US010982249B2

(12) United States Patent
Douchin et al.

(10) Patent No.: US 10,982,249 B2

(45) Date of Patent: Apr. 20, 2021

(54) PRODUCTION OF STEVIOL GLYCOSIDES IN RECOMBINANT HOSTS

(71) Applicant: EVOLVA SA, Reinach (CH)

(72) Inventors: Veronique Douchin, Frederiksberg (DK); Swee Chuang Lim Hallwyl, Vallensbaek Strand (DK); Kim Olsson, Copenhagen (DK)

(73) Assignee: Evolva SA, Reinach (CH)

( * ) Notice: Subject to any disclaimer, the term of this patent is extended or adjusted under 35 U.S.C. 154(b) by 48 days.

(21) Appl. No.: 16/091,536

(22) PCT Filed: Apr. 13, 2017

(86) PCT No.: PCT/EP2017/059028

§ 371 (c)(1),
(2) Date: Oct. 5, 2018

(87) PCT Pub. No.: WO2017/178632

PCT Pub. Date: Oct. 19, 2017

(65) Prior Publication Data

US 2019/0203245 A1 Jul. 4, 2019

Related U.S. Application Data

(60) Provisional application No. 62/321,850, filed on Apr. 13, 2016.

(51) Int. Cl.

| | |
|---|---|
| ***C12P 19/44*** | (2006.01) |
| ***C12P 19/56*** | (2006.01) |
| ***A23L 2/60*** | (2006.01) |
| ***C12N 15/63*** | (2006.01) |
| ***A23L 27/30*** | (2016.01) |
| ***G01N 30/02*** | (2006.01) |

(52) U.S. Cl.

CPC ................. *C12P 19/56* (2013.01); *A23L 2/60* (2013.01); *A23L 27/36* (2016.08); *C12N 15/63* (2013.01); *G01N 30/02* (2013.01); *G01N 2030/027* (2013.01)

(58) Field of Classification Search

CPC ................................ C12N 15/63; C12N 19/56

See application file for complete search history.

(56) References Cited

U.S. PATENT DOCUMENTS

| | | | |
|---|---|---|---|
| 4,590,160 | A | 5/1986 | Nishihashi et al. |
| 5,198,360 | A | 3/1993 | Ballou et al. |
| 5,204,253 | A | 4/1993 | Sanford et al. |
| 5,306,862 | A | 4/1994 | Chappell et al. |
| 5,460,949 | A | 10/1995 | Saunders et al. |
| 5,538,880 | A | 7/1996 | Lundquist et al. |
| 6,013,863 | A | 1/2000 | Lundquist et al. |
| 6,215,051 | B1 | 4/2001 | Yu et al. |
| 6,255,557 | B1 | 7/2001 | Brandle |
| 6,284,493 | B1 | 9/2001 | Roth |
| 6,284,506 | B1 | 9/2001 | Hoshino et al. |
| 6,329,571 | B1 | 12/2001 | Hiei |
| 6,586,202 | B2 | 7/2003 | Hoshino et al. |
| 6,660,507 | B2 | 12/2003 | Cheng et al. |
| 6,806,076 | B1 | 10/2004 | Miyake et al. |
| 6,969,595 | B2 | 11/2005 | Brzostowicz et al. |
| 7,034,140 | B2 | 4/2006 | Bramucci et al. |
| 7,056,717 | B2 | 6/2006 | Cheng et al. |
| 7,098,000 | B2 | 8/2006 | Cheng et al. |
| 7,129,392 | B2 | 10/2006 | Hahn et al. |
| 7,132,268 | B2 | 11/2006 | Miyake et al. |
| 7,172,886 | B2 | 2/2007 | Keasling et al. |
| 7,183,089 | B2 | 2/2007 | Keasling et al. |
| 7,186,891 | B1 | 3/2007 | Chappell et al. |
| 7,208,298 | B2 | 4/2007 | Miyake et al. |
| 7,335,815 | B2 | 2/2008 | Boronat et al. |
| 7,364,885 | B2 | 4/2008 | Miyake et al. |
| 7,422,884 | B2 | 9/2008 | Bai et al. |
| 7,514,597 | B2 | 4/2009 | Nakamura et al. |
| 7,569,389 | B2 | 9/2009 | Feldmann et al. |
| 7,692,065 | B2 | 4/2010 | Harper et al. |
| 7,838,287 | B2 | 11/2010 | Goldsmith et al. |
| 7,923,541 | B2 | 4/2011 | Yang et al. |
| 7,927,851 | B2 | 4/2011 | Brandle et al. |
| 7,981,647 | B2 | 7/2011 | Berry et al. |
| 9,562,251 | B2 | 2/2017 | Kishore et al. |
| 9,957,540 | B2 | 5/2018 | Mikkelsen et al. |
| 2002/0142408 | A1 | 10/2002 | DiCosimo et al. |
| 2003/0033626 | A1 | 2/2003 | Hahn et al. |
| 2003/0148416 | A1 | 8/2003 | Berry et al. |
| 2003/0148479 | A1 | 8/2003 | Keasling et al. |
| 2003/0190734 | A1 | 10/2003 | Hoshino et al. |
| 2003/0219798 | A1 | 11/2003 | Gokarn et al. |
| 2004/0010815 | A1 | 1/2004 | Lange et al. |

(Continued)

FOREIGN PATENT DOCUMENTS

| | | |
|---|---|---|
| CN | 101720910 | 6/2010 |
| CN | 102216313 | 10/2011 |

(Continued)

OTHER PUBLICATIONS

International Search Report issued by the International Searching Authority for International Application No. PCT/US2011/038967, dated Sep. 1, 2011 (10 pages).

Written Opinion of the International Searching Authority for International Application No. PCT/US2011/038967, dated Sep. 1, 2011 (12 pages).

International Preliminary Report on Patentability issued by the International Bureau for International Application No. PCT/US2011/038967, dated Dec. 4, 2012 (13 pages).

(Continued)

*Primary Examiner* — Tekchand Saidha

(74) *Attorney, Agent, or Firm* — McDonnell Boehnen Hulbert & Berghoff LLP

(57) ABSTRACT

The invention relates to recombinant microorganisms and methods for producing steviol glycosides and steviol glycoside precursors.

22 Claims, 3 Drawing Sheets

Specification includes a Sequence Listing.

(56) References Cited

U.S. PATENT DOCUMENTS

| | | | |
|---|---|---|---|
| 2004/0072311 | A1 | 4/2004 | DiCosimo et al. |
| 2004/0078846 | A1 | 4/2004 | Desouza et al. |
| 2004/0176570 | A1 | 9/2004 | Bacher et al. |
| 2004/0194162 | A1 | 9/2004 | Hahn et al. |
| 2005/0003474 | A1 | 1/2005 | Desouza |
| 2005/0032169 | A1 | 2/2005 | Miyake et al. |
| 2006/0014264 | A1 | 1/2006 | Sauer |
| 2006/0079476 | A1 | 4/2006 | Keasling et al. |
| 2006/0083838 | A1 | 4/2006 | Jackson et al. |
| 2007/0004000 | A1 | 1/2007 | Miyake et al. |
| 2007/0077616 | A1 | 4/2007 | Keasling et al. |
| 2007/0099261 | A1 | 5/2007 | Keasling et al. |
| 2007/0118916 | A1 | 5/2007 | Puzio et al. |
| 2007/0128311 | A1 | 6/2007 | Prakash et al. |
| 2007/0166782 | A1 | 7/2007 | Keasling et al. |
| 2007/0202579 | A1 | 8/2007 | Berry et al. |
| 2007/0238157 | A1 | 10/2007 | Millis et al. |
| 2007/0238159 | A1 | 10/2007 | Millis et al. |
| 2007/0238160 | A1 | 10/2007 | Millis et al. |
| 2007/0254354 | A1 | 11/2007 | Millis et al. |
| 2007/0269857 | A1 | 11/2007 | Miyake et al. |
| 2007/0286850 | A1 | 12/2007 | Bai et al. |
| 2008/0064063 | A1 | 3/2008 | Brandle |
| 2008/0081358 | A1 | 4/2008 | Vittanen et al. |
| 2008/0131926 | A1 | 6/2008 | Miyake et al. |
| 2008/0216397 | A1 | 9/2008 | Busby et al. |
| 2008/0261280 | A1 | 10/2008 | Hahn et al. |
| 2008/0271205 | A1 | 10/2008 | Yamaguchi et al. |
| 2008/0286870 | A1 | 11/2008 | Vittanen et al. |
| 2008/0292775 | A1 | 11/2008 | Prakash et al. |
| 2008/0318227 | A1 | 12/2008 | Bacher et al. |
| 2009/0004724 | A1 | 1/2009 | Keasling et al. |
| 2009/0047718 | A1 | 2/2009 | Blaschek et al. |
| 2009/0055974 | A1 | 2/2009 | Tanksley et al. |
| 2009/0074935 | A1 | 3/2009 | Lee |
| 2009/0143308 | A1 | 6/2009 | Monk et al. |
| 2009/0286262 | A1 | 11/2009 | Slack |
| 2009/0298706 | A1 | 12/2009 | Lee et al. |
| 2010/0112156 | A1 | 5/2010 | Abelyan et al. |
| 2010/0120096 | A1 | 5/2010 | Kitaoka et al. |
| 2010/0221801 | A1 | 9/2010 | Van Dyk |
| 2010/0297722 | A1 | 11/2010 | Anterola et al. |
| 2010/0316782 | A1 | 12/2010 | Shi et al. |
| 2011/0087011 | A1 | 4/2011 | Chiang et al. |
| 2011/0092684 | A1 | 4/2011 | Abelyan et al. |
| 2011/0126318 | A1 | 5/2011 | Allen et al. |
| 2011/0160311 | A1 | 6/2011 | Prakash et al. |
| 2012/0021111 | A1 | 1/2012 | Pfister et al. |
| 2012/0083593 | A1 | 4/2012 | Liu et al. |
| 2012/0164678 | A1 | 6/2012 | Stephanopoulos et al. |
| 2012/0178169 | A1 | 7/2012 | Voytas et al. |
| 2013/0137138 | A1 | 5/2013 | Hansen |
| 2013/0171328 | A1 | 7/2013 | Kishore et al. |
| 2014/0329281 | A1 | 11/2014 | Houghton-Larsen et al. |
| 2015/0159188 | A1 | 6/2015 | Ono et al. |
| 2015/0342234 | A1 | 12/2015 | Hicks et al. |
| 2016/0186225 | A1 | 6/2016 | Mikkelsen et al. |

FOREIGN PATENT DOCUMENTS

| | | |
|---|---|---|
| CN | 103397064 | 11/2013 |
| CN | 104845990 | 8/2015 |
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2575432 | 4/2013 |
| EP | 2902410 | 8/2015 |
| JP | 59101408 | 6/1984 |
| JP | 3-277275 | 12/1991 |
| JP | 05-115298 | 5/1993 |
| JP | 2009034080 | 2/2009 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006069610 | 7/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2008/091547 | 7/2008 |
| WO | WO 2009/005704 | 1/2009 |
| WO | WO 2009/037329 | 3/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | WO 2009/111513 | 9/2009 |
| WO | 2009/140394 | 11/2009 |
| WO | WO 2009/140394 | 11/2009 |
| WO | WO 2010/021001 | 2/2010 |
| WO | WO 2010/038911 | 4/2010 |
| WO | WO 2010/044960 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | WO 2011/060057 | 5/2011 |
| WO | WO 2011/153378 | 8/2011 |
| WO | 2011/140329 | 11/2011 |
| WO | 2011/151326 | 12/2011 |
| WO | 2011/153378 | 12/2011 |
| WO | WO 2011/151326 | 12/2011 |
| WO | WO 2011/153144 | 12/2011 |
| WO | WO 2012/075030 | 6/2012 |
| WO | 2013/022989 | 2/2013 |
| WO | WO 2013/019050 | 2/2013 |
| WO | WO 2013/022989 | 2/2013 |
| WO | WO 2013/021261 | 5/2013 |
| WO | WO 2013/076577 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |
| WO | WO 2014/086890 | 6/2014 |
| WO | WO 2014/122227 | 8/2014 |
| WO | WO 2014/122328 | 8/2014 |
| WO | 2014/191580 | 12/2014 |
| WO | 2014/191581 | 12/2014 |
| WO | WO2014/191580 | 12/2014 |
| WO | 2015/011209 | 1/2015 |
| WO | WO 2015/007748 | 1/2015 |
| WO | 2015/014959 | 2/2015 |
| WO | 2015/016393 | 2/2015 |
| WO | WO 2015/014969 | 2/2015 |
| WO | WO 2015/028324 | 3/2015 |
| WO | WO 2015051454 | 4/2015 |
| WO | WO 2015/132411 | 9/2015 |
| WO | 2016/023844 | 2/2016 |
| WO | WO 2016/038095 | 3/2016 |

(56) References Cited

FOREIGN PATENT DOCUMENTS

WO WO 2016/120486 8/2016
WO WO 2017/025362 2/2017
WO WO 2017/098017 6/2017

OTHER PUBLICATIONS

Third-Party Submission under 37 CFR 1.290 for U.S. Appl. No. 13/701,406, dated Mar. 7, 2014 (238 pages).
Extended European Search Report and Opinion issued by the European Patent Office for European Application No. 11790428.4, dated Dec. 20, 2013.
Non-Final Office Action for U.S. Appl. No. 14/237,540, dated Dec. 30, 2015 (pp. 1-19).
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
International Preliminary Report on Patentability issued by the International Bureau for International Application No. PCT/US2012/050021, dated Feb. 11, 2014.
Extended European Search Report issued in EP 15193074.0; dated Feb. 12, 2016, pp. 1-9.
International Search Report from the International Searching Authority for International Application No. PCT/EP2014/052363, dated Sep. 22, 2014 (12 pages).
Written Opinion of the International Searching Authority for International Application No. PCT/EP2014/052363, dated Sep. 22, 2014 (10 pages).
International Preliminary Report on Patentability issued by the International Bureau for International Application No. PCT/EP2014/052363, dated Aug. 11, 2015 (11 pages).
International Preliminary Report on Patentability issued by the International Bureau for International Application No. PCT/EP2014/052675, dated Aug. 11, 2015 (8 pages).
International Search Report of the International Searching Authority for International Application No. PCT/EP2013/075587, dated Feb. 20, 2014 (pp. 1-5).
Written Opinion of the International Searching Authority for International Application No. PCT/EP2013/075587, dated Feb. 20, 2014 (pp. 1-9).
International Preliminary Report on Patentability from the International Bureau for International Application No. PCT/EP2013/075587, dated Jun. 9, 2015 (pp. 1-10).
Invitation to Pay Additional Fees and, Where Applicable, Protest Fee by the International Searching Authority for International Application No. PCT/EP2015/070620, dated Nov. 27, 2015 (pp. 1-14).
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).
Garber et al., "Computational methods for transcriptome annotation and quantification using RNA-seq," Nat Methods 8(6):469-77 (2011).
Kawai et al., "Transformation of *Saccharomyces cerevisiae* and other fungi: methods and possible underlying mechanism," Bioeng Bugs. 1(6):395-403 (2010).
Lin et al., "Arrestin-related ubiquitin-ligase adaptors regulate endocytosis and protein turnover at the cell surface," Cell 135(4):714-25 (2008).
Nagalakshmi et al., "The transcriptional landscape of the yeast genome defined by RNA sequencing," Science 320(5881 ): 1344-9 (2008).
Nikko & Pelham, "Arrestin-mediated endocytosis of yeast plasma membrane transporters," Traffic 10(12):1856-67 (2009).
Nikko et al. "Arrestin-like proteins mediate ubiquitination and endocytosis of the yeast metal transporter Smf1," EMBO Rep. 9(12):1216-21 (2008).
Olsson et al., "Microbial production of next-generation stevia sweeteners," Microbial Cell Factories, 15:11-14 (2016).
Partow et al., "Characterization of different promoters for designing a new expression vector in *Saccharomyces cerevisiae*," Yeast 27:955-64 (2010).
Robinson & Oshlack et al., "A scaling normalization method for differential expression analysis of RNA-seq data," Genome Bioi. 11(3):R25 (2010).
Saier Jr. et al., "The transporter classification database," Nucl. Acids Res., 42(1):D251-258 (2014).
Wang et al., "RNA-Seq: a revolutionary tool for transcriptomics," Nat Rev Genet. 10(1):57-63 (2009).
Wilhelm et al., "Defining transcribed regions using RNA-seq," Nature Protocols 5:255-66 (2010).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Abraham & Bhat, "Permeabilization of baker's yeast with N-lauroyl sarcosine," J Ind Microbial Biotechnol. 35(8):799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31(10):3307-30 (1992).
Ajikumar et al., "Terpenoids: opportunities for biosynthsis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42(4):2827-37 (2010).
Bankar et al., "Environmental and industrial applications of Yarrowia lipolytica," Appl Microbiol Biotechnol. 84(5):847-65 (Oct. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis," Plant Mol Biol. 50(4-5):613-22 (2002).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Carretero-Paulet et al., "Expression and Molecular Analysis of the *Arabidopsis* DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Chemler et al., "Biosynthesis of isoprenoids, polyunsaturated fatty acids and flavonoids in *Saccharomyces cerevisiae*," Microb Cell Fact. 5:20 (2006).
Chen, "Summary on Study of Stevioside," China Pharmacist, 10(6):598-599 (2007).
Chen et al., "MolProbity: all-atom structure validation for macromolecular crystallography," Acta Crystallogr D Biol Crystallogr 66(Pt 1):12-21 (Jan. 2010).
Chica et al., "Semi-rational approaches to engineering enzyme activity: combining the benefits of directed evolution and rational design," Curr Opin Biotechnol. 16(4):378-84 (2005).
Chow & Palecek, "Enzyme encapsulation in permeabilized *Saccharomyces cerevisiae* cells," Biotechnol Prog. 20(2):449-56 (2004).
Correa et al., "Genetic mapping of 1,3-beta-glucanase-encoding genes in *Saccharomyces cerevisiae*," Current Genet. 22(4):283-8 (1992).

(56) References Cited

OTHER PUBLICATIONS

Darise et al., "Enzymic Transglucosylation of Rubusoside and the Structure-Sweetness Relationship of Steviol-Bisglycosides," Agric. Biol. Chem. 48(10):2483-8 (Jan. 1984).

Davis et al., "MolProbity: all-atom contacts and structure validation for proteins and nucleic acids," Nucleic Acids Res. 35:W375-83 (Apr. 2007).

Del Sorbo et al., "Fungal transporters involved in efflux of natural toxic compounds and fungicides," Fungal. Genet. Biol. 30(1):1-15 (Jun. 2000).

Diener et al., "*Arabidopsis* ALF5, a multidrug efflux transporter gene family member, confers resistance to toxins," Plant Cell 13(7):1625-38 (Jul. 2001).

Dodhia et al., "Engineering human cytochrome P450 enzymes into catalytically self-sufficient chimeras using molecular Lego," J Biol Inorg Chem. 11(7):903-16 (Oct. 2006).

Dubey, et al., An overview of the non-mevalonate pathway for terpenoid biosynthesis in plants, J. Biosci. 28(5):637-46 (2003).

Dubois & Stephenson, "Diterpenoid sweeteners. Synthesis and sensory evaluation of stevioside analogues with improved organoleptic properties," J. Med. Chem. 28(1):93-8 (Jan. 1985).

EFSA Panel on Food Additives and Nutrient Sources added to Food (ANS), "Scientific Opinion on the safety of steviol glycosides for the proposed uses as a food additive," EFSA Journal 8(4):1537 (2010).

Eisenreich et al., "Biosynthesis of isoprenoids via the non-mevalonate pathway," Cell Mol Life Sci. 61(12):1401-6 (2004).

Emboss Needle results for Pairwise Sequence Alignment of UGT91D1 and UGT91D2; dated Apr. 4, 2016, 2 pages.

Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).

Estrada De Martin et al., "Ice2p is important for the distribution and structure of the cortical ER network in *Saccharomyces cerevisiae*," J Cell Sci. 118(Pt 1):65-77 (Oct. 2006).

Fernandez et al., "Activation of chitin synthetase in permeabilized cells of a *Saccharomyces cerevisiae* mutant lacking proteinase B," J Bacteriol. 152(3):1255-64 (1982).

Flores et al., "Permeabilization of yeast cells (*Kluyveromyces lactis*) with organic solvents," Enzyme Microb Technol. 16(4):340-6 (1994).

Fowler & Zabin, "Effects of Dimethylsulfoxide on the Lactose Operon in *Escherichia coli*," J Bacteriol. 92(2):353-7 (1966).

Freire, "Differential scanning calorimetry," Methods Mol Biol. 40:191-218 (1995).

Fukunaga et al., "Enzymatic transglucosylation products of stevioside: separation and sweetness-evaluation," Agric. Biol. Chem. 53(6):1603-7 (Jan. 1989).

Geuns, "Stevioside," Phytochemistry 64(5):913-21 (2003).

Giaever & Nislow, "The yeast deletion collection: a decade of functional genomics," Genetics 197(2):451-65 (Jun. 2014).

Gietz & Schiestl, "High-efficiency yeast transformation using the LiAc/SS carrier DNA/PEG method," Nat Protoc. 2(1):31-4 (2007).

Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).

Goralczyk, "Compounds from Stevia for Improving and Maintaining Mental Performance," Stevia World Forum, Feb. 24-25, 2010, 17 pages.

Guleria & Yadav, "Insights into Steviol Glycoside Biosynthesis Pathway Enzymes Through Structural Homology Modeling," Am. J. Biochem. Molec. Biol. 3(1):1-19 (2013).

Gunel et al., "Metabolic Engineering for Production of Geranylgeranyl Pyrophosphate Synthase in Non-Carotenogenic Yeast *Schizosaccharomyces pombe*," Biotechnol. & Biotechnol. Eq. 20(3):76-82 (2006).

Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).

Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).

Hellfritsch et al., "Human psychometric and taste receptor responses to steviol glycosides," J. Agric. Food Chem. 60(27):6782-93 (Jul. 2012).

Humphrey et al., "Spatial organisation of four enzymes from Stevia rebaudiana that are involved in steviol glycoside synthesis," Plant Mol Bio. 61(1-2):47-62 (2006).

Iandolino et al., "High-Quality RNA, cDNA, and Derived EST Libraries From Grapevine (*Vitis vinifera* L.)," Plant Mol Biol Reporter 22:269-78 (2004).

Irmler et al., "Indole alkaloid biosynthesis in Catharanthus roseus: new enzyme activities and identification of cytochrome P450 CYP72A1 as secologanin synthase," Plant J. 24(6):797-804 (2000).

Jennewein et al., "Taxol biosythesis: baxane 13 alpha-hydroxylase is a cytochrome P450-dependent monooxygenase," Proc Natl Acad Sci U S A 98(24):13595-600 (2001).

Bateman et al., "Pfam 3.1: 1313 multiple alignments and profile HMMs match the majority of proteins," Nucleic Acids Res. 27(1):260-2 (Jan. 1999).

Bay & Turner, "Diversity and evolution of the small multidrug resistance protein family," BMC Evol. Biol. 9:140 (Jun. 2009).

Brachmann et al., "Designer deletion strains derived from *Saccharomyces cerevisiae* S288C: a useful set of strains and plasmids for PCR-mediated gene disruption and other applications," Yeast 14:115-32 (1998).

Chen et al., "Transferring a biosynthetic cycle into a productive *Escherichia coli* strain: large-scale synthesis of galactosides," J. Am. Chem. Soc. 123(36):8866-7 (Sep. 2001).

Chenna et al., "Multiple sequence alignment with the Clustal series of programs," Nucleic Acids Res. 31(13):3497-500 (Jul. 2003).

GenBank Accession No. AAB62280, dated Jul. 2, 1997 (2 pages).

GenBank Accession No. AAB87091, dated Mar. 22, 2000 (2 pages).

GenBank Accession No. AAC28895.1, dated Aug. 6, 1998 (2 pages).

GenBank Accession No. AAC39505, dated Jul. 26, 1998 (1 page).

GenBank Accession No. AAD34294, dated Mar. 22, 2000 (2 pages).

GenBank Accession No. AAD34295, dated Mar. 22, 2000 (2 pages).

GenBank Accession No. AAD47596, dated Aug. 9, 1999 (2 pages).

GenBank Accession No. AAH69913, dated Jul. 15, 2006 (2 pages).

GenBank Accession No. AEE36246, dated Oct. 6, 2014 (3 pages).

GenBank Accession No. AAR06912, dated Dec. 28, 2004 (2 pages).

GenBank Accession No. AAR06916.1, dated Dec. 28, 2004 (2 pages).

GenBank Accession No. AAR06920.1, dated Dec. 28, 2004 (2 pages).

GenBank Accession No. ABA42921, dated Jun. 21, 2006 (1 page).

GenBank Accession No. ABB88839, dated May 28, 2008 (2 pages).

GenBank Accession No. ABC59076, dated Jun. 6, 2007 (1 page).

GenBank Accession No. ABC98596, dated Jan. 31, 2014 (2 pages).

GenBank Accession No. ABD60225, dated May 28, 2008 (2 pages).

GenBank Accession No. ABD92926, dated Oct. 10, 2007 (2 pages).

GenBank Accession No. AC133334, dated Jan. 31, 2004 (44 pages).

GenBank Accession No. ACD93722, dated Jun. 10, 2008 (1 page).

GenBank Accession No. AF034774, dated Apr. 17, 1998 (2 pages).

GenBank Accession No. AY562490, dated May 23, 2006 (3 pages).

GenBank Accession No. BAA43200, dated Mar. 13, 1999 (2 pages).

GenBank Accession No. BAB59027, dated Jan. 30, 2002 (1 page).

GenBank Accession No. BAF61135, dated May 9, 2007 (2 pages).

GenBank Accession No. BAG30962, dated Nov. 12, 2012 (2 pages).

GenBank Accession No. BC153262, dated Oct. 4, 2007 (3 pages).

GenBank Accession No. CAA75568, dated Nov. 14, 2006 (2 pages).

GenBank Accession No. CAA76703, dated Nov. 14, 2006 (1 page).

GenBank Accession No. CAE09055, dated Nov. 14, 2006 (2 pages).

GenBank Accession No. CAG41604, dated Feb. 6, 2015 (2 pages).

GenBank Accession No. DQ3988713, dated May 28, 2008 (2 pages).

GenBank Accession No. EDY51667, dated Sep. 2, 2008 (2 pages).

GenBank Accession No. EU263989, dated Jun. 11, 2008 (2 pages).

(56) References Cited

OTHER PUBLICATIONS

GenBank Accession No. NM_116512, dated Jan. 22, 2014 (3 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. NP_194183, dated Jan. 22, 2014 (4 pages).
GenBank Accession No. NP_195399, dated Jan. 22, 2014 (3 pages).
GenBank Accession No. NP_197872.1, dated Jan. 22, 2014 (2 pages).
GenBank Accession No. Q9UVY5.1, dated Apr. 1, 2015 (3 pages).
GenBank Accession No. AAS07253.1, dated Jan. 31, 2004 (3 pages).
Gloster, "Advances in understanding glycosyltransferases from a structural perspective," Curr Opin Struct Biol. 28:131-41 (2014).
Guo et al., "Protein tolerance to random amino acid change", Proceedings of the National Academy of Sciences USA, vol. 101, No. 25, pp. 9205-9210 (2004).
Liu et al., "Biosynthesis of Rebaudioside A by Whole Cell of Recombinant *Saccharomyces cerevisiae*," Food and Fermentation Industries, 38(7) : 6-10 (2012) (Abstract translation).
Ni et al., "Outer membrane mutation effects on UDP-glucose permeability and whole-cell catalysis rate," Appl Microbiol Biotechnol. 73(2):384-93 (2006).
Prisic et al, "Synergistic substrate inhibition of ent-copalyl diphosphate synthase: a potential feed-forward inhibition mechanism limiting gibberellin metabolism," Plant Physiol. 144(1):445-54 (2007).
Unligil et al., "Glycosyltransferase structure and mechanism," Curr Opin Struct Biol. 10(5):510-7 (2000).
Wanchao et al., "Advances on the Stevoil Glycoside Biosynthesis and Its Key Enzymes," Biotechnology Bulletin, Feb. 2008 (English Abstract translation).
International Search Report by the International Searching Authority for International Application No. PCT/EP2015/070620; dated Mar. 29, 2016, pp. 1-10.
Written Opinion of the International Searching Authority for International Application No. PCT/EP2015/070620; dated Mar. 29, 2016, pp. 1-24.
Shao et al., "Crystal structures of a multifunctional triterpene/flavonoid glycosyltransferase from Medicago truncatula," Plant Cell 17(11):3141-54 (2005).
Shibata et al., "Glucosylation of Steviol and Steviol-Glucosides in Extracts from *Stevia rebaudiana Bertoni*" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast *Kluyveromyces lactis*," FEMS Yeast Res. 6(3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73(13):4342-50 (2007).
Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583(20):3303-9 (2009).
Xu et al., "Generation of hepatitis B virus PreS2-S antigen in Hansenula polymorpha," Virol Sin. 29(6):403-9 (Dec. 2014).
Yadav et al., "A review on the improvement of stevia [*Stevia rebaudiana* (*Bertoni*)]," Can J Plant Sci. 91:1-27 (2011).
Yao et al., "A genetic linkage map for Stevia rebaudiana," Genome 42:657-61 (1999).
Yazaki, "ABC transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast *Rhodosporidium toruloides*," Nature Commun. 3:1112 (Oct. 2012).
GenBank Accession No. AAF61439.1, dated Sep. 25, 2000 (2 pages).
GenBank Accession No. AAM53963.1, dated Jun. 17, 2002 (2 pages).
GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454A, dated May 28, 2008 (2 pages).
GenBank Accession No. EU722415.1, dated Jun. 10, 2008 (2 pages).
GenBank Accession No. EU751291.1, dated Jun. 24, 2008 (2 pages).
EBI Accession No. AAY05902, "Jerusalem artichoke in-chain hydroxylase CYP8161" (1 page), Jun. 15, 2009.
EBI Accession No. ABM86477, "Rice abiotic stress responsive polypeptide Seq ID No. 4723" (1 page), dated Jun. 2, 2005.
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Liu et al., "Functional and Biochemical Characteritzation of *Escherichia coli* Sugar Efflux Transporters," JBC, 274(33):22977-22984 (Aug. 1999).
Sun et al., "Regulation and Function of *Escherichia coli* Sugar Efflux Transporter A (Set A) during Glucose-Phosphate Stress," J of Bacteriology, 193(1):143-153 (Jan. 2011).
Chen et al., "Sugar transporters for intercellular exchange and nutrition of pathogens," Nature 468(7323):527-32 (2010).
Chen et al., "Fusion protein linkers: Property, design, and functionality", Advanced Drug Delivery reviews, 65(0):1257-69 (2013).

(56) References Cited

OTHER PUBLICATIONS

Daran et al., "Genetic and biochemical characterization of the UGP1 gene encoding the UDP-glucose pyrophosphorylase from *Saccharomyces cerevisiae*," Eur J Biochem. 233(2):520-30 (Jul. 1995).
Husar et al., "Overexpression of the UGT73C6 alters brassinosteriod glucoside formation in *Arabidopsis thaliana*", BMC Plant Biology, 11:1-14 (2011).
Khan et al., "Physical and chemical mutagenesis in Stevia rebaudiana: variant generation with higher UGT expression and glycosidic profile but with low photosynthetic capabilities," Acta Physiologiae Plantarum 38(1) (2016).
Malonek et al., "The NADPH-cytochrome P450 Reductase Gene from Gibberalla fujikuroi is Essential for Gibberellin Biosynthesis", J Bio Chem. 279(24):25075-84 (Jun. 2004).
Mao et al., "Produce steviol glycosides in engineered yeast", 2015 Synthetic Biology: Engineering, Evolution & Design (SEED), Poster Abstract (Jun. 2015).
Nagatoshi et al., "UGT75L6 and UGT94E5 mediate sequential glucosylation of crocetin to crocin in Gardenia asminoides", FEBS Letters, 586:1055-1061 (2012).
Wang et al., "Pathway mining-based integration of critical enzyme parts for de novo biosynthesis of steviol glycoside sweetener in *Escherichia coli*", Cell Research, 26:258-261 (Sep. 2015).
Wang et al., "Efficient enzymatic production of rebaudioside A from stevioside", Bioscience, Biotechnology, and Biochemistry, 80:67-73 (Aug. 2015).
Wang et al., "Design and construction of artificial biological systems for complex natural products biosynthesis", Chinese Journal of Biotechnology, 29:1146-1160 (2013).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside: In-house validation and application to wheat," Journal of Chromatography A, 1423, pp. 183-189 (2015).
Yang et al., "Base substitution mutations in uridinediphosphate-dependent glycosyltransferase 76G1 gene of Stevia rebaudioside A; Mustation in UGT76G1, a key gene of steviol glycoside synthesis", Plant Physiology and Biochemistry, 80:220-225 (2014).
Examination Report issued by the European Patent Office for European Application No. 12750513.9, dated Nov. 26, 2014.
Mahe et al., "The ATP Binding Cassette Transporters Pdr5 and Snq2 of *Saccharomyces cerevisiae* Can Mediate Transport of Sterids via in Vivo", JBC, 271(41):25167-25172. (Oct. 1996).
Starratt et al., "Rebaudioside F, a diterpene glycoside from Stevia redaudiana", Phytochemistry, 59(4):367-370. (Feb. 2002). Abstract.
Uniprot Accession No. Q75183, dated Jul. 5, 2004 (pp. 1-2).
Uniprot Accession No. Q75183, dated Jul. 22, 2008 (pp. 1-4).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).
Hallstrom & Moye-Rowley, "Divergent transcriptional control of multidrug resistance genes in *Saccharomyces cerevisiae*," J. Biol. Chem. 273(4):2098-104 (Jan. 1998).
Katzmann et al., "Expression of an ATP-binding cassette transporter-encoding gene (YOR1) is required for oligomycin resistance in *Saccharomyces cerevisiae*," Mol. Cell Biol. 15(12):6875-83 (Dec. 1995).
Li et al., "Phylogenetic analysis of the UDP-glycosyltransferase multigene family of *Arabidopsis thaliana*," J. Biol. Chem. 276(6):4338-43 (Oct. 2000).
Masada et al., "An efficient chemoenzymatic production of small molecule glucosides with in situ UDP-glucose recycling," FEBS Lett. 581(13):2562-6 (May 2007).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (May 2005).
Nagy et al., "Role of the yeast ABC transporter Yor1p in cadmium detoxification," Biochimie 88(11):1665-71 (Jun. 2006).
Nikaido & Takatsuk, "Mechanisms of RND multidrug efflux pumps," Biochim. Biophys. Acta. 1794(5):769-81 (May 2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).
Osmani et al., "Substrate specificity of plant UDP-dependent glycosyltransferases predicted from crystal structures and homology modeling," Phytochemistry 70(3):325-47 (Feb. 2009).
Richman et al., "Functional genomics uncovers three glucosyltransferases involved in the synthesis of the major sweet glucosides of Stevia rebaudiana," Plant J. 41(1):56-67 (Jan. 2005).
Riesmeier et al., "Isolation and characterization of a sucrose carrier cDNA from spinach by functional expression in yeast," EMBO J. 11(13):4705-13 (Dec. 1992).
Rodríguez-Concepción & Boronat, "Elucidation of the methylerythritol phosphate pathway for isoprenoid biosynthesis in bacteria and plastids. A metabolic milestone achieved through genomics," Plant Physiol. 130(3):1079-89 (Nov. 2002).
Saier Jr et al., "The major facilitator superfamily," J. Mol. Microbiol. Biotechnol. 1(2):257-79 (Nov. 1999).
Saier Jr et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coli*," J. Biol. Chem. 279(8):6613-9 (Dec. 2003).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J. Biol. Chem. 280(2):899-906 (Jan. 2005).
Shao et al., "Enhanced production of alpha-galactosyl epitopes by metabolically engineered Pichia pastoris," Appl. Environ. Microbiol. 69(9):5238-42 (Sep. 2003).
Son et al., "Production of flavonoid O-glucoside using sucrose synthase and flavonoid O-glucosyltransferase fusion protein," J. Microbiol. Biotechnol. 19(7):709-12 (Jul. 2009).
Sonnhammer et al., "Pfam: a comprehensive database of protein domain families based on seed alignments," Proteins 28(3):405-20 (Jul. 1997).
Sonnhammer et al., "Pfam: multiple sequence alignments and HMM-profiles of protein domains," Nucleic Acids Res. 26(1):320-2 (Jan. 1998).
Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).
International Search Report by the International Searching Authority for International Application No. PCT/EP2014/052675, dated Apr. 23, 2014 (5 pages).
Written Opinion of the International Searching Authority for International Application No. PCT/EP2014/052675, dated Apr. 23, 2014 (7 pages).
Arnold, F. H. "Combinatorial and computational challenges for biocatalyst design," Nature 409(6817):253-257 (2001) .

(56) References Cited

OTHER PUBLICATIONS

Bruyn et al., "Metabolic engineering of *Escherichia coli* into a versatile glycosylation platform: production of bio-active quercetin glycosides," Microb Cell Fact., 14:138 (2015).
Bruyn et al., "Development of an in vivo glucosylation platform by coupling production to growth: production of phenolic glucosides by a glycosyltransferase of Vitis vinifera," Biotechnol Bioeng., 112(8):1594-603 (2015).
Duetz, "Microtiter plates as mini-bioreactors: miniaturization of fermentation methods," Trends Microbiol 15(10):469-75 (2007).
François et al., "Reserve carbohydrates metabolism in the yeast *Saccharomyces cerevisiae*," FEMS Microbiol Rev., 25(1):125-45 (2001).
Li et al., "Production of rebaudioside A from stevioside catalyzed by the engineered *Saccharomyces cerevisiae*," Appl Biochem Biotechnol., 178(8):1586-98 (2016).
Mikayama et al., "Molecular cloning and functional expression of a cDNA encoding glycosylation-inhibiting factor," Proc Natl Acad Sci U S A. 90(21):10056-60 (1993).
Rudinger et al., "Characteristics of the amino acids as components of a peptide hormone sequence," Peptide Hormones. Biol. Council. pp. 5-7 (1976).
Saier, "Families of transmembrane sugar transport proteins," Mol Microbiol., 35(4):699-710 (2000).
Tiwari et al., "Plant secondary metabolism linked glycosyltransferases: An update on expaning knowledge and scopes", Biotechnology Advances, 34:714-739 (May 2016).
GenBank Accession No. AZF53544, dated Apr. 14, 2011 (2 pages).
UniProt Accession No. B5MEX6, Nov. 4, 2008 (1 page).
UniProt Accession No. E4MVV7, Feb. 8, 2011 (1 page).
UniProt Accession No. F6KWJ2, Jul. 27, 2011 (1 page).
UniProt Accession No. H9BYK3, May 16, 2012 (1 page).
International Preliminary Report on Patentability from the International Bureau for International Application PCT/EP2015/070620; dated Mar. 14, 2017 (pp. 1-25).
International Preliminary Report on Patentability from the International Bureau for International Application PCTEP2015/068314; dated Feb. 14, 2017 (pp. 1-10).
International Search Report and Written Opinion of the International Searching Authority for International Application No. PCT/EP2015/052007; dated Jul. 4, 2016, pp. 1-24.
International Preliminary Report on Patentability from the International Bureau for International Application PCT/EP2015/052007; dated Aug. 1, 2017 (pp. 1-16).
International Search Report and Written Opinion of the International Searching Authority for International Application No. PCT/EP2016/068259; dated Jan. 24, 2017, pp. 1-18.
International Preliminary Report on Patentability from the International Bureau for International Application PCT/EP2016/068259; dated Feb. 13, 2018 (pp. 1-11).
International Search Report and Written Opinion of International Search Authority for International Application No. PCTEP2016/080516; dated Mar. 15, 2017, pp. 1-22.
International Preliminary Report on Patentability from the International Bureau for International Application PCTEP2016/080516; dated Jun. 12, 2018 (pp. 1-11).
International Search Report and Written Opinion of the International Searching Authority for International Application No. PCT/EP2017/061775; dated Sep. 6, 2017, pp. 1-17.
International Preliminary Report on Patentability from the International Bureau for International Application PCT/EP2017/061775; dated Nov. 20, 2018 (pp. 1-9).
International Search Report of the International Searching Authority for International Application No. PCT/EP2017/061774; dated Aug. 30, 2017, pp. 1-20.
Written Opinion of the International Searching Authority for International Application No. PCT/EP2017/061774; dated Aug. 30, 2017, pp. 1-13.
International Preliminary Report on Patentability from then International Search Authority for International Application No. PCT/EP2017/061774; dated Nov. 20, 2018, pp. 1-14.
Ceunen & Geuns, "Steviol glycosides: chemical diversity, metabolism, and function," J. Nat. Prod. 76(6):1201-28 (Jun. 2013).
Olsson et al., "Microbial production of next-generation stevia sweeteners," Microbial Cell Factories, 15:1-14 (2016).
Song et al., "The Aspergillus fumigatus 1-29 damage resistance protein family coordinately regulates ergosterol biosynthesis and azole susceptibility," MBIO, 7:1-13 (2016).
Chen et al., "Progress in the Application of Affinity Tags for the Expression and Purification of Recombinant Proteins," China Biotechnology, vol. 32, No. 12, pp. 93-103, Dec. 15, 2012 (English Abstract).
Ohta et al., MassBank Accession No. FU000299 (May 2016).
Ohta et al., MassBank Accession No. FU000332 (May 2016).
Third Party Submission in U.S. Appl. No. 14/648,747; dated Mar. 28, 2016, pp. 1-231.
International Search Report and Written Opinion of International Search Authority for International Application No. PCTEP2017/059028; dated Jun. 27, 2017, pp. 1-15.
International Preliminary Report on Patentability from the International Bureau for International Application PCTEP2017/059028; dated Oct. 16, 2018 (pp. 1-7).
Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in *Stevia rebaudiana Bertoni*—Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of *Stevia rebaudiana Bertoni*," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathwayin *Stevia rebaudiana* (*Bertoni*)" Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast *Rhodosporidium toruloides* Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Experimentalis Sinica 36(2):123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Madan et al., "*Stevia rebaudiana* (*Bert.*) *Bertoni*A Review," Indian Journal of Natural Products and Resources 1(3)267-86 (2010).

(56) References Cited

OTHER PUBLICATIONS

Madhav et al., "Functional and structural variation of uridine diphosphate glycosyltransferase (UGT) gene of Stevia rebaudiana—UGTSr involved in the synthesis of rebaudioside A," Plant Physiol. Biochern. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing *Stevia rebaudiana*, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of ent-copalyl diphosphate synthase from *Scoparia dulcis* L.," Plant Sci. 169:760-7 (2005).
Nelson et al., "P450 superfamily: update on new sequences, gene mapping, accession numbers and nomenclature," Pharmacogenetics 6:1-42 (1996).
Newman et al., "High-level production of amorpha-4,11-diene in a two-phase partitioning bioreactor of metabolically engineered *Escherichia coli*," Biotechnol Bioeng 95(4):684-91 (2006).
Nicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Nour-Eldin et al., "USER cloning and USER fusion: the ideal cloning techniques for small and big laboratories," Methods Mol Biol. 643:185-200 (2010).
Ohta et al., "Characterization of Novel Steviol Glycosides from Leaves of *Stevia rebaudiana Morita*," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31(6):532-7 (Dec. 2014).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).
Presecki & Vasic-Racki, "Production of L-malic acid by permeabilized cells of commercial *Saccharomyces* sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast *Rhodotorula glutinis* for the bioconversion of crude glycerol from biodiesel plant to lipids and carotenoids," Process Biochemistry 46(1):210-8 (Jan. 2011).
Schwab et al., Poster, "Watchmaker®—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol. 143(3):212-23 (2007).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
Jones et al., "UGT73C6 and UGT78D1, Glycosyltransferases Involved in Flavonol Glycoside Biosynthesis in *Arabidopsis thaliana*," J. Biol. Chem., vol. 278, No. 45, pp. 43910-43918 (2003).
Popenberger et al., Heterologous Expression of *Arabidopsis* UDP-Glucosyltransferases in *Saccharomyces cerevisiae* for Production ofZearalenone-4-0-Glucoside, Appl. Environ. Microbial., vol. 72, pp. 4404-4410 (2006).
Wang, et al., "Glycosylation and Glycosyltransferase of Small Molecular Compounds of Plan", Plant Physiology Communications 44(5):997-1003, Oct. 2008.

Steviol
Steviol-13-O-glucoside
Steviol-19-O-Glucoside
Steviol-1,3-bioside
Steviol-1,2-bioside
Rubusoside
RebB
1,3-Stevioside (RebG)
Stevioside
RebQ
RebA
RebE
RebI
RebD
RebM

PRODUCTION OF STEVIOL GLYCOSIDES IN RECOMBINANT HOSTS

This application is a U.S. National Stage Application of International Application No. PCT/EP2017/059028, filed on Apr. 13, 2017, and claims the benefit of U.S. Provisional Application No. 62/321,850, filed on Apr. 13, 2016, the disclosures of each of which are explicitly incorporated by reference herein in their entirety.

BACKGROUND OF THE INVENTION

Field of the Invention

This disclosure relates to recombinant production of steviol glycosides and steviol glycoside precursors in recombinant hosts. In particular, this disclosure relates to production of steviol glycosides comprising steviol-13-O-glucoside (13-SMG), rubusoside, rebaudioside B (RebB), rebaudioside A (RebA), rebaudioside D (RebD), and rebaudioside M (RebM) in recombinant hosts comprising genes involved in uridine diphosphate (UDP)-glucose formation.

Description of Related Art

Sweeteners are well known as ingredients used most commonly in the food, beverage, or confectionary industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine, and sucralose. *Stevia* extract is a natural sweetener that can be isolated and extracted from a perennial shrub, *Stevia rebaudiana*. *Stevia* is commonly grown in South America and Asia for commercial production of *stevia* extract. *Stevia* extract, purified to various degrees, is used commercially as a high intensity sweetener in foods and in blends or alone as a tabletop sweetener. Extracts of the *Stevia* plant generally comprise steviol glycosides that contribute to the sweet flavor, although the amount of each steviol glycoside often varies, inter alia, among different production batches.

Chemical structures for several steviol glycosides are shown in FIG. 2, including the diterpene steviol and various steviol glycosides. Extracts of the *Stevia* plant generally comprise steviol glycosides that contribute to the sweet flavor, although the amount of each steviol glycoside often varies, inter alia, among different production batches.

As recovery and purification of steviol glycosides from the *Stevia* plant have proven to be labor intensive and inefficient, there remains a need for a recombinant production system that can accumulate high yields of desired steviol glycosides, such as RebM. There also remains a need for improved production of steviol glycosides in recombinant hosts for commercial uses. As well, there remains a need for increasing UDP-glucose formation in recombinant hosts in order to produce higher yields of steviol glycosides, including RebM.

SUMMARY OF THE INVENTION

It is against the above background that the present invention provides certain advantages and advancements over the prior art.

Although this invention as disclosed herein is not limited to specific advantages or functionalities, the invention provides a recombinant host cell capable of producing one or more steviol glycosides or a steviol glycoside composition in a cell culture, comprising:

(a) a recombinant gene encoding a polypeptide capable of synthesizing uridine 5'-triphosphate (UTP) from uridine diphosphate (UDP);

(b) a recombinant gene encoding a polypeptide capable of converting glucose-6-phosphate to glucose-1-phosphate; and/or (c) a recombinant gene encoding a polypeptide capable of synthesizing uridine diphosphate glucose (UDP-glucose) from UTP and glucose-1-phosphate.

In one aspect of the recombinant host cell disclosed herein:

(a) the polypeptide capable of synthesizing UTP from UDP comprises a polypeptide having at least 60% sequence identity to the amino acid sequence set forth in SEQ ID NO:123;

(b) the polypeptide capable of converting glucose-6-phosphate to glucose-1-phosphate comprises a polypeptide having at least 60% sequence identity to the amino acid sequence set forth in SEQ ID NO:2, SEQ ID NO:119, SEQ ID NO:143 or a polypeptide having at least 55% sequence identity to the amino acid sequence set forth in SEQ ID NO:141, SEQ ID NO:145, or SEQ ID NO:147; and/or (c) the polypeptide capable of synthesizing UDP-glucose from UTP and glucose-1-phosphate comprises a polypeptide having at least 60% sequence identity to the amino acid sequence set forth in SEQ ID NO:121, SEQ ID NO:127, a polypeptide having at least 55% sequence identity to the amino acid sequence set forth in SEQ ID NO:125, SEQ ID NO:129, SEQ ID NO:133, SEQ ID NO:135, SEQ ID NO:137, or SEQ ID NO:139 or a polypeptide having at least 70% sequence identity to the amino acid sequence set forth in SEQ ID NO:131.

In one aspect, the recombinant host cell disclosed herein further comprises:

(a) a gene encoding a polypeptide capable of glycosylating steviol or a steviol glycoside at its C-13 hydroxyl group thereof;

(b) a gene encoding a polypeptide capable of beta 1,3 glycosylation of the C3' of the 13-O-glucose, 19-O-glucose, or both 13-O-glucose and 19-O-glucose of a steviol glycoside;

(c) a gene encoding a polypeptide capable of glycosylating steviol or a steviol glycoside at its C-19 carboxyl group thereof; and/or (d) a gene encoding a polypeptide capable of beta 1,2 glycosylation of the C2' of the 13-O-glucose, 19-O-glucose, or both 13-O-glucose and 19-O-glucose of a steviol glycoside.

In one aspect, the recombinant host cell disclosed herein further comprises:

(e) a gene encoding a polypeptide capable of synthesizing geranylgeranyl pyrophosphate (GGPP) from farnesyl diphosphate (FPP) and isopentenyl diphosphate (IPP);

(f) a gene encoding a polypeptide capable of synthesizing ent-copalyl diphosphate from GGPP;

(g) a gene encoding an a polypeptide capable of synthesizing ent-kaurene from ent-copalyl diphosphate;

(h) a gene encoding a polypeptide capable of synthesizing ent-kaurenoic acid from ent-kaurene;

(i) a gene encoding a polypeptide capable of reducing cytochrome P450 complex; and/or (j) a gene encoding a polypeptide capable of synthesizing steviol from ent-kaurenoic acid.

In one aspect of the recombinant host cell disclosed herein:

(a) the polypeptide capable of glycosylating steviol or a steviol glycoside at its C-13 hydroxyl group thereof comprises a polypeptide having at least 55% sequence identity to the amino acid sequence set forth in SEQ ID NO:7;

(b) the polypeptide capable of beta 1,3 glycosylation of the C3' of the 13-O-glucose, 19-O-glucose, or both 13-O-glucose and 19-O-glucose of a steviol glycoside comprises a polypeptide having at least 50% sequence identity to the amino acid sequence set forth in SEQ ID NO:9;

(c) the polypeptide capable of glycosylating steviol or a steviol glycoside at its C-19 carboxyl group thereof comprises a polypeptide having at least 55% sequence identity to the amino acid sequence set forth in SEQ ID NO:4;

(d) the polypeptide capable of beta 1,2 glycosylation of the C2' of the 13-O-glucose, 19-O-glucose, or both 13-O-glucose and 19-O-glucose of a steviol glycoside comprises a polypeptide having 80% or greater identity to the amino acid sequence set forth in SEQ ID NO:11; a polypeptide having 80% or greater identity to the amino acid sequence set forth in SEQ ID NO:13; or a polypeptide having at least 65% sequence identity to the amino acid sequence set forth in SEQ ID NO:16;

(e) the polypeptide capable of synthesizing GGPP comprises a polypeptide having at least 70% sequence identity to the amino acid sequence set forth in SEQ ID NO:20, SEQ ID NO:22, SEQ ID NO:24, SEQ ID NO:26, SEQ ID NO:28, SEQ ID NO:30, SEQ ID NO:32, or SEQ ID NO:116;

(f) the polypeptide capable of synthesizing ent-copalyl diphosphate comprises a polypeptide having at least 70% sequence identity to the amino acid sequence set forth in SEQ ID NO:34, SEQ ID NO:36, SEQ ID NO:38, SEQ ID NO:40, SEQ ID NO:42, or SEQ ID NO:120;

(g) the polypeptide capable of synthesizing ent-kaurene comprises a polypeptide having at least 70% sequence identity to the amino acid sequence set forth in SEQ ID NO:44, SEQ ID NO:46, SEQ ID NO:48, SEQ ID NO:50, or SEQ ID NO:52;

(h) the polypeptide capable of synthesizing ent-kaurenoic acid comprises a polypeptide having at least 70% sequence identity to the amino acid sequence set forth in SEQ ID NO:60, SEQ ID NO:62, SEQ ID NO:117, SEQ ID NO:66, SEQ ID NO:68, SEQ ID NO:70, SEQ ID NO:72, SEQ ID NO:74, or SEQ ID NO:76;

(i) the polypeptide capable of reducing cytochrome P450 complex comprises a polypeptide having at least 70% sequence identity to the amino acid sequence set forth in SEQ ID NO:78, SEQ ID NO:80, SEQ ID NO:82, SEQ ID NO:84, SEQ ID NO:86, SEQ ID NO:88, SEQ ID NO:90, SEQ ID NO:92; and/or (k) the polypeptide capable of synthesizing steviol comprises a polypeptide having at least 70% sequence identity to the amino acid sequence set forth in SEQ ID NO:94, SEQ ID NO:97, SEQ ID NO:100, SEQ ID NO:101, SEQ ID NO:102, SEQ ID NO:103, SEQ ID NO:104, SEQ ID NO:106, SEQ ID NO:108, SEQ ID NO:110, SEQ ID NO:112, or SEQ ID NO:114.

In one aspect, the recombinant host cell disclosed herein comprises:

(a) a gene encoding a polypeptide capable of synthesizing uridine 5'-triphosphate (UTP) from uridine diphosphate (UDP) having at least 60% sequence identity to the amino acid sequence set forth in SEQ ID NO:123;

(b) one or more genes encoding a polypeptide capable of converting glucose-6-phosphate to glucose-1-phosphate, each having at least 60% sequence identity to the amino acid sequence set forth in SEQ ID NO:2 and/or SEQ ID NO:119; and (c) a gene encoding a polypeptide capable of synthesizing UDP-glucose from UTP and glucose-1-phosphate having at least 60% sequence identity to the amino acid sequence set forth in SEQ ID NO:121.

In one aspect, the recombinant host cell disclosed herein comprises:

(a) a gene encoding a polypeptide capable of synthesizing uridine 5'-triphosphate (UTP) from uridine diphosphate (UDP);

(b) a gene encoding a polypeptide capable of converting glucose-6-phosphate to glucose-1-phosphate;

(c) a gene encoding a polypeptide capable of synthesizing UDP-glucose from UTP and glucose-1-phosphate having at least 60% sequence identity to the amino acid sequence set forth in SEQ ID NO:121;

(d) a gene encoding a polypeptide capable of synthesizing UDP-glucose from UTP and glucose-1-phosphate having at least 55% sequence identity to the amino acid sequence set forth in SEQ ID NO:125, SEQ ID NO:129, SEQ ID NO:133, SEQ ID NO:135, SEQ ID NO:137, or SEQ ID NO:139; at least 60% sequence identity to the amino acid sequence set forth in SEQ ID NO:127; or at least 70% sequence identity to the amino acid sequence set forth in SEQ ID NO:131; and one or more of:

(e) a gene encoding a polypeptide capable of glycosylating steviol or a steviol glycoside at its C-13 hydroxyl group thereof having at least 55% sequence identity to the amino acid sequence set forth in SEQ ID NO:7;

(b) a gene encoding a polypeptide capable of beta 1,3 glycosylation of the C3' of the 13-O-glucose, 19-O-glucose, or both 13-O-glucose and 19-O-glucose of a steviol glycoside having at least 50% sequence identity to the amino acid sequence set forth in SEQ ID NO:9;

(c) a gene encoding a polypeptide capable of glycosylating steviol or a steviol glycoside at its C-19 carboxyl group thereof having at least 55% sequence identity to the amino acid sequence set forth in SEQ ID NO:4;

(d) a gene encoding a polypeptide capable of beta 1,2 glycosylation of the C2' of the 13-O-glucose, 19-O-glucose, or both 13-O-glucose and 19-O-glucose of a steviol glycoside comprises a polypeptide having 80% or greater identity to the amino acid sequence set forth in SEQ ID NO:11; a polypeptide having 80% or greater identity to the amino acid sequence set forth in SEQ ID NO:13; or a polypeptide having at least 65% sequence identity to the amino acid sequence set forth in SEQ ID NO:16.

In one aspect, the recombinant host cell disclosed herein comprises:

(a) a recombinant gene encoding a polypeptide capable of synthesizing uridine 5'-triphosphate (UTP) from uridine diphosphate (UDP) having at least 60% sequence identity to the amino acid sequence set forth in SEQ ID NO:123;

(b) one or more recombinant genes encoding a polypeptide capable of converting glucose-6-phosphate to glucose-1-phosphate, each having at least 60% sequence identity to the amino acid sequence set forth in SEQ ID NO:2 and/or SEQ ID NO:119; and/or (c) a recombinant gene encoding a polypeptide capable of synthesizing UDP-glucose from UTP and glucose-1-phosphate having at least 60% sequence identity to the amino acid sequence set forth in SEQ ID NO:121;

wherein the gene encoding a polypeptide capable of synthesizing uridine 5'-triphosphate (UTP) from uridine diphosphate (UDP), the one or more genes encoding a polypeptide capable of converting glucose-6-phosphate to glucose-1-phosphate, and/or the gene encoding a polypeptide capable of synthesizing UDP-glucose from UTP and glucose-1-phosphate are overexpressed relative to a corresponding host cell lacking the one or more recombinant genes.

In one aspect of the recombinant host cell disclosed herein, the gene encoding a polypeptide capable of synthesizing uridine 5'-triphosphate (UTP) from uridine diphosphate (UDP), the one or more genes encoding a polypeptide capable of converting glucose-6-phosphate to glucose-1-phosphate, and/or the gene encoding a polypeptide capable of synthesizing UDP-glucose from UTP and glucose-1-phosphate are overexpressed by at least 10%, or at least 15%, or at least 20%, or at least 30%, or at least 40%, or at least 50%, or at least 60%, or at least 70%, or at least 80%, or at least 90%, or at least 100%, or at least 125%, or at least 150%, or at least 175%, or at least 200% relative to a corresponding host cell lacking the one or more recombinant genes.

In one aspect of the recombinant host cell disclosed herein, expression of the one or more recombinant genes increase the amount of UDP-glucose accumulated by the cell relative to a corresponding host lacking the one or more recombinant genes.

In one aspect of the recombinant host cell disclosed herein, expression of the one or more recombinant genes increases the amount of UDP-glucose accumulated by the cell by at least about 10%, at least about 25%, or at least about 50%, at least about 100%, at least about 150%, at least about 200%, or at least about 250% relative to a corresponding host lacking the one or more recombinant genes.

In one aspect of the recombinant host cell disclosed herein, expression of the one or more recombinant genes increases an amount of the one or more steviol glycosides or the steviol glycoside composition produced by the cell relative to a corresponding host lacking the one or more recombinant genes.

In one aspect of the recombinant host cell disclosed herein, expression of the one or more recombinant genes increases the amount of the one or more steviol glycosides produced by the cell by at least about 5%, at least about 10%, at least about 25%, at least about 50%, at least about 75%, or at least about 100% relative to a corresponding host lacking the one or more recombinant genes.

In one aspect of the recombinant host cell disclosed herein, expression of the one or more recombinant genes increases the amount of RebA, RebB, Reb D, and/or RebM produced by the cell relative to a corresponding host lacking the one or more recombinant genes.

In one aspect of the recombinant host cell disclosed herein, expression of the one or more recombinant genes decreases the one of one or more steviol glycosides or the steviol glycoside composition accumulated by the cell relative to a corresponding host lacking the one or more recombinant genes.

In one aspect of the recombinant host cell disclosed herein, expression of the one or more recombinant genes decreases the amount of the one or more steviol glycosides accumulated by the cell by at least about 5%, at least about 10%, at least about 25%, or at least about 50% relative to a corresponding host lacking the one or more recombinant genes.

In one aspect of the recombinant host cell disclosed herein, expression of the one or more recombinant genes decreases the amount of RebB, RebD, and/or 13-SMG accumulated by the cell relative to a corresponding host lacking the one or more recombinant genes.

In one aspect of the recombinant host cell disclosed herein, expression of the one or more recombinant genes increases or decreases the amount of total steviol glycosides produced by the cell by less than 5%, less than 2.5%, or less than 1% relative to a corresponding host lacking the one or more recombinant genes.

In one aspect of the recombinant host cell disclosed herein, expression of the one or more recombinant genes increases the amount of total steviol glycosides produced by the cell by at least about 5%, at least about 10%, or at least about 25% relative to a corresponding host lacking the one or more recombinant genes.

In one aspect of the recombinant host cell disclosed herein, the one or more steviol glycosides is, or the steviol glycoside composition comprises, steviol-13-O-glucoside (13-SMG), steviol-1,2-Bioside, steviol-1,3-Bioside, steviol-19-O-glucoside (19-SMG), 1,2-Stevioside, 1,3-stevioside (RebG), rubusoside, rebaudioside A (RebA), rebaudioside B (RebB), rebaudioside C (RebC), rebaudioside D (RebD), rebaudioside E (RebE), rebaudioside F (RebF), rebaudioside M (RebM), rebaudioside Q (RebQ), rebaudioside I (RebI), dulcoside A, and/or an isomer thereof.

In one aspect of the recombinant host cell disclosed herein, the recombinant host cell is a plant cell, a mammalian cell, an insect cell, a fungal cell, an algal cell or a bacterial cell.

The invention also provides method of producing one or more steviol glycosides or a steviol glycoside composition in a cell culture, comprising culturing the recombinant host cell disclosed herein, under conditions in which the genes are expressed, and wherein the one or more steviol glycosides or the steviol glycoside composition is produced by the recombinant host cell.

In one aspect of the methods disclosed herein, the genes are constitutively expressed and/or expression of the genes is induced.

In one aspect of the methods disclosed herein, the amount of UDP-glucose accumulated by the cell is increased by at least by at least about 10% relative to a corresponding host lacking the one or more recombinant genes.

In one aspect of the methods disclosed herein, the amount of RebA, RebB, RebD, and/or RebM produced by the cell is increased by at least about 5% relative to a corresponding host lacking the one or more recombinant genes.

In one aspect of the methods disclosed herein, the amount of RebB, RebD, and/or 13-SMG accumulated by the cell is decreased by at least about 5% relative to a corresponding host lacking the one or more recombinant genes.

In one aspect of the methods disclosed herein, the amount of total steviol glycosides produced by the cell is increased or decreased by less than about 5% relative to a corresponding host lacking the one or more recombinant genes.

In one aspect of the methods disclosed herein, the amount of total steviol glycosides produced by the cell is increased by at least about 5% relative to a corresponding host lacking the one or more recombinant genes.

In one aspect of the methods disclosed herein, the recombinant host cell is grown in a fermentor at a temperature for a period of time, wherein the temperature and period of time facilitate the production of the one or more steviol glycosides or the steviol glycoside composition.

In one aspect of the methods disclosed herein, the amount of UDP-glucose present in the cell culture is increased by at least about 10%, at least about 25%, or at least about 50%, at least about 100%, at least about 150%, at least about 200%, or at least about 250% at any point throughout the period of time.

In one aspect, the methods disclosed herein further comprise isolating the produced one or more steviol glycosides or the steviol glycoside composition from the cell culture.

In one aspect of the methods disclosed herein, the isolating step comprises:

(a) providing the cell culture comprising the one or more steviol glycosides or the steviol glycoside composition;
(b) separating a liquid phase of the cell culture from a solid phase of the cell culture to obtain a supernatant comprising the produced one or more steviol glycosides or the steviol glycoside composition;
(c) providing one or more adsorbent resins, comprising providing the adsorbent resins in a packed column; and
(d) contacting the supernatant of step (b) with the one or more adsorbent resins in order to obtain at least a portion of the produced one or more steviol glycosides or the steviol glycoside composition, thereby isolating the produced one or more steviol glycosides or the steviol glycoside composition;

or (a) providing the cell culture comprising the one or more steviol glycosides or the steviol glycoside composition;
(b) separating a liquid phase of the cell culture from a solid phase of the cell culture to obtain a supernatant comprising the produced one or more steviol glycosides or the steviol glycoside composition;
(c) providing one or more ion exchange or ion exchange or reversed-phase chromatography columns; and
(d) contacting the supernatant of step (b) with the one or more ion exchange or ion exchange or reversed-phase chromatography columns in order to obtain at least a portion of the produced one or more steviol glycosides or the steviol glycoside composition, thereby isolating the produced one or more steviol glycosides or the steviol glycoside composition;

or (a) providing the cell culture comprising the one or more steviol glycosides or the steviol glycoside composition;
(b) separating a liquid phase of the cell culture from a solid phase of the cell culture to obtain a supernatant comprising the produced one or more steviol glycosides or the steviol glycoside composition;
(c) crystallizing or extracting the produced one or more steviol glycosides or the steviol glycoside composition, thereby isolating the produced one or more steviol glycosides or the steviol glycoside composition.

In one aspect, the methods disclosed herein further comprise recovering the one or more steviol glycosides or the steviol glycoside composition from the cell culture.

In one aspect of the methods disclosed herein, the recovered one or more steviol glycosides or the steviol glycoside composition has a reduced level of *Stevia* plant-derived components relative to a plant-derived *Stevia* extract.

The invention also provides a method for producing one or more steviol glycosides or a steviol glycoside composition, comprising whole-cell bioconversion of plant-derived or synthetic steviol and/or steviol glycosides in a cell culture medium of a recombinant host cell using:

(a) a polypeptide capable of synthesizing UTP from UDP having at least 60% sequence identity to the amino acid sequence set forth in SEQ ID NO:123;
(b) a polypeptide capable of converting glucose-6-phosphate to glucose-1-phosphate having at least 60% sequence identity to the amino acid sequence set forth in SEQ ID NO:2, SEQ ID NO:119, or SEQ ID NO:143; at least 55% sequence identity to the amino acid sequence set forth in SEQ ID NO:141, SEQ ID NO:145, or SEQ ID NO:147; and/or
(c) a polypeptide capable of synthesizing UDP-glucose from UTP and glucose-1-phosphate having at least 60% sequence identity to the amino acid sequence set forth in SEQ ID NO:121, SEQ ID NO:127; at least 55% sequence identity to the amino acid sequence set forth in SEQ ID NO:125, SEQ ID NO:129, SEQ ID NO:133, SEQ ID NO:135, SEQ ID NO:137, or SEQ ID NO:139; or at least 70% sequence identity to the amino acid sequence set forth in SEQ ID NO:131; and one or more of:

(d) a polypeptide capable of glycosylating steviol or a steviol glycoside at its C-13 hydroxyl group thereof;
(e) a polypeptide capable of beta 1,3 glycosylation of the C3' of the 13-O-glucose, 19-O-glucose, or both 13-O-glucose and 19-O-glucose of a steviol glycoside;
(f) a polypeptide capable of glycosylating steviol or a steviol glycoside at its C-19 carboxyl group thereof; and/or
(g) a polypeptide capable of beta 1,2 glycosylation of the C2' of the 13-O-glucose, 19-O-glucose, or both 13-O-glucose and 19-O-glucose of a steviol glycoside;
wherein at least one of the polypeptides is a recombinant polypeptide expressed in the recombinant host cell; and producing the one or more steviol glycosides or the steviol glycoside composition thereby.

In one aspect of the methods disclosed herein:

(d) the polypeptide capable of glycosylating steviol or a steviol glycoside at its C-13 hydroxyl group thereof comprises a polypeptide having at least 55% sequence identity to the amino acid sequence set forth in SEQ ID NO:7;
(e) the polypeptide capable of beta 1,3 glycosylation of the C3' of the 13-O-glucose, 19-O-glucose, or both 13-O-glucose and 19-O-glucose of a steviol glycoside comprises a polypeptide having at least 50% sequence identity to the amino acid sequence set forth in SEQ ID NO:9;
(f) the polypeptide capable of glycosylating steviol or a steviol glycoside at its C-19 carboxyl group thereof comprises a polypeptide having at least 55% sequence identity to the amino acid sequence set forth in SEQ ID NO:4;
(g) the polypeptide capable of beta 1,2 glycosylation of the C2' of the 13-O-glucose, 19-O-glucose, or both 13-O-glucose and 19-O-glucose of a steviol glycoside comprises a polypeptide having 80% or greater identity to the amino acid sequence set forth in SEQ ID NO:11; a polypeptide having 80% or greater identity to the amino acid sequence set forth in SEQ ID NO:13; or a polypeptide having at least 65% sequence identity to the amino acid sequence set forth in SEQ ID NO:16.

In one aspect of the methods disclosed herein, the recombinant host cell is a plant cell, a mammalian cell, an insect cell, a fungal cell, an algal cell or a bacterial cell.

In one aspect of the methods disclosed herein, the one or more steviol glycosides is, or the steviol glycoside composition comprises, steviol-13-O-glucoside (13-SMG), steviol-1,2-Bioside, steviol-1,3-Bioside, steviol-19-O-glucoside (19-SMG), 1,2-stevioside, 1,3-stevioside (RebG), rubusoside, rebaudioside A (RebA), rebaudioside B (RebB), rebaudioside C (RebC), rebaudioside D (RebD), rebaudioside E (RebE), rebaudioside F (RebF), rebaudioside M (RebM), rebaudioside Q (RebQ), rebaudioside I (RebI), dulcoside A, and/or an isomer thereof.

The invention also provides a cell culture, comprising the recombinant host cell disclosed herein, the cell culture further comprising:

(a) the one or more steviol glycosides or the steviol glycoside composition produced by the recombinant host cell;

(b) glucose, fructose, sucrose, xylose, rhamnose, UDP-glucose, UDP-rhamnose, UDP-xylose, and/or N-acetyl-glucosamine; and (c) supplemental nutrients comprising trace metals, vitamins, salts, YNB, and/or amino acids;

wherein the one or more steviol glycosides or the steviol glycoside composition is present at a concentration of at least 1 mg/liter of the cell culture;

wherein the cell culture is enriched for the one or more steviol glycosides or the steviol glycoside composition relative to a steviol glycoside composition from a *Stevia* plant and has a reduced level of *Stevia* plant-derived components relative to a plant-derived *Stevia* extract.

The invention also provides a cell culture, comprising the recombinant host cell disclosed herein, the cell culture further comprising:

(a) the one or more steviol glycosides or the steviol glycoside composition produced by the recombinant host cell;

(b) glucose, fructose, sucrose, xylose, rhamnose, UDP-glucose, UDP-rhamnose, UDP-xylose, and/or N-acetyl-glucosamine; and (c) supplemental nutrients comprising trace metals, vitamins, salts, YNB, and/or amino acids;

wherein UDP-glucose is present in the cell culture at a concentration of at least 100 μM;

wherein the cell culture is enriched for UGP-glucose relative to a steviol glycoside composition from a *Stevia* plant and has a reduced level of *Stevia* plant-derived components relative to a plant-derived *Stevia* extract.

The invention also provides cell lysate from the recombinant host cell disclosed herein grown in the cell culture, comprising:

(a) the one or more steviol glycosides or the steviol glycoside composition produced by the recombinant host cell;

(b) glucose, fructose, sucrose, xylose, rhamnose, UDP-glucose, UDP-rhamnose, UDP-xylose, and/or N-acetyl-glucosamine; and/or (c) supplemental nutrients comprising trace metals, vitamins, salts, yeast nitrogen base, YNB, and/or amino acids;

wherein the one or more steviol glycosides or the steviol glycoside composition produced by the recombinant host cell is present at a concentration of at least 1 mg/liter of the cell culture.

The invention also provides one or more steviol glycosides produced by the recombinant host cell disclosed herein;

wherein the one or more steviol glycosides produced by the recombinant host cell are present in relative amounts that are different from a steviol glycoside composition from a *Stevia* plant and have a reduced level of *Stevia* plant-derived components relative to a plant-derived *Stevia* extract.

The invention also provides one or more steviol glycosides produced by the method disclosed herein;

wherein the one or more steviol glycosides produced by the recombinant host cell are present in relative amounts that are different from a steviol glycoside composition from a *Stevia* plant and have a reduced level of *Stevia* plant-derived components relative to a plant-derived *Stevia* extract.

The invention also provides a sweetener composition, comprising the one or more steviol glycosides disclosed herein.

The invention also provides a food product comprising, the sweetener composition disclosed herein.

The invention also provides a beverage or a beverage concentrate, comprising the sweetener composition disclosed herein.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
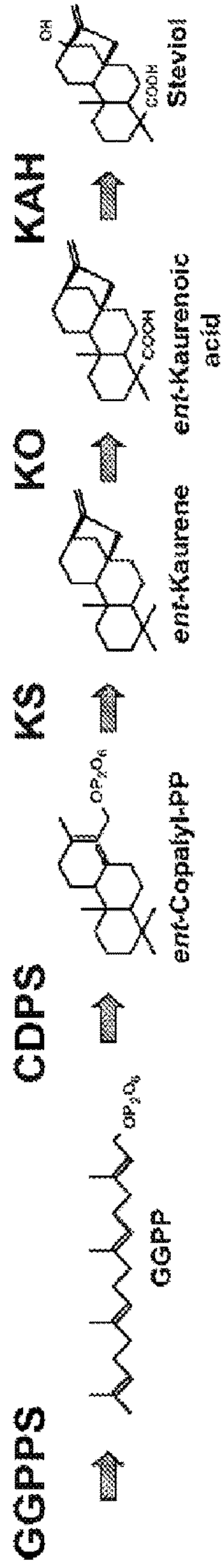
FIG. 1 shows the biochemical pathway for producing steviol from geranylgeranyl diphosphate using geranylgeranyl diphosphate synthase (GGPPS), ent-copalyl diphosphate synthase (CDPS), ent-kaurene synthase (KS), ent-kaurene oxidase (KO), and ent-kaurenoic acid hydroxylase (KAH) polypeptides.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

All publications, patents and patent applications cited herein are hereby expressly incorporated by reference for all purposes.

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide," "nucleotide," "oligonucleotide," and "nucleic acid" can be used interchangeably to refer to nucleic acid comprising DNA, RNA, derivatives thereof, or combinations thereof, in either single-stranded or double-stranded embodiments depending on context as understood by the skilled worker.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In some aspects, said recombinant genes are encoded by cDNA. In other embodiments, recombinant genes are synthetic and/or codon-optimized for expression in *S. cerevisiae.*

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to *S. cerevisiae*, including, but not limited to *S. cerevisiae* strain S288C. In some embodiments, an endogenous yeast gene is overexpressed. As used herein, the term "overexpress" is used to refer to the expression of a gene in an organism at levels higher than the level of gene expression in a wild type organism. See, e.g., Prelich, 2012, *Genetics* 190:841-54. See, e.g., Giaever & Nislow, 2014, *Genetics* 197(2):451-65. In some aspects, overexpression can be performed by integration using the USER cloning system; see, e.g., Nour-Eldin et al., 2010, Methods Mol Biol. 643:185-200. As used herein, the terms "deletion," "deleted," "knockout," and "knocked out" can be used interchangeably to refer to an endogenous gene that has been manipulated to no longer be expressed in an organism, including, but not limited to, *S. cerevisiae.*

As used herein, the terms "heterologous sequence" and "heterologous coding sequence" are used to describe a sequence derived from a species other than the recombinant host. In some embodiments, the recombinant host is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, *Ann. Rev. Genetics* 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

Figure 2:
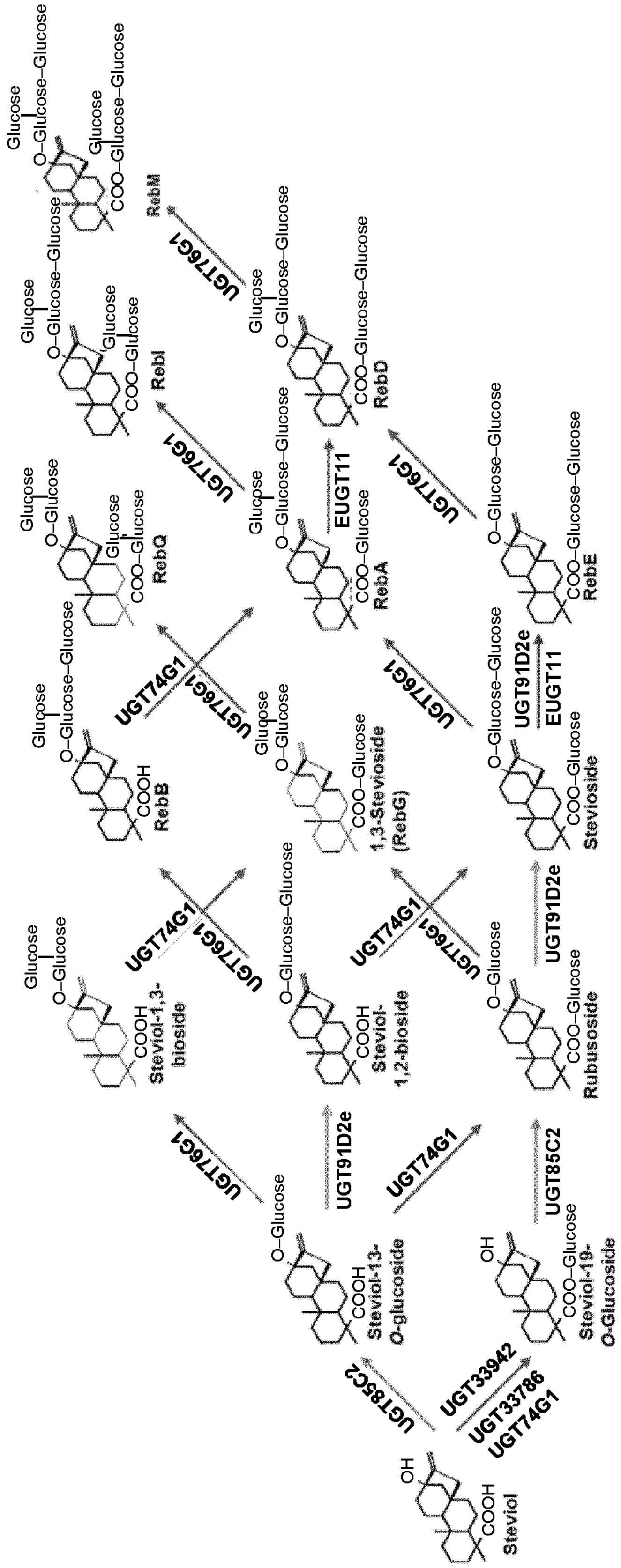
FIG. 2 shows representative primary steviol glycoside glycosylation reactions catalyzed by suitable UGT enzymes and chemical structures for several of the compounds found in *Stevia* extracts.

As used herein, the term "steviol glycoside" refers to rebaudioside A (RebA) (CAS #58543-16-1), rebaudioside B (RebB) (CAS #58543-17-2), rebaudioside C (RebC) (CAS #63550-99-2), rebaudioside D (RebD) (CAS #63279-13-0), rebaudioside E (RebE) (CAS #63279-14-1), rebaudioside F (RebF) (CAS #438045-89-7), rebaudioside M (RebM) (CAS #1220616-44-3), Rubusoside (CAS #63849-39-4), Dulcoside A (CAS #64432-06-0), rebaudioside I (RebI) (MassBank Record: FU000332), rebaudioside Q (RebQ), 1,2-Stevioside (CAS #57817-89-7), 1,3-Stevioside (RebG), Steviol-1,2-Bioside (MassBank Record: FU000299), Steviol-1,3-Bioside, Steviol-13-O-glucoside (13-SMG), Steviol-19-O-glucoside (19-SMG), a tri-glycosylated steviol glycoside, a tetra-glycosylated steviol glycoside, a penta-glycosylated steviol glycoside, a hexa-glycosylated steviol glycoside, a hepta-glycosylated steviol glycoside, and isomers thereof. See FIG. 2; see also, Steviol Glycosides Chemical and Technical Assessment 69th JECFA, 2007, prepared by Harriet Wallin, Food Agric. Org.

As used herein, the terms "steviol glycoside precursor" and "steviol glycoside precursor compound" are used to refer to intermediate compounds in the steviol glycoside biosynthetic pathway. Steviol glycoside precursors include, but are not limited to, geranylgeranyl diphosphate (GGPP), ent-copalyl-diphosphate, ent-kaurene, ent-kaurenol, ent-kaurenal, ent-kaurenoic acid, and steviol. See FIG. 1. In some embodiments, steviol glycoside precursors are themselves steviol glycoside compounds. For example, 19-SMG, rubusoside, 1,2-stevioside, and RebE are steviol glycoside precursors of RebM. See FIG. 2.

Also as used herein, the terms "steviol precursor" and "steviol precursor compound" are used to refer to intermediate compounds in the steviol biosynthetic pathway. Steviol precursors may also be steviol glycoside precursors, and include, but are not limited to, geranylgeranyl diphosphate (GGPP), ent-copalyl-diphosphate, ent-kaurene, ent-kaurenol, ent-kaurenal, and ent-kaurenoic acid. Steviol glycosides and/or steviol glycoside precursors can be produced in vivo (i.e., in a recombinant host), in vitro (i.e., enzymatically), or by whole cell bioconversion. As used herein, the terms "produce" and "accumulate" can be used interchangeably to describe synthesis of steviol glycosides and steviol glycoside precursors in vivo, in vitro, or by whole cell bioconversion.

As used herein, the terms "culture broth," "culture medium," and "growth medium" can be used interchangeably to refer to a liquid or solid that supports growth of a cell. A culture broth can comprise glucose, fructose, sucrose, trace metals, vitamins, salts, yeast nitrogen base (YNB), and/or amino acids. The trace metals can be divalent cations, including, but not limited to, $Mn^{2+}$ and/or $Mg^{2+}$. In some embodiments, $Mn^{2+}$ can be in the form of $MnCl_2$ dihydrate and range from approximately 0.01 g/L to 100 g/L. In some embodiments, $Mg^{2+}$ can be in the form of $MgSO_4$ heptahydrate and range from approximately 0.01 g/L to 100 g/L. For example, a culture broth can comprise i) approximately 0.02-0.03 g/L $MnCl_2$ dihydrate and approximately 0.5-3.8 g/L $MgSO_4$ heptahydrate, ii) approximately 0.03-0.06 g/L $MnCl_2$ dihydrate and approximately 0.5-3.8 g/L $MgSO_4$ heptahydrate, and/or iii) approximately 0.03-0.17 g/L $MnCl_2$ dihydrate and approximately 0.5-7.3 g/L $MgSO_4$ heptahydrate. Additionally, a culture broth can comprise one or more steviol glycosides produced by a recombinant host, as described herein.

Recombinant steviol glycoside-producing *Saccharomyces cerevisiae* (*S. cerevisiae*) strains are described in WO 2011/153378, WO 2013/022989, WO 2014/122227, and WO 2014/122328, each of which is incorporated by reference in their entirety. Methods of producing steviol glycosides in recombinant hosts, by whole cell bio-conversion, and in vitro are also described in WO 2011/153378, WO 2013/022989, WO 2014/122227, and WO 2014/122328.

In some embodiments, a recombinant host comprising a gene encoding a polypeptide capable of synthesizing geranylgeranyl pyrophosphate (GGPP) from farnesyl diphosphate (FPP) and isopentenyl diphosphate (IPP) (e.g., geranylgeranyl diphosphate synthase (GGPPS)); a gene encoding a polypeptide capable of synthesizing ent-copalyl diphosphate from GGPP (e.g., ent-copalyl diphosphate synthase (CDPS)); a gene encoding a polypeptide capable of synthesizing ent-kaurene from ent-copalyl diphosphate (e.g., kaurene synthase (KS)); a gene encoding a polypeptide capable of synthesizing ent-kaurenoic acid, ent-kaurenol, and/or ent-kaurenal from ent-kaurene (e.g., kaurene oxidase (KO)); a gene encoding a polypeptide capable of reducing cytochrome P450 complex (e.g., cytochrome P450 reductase (CPR) or P450 oxidoreductase (POR); for example, but not limited to a polypeptide capable of electron transfer from NADPH to cytochrome P450 complex during conversion of NADPH to $NADP^+$, which is utilized as a cofactor for terpenoid biosynthesis); a gene encoding a polypeptide capable of synthesizing steviol from ent-kaurenoic acid (e.g., steviol synthase (KAH)); and/or a gene encoding a bifunctional polypeptide capable of synthesizing ent-copalyl diphosphate from GGPP and synthesizing ent-kaurene from ent-copalyl diphosphate (e.g., an ent-copalyl diphosphate synthase (CDPS)—ent-kaurene synthase (KS) polypeptide)

can produce steviol in vivo. See, e.g., FIG. 1. The skilled worker will appreciate that one or more of these genes can be endogenous to the host provided that at least one (and in some embodiments, all) of these genes is a recombinant gene introduced into the recombinant host.

In some embodiments, a recombinant host comprising a gene encoding a polypeptide capable of glycosylating steviol or a steviol glycoside at its C-13 hydroxyl group (e.g., UGT85C2 polypeptide); a gene encoding a polypeptide capable of beta 1,3 glycosylation of the C3' of the 13-O-glucose, 19-O-glucose, or both 13-O-glucose and 19-O-glucose of a steviol glycoside (e.g., UGT76G1 polypeptide); a gene encoding a polypeptide capable of glycosylating steviol or a steviol glycoside at its C-19 carboxyl group (e.g., UGT74G1 polypeptide); and/or a gene encoding a polypeptide capable of beta 1,2 glycosylation of the C2' of the 13-O-glucose, 19-O-glucose, or both 13-O-glucose and 19-O-glucose of a steviol glycoside (e.g., UGT91D2 and EUGT11 polypeptide) can produce a steviol glycoside in vivo. The skilled worker will appreciate that one or more of these genes can be endogenous to the host provided that at least one (and in some embodiments, all) of these genes is a recombinant gene introduced into the recombinant host.

In some embodiments, steviol glycosides and/or steviol glycoside precursors are produced in vivo through expression of one or more enzymes involved in the steviol glycoside biosynthetic pathway in a recombinant host. For example, a recombinant host comprising a gene encoding a polypeptide capable of synthesizing geranylgeranyl pyrophosphate (GGPP) from farnesyl diphosphate (FPP) and isopentenyl diphosphate (IPP); a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; a gene encoding a bifunctional polypeptide capable of synthesizing ent-copalyl diphosphate from GGPP and synthesizing ent-kaurene from ent-copalyl diphosphate; a gene encoding a polypeptide capable of glycosylating steviol or a steviol glycoside at its C-13 hydroxyl group (e.g., UGT85C2 polypeptide); a gene encoding a polypeptide capable of beta 1,3 glycosylation of the C3' of the 13-O-glucose, 19-O-glucose, or both 13-O-glucose and 19-O-glucose of a steviol glycoside (e.g., UGT76G1 polypeptide); a gene encoding a polypeptide capable of glycosylating steviol or a steviol glycoside at its C-19 carboxyl group (e.g., UGT74G1 polypeptide); and/or a gene encoding a polypeptide capable of beta 1,2 glycosylation of the C2' of the 13-O-glucose, 19-O-glucose, or both 13-O-glucose and 19-O-glucose of a steviol glycoside (e.g., UGT91D2 and EUGT11 polypeptide) can produce a steviol glycoside and/or steviol glycoside precursors in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

In some embodiments, a steviol-producing recombinant microorganism comprises heterologous nucleic acids encoding a polypeptide capable of glycosylating steviol or a steviol glycoside at its C-13 hydroxyl group; a polypeptide capable of beta 1,3 glycosylation of the C3' of the 13-O-glucose, 19-O-glucose, or both 13-O-glucose and 19-O-glucose of a steviol glycoside; a polypeptide capable of glycosylating steviol or a steviol glycoside at its C-19 carboxyl group; and a polypeptide capable of beta 1,2 glycosylation of the C2' of the 13-O-glucose, 19-O-glucose, or both 13-O-glucose and 19-O-glucose of a steviol glycoside.

In some embodiments, a steviol-producing recombinant microorganism comprises heterologous nucleic acids encoding a polypeptide capable of glycosylating steviol or a steviol glycoside at its C-13 hydroxyl group, a polypeptide capable of beta 1,3 glycosylation of the C3' of the 13-O-glucose, 19-O-glucose, or both 13-O-glucose and 19-O-glucose of a steviol glycoside, and a polypeptide capable of beta 1,2 glycosylation of the C2' of the 13-O-glucose, 19-O-glucose, or both 13-O-glucose and 19-O-glucose of a steviol glycoside polypeptides.

In some aspects, a polypeptide capable of glycosylating steviol or a steviol glycoside at its C-13 hydroxyl group, a polypeptide capable of beta 1,3 glycosylation of the C3' of the 13-0-glucose, 19-O-glucose, or both 13-O-glucose and 19-O-glucose of a steviol glycoside, a polypeptide capable of glycosylating steviol or a steviol glycoside at its C-19 carboxyl group, and/or a polypeptide capable of beta 1,2 glycosylation of the C2' of the 13-O-glucose, 19-O-glucose, or both 13-O-glucose and 19-O-glucose of a steviol glycoside, transfers a glucose molecule from uridine diphosphate glucose (UDP-glucose) to steviol and/or a steviol glycoside.

Figure 3:
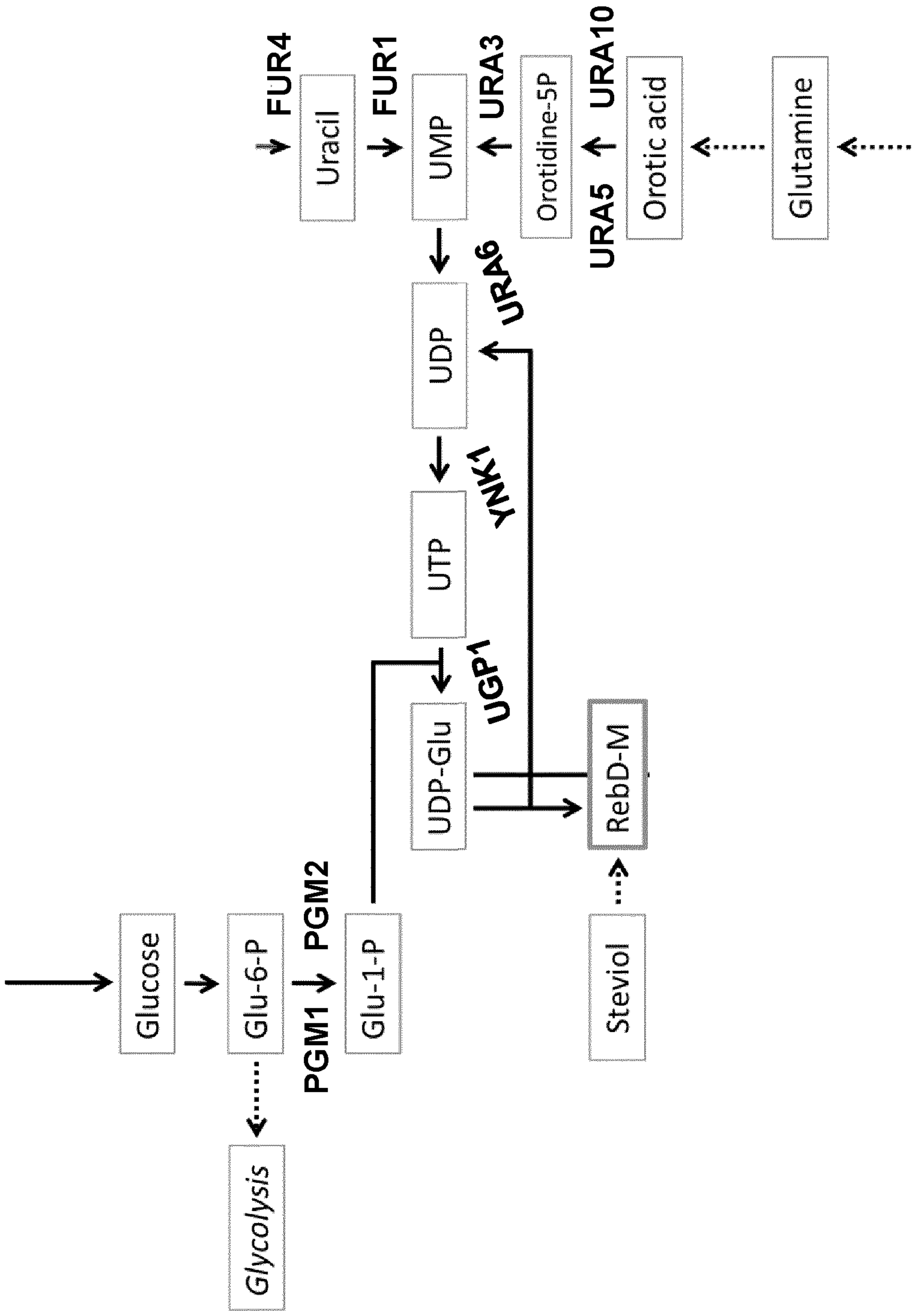
FIG. 3 shows representative reactions catalyzed by enzymes involved in the UDP-glucose biosynthetic pathway, including uracil permease (FUR4), uracil phosphoribosyltransferase (FUR1), orotate phosphoribosyltransferase 1 (URA5), orotate phosphoribosyltransferase 2 (URA10), orotidine 5'-phosphate decarboxylase (URA3), uridylate kinase (URA6), nucleoside diphosphate kinase (YNK1), phosphoglucomutase-1 (PGM1), phosphoglucomutase-2 (PGM2), and UTP-glucose-1-phosphate uridylyltransferase (UGP1). See, e.g., Daran et al., 1995, *Eur J Biochem.* 233(2):520-30.

In some aspects, UDP-glucose is produced in vivo through expression of one or more enzymes involved in the UDP-glucose biosynthetic pathway in a recombinant host. For example, a recombinant host comprising a gene encoding a polypeptide capable of transporting uracil into the host cell (e.g., uracil permease (FUR4)); a gene encoding a polypeptide capable of synthesizing uridine monophosphate (UMP) from uracil (e.g., uracil phosphoribosyltransferase (FUR1)); a gene encoding a polypeptide capable of synthesizing orotidine monophosphate (OMP) from orotate or orotic acid (e.g., orotate phosphoribosyltransferase 1 (URA5) and orotate phosphoribosyltransferase 2 (URA10)); a gene encoding a polypeptide capable of synthesizing UMP from OMP (e.g., orotidine 5'-phosphate decarboxylase (URA3)); a gene encoding a polypeptide capable of synthesizing uridine diphosphate (UDP) from UMP (e.g., uridylate kinase (URA6)); a gene encoding a polypeptide capable of synthesizing uridine 5'-triphosphate (UTP) from UDP (i.e., a polypeptide capable of catalyzing the transfer of gamma phosphates from nucleoside triphosphates, e.g., nucleoside diphosphate kinase (YNK1)); a gene encoding a polypeptide capable of converting glucose-6-phosphate to glucose-1-phosphate (e.g., phosphoglucomutase-1 (PGM1) and phosphoglucomutase-2 (PGM2)); and/or a gene encoding a polypeptide capable of synthesizing UDP-glucose from UTP and glucose-1-phosphate (e.g., UTP-glucose-1-phosphate uridylyltransferase (UGP1) can produce UDP-glucose in vivo. See, e.g., FIG. 3. The skilled worker will appreciate that one or more of these genes may be endogenous to the host.

In some embodiments, a recombinant host comprises a gene encoding a polypeptide capable of synthesizing UTP from UDP. In some aspects, the gene encoding a polypeptide capable of synthesizing UTP from UDP is a recombinant gene. In some aspects, the recombinant gene comprises a nucleotide sequence native to the host. In other aspects, the recombinant gene comprises a heterologous nucleotide sequence. In some aspects, the recombinant gene is operably linked to a promoter. In some aspects, the recombinant gene is operably linked to a terminator, for example but not limited to, tCYC1 (SEQ ID NO:154) or tADH1 (SEQ ID NO:155). In some aspects, the promoter and terminator drive high expression of the recombinant gene. In some aspects, the recombinant gene is operably linked to a strong promoter, for example but not limited to, pTEF1 (SEQ ID NO:148), pPGK1 (SEQ ID NO:149), pTDH3 (SEQ ID NO:150), pTEF2 (SEQ ID NO:151), pTPI1 (SEQ ID NO:152), or pPDC1 (SEQ ID NO:153). In some aspects, the recombinant gene comprises a nucleotide sequence that originated from or is present in the same species as the recombinant host. In some aspects, expression of a recombinant gene encoding a polypeptide capable of synthesizing UTP from UDP results in a total expression level of genes encoding a polypeptide capable of synthesizing UTP from UDP that is higher than the expression level of endogenous genes encoding a polypeptide capable of synthesizing UTP from UDP, i.e., an overexpression of a polypeptide capable of synthesizing UTP from UDP.

In some aspects, the gene encoding the polypeptide capable of synthesizing UTP from UDP is a gene present in the same species as the recombinant host, i.e., an endogenous gene. In some embodiments, the wild-type promoter of an endogenous gene encoding the polypeptide capable of synthesizing UTP from UDP can be exchanged for a strong promoter. In some aspects, the strong promoter drives high expression of the endogenous gene (i.e., overexpression of the gene). In other embodiments, the wild-type enhancer of an endogenous gene encoding a polypeptide capable of synthesizing UTP from UDP can be exchanged for a strong enhancer. In some embodiments, the strong enhancer drives high expression of the endogenous gene (i.e., overexpression of the gene). In some embodiments, both the wild-type enhancer (i.e., operably linked to the promoter) and the wild-type promoter (i.e., operably linked to the endogenous gene) of the endogenous gene can be exchanged for a strong enhancer and strong promoter, respectively, resulting in overexpression of a polypeptide capable of synthesizing UTP from UDP (i.e., relative to the expression level of endogenous genes operably linked to wild-type enhancers and/or promoters). The endogenous gene operably linked to the strong enhancer and/or promoter may be located at the native loci, and/or may be located elsewhere in the genome.

For example, in some embodiments, a recombinant host comprising an endogenous gene encoding a polypeptide capable of synthesizing UTP from UDP, operably linked to a wild-type promoter, further comprises a recombinant gene encoding a polypeptide capable of synthesizing UTP from UDP, comprising a nucleotide sequence native to the host, operably linked to, e.g., a wild-type promoter, a promoter native to the host, or a heterologous promoter. In another example, in some embodiments, a recombinant host comprising an endogenous gene encoding a polypeptide capable of synthesizing UTP from UDP, operably linked to a wild-type promoter, further comprises a recombinant gene encoding a polypeptide capable of synthesizing UTP from UDP, comprising a heterologous nucleotide sequence, operably linked to, e.g., a wild-type promoter, a promoter native to the host, or a heterologous promoter. In yet another example, in some embodiments, a recombinant host comprises an endogenous gene encoding a polypeptide capable of synthesizing UTP from UDP, operably linked to, e.g., a strong promoter native to the host, or a heterologous promoter.

The person of ordinary skill in the art will appreciate that, e.g., expression of a recombinant gene encoding a polypeptide capable of synthesizing UTP from UDP; expression of a recombinant gene and an endogenous gene encoding a polypeptide capable of synthesizing UTP from UDP, and expression of an endogenous gene encoding a polypeptide capable of synthesizing UTP from UDP, wherein the wild-type promoter and/or enhancer of the endogenous gene are exchanged for a strong promoter and/or enhancer, each result in overexpression of a polypeptide capable of synthesizing UTP from UDP relative to a corresponding host not expressing a recombinant gene encoding a polypeptide capable of synthesizing UTP from UDP and/or a corresponding host expressing only a native gene encoding a polypeptide capable of synthesizing UTP from UDP, operably linked to the wild-type promoter and enhancer—i.e., as used herein, the term "expression" may include "overexpression."

In some embodiments, a polypeptide capable of synthesizing UTP from UDP is overexpressed such that the total expression level of genes encoding the polypeptide capable of synthesizing UTP from UDP is at least 5% higher than the expression level of endogenous genes encoding a polypeptide capable of synthesizing UTP from UDP. In some embodiments, the total expression level of genes encoding a polypeptide capable of synthesizing UTP from UDP is at least 10%, or at least 15%, or at least 20%, or at least 30%, or at least 40%, or at least 50%, or at least 60%, or at least 70%, or at least 80%, or at least 90%, or at least 100%, or at least 125%, or at least 150%, or at least 175%, or at least 200% higher than the expression level of endogenous genes encoding a polypeptide capable of synthesizing UTP from UDP.

In some embodiments, a recombinant host comprises a gene encoding a polypeptide capable of converting glucose-6-phosphate to glucose-1-phosphate. In some aspects, the gene encoding a polypeptide capable of converting glucose-6-phosphate to glucose-1-phosphate is a recombinant gene. In some aspects, the recombinant gene comprises a nucleotide sequence native to the host. In other aspects, the recombinant gene comprises a heterologous nucleotide sequence. In some aspects, the recombinant gene is operably linked to a promoter. In some aspects, the recombinant gene is operably linked to a terminator, for example but not limited to, tCYC1 (SEQ ID NO:154) or tADH1 (SEQ ID NO:155). In some aspects, the promoter and terminator drive high expression of the recombinant gene. In some aspects, the recombinant gene is operably linked to a strong promoter, for example but not limited to, pTEF1 (SEQ ID NO:148), pPGK1 (SEQ ID NO:149), pTDH3 (SEQ ID NO:150), pTEF2 (SEQ ID NO:151), pTPI1 (SEQ ID NO:152), or pPDC1 (SEQ ID NO:153). In some aspects, the recombinant gene comprises a nucleotide sequence that originated from or is present in the same species as the recombinant host. In some aspects, expression of a recombinant gene encoding a polypeptide capable of converting glucose-6-phosphate to glucose-1-phosphate results in a total expression level of genes encoding a polypeptide capable of converting glucose-6-phosphate to glucose-1-phosphate that is higher than the expression level of endogenous genes encoding a polypeptide capable of converting glucose-6-phosphate to glucose-1-phosphate, i.e., an overexpression of a polypeptide capable of converting glucose-6-phosphate to glucose-1-phosphate.

In some aspects, the gene encoding the polypeptide capable of converting glucose-6-phosphate to glucose-1-phosphate is a gene present in the same species as the recombinant host, i.e., an endogenous gene. In some embodiments, the wild-type promoter of an endogenous gene encoding the polypeptide capable of converting glucose-6-phosphate to glucose-1-phosphate can be exchanged for a strong promoter. In some aspects, the strong promoter drives high expression of the endogenous gene (i.e., overexpression of the gene). In other embodiments, the wild-type enhancer of an endogenous gene encoding a polypeptide capable of converting glucose-6-phosphate to glucose-1-phosphate can be exchanged for a strong enhancer. In some embodiments, the strong enhancer drives high expression of the endogenous gene (i.e., overexpression of the gene). In some embodiments, both the wild-type enhancer (i.e., operably linked to the promoter) and the wild-type promoter (i.e., operably linked to the endogenous gene) of the endogenous gene can be exchanged for a strong enhancer and strong promoter, respectively, resulting in overexpression of a polypeptide capable of converting glucose-6-phosphate to glucose-1-phosphate (i.e., relative to the expression level of endogenous genes operably linked to wild-type enhancers and/or promoters). The endogenous gene operably linked to the strong enhancer and/or promoter may be located at the native loci, and/or may be located elsewhere in the genome.

For example, in some embodiments, a recombinant host comprising an endogenous gene encoding a polypeptide capable of converting glucose-6-phosphate to glucose-1-phosphate, operably linked to a wild-type promoter, further comprises a recombinant gene encoding a polypeptide capable of converting glucose-6-phosphate to glucose-1-phosphate, comprising a nucleotide sequence native to the host, operably linked to, e.g., a wild-type promoter, a promoter native to the host, or a heterologous promoter. In another example, in some embodiments, a recombinant host comprising an endogenous gene encoding a polypeptide capable of converting glucose-6-phosphate to glucose-1-phosphate, operably linked to a wild-type promoter, further comprises a recombinant gene encoding a polypeptide capable of converting glucose-6-phosphate to glucose-1-phosphate, comprising a heterologous nucleotide sequence, operably linked to, e.g., a wild-type promoter, a promoter native to the host, or a heterologous promoter. In yet another example, in some embodiments, a recombinant host comprises an endogenous gene encoding a polypeptide capable of converting glucose-6-phosphate to glucose-1-phosphate, operably linked to, e.g., a strong promoter native to the host, or a heterologous promoter.

In some embodiments, a polypeptide capable of converting glucose-6-phosphate to glucose-1-phosphate is overexpressed such that the total expression level of genes encoding the polypeptide capable of converting glucose-6-phosphate to glucose-1-phosphate is at least 5% higher than the expression level of endogenous genes encoding a polypeptide capable of converting glucose-6-phosphate to glucose-1-phosphate. In some embodiments, the total expression level of genes encoding a polypeptide capable of converting glucose-6-phosphate to glucose-1-phosphate is at least 10%, or at least 15%, or at least 20%, or at least 30%, or at least 40%, or at least 50%, or at least 60%, or at least 70%, or at least 80%, or at least 90%, or at least 100%, or at least 125%, or at least 150%, or at least 175%, or at least 200% higher than the expression level of endogenous genes encoding a polypeptide capable of converting glucose-6-phosphate to glucose-1-phosphate.

In some embodiments, a recombinant host comprises a gene encoding a polypeptide capable of synthesizing UDP-glucose from UTP and glucose-1-phosphate. In some aspects, the gene encoding a polypeptide capable of synthesizing UDP-glucose from UTP and glucose-1-phosphate is a recombinant gene. In some aspects, the recombinant gene comprises a nucleotide sequence native to the host. In other aspects, the recombinant gene comprises a heterologous nucleotide sequence. In some aspects, the recombinant gene is operably linked to a promoter. In some aspects, the recombinant gene is operably linked to a terminator, for example but not limited to, tCYC1 (SEQ ID NO:154) or tADH1 (SEQ ID NO:155). In some aspects, the promoter and terminator drive high expression of the recombinant gene. In some aspects, the recombinant gene is operably linked to a strong promoter, for example but not limited to, pTEF1 (SEQ ID NO:148), pPGK1 (SEQ ID NO:149), pTDH3 (SEQ ID NO:150), pTEF2 (SEQ ID NO:151), pTPI1 (SEQ ID NO:152), or pPDC1 (SEQ ID NO:153). In some aspects, the recombinant gene comprises a nucleotide sequence that originated from or is present in the same species as the recombinant host. In some aspects, expression of a recombinant gene encoding a polypeptide capable of synthesizing UDP-glucose from UTP and glucose-1-phosphate results in a total expression level of genes encoding a polypeptide capable of synthesizing UDP-glucose from UTP and glucose-1-phosphate that is higher than the expression level of endogenous genes encoding a polypeptide capable of synthesizing UDP-glucose from UTP and glucose-1-phosphate, i.e., an overexpression of a polypeptide capable of synthesizing UDP-glucose from UTP and glucose-1-phosphate.

In some aspects, the gene encoding the polypeptide capable of synthesizing UDP-glucose from UTP and glucose-1-phosphate is a gene present in the same species as the recombinant host, i.e., an endogenous gene. In some embodiments, the wild-type promoter of an endogenous gene encoding the polypeptide capable of synthesizing UDP-glucose from UTP and glucose-1-phosphate can be exchanged for a strong promoter. In some aspects, the strong promoter drives high expression of the endogenous gene (i.e., overexpression of the gene). In other embodiments, the wild-type enhancer of an endogenous gene encoding a polypeptide capable of synthesizing UDP-glucose from UTP and glucose-1-phosphate can be exchanged for a strong enhancer. In some embodiments, the strong enhancer drives high expression of the endogenous gene (i.e., overexpression of the gene). In some embodiments, both the wild-type enhancer (i.e., operably linked to the promoter) and the wild-type promoter (i.e., operably linked to the endogenous gene) of the endogenous gene can be exchanged for a strong enhancer and strong promoter, respectively, resulting in overexpression of a polypeptide capable of synthesizing UDP-glucose from UTP and glucose-1-phosphate (i.e., relative to the expression level of endogenous genes operably linked to wild-type enhancers and/or promoters). The endogenous gene operably linked to the strong enhancer and/or promoter may be located at the native loci, and/or may be located elsewhere in the genome.

For example, in some embodiments, a recombinant host comprising an endogenous gene encoding a polypeptide capable of synthesizing UDP-glucose from UTP and glucose-1-phosphate, operably linked to a wild-type promoter, further comprises a recombinant gene encoding a polypeptide capable of synthesizing UDP-glucose from UTP and glucose-1-phosphate, comprising a nucleotide sequence native to the host, operably linked to, e.g., a wild-type promoter, a promoter native to the host, or a heterologous promoter. In another example, in some embodiments, a recombinant host comprising an endogenous gene encoding a polypeptide capable of synthesizing UDP-glucose from UTP and glucose-1-phosphate, operably linked to a wild-type promoter, further comprises a recombinant gene encoding a polypeptide capable of synthesizing UDP-glucose from UTP and glucose-1-phosphate, comprising a heterologous nucleotide sequence, operably linked to, e.g., a wild-type promoter, a promoter native to the host, or a heterologous promoter. In yet another example, in some embodiments, a recombinant host comprises an endogenous gene encoding a polypeptide capable of synthesizing UDP-glucose from UTP and glucose-1-phosphate, operably linked to, e.g., a strong promoter native to the host, or a heterologous promoter.

In some embodiments, a recombinant host comprising a polypeptide capable of synthesizing UDP-glucose from UTP and glucose-1-phosphate is overexpressed such that the total expression level of genes encoding the polypeptide capable of synthesizing UDP-glucose from UTP and glucose-1-phosphate is at least 5% higher than the expression level of endogenous genes encoding a polypeptide capable of synthesizing UDP-glucose from UTP and glucose-1-phosphate. In some embodiments, the total expression level of genes encoding a polypeptide capable of synthesizing UDP-glucose from UTP and glucose-1-phosphate is at least 10%, or at least 15%, or at least 20%, or at least 30%, or at least 40%, or at least 50%, or at least 60%, or at least 70%, or at least 80%, or at least 90%, or at least 100%, or at least 125%, or at least 150%, or at least 175%, or at least 200% higher than the expression level of endogenous genes encoding a polypeptide capable of synthesizing UDP-glucose from UTP and glucose-1-phosphate.

In some aspects, a recombinant host comprising one or more genes encoding one or more polypeptides capable of synthesizing UTP from UDP, one or more genes encoding one or more polypeptides capable of converting glucose-6-phosphate to glucose-1-phosphate, and/or one or more genes encoding one or more polypeptides capable of synthesizing UDP-glucose from UTP and glucose-1-phosphate may further comprise a recombinant gene encoding a polypeptide capable of transporting uracil into the host cell; a recombinant gene encoding a polypeptide capable of synthesizing uridine monophosphate (UMP) from uracil; a recombinant gene encoding a polypeptide capable of synthesizing orotidine monophosphate (OMP) from orotate or orotic acid; a recombinant gene encoding a polypeptide capable of synthesizing UMP from OMP; and/or a recombinant gene encoding a polypeptide capable of synthesizing uridine diphosphate (UDP) from UMP. In some embodiments, a recombinant host comprising one or more genes encoding one or more polypeptides capable of synthesizing UTP from UDP, one or more genes encoding one or more polypeptides capable of converting glucose-6-phosphate to glucose-1-phosphate, and/or one or more genes encoding one or more polypeptides capable of synthesizing UDP-glucose from UTP and glucose-1-phosphate may overexpress a gene encoding a polypeptide capable of transporting uracil into the host cell; a gene encoding a polypeptide capable of synthesizing uridine monophosphate (UMP) from uracil; a gene encoding a polypeptide capable of synthesizing orotidine monophosphate (OMP) from orotate or orotic acid; a gene encoding a polypeptide capable of synthesizing UMP from OMP; and/or a gene encoding a polypeptide capable of synthesizing uridine diphosphate (UDP) from UMP.

In some aspects, the polypeptide capable of synthesizing UTP from UDP comprises a polypeptide having the amino acid sequence set forth in SEQ ID NO:123 (which can be encoded by the nucleotide sequence set forth in SEQ ID NO:122).

In some aspects, the polypeptide capable of converting glucose-6-phosphate to glucose-1-phosphate comprises a polypeptide having the amino acid sequence set forth in SEQ ID NO:2 (which can be encoded by the nucleotide sequence set forth in SEQ ID NO:1), SEQ ID NO:119 (encoded by the nucleotide sequence set forth in SEQ ID NO:118), SEQ ID NO:141 (encoded by the nucleotide sequence set forth in SEQ ID NO:140), SEQ ID NO:143 (encoded by the nucleotide sequence set forth in SEQ ID NO:142), SEQ ID NO:145 (encoded by the nucleotide sequence set forth in SEQ ID NO:144), or SEQ ID NO:147 (encoded by the nucleotide sequence set forth in SEQ ID NO:146).

In some aspects, the polypeptide capable of synthesizing UDP-glucose from UTP and glucose-1-phosphate comprises a polypeptide having the amino acid sequence set forth in SEQ ID NO:121 (which can be encoded by the nucleotide sequence set forth in SEQ ID NO:120), SEQ ID NO:125 (encoded by the nucleotide sequence set forth in SEQ ID NO:124), SEQ ID NO:127 (encoded by the nucleotide sequence set forth in SEQ ID NO:126), SEQ ID NO:129 (encoded by the nucleotide sequence set forth in SEQ ID NO:128), SEQ ID NO:131 (encoded by the nucleotide sequence set forth in SEQ ID NO:130), SEQ ID NO:133 (encoded by the nucleotide sequence set forth in SEQ ID NO:132), SEQ ID NO:135 (encoded by the nucleotide sequence set forth in SEQ ID NO:134), SEQ ID NO:137 (encoded by the nucleotide sequence set forth in SEQ ID NO:136), or SEQ ID NO:139 (encoded by the nucleotide sequence set forth in SEQ ID NO:138).

In some embodiments, a recombinant host comprises a recombinant gene encoding a polypeptide capable of synthesizing UTP from UDP and a recombinant gene encoding a polypeptide capable of converting glucose-6-phosphate to glucose-1-phosphate. In some embodiments, a recombinant host comprises a recombinant gene encoding a polypeptide capable of synthesizing UTP from UDP and a recombinant gene encoding a polypeptide capable of synthesizing UDP-glucose from UTP and glucose-1-phosphate. In some embodiments, a recombinant host comprises a recombinant gene encoding a polypeptide capable of converting glucose-6-phosphate to glucose-1-phosphate and a recombinant gene encoding a polypeptide capable of synthesizing UDP-glucose from UTP and glucose-1-phosphate. In some embodiments, a recombinant host comprises a recombinant gene encoding a polypeptide capable of synthesizing UTP from UDP, a recombinant gene encoding a polypeptide capable of converting glucose-6-phosphate to glucose-1-phosphate, and a recombinant gene encoding a polypeptide capable of synthesizing UDP-glucose from UTP and glucose-1-phosphate.

In some embodiments, a recombinant host comprises two or more recombinant genes encoding a polypeptide involved in the UDP-glucose biosynthetic pathway, e.g., a gene encoding a polypeptide capable of converting glucose-6-phosphate having a first amino acid sequence and a gene encoding a polypeptide capable of converting glucose-6-phosphate having a second amino acid sequence distinct from the first amino acid sequence. For example, in some embodiments, a recombinant host comprises a gene encoding a polypeptide having the amino acid sequence of PGM1 (e.g., a polypeptide having the amino acid sequence set forth in SEQ ID NO:2) and a gene encoding a polypeptide having the amino acid sequence of PGM2 (e.g., a polypeptide having the amino acid sequence set forth in SEQ ID NO:119, SEQ ID NO:141, SEQ ID NO:143, SEQ ID NO:145, or SEQ ID NO:147). In certain such embodiments, the two or more genes encoding a polypeptide involved in the UDP-glucose biosynthetic pathway comprise nucleotide sequences native to the recombinant host cell (e.g., a recombinant *S. cerevisiae* host cell comprising a gene encoding a polypeptide having the amino acid sequence set forth in SEQ ID NO:2 and a gene encoding a polypeptide having the amino acid sequence set forth in SEQ ID NO:119). In other such embodiments, one of the two or more genes encoding a polypeptide involved in the UDP-glucose biosynthetic pathway comprises a nucleotide sequence native to the recombinant host cell, while one or more of the two or more genes encoding a polypeptide involved in the UDP-glucose biosynthetic pathway comprises a heterologous nucleotide sequence. For example, in some embodiments, a recombinant *S. cerevisiae* host cell expressing a recombinant gene encoding a polypeptide capable of synthesizing UDP-glucose from UTP and glucose-1-phosphate having the amino acid sequence set forth in SEQ ID NO:121 (i.e., a recombinant host overexpressing the polypeptide) further expresses a recombinant gene encoding a polypeptide capable of synthesizing UDP-glucose from UTP and glucose-1-phosphate having the amino acid sequence set forth in, e.g., SEQ ID NO:125, SEQ ID NO:127, SEQ ID NO:129, SEQ ID NO:131, SEQ ID NO:133, SEQ ID NO:135, SEQ ID NO:137, or SEQ ID NO:139. In another example, in some embodiments, a recombinant *S. cerevisiae* host cell expressing a recombinant gene encoding a polypeptide capable of converting glucose-6-phosphate to glucose-1-phosphate having the amino acid sequence set forth in SEQ ID NO:119 (i.e., a recombinant host overexpressing the polypeptide) further expresses a recombinant gene encoding a polypeptide capable of converting glucose-6-phosphate to glucose-1-phosphate having the amino acid sequence set forth in, e.g., SEQ ID NO:141, SEQ ID NO:143, SEQ ID NO:145, or SEQ ID NO:147. Accordingly, as used herein, the term "a recombinant gene" may include "one or more recombinant genes."

In some embodiments, a recombinant host comprises two or more copies of a recombinant gene encoding a polypeptide involved in the UDP-glucose biosynthetic pathway or the steviol glycoside biosynthetic pathway. In some embodiments, a recombinant host is preferably transformed with, e.g., two copies, three copies, four copies, or five copies of a recombinant gene encoding a polypeptide involved in the UDP-glucose biosynthetic pathway or the steviol glycoside biosynthetic pathway. For example, in some embodiments, a recombinant host is transformed with two copies of a recombinant gene encoding a polypeptide capable of synthesizing UTP from UDP (e.g., a polypeptide having the amino acid sequence set forth in SEQ ID NO:123). The person of ordinary skill in the art will appreciate that, in some embodiments, recombinant genes may be replicated in a host cell independently of cell replication; accordingly, a recombinant host cell may comprise, e.g., more copies of a recombinant gene than the number of copies the cell was transformed with. Accordingly, as used herein, the term "a recombinant gene" may include "one or more copies of a recombinant gene."

In some aspects, expression of a polypeptide capable of synthesizing UTP from UDP, a polypeptide capable of converting glucose-6-phosphate to glucose-1-phosphate, and/or a polypeptide capable of synthesizing UDP-glucose from UTP and glucose-1-phosphate in a recombinant host cell increases the amount of UDP-glucose produced by the cell. In some aspects, expression of a polypeptide capable of synthesizing UTP from UDP, a polypeptide capable of converting glucose-6-phosphate to glucose-1-phosphate, and/or a polypeptide capable of synthesizing UDP-glucose from UTP and glucose-1-phosphate in a recombinant host cell maintains, or even increases, the pool of UDP-glucose available for, e.g., glycosylation of steviol or a steviol glycoside. In some aspects, expression of a polypeptide capable of synthesizing UTP from UDP, a polypeptide capable of converting glucose-6-phosphate to glucose-1-phosphate, and/or a polypeptide capable sunthesizing UDP-glucose from UTP and glucose-1-phosphate in a recombinant host cell increases the speed which UDP-glucose is regenerated, thus maintaining, or even increasing, the UDP-glucose pool, which can be used to synthesize one or more steviol glycosides.

In some embodiments, expression of a recombinant gene encoding a polypeptide capable of synthesizing UTP from UDP (e.g., a polypeptide having the amino acid sequence set forth in SEQ ID NO:123), a recombinant gene encoding a polypeptide capable of converting glucose-6-phosphate to glucose-1-phosphate (e.g. a polypeptide having the amino acid sequence set forth in SEQ ID NO:2, SEQ ID NO:119, SEQ ID NO:141, SEQ ID NO:143, SEQ ID NO:145, or SEQ ID NO:147), and a recombinant gene encoding a polypeptide capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, or SEQ ID NO:139) in a recombinant host cell increases the amount of UDP-glucose produced by the cell by at least about 10%, e.g., at least about 25%, or at least about 50%, or at least about 75%, or at least about 100%, or at least about 125%, or at least about 150%, or at least about 175%, or at least about 200%, or at least about 225%, or at least about 250%, or at least about 275%, or at least about 300%, calculated as an increase in intracellular UDP-glucose concentration relative to a corresponding host lacking the recombinant genes.

In certain such embodiments, one or more of the recombinant gene encoding a polypeptide capable of synthesizing UTP from UDP, the recombinant gene encoding a polypeptide capable of converting glucose-6-phosphate to glucose-1-phosphate, and the recombinant gene encoding a polypeptide capable of synthesizing UDP-glucose from UTP and glucose-1-phosphate comprise a nucleotide sequence native to the host cell. For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2 and/or SEQ ID NO:119, and a recombinant gene encoding a polypeptide capable of synthesizing UDP-glucose from UTP and glucose-1-phosphate having the amino acid sequence set forth in SEQ ID NO:121 in a steviol glycoside-producing *S. cerevisiae* host cell (i.e., providing a recombinant host overexpressing the polypeptides) increases the amount of UDP-glucose produced by the cell by at least about 10%, e.g., at least about 25%, or at least about 50%, or at least about 75%, or at least about 100%, or at least about 125%, or at least about 150%, or at least about 175%, or at least about 200%, or at least about 225%, or at least about 250%, or at least about 275%, or at least about 300%, calculated as an increase in intracellular UDP-glucose concentration relative to a corresponding host lacking the recombinant genes.

In some aspects, expression of a polypeptide capable of synthesizing UTP from UDP, a polypeptide capable of converting glucose-6-phosphate to glucose-1-phosphate, and/or a polypeptide capable of synthesizing UDP-glucose from UTP and glucose-1-phosphate in a steviol-glycoside producing recombinant host cell further expressing a gene encoding a polypeptide capable of glycosylating steviol or a steviol glycoside at its C-13 hydroxyl group; a gene encoding a polypeptide capable of beta 1,3 glycosylation of the C3' of the 13-O-glucose, 19-O-glucose, or both 13-O-glucose and 19-O-glucose of a steviol glycoside; a gene encoding a polypeptide capable of glycosylating steviol or a steviol glycoside at its C-19 carboxyl group; and/or a gene encoding a polypeptide capable of beta 1,2 glycosylation of the C2' of the 13-O-glucose, 19-O-glucose, or both 13-O-glucose and 19-O-glucose of a steviol glycoside, increases the amount of one or more steviol glycosides produced by the cell, and/or decreases the amount of one or more steviol glycosides produced by the cell. In some embodiments, the steviol glycoside-producing host further expresses a gene encoding a polypeptide capable of synthesizing GGPP from FPP and IPP; a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; and a gene encoding a polypeptide capable of synthesizing steviol from ent-kaurenoic acid; and/or a gene encoding a bifunctional polypeptide capable of synthesizing ent-copalyl diphosphate from GGPP and synthesizing ent-kaurene from ent-copalyl diphosphate.

In some aspects, the polypeptide capable of synthesizing geranylgeranyl pyrophosphate (GGPP) from farnesyl diphosphate (FPP) and isopentenyl diphosphate (IPP) comprises a polypeptide having an amino acid sequence set forth in SEQ ID NO:20 (which can be encoded by the nucleotide sequence set forth in SEQ ID NO:19), SEQ ID NO:22 (encoded by the nucleotide sequence set forth in SEQ ID NO:21), SEQ ID NO:24 (encoded by the nucleotide sequence set forth in SEQ ID NO:23), SEQ ID NO:26 (encoded by the nucleotide sequence set forth in SEQ ID NO:25), SEQ ID NO:28 (encoded by the nucleotide sequence set forth in SEQ ID NO:27), SEQ ID NO:30 (encoded by the nucleotide sequence set forth in SEQ ID NO:29), SEQ ID NO:32 (encoded by the nucleotide sequence set forth in SEQ ID NO:31), or SEQ ID NO:116 (encoded by the nucleotide sequence set forth in SEQ ID NO:115). In some embodiments, a recombinant host comprising a gene encoding a polypeptide capable of synthesizing geranylgeranyl pyrophosphate (GGPP) from farnesyl diphosphate (FPP) and isopentenyl diphosphate (IPP) further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of synthesizing ent-copalyl diphosphate from GGPP comprises a polypeptide having an amino acid sequence set forth in SEQ ID NO:34 (which can be encoded by the nucleotide sequence set forth in SEQ ID NO:33), SEQ ID NO:36 (encoded by the nucleotide sequence set forth in SEQ ID NO:35), SEQ ID NO:38 (encoded by the nucleotide sequence set forth in SEQ ID NO:37), SEQ ID NO:40 (encoded by the nucleotide sequence set forth in SEQ ID NO:39), or SEQ ID NO:42 (encoded by the nucleotide sequence set forth in SEQ ID NO:41). In some embodiments, the polypeptide capable of synthesizing ent-copalyl diphosphate from GGPP lacks a chloroplast transit peptide. In some embodiments, a recombinant host comprising a gene encoding a polypeptide capable of synthesizing ent-copalyl diphosphate from GGPP further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of synthesizing ent-kaurene from ent-copalyl diphosphate comprises a polypeptide having an amino acid sequence set forth in SEQ ID NO:44 (which can be encoded by the nucleotide sequence set forth in SEQ ID NO:43), SEQ ID NO:46 (encoded by the nucleotide sequence set forth in SEQ ID NO:45), SEQ ID NO:48 (encoded by the nucleotide sequence set forth in SEQ ID NO:47), SEQ ID NO:50 (encoded by the nucleotide sequence set forth in SEQ ID NO:49), or SEQ ID NO:52 (encoded by the nucleotide sequence set forth in SEQ ID NO:51). In some embodiments, a recombinant host comprising a gene encoding a polypeptide capable of synthesizing ent-kaurene from ent-copalyl diphosphate further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some embodiments, a recombinant host comprises a gene encoding a bifunctional polypeptide capable of synthesizing ent-copalyl diphosphate from GGPP and synthesizing ent-kaurene from ent-copalyl diphosphate. In some aspects, the bifunctional polypeptide comprises a polypeptide having an amino acid sequence set forth in SEQ ID NO:54 (which can be encoded by the nucleotide sequence set forth in SEQ ID NO:53), SEQ ID NO:56 (encoded by the nucleotide sequence set forth in SEQ ID NO:55), or SEQ ID NO:58 (encoded by the nucleotide sequence set forth in SEQ ID NO:57). In some embodiments, a recombinant host comprising a gene encoding a bifunctional polypeptide capable of synthesizing ent-copalyl diphosphate from GGPP and synthesizing ent-kaurene from ent-copalyl diphosphate further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of synthesizing ent-kaurenoic acid, ent-kaurenol, and/or ent-kaurenal from ent-kaurene comprises a polypeptide having an amino acid sequence set forth in SEQ ID NO:60 (which can be encoded by the nucleotide sequence set forth in SEQ ID NO:59), SEQ ID NO:62 (encoded by the nucleotide sequence set forth in SEQ ID NO:61), SEQ ID NO:117 (encoded by the nucleotide sequence set forth in SEQ ID NO:63 or SEQ ID NO:64), SEQ ID NO:66 (encoded by the nucleotide sequence set forth in SEQ ID NO:65), SEQ ID NO:68 (encoded by the nucleotide sequence set forth in SEQ ID NO:67), SEQ ID NO:70 (encoded by the nucleotide sequence set forth in SEQ ID NO:69), SEQ ID NO:72 (encoded by the nucleotide sequence set forth in SEQ ID NO:71), SEQ ID NO:74 (encoded by the nucleotide sequence set forth in SEQ ID NO:73), or SEQ ID NO:76 (encoded by the nucleotide sequence set forth in SEQ ID NO:75). In some embodiments, a recombinant host comprising a gene encoding a polypeptide capable of synthesizing ent-kaurenoic acid, ent-kaurenol, and/or ent-kaurenal from ent-kaurene further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of reducing cytochrome P450 complex comprises a polypeptide having an amino acid sequence set forth in SEQ ID NO:78 (which can be encoded by the nucleotide sequence set forth in SEQ ID NO:77), SEQ ID NO:80 (encoded by the nucleotide sequence set forth in SEQ ID NO:79), SEQ ID NO:82 (encoded by the nucleotide sequence set forth in SEQ ID NO:81), SEQ ID NO:84 (encoded by the nucleotide sequence set forth in SEQ ID NO:83), SEQ ID NO:86 (encoded by the nucleotide sequence set forth in SEQ ID NO:85), SEQ ID NO:88 (encoded by the nucleotide sequence set forth in SEQ ID NO:87), SEQ ID NO:90 (encoded by the nucleotide sequence set forth in SEQ ID NO:89), or SEQ ID NO:92 (encoded by the nucleotide sequence set forth in SEQ ID NO:91). In some embodiments, a recombinant host comprising a gene encoding a polypeptide capable of reducing cytochrome P450 complex further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of synthesizing steviol from ent-kaurenoic acid comprises a polypeptide having an amino acid sequence set forth in SEQ ID NO:94 (which can be encoded by the nucleotide sequence set forth in SEQ ID NO:93), SEQ ID NO:97 (encoded by the nucleotide sequence set forth in SEQ ID NO:95 or SEQ ID NO:96), SEQ ID NO:100 (encoded by the nucleotide sequence set forth in SEQ ID NO:98 or SEQ ID NO:99), SEQ ID NO:101, SEQ ID NO:102, SEQ ID NO:103, SEQ ID NO:104, SEQ ID NO:106 (encoded by the nucleotide sequence set forth in SEQ ID NO:105), SEQ ID NO:108 (encoded by the nucleotide sequence set forth in SEQ ID NO:107), SEQ ID NO:110 (encoded by the nucleotide sequence set forth in SEQ ID NO:109), SEQ ID NO:112 (encoded by the nucleotide sequence set forth in SEQ ID NO:111), or SEQ ID NO:114 (encoded by the nucleotide sequence set forth in SEQ ID NO:113). In some embodiments, a recombinant host comprising a gene encoding a polypeptide capable of synthesizing steviol from ent-kaurenoic acid further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some embodiments, a recombinant host comprises a nucleic acid encoding a polypeptide capable of glycosylating steviol or a steviol glycoside at its C-13 hydroxyl group (e.g., UGT85C2 polypeptide) (SEQ ID NO:7), a nucleic acid encoding a polypeptide capable of beta 1,3 glycosylation of the C3' of the 13-O-glucose, 19-O-glucose, or both 13-O-glucose and 19-O-glucose of a steviol glycoside (e.g., UGT76G1 polypeptide) (SEQ ID NO:9), a nucleic acid encoding a polypeptide capable of glycosylating steviol or a steviol glycoside at its C-19 carboxyl group (e.g., UGT74G1 polypeptide) (SEQ ID NO:4), a nucleic acid encoding a polypeptide capable of beta 1,2 glycosylation of the C2' of the 13-O-glucose, 19-O-glucose, or both 13-O-glucose and 19-O-glucose of a steviol glycoside (e.g., EUGT11 polypeptide) (SEQ ID NO:16). In some aspects, the polypeptide capable of beta 1,2 glycosylation of the C2' of the 13-0-glucose, 19-O-glucose, or both 13-O-glucose and 19-O-glucose of a steviol glycoside (e.g., UGT91D2 polypeptide) can be a UGT91D2e polypeptide (SEQ ID NO:11) or a UGT91D2e-b polypeptide (SEQ ID NO:13). In some embodiments, a recombinant host comprising a gene encoding a polypeptide capable of glycosylating steviol or a steviol glycoside further comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139). In some embodiments, the recombinant host is an *S. cerevisiae* host cell overexpressing one or more genes encoding one or more polypeptides involved in the UDP-glucose biosynthetic pathway (e.g., a polypeptide having the amino acid sequence set forth in SEQ ID NO:2, SEQ ID NO:119, SEQ ID NO:121, and/or SEQ ID NO:123).

In some aspects, the polypeptide capable of glycosylating steviol or a steviol glycoside at its C-13 hydroxyl group is encoded by the nucleotide sequence set forth in SEQ ID NO:5 or SEQ ID NO:6, the polypeptide capable of beta 1,3 glycosylation of the C3' of the 13-O-glucose, 19-O-glucose, or both 13-O-glucose and 19-O-glucose of a steviol glycoside is encoded by the nucleotide sequence set forth in SEQ ID NO:8, the polypeptide capable of glycosylating steviol or a steviol glycoside at its C-19 carboxyl group is encoded by the nucleotide sequence set forth in SEQ ID NO:3, the polypeptide capable of beta 1,2 glycosylation of the C2' of the 13-O-glucose, 19-O-glucose, or both 13-O-glucose and 19-O-glucose of a steviol glycoside is encoded by the nucleotide sequence set forth in SEQ ID NO:10, SEQ ID NO:12, SEQ ID NO:14, or SEQ ID NO:15. The skilled worker will appreciate that expression of these genes may be necessary to produce a particular steviol glycoside but that one or more of these genes can be endogenous to the host provided that at least one (and in some embodiments, all) of these genes is a recombinant gene introduced into the recombinant host.

In some embodiments, expression of a recombinant gene encoding a polypeptide capable of synthesizing UTP from UDP, a recombinant gene encoding a polypeptide capable of converting glucose-6-phosphate to glucose-1-phosphate, and a recombinant gene encoding a polypeptide capable of synthesizing UDP-glucose from UTP and glucose-1-phosphate in a steviol glycoside-producing recombinant host increases the amount of one or more steviol glycosides, e.g., rubusoside, RebB, RebA, RebD, and RebM, produced by the cell by at least about 5%, e.g., at least about 10%, or at least about 15%, or at least about 20%, or at least about 25%, or at least about 30%, or at least about 35%, or at least about 40%, or at least about 45%, or at least about 50%, or at least about 60%, or at least about 70%, or at least about 80%, or at least about 90%, or at least about 100%, calculated as an increase in intracellular steviol glycoside concentration relative to a corresponding steviol glycoside-producing host lacking the recombinant genes.

For example, in some embodiments, expression of a recombinant gene encoding a polypeptide capable of synthesizing UTP from UDP (e.g., a polypeptide having the amino acid sequence set forth in SEQ ID NO:123), a recombinant gene encoding a polypeptide capable of converting glucose-6-phosphate to glucose-1-phosphate (e.g. a polypeptide having the amino acid sequence set forth in SEQ ID NO:2, SEQ ID NO:119, SEQ ID NO:141, SEQ ID NO:143, SEQ ID NO:145, or SEQ ID NO:147), and a recombinant gene encoding a polypeptide capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, or SEQ ID NO:139) in a steviol glycoside-producing host increases the amount of one or more steviol glycosides, e.g., rubusoside, RebB, RebA, RebD, and RebM, produced by the cell by at least about 5%, e.g., at least about 10%, or at least about 15%, or at least about 20%, or at least about 25%, or at least about 30%, or at least about 35%, or at least about 40%, or at least about 45%, or at least about 50%, or at least about 60%, or at least about 70%, or at least about 80%, or at least about 90%, or at least about 100%, calculated as an increase in intracellular glycoside concentration relative to a corresponding steviol glycoside-producing host lacking the recombinant genes.

In some embodiments, expression of a recombinant gene encoding a polypeptide capable of synthesizing UTP from UDP, a recombinant gene encoding a polypeptide capable of converting glucose-6-phosphate to glucose-1-phosphate, and a recombinant gene encoding a polypeptide capable of synthesizing UDP-glucose from UTP and glucose-1-phosphate in a steviol glycoside-producing recombinant host decreases the amount of one or more steviol glycosides, e.g., 13-SMG and RebD, produced by the cell by at least about 5%, e.g., at least about 10%, or at least about 15%, or at least about 20%, or at least about 25%, or at least about 30%, or at least about 35%, or at least about 40%, or at least about 45%, or at least about 50%, calculated as a decrease in intracellular steviol glycoside concentration relative to a corresponding steviol glycoside-producing host lacking the recombinant genes.

For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2, a recombinant gene encoding a polypeptide capable of converting glucose-6-phosphate to glucose-1-phosphate having the amino acid sequence set forth in SEQ ID NO:119, a recombinant gene encoding a polypeptide capable of synthesizing UDP-glucose from UTP and glucose-1-phosphate having the amino acid sequence set forth in SEQ ID NO:121, and further expression of a recombinant gene encoding a polypeptide capable of synthesizing UDP-glucose from UTP and glucose-1-phosphate having the amino acid sequence set forth in, e.g., SEQ ID NO:127, SEQ ID NO:133, SEQ ID NO:129, SEQ ID NO:125, SEQ ID NO:139, or SEQ ID NO:135, in a steviol glycoside-producing recombinant host decreases the amount of 13-SMG produced by the cell by at least about 5%, e.g., at least about 7.5%, or at least about 10%, or at least about 15%, or at least about 20%, or at least about 25%, or at least about 30%, or at least about 35%.

In some embodiments, expression of a recombinant gene encoding a polypeptide capable of synthesizing UTP from UDP, a recombinant gene encoding a polypeptide capable of converting glucose-6-phosphate to glucose-1-phosphate, and a recombinant gene encoding a polypeptide capable of synthesizing UDP-glucose from UTP and glucose-1-phosphate in a steviol glycoside-producing recombinant host increases the total amount of steviol glycosides (i.e., the total amount of mono-, di-, tri-, tetra- penta-, hexa-, and hepta-glycosylated steviol compounds) by at least about 5%, e.g., at least about 7.5%, or at least about 10%, or at least about 12.5%, or at least about 15%, or at least about 17.5%, or at least about 20%, or at least about 25%, or at least about 27.5%, or at least about 30%, or at least about 35%, calculated as an increase in intracellular steviol glycoside concentration relative to a corresponding steviol glycoside-producing host lacking the recombinant genes.

For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2, a recombinant gene encoding a polypeptide capable of converting glucose-6-phosphate to glucose-1-phosphate having the amino acid sequence set forth in SEQ ID NO:119, a recombinant gene encoding a polypeptide capable of synthesizing UDP-glucose from UTP and glucose-1-phosphate having the amino acid sequence set forth in SEQ ID NO:121, and further expression of a recombinant gene encoding a polypeptide capable of synthesizing UDP-glucose from UTP and glucose-1-phosphate having the amino acid sequence set forth in, e.g., SEQ ID NO:133, SEQ ID NO:129, SEQ ID NO:131, SEQ ID NO:125, SEQ ID NO:139, or SEQ ID NO:135, in a steviol glycoside-producing recombinant host increases the total amount of steviol glycosides (i.e., the total amount of mono-, di-, tri-, tetra- penta-, hexa-, and hepta-glycosylated steviol compounds) by at least about 5%, e.g., at least about 7.5%, or at least about 10%, or at least about 12.5%, or at least about 15%, or at least about 17.5%, or at least about 20%, or at least about 25%, or at least about 27.5%, or at least about 30%, or at least about 35%, calculated as an increase in intracellular steviol glycoside concentration relative to a corresponding steviol glycoside-producing host lacking the recombinant genes.

In some other embodiments, the total amount of steviol glycosides produced by a steviol glycoside-producing recombinant host cell is unchanged (i.e., increased or decreased by less than about 5%, or less than about 4%, or less than about 3%, or less than about 2%, or less than about 1%) by expression in the host of a recombinant gene encoding a polypeptide capable of synthesizing UTP from UDP, a recombinant gene encoding a polypeptide capable of converting glucose-6-phosphate to glucose-1-phosphate, and/or a recombinant gene encoding a polypeptide capable of synthesizing UDP-glucose from UTP and glucose-1-phosphate. For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2, a recombinant gene encoding a polypeptide capable of converting glucose-6-phosphate to glucose-1-phosphate having the amino acid sequence set forth in SEQ ID NO:119, a recombinant gene encoding a polypeptide capable of synthesizing UDP-glucose from UTP and glucose-1-phosphate having the amino acid sequence set forth in SEQ ID NO:121 in a steviol glycoside-producing recombinant host increases the total amount of steviol glycosides produced by the host by less than about 5%, e.g., less than about 4%, or less than about 3%, or less than about 2%.

The person of ordinary skill in the art will appreciate that, in such embodiments, expression of one or more genes encoding a polypeptide involved in the involved in the UDP-glucose biosynthetic pathway may affect the relative levels of steviol glycosides produced by the recombinant host, e.g., by increasing the level of UDP-glucose available as a substrate for a polypeptide capable of glycosylating steviol or a steviol glycoside. For example, in some embodiments, expression of a recombinant gene encoding a polypeptide capable of synthesizing UTP from UDP having the amino acid sequence set forth in SEQ ID NO:123, a recombinant gene encoding a polypeptide capable of converting glucose-6-phosphate to glucose-1-phosphate having the amino acid sequence set forth in SEQ ID NO:2, a recombinant gene encoding a polypeptide capable of converting glucose-6-phosphate to glucose-1-phosphate having the amino acid sequence set forth in SEQ ID NO:119, a recombinant gene encoding a polypeptide capable of synthesizing UDP-glucose from UTP and glucose-1-phosphate having the amino acid sequence set forth in SEQ ID NO:121 in a steviol glycoside-producing recombinant host increases the total amount of steviol glycosides produced by the host by less than about 5%, e.g., less than about 4%, or less than about 3%, or less than about 2%, increases the amount of RebM produced by the host by at least about 50%, e.g., at least about 60%, or at least about 70%, or at least about 80%, or at least about 90%, and decreases the amount of RebD produced by the host by at least about 10%, e.g., at least about 20%, or at least about 30%, or at least about 40%.

In some embodiments, a recombinant host cell comprises one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139).

In certain embodiments, a recombinant host comprises one or more recombinant genes having a nucleotide sequence native to the host that encode one or more polypeptides capable of synthesizing UTP from UDP, one or more polypeptides capable of converting glucose-6-phosphate to glucose-1-phosphate, and/or one or more polypeptides capable of synthesizing UDP-glucose from UTP and glucose-1-phosphate, i.e., a recombinant host overexpresses one or more polypeptides capable of synthesizing UTP from UDP, one or more polypeptides capable of converting glucose-6-phosphate to glucose-1-phosphate, and/or one or more polypeptides capable of synthesizing UDP-glucose from UTP and glucose-1-phosphate.

In certain such embodiments, a recombinant host cell overexpresses one or more genes encoding one or more polypeptides capable of synthesizing UTP from UDP (e.g., an *S. cerevisiae* host cell expressing a recombinant gene encoding a polypeptide having the amino acid sequence set forth in SEQ ID NO:123), one or more genes encoding one or more polypeptides capable of converting glucose-6-phosphate to glucose-1-phosphate (e.g., an *S. cerevisiae* host cell expressing a recombinant gene encoding a polypeptide having the amino acid sequence set forth in SEQ ID NO:2, and/or SEQ ID NO:119), and/or one or more genes encoding one or more polypeptides capable of synthesizing UDP-glucose from UTP and glucose-1-phosphate (e.g., an *S. cerevisiae* host cell expressing a recombinant gene encoding a polypeptide having the amino acid sequence set forth in SEQ ID NO:121). In one example, a recombinant *S. cerevisiae* host cell overexpresses a gene encoding a polypeptide having the amino acid sequence set forth in SEQ ID NO:123, a gene encoding a polypeptide having the amino acid sequence set forth in SEQ ID NO:2, a gene encoding a polypeptide having the amino acid sequence set forth in SEQ ID NO:119, and a gene encoding a polypeptide having the amino acid sequence set forth in SEQ ID NO:121.

In certain embodiments, a recombinant host cell comprising one or more genes encoding one or more polypeptides capable of synthesizing UTP from UDP (e.g., a polypeptide having the amino acid sequence set forth in SEQ ID NO:123), one or more genes encoding one or more polypeptides capable of converting glucose-6-phosphate to glucose-1-phosphate (e.g., a polypeptide having the amino acid sequence set forth in SEQ ID NO:2, SEQ ID NO:119, SEQ ID NO:141, SEQ ID NO:143, SEQ ID NO:145, and/or SEQ ID NO:147), and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139), further comprises a gene encoding a polypeptide capable of glycosylating steviol or a steviol glycoside at its C-13 hydroxyl group (e.g., a polypeptide having the amino acid sequence set forth in SEQ ID NO:7); a gene encoding a polypeptide capable of beta 1,3 glycosylation of the C3' of the 13-O-glucose, 19-O-glucose, or both 13-O-glucose and 19-O-glucose of a steviol glycoside (e.g., a polypeptide having the amino acid sequence set forth in SEQ ID NO:9); a gene encoding a polypeptide capable of glycosylating steviol or a steviol glycoside at its C-19 carboxyl group (e.g., a polypeptide having the amino acid sequence set forth in SEQ ID NO:4); and/or a gene encoding a polypeptide capable of beta 1,2 glycosylation of the C2' of the 13-O-glucose, 19-O-glucose, or both 13-O-glucose and 19-O-glucose of a steviol glycoside (e.g., a polypeptide having the amino acid sequence set forth in SEQ ID NO:11, SEQ ID NO:13, or SEQ ID NO:16). In certain such embodiments, the recombinant host cell further comprises a gene encoding a polypeptide capable of synthesizing GGPP from FPP and IPP (e.g., a polypeptide having the amino acid sequence set forth in SEQ ID NO:20); a gene encoding a polypeptide capable of synthesizing ent-copalyl diphosphate from GGPP (e.g., a polypeptide having the amino acid sequence set forth in SEQ ID NO:40); a gene encoding a polypeptide capable of synthesizing ent-kaurene from ent-copalyl diphosphate (e.g., a polypeptide having the amino acid sequence set forth in SEQ ID NO:52); a gene encoding a polypeptide capable of synthesizing ent-kaurenoic acid, ent-kaurenol, and/or ent-kaurenal from ent-kaurene (e.g., a polypeptide having the amino acid sequence set forth in SEQ ID NO:60 or SEQ ID NO:117); a gene encoding a polypeptide capable of reducing cytochrome P450 complex (e.g., a polypeptide having the amino acid sequence set forth in SEQ ID NO:78, SEQ ID NO:86, or SEQ ID NO:92); and/or a gene encoding a polypeptide capable of synthesizing steviol from ent-kaurenoic acid (e.g., a polypeptide having the amino acid sequence set forth in SEQ ID NO:94).

In some embodiments, a recombinant host comprises two or more genes encoding two or more polypeptides capable of converting glucose-6-phosphate to glucose-1-phosphate (e.g., two or more polypeptides having the amino acid sequence set forth in SEQ ID NO:2, SEQ ID NO:119, SEQ ID NO:141, SEQ ID NO:143, SEQ ID NO:145, and/or SEQ ID NO:147), and/or two or more genes encoding two or more polypeptides capable of synthesizing UDP-glucose from UTP and glucose-1-phosphate (e.g., two or more polypeptides having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139).

In certain such embodiments, a recombinant host comprises two or more genes encoding two or more polypeptides capable of converting glucose-6-phosphate to glucose-1-phosphate, e.g., two or more genes encoding two or more polypeptides having the amino acid sequence set forth in SEQ ID NO:2, SEQ ID NO:119, SEQ ID NO:141, SEQ ID NO:143, SEQ ID NO:145, and/or SEQ ID NO:147. In one example, a recombinant host comprises a gene encoding a polypeptide having the amino acid sequence set forth in SEQ ID NO:2 and a polypeptide having the amino acid sequence set forth in SEQ ID NO:119. In another example, a recombinant host comprises a gene encoding a polypeptide having the amino acid sequence set forth in SEQ ID NO:2, a polypeptide having the amino acid sequence set forth in SEQ ID NO:119, and a polypeptide having the amino acid sequence set forth in SEQ ID NO:145. In some embodiments, the recombinant host further comprises a gene encoding a polypeptide capable of synthesizing UTP from UDP (e.g., a polypeptide having the amino acid sequence set forth in SEQ ID NO:123) and/or one or more genes encoding one or more polypeptides capable of synthesizing UDP-glucose from UTP and glucose-1-phosphate (e.g., a polypeptide having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139).

In certain such embodiments, a recombinant host comprises two or more genes encoding two or more polypeptides capable of synthesizing UDP-glucose from UTP and glucose-1-phosphate, e.g., two or more genes encoding two or more polypeptides having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139. In one example, a recombinant host comprises a gene encoding a polypeptide having the amino acid sequence set forth in SEQ ID NO:121 and a polypeptide having the amino acid sequence set forth in SEQ ID NO:125. In another example, a recombinant host comprises a gene encoding a polypeptide having the amino acid sequence set forth in SEQ ID NO:121 and a polypeptide having the amino acid sequence set forth in SEQ ID NO:127. In another example, a recombinant host comprises a gene encoding a polypeptide having the amino acid sequence set forth in SEQ ID NO:121 and a polypeptide having the amino acid sequence set forth in SEQ ID NO:129. In another example, a recombinant host comprises a gene encoding a polypeptide having the amino acid sequence set forth in SEQ ID NO:121 and a polypeptide having the amino acid sequence set forth in SEQ ID NO:131. In another example, a recombinant host comprises a gene encoding a polypeptide having the amino acid sequence set forth in SEQ ID NO:121 and a gene encoding a gene encoding a polypeptide having the amino acid sequence set forth in SEQ ID NO:133. In another example, a recombinant host comprises a gene encoding a polypeptide having the amino acid sequence set forth in SEQ ID NO:121 and a gene encoding a polypeptide having the amino acid sequence set forth in SEQ ID NO:135. In another example, a recombinant host comprises a gene encoding a polypeptide having the amino acid sequence set forth in SEQ ID NO:121 and a gene encoding a polypeptide having the amino acid sequence set forth in SEQ ID NO:137. In another example, a recombinant host comprises a gene encoding a polypeptide having the amino acid sequence set forth in SEQ ID NO:121 and a gene encoding a polypeptide having the amino acid sequence set forth in SEQ ID NO:139. In some embodiments, the recombinant host further comprises a gene encoding a polypeptide capable of synthesizing UTP from UDP (e.g., a polypeptide having the amino acid sequence set forth in SEQ ID NO:123) and/or one or more genes encoding one or more polypeptides capable of converting glucose-6-phosphate to glucose-1-phosphate (e.g., one or more polypeptides having the amino acid sequence set forth in SEQ ID NO:2, SEQ ID NO:119, SEQ ID NO:141, SEQ ID NO:143, SEQ ID NO:145, and/or SEQ ID NO:147).

In certain such embodiments, a recombinant host comprising two or more genes encoding two or more polypeptides capable of converting glucose-6-phosphate to glucose-1-phosphate (e.g., two or more polypeptides having the amino acid sequence set forth in SEQ ID NO:2, SEQ ID NO:119, SEQ ID NO:141, SEQ ID NO:143, SEQ ID NO:145, and/or SEQ ID NO:147), and/or two or more genes encoding two or more polypeptides capable of synthesizing UDP-glucose from UTP and glucose-1-phosphate (e.g., two or more polypeptides having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139) is a host cell overexpressing one or more genes encoding one or more polypeptides involved in the UDP-glucose biosynthetic pathway (e.g., an *S. cerevisiae* host cell expressing one or more genes encoding one or more polypeptides having the amino acid sequence set forth in SEQ ID NO:2, SEQ ID NO:119, SEQ ID NO:121, and/or SEQ ID NO:123).

In certain embodiments, a recombinant host cell comprising two or more genes encoding two or more polypeptides capable of converting glucose-6-phosphate to glucose-1-phosphate (e.g., two or more polypeptides having the amino acid sequence set forth in SEQ ID NO:2, SEQ ID NO:119, SEQ ID NO:141, SEQ ID NO:143, SEQ ID NO:145, and/or SEQ ID NO:147), and/or two or more genes encoding two or more polypeptides capable of synthesizing UDP-glucose from UTP and glucose-1-phosphate (e.g., two or more polypeptides having the amino acid sequence set forth in SEQ ID NO:121, SEQ ID NO:125, SEQ ID NO:127, SEQ ID NO:129, SEQ ID NO:131, SEQ ID NO:133, SEQ ID NO:135, SEQ ID NO:137, and/or SEQ ID NO:139), further comprises a gene encoding polypeptide capable of synthesizing UTP from UDP (e.g., a polypeptide having the amino acid sequence set forth in SEQ ID NO:123), a gene encoding a polypeptide capable of glycosylating steviol or a steviol glycoside at its C-13 hydroxyl group (e.g., a polypeptide having the amino acid sequence set forth in SEQ ID NO:7); a gene encoding a polypeptide capable of beta 1,3 glycosylation of the C3' of the 13-O-glucose, 19-O-glucose, or both 13-O-glucose and 19-O-glucose of a steviol glycoside (e.g., a polypeptide having the amino acid sequence set forth in SEQ ID NO:9); a gene encoding a polypeptide capable of glycosylating steviol or a steviol glycoside at its C-19 carboxyl group (e.g., a polypeptide having the amino acid sequence set forth in SEQ ID NO:4); and/or a gene encoding a polypeptide capable of beta 1,2 glycosylation of the C2' of the 13-O-glucose, 19-O-glucose, or both 13-O-glucose and 19-O-glucose of a steviol glycoside (e.g., a polypeptide having the amino acid sequence set forth in SEQ ID NO:11, SEQ ID NO:13, or SEQ ID NO:16). In certain such embodiments, the recombinant host cell further comprises a gene encoding a polypeptide capable of synthesizing GGPP from FPP and IPP (e.g., a polypeptide having the amino acid sequence set forth in SEQ ID NO:20); a gene encoding a polypeptide capable of synthesizing ent-copalyl diphosphate from GGPP (e.g., a polypeptide having the amino acid sequence set forth in SEQ ID NO:40); a gene encoding a polypeptide capable of synthesizing ent-kaurene from ent-copalyl diphosphate (e.g., a polypeptide having the amino acid sequence set forth in SEQ ID NO:52); a gene encoding a polypeptide capable of synthesizing ent-kaurenoic acid, ent-kaurenol, and/or ent-kaurenal from ent-kaurene (e.g., a polypeptide having the amino acid sequence set forth in SEQ ID NO:60 or SEQ ID NO:117); a gene encoding a polypeptide capable of reducing cytochrome P450 complex (e.g., a polypeptide having the amino acid sequence set forth in SEQ ID NO:78, SEQ ID NO:86, or SEQ ID NO:92); and/or a gene encoding a polypeptide capable of synthesizing steviol from ent-kaurenoic acid (e.g., a polypeptide having the amino acid sequence set forth in SEQ ID NO:94).

In some embodiments, a steviol glycoside or steviol glycoside precursor is produced by whole cell bioconversion. For whole cell bioconversion to occur, a host cell expressing one or more enzymes involved in the steviol glycoside pathway takes up and modifies a steviol glycoside precursor in the cell; following modification in vivo, a steviol glycoside remains in the cell and/or is excreted into the culture medium. For example, a host cell expressing a gene encoding a polypeptide capable of synthesizing UTP from UDP, a gene encoding a polypeptide capable of converting glucose-6-phosphate to glucose-1-phosphate, and/or a gene encoding a polypeptide capable of synthesizing UDP-glucose from UTP and glucose-1-phosphate; and further expressing a gene encoding a polypeptide capable of glycosylating steviol or a steviol glycoside at its C-13 hydroxyl group; a gene encoding a polypeptide capable of beta 1,3 glycosylation of the C3' of the 13-O-glucose, 19-O-glucose, or both 13-O-glucose and 19-O-glucose of a steviol glycoside; a gene encoding a polypeptide capable of glycosylating steviol or a steviol glycoside at its C-19 carboxyl group; and/or a gene encoding a polypeptide capable of beta 1,2 glycosylation of the C2' of the 13-O-glucose, 19-O-glucose, or both 13-O-glucose and 19-O-glucose of a steviol glycoside can take up steviol and glycosylate steviol in the cell; following glycosylation in vivo, a steviol glycoside can be excreted into the culture medium. In certain such embodiments, the host cell may further express a gene encoding a polypeptide capable of synthesizing GGPP from FPP and IPP; a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; a gene encoding a polypeptide capable of synthesizing steviol from ent-kaurenoic acid; and/or a gene encoding a bifunctional polypeptide capable of synthesizing ent-copalyl diphosphate from GGPP and synthesizing ent-kaurene from ent-copalyl diphosphate.

In some embodiments, the method for producing one or more steviol glycosides or a steviol glycoside composition disclosed herein comprises whole-cell bioconversion of plant-derived or synthetic steviol and/or steviol glycosides in a cell culture medium of a recombinant host cell using: (a) a polypeptide capable of synthesizing UTP from UDP; (b) a polypeptide capable of converting glucose-6-phosphate to glucose-1-phosphate; and/or (c) a polypeptide capable of synthesizing UDP-glucose from UTP and glucose-1-phosphate, and one or more of: (d) a polypeptide capable of glycosylating steviol or a steviol glycoside at its C-13 hydroxyl group thereof; (e) a polypeptide capable of beta 1,3 glycosylation of the C3' of the 13-O-glucose, 19-O-glucose, or both 13-O-glucose and 19-O-glucose of a steviol glycoside; (f) a polypeptide capable of glycosylating steviol or a steviol glycoside at its C-19 carboxyl group thereof; and/or (g) a polypeptide capable of beta 1,2 glycosylation of the C2' of the 13-O-glucose, 19-O-glucose, or both 13-O-glucose and 19-O-glucose of a steviol glycoside; wherein at least one of the polypeptides is a recombinant polypeptide expressed in the recombinant host cell; and producing the one or more steviol glycosides or the steviol glycoside composition thereby.

In some embodiments of the methods for producing one or more steviol glycosides or a steviol glycoside composition disclosed herein comprises whole-cell bioconversion of plant-derived or synthetic steviol and/or steviol glycosides in a cell culture medium of a recombinant host cell disclosed herein, the polypeptide capable of synthesizing UTP from UDP comprises a polypeptide having at least 60% sequence identity to the amino acid sequence set forth in SEQ ID NO:123; the polypeptide capable of converting glucose-6-phosphate to glucose-1-phosphate comprises a polypeptide having at least 60% sequence identity to the amino acid sequence set forth in SEQ ID NO:2, SEQ ID NO:119, or SEQ ID NO:143; or at least 55% sequence identity to the amino acid sequence set forth in SEQ ID NO:141, SEQ ID NO:145, or SEQ ID NO:147; and/or the polypeptide capable of synthesizing UDP-glucose from UTP and glucose-1-phosphate comprises a polypeptide having at least 60% sequence identity to the amino acid sequence set forth in SEQ ID NO:121, SEQ ID NO:127; at least 55% sequence identity to the amino acid sequence set forth in SEQ ID NO:125, SEQ ID NO:129, SEQ ID NO:133, SEQ ID NO:135, SEQ ID NO:137, or SEQ ID NO:139; or at least 70% sequence identity to the amino acid sequence set forth in SEQ ID NO:131.

In some embodiments, a polypeptide capable of synthesizing UTP from UDP, a polypeptide capable of converting glucose-6-phosphate to glucose-1-phosphate, and/or a polypeptide capable of synthesizing UDP-glucose from UTP and glucose-1-phosphate can be displayed on the surface of the recombinant host cells disclosed herein by fusing it with the anchoring motifs.

In some embodiments, the cell is permeabilized to take up a substrate to be modified or to excrete a modified product. In some embodiments, a permeabilizing agent can be added to aid the feedstock entering into the host and product getting out. In some embodiments, the cells are permeabilized with a solvent such as toluene, or with a detergent such as Triton-X or Tween. In some embodiments, the cells are permeabilized with a surfactant, for example a cationic surfactant such as cetyltrimethylammonium bromide (CTAB). In some embodiments, the cells are permeabilized with periodic mechanical shock such as electroporation or a slight osmotic shock. For example, a crude lysate of the cultured microorganism can be centrifuged to obtain a supernatant. The resulting supernatant can then be applied to a chromatography column, e.g., a C18 column, and washed with water to remove hydrophilic compounds, followed by elution of the compound(s) of interest with a solvent such as methanol. The compound(s) can then be further purified by preparative HPLC. See also, WO 2009/140394.

In some embodiments, steviol, one or more steviol glycoside precursors, and/or one or more steviol glycosides are produced by co-culturing of two or more hosts. In some embodiments, one or more hosts, each expressing one or more enzymes involved in the steviol glycoside pathway, produce steviol, one or more steviol glycoside precursors, and/or one or more steviol glycosides. For example, a host expressing a gene encoding a polypeptide capable of synthesizing GGPP from FPP and IPP; a gene encoding a polypeptide capable of synthesizing ent-copalyl diphosphate from GGPP; a gene encoding a polypeptide capable of synthesizing ent-kaurene from ent-copalyl diphosphate; a gene encoding a polypeptide capable of synthesizing ent-kaurenoic acid, ent-kaurenol, and/or ent-kaurenal from ent-kaurene; a gene encoding a polypeptide capable of reducing cytochrome P450 complex; a gene encoding a polypeptide capable of synthesizing steviol from ent-kaurenoic acid; and/or a gene encoding a bifunctional polypeptide capable of synthesizing ent-copalyl diphosphate from GGPP and synthesizing ent-kaurene from ent-copalyl diphosphate and a host expressing a gene encoding a polypeptide capable of synthesizing UTP from UDP, a gene encoding a polypeptide capable of converting glucose-6-phosphate to glucose-1- phosphate, and/or a gene encoding a polypeptide capable of synthesizing UDP-glucose from UTP and glucose-1-phosphate; and further expressing a gene encoding a polypeptide capable of glycosylating steviol or a steviol glycoside at its C-13 hydroxyl group; a gene encoding a polypeptide capable of beta 1,3 glycosylation of the C3' of the 13-O-glucose, 19-O-glucose, or both 13-O-glucose and 19-O-glucose of a steviol glycoside; a gene encoding a polypeptide capable of glycosylating steviol or a steviol glycoside at its C-19 carboxyl group; and/or a gene encoding a polypeptide capable of beta 1,2 glycosylation of the C2' of the 13-O-glucose, 19-O-glucose, or both 13-O-glucose and 19-O-glucose of a steviol glycoside, produce one or more steviol glycosides.

In some embodiments, the steviol glycoside comprises, for example, but not limited to, 13-SMG, steviol-1,2-bioside, steviol-1,3-bioside, 19-SMG, 1,2-stevioside, 1,3-stevioside (RebG), rubusoside, RebA, RebB, RebC, RebD, RebE, RebF, RebM, RebQ, RebI, dulcoside A, di-glycosylated steviol, tri-glycosylated steviol, tetra-glycosylated steviol, penta-glycosylated steviol, hexa-glycosylated steviol, hepta-glycosylated steviol, or isomers thereof.

In some embodiments, a steviol glycoside or steviol glycoside precursor composition produced in vivo, in vitro, or by whole cell bioconversion does not comprise or comprises a reduced amount or reduced level of plant-derived components than a *Stevia* extract from, inter alia, a *Stevia* plant. Plant-derived components can contribute to off-flavors and include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α- and β-amyrin, lupeol, β-amryin acetate, pentacyclic triterpenes, centauredin, quercitin, epi-alpha-cadinol, carophyllenes and derivatives, beta-pinene, beta-sitosterol, and gibberellin. In some embodiments, the plant-derived components referred to herein are non-glycoside compounds.

As used herein, the terms "detectable amount," "detectable concentration," "measurable amount," and "measurable concentration" refer to a level of steviol glycosides measured in AUC, $\mu M/OD_{600}$, mg/L, μM, or mM. Steviol glycoside production (i.e., total, supernatant, and/or intracellular steviol glycoside levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vis), mass spectrometry (MS), and nuclear magnetic resonance spectroscopy (NMR).

As used herein, the term "undetectable concentration" refers to a level of a compound that is too low to be measured and/or analyzed by techniques such as TLC, HPLC, UV-Vis, MS, or NMR. In some embodiments, a compound of an "undetectable concentration" is not present in a steviol glycoside or steviol glycoside precursor composition.

After the recombinant microorganism has been grown in culture for the period of time, wherein the temperature and period of time facilitate the production of a steviol glycoside, steviol and/or one or more steviol glycosides can then be recovered from the culture using various techniques known in the art. Steviol glycosides can be isolated using a method described herein. For example, following fermentation, a culture broth can be centrifuged for 30 min at 7000 rpm at 4° C. to remove cells, or cells can be removed by filtration. The cell-free lysate can be obtained, for example, by mechanical disruption or enzymatic disruption of the host cells and additional centrifugation to remove cell debris. Mechanical disruption of the dried broth materials can also be performed, such as by sonication. The dissolved or suspended broth materials can be filtered using a micron or sub-micron prior to further purification, such as by preparative chromatography. The fermentation media or cell-free lysate can optionally be treated to remove low molecular weight compounds such as salt; and can optionally be dried prior to purification and re-dissolved in a mixture of water and solvent.

The supernatant or cell-free lysate can be purified as follows: a column can be filled with, for example, HP20 Diaion resin (aromatic type Synthetic Adsorbent; Supelco) or other suitable non-polar adsorbent or reversed-phase chromatography resin, and an aliquot of supernatant or cell-free lysate can be loaded on to the column and washed with water to remove the hydrophilic components. The steviol glycoside product can be eluted by stepwise incremental increases in the solvent concentration in water or a gradient from, e. g., 0%→100% methanol). The levels of steviol glycosides, glycosylated ent-kaurenol, and/or glycosylated ent-kaurenoic acid in each fraction, including the flow-through, can then be analyzed by LC-MS. Fractions can then be combined and reduced in volume using a vacuum evaporator. Additional purification steps can be utilized, if desired, such as additional chromatography steps and crystallization. For example, steviol glycosides can be isolated by methods not limited to ion exchange chromatography, reversed-phase chromatography (i.e., using a C18 column), extraction, crystallization, and carbon columns and/or decoloring steps.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of steviol glycosides and/or steviol glycoside precursors. In some embodiments, "and/or" is used to refer to production of steviol glycosides, wherein one or more steviol glycosides are produced. In some embodiments, "and/or" is used to refer to production of steviol glycosides, wherein one or more steviol glycosides are produced through one or more of the following steps: culturing a recombinant microorganism, synthesizing one or more steviol glycosides in a recombinant microorganism, and/or isolating one or more steviol glycosides.

Functional Homologs

Functional homologs of the polypeptides described above are also suitable for use in producing steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol glycoside biosynthesis polypeptides. Sequence analysis can involve BLAST, Reciprocal BLAST, or PSI-BLAST analysis of non-redundant databases using a UGT amino acid sequence as the reference sequence. Amino acid sequence is, in some instances, deduced from the nucleotide sequence. Those polypeptides in the database that have greater than 40% sequence identity are candidates for further evaluation for suitability as a steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol glycoside biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. The information included at the Pfam database is described in Sonnhammer et al., *Nucl. Acids Res.,* 26:320-322 (1998); Sonnhammer et al., Proteins, 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol in a recombinant host include functional homologs of UGTs.

Methods to modify the substrate specificity of, for example, a UGT, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, *Phytochemistry* 70: 325-347.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program Clustal Omega (version 1.2.1, default parameters), which allows alignments of nucleic acid or polypeptide sequences to be carried out across their entire length (global alignment). Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: % age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine a % identity of a candidate nucleic acid or amino acid sequence to a reference sequence, the sequences are aligned using Clustal Omega, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional UGT proteins (e.g., a polypeptide capable of glycosylating steviol or a steviol glycoside at its C-19 carboxyl group) can include additional amino acids that are not involved in the enzymatic activities carried out by the enzymes. In some embodiments, UGT proteins are fusion proteins. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins. In some embodiments, a nucleic acid sequence encoding a UGT polypeptide (e.g., a polypeptide capable of glycosylating steviol or a steviol glycoside at its C-19 carboxyl group) can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), and Flag™ tag (Kodak, New Haven, Conn.). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a UGT polypeptide (e.g., a polypeptide capable of glycosylating steviol or a steviol glycoside at its C-19 carboxyl group) is altered by domain swapping.

In some embodiments, a fusion protein is a protein altered by circular permutation, which consists in the covalent attachment of the ends of a protein that would be opened elsewhere afterwards. Thus, the order of the sequence is altered without causing changes in the amino acids of the protein. In some embodiments, a targeted circular permutation can be produced, for example but not limited to, by designing a spacer to join the ends of the original protein. Once the spacer has been defined, there are several possibilities to generate permutations through generally accepted molecular biology techniques, for example but not limited to, by producing concatemers by means of PCR and subsequent amplification of specific permutations inside the concatemer or by amplifying discrete fragments of the protein to exchange to join them in a different order. The step of generating permutations can be followed by creating a circular gene by binding the fragment ends and cutting back at random, thus forming collections of permutations from a unique construct. In some embodiments, DAP1 polypeptide is altered by circular permutation.

Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a yeast strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites or phosphatases as discussed herein. In such cases, a nucleic acid that overexpresses the polypeptide or gene product may be included in a recombinant construct that is transformed into the strain. Alternatively, mutagenesis can be used to generate mutants in genes for which it is desired to increase or enhance function.

Host Microorganisms

Recombinant hosts can be used to express polypeptides for the producing steviol glycosides, including mammalian, insect, plant, and algal cells. A number of prokaryotes and eukaryotes are also suitable for use in constructing the recombinant microorganisms described herein, e.g., gram-negative bacteria, yeast, and fungi. A species and strain selected for use as a steviol glycoside production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a temperature(s) for a period of time, wherein the temperature and period of time facilitate the production of a steviol glycoside. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, GGPP, ent-kaurene and ent-kaurenoic acid, can be determined by extracting samples from culture media for analysis according to published methods.

Carbon sources of use in the instant method include any molecule that can be metabolized by the recombinant host cell to facilitate growth and/or production of the steviol glycosides. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

It will be appreciated that the various genes and modules discussed herein can be present in two or more recombinant hosts rather than a single host. When a plurality of recombinant hosts is used, they can be grown in a mixed culture to accumulate steviol and/or steviol glycosides.

Alternatively, the two or more hosts each can be grown in a separate culture medium and the product of the first culture medium, e.g., steviol, can be introduced into second culture medium to be converted into a subsequent intermediate, or into an end product such as, for example, RebA. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* or *Yarrowia*. Exemplary species from such genera include *Lentinus tigrinus, Laetiporus sulphureus, Phanerochaete chrysosporium, Pichia pastoris, Cyberlindnera jadinii, Physcomitrella patens, Rhodoturula glutinis, Rhodoturula mucilaginosa, Phaffia rhodozyma, Xanthophyllomyces dendrorhous, Fusarium fujikuroi/Gibberella fujikuroi, Candida utilis, Candida glabrata, Candida albicans*, and *Yarrowia lipolytica.*

In some embodiments, a microorganism can be a prokaryote such as *Escherichia* bacteria cells, for example, *Escherichia coli* cells; *Lactobacillus* bacteria cells; *Lactococcus* bacteria cells; *Comebacterium* bacteria cells; *Acetobacter* bacteria cells; *Acinetobacter* bacteria cells; or *Pseudomonas* bacterial cells.

In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii*, or *S. cerevisiae.*

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be a cyanobacterial cell such as *Blakeslea trispora, Dunaliella salina,*

*Haematococcus pluvialis, Chlorella* sp., *Undaria pinnatifida, Sargassum, Laminaria japonica, Scenedesmus almeriensis.*

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms.

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for producing steviol glycosides.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella*, and *Phanerochaete* spp.

*Agaricus, Gibberella*, and *Phanerochaete* spp. can be useful because they are known to produce large amounts of isoprenoids in culture. Thus, the terpene precursors for producing large amounts of steviol glycosides are already produced by endogenous genes. Thus, modules comprising recombinant genes for steviol glycoside biosynthesis polypeptides can be introduced into species from such genera without the necessity of introducing mevalonate or MEP pathway genes.

*Arxula adeninivorans* (*Blastobotrys adeninivorans*)

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g., alkanes, fatty acids, oils) and can grow on sugars. It has a high potential for industrial applications and is an oleaginous microorgamism. *Yarrowia lipolyptica* can accumulate lipid content to approximately 40% of its dry cell weight and is a model organism for lipid accumulation and remobilization. See e.g., Nicaud, 2012, Yeast 29(10):409-18; Beopoulos et al., 2009, *Biochimie* 91(6):692-6; Bankar et al., 2009, *Appl Microbiol Biotechnol.* 84(5):847-65.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Rhodosporidium toruloides*

*Rhodosporidium toruloides* is oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

*Hansenula polymorpha* (*Pichia angusta*)

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

*Pichia pastoris*

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

*Physcomitrella* spp.

*Physcomitrella mosses*, when grown in suspension culture, have characteristics similar to yeast or other fungal cultures. This genera can be used for producing plant secondary metabolites, which can be difficult to produce in other types of cells.

It can be appreciated that the recombinant host cell disclosed herein can comprise a plant cell, comprising a plant cell that is grown in a plant, a mammalian cell, an insect cell, a fungal cell, comprising a yeast cell, wherein the yeast cell is a cell from *Saccharomyces cerevisiae, Schizosaccharomyces pombe, Yarrowia lipolytica, Candida*

*glabrata*, *Ashbya gossypii*, *Cyberlindnera jadinii*, *Pichia pastoris*, *Kluyveromyces lactis*, *Hansenula polymorpha*, *Candida boidinii*, *Arxula adeninivorans*, *Xanthophyllomyces dendrorhous*, or *Candida albicans* species or is a Saccharomycete or is a *Saccharomyces cerevisiae* cell, an algal cell or a bacterial cell, comprising *Escherichia* cells, *Lactobacillus* cells, *Lactococcus* cells, *Cornebacterium* cells, *Acetobacter* cells, *Acinetobacter* cells, or *Pseudomonas* cells.

Steviol Glycoside Compositions

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., RebD or RebM) and have a consistent taste profile. As used herein, the term "enriched" is used to describe a steviol glycoside composition with an increased proportion of a particular steviol glycoside, compared to a steviol glycoside composition (extract) from a *stevia* plant. Thus, the recombinant hosts described herein can facilitate the production of compositions that are tailored to meet the sweetening profile desired for a given food product and that have a proportion of each steviol glycoside that is consistent from batch to batch. In some embodiments, hosts described herein do not produce or produce a reduced amount of undesired plant by-products found in *Stevia* extracts. Thus, steviol glycoside compositions produced by the recombinant hosts described herein are distinguishable from compositions derived from *Stevia* plants.

The amount of an individual steviol glycoside (e.g., RebA, RebB, RebD, or RebM) accumulated can be from about 1 to about 7,000 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L, at least about 1,000 mg/L, at least about 1,200 mg/L, at least about at least 1,400 mg/L, at least about 1,600 mg/L, at least about 1,800 mg/L, at least about 2,800 mg/L, or at least about 7,000 mg/L. In some aspects, the amount of an individual steviol glycoside can exceed 7,000 mg/L. The amount of a combination of steviol glycosides (e.g., RebA, RebB, RebD, or RebM) accumulated can be from about 1 mg/L to about 7,000 mg/L, e.g., about 200 to about 1,500, at least about 2,000 mg/L, at least about 3,000 mg/L, at least about 4,000 mg/L, at least about 5,000 mg/L, at least about 6,000 mg/L, or at least about 7,000 mg/L. In some aspects, the amount of a combination of steviol glycosides can exceed 7,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing a steviol glycoside precursor, while a second microorganism comprises steviol glycoside biosynthesis genes. The product produced by the second, or final microorganism is then recovered. It will also be appreciated that in some embodiments, a recombinant microorganism is grown using nutrient sources other than a culture medium and utilizing a system other than a fermenter.

Alternatively, the two or more microorganisms each can be grown in a separate culture medium and the product of the first culture medium, e.g., steviol, can be introduced into second culture medium to be converted into a subsequent intermediate, or into an end product such as RebA. The product produced by the second, or final microorganism is then recovered. It will also be appreciated that in some embodiments, a recombinant microorganism is grown using nutrient sources other than a culture medium and utilizing a system other than a fermenter.

Steviol glycosides and compositions obtained by the methods disclosed herein can be used to make food products, dietary supplements and sweetener compositions. See, e.g., WO 2011/153378, WO 2013/022989, WO 2014/122227, and WO 2014/122328.

For example, substantially pure steviol or steviol glycoside such as RebM or RebD can be included in food products such as ice cream, carbonated 2s, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately, each producing a specific steviol or steviol glycoside, recovering the steviol or steviol glycoside in substantially pure form from each microorganism and then combining the compounds to obtain a mixture comprising each compound in the desired proportion. The recombinant microorganisms described herein permit more precise and consistent mixtures to be obtained compared to current *Stevia* products.

In another alternative, a substantially pure steviol or steviol glycoside can be incorporated into a food product along with other sweeteners, e.g., saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. 2007/0128311. In some embodiments, the steviol or steviol glycoside may be provided with a flavor (e.g., citrus) as a flavor modulator.

Compositions produced by a recombinant microorganism described herein can be incorporated into food products. For example, a steviol glycoside composition produced by a recombinant microorganism can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism can be incorporated into a baked good (e.g., a biscuit) such that the food product has a maximum of 300 mg steviol glycoside/kg food on a dry weight basis. A steviol glycoside composition produced by a recombinant microorganism can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism can be incorporated into bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis. In some embodiments, a steviol glycoside composition produced herein is a component of a pharmaceutical composition. See, e.g., Steviol Glycosides Chemical and Technical Assessment 69th JECFA, 2007, prepared by Harriet Wallin, Food Agric. Org.; EFSA Panel on Food Additives and Nutrient Sources added to Food (ANS), "Scientific Opinion on the safety of steviol glycosides for the proposed uses as a food additive," 2010, *EFSA Journal* 8(4):1537; U.S. Food and Drug Administration GRAS Notice 323; U.S Food and Drug Administration GRAS Notice 329; WO 2011/037959; WO 2010/146463; WO 2011/046423; and WO 2011/056834.

For example, such a steviol glycoside composition can have from 90-99 weight % RebA and an undetectable amount of *stevia* plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a RebB-enriched composition having greater than 3 weight % RebB and be incorporated into the food product such that the amount of RebB in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebB-enriched composition has an undetectable amount of *stevia* plant-derived contaminants.

Such a steviol glycoside composition can be a RebD-enriched composition having greater than 3 weight % RebD and be incorporated into the food product such that the amount of RebD in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebD-enriched composition has an undetectable amount of *stevia* plant-derived contaminants.

Such a steviol glycoside composition can be a RebE-enriched composition having greater than 3 weight % RebE and be incorporated into the food product such that the amount of RebE in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebE-enriched composition has an undetectable amount of *stevia* plant-derived contaminants.

Such a steviol glycoside composition can be a RebM-enriched composition having greater than 3 weight % RebM and be incorporated into the food product such that the amount of RebM in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebM-enriched composition has an undetectable amount of *stevia* plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for RebA, RebB, RebD, RebE, or RebM, can be package in a sachet, for example, at from 10,000 to 30,000 mg steviol glycoside/kg product on a dry weight basis, for tabletop use. In some embodiments, a steviol glycoside produced in vitro, in vivo, or by whole cell bioconversion The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1: Strain Engineering

Steviol glycoside-producing *S. cerevisiae* strains were constructed as described in WO 2011/153378, WO 2013/022989, WO 2014/122227, and WO 2014/122328, each of which is incorporated by reference in its entirety. For example, yeast strains comprising and expressing a native gene encoding a YNK1 polypeptide (SEQ ID NO:122, SEQ ID NO:123), a native gene encoding a PGM1 polypeptide (SEQ ID NO:1, SEQ ID NO:2), a native gene encoding a PGM2 polypeptide (SEQ ID NO:118, SEQ ID NO:119), a native gene encoding a UGP1 polypeptide (SEQ ID NO:120, SEQ ID NO:121), a recombinant gene encoding a GGPPS polypeptide (SEQ ID NO:19, SEQ ID NO:20), a recombinant gene encoding a truncated CDPS polypeptide (SEQ ID NO:39, SEQ ID NO:40), a recombinant gene encoding a KS polypeptide (SEQ ID NO:51, SEQ ID NO:52), a recombinant gene encoding a KO polypeptide (SEQ ID NO:59, SEQ ID NO:60), a recombinant gene encoding a KO polypeptide (SEQ ID NO:63, SEQ ID NO:64), a recombinant gene encoding an ATR2 polypeptide (SEQ ID NO:91, SEQ ID NO:92), a recombinant gene encoding a KAHe1 polypeptide (SEQ ID NO:93, SEQ ID NO:94), a recombinant gene encoding a CPR8 polypeptide (SEQ ID NO:85, SEQ ID NO:86), a recombinant gene encoding a CPR1 polypeptide (SEQ ID NO:77, SEQ ID NO:78), a recombinant gene encoding a UGT76G1 polypeptide (SEQ ID NO:8, SEQ ID NO:9), a recombinant gene encoding a UGT85C2 polypeptide (SEQ ID NO:5/SEQ ID NO:6, SEQ ID NO:7), a recombinant gene encoding a UGT74G1 polypeptide (SEQ ID NO:3, SEQ ID NO:4), a recombinant gene encoding a UGT91d2e-b polypeptide (SEQ ID NO:12, SEQ ID NO:13) and a recombinant gene encoding an EUGT11 polypeptide (SEQ ID NO:14, SEQ ID NO:15, SEQ ID NO:16) were engineered to accumulate steviol glycosides.

Example 2: Overexpression of PGM1, PGM2, UGP1, and YNK1

A steviol glycoside-producing *S. cerevisiae* strain as described in Example 1, further engineered to comprise and express a recombinant gene encoding a KAH polypeptide (SEQ ID NO:96, SEQ ID NO:97) and a recombinant gene encoding a KO polypeptide (SEQ ID NO:117, SEQ ID NO:64), was transformed with vectors comprising an additional copy of the gene encoding a YNK1 polypeptide (SEQ ID NO:122, SEQ ID NO:123), operably linked to a pTEF1 promoter (SEQ ID NO:148) and a CYC1 terminator (SEQ ID NO:154), an additional copy of the gene encoding a PGM1 polypeptide (SEQ ID NO:1, SEQ ID NO:2), operably linked to a pTEF1 promoter (SEQ ID NO:148) and a CYC1 terminator (SEQ ID NO:154), an additional copy of the gene encoding a PGM2 polypeptide (SEQ ID NO:118, SEQ ID NO:119), operably linked to a pPGK1 promoter (SEQ ID NO:149) and a tADH1 terminator (SEQ ID NO:155), and an additional copy of the gene encoding a UGP1 polypeptide (SEQ ID NO:120, SEQ ID NO:121), operably linked to a pPGK1 promoter (SEQ ID NO:149) and a tADH1 terminator (SEQ ID NO:155).

Fed-batch fermentation with cultures of the transformed *S. cerevisiae* strain and a control *S. cerevisiae* strain (a steviol glycoside-producing *S. cerevisiae* strain as described in Example 2, further engineered to comprise and express a recombinant gene encoding a KAH polypeptide and a recombinant gene encoding a KO polypeptide) was carried out aerobically in 2 L fermenters at 30° C. with an approximate 16 h growth phase in minimal medium comprising glucose, ammonium sulfate, trace metals, vitamins, salts, and buffer followed by an approximate 100 h feeding phase with a glucose-comprising defined feed medium. A pH near 6.0 and glucose-limiting conditions were maintained. Extractions of whole culture samples (without cell removal) were performed and extracts were analyzed by LC-UV to determine levels of steviol glycosides.

LC-UV was conducted with an Agilent 1290 instrument comprising a variable wavelength detector (VWD), a thermostatted column compartment (TCC), an autosampler, an autosampler cooling unit, and a binary pump, using SB-C18 rapid resolution high definition (RRHD) 2.1 mm×300 mm, 1.8 μm analytical columns (two 150 mm columns in series; column temperature of 65° C.). Steviol glycosides were separated by a reversed-phase C18 column followed by detection by UV absorbance at 210 mm. Quantification of steviol glycosides was done by comparing the peak area of each analyte to standards of RebA and applying a correction factor for species with differing molar absorptivities. For LC-UV, 0.5 mL cultures were spun down, the supernatant was removed, and the wet weight of the pellets was calculated. The LC-UV results were normalized by pellet wet weight. Total steviol glycoside values of the fed-batch fermentation were calculated based upon the measured levels of steviol glycosides calculated as a sum (in g/L RebD equivalents) of measured RebA, RebB, RebD, RebE, RebM, 13-SMG, rubusoside, steviol-1,2-bioside, di-glycosylated steviol, tri-glycosylated steviol, tetra-glycosylated steviol, penta-glycosylated steviol, hexa-glycosylated steviol, and hepta-glycosylated steviol. Results are shown in Table 1.

TABLE 1

Steviol Glycoside accumulation by transformed *S. cerevisiae* strain and *S. cerevisiae* control strain.

| | Transformed Strain | | Control Strain | |
|---|---|---|---|---|
| | Accumulation (g/L RebD Equiv.) | Std. Error (g/L RebD Equiv.) | Accumulation (g/L RebD Equiv.) | Std. Error (g/L RebD Equiv.) |
| 13-SMG | 2.40 | 0.14 | 4.2 | 0.02 |
| RebA | 0.59 | 0.007 | 0.45 | 0.07 |
| RebD | 1.21 | 0.16 | 2.16 | 0.12 |
| RebM | 6.31 | 0.22 | 3.22 | 0.06 |
| Total SG | 11.90 | 0.33 | 11.76 | 0.34 |

A decrease in 13-SMG and RebD accumulation, and an increase in RebA and RebM accumulation were observed for the *S. cerevisiae* strain overexpressing UGP1, YNK1, PGM1, and PGM2, relative to the control strain. Furthermore, RebD+RebM accumulation levels increased upon overexpression of UGP1, YNK1, PGM1, and PGM2, while the total steviol glycosides produced by the experimental strain increased negligibly. In addition, RebD/RebM ratios of 0.2 and below were observed for the *S. cerevisiae* strain overexpressing UGP1, YNK1, PGM1, and PGM2, relative to the control strain.

Example 3: UGP1, PGM2 Activity Assay

Fed-batch fermentation with cultures of a *S. cerevisiae* strain overexpressing PGM1, PGM2, UGP1, and YNK1, as described in Example 2, and a control *S. cerevisiae* strain (a steviol glycoside-producing *S. cerevisiae* strain as described in Example 1) was carried out aerobically in 2 L fermenters at 30° C. with an approximate 16 h growth phase in minimal medium comprising glucose, ammonium sulfate, trace metals, vitamins, salts, and buffer followed by an approximate 100 h feeding phase with a glucose-comprising defined feed medium. A pH near 6.0 and glucose-limiting conditions were maintained. Whole culture samples (without cell removal) were analyzed to determine the activity levels of PGM and UGP.

For both assays, frozen fermentation cell pellets were resuspended in CelLytic™ Y Cell Lysis Reagent (Sigma) to an $OD_{600}$ of 44. Samples were shaken 30 min at 25° C. and then centrifuged at 13,000 rpm for 10 min. The supernatant was recovered and stored on ice.

The PGM enzyme assay relies on a coupled activity assay wherein supplied glucose-1-phosphate is first converted to glucose-6-phosphate by a PGM polypeptide/PGM polypeptide containing cell lysate, followed by glucose-6-phosphate conversion by a glucose-6-phosphate dehydrogenase (added to the assay as a purified enzyme in excess) to phosphogluconolactone under β-$NADP^+$ consumption. The kinetics of the concomitant β-NAPDH released are recorded by monitoring the absorbance at 340 nm.

180 mM glycylglycine, pH 7.4 (adjusted with NaOH/HCl); 5.0 mM glucose-1-phosphate; 3.00 mM β-$NADP^+$; 0.4 mM G1,6-bisphosphate; 30 mM $MgCl_2$, 43 mM L-cysteine; 0.65 U/ml G6P-DH, and previously stored cell lysate were mixed together at 30° C. at different cell-lysate/buffer concentrations (0.5% (v/v), 1% (v/v), 2% (v/v), and 3% (v/v)). The kinetics for the release of β-NAPDH were followed over a maximum of 1000 sec. for each concentration of supernatant added. PGM activity for each cell-lysate/buffer concentration was defined by the maximum slope of the curve of $OD_{340}$ versus time. Cell-lysate/buffer concentration corrected PGM activity was defined as the slope of the curve of OD340/sec as a function of Cell-lysate/buffer concentrations. The value obtained in this way for a certain strain can be compared to the values from other strains and differences in PGM activity can be pointed out. The increase in activity of the cell-lysate of the *S. cerevisiae* strain overexpressing PGM1, PGM2, UGP1, and YNK1 is shown in Table 3, below, relative to that of the control strain.

The UGP assay relies on a coupled activity assay of the yeast UDP-glucose pyrophosphorylase wherein supplied glucose-1-phosphate is first converted to UDP-glucose by a UGP polypeptide/UGP polypeptide-containing cell-lysate under UTP consumption, followed by UDP-glucose conversion to UDP-Glucuronate and β-NADH by UDP-glucose dehydrogenase (added to the assay as a purified enzyme in excess) under β-$NAD^+$ consumption. The kinetics for the release of β-NADH are followed by monitoring the change in absorbance at 340 nm. Alternative UGP assays using, for example but not limited to, hydrophilic interaction liquid chromatography coupled with tandem mass spectrometry for the quantification of UDP-glucose (see Warth et al., Journal of Chromatography A, 1423, pp. 183-189 (2016)) may be used as well.

100 mM Tris/HCl, pH 8.5; 10 mM MgCl2; 100 mM NaCl; 5.0 mM β-$NAD^+$; 2 mM UTP; 2 mM ATP; 0.12 mg/ml UDPG-DH; 5 mM; and previously stored cell lysate were mixed together at 30° C. at different supernatant/buffer concentrations (0.5% (v/v), 1% (v/v), 1.5% (v/v), and 2% (v/v)). The kinetics for the release of β-NADH were followed over a maximum of 1000 sec. for each supernatant/buffer concentration. UGP activity for each cell-lysate/buffer concentration was defined by the maximum slope of the curve of $OD_{340}$ versus time. Cell-lysate/buffer concentration corrected UGP activity was defined as the slope of the curve of OD340/sec as a function of Cell-lysate/buffer concentrations. The value obtained in this way for a certain strain can be compared to the values from other strains and differences in UGP activity can be pointed out. The increase in activity of the lysate of the *S. cerevisiae* strain overexpressing PGM1, PGM2, UGP1, and YNK1 is shown in Table 2, below, relative to that of the control strain.

TABLE 2

Relative UGP and PGM activity

| | Transformed Strain | Control Strain |
|---|---|---|
| UGP Activity relative to control strain | 250% | 100% |
| PGM Activity relative to control stain | 160% | 100% |

Individual and total steviol glycoside values of the fed-batch fermentation were calculated according to Example 2. Results are shown in Table 3.

TABLE 3

Steviol Glycoside accumulation by transformed *S. cerevisiae* strain and *S. cerevisiae* control strain.

| | Transformed Strain Accumulation (g/L RebD Equiv.) | Control Strain Accumulation (g/L RebD Equiv.) |
|---|---|---|
| RebD | 2.19 | 1.21 |
| RebM | 5.71 | 5.12 |
| Total SG | 12.10 | 9.43 |

An increase in both UGP and PGM activity was observed for the *S. cerevisiae* strain overexpressing UGP1, YNK1, PGM1, and PGM2, relative to the control strain. As shown in Table 3, RebD and total steviol glycoside accumulation increased upon overexpression of UGP1, YNK1, PGM1, and PGM2. Without being bound to a particular theory, the results suggest that increasing UGP and PGM activity (i.e., by expressing genes encoding polypeptides involved in the UDP-glucose biosynthetic pathway) allows for conversion of partially glycosylated steviol glycosides to higher molecular weight steviol glycosides, including, e.g., RebD.

Example 4: LC-MS Analytical Procedures (UDP-Glucose Analysis)

LC-MS analyses were performed on a Thermo Scientific Accela UPLC (Ultra Performance Liquid Chromatography system; Thermo Scientific) with a Thermo Scientific PAL autosampler system (Thermo Scientific) SeQuant ZIC-cHILIC column (2.1 mm×150 mm, 3.0 μm analytical column, 100 Å pore size) coupled to a Thermo Scientific Exactive Orbitrap mass spectrometer with electrospray ionization (ESI) operated in negative ionization mode. Compound separation was achieved using a gradient of the two mobile phases: A (water with 0.1% ammonium acetate) and B (MeCN). Separation was achieved by using a gradient from time 0 min with 15% A holding until 0.5 min and increasing to 50% A at time 15.50 min, holding until time 17.50 min, and reducing to 15% A at time 17.60 min, equilibrating at 15% A until 25.50 min. The flow rate was 0.3 mL/min, and the column was maintained at room temperature. UDP-glucose was monitored by full-scan analysis in the mass range 130-1400 m/z. EIC (Extracted ion chromatogram) of 565.04492-565.05058 corresponding to UDP-glucose was extracted and quantified by comparing against authentic standards. See Table 4 for m/z trace and retention time values of UDP-glucose.

TABLE 4

LC-MS Analytical Data for UDP-glucose

| Compound | MS Trace | RT (mins) |
|---|---|---|
| UDP-glucose | 565.04775 | 8.4 |

To determine the intracellular concentration of UDP-Glucose, full fermentation broth was sampled (via syringe) at desired time points during different stages of fermentation. Biomass (cells) was quickly separated by centrifugation and supernatant was removed. Cell pellets were quenched and extracted using a mixture of methanol, chloroform and an aqueous buffer solution. The final intracellular extracts were stored at −80° C. prior to LC-MS analysis.

Example 5: UDP-Glucose Accumulation Quantification

Fed-batch fermentation with cultures of a *S. cerevisiae* strain overexpressing PGM1, PGM2, UGP1, and YNK1, as described in Example 2, and a control *S. cerevisiae* strain (a *S. cerevisiae* strain comprising and expressing a native gene encoding a YNK1 polypeptide (SEQ ID NO:122, SEQ ID NO:123), a native gene encoding a PGM1 polypeptide (SEQ ID NO:1, SEQ ID NO:2), a native gene encoding a PGM2 polypeptide (SEQ ID NO:118, SEQ ID NO:119), a native gene encoding a UGP1 polypeptide (SEQ ID NO:120, SEQ ID NO:121), a recombinant gene encoding a GGPPS polypeptide (SEQ ID NO:19, SEQ ID NO:20), a recombinant gene encoding a truncated CDPS polypeptide (SEQ ID NO:39, SEQ ID NO:40), a recombinant gene encoding a KS polypeptide (SEQ ID NO:51, SEQ ID NO:52), a recombinant gene encoding a KO polypeptide (SEQ ID NO:59, SEQ ID NO:60), a recombinant gene encoding a KAHe1 polypeptide (SEQ ID NO:93, SEQ ID NO:94), a recombinant gene encoding a CPR8 polypeptide (SEQ ID NO:85, SEQ ID NO:86), a recombinant gene encoding a CPR1 polypeptide (SEQ ID NO:77, SEQ ID NO:78), a recombinant gene encoding an ATR2 polypeptide (SEQ ID NO:91, SEQ ID NO:92), a recombinant gene encoding a UGT85C2 polypeptide (SEQ ID NO:5/SEQ ID NO:6, SEQ ID NO:7), and a recombinant gene encoding a UGT74G1 polypeptide (SEQ ID NO:3, SEQ ID NO:4)) was carried out aerobically in 2 L fermenters at 30° C. with an approximate 16 h growth phase in minimal medium comprising glucose, ammonium sulfate, trace metals, vitamins, salts, and buffer followed by an approximate 100 h feeding phase with a glucose-comprising defined feed medium. A pH near 6.0 and glucose-limiting conditions were maintained. Whole culture samples (without cell removal) were analyzed by LC-UV to determine the levels of steviol glycosides, according to Example 2, and by LC-MS to analyze the intracellular level of UDP-glucose, according to Example 4. Results are shown in Tables 5-6.

TABLE 5

Steviol Glycoside accumulation by transformed *S. cerevisiae* strain and *S. cerevisiae* control strain.

| | Transformed Strain Accumulation (g/L RebD Equiv.) | Control Strain Accumulation (g/L RebD Equiv.) |
|---|---|---|
| RebD | 1.05 | 1.92 |
| RebM | 5.75 | 2.23 |
| Total SG | 10.18 | 7.40 |

TABLE 6

UDP-glucose accumulation by transformed *S. cerevisiae* strain and *S. cerevisiae* control strain.

| | Transformed Strain | | Control Strain | |
|---|---|---|---|---|
| Time (h) | UDP-glucose Accumulation (μM) | Std. Deviation (μM) | UDP-glucose Accumulation (μM) | Std. Deviation (μM) |
| 22 | 450.52 | 54.96 | 306.50 | 51.75 |
| 30 | 495.66 | 10.83 | 198.88 | 36.95 |
| 46 | 518.26 | 26.13 | 241.30 | 45.69 |
| 55 | 425.39 | 70.01 | 221.35 | 64.36 |
| 72 | 398.08 | 41.85 | 206.26 | 19.54 |
| 76 | 299.16 | 33.57 | 159.96 | 5.06 |
| 96 | 270.53 | 82.67 | 160.74 | 9.19 |
| 104 | 310.97 | 24.57 | 132.08 | 21.17 |
| 120 | 359.92 | 24.30 | 119.32 | 37.39 |

An increase in UDP-glucose accumulation, by up to 300%, was observed for the *S. cerevisiae* strain overexpressing UGP1, YNK1, PGM1, and PGM2, relative to the control strain. RebD+RebM accumulation levels increased upon overexpression of UGP1, YNK1, PGM1, and PGM2; this result further demonstrates a beneficial effect of expression of UDP-glucose biosynthetic pathway genes on the production of higher molecular weight steviol glycosides such as RebD or RebM.

One of skill in the art would appreciate a disctinction between improving the total amount of UDP-glucose as compared to the recycling of UDP-glucose. As shown in Table 6 above, taking the highest and lowest number over fermentation time, the worst decrease in parental strain is 2.5 while the worst decrease in UDP-glucose boosted strain (i.e., the *S. cerevisiae* strain overexpressing UGP1, YNK1, PGM1, and PGM2) is 1.9 times. This demonstrates that overexpressing UGP1, YNK1, PGM1, and PGM2 increases the UDP-glucose pool and UDP-glucose. In fact, the net increase (consumption/formation) is higher is the UDP-glucose boosted strain.

Without being bound to a particular theory, the results observed in Examples 2-5 suggest that increasing UDP-glucose levels (i.e., by expressing genes encoding polypeptides involved in the UDP-glucose biosynthetic pathway) allows for conversion of 13-SMG and other partially glycosylated steviol glycosides to higher molecular weight steviol glycosides, including, e.g., RebM. Furthermore, the difference between the magnitude of the increase in accumulation levels of, e.g., RebM and/or RebD and that of the increase in accumulation levels of the total steviol glycosides suggests that maintaining and/or increasing UDP-glucose levels allows for more efficient production of higher molecular weight steviol glycosides, including, e.g., RebM (i.e., by shifting the profile of produced steviol glycosides away from lower molecular weight steviol glycosides).

Example 6: Expression of Heterologous UGP1 and PGM2

A steviol glycoside-producing *S. cerevisiae* strain overexpressing UGP1, YNK1, PGM1, and PGM2, as described in Example 2, was transformed with vectors comprising a gene encoding a UGP1 polypeptide (SEQ ID NO:132, SEQ ID NO:133) operably linked to a pPDC1 promoter (SEQ ID NO:153) and a tCYC1 terminator (SEQ ID NO:154) and a gene encoding a PGM2 polypeptide (SEQ ID NO:144, SEQ ID NO:145), operably linked to a pTPI1 promoter (SEQ ID NO:152) and an tADH1 terminator (SEQ ID NO:155).

Fed-batch fermentation with cultures of the transformed *S. cerevisiae* strain and a control *S. cerevisiae* strain (a steviol glycoside-producing *S. cerevisiae* strain as described in Example 2, further engineered to comprise and express a recombinant gene encoding a KAH polypeptide and a recombinant gene encoding a KO polypeptide) was carried out aerobically in 2 L fermenters at 30° C. with an approximate 16 h growth phase in minimal medium comprising glucose, ammonium sulfate, trace metals, vitamins, salts, and buffer followed by an approximate 100 h feeding phase with a glucose-comprising defined feed medium. A pH near 6.0 and glucose-limiting conditions were maintained. Whole culture samples (without cell removal) were analyzed by LC-UV to determine levels of steviol glycosides, as described in Example 2. Results are shown in Table 7.

TABLE 7

Steviol Glycoside accumulation by transformed *S. cerevisiae* strain and *S. cerevisiae* control strain.

| | Transformed Strain Accumulation (g/L RebD Equiv.) | Control Strain Accumulation (g/L RebD Equiv.) |
|---|---|---|
| RebD | 2.27 | 1.80 |
| RebM | 5.33 | 4.50 |
| Total SG | 14.27 | 12.39 |

An increase in RebD and RebM accumulation were observed for the *S. cerevisiae* strain expressing PGM2 and UGP1, relative to the control strain. Furthermore, total steviol glycosides produced by the experimental strain also increased. Without being bound to a particular theory, the results observed in Table 7 suggest that increasing UDP-glucose levels (i.e., by expressing genes encoding polypeptides involved in the UDP-glucose biosynthetic pathway) allows for conversion of 13-SMG and other partially glycosylated steviol glycosides to higher molecular weight steviol glycosides, including, e.g., RebM.

Example 7: LC-MS Analytical Procedures (Steviol Glycoside Analysis)

LC-MS analyses were performed on a Waters ACQUITY UPLC (Ultra Performance Liquid Chromatography system; Waters Corporation) with a Waters ACQUITY UPLC (Ultra Performance Liquid Chromatography system; Waters Corporation) BEH C18 column (2.1×50 mm, 1.7 μm particles, 130 Å pore size) equipped with a pre-column (2.1×5 mm, 1.7 μm particles, 130 Å pore size) coupled to a Waters ACQUITY TQD triple quadropole mass spectrometer with electrospray ionization (ESI) operated in negative ionization mode. Compound separation was achieved using a gradient of the two mobile phases, A (water with 0.1% formic acid) and B (MeCN with 0.1% formic acid), by increasing from 20% to 50% B between 0.3 to 2.0 min, increasing to 100% B at 2.01 min and holding 100% B for 0.6 min, and re-equilibrating for 0.6 min. The flow rate was 0.6 mL/min, and the column temperature was set at 55° C. Steviol glycosides were monitored using SIM (Single Ion Monitoring) and quantified by comparing against authentic standards. See Table 1 for m/z trace and retention time values of steviol glycosides and glycosides of steviol precursors detected.

TABLE 8

LC-MS Analytical Data for Steviol and Glycosides of Steviol and Steviol Precursors

| Compound | MS Trace | RT (mins) |
|---|---|---|
| steviol + 5Glc (#22) [also referred to as compound 5.22] | 1127.48 | 0.85 |
| steviol + 6Glc (isomer 1) [also referred to as compound 6.1] | 1289.53 | 0.87 |
| steviol + 7Glc (isomer 2) [also referred to as compound 7.2] | 1451.581 | 0.94 |
| steviol + 6Glc (#23) [also referred to as compound 6.23] | 1289.53 | 0.97 |
| RebE | 965.42 | 1.06 |
| RebD | 1127.48 | 1.08 |
| RebM | 1289.53 | 1.15 |
| steviol + 7Glc (isomer 5) [also referred to as compound 7.5] | 1451.581 | 1.09 |
| steviol + 4Glc (#26) [also referred to as compound 4.26] | 965.42 | 1.21 |
| steviol + 5Glc (#24) [also referred to as compound 5.24] | 1127.48 | 1.18 |
| steviol + 4Glc (#25) [also referred to as compound 5.25] | 1127.48 | 1.40 |
| RebA | 965.42 | 1.43 |
| 1,2-Stevioside | 803.37 | 1.43 |
| steviol + 4Glc (#33) [also referred to as compound 4.33] | 965.42 | 1.49 |
| steviol + 3Glc (#1) [also referred to as compound 3.1] | 803.37 | 1.52 |
| steviol + 2Glc (#57) [also referred to as compound 2.57] | 641.32 | 1.57 |
| RebQ | 965.42 | 1.59 |
| 1,3-Stevioside (RebG) | 803.37 | 1.60 |
| Rubusoside | 641.32 | 1.67 |
| RebB | 803.37 | 1.76 |
| Steviol-1,2-Bioside | 641.32 | 1.80 |
| Steviol-1,3-Bioside | 641.32 | 1.95 |
| 19-SMG | 525.27 | 1.98 |
| 13-SMG | 479.26 | 2.04 |
| ent-kaurenoic acid + 3Glc (isomer 1) [also referred to as compound KA3.1] | 787.37 | 2.16 |
| ent-kaurenoic acid + 3Glc (isomer 2) [also referred to as compound KA3.2] | 787.37 | 2.28 |
| ent-kaurenol + 3Glc (isomer 1) co-eluted with ent-kaurenol + 3Glc (#6) [also referred to as compounds KL3.1 and KL3.6] | 773.4 | 2.36 |
| ent-kaurenoic acid + 2Glc (#7) [also referred to as compound KA2.7] | 625.32 | 2.35 |
| ent-kaurenol + 2Glc (#8) [also referred to as compound KL2.8] | 611.34 | 2.38 |
| Steviol | 317.21 | 2.39 |

Steviol glycosides can be isolated using a method described herein. For example, following fermentation, a culture broth can be centrifuged for 30 min at 7000 rpm at 4° C. to remove cells, or cells can be removed by filtration. The cell-free lysate can be obtained, for example, by mechanical disruption or enzymatic disruption of the host cells and additional centrifugation to remove cell debris. Mechanical disruption of the dried broth materials can also be performed, such as by sonication. The dissolved or suspended broth materials can be filtered using a micron or sub-micron filter prior to further purification, such as by preparative chromatography. The fermentation media or cell-free lysate can optionally be treated to remove low molecular weight compounds such as salt, and can optionally be dried prior to purification and re-dissolved in a mixture of water and solvent. The supernatant or cell-free lysate can be purified as follows: a column can be filled with, for example, HP20 Diaion resin (aromatic-type Synthetic Adsorbent; Supelco) or another suitable non-polar adsorbent or reverse phase chromatography resin, and an aliquot of supernatant or cell-free lysate can be loaded on to the column and washed with water to remove the hydrophilic components. The steviol glycoside product can be eluted by stepwise incremental increases in the solvent concentration in water or a gradient from, e.g., 0%→100% methanol. The levels of steviol glycosides, glycosylated ent-kaurenol, and/or glycosylated ent-kaurenoic acid in each fraction, including the flow-through, can then be analyzed by LC-MS. Fractions can then be combined and reduced in volume using a vacuum evaporator. Additional purification steps can be utilized, if desired, such as additional chromatography steps and crystallization.

Example 8: Expression of Heterologous UGP1

A steviol glycoside-producing *S. cerevisiae* strain overexpressing UGP1, YNK1, PGM1, and PGM2, as described in Example 2, was transformed with a vector comprising a codon-optimized nucleotide sequence encoding a UGP1 polypeptide (SEQ ID NO:132, SEQ ID NO:133) operably linked to a pTDH3 promoter (SEQ ID NO:150) and a tCYC1 terminator (SEQ ID NO:154), as summarized in Table 9, below.

TABLE 9

UGP1 Polypeptides Expressed

| Strain | SEQ ID |
|---|---|
| 1 | 126, 127 |
| 2 | 132, 133 |
| 3 | 128, 129 |
| 4 | 130, 131 |
| 5 | 124, 125 |
| 6 | 138, 139 |
| 7 | 136, 137 |
| 8 | 134, 135 |

Single colonies of the transformed strains provided in Table 9, and a control strain, transformed with a blank vector, were grown in 500 μL of Delft medium in a 96-well plate for 2 days at 30° C., shaking at 280 rpm. 50 μL of the cell culture of each strain was then transferred to a second 96-well plate and grown in 450 μL Feed-in-Time medium (m2p-labs GmbH, Baesweiler, Germany) for 4 days at 30° C., shaking at 280 rpm. Samples for LC-MS analysis were prepared by extracting 100 μL of cell solution with 100 μL of DMSO, vortexing until mixed, and incubating at 80° C. for 10 minutes. The resultant extract was clarified by centrifugation at 15,000 g for 10 min. 20 μL of the supernatant was diluted with 140 μL of 50% (v/v) DMSO for LC-MS injection. LC-MS data was normalized to the $OD_{600}$ of a mixture of 100 μL of the cell solution and 100 μL of water, measured on an ENVISION® Multilabel Reader (PerkinElmer, Waltham, Mass.).

LC-MS analysis was performed according to Example 7. Whole culture accumulation of compounds in μM/$OD_{600}$ was quantified by LC-MS against a known standard. Results are shown in Table 10, below. Each value is an average of 6 independent clones.

TABLE 10

| Concentration of Steviol Glycosides | | | | | | | |
|---|---|---|---|---|---|---|---|
| | Accumulated Concentration (μM/$OD_{600}$) | | | | | | |
| Strain | 13-SMG | Rubu. | RebB | RebA | RebD | RebM | Total |
| Control | 9.96 ± 2.19 | 0.05 ± 0.08 | 0.67 ± 0.14 | 1.95 ± 0.79 | 3.89 ± 0.60 | 20.73 ± 4.48 | 37.38 ± 6.71 |
| 1 | 6.15 ± 1.83 | 0.26 ± 0.04 | 0.59 ± 0.09 | 2.37 ± 0.65 | 1.49 ± 0.36 | 25.91 ± 1.35 | 37.38 ± 3.03 |
| 2 | 7.06 ± 2.48 | 0.23 ± 0.12 | 0.76 ± 0.30 | 2.03 ± 0.37 | 1.34 ± 0.24 | 27.99 ± 3.17 | 39.43 ± 5.88 |
| 3 | 8.73 ± 3.20 | 0.25 ± 0.08 | 0.69 ± 0.24 | 2.50 + 0.81 | 1.69 ± 0.43 | 29.41 ± 6.19 | 43.34 ± 9.22 |
| 4 | 13.02 ± 2.39 | 0.14 ± 0.08 | 0.99 ± 0.23 | 2.88 ± 0.51 | 4.89 ± 0.75 | 30.41 ± 5.90 | 52.50 ± 9.51 |
| 5 | 7.91 ± 2.30 | 0.28 ± 0.08 | 0.62 ± 0.14 | 2.55 ± 0.96 | 1.42 ± 0.33 | 29.54 ± 4.23 | 42.37 ± 5.98 |
| 6 | 8.89 ± 2.94 | 0.28 ± 0.04 | 0.68 ± 0.18 | 2.36 ± 0.66 | 1.43 ± 0.49 | 27.64 ± 3.49 | 41.32 ± 5.08 |
| 7 | 5.68 ± 2.05 | 0.23 ± 0.09 | 0.51 ± 0.19 | 2.04 ± 0.50 | 1.26 ± 0.28 | 23.63 ± 2.27 | 33.38 ± 4.98 |
| 8 | 6.59 ± 2.65 | 0.22 ± 0.12 | 0.63 ± 0.17 | 2.28 ± 1.03 | 1.49 ± 0.59 | 26.64 ± 6.51 | 37.90 ± 10.21 |

Increases in steviol glycoside accumulation, by up to about 600%, was observed for the *S. cerevisiae* strain overexpressing UGP1, YNK1, PGM1, and PGM2, and further expressing heterologous UGP1, relative to the control strain. RebD+RebM accumulation levels increased upon expression of heterologous UGP1, further demonstrating a beneficial effect of expression of heterologous UDP-glucose biosynthetic pathway genes on the production of higher molecular weight steviol glycosides such as RebD or RebM.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

TABLE 11

| Sequences disclosed herein. |
|---|
| SEQ ID NO: 1 |
| *S. cerevisiae* |
| atgtcacttc taatagattc tgtaccaaca gttgcttata aggaccaaaa accgggtact 60 |
| tcaggtttac gtaagaagac caaggttttc atggatgagc ctcattatac tgagaacttc 120 |
| attcaagcaa caatgcaatc tatccctaat ggctcagagg gaaccacttt agttgttgga 180 |
| ggagatggtc gtttctacaa cgatgttatc atgaacaaga ttgccgcagt aggtgctgca 240 |
| aacggtgtca gaaagttagt cattggtcaa ggcggtttac tttcaacacc agctgcttct 300 |
| catataatta gaacatacga ggaaaagtgt accggtggtg gtatcatatt aactgcctca 360 |
| cacaacccag gcggtccaga gaatgattta ggtatcaagt ataatttacc taatggtggg 420 |
| ccagctccag agagtgtcac taacgctatc tgggaagcgt ctaaaaaatt aactcactat 480 |
| aaaattataa agaacttccc caagttgaat ttgaacaagc ttggtaaaaa ccaaaaatat 540 |
| ggcccattgt tagtggacat aattgatcct gccaaagcat acgttcaatt tctgaaggaa 600 |
| atttttgatt ttgacttaat taaaagcttc ttagcgaaac agcgcaaaga caaagggtgg 660 |
| aagttgttgt ttgactcctt aaatggtatt acaggaccat atggtaaggc tatatttgtt 720 |
| gatgaatttg gtttaccggc agaggaagtt cttcaaaatt ggcacccttt acctgatttc 780 |
| ggcggtttac atcccgatcc gaatctaacc tatgcacgaa ctcttgttga cagggttgac 840 |
| cgcgaaaaaa ttgcctttgg agcagcctcc gatggtgatg gtgataggaa tatgatttac 900 |
| ggttatggcc ctgctttcgt ttcgccaggt gattctgttg ccattattgc cgaatatgca 960 |
| cccgaaattc catacttcgc caaacaaggt atttatggct tggcacgttc atttcctaca 1020 |
| tcctcagcca ttgatcgtgt tgcagcaaaa aagggattaa gatgttacga agttccaacc 1080 |
| ggctggaaat tcttctgtgc cttatttgat gctaaaaagc tatcaatctg tggtgaagaa 1140 |
| tccttcggta caggttccaa tcatatcaga gaaaaggacg gtctatgggc cattattgct 1200 |
| tggttaaata tcttggctat ctaccatagg cgtaaccctg aaaaggaagc ttcgatcaaa 1260 |
| actattcagg acgaattttg gaacgagtat ggccgtactt tcttcacaag atacgattac 1320 |
| gaacatatcg aatgcgagca ggccgaaaaa gttgtagctc ttttgagtga atttgtatca 1380 |
| aggccaaacg tttgtggctc ccacttccca gctgatgagt ctttaaccgt tatcgattgt 1440 |
| ggtgattttt cgtatagaga tctagatggc tccatctctg aaaatcaagg ccttttcgta 1500 |
| aagttttcga atgggactaa atttgttttg aggttatccg gcacaggcag ttctggtgca 1560 |
| acaataagat tatacgtaga aaagtatact gataaaaagg agaactatgg ccaaacagct 1620 |
| gacgtcttct tgaaacccgt catcaactcc attgtaaaat tcttaagatt taaagaaatt 1680 |
| ttaggaacag acgaaccaac agtccgcaca tag 1713 |
| |
| SEQ ID NO: 2 |
| *S. cerevisiae* |
| MSLLIDSVPT VAYKDQKPGT SGLRKKTKVF MDEPHYTENF IQATMQSIPN GSEGTTLVVG 60 |
| GDGRFYNDVI MNKIAAVGAA NGVRKLVIGQ GGLLSTPAAS HIIRTYEEKC TGGGIILTAS 120 |
| HNPGGPENDL GIKYNLPNGG PAPESVTNAI WEASKKLTHY KIIKNFPKLN LNKLGKNQKY 180 |
| GPLLVDIIDP AKAYVQFLKE IFDFDLIKSF LAKQRKDKGW KLLFDSLNGI TGPYGKAIFV 240 |
| DEFGLPAEEV LQNWHPLPDF GGLHPDPNLT YARTLVDRVD REKIAFGAAS DGDGDRNMIY 300 |
| GYGPAFVSPG DSVAIIAEYA PEIPYFAKQG IYGLARSFPT SSAIDRVAAK KGLRCYEVPT 360 |
| GWKFFCALFD AKKLSICGEE SFGIGSNHIR EKDGLWAIIA WLNILAIYHR RNPEKEASIK 420 |
| TIQDEFWNEY GRTFFTRYDY EHIECEQAEK VVALLSEFVS RPNVCGSHFP ADESLTVIDC 480 |
| GDFSYRDLDG SISENQGLFV KFSNGTKFVL RLSGTGSSGA TIRLYVEKYT DKKENYGQTA 540 |
| DVFLKPVINS IVKFLRFKEI LGTDEPTVRT 570 |

TABLE 11-continued

| Sequences disclosed herein. |
|---|
| SEQ ID NO: 3<br>*S. rebaudiana*<br>atggcagagc aacaaaagat caaaaagtca cctcacgtct tacttattcc atttcctctg 60<br>caaggacata tcaacccatt catacaattt gggaaaagat tgattagtaa gggtgtaaag 120<br>acaacactgg taaccactat ccacactttg aattctactc tgaaccactc aaatactact 180<br>actacaagta tagaaattca agctatatca gacggatgcg atgagggtgg ctttatgtct 240<br>gccggtgaat cttacttgga aacattcaag caagtgggat ccaagtctct ggccgatcta 300<br>atcaaaaagt tacagagtga aggcaccaca attgacgcca taatctacga ttctatgaca 360<br>gagtgggttt tagacgttgc tatcgaattt ggtattgatg gaggttcctt tttcacacaa 420<br>gcatgtgttg tgaattctct atactaccat gtgcataaag ggttaatctc tttaccattg 480<br>ggtgaaactg tttcagttcc aggttttcca gtgttacaac gttgggaaac cccattgatc 540<br>ttacaaaatc atgaacaaat acaatcacct tggtcccaga tgttgtttgg tcaattcgct 600<br>aacatcgatc aagcaagatg ggtctttact aattcattct ataagttaga ggaagaggta 660<br>attgaatgga ctaggaagat ctggaatttg aaagtcattg gtccaacatt gccatcaatg 720<br>tatttggaca aaagacttga tgatgataaa gataatggtt tcaatttgta caaggctaat 780<br>catcacgaat gtatgaattg gctggatgac aaaccaaagg aatcagttgt atatgttgct 840<br>ttcggctctc ttgttaaaca tggtccagaa caagttgagg agattacaag agcacttata 900<br>gactctgacg taaacttttt gtgggtcatt aagcacaaag aggaggggaa actgccagaa 960<br>aacctttctg aagtgataaa gaccggaaaa ggtctaatcg ttgcttggtg taaacaattg 1020<br>gatgttttag ctcatgaatc tgtaggctgt tttgtaacac attgcggatt caactctaca 1080<br>ctagaagcca tttccttagg cgtacctgtc gttgcaatgc ctcagttctc cgatcagaca 1140<br>accaacgcta aacttttgga cgaaatacta ggggtgggtg tcagagttaa agcagacgag 1200<br>aatggtatcg tcagaagagg gaacctagct tcatgtatca aaatgatcat ggaagaggaa 1260<br>agaggagtta tcataaggaa aaacgcagtt aagtggaagg atcttgcaaa ggttgccgtc 1320<br>catgaaggcg gctcttcaga taatgatatt gttgaatttg tgtccgaact aatcaaagcc 1380<br>taa 1383<br><br>SEQ ID NO: 4<br>*S. rebaudiana*<br>MAEQQKIKKS PHVLLIPFPL QGHINPFIQF GKRLISKGVK TTLVTTIHTL NSTLNHSNTT 60<br>TTSIEIQAIS DGCDEGGFMS AGESYLETFK QVGSKSLADL IKKLQSEGTT IDAIIYDSMT 120<br>EWVLDVAIEF GIDGGSFFTQ ACVVNSLYYH VHKGLISLPL GETVSVPGFP VLQRWETPLI 180<br>LQNHEQIQSP WSQMLFGQFA NIDQARWVFT NSFYKLEEEV IEWTRKIWNL KVIGPTLPSM 240<br>YLDKRLDDDK DNGFNLYKAN HHECMNWLDD KPKESVVYVA FGSLVKHGPE QVEEITRALI 300<br>DSDVNFLWVI KHKEEGKLPE NLSEVIKTGK GLIVAWCKQL DVLAHESVGC FVTHCGFNST 360<br>LEAISLGVPV VAMPQFSDQT TNAKLLDEIL GVGVRVKADE NGIVRRGNLA SCIKMIMEEE 420<br>RGVIIRKNAV KWKDLAKVAV HEGGSSDNDI VEFVSELIKA 460<br><br>SEQ ID NO: 5<br>*S. rebaudiana*<br>atggatgcaa tggctacaac tgagaagaaa ccacacgtca tcttcatacc atttccagca 60<br>caaagccaca ttaaagccat gctcaaacta gcacaacttc tccaccacaa aggactccag 120<br>ataaccttcg tcaacaccga cttcatccac aaccagtttc ttgaatcatc gggcccacat 180<br>tgtctagacg gtgcaccggg tttccggttc gaaaccattc cggatggtgt ttctcacagt 240<br>ccggaagcga gcatcccaat cagagaatca ctcttgagat ccattgaaac caacttcttg 300<br>gatcgtttca ttgatcttgt aaccaaactt ccggatcctc cgacttgtat tatctcagat 360<br>gggttcttgt cggttttcac aattgacgct gcaaaaaagc ttggaattcc ggtcatgatg 420<br>tattggacac ttgctgcctg tgggttcatg ggtttttacc atattcattc tctcattgag 480<br>aaaggatttg caccacttaa agatgcaagt tacttgacaa atgggtattt ggacaccgtc 540<br>attgattggg ttccgggaat ggaaggcatc cgtctcaagg atttcccgct ggactggagc 600<br>actgacctca atgacaaagt tttgatgttc actacggaag ctcctcaaag gtcacacaag 660<br>gtttcacatc atattttcca cacgttcgat gagttggagc ctagtattat aaaaactttg 720<br>tcattgaggt ataatcacat ttacaccatc ggcccactgc aattacttct tgatcaaata 780<br>cccgaagaga aaaagcaaac tggaattacg agtctccatg gatacagttt agtaaaagaa 840<br>gaaccagagt gtttccagtg gcttcagtct aaagaaccaa attccgtcgt ttatgtaaat 900<br>tttggaagta ctacagtaat gtctttagaa gacatgacgg aatttggttg gggacttgct 960<br>aatagcaacc attatttcct ttggatcatc cgatcaaact tggtgatagg ggaaaatgca 1020<br>gttttgcccc ctgaacttga ggaacatata aagaaaagag gctttattgc tagctggtgt 1080<br>tcacaagaaa aggtcttgaa gcacccttcg gttggagggt tcttgactca ttgtgggtgg 1140<br>ggatcgacca tcgagagctt gtctgctggg gtgccaatga tatgctggcc ttattcgtgg 1200<br>gaccagctga ccaactgtag gtatatatgc aaagaatggg aggttgggct cgagatggga 1260<br>accaaagtga aacgagatga agtcaagagg cttgtacaag agttgatggg agaaggaggt 1320<br>cacaaaatga ggaacaaggc taaagattgg aaagaaaagg ctcgcattgc aatagctcct 1380<br>aacggttcat cttctttgaa catagacaaa atggtcaagg aaatcaccgt gctagcaaga 1440<br>aactagttac aaagttgttt cacattgtgc tttctattta agatgtaact ttgttctaat 1500<br>ttaatattgt ctagatgtat tgaaccataa gtttagttgg tctcaggaat tgatttttaa 1560<br>tgaaataatg gtcattaggg gtgagt 1586<br><br>SEQ ID NO: 6<br>*S. rebaudiana*<br>atggatgcaa tggcaactac tgagaaaaag cctcatgtga tcttcattcc atttcctgca 60<br>caatctcaca taaaggcaat gctaaagtta gcacaactat tacaccataa gggattacag 120<br>ataactttcg tgaataccga cttcatccat aatcaatttc tggaatctag tggccctcat 180<br>tgtttggacg gagccccagg gtttagattc gaaacaattc ctgacggtgt ttcacattcc 240<br>ccagaggcct ccatcccaat aagagagagt ttactgaggt caatagaaac caactttttg 300<br>gatcgtttca ttgacttggt cacaaaactt ccagacccac caacttgcat aatctctgat 360<br>ggctttctgt cagtgtttac tatcgacgct gccaaaaagt tgggtatccc agttatgatg 420<br>tactggactc ttgctgcatg cggtttcatg ggtttctatc acatccattc tcttatcgaa 480 |

TABLE 11-continued

| Sequences disclosed herein. |
|---|
| aagggttttg ctccactgaa agatgcatca tacttaacca acggctacct ggatactgtt 540<br>attgactggg taccaggtat ggaaggtata agacttaaag attttccttt ggattggtct 600<br>acagacctta atgataaagt attgatgttt actacagaag ctccacaaag atctcataag 660<br>gtttcacatc atatctttca cacctttgat gaattggaac catcaatcat caaaaccttg 720<br>tctctaagat acaatcatat ctacactatt ggtccattac aattacttct agatcaaatt 780<br>cctgaagaga aaaagcaaac tggtattaca tccttacacg gctactcttt agtgaaagag 840<br>gaaccagaat gttttcaatg gctacaaagt aaagagccta attctgtggt ctacgtcaac 900<br>ttcggaagta caacagtcat gtccttggaa gatatgactg aatttggttg gggccttgct 960<br>aattcaaatc attactttct atggattatc aggtccaatt tggtaatagg ggaaaacgcc 1020<br>gtattacctc cagaattgga ggaacacatc aaaaagagag gtttcattgc ttcctggtgt 1080<br>tctcaggaaa aggtattgaa acatccttct gttggtggtt tccttactca ttgcggttgg 1140<br>ggctctacaa tcgaatcact aagtgcagga gttccaatga tttgttggcc atattcatgg 1200<br>gaccaactta caaattgtag gtatatctgt aaagagtggg aagttggatt agaaatggga 1260<br>acaaaggtta aacgtgatga agtgaaaaga ttggttcagg agttgatggg ggaaggtggc 1320<br>cacaagatga gaaacaaggc caaagattgg aaggaaaaag ccagaattgc tattgctcct 1380<br>aacgggtcat cctctctaaa cattgataag atggtcaaag agattacagt cttagccaga 1440<br>aactaa 1446 |
| SEQ ID NO: 7<br>*S. rebaudiana*<br>MDAMATTEKK PHVIFIPFPA QSHIKAMLKL AQLLHHKGLQ ITFVNTDFIH NQFLESSGPH 60<br>CLDGAPGFRF ETIPDGVSHS PEASIPIRES LLRSIETNFL DRFIDLVTKL PDPPTCIISD 120<br>GFLSVFTIDA AKKLGIPVMM YWTLAACGFM GFYHIHSLIE KGFAPLKDAS YLTNGYLDTV 180<br>IDWVPGMEGI RLKDFPLDWS TDLNDKVLMF TTEAPQRSHK VSHHIFHTFD ELEPSIIKTL 240<br>SLRYNHIYTI GPLQLLLDQI PEEKKQTGIT SLHGYSLVKE EPECFQWLQS KEPNSVVYVN 300<br>FGSTTVMSLE DMTEFGWGLA NSNHYFLWII RSNLVIGENA VLPPELEEHI KKRGFIASWC 360<br>SQEKVLKHPS VGGFLTHCGW GSTIESLSAG VPMICWPYSW DQLTNCRYIC KEWEVGLEMG 420<br>TKVKRDEVKR LVQELMGEGG HKMRNKAKDW KEKARIAIAP NGSSSLNIDK MVKEITVLAR 480<br>N 481 |
| SEQ ID NO: 8<br>*S. rebaudiana*<br>atggaaaaca agaccgaaac aacagttaga cgtaggcgta gaatcattct gtttccagta 60<br>ccttttcaag ggcacatcaa tccaatacta caactagcca acgttttgta ctctaaaggt 120<br>ttttctatta caatctttca caccaatttc aacaaaccaa aaacatccaa ttacccacat 180<br>ttcacattca gattcatact tgataatgat ccacaagatg aacgtatttc aaacttacct 240<br>acccacggtc ctttagctgg aatgagaatt ccaatcatca atgaacatgg tgccgatgag 300<br>cttagaagag aattagagtt acttatgttg gcatccgaag aggacgagga agtctcttgt 360<br>ctgattactg acgctctatg gtactttgcc caatctgtgg ctgatagttt gaatttgagg 420<br>agattggtac taatgacatc cagtctgttt aactttcacg ctcatgttag tttaccacaa 480<br>tttgacgaat tgggatactt ggaccctgat gacaagacta ggttagagga acaggcctct 540<br>ggttttccta tgttgaaagt caaagatatc aagtctgcct attctaattg gcaaatcttg 600<br>aaagagatct taggaaagat gatcaaacag acaaaggctt catctggagt gatttggaac 660<br>agtttcaaag agttagaaga gtctgaattg gagactgtaa tcagagaaat tccagcacct 720<br>tcattcctga taccattacc aaaacatttg actgcttcct cttcctcttt gttggatcat 780<br>gacagaacag tttttcaatg gttggaccaa caaccaccta gttctgtttt gtacgtgtca 840<br>tttggtagta cttctgaagt cgatgaaaag gacttccttg aaatcgcaag aggcttagtc 900<br>gatagtaagc agtcattcct ttgggtcgtg cgtccaggtt tcgtgaaagg ctcaacatgg 960<br>gtcgaaccac ttccagatgg ttttctaggc gaaagaggta gaatagtcaa atgggttcct 1020<br>caacaggaag ttttagctca tggcgctatt ggggcattct ggactcattc cggatggaat 1080<br>tcaactttag aatcagtatg cgaaggggta cctatgatct tttcagattt tggtcttgat 1140<br>caaccactga acgcaagata catgtctgat gttttgaaag tgggtgtata tctagaaaat 1200<br>ggctgggaaa ggggtgaaat agctaatgca ataagacgtg ttatggttga tgaagagggg 1260<br>gagtatatca gacaaaacgc aagagtgctg aagcaaaagg ccgacgtttc tctaatgaag 1320<br>ggaggctctt catacgaatc cttagaatct cttgtttcct acatttcatc actgtaa 1377 |
| SEQ ID NO: 9<br>*S. rebaudiana*<br>MENKTETTVR RRRRIILFPV PFQGHINPIL QLANVLYSKG FSITIFHTNF NKPKTSNYPH 60<br>FTFRFILDND PQDERISNLP THGPLAGMRI PIINEHGADE LRRELELLML ASEEDEEVSC 120<br>LITDALWYFA QSVADSLNLR RLVLMTSSLF NFHAHVSLPQ FDELGYLDPD DKTRLEEQAS 180<br>GFPMLKVKDI KSAYSNWQIL KEILGKMIKQ TKASSGVIWN SFKELEESEL ETVIREIPAP 240<br>SFLIPLPKHL TASSSSLLDH DRTVFQWLDQ QPPSSVLYVS FGSTSEVDEK DFLEIARGLV 300<br>DSKQSFLWVV RPGFVKGSTW VEPLPDGFLG ERGRIVKWVP QQEVLAHGAI GAFWTHSGWN 360<br>STLESVCEGV PMIFSDFGLD QPLNARYMSD VLKVGVYLEN GWERGEIANA IRRVMVDEEG 420<br>EYIRQNARVL KQKADVSLMK GGSSYESLES LVSYISSL 458 |
| SEQ ID NO: 10<br>atggctacat ctgattctat tgttgatgac aggaagcagt tgcatgtggc tactttccct 60<br>tggcttgctt tcggtcatat actgccttac ctacaactat caaaactgat agctgaaaaa 120<br>ggacataaag tgtcattcct ttcaacaact agaaacattc aaagattatc ttcccacata 180<br>tcaccattga ttaacgtcgt tcaattgaca cttccaagag tacaggaatt accagaagat 240<br>gctgaagcta caacagatgt gcatcctgaa gatatccctt acttgaaaaa ggcatccgat 300<br>ggattacagc ctgaggtcac tagattcctt gagcaacaca gtccagattg gatcatatac 360<br>gactacactc actattggtt gccttcaatt gcagcatcac taggcatttc tagggcacat 420<br>ttcagtgtaa ccacaccttg ggccattgct tacatgggtc catccgctga tgctatgatt 480<br>aacggcagtg atggtagaac taccgttgaa gatttgacaa ccccaccaaa gtggtttcca 540<br>tttccaacta aagtctgttg gagaaaacac gacttagcaa gactggttcc atacaaggca 600 |

TABLE 11-continued

Sequences disclosed herein.

```
ccaggaatct cagacggcta tagaatgggt ttagtcctta aagggtctga ctgcctattg    660
tctaagtgtt accatgagtt tgggacacaa tggctaccac ttttggaaac attacaccaa    720
gttcctgtcg taccagttgg tctattacct ccagaaatcc ctggtgatga gaaggacgag    780
acttgggttt caatcaaaaa gtggttagac gggaagcaaa aaggctcagt ggtatatgtg    840
gcactgggtt ccgaagtttt agtatctcaa acagaagttg tggaacttgc cttaggtttg    900
gaactatctg gattgccatt tgtctgggcc tacagaaaac caaaaggccc tgcaaagtcc    960
gattcagttg aattgccaga cggctttgtc gagagaacta gagatagagg gttggtatgg   1020
acttcatggg ctccacaatt gagaatcctg agtcacgaat ctgtgtgcgg tttcctaaca   1080
cattgtggtt ctggttctat agttgaagga ctgatgtttg gtcatccact tatcatgttg   1140
ccaatctttg gtgaccagcc tttgaatgca cgtctgttag aagataaaca agttggaatt   1200
gaaatcccac gtaatgagga agatggatgt ttaaccaagg agtctgtggc cagatcatta   1260
cgttccgttg tcgttgaaaa ggaaggcgaa atctacaagg ccaatgcccg tgaactttca   1320
aagatctaca atgacacaaa agtagagaag gaatatgttt ctcaatttgt agattaccta   1380
gagaaaaacg ctagagccgt agctattgat catgaatcct aa                      1422
```

SEQ ID NO: 11

```
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARLVPYKA PGISDGYRMG LVLKGSDCLL SKCYHEFGTQ WLPLLETLHQ   240
VPVVPVGLLP PEIPGDEKDE TWVSIKKWLD GKQKGSVVYV ALGSEVLVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFGDQPLNA RLLEDKQVGI EIPRNEEDGC LTKESVARSL   420
RSVVVEKEGE IYKANARELS KIYNDTKVEK EYVSQFVDYL EKNARAVAID HES          473
```

SEQ ID NO: 12

```
atggctactt ctgattccat cgttgacgat agaaagcaat tgcatgttgc tacttttcca     60
tggttggctt tcggtcatat tttgccatac ttgcaattgt ccaagttgat tgctgaaaag    120
ggtcacaagg tttcattctt gtctaccacc agaaacatcc aaagattgtc ctctcatatc    180
tccccattga tcaacgttgt tcaattgact ttgccaagag tccaagaatt gccagaagat    240
gctgaagcta ctactgatgt tcatccagaa gatatccctt acttgaaaaa ggcttccgat    300
ggtttacaac cagaagttac tagattcttg gaacaacatt ccccagattg gatcatctac    360
gattatactc attactggtt gccatccatt gctgcttcat tgggtatttc tagagcccat    420
ttctctgtta ctactccatg ggctattgct tatatgggtc catctgctga tgctatgatt    480
aacggttctg atggtagaac taccgttgaa gatttgacta ctccaccaaa gtggtttcca    540
tttccaacaa aagtctgttg gagaaaacac gatttggcta gattggttcc atacaaagct    600
ccaggtattt ctgatggtta cagaatgggt atggttttga aaggttccga ttgcttgttg    660
tctaagtgct atcatgaatt cggtactcaa tggttgcctt tgttggaaac attgcatcaa    720
gttccagttg ttccagtagg tttgttgcca ccagaaattc caggtgacga aaaagacgaa    780
acttgggttt ccatcaaaaa gtggttggat ggtaagcaaa agggttctgt tgtttatgtt    840
gctttgggtt ccgaagcttt ggtttctcaa accgaagttg ttgaattggc tttgggtttg    900
gaattgtctg gtttgccatt tgtttgggct tacagaaaac ctaaaggtcc agctaagtct    960
gattctgttg aattgccaga tggtttcgtt gaaagaacta gagatagagg tttggtttgg   1020
acttcttggg ctccacaatt gagaattttg tctcatgaat ccgtctgtgg tttcttgact   1080
cattgtggtt ctggttctat cgttgaaggt ttgatgtttg gtcacccatt gattatgttg   1140
ccaatctttg gtgaccaacc attgaacgct agattattgg aagataagca agtcggtatc   1200
gaaatcccaa gaaatgaaga agatggttgc ttgaccaaag aatctgttgc tagatctttg   1260
agatccgttg tcgttgaaaa agaaggtgaa atctacaagg ctaacgctag agaattgtcc   1320
aagatctaca acgataccaa ggtcgaaaaa gaatacgttt cccaattcgt tgactacttg   1380
gaaaagaatg ctagagctgt tgccattgat catgaatctt ga                      1422
```

SEQ ID NO: 13

```
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARLVPYKA PGISDGYRMG MVLKGSDCLL SKCYHEFGTQ WLPLLETLHQ   240
VPVVPVGLLP PEIPGDEKDE TWVSIKKWLD GKQKGSVVYV ALGSEALVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFGDQPLNA RLLEDKQVGI EIPRNEEDGC LTKESVARSL   420
RSVVVEKEGE IYKANARELS KIYNDTKVEK EYVSQFVDYL EKNARAVAID HES          473
```

SEQ ID NO: 14

*O. sativa*

```
atggactccg gctactcctc ctcctacgcc gccgccgccg ggatgcacgt cgtgatctgc     60
ccgtggctcg ccttcggcca cctgctcccg tgcctcgacc tcgcccagcg cctcgcgtcg    120
cggggccacc gcgtgtcgtt cgtctccacg ccgcggaaca tatcccgcct cccgccggtg    180
cgccccgcgc tcgcgccgct cgtcgccttc gtggcgctgc cgctcccgcg cgtcgagggg    240
ctccccgacg gcgccgagtc caccaacgac gtcccccacg acaggccgga catggtcgag    300
ctccaccgga gggccttcga cgggctcgcc gcgcccttct cggagttctt gggcaccgcg    360
tgcgccgact gggtcatcgt cgacgtcttc caccactggg ccgcagccgc cgctctcgag    420
cacaaggtgc catgtgcaat gatgttgttg ggctctgcac atatgatcgc ttccatagca    480
gacagacggc tcgagcgcgc ggagacagag tcgcctgcgg ctgccgggca gggacgccca    540
gcggcggcgc caacgttcga ggtggcgagg atgaagttga tacgaaccaa aggctcatcg    600
ggaatgtccc tcgccgagcg cttctccttg acgctctcga ggagcagcct cgtcgtcggg    660
cggagctgcg tggagttcga gccggagacc gtcccgctcc tgtcgacgct ccgcggtaag    720
cctattacct tccttggcct tatgccgccg ttgcatgaag gccgccgcga ggacggcgag    780
gatgccaccg tccgctggct cgacgcgcag ccggccaagt ccgtcgtgta cgtcgcgcta    840
ggcagcgagg tgccactggg agtggagaag gtccacgagc tcgcgctcgg gctggagctc    900
```

TABLE 11-continued

Sequences disclosed herein.

```
gccgggacgc gcttcctctg ggctcttagg aagcccactg gcgtctccga cgccgacctc   960
ctccccgccg gcttcgagga gcgcacgcgc ggccgcggcg tcgtggcgac gagatgggtt  1020
cctcagatga gcatactggc gcacgccgcc gtgggcgcgt tcctgaccca ctgcggctgg  1080
aactcgacca tcgaggggct catgttcggc cacccgctta tcatgctgcc gatcttcggc  1140
gaccagggac cgaacgcgcg gctaatcgag gcgaagaacg ccggattgca ggtggcaaga  1200
aacgacggcg atggatcgtt cgaccgagaa ggcgtcgcgg cggcgattcg tgcagtcgcg  1260
gtggaggaag aaagcagcaa agtgtttcaa gccaaagcca agaagctgca ggagatcgtc  1320
gcggacatgg cctgccatga gaggtacatc gacggattca ttcagcaatt gagatcttac  1380
aaggattga                                                          1389
```

SEQ ID NO: 15
*O. sativa*

```
atggatagtg gctactcctc atcttatgct gctgccgctg gtatgcacgt tgtgatctgc    60
ccttggttgg cctttggtca cctgttacca tgtctggatt tagcccaaag actggcctca   120
agaggccata gagtatcatt tgtgtctact cctagaaata tctctcgttt accaccagtc   180
agacctgctc tagctcctct agttgcattc gttgctcttc cacttccaag agtagaagga   240
ttgccagacg gcgctgaatc tactaatgac gtaccacatg atagacctga catggtcgaa   300
ttgcatagaa gagcctttga tggattggca gctccatttt ctgagttcct gggcacagca   360
tgtgcagact gggttatagt cgatgtattt catcactggg ctgctgcagc cgcattggaa   420
cataaggtgc cttgtgctat gatgttgtta gggtcagcac acatgatcgc atccatagct   480
gatagaagat tggaaagagc tgaaacagaa tccccagccg cagcaggaca aggtaggcca   540
gctgccgccc caacctttga agtggctaga atgaaattga ttcgtactaa aggtagttca   600
gggatgagtc ttgctgaaag gttttctctg acattatcta gatcatcatt agttgtaggt   660
agatcctgcg tcgagttcga acctgaaaca gtacctttac tatctacttt gagaggcaaa   720
cctattactt tccttggtct aatgcctcca ttacatgaag gaaggagaga agatggtgaa   780
gatgctactg ttaggtggtt agatgcccaa cctgctaagt ctgttgttta cgttgcattg   840
ggttctgagg taccactagg ggtggaaaag gtgcatgaat tagcattagg acttgagctg   900
gccggaacaa gattcctttg ggctttgaga aaaccaaccg gtgtttctga cgccgacttg   960
ctaccagctg ggttcgaaga gagaacaaga ggccgtggtg tcgttgctac tagatgggtc  1020
ccacaaatga gtattctagc tcatgcagct gtaggggcct ttctaaccca ttgcggttgg  1080
aactcaacaa tagaaggact gatgtttggt catccactta ttatgttacc aatctttggc  1140
gatcagggac ctaacgcaag attgattgag gcaaagaacg caggtctgca ggttgcacgt  1200
aatgatggtg atggttcctt tgatagagaa ggcgttgcag ctgccatcag agcagtcgcc  1260
gttgaggaag agtcatctaa agttttccaa gctaaggcca aaaaattaca agagattgtg  1320
gctgacatgg cttgtcacga aagatacatc gatggtttca tccaacaatt gagaagttat  1380
aaagactaa                                                          1389
```

SEQ ID NO: 16
*O. sativa*

```
MDSGYSSSYA AAAGMHVVIC PWLAFGHLLP CLDLAQRLAS RGHRVSFVST PRNISRLPPV    60
RPALAPLVAF VALPLPRVEG LPDGAESTND VPHDRPDMVE LHRRAFDGLA APFSEFLGTA   120
CADWVIVDVF HHWAAAAALE HKVPCAMMLL GSAHMIASIA DRRLERAETE SPAAAGQGRP   180
AAAPTFEVAR MKLIRTKGSS GMSLAERFSL TLSRSSLVVG RSCVEFEPET VPLLSTLRGK   240
PITFLGLMPP LHEGRREDGE DATVRWLDAQ PAKSVVYVAL GSEVPLGVEK VHELALGLEL   300
AGTRFLWALR KPTGVSDADL LPAGFEERTR GRGVVATRWV PQMSILAHAA VGAFLTHCGW   360
NSTIEGLMFG HPLIMLPIFG DQGPNARLIE AKNAGLQVAR NDGDGSFDRE GVAAAIRAVA   420
VEEESSKVFQ AKAKKLQEIV ADMACHERYI DGFIQQLRSY KD                     462
```

SEQ ID NO: 17

```
MDSGYSSSYA AAAGMHVVIC PWLAFGHLLP CLDLAQRLAS RGHRVSFVST PRNISRLPPV    60
RPALAPLVAF VALPLPRVEG LPDGAESTND VPHDRPDMVE LHRRAFDGLA APFSEFLGTA   120
CADWVIVDVF HHWAAAAALE HKVPCAMMLL GSAHMIASIA DRRLERAETE SPAAAGQGRP   180
AAAPTFEVAR MKLIRTKGSS GMSLAERFSL TLSRSSLVVG RSCVEFEPET VPLLSTLRGK   240
PITFLGLLPP EIPGDEKDET WVSIKKWLDG KQKGSVVYVA LGSEALVSQT EVVELALGLE   300
LSGLPFVWAY RKPKGPAKSD SVELPDGFVE RTRDRGLVWT SWAPQLRILS HESVCGFLTH   360
CGSGSIVEGL MFGHPLIMLP IFGDQPLNAR LLEDKQVGIE IARNDGDGSF DREGVAAAIR   420
AVAVEEESSK VFQAKAKKLQ EIVADMACHE RYIDGFIQQL RSYKD                  465
```

SEQ ID NO: 18

```
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARLVPYKA PGISDGYRMG MVLKGSDCLL SKCYHEFGTQ WLPLLETLHQ   240
VPVVPVGLMP PLHEGRREDG EDATVRWLDA QPAKSVVYVA LGSEVPLGVE KVHELALGLE   300
LAGTRFLWAL RKPTGVSDAD LLPAGFEERT RGRGVVATRW VPQMSILAHA AVGAFLTHCG   360
WNSTIEGLMF GHPLIMLPIF GDQGPNARLI EAKNAGLQVP RNEEDGCLTK ESVARSLRSV   420
VVEKEGEIYK ANARELSKIY NDTKVEKEYV SQFVDYLEKN ARAVAIDHES              470
```

SEQ ID NO: 19
*Synechococcus* sp.

```
atggctttgg taaacccaac cgctcttttc tatggtacct ctatcagaac aagacctaca    60
aacttactaa atccaactca aaagctaaga ccagtttcat catcttcctt accttctttc   120
tcatcagtta gtgcgattct tactgaaaaa catcaatcta atccttctga gaacaacaat   180
ttgcaaactc atctagaaac tcctttcaac tttgatagtt atatgttgga aaaagtcaac   240
atggttaacg aggcgcttga tgcatctgtc ccactaaaag acccaatcaa aatccatgaa   300
tccatgagat actctttatt ggcaggcggt aagagaatca gaccaatgat gtgtattgca   360
gcctgcgaaa tagtcggagg taatatcctt aacgccatgc cagccgcatg tgccgtggaa   420
atgattcata ctatgtcttt ggtgcatgac gatcttccat gtatggataa tgatgacttc   480
```

TABLE 11-continued

Sequences disclosed herein.

agaagaggta aacctatttc acacaaggtc tacggggagg aaatggcagt attgaccggc 540
gatgctttac taagtttatc tttcgaacat atagctactg ctacaaaggg tgtatcaaag 600
gatagaatcg tcagagctat aggggagttg gcccgttcag ttggctccga aggtttagtg 660
gctggacaag ttgtagatat cttgtcagag ggtgctgatg ttggattaga tcacctagaa 720
tacattcaca tccacaaaac agcaatgttg cttgagtcct cagtagttat tggcgctatc 780
atgggaggag gatctgatca gcagatcgaa aagttgagaa aattcgctag atctattggt 840
ctactattcc aagttgtgga tgacattttg gatgttacaa aatctaccga agagttgggg 900
aaaacagctg gtaaggattt gttgacagat aagacaactt acccaaagtt gttaggtata 960
gaaaagtcca gagaatttgc cgaaaaactt aacaaggaag cacaagagca attaagtggc 1020
tttgatagac gtaaggcagc tcctttgatc gcgttagcca actacaatgc gtaccgtcaa 1080
aattga 1086

SEQ ID NO: 20
*Synechococcus* sp.
MALVNPTALF YGTSIRTRPT NLLNPTQKLR PVSSSSLPSF SSVSAILTEK HQSNPSENNN 60
LQTHLETPFN FDSYMLEKVN MVNEALDASV PLKDPIKIHE SMRYSLLAGG KRIRPMMCIA 120
ACEIVGGNIL NAMPAACAVE MIHTMSLVHD DLPCMDNDDF RRGKPISHKV YGEEMAVLTG 180
DALLSLSFEH IATATKGVSK DRIVRAIGEL ARSVGSEGLV AGQVVDILSE GADVGLDHLE 240
YIHIHKTAML LESSVVIGAI MGGGSDQQIE KLRKFARSIG LLFQVVDDIL DVTKSTEELG 300
KTAGKDLLTD KTTYPKLLGI EKSREFAEKL NKEAQEQLSG FDRRKAAPLI ALANYNAYRQ 360
N 361

SEQ ID NO: 21
atggctgagc aacaaatatc taacttgctg tctatgtttg atgcttcaca tgctagtcag 60
aaattagaaa ttactgtcca aatgatggac acataccatt acagagaaac gcctccagat 120
tcctcatctt ctgaaggcgg ttcattgtct agatacgacg agagaagagt ctctttgcct 180
ctcagtcata atgctgcctc tccagatatt gtatcacaac tatgtttttc cactgcaatg 240
tcttcagagt tgaatcacag atggaaatct caaagattaa aggtggccga ttctccttac 300
aactatatcc taacattacc atcaaaagga attagaggtg cctttatcga ttccctgaac 360
gtatggttgg aggttccaga ggatgaaaca tcagtcatca aggaagttat tggtatgctc 420
cacaactctt cattaatcat tgatgacttc caagataatt ctccacttag aagaggaaag 480
ccatctaccc atacagtctt cggccctgcc caggctatca atactgctac ttacgttata 540
gttaaagcaa tcgaaaagat acaagacata gtgggacacg atgcattggc agatgttacg 600
ggtactatta caactatttt ccaaggtcag gccatggact tgtggtggac agcaaatgca 660
atcgttccat caatacagga atacttactt atggtaaacg ataaaaccgg tgctctcttt 720
agactgagtt tggagttgtt agctctgaat tccgaagcca gtatttctga ctctgcttta 780
gaaagtttat ctagtgctgt ttccttgcta ggtcaatact tccaaatcag agacgactat 840
atgaacttga tcgataacaa gtatacagat cagaaaggct tctgcgaaga tcttgatgaa 900
ggcaagtact cactaacact tattcatgcc ctccaaactg attcatccga tctactgacc 960
aacatccttt caatgagaag agtgcaagga aagttaacgg cacaaaagag atgttggttc 1020
tggaaatga 1029

SEQ ID NO: 22
MAEQQISNLL SMFDASHASQ KLEITVQMMD TYHYRETPPD SSSSEGGSLS RYDERRVSLP 60
LSHNAASPDI VSQLCFSTAM SSELNHRWKS QRLKVADSPY NYILTLPSKG IRGAFIDSLN 120
VWLEVPEDET SVIKEVIGML HNSSLIIDDF QDNSPLRRGK PSTHTVEGPA QAINTATYVI 180
VKAIEKIQDI VGHDALADVT GTITTIFQGQ AMDLWWTANA IVPSIQEYLL MVNDKTGALF 240
RLSLELLALN SEASISDSAL ESLSSAVSLL GQYFQIRDDY MNLIDNKYTD QKGFCEDLDE 300
GKYSLTLIHA LQTDSSDLLT NILSMRRVQG KLTAQKRCWF WK 342

SEQ ID NO: 23
atggaaaaga ctaaggagaa agcagaacgt atcttgctgg agccatacag atacttatta 60
caactaccag gaaagcaagt ccgttctaaa ctatcacaag cgttcaatca ctggttaaaa 120
gttcctgaag ataagttaca aatcattatt gaagtcacag aaatgctaca caatgcttct 180
ttactgatcg atgatataga ggattcttcc aaactgagaa gaggttttcc tgtcgctcat 240
tccatatacg gggtaccaag tgtaatcaac tcagctaatt acgtctactt cttgggattg 300
gaaaaagtat tgacattaga tcatccagac gctgtaaagc tattcaccag acaacttctt 360
gaattgcatc aaggtcaagg tttggatatc tattggagag acacttatac ttgcccaaca 420
gaagaggagt acaaagcaat ggttctacaa aagactggcg gtttgttcgg acttgccgtt 480
ggtctgatgc aacttttctc tgattacaag gaggacttaa agcctctgtt ggataccttg 540
ggcttgtttt tccagattag agatgactac gctaacttac attcaaagga atattcagaa 600
aacaaatcat tctgtgaaga tttgactgaa gggaagttta gttttccaac aatccacgcc 660
atttggtcaa gaccagaatc tactcaagtg caaaacattc tgcgtcagag aacagagaat 720
attgacatca aaaagtattg tgttcagtac ttggaagatg ttggttcttt tgcttacaca 780
agacatacac ttagagaatt agaggcaaaa gcatacaagc aaatagaagc ctgtggaggc 840
aatccttctc tagtggcatt ggttaaacat ttgtccaaaa tgttcaccga ggaaaacaag 900
taa 903

SEQ ID NO: 24
MEKTKEKAER ILLEPYRYLL QLPGKQVRSK LSQAFNHWLK VPEDKLQIII EVTEMLHNAS 60
LLIDDIEDSS KLRRGFPVAH SIYGVPSVIN SANYVYFLGL EKVLTLDHPD AVKLFTRQLL 120
ELHQGQGLDI YWRDTYTCPT EEEYKAMVLQ KTGGLFGLAV GLMQLFSDYK EDLKPLLDTL 180
GLFFQIRDDY ANLHSKEYSE NKSFCEDLTE GKFSFPTIHA IWSRPESTQV QNILRQRTEN 240
IDIKKYCVQY LEDVGSFAYT RHTLRELEAK AYKQIEACGG NPSLVALVKH LSKMFTEENK 300

SEQ ID NO: 25
atggcaagat tctattttct taacgcacta ttgatggtta tctcattaca atcaactaca 60
gccttcactc cagctaaact tgcttatcca acaacaacaa cagctctaaa tgtcgcctcc 120

TABLE 11-continued

Sequences disclosed herein.

```
gccgaaactt ctttcagtct agatgaatac ttggcctcta agataggacc tatagagtct   180
gccttggaag catcagtcaa atccagaatt ccacagaccg ataagatctg cgaatctatg   240
gcctactctt tgatggcagg aggcaagaga attagaccag tgttgtgtat cgctgcatgt   300
gagatgttcg gtggatccca agatgtcgct atgcctactg ctgtggcatt agaaatgata   360
cacacaatgt ctttgattca tgatgatttg ccatccatgg ataacgatga cttgagaaga   420
ggtaaaccaa caaaccatgt cgttttcggc gaagatgtag ctattcttgc aggtgactct   480
ttattgtcaa cttccttcga gcacgtcgct agagaaacaa aaggagtgtc agcagaaaag   540
atcgtggatg ttatcgctag attaggcaaa tctgttggtg ccgagggcct tgctggcggt   600
caagttatgg acttagaatg tgaagctaaa ccaggtacca cattagacga cttgaaatgg   660
attcatatcc ataaaaccgc tacattgtta caagttgctg tagcttctgg tgcagttcta   720
ggtggtgcaa ctcctgaaga ggttgctgca tgcgagttgt ttgctatgaa tataggtctt   780
gcctttcaag ttgccgacga tatccttgat gtaaccgctt catcagaaga tttgggtaaa   840
actgcaggca aagatgaagc tactgataag acaacttacc caaagttatt aggattagaa   900
gagagtaagg catacgcaag acaactaatc gatgaagcca aggaaagttt ggctcctttt   960
ggagatagag ctgccccttt attggccatt gcagatttca ttattgatag aaagaattga  1020

SEQ ID NO: 26
MARFYFLNAL LMVISLQSTT AFTPAKLAYP TTTTALNVAS AETSFSLDEY LASKIGPIES    60
ALEASVKSRI PQTDKICESM AYSLMAGGKR IRPVLCIAAC EMFGGSQDVA MPTAVALEMI   120
HTMSLIHDDL PSMDNDDLRR GKPTNHVVFG EDVAILAGDS LLSTSFEHVA RETKGVSAEK   180
IVDVIARLGK SVGAEGLAGG QVMDLECEAK PGTTLDDLKW IHIHKTATLL QVAVASGAVL   240
GGATPEEVAA CELFAMNIGL AFQVADDILD VTASSEDLGK TAGKDEATDK TTYPKLLGLE   300
ESKAYARQLI DEAKESLAPF GDRAAPLLAI ADFIIDRKN                          339

SEQ ID NO: 27
atgcacttag caccacgtag agtccctaga ggtagaagat caccacctga cagagttcct    60
gaaagacaag gtgccttggg tagaagacgt ggagctggct ctactggctg tgcccgtgct   120
gctgctggtg ttcaccgtag aagaggagga ggcgaggctg atccatcagc tgctgtgcat   180
agaggctggc aagccggtgg tggcaccggt ttgcctgatg aggtggtgtc taccgcagcc   240
gccttagaaa tgtttcatgc ttttgcttta atccatgatg atatcatgga tgatagtgca   300
actagaagag gctccccaac tgttcacaga gccctagctg atcgtttagg cgctgctctg   360
gacccagatc aggccggtca actaggagtt tctactgcta tcttggttgg agatctggct   420
ttgacatggt ccgatgaatt gttatacgct ccattgactc cacatagact ggcagcagta   480
ctaccattgg taacagctat gagagctgaa accgttcatg gccaatatct tgatataact   540
agtgctagaa gacctgggac cgatacttct cttgcattga gaatagccag atataagaca   600
gcagcttaca caatggaacg tccactgcac attggtgcag ccctggctgg ggcaagacca   660
gaactattag cagggctttc agcatacgcc ttgccagctg gagaagcctt ccaattggca   720
gatgacctgc taggcgtctt cggtgatcca agacgtacag ggaaacctga cctagatgat   780
cttagaggtg gaaagcatac tgtcttagtc gccttggcaa gagaacatgc cactccagaa   840
cagagacaca cattggatac attattgggt acaccaggtc ttgatagaca aggcgcttca   900
agactaagat gcgtattggt agcaactggt gcaagagccg aagccgaaag acttattaca   960
gagagaagag atcaagcatt aactgcattg aacgcattaa cactgccacc tcctttagct  1020
gaggcattag caagattgac attagggtct acagctcatc ctgcctaa               1068

SEQ ID NO: 28
MHLAPRRVPR GRRSPPDRVP ERQGALGRRR GAGSTGCARA AAGVHRRRGG GEADPSAAVH    60
RGWQAGGGTG LPDEVVSTAA ALEMFHAFAL IHDDIMDDSA TRRGSPTVHR ALADRLGAAL   120
DPDQAGQLGV STAILVGDLA LTWSDELLYA PLTPHRLAAV LPLVTAMRAE TVHGQYLDIT   180
SARRPGTDTS LALRIARYKT AAYTMERPLH IGAALAGARP ELLAGLSAYA LPAGEAFQLA   240
DDLLGVFGDP RRTGKPDLDD LRGGKHTVLV ALAREHATPE QRHTLDTLLG TPGLDRQGAS   300
RLRCVLVATG ARAEAERLIT ERRDQALTAL NALTLPPPLA EALARLTLGS TAHPA        355

SEQ ID NO: 29
atgtcatatt tcgataacta cttcaatgag atagttaatt ccgtgaacga catcattaag    60
tcttacatct ctggcgacgt accaaaacta tacgaagcct cctaccattt gtttacatca   120
ggaggaaaga gactaagacc attgatcctt acaatttctt ctgatctttt cggtggacag   180
agagaaagag catactatgc tggcgcagca atcgaagttt tgcacacatt cactttggtt   240
cacgatgata tcatggatca agataacatt cgtagaggtc ttcctactgt acatgtcaag   300
tatggcctac ctttggccat tttagctggt gacttattgc atgcaaaagc ctttcaattg   360
ttgactcagg cattgagagg tctaccatct gaaactatca tcaaggcgtt tgatatcttt   420
acaagatcta tcattatcat atcagaaggt caagctgtcg atatggaatt cgaagataga   480
attgatatca aggaacaaga gtatttggat atgatatctc gtaaaaccgc tgccttattc   540
tcagcttctt cttccattgg ggcgttgata gctggagcta atgataacga tgtgagatta   600
atgtccgatt tcggtacaaa tcttgggatc gcatttcaaa ttgtagatga tatacttggt   660
ttaacagctg atgaaaaaga gctaggaaaa cctgttttca gtgatatcag agaaggtaaa   720
aagaccatat tagtcattaa gactttagaa ttgtgtaagg aagacgagaa aaagattgtg   780
ttaaaagcgc taggcaacaa gtcagcatca aaggaagagt tgatgagttc tgctgacata   840
atcaaaaagt actcattgga ttacgcctac aacttagctg agaaatacta caaaaacgcc   900
atcgattctc taaatcaagt ttcaagtaaa agtgatattc cagggaaggc attgaaatat   960
cttgctgaat tcaccatcag aagacgtaag taa                                993

SEQ ID NO: 30
MSYFDNYFNE IVNSVNDIIK SYISGDVPKL YEASYHLFTS GGKRLRPLIL TISSDLFGGQ    60
RERAYYAGAA IEVLHTFTLV HDDIMDQDNI RRGLPTVHVK YGLPLAILAG DLLHAKAFQL   120
LTQALRGLPS ETIIKAFDIF TRSIIIISEG QAVDMEFEDR IDIKEQEYLD MISRKTAALF   180
SASSSIGALI AGANDNDVRL MSDFGTNLGI AFQIVDDILG LTADEKELGK PVFSDIREGK   240
KTILVIKTLE LCKEDEKKIV LKALGNKSAS KEELMSSADI IKKYSLDYAY NLAEKYYKNA   300
IDSLNQVSSK SDIPGKALKY LAEFTIRRRK                                    330
```

TABLE 11-continued

Sequences disclosed herein.

SEQ ID NO: 31
```
atggtcgcac aaactttcaa cctggatacc tacttatccc aaagacaaca acaagttgaa    60
gaggccctaa gtgctgctct tgtgccagct tatcctgaga gaatatacga agctatgaga   120
tactccctcc tggcaggtgg caaaagatta agacctatct tatgtttagc tgcttgcgaa   180
ttggcaggtg gttctgttga acaagccatg ccaactgcgt gtgcacttga aatgatccat   240
acaatgtcac taattcatga tgacctgcca gccatggata acgatgattt cagaagagga   300
aagccaacta atcacaaggt gttcggggaa gatatagcca tcttagcggg tgatgcgctt   360
ttagcttacg cttttgaaca tattgcttct caaacaagag gagtaccacc tcaattggtg   420
ctacaagtta ttgctagaat cggacacgcc gttgctgcaa caggcctcgt tggaggccaa   480
gtcgtagacc ttgaatctga aggtaaagct atttccttag aaacattgga gtatattcac   540
tcacataaga ctggagcctt gctggaagca tcagttgtct caggcggtat tctcgcaggg   600
gcagatgaag agcttttggc cagattgtct cattacgcta gagatatagg cttggctttt   660
caaatcgtcg atgatatcct ggatgttact gctacatctg aacagttggg gaaaaccgct   720
ggtaaagacc aggcagccgc aaaggcaact tatccaagtc tattgggttt agaagcctct   780
agacagaaag cggaagagtt gattcaatct gctaaggaag ccttaagacc ttacggttca   840
caagcagagc cactcctagc gctggcagac ttcatcacac gtcgtcagca ttaa         894
```

SEQ ID NO: 32
```
MVAQTFNLDT YLSQRQQQVE EALSAALVPA YPERIYEAMR YSLLAGGKRL RPILCLAACE    60
LAGGSVEQAM PTACALEMIH TMSLIHDDLP AMDNDDFRRG KPTNHKVFGE DIAILAGDAL   120
LAYAFEHIAS QTRGVPPQLV LQVIARIGHA VAATGLVGGQ VVDLESEGKA ISLETLEYIH   180
SHKTGALLEA SVVSGGILAG ADEELLARLS HYARDIGLAF QIVDDILDVT ATSEQLGKTA   240
GKDQAAAKAT YPSLLGLEAS RQKAEELIQS AKEALRPYGS QAEPLLALAD FITRRQH      297
```

SEQ ID NO: 33
```
atgaaaaccg ggtttatctc accagcaaca gtatttcatc acagaatctc accagcgacc    60
actttcagac atcacttatc acctgctact acaaactcta caggcattgt cgccttaaga   120
gacatcaact tcagatgtaa agcagtttct aaagagtact ctgatctgtt gcagaaagat   180
gaggcttctt tcacaaaatg ggacgatgac aaggtgaaag atcatcttga taccaacaaa   240
aacttatacc caaatgatga gattaaggaa tttgttgaat cagtaaaggc tatgttcggt   300
agtatgaatg acggggagat aaacgtctct gcatacgata ctgcatgggt tgctttggtt   360
caagatgtcg atggatcagg tagtcctcag ttcccttctt ctttagaatg gattgccaac   420
aatcaattgt cagatggatc atggggagat catttgctgt tctcagctca cgatagaatc   480
atcaacacat tagcatgcgt tattgcactt acaagttgga atgttcatcc ttctaagtgt   540
gaaaaaggtt tgaatttttct gagagaaaac atttgcaaat tagaagatga aaacgcagaa   600
catatgccaa ttggttttga agtaacattc ccatcactaa ttgatatcgc gaaaaagttg   660
aacattgaag tacctgagga tactccagca cttaaagaga tctacgcacg tagagatatc   720
aagttaacta agatcccaat ggaagttctt cacaaggtac ctactacttt gttacattct   780
ttggaaggaa tgcctgattt ggagtgggaa aaactgttaa agctacaatg taaagatggt   840
agtttcttgt tttccccatc tagtaccgca ttcgccctaa tgcaaacaaa agatgagaaa   900
tgcttacagt atctaacaaa tatcgtcact aagttcaacg gtggcgtgcc taatgtgtac   960
ccagtcgatt tgtttgaaca tatttgggtt gttgatagac tgcagagatt ggggattgcc  1020
agatacttca aatcagagat aaaagattgt gtagagtata tcaataagta ctggaccaaa  1080
aatggaattt gttgggctag aaatactcac gttcaagata tcgatgatac agccatggga  1140
ttcagagtgt tgagagcgca cggttatgac gtcactccag atgtttttag acaatttgaa  1200
aaagatggta aattcgtttg ctttgcaggg caatcaacac aagccgtgac aggaatgttt  1260
aacgtttaca gagcctctca aatgttgttc ccaggggaga gaattttgga agatgccaaa  1320
aagttctctt acaattactt aaaggaaaag caaagtacca acgaattgct ggataaatgg  1380
ataatcgcta aagatctacc tggtgaagtt ggttatgctc tggatatccc atggtatgct  1440
tccttaccaa gattggaaac tcgttattac cttgaacaat acggcggtga agatgatgtc  1500
tggataggca agacattata cagaatgggt tacgtgtcca ataacacata tctagaaatg  1560
gcaaagctgg attacaataa ctatgttgca gtccttcaat tagaatggta cacaatacaa  1620
caatggtacg tcgatattgg tatagagaag ttcgaatctg acaacatcaa gtcagtcctg  1680
```

SEQ ID NO: 34
```
MKTGFISPAT VFHHRISPAT TFRHHLSPAT TNSTGIVALR DINFRCKAVS KEYSDLLQKD    60
EASFTKWDDD KVKDHLDTNK NLYPNDEIKE FVESVKAMFG SMNDGEINVS AYDTAWVALV   120
QDVDGSGSPQ FPSSLEWIAN NQLSDGSWGD HLLFSAHDRI INTLACVIAL TSWNVHPSKC   180
EKGLNFLREN ICKLEDENAE HMPIGFEVTF PSLIDIAKKL NIEVPEDTPA LKEIYARRDI   240
KLTKIPMEVL HKVPTTLLHS LEGMPDLEWE KLLKLQCKDG SFLFSPSSTA FALMQTKDEK   300
CLQYLTNIVT KFNGGVPNVY PVDLFEHIWV VDRLQRLGIA RYFKSEIKDC VEYINKYWTK   360
NGICWARNTH VQDIDDTAMG FRVLRAHGYD VTPDVFRQFE KDGKFVCFAG QSTQAVTGMF   420
NVYRASQMLF PGERILEDAK KFSYNYLKEK QSTNELLDKW IIAKDLPGEV GYALDIPWYA   480
SLPRLETRYY LEQYGGEDDV WIGKTLYRMG YVSNNTYLEM AKLDYNNYVA VLQLEWYTIQ   540
QWYVDIGIEK FESDNIKSVL VSYYLAAASI FEPERSKERI AWAKTTILVD KITSIFDSSQ   600
SSKEDITAFI DKFRNKSSSK KHSINGEPWH EVMVALKKTL HGFALDALMT HSQDIHPQLH   660
QAWEMWLTKL QDGVDVTAEL MVQMINMTAG RWVSKELLTH PQYQRLSTVT NSVCHDITKL   720
HNFKENSTTV DSKVQELVQL VFSDTPDDLD QDMKQTFLTV MKTFYYKAWC DPNTINDHIS   780
KVFEIVI                                                            787
```

SEQ ID NO: 35
```
atgcctgatg cacacgatgc tccacctcca caaataagac agagaacact agtagatgag    60
gctacccaac tgctaactga gtccgcagaa gatgcatggg gtgaagtcag tgtgtcagaa   120
tacgaaacag caaggctagt tgcccatgct acatggttag gtggacacgc cacaagagtg   180
gccttccttc tggagagaca acacgaagac gggtcatggg gtccaccagg tggatatagg   240
ttagtcccta cattatctgc tgttcacgca ttattgacat gtcttgcctc tcctgctcag   300
gatcatggcg ttccacatga tagactttta agagctgttg acgcaggctt gactgccttg   360
```

TABLE 11-continued

Sequences disclosed herein.

```
agaagattgg ggacatctga ctccccacct gatactatag cagttgagct ggttatccca   420
tctttgctag agggcattca acacttactg gaccctgctc atcctcatag tagaccagcc   480
ttctctcaac atagaggctc tcttgtttgt cctggtggac tagatgggag aactctagga   540
gctttgagat cacacgccgc agcaggtaca ccagtaccag gaaaagtctg gcacgcttcc   600
gagactttgg gcttgagtac cgaagctgct tctcacttgc aaccagccca aggtataatc   660
ggtggctctg ctgctgccac agcaacatgg ctaaccaggg ttgcaccatc tcaacagtca   720
gattctgcca gaagatacct tgaggaatta caacacagat actctggccc agttccttcc   780
attaccccta tcacatactt cgaaagagca tggttattga acaattttgc agcagccggt   840
gttccttgtg aggctccagc tgctttgttg gattccttag aagcagcact tacaccacaa   900
ggtgctcctg ctggagcagg attgcctcca gatgctgatg atacagccgc tgtgttgctt   960
gcattggcaa cacatgggag aggtagaaga ccagaagtac tgatggatta caggactgac  1020
gggtatttcc aatgctttat tggggaaagg actccatcaa tttcaacaaa cgctcacgta  1080
ttggaaacat tagggcatca tgtggcccaa catccacaag atagagccag atacggatca  1140
gccatggata ccgcatcagc ttggctgctg gcagctcaaa agcaagatgg ctcttggtta  1200
gataaatggc atgcctcacc atactacgct actgtttgtt gcacacaagc cctagccgct  1260
catgcaagtc ctgcaactgc accagctaga cagagagctg tcagatgggt tttagccaca  1320
caaagatccg atggcggttg ggtctatgg cattcaactg ttgaagagac tgcttatgcc  1380
ttacagatct tggccccacc ttctggtggt ggcaatatcc cagtccaaca agcacttact  1440
agaggcagag caagattgtg tggagccttg ccactgactc ctttatggca tgataaggat  1500
ttgtatactc cagtaagagt agtcagagct gccagagctg ctgctctgta cactaccaga  1560
gatctattgt taccaccatt gtaa                                        1584
```

SEQ ID NO: 36

```
MPDAHDAPPP QIRQRTLVDE ATQLLTESAE DAWGEVSVSE YETARLVAHA TWLGGHATRV    60
AFLLERQHED GSWGPPGGYR LVPTLSAVHA LLTCLASPAQ DHGVPHDRLL RAVDAGLTAL   120
RRLGTSDSPP DTIAVELVIP SLLEGIQHLL DPAHPHSRPA FSQHRGSLVC PGGLDGRTLG   180
ALRSHAAAGT PVPGKVWHAS ETLGLSTEAA SHLQPAQGII GGSAAATATW LTRVAPSQQS   240
DSARRYLEEL QHRYSGPVPS ITPITYFERA WLLNNFAAAG VPCEAPAALL DSLEAALTPQ   300
GAPAGAGLPP DADDTAAVLL ALATHGRGRR PEVLMDYRTD GYFQCFIGER TPSISTNAHV   360
LETLGHHVAQ HPQDRARYGS AMDTASAWLL AAQKQDGSWL DKWHASPYYA TVCCTQALAA   420
HASPATAPAR QRAVRWVLAT QRSDGGWGLW HSTVEETAYA LQILAPPSGG GNIPVQQALT   480
RGRARLCGAL PLTPLWHDKD LYTPVRVVRA ARAAALYTTR DLLLPPL                 527
```

SEQ ID NO: 37

```
atgaacgccc tatccgaaca cattttgtct gaattgagaa gattattgtc tgaaatgagt    60
gatggcggat ctgttggtcc atctgtgtat gatacggccc aggccctaag attccacggt   120
aacgtaacag gtagacaaga tgcatatgct tggttgatcg cccagcaaca agcagatgga   180
ggttggggct ctgccgactt tccactcttt agacatgctc caacatgggc tgcacttctc   240
gcattacaaa gagctgatcc acttcctggc gcagcagacg cagttcagac cgcaacaaga   300
ttcttgcaaa gacaaccaga tccatacgct catgccgttc ctgaggatgc ccctattggt   360
gctgaactga tcttgcctca gttttgtgga gaggctgctt ggttgttggg aggtgtggcc   420
ttccctagac acccagccct attaccatta agacaggctt gtttagtcaa actgggtgca   480
gtcgccatgt tgccttcagg acacccattg ctccactcct gggaggcatg gggtacttct   540
ccaacaacag cctgtccaga cgatgatggt tctataggta tctcaccagc agctacagcc   600
gcctggagag cccaggctgt gaccagaggc tcaactcctc aagtgggcag agctgacgca   660
tacttacaaa tggcttcaag agcaacgaga tcaggcatag aaggagtctt ccctaatgtt   720
tggcctataa acgtattcga accatgctgg tcactgtaca ctctccatct tgccggtctg   780
ttcgcccatc cagcactggc tgaggctgta agagttatcg ttgctcaact tgaagcaaga   840
ttgggagtgc atggcctcgg accagcttta cattttgctg ccgacgctga tgatactgca   900
gttgccttat gcgttctgca tttggctggc agagatcctg cagttgacgc attgagacat   960
tttgaaattg gtgagctctt tgttacattc ccaggagaga gaaatgctag tgtctctacg  1020
aacattcacg ctcttcatgc tttgagattg ttaggtaaac cagctgccgg agcaagtgca  1080
tacgtcgaag caaatagaaa tccacatggt ttgtgggaca acgaaaaatg gcacgtttca  1140
tggctttatc caactgcaca cgccgttgca gctctagctc aaggcaagcc tcaatggaga  1200
gatgaaagag cactagccgc tctactacaa gctcaaagag atgatggtgg ttggggagct  1260
ggtagaggat ccactttcga ggaaaccgcc tacgctcttt tcgctttaca cgttatggac  1320
ggatctgagg aagccacagg cagaagaaga atcgctcaag tcgtcgcaag agccttagaa  1380
tggatgctag ctagacatgc cgcacatgga ttaccacaaa caccactctg gattggtaag  1440
gaattgtact gtcctactag agtcgtaaga gtagctgagc tagctggcct gtggttagca  1500
ttaagatggg gtagaagagt attagctgaa ggtgctggtg ctgcacctta a           1551
```

SEQ ID NO: 38

```
MNALSEHILS ELRRLLSEMS DGGSVGPSVY DTAQALRFHG NVTGRQDAYA WLIAQQQADG    60
GWGSADFPLF RHAPTWAALL ALQRADPLPG AADAVQTATR FLQRQPDPYA HAVPEDAPIG   120
AELILPQFCG EAAWLLGGVA FPRHPALLPL RQACLVKLGA VAMLPSGHPL LHSWEAWGTS   180
PTTACPDDDG SIGISPAATA AWRAQAVTRG STPQVGRADA YLQMASRATR SGIEGVFPNV   240
WPINVFEPCW SLYTLHLAGL FAHPALAEAV RVIVAQLEAR LGVHGLGPAL HFAADADDTA   300
VALCVLHLAG RDPAVDALRH FEIGELFVTF PGERNASVST NIHALHALRL LGKPAAGASA   360
YVEANRNPHG LWDNEKWHVS WLYPTAHAVA ALAQGKPQWR DERALAALLQ AQRDDGGWGA   420
GRGSTFEETA YALFALHVMD GSEEATGRRR IAQVVARALE WMLARHAAHG LPQTPLWIGK   480
ELYCPTRVVR VAELAGLWLA LRWGRRVLAE GAGAAP                              516
```

SEQ ID NO: 39

*Z. mays*

```
atggtttgt cttcttcttg tactacagta ccacacttat cttcattagc tgtcgtgcaa    60
cttggtcctt ggagcagtag gattaaaaag aaaaccgata ctgttgcagt accagccgct   120
gcaggaaggt ggagaagggc cttggctaga gcacagcaca catcagaatc cgcagctgtc   180
gcaaagggca gcagtttgac ccctatagtg agaactgacg ctgagtcaag gagaacaaga   240
```

TABLE 11-continued

Sequences disclosed herein.

```
tggccaaccg atgacgatga cgccgaacct ttagtggatg agatcagggc aatgcttact   300
tccatgtctg atggtgacat ttccgtgagc gcatacgata cagcctgggt cggattggtt   360
ccaagattag acggcggtga aggtcctcaa tttccagcag ctgtgagatg gataagaaat   420
aaccagttgc ctgacggaag ttggggcgat gccgcattat tctctgccta tgacaggctt   480
atcaataccc ttgcctgcgt tgtaactttg acaaggtggt ccctagaacc agagatgaga   540
ggtagaggac tatctttttt gggtaggaac atgtggaaat tagcaactga agatgaagag   600
tcaatgccta ttggcttcga attagcattt ccatctttga tagagcttgc taagagccta   660
ggtgtccatg acttccctta tgatcaccag gccctacaag gaatctactc ttcaagagag   720
atcaaaatga agaggattcc aaaagaagtg atgcataccg ttccaacatc aatattgcac   780
agtttggagg gtatgcctgg cctagattgg gctaaactac ttaaactaca gagcagcgac   840
ggaagttttt tgttctcacc agctgccact gcatatgctt taatgaatac cggagatgac   900
aggtgtttta gctacatcga tagaacagta aagaaattca acggcggcgt ccctaatgtt   960
tatccagtgg atctatttga acatatttgg gccgttgata gacttgaaag attaggaatc  1020
tccaggtact tccaaaagga gatcgaacaa tgcatggatt atgtaaacag gcattggact  1080
gaggacggta tttgttgggc aaggaactct gatgtcaaag aggtggacga cacagctatg  1140
gcctttagac ttcttaggtt gcacggctac agcgtcagtc ctgatgtgtt taaaaacttc  1200
gaaaaggacg gtgaattttt cgcatttgtc ggacagtcta atcaagctgt taccggtatg  1260
tacaacttaa acagagcaag ccagatatcc ttcccaggcg aggatgtgct tcatagagct  1320
ggtgccttct catatgagtt cttgaggaga aaagaagcag agggagcttt gagggacaag  1380
tggatcattt ctaaagatct acctggtgaa gttgtgtata ctttggattt tccatggtac  1440
ggcaacttac ctagagtcga ggccagagac tacctagagc aatacggagg tggtgatgac  1500
gtttggattg gcaagacatt gtataggatg ccacttgtaa acaatgatgt atatttggaa  1560
ttggcaagaa tggatttcaa ccactgccag gctttgcatc agttagagtg gcaaggacta  1620
aaaagatggt atactgaaaa taggttgatg gactttggtg tcgcccaaga agatgccctt  1680
agagcttatt ttcttgcagc cgcatctgtt tacgagcctt gtagagctgc cgagaggctt  1740
gcatgggcta gagccgcaat actagctaac gccgtgagca cccacttaag aaatagccca  1800
tcattcagag aaaggttaga gcattctctt aggtgtagac ctagtgaaga gacagatggc  1860
tcctggttta actcctcaag tggctctgat gcagttttag taaaggctgt cttaagactt  1920
actgattcat tagccaggga agcacagcca atccatggag gtgacccaga agatattata  1980
cacaagttgt taagatctgc ttgggccgag tgggttaggg aaaaggcaga cgctgccgat  2040
agcgtgtgca atggtagttc tgcagtagaa caagagggat caagaatggt ccatgataaa  2100
cagacctgtc tattattggc tagaatgatc gaaatttctg ccggtagggc agctggtgaa  2160
gcagccagtg aggacggcga tagaagaata attcaattaa caggctccat ctgcgacagt  2220
cttaagcaaa aaatgctagt ttcacaggac cctgaaaaaa atgaagagat gatgtctcac  2280
gtggatgacg aattgaagtt gaggattaga gagttcgttc aatatttgct tagactaggt  2340
gaaaaaaaga ctggatctag cgaaaccagg caaacatttt taagtatagt gaaatcatgt  2400
tactatgctg ctcattgccc acctcatgtc gttgatagac acattagtag agtgattttc  2460
gagccagtaa gtgccgcaaa gtaaccgcgg                                  2490
```

SEQ ID NO: 40

*Z. mays*

```
MVLSSSCTTV PHLSSLAVVQ LGPWSSRIKK KTDTVAVPAA AGRWRRALAR AQHTSESAAV    60
AKGSSLTPIV RTDAESRRTR WPTDDDDAEP LVDEIRAMLT SMSDGDISVS AYDTAWVGLV   120
PRLDGGEGPQ FPAAVRWIRN NQLPDGSWGD AALFSAYDRL INTLACVVTL TRWSLEPEMR   180
GRGLSFLGRN MWKLATEDEE SMPIGFELAF PSLIELAKSL GVHDFPYDHQ ALQGIYSSRE   240
IKMKRIPKEV MHTVPTSILH SLEGMPGLDW AKLLKLQSSD GSFLFSPAAT AYALMNTGDD   300
RCFSYIDRTV KKFNGGVPNV YPVDLFEHIW AVDRLERLGI SRYFQKEIEQ CMDYVNRHWT   360
EDGICWARNS DVKEVDDTAM AFRLLRLHGY SVSPDVFKNF EKDGEFFAFV GQSNQAVTGM   420
YNLNRASQIS FPGEDVLHRA GAFSYEFLRR KEAEGALRDK WIISKDLPGE VVYTLDFPWY   480
GNLPRVEARD YLEQYGGGDD VWIGKTLYRM PLVNNDVYLE LARMDFNHCQ ALHQLEWQGL   540
KRWYTENRLM DFGVAQEDAL RAYFLAAASV YEPCRAAERL AWARAAILAN AVSTHLRNSP   600
SFRERLEHSL RCRPSEETDG SWFNSSSGSD AVLVKAVLRL TDSLAREAQP IHGGDPEDII   660
HKLLRSAWAE WVREKADAAD SVCNGSSAVE QEGSRMVHDK QTCLLLARMI EISAGRAAGE   720
AASEDGDRRI IQLTGSICDS LKQKMLVSQD PEKNEEMMSH VDDELKLRIR EFVQYLLRLG   780
EKKTGSSETR QTFLSIVKSC YYAAHCPPHV VDRHISRVIF EPVSAAK                 827
```

SEQ ID NO: 41

```
cttcttcact aaatacttag acagagaaaa cagagctttt taaagccatg tctcttcagt    60
atcatgttct aaactccatt ccaagtacaa cctttctcag ttctactaaa acaacaatat   120
cttcttcttt ccttaccatc tcaggatctc ctctcaatgt cgctagagac aaatccagaa   180
gcggttccat acattgttca aagcttcgaa ctcaagaata cattaattct caagaggttc   240
aacatgattt gcctctaata catgagtggc aacagcttca aggagaagat gctcctcaga   300
ttagtgttgg aagtaatagt aatgcattca aagaagcagt gaagagtgtg aaaacgatct   360
tgagaaacct aacggacggg gaaattacga tatcggctta cgatacagct tgggttgcat   420
tgatcgatgc cggagataaa actccggcgt ttccctccgc cgtgaaatgg atcgccgaga   480
accaactttc cgatggttct tggggagatg cgtatctctt ctcttatcat gatcgtctca   540
tcaataccct tgcatgcgtc gttgctctaa gatcatggaa tctctttcct catcaatgca   600
acaaaggaat cacgtttttc cgggaaaata ttgggaagct agaagacgaa aatgatgagc   660
atatgccaat cggattcgaa gtagcattcc catcgttgct tgagatagct cgaggaataa   720
acattgatgt accgtacgat tctccggtct taaaagatat atacgccaag aaagagctaa   780
agcttacaag gataccaaaa gagataatgc acaagatacc aacaacattg ttgcatagtt   840
tggaggggat gcgtgattta gattgggaaa agctcttgaa acttcaatct caagacggat   900
ctttcctctt ctctccttcc tctaccgctt ttgcattcat gcagacccga gacagtaact   960
gcctcgagta tttgcgaaat gccgtcaaac gtttcaatgg aggagttccc aatgtctttc  1020
ccgtggatct tttcgagcac atatggatag tggatcggtt acaacgttta gggatatcga  1080
gatactttga agaagagatt aaagagtgtc ttgactatgt ccacagatat tggaccgaca  1140
atggcatatg ttgggctaga tgttcccatg tccaagacat cgatgataca gccatggcat  1200
ttaggctctt aagacaacat ggataccaag tgtccgcaga tgtattcaag aactttgaga  1260
```

TABLE 11-continued

Sequences disclosed herein.

```
aagagggaga gtttttctgc tttgtggggc aatcaaacca agcagtaacc ggtatgttca 1320
acctataccg ggcatcacaa ttggcgtttc caagggaaga gatattgaaa aacgccaaag 1380
agttttctta taattatctg ctagaaaaac gggagagaga ggagttgatt gataagtgga 1440
ttataatgaa agacttacct ggcgagattg ggtttgcgtt agagattcca tggtacgcaa 1500
gcttgcctcg agtagagacg agattctata ttgatcaata tggtggagaa aacgacgttt 1560
ggattggcaa gactctttat aggatgccat acgtgaacaa taatggatat ctggaattag 1620
caaaacaaga ttacaacaat tgccaagctc agcatcagct cgaatgggac atattccaaa 1680
agtggtatga agaaaatagg ttaagtgagt ggggtgtgcg cagaagtgag cttctcgagt 1740
gttactactt agcggctgca actatatttg aatcagaaag gtcacatgag agaatggttt 1800
gggctaagtc aagtgtattg gttaaagcca tttcttcttc ttttggggaa tcctctgact 1860
ccagaagaag cttctccgat cagtttcatg aatacattgc caatgctcga cgaagtgatc 1920
atcactttaa tgacaggaac atgagattgg accgaccagg atcggttcag gccagtcggc 1980
ttgccggagt gttaatcggg actttgaatc aaatgtcttt tgaccttttc atgtctcatg 2040
gccgtgacgt taacaatctc ctctatctat cgtggggaga ttggatggaa aaatggaaac 2100
tatatggaga tgaaggagaa ggagagctca tggtgaagat gataattcta atgaagaaca 2160
atgacctaac taacttcttc acccacactc acttcgttcg tctcgcggaa atcatcaatc 2220
gaatctgtct tcctcgccaa tacttaaagg caaggagaaa cgatgagaag gagaagacaa 2280
taaagagtat ggagaaggag atggggaaaa tggttgagtt agcattgtcg gagagtgaca 2340
catttcgtga cgtcagcatc acgtttcttg atgtagcaaa agcattttac tactttgctt 2400
tatgtggcga tcatctccaa actcacatct ccaaagtctt gtttcaaaaa gtctagtaac 2460
ctcatcatca tcatcgatcc attaacaatc agtggatcga tgtatccata gatgcgtgaa 2520
taatatttca tgtagagaag gagaacaaat tagatcatgt agggttatca 2570
```

SEQ ID NO: 42

```
MSLQYHVLNS IPSTTFLSST KTTISSSFLT ISGSPLNVAR DKSRSGSIHC SKLRTQEYIN 60
SQEVQHDLPL IHEWQQLQGE DAPQISVGSN SNAFKEAVKS VKTILRNLTD GEITISAYDT 120
AWVALIDAGD KTPAFPSAVK WIAENQLSDG SWGDAYLFSY HDRLINTLAC VVALRSWNLF 180
PHQCNKGITF FRENIGKLED ENDEHMPIGF EVAFPSLLEI ARGINIDVPY DSPVLKDIYA 240
KKELKLTRIP KEIMHKIPTT LLHSLEGMRD LDWEKLLKLQ SQDGSFLFSP SSTAFAFMQT 300
RDSNCLEYLR NAVKRFNGGV PNVFPVDLFE HIWIVDRLQR LGISRYFEEE IKECLDYVHR 360
YWTDNGICWA RCSHVQDIDD TAMAFRLLRQ HGYQVSADVF KNFEKEGEFF CFVGQSNQAV 420
TGMFNLYRAS QLAFPREEIL KNAKEFSYNY LLEKREREEL IDKWIIMKDL PGEIGFALEI 480
PWYASLPRVE TRFYIDQYGG ENDVWIGKTL YRMPYVNNNG YLELAKQDYN NCQAQHQLEW 540
DIFQKWYEEN RLSEWGVRRS ELLECYYLAA ATIFESERSH ERMVWAKSSV LVKAISSSFG 600
ESSDSRRSFS DQFHEYIANA RRSDHHFNDR NMRLDRPGSV QASRLAGVLI GTLNQMSFDL 660
FMSHGRDVNN LLYLSWGDWM EKWKLYGDEG EGELMVKMII LMKNNDLTNF FTHTHFVRLA 720
EIINRICLPR QYLKARRNDE KEKTIKSMEK EMGKMVELAL SESDTFRDVS ITFLDVAKAF 780
YYFALCGDHL QTHISKVLFQ KV 802
```

SEQ ID NO: 43

```
atgaatttga gtttgtgtat agcatctcca ctattgacca aatctaatag accagctgct 60
ttatcagcaa ttcatacagc tagtacatcc catggtggcc aaaccaaccc tacgaatctg 120
ataatcgata cgaccaagga gagaatacaa aaacaattca aaaatgttga aatttcagtt 180
tcttcttatg atactgcgtg ggttgccatg gttccatcac ctaattctcc aaagtctcca 240
tgtttcccag aatgtttgaa ttggctgatt aacaaccagt tgaatgatgg atcttggggt 300
ttagtcaatc acacgcacaa tcacaaccat ccacttttga aagattcttt atcctcaact 360
ttggcttgca tcgtggccct aaagagatgg aacgtaggtg aggatcagat taacaagggg 420
cttagtttca ttgaatctaa cttggcttcc gcgactgaaa aatctcaacc atctccaata 480
ggattcgata tcatctttcc aggtctgtta gagtacgcca aaaatctaga tatcaactta 540
ctgtctaagc aaactgattt ctcactaatg ttacacaaga gagaattaga acaaaagaga 600
tgtcattcaa acgaaatgga tggttaccta gcttatatct ctgaaggtct tggtaatctt 660
tacgattgga atatggtgaa aaagtaccag atgaaaaatg gctcagtttt caattcccct 720
tctgcaactg cggcagcatt cattaaccat caaaatccag gatgcctgaa ctatttgaat 780
tcactactag acaaattcgg caacgcagtt ccaactgtat accctcacga tttgtttatc 840
agattgagta tggtggatac aattgaaaga cttggtatat ccccaccact tagagtcgag 900
atcaaaaatg ttttggatga gacataccgt tgttgggtgg agagagatga acaaatcttt 960
atggatgttg tgacgtgcgc gttggccttt agattgttgc gtattaacgg ttacgaagtt 1020
agtccagatc cacttgccga aattacaaac gaattagctt taaaggatga atacgccgct 1080
cttgaaacat atcatgcgtc acatatcctt taccaagagg acttatcatc tggaaaacaa 1140
attcttaaat ctgctgattt cctgaaggaa atcatatcca ctgatagtaa tagactgtcc 1200
aaactgatcc ataaagaggt tgaaaatgca cttaagttcc ctattaacac cggcttagaa 1260
cgtattaaca caagacgtaa catccagctt tacaacgtag acaatactag aatcttgaaa 1320
accacttacc attcttccaa catatcaaac actgattacc taagattagc tgttgaagat 1380
ttctacacat gtcagtctat ctatagagaa gagctgaaag gattagagag atgggtcgtt 1440
gagaataagc tagatcaatt gaaatttgcc agacaaaaga cagcttattg ttacttctca 1500
gttgccgcca ctttatcaag tccagaattg tcagatgcac gtatttcttg ggctaaaaac 1560
ggaattttga caactgttgt tgatgatttc tttgatattg gcgggacaat cgacgaattg 1620
acaaacctga ttcaatgcgt tgaaaagtgg aatgtcgatg tcgataaaga ctgttgctca 1680
gaacatgtta gaatactgtt cttggctctg aaagatgcta tctgttggat cggggatgag 1740
gctttcaaat ggcaagctag agatgtgacg tctcacgtca ttcaaacctg gctagaactg 1800
atgaactcta tgttgagaga agcaatttgg actagagatg catacgttcc tacattaaac 1860
gagtatatgg aaaacgctta tgtctccttt gctttgggtc ctatcgttaa gcctgccata 1920
tactttgtag gaccaaagct atccgaggaa atcgtcgaat catcagaata ccataacttg 1980
ttcaagttaa tgtccacaca aggcagatta cttaatgata ttcattcttt caaaagagag 2040
tttaaggaag gaaagttaaa tgctgttgct ctgcatcttt ctaatggcga aagtggtaaa 2100
gtcgaagagg aagtagttga ggaaatgatg atgatgatca aaaacaagag aaaggagttg 2160
atgaaactaa tcttcgaaga gaacggttca attgttccta gagcatgtaa ggatgcattt 2220
tggaacatgt gtcatgtgct aaacttttttc tacgcaaacg acgatggttt tactgggaac 2280
```

TABLE 11-continued

Sequences disclosed herein.

```
acaatactag atacagtaaa agacatcata tacaaccctt tggtcttagt aaacgaaaac  2340
gaggagcaaa gataa                                                   2355

SEQ ID NO: 44
MNLSLCIASP LLTKSNRPAA LSAIHTASTS HGGQTNPTNL IIDTTKERIQ KQFKNVEISV    60
SSYDTAWVAM VPSPNSPKSP CFPECLNWLI NNQLNDGSWG LVNHTHNHNH PLLKDSLSST   120
LACIVALKRW NVGEDQINKG LSFIESNLAS ATEKSQPSPI GFDIIFPGLL EYAKNLDINL   180
LSKQTDFSLM LHKRELEQKR CHSNEMDGYL AYISEGLGNL YDWNMVKKYQ MKNGSVFNSP   240
SATAAAFINH QNPGCLNYLN SLLDKFGNAV PTVYPHDLFI RLSMVDTIER LGISHHFRVE   300
IKNVLDETYR CWVERDEQIF MDVVTCALAF RLLRINGYEV SPDPLAEITN ELALKDEYAA   360
LETYHASHIL YQEDLSSGKQ ILKSADFLKE IISTDSNRLS KLIHKEVENA LKFPINTGLE   420
RINTRRNIQL YNVDNTRILK TTYHSSNISN TDYLRLAVED FYTCQSIYRE ELKGLERWVV   480
ENKLDQLKFA RQKTAYCYFS VAATLSSPEL SDARISWAKN GILTTVVDDF FDIGGTIDEL   540
TNLIQCVEKW NVDVDKDCCS EHVRILFLAL KDAICWIGDE AFKWQARDVT SHVIQTWLEL   600
MNSMLREAIW TRDAYVPTLN EYMENAYVSF ALGPIVKPAI YFVGPKLSEE IVESSEYHNL   660
FKLMSTQGRL LNDIHSFKRE FKEGKLNAVA LHLSNGESGK VEEEVVEEMM MMIKNKRKEL   720
MKLIFEENGS IVPRACKDAF WNMCHVLNFF YANDDGFTGN TILDTVKDII YNPLVLVNEN   780
EEQR                                                               784

SEQ ID NO: 45
atgaatctgt ccctttgtat agctagtcca ctgttgacaa aatcttctag accaactgct    60
ctttctgcaa ttcatactgc cagtactagt catggaggtc aaacaaaccc aacaaatttg   120
ataatcgata ctactaagga gagaatccaa aagctattca aaaatgttga aatctcagta   180
tcatcttatg acaccgcatg ggttgcaatg gtgccatcac ctaattcccc aaaaagtcca   240
tgttttccag agtgcttgaa ttggttaatc aataatcagt taaacgatgg ttcttggggt   300
ttagtcaacc acactcataa ccacaatcat ccattattga aggactcttt atcatcaaca   360
ttagcctgta ttgttgcatt gaaaagatgg aatgtaggtg aagatcaaat caacaagggt   420
ttatcattca tagaatccaa tctagcttct gctaccgaca aatcacaacc atctccaatc   480
gggttcgaca taatcttccc tggtttgctg gagtatgcca aaaaccttga tatcaactta   540
ctgtctaaac aaacagattt ctctttgatg ctacacaaaa gagagttaga gcagaaaaga   600
tgccattcta acgaaattga cgggtactta gcatatatct cagaaggttt gggtaatttg   660
tatgactgga acatggtcaa aaagtatcag atgaaaaatg gatccgtatt caattctcct   720
tctgcaactg ccgcagcatt cattaatcat caaaaccctg ggtgtcttaa ctacttgaac   780
tcactattag ataagtttgg aaatgcagtt ccaacagtct atcctttgga cttgtacatc   840
agattatcta tggttgacac tatagagaga ttaggtattt ctcatcattt cagagttgag   900
atcaaaaatg ttttggacga gacatacaga tgttgggtcg aaagagatga gcaaatcttt   960
atggatgtcg tgacctgcgc tctggctttt agattgctaa ggatacacgg atacaaagta  1020
tctcctgatc aactggctga gattacaaac gaactggctt tcaaagacga atacgccgca  1080
ttagaaacat accatgcatc ccaaatactt taccaggaag acctaagttc aggaaaacaa  1140
atcttgaagt ctgcagattt cctgaaaggc attctgtcta cagatagtaa taggttgtct  1200
aaattgatac acaaggaagt agaaaacgca ctaaagtttc ctattaacac tggtttagag  1260
agaatcaata ctaggagaaa cattcagctg tacaacgtag ataatacaag gattcttaag  1320
accacctacc atagttcaaa catttccaac acctattact taagattagc tgtcgaagac  1380
ttttacactt gtcaatcaat ctacagagag gagttaaagg gcctagaaag atgggtagtt  1440
caaaacaagt tggatcaact gaagtttgct agacagaaga cagcatactg ttatttctct  1500
gttgctgcta ccctttcatc cccagaattg tctgatgcca gaataagttg ggccaaaaat  1560
ggtattctta caactgtagt cgatgatttc tttgatattg gaggtactat tgatgaactg  1620
acaaatctta ttcaatgtgt tgaaaagtgg aacgtggatg tagataagga ttgctgcagt  1680
gaacatgtga gaatactttt cctggctcta aaagatgcaa tatgttggat tggcgacgag  1740
gccttcaagt ggcaagctag agatgttaca tctcatgtca tccaaacttg gcttgaactg  1800
atgaactcaa tgctaagaga agcaatctgg acaagagatg catacgttcc aacattgaac  1860
gaatacatgg aaaacgctta cgtctcattt gccttgggtc ctattgttaa gccagccata  1920
tactttgttg ggccaaagtt atccgaagag attgttgagt cttccgaata tcataaccta  1980
ttcaagttaa tgtcaacaca aggcagactt ctgaacgata tccactcctt caaaagagaa  2040
ttcaaggaag gtaagctaaa cgctgttgct ttgcacttgt ctaatggtga atctggcaaa  2100
gtggaagagg aagtcgttga ggaaatgatg atgatgatca aaaacaagag aaaggaattg  2160
atgaaattga ttttcgagga aaatggttca atcgtaccta gagcttgtaa agatgctttt  2220
tggaatatgt gccatgttct taacttcttt tacgctaatg atgatggctt cactggaaat  2280
acaatattgg atacagttaa agatatcatc tacaacccac ttgttttggt caatgagaac  2340
gaggaacaaa gataa                                                   2355

SEQ ID NO: 46
MNLSLCIASP LLTKSSRPTA LSAIHTASTS HGGQTNPTNL IIDTTKERIQ KLFKNVEISV    60
SSYDTAWVAM VPSPNSPKSP CFPECLNWLI NNQLNDGSWG LVNHTHNHNH PLLKDSLSST   120
LACIVALKRW NVGEDQINKG LSFIESNLAS ATDKSQPSPI GFDIIFPGLL EYAKNLDINL   180
LSKQTDFSLM LHKRELEQKR CHSNEIDGYL AYISEGLGNL YDWNMVKKYQ MKNGSVFNSP   240
SATAAAFINH QNPGCLNYLN SLLDKFGNAV PTVYPLDLYI RLSMVDTIER LGISHHFRVE   300
IKNVLDETYR CWVERDEQIF MDVVTCALAF RLLRIHGYKV SPDQLAEITN ELAFKDEYAA   360
LETYHASQIL YQEDLSSGKQ ILKSADFLKG ILSTDSNRLS KLIHKEVENA LKFPINTGLE   420
RINTRRNIQL YNVDNTRILK TTYHSSNISN TYYLRLAVED FYTCQSIYRE ELKGLERWVV   480
QNKLDQLKFA RQKTAYCYFS VAATLSSPEL SDARISWAKN GILTTVVDDF FDIGGTIDEL   540
TNLIQCVEKW NVDVDKDCCS EHVRILFLAL KDAICWIGDE AFKWQARDVT SHVIQTWLEL   600
MNSMLREAIW TRDAYVPTLN EYMENAYVSF ALGPIVKPAI YFVGPKLSEE IVESSEYHNL   660
FKLMSTQGRL LNDIHSFKRE FKEGKLNAVA LHLSNGESGK VEEEVVEEMM MMIKNKRKEL   720
MKLIFEENGS IVPRACKDAF WNMCHVLNFF YANDDGFTGN TILDTVKDII YNPLVLVNEN   780
EEQR                                                               784
```

TABLE 11-continued

Sequences disclosed herein.

SEQ ID NO: 47
atggctatgc cagtgaagct aacacctgcg tcattatcct taaaagctgt gtgctgcaga 60
ttctcatccg gtggccatgc tttgagattc gggagtagtc tgccatgttg gagaaggacc 120
cctacccaaa gatctacttc ttcctctact actagaccag ctgccgaagt gtcatcaggt 180
aagagtaaac aacatgatca ggaagctagt gaagcgacta tcagacaaca attacaactt 240
gtggatgtcc tggagaatat gggaatatcc agacattttg ctgcagagat aaagtgcata 300
ctagacagaa cttacagatc ttggttacaa agacacgagg aaatcatgct ggacactatg 360
acatgtgcta tggcttttag aatcctaaga ttgaacggat acaacgtttc atcagatgaa 420
ctataccacg ttgtagaggc atctggtctg cataattctt tgggtgggta tcttaacgat 480
accagaacac tacttgaatt acacaaggct tcaacagtta gtatctctga ggatgaatct 540
atcttagatt caattggctc tagatccaga acattgctta gagaacaatt ggagtctggt 600
ggcgcactga gaaagccttc tttattcaaa gaggttgaac atgcactgga tggacctttt 660
tacaccacac ttgatagact tcatcatagg tggaatattg aaaacttcaa cattattgag 720
caacacatgt tggagactcc atacttatct aaccagcata catcaaggga tatcctagca 780
ttgtcaatta gagatttttc ctcctcacaa ttcacttatc aacaagagct acagcatctg 840
gagagttggg ttaaggaatg tagattagat caactacagt tcgcaagaca gaaattagcg 900
tacttttacc tatcagccgc aggcaccatg ttttctcctg agctttctga tgcgagaaca 960
ttatgggcca aaaacggggt gttgacaact attgttgatg atttctttga tgttgccggt 1020
tctaaagagg aattggaaaa cttagtcatg ctggtcgaaa tgtgggatga acatcacaaa 1080
gttgaattct attctgagca ggtcgaaatc atcttctctt ccatctacga ttctgtcaac 1140
caattgggtg agaaggcctc tttggttcaa gacagatcaa ttacaaaaca ccttgttgaa 1200
atatggttag acttgttaaa gtccatgatg acggaagttg aatggagact gtcaaaatac 1260
gtgcctacag aaaaggaata catgattaat gcctctctta tcttcggcct aggtccaatc 1320
gttttaccag ctttgtattt cgttggtcca aagatttcag aaagtatagt aaaggaccca 1380
gaatatgatg aattgttcaa actaatgtca acatgtggta gattgttgaa tgacgtgcaa 1440
acgttcgaaa gagaatacaa tgagggtaaa ctgaattctg tcagtctatt ggttcttcac 1500
ggaggcccaa tgtctatttc agacgcaaag aggaaattac aaaagcctat tgatacgtgt 1560
agaagagatc ttctttcttt ggtccttaga gaagagtctg tagtaccaag accatgtaag 1620
gaactattct ggaaaatgtg taaagtgtgc tatttctttt actcaacaac tgatgggttt 1680
tctagtcaag tcgaaagagc aaaagaggta gacgctgtca taaatgagcc actgaagttg 1740
caaggttctc atacactggt atctgatgtt taa 1773

SEQ ID NO: 48
MAMPVKLTPA SLSLKAVCCR FSSGGHALRF GSSLPCWRRT PTQRSTSSST TRPAAEVSSG 60
KSKQHDQEAS EATIRQQLQL VDVLENMGIS RHFAAEIKCI LDRTYRSWLQ RHEEIMLDTM 120
TCAMAFRILR LNGYNVSSDE LYHVVEASGL HNSLGGYLND TRTLLELHKA STVSISEDES 180
ILDSIGSRSR TLLREQLESG GALRKPSLFK EVEHALDGPF YTTLDRLHHR WNIENFNIIE 240
QHMLETPYLS NQHTSRDILA LSIRDFSSSQ FTYQQELQHL ESWVKECRLD QLQFARQKLA 300
YFYLSAAGTM FSPELSDART LWAKNGVLTT IVDDFFDVAG SKEELENLVM LVEMWDEHHK 360
VEFYSEQVEI IFSSIYDSVN QLGEKASLVQ DRSITKHLVE IWLDLLKSMM TEVEWRLSKY 420
VPTEKEYMIN ASLIFGLGPI VLPALYFVGP KISESIVKDP EYDELFKLMS TCGRLLNDVQ 480
TFEREYNEGK LNSVSLLVLH GGPMSISDAK RKLQKPIDTC RRDLLSLVLR EESVVPRPCK 540
ELFWKMCKVC YFFYSTTDGF SSQVERAKEV DAVINEPLKL QGSHTLVSDV 590

SEQ ID NO: 49
atgcagaact tccatggtac aaaggaaagg atcaaaaaga tgtttgacaa gattgaattg 60
tccgtttctt cttatgatac agcctgggtt gcaatggtcc catcccctga ttgcccagaa 120
acaccttgtt ttccagaatg tactaaatgg atcctagaaa atcagttggg tgatggtagt 180
tggtcacttc ctcatggcaa tccacttcta gttaaagatg cattatcttc cactcttgct 240
tgtattctgg ctcttaaaag atggggaatc ggtgaggaac agattaacaa aggactgaga 300
ttcatagaac tcaactctgc tagtgtaacc gataacgaac aacacaaacc aattggattt 360
gacattatct ttccaggtat gattgaatac gctatagact tagacctgaa tctaccacta 420
aaaccaactg acattaactc catgttgcat cgtagagccc ttgaattgac atcaggtgga 480
ggcaaaaatc tagaaggtag aagagcttac ttggcctacg tctctgaagg aatcggtaag 540
ctgcaagatt gggaaatggc tatgaaatac caacgtaaaa acggatctct gttcaatagt 600
ccatcaacaa ctgcagctgc attcatccat atacaagatg ctgaatgcct ccactatatt 660
cgttctcttc tccagaaatt tggaaacgca gtccctacaa tataccctct cgatatctat 720
gccagacttt caatggtaga tgccctggaa cgtcttggta ttgatagaca tttcagaaag 780
gagagaaagt tcgttctgga tgaaacatac agattttggt tgcaaggaga agaggagatt 840
ttctccgata acgcaacctg tgctttggcc ttcagaatat tgagacttaa tggttacgat 900
gtctctcttg aagatcactt ctctaactct ctgggcggtt acttaaagga ctcaggagca 960
gctttagaac tgtacagagc cctccaattg tcttacccag acgagtccct cctggaaaag 1020
caaaattcta gaacttctta cttcttaaaa caaggtttat ccaatgtctc cctctgtggt 1080
gacagattgc gtaaaaacat aattggagag gtgcatgatg ctttaaactt ttccgaccac 1140
gctaacttac aaagattagc tattcgtaga aggattaagc attacgctac tgacgataca 1200
aggattctaa aaacttccta cagatgctca acaatcggta accaagattt tctaaaactt 1260
gcagtggaag atttcaatat ctgtcaatca atacaaagag aggaattcaa gcatattgaa 1320
agatgggtcg ttgaaagacg tctagacaag ttaaagttcg ctagacaaaa agaggcctat 1380
tgctatttct cagccgcagc aacattgttt gcccctgaat tgtctgatgc tagaatgtct 1440
tgggccaaaa atggtgtatt gacaactgtg gttgatgatt tcttcgatgt cggaggctct 1500
gaagaggaat tagttaactt gatagaattg atcgagcgtt gggatgtgaa tggcagtgca 1560
gatttttgta gtgaggaagt tgagattatc tattctgcta tccactcaac tatctctgaa 1620
ataggtgata agtcatttgg ctggcaaggt agagatgtaa agtctcaagt tatcaagatc 1680
tggctggact tattgaaatc aatgttaact gaagctcaat ggtcttcaaa caagtctgtt 1740
cctaccctag atgagtatat gacaaccgcc catgtttcat tcgcacttgg tccaattgta 1800
cttccagcct tatacttcgt tggcccaaag ttgtcagaag aggttgcagg tcatcctgaa 1860
ctactaaacc tctacaaagt cacatctact tgtggcagac tactgaatga ttggagaagt 1920
tttaagagag aatccgagga aggtaagctc aacgctatta gtttatacat gatccactcc 1980

TABLE 11-continued

Sequences disclosed herein.

```
ggtggtgctt ctacagaaga ggaaacaatc gaacatttca aaggtttgat tgattctcag  2040
agaaggcaac tgttacaatt ggtgttgcaa gagaaggata gtatcatacc tagaccatgt  2100
aaagatctat tttggaatat gattaagtta ttacacactt tctacatgaa agatgatggc  2160
ttcacctcaa atgagatgag gaatgtagtt aaggcaatca ttaacgaacc aatctcactg  2220
gatgaattat ga                                                     2232
```

SEQ ID NO: 50

```
MSCIRPWFCP SSISATLTDP ASKLVTGEFK TTSLNFHGTK ERIKKMFDKI ELSVSSYDTA    60
WVAMVPSPDC PETPCFPECT KWILENQLGD GSWSLPHGNP LLVKDALSST LACILALKRW   120
GIGEEQINKG LRFIELNSAS VTDNEQHKPI GFDIIFPGMI EYAKDLDLNL PLKPTDINSM   180
LHRRALELTS GGGKNLEGRR AYLAYVSEGI GKLQDWEMAM KYQRKNGSLF NSPSTTAAAF   240
IHIQDAECLH YIRSLLQKFG NAVPTIYPLD IYARLSMVDA LERLGIDRHF RKERKFVLDE   300
TYRFWLQGEE EIFSDNATCA LAFRILRLNG YDVSLEDHFS NSLGGYLKDS GAALELYRAL   360
QLSYPDESLL EKQNSRTSYF LKQGLSNVSL CGDRLRKNII GEVHDALNFP DHANLQRLAI   420
RRRIKHYATD DTRILKTSYR CSTIGNQDFL KLAVEDFNIC QSIQREEFKH IERWVVERRL   480
DKLKFARQKE AYCYFSAAAT LFAPELSDAR MSWAKNGVLT TVVDDFFDVG GSEEELVNLI   540
ELIERWDVNG SADFCSEEVE IIYSAIHSTI SEIGDKSFGW QGRDVKSHVI KIWLDLLKSM   600
LTEAQWSSNK SVPTLDEYMT TAHVSFALGP IVLPALYFVG PKLSEEVAGH PELLNLYKVM   660
STCGRLLNDW RSFKRESEEG KLNAISLYMI HSGGASTEEE TIEHFKGLID SQRRQLLQLV   720
LQEKDSIIPR PCKDLFWNMI KLLHTFYMKD DGFTSNEMRN VVKAIINEPI SLDEL        775
```

SEQ ID NO: 51

*A. thaliana*

```
atgtctatca accttcgctc ctccggttgt tcgtctccga tctcagctac tttggaacga    60
ggattggact cagaagtaca gacaagagct aacaatgtga gctttgagca aacaaaggag   120
aagattagga agatgttgga gaaagtggag ctttctgttt cggcctacga tactagttgg   180
gtagcaatgg ttccatcacc gagctcccaa aatgctccac ttttcccaca gtgtgtgaaa   240
tggttattgg ataatcaaca tgaagatgga tcttggggac ttgataacca tgaccatcaa   300
tctcttaaga aggatgtgtt atcatctaca ctggctagta tcctcgcgtt aaagaagtgg   360
ggaattggtg aaagacaaat aaacaagggt ctccagttta ttgagctgaa ttctgcatta   420
gtcactgatg aaaccataca gaaaccaaca gggtttgata ttatatttcc tgggatgatt   480
aaatatgcta gagatttgaa tctgacgatt ccattgggct cagaagtggt ggatgacatg   540
atacgaaaaa gagatctgga tcttaaatgt gatagtgaaa agttttcaaa gggaagagaa   600
gcatatctgg cctatgtttt agaggggaca agaaacctaa aagattggga tttgatagtc   660
aaatatcaaa ggaaaaatgg gtcactgttt gattctccag ccacaacagc agctgctttt   720
actcagtttg ggaatgatgg ttgtctccgt tatctctgtt ctctccttca gaaattcgag   780
gctgcagttc cttcagttta tccatttgat caatatgcac gccttagtat aattgtcact   840
cttgaaagct taggaattga tagagatttc aaaaccgaaa tcaaaagcat attggatgaa   900
acctatagat attggcttcg tggggatgaa gaaatatgtt tggacttggc cacttgtgct   960
ttggctttcc gattattgct tgctcatggc tatgatgtgt cttacgatcc gctaaaacca  1020
tttgcagaag aatctggttt ctctgatact ttggaaggat atgttaagaa tacgtttttct 1080
gtgttagaat tatttaaggc tgctcaaagt tatccacatg aatcagcttt gaagaagcag  1140
tgttgttgga ctaaacaata tctggagatg gaattgtcca gctgggttaa gacctctgtt  1200
cgagataaat acctcaagaa agaggtcgag gatgctcttg cttttccctc ctatgcaagc  1260
ctagaaagat cagatcacag gagaaaaata ctcaatggtt ctgctgtgga aaacaccaga  1320
gttacaaaaa cctcatatcg tttgcacaat atttgcacct ctgatatcct gaagttagct  1380
gtggatgact tcaatttctg ccagtccata caccgtgaag aaatggaacg tcttgatagg  1440
tggattgtgg agaatagatt gcaggaactg aaatttgcca gacagaagct ggcttactgt  1500
tatttctctg ggctgcaac tttattttct ccagaactat ctgatgctcg tatatcgtgg   1560
gccaaaggtg gagtacttac aacggttgta gacgacttct ttgatgttgg agggtccaaa  1620
gaagaactgg aaaacctcat acacttggtc gaaaagtggg atttgaacgg tgttcctgag  1680
tacagctcag aacatgttga gatcatattc tcagttctaa gggacaccat tctcgaaaca  1740
ggagacaaag cattcaccta tcaaggacgc aatgtgacac accacattgt gaaaatttgg  1800
ttggatctgc tcaagtctat gttgagagaa gccgagtggt ccagtgacaa gtcaacacca  1860
agcttggagg attacatgga aaatgcgtac atatcatttg cattaggacc aattgtcctc  1920
ccagctacct atctgatcgg acctccactt ccagagaaga cagtcgatag ccaccaatat  1980
aatcagctct acaagctcgt gagcactatg ggtcgtcttc taaatgacat acaaggtttt  2040
aagagagaaa gcgcggaagg gaagctgaat gcggtttcat tgcacatgaa acacgagaga  2100
gacaatcgca gcaaagaagt gatcatagaa tcgatgaaag gtttagcaga gagaaagagg  2160
gaagaattgc ataagctagt tttggaggag aaaggaagtg tggttccaag ggaatgcaaa  2220
gaagcgttct tgaaaatgag caaagtgttg aacttatttt acaggaagga cgatggattc  2280
acatcaaatg atctgatgag tcttgttaaa tcagtgatct acgagcctgt tagcttacag  2340
aaagaatctt taacttga                                               2358
```

SEQ ID NO: 52

*A. thaliana*

```
MSINLRSSGC SSPISATLER GLDSEVQTRA NNVSFEQTKE KIRKMLEKVE LSVSAYDTSW    60
VAMVPSPSSQ NAPLFPQCVK WLLDNQHEDG SWGLDNHDHQ SLKKDVLSST LASILALKKW   120
GIGERQINKG LQFIELNSAL VTDETIQKPT GFDIIFPGMI KYARDLNLTI PLGSEVVDDM   180
IRKRDLDLKC DSEKFSKGRE AYLAYVLEGT RNLKDWDLIV KYQRKNGSLF DSPATTAAAF   240
TQFGNDGCLR YLCSLLQKFE AAVPSVYPFD QYARLSIIVT LESLGIDRDF KTEIKSILDE   300
TYRYWLRGDE EICLDLATCA LAFRLLLAHG YDVSYDPLKP FAEESGFSDT LEGYVKNTFS   360
VLELFKAAQS YPHESALKKQ CCWTKQYLEM ELSSWVKTSV RDKYLKKEVE DALAFPSYAS   420
LERSDHRRKI LNGSAVENTR VTKTSYRLHN ICTSDILKLA VDDFNFCQSI HREEMERLDR   480
WIVENRLQEL KFARQKLAYC YFSGAATLFS PELSDARISW AKGGVLTTVV DDFFDVGGSK   540
EELENLIHLV EKWDLNGVPE YSSEHVEIIF SVLRDTILET GDKAFTYQGR NVTHHIVKIW   600
LDLLKSMLRE AEWSSDKSTP SLEDYMENAY ISFALGPIVL PATYLIGPPL PEKTVDSHQY   660
NQLYKLVSTM GRLLNDIQGF KRESAEGKLN AVSLHMKHER DNRSKEVIIE SMKGLAERKR   720
```

TABLE 11-continued

| Sequences disclosed herein. |
|---|
| EELHKLVLEE KGSVVPRECK EAFLKMSKVL NLFYRKDDGF TSNDLMSLVK SVIYEPVSLQ 780 |
| KESLT 785 |
| |
| SEQ ID NO: 53 |
| atggaatttg atgaaccatt ggttgacgaa gcaagatctt tagtgcagcg tactttacaa 60 |
| gattatgatg acagatacgg cttcggtact atgtcatgtg ctgcttatga tacagcctgg 120 |
| gtgtctttag ttacaaaaac agtcgatggg agaaaacaat ggcttttccc agagtgtttt 180 |
| gaatttctac tagaaacaca atctgatgcc ggaggatggg aaatcgggaa ttcagcacca 240 |
| atcgacggta tattgaatac agctgcatcc ttacttgctc taaaacgtca cgttcaaact 300 |
| gagcaaatca tccaacctca acatgaccat aaggatctag caggtagagc tgaacgtgcc 360 |
| gctgcatctt tgagagcaca attggctgca ttggatgtgt ctacaactga acacgtcggt 420 |
| tttgagataa ttgttcctgc aatgctagac ccattagaag ccgaagatcc atctctagtt 480 |
| ttcgattttc cagctaggaa acctttgatg aagattcatg atgctaagat gagtagattc 540 |
| aggccagaat acttgtatgg caaacaacca atgaccgcct tacattcatt agaggctttc 600 |
| ataggcaaaa tcgacttcga taaggtaaga caccaccgta cccatgggtc tatgatgggt 660 |
| tctccttcat ctaccgcagc ctacttaatg cacgcttcac aatgggatgg tgactcagag 720 |
| gcttacctta gacacgtgat taaacacgca gcagggcagg gaactggtgc tgtaccatct 780 |
| gctttcccat caacacattt tgagtcatct tggattctta ccacattgtt tagagctgga 840 |
| ttttcagctt ctcatcttgc ctgtgatgag ttgaacaagt tggtcgagat acttgagggc 900 |
| tcattcgaga aggaaggtgg ggcaatcggt tacgctccag ggtttcaagc agatgttgat 960 |
| gatactgcta aaacaataag tacattagca gtccttggaa gagatgctac accaagacaa 1020 |
| atgatcaagg tatttgaagc taatacacat tttagaacat accctggtga aagagatcct 1080 |
| tctttgacag ctaattgtaa tgctctatca gccttactac accaaccaga tgcagcaatg 1140 |
| tatggatctc aaattcaaaa gattaccaaa tttgtctgtg actattggtg gaagtctgat 1200 |
| ggtaagatta aagataagtg gaacacttgc tacttgtacc catctgtctt attagttgag 1260 |
| gttttggttg atcttgttag tttattggag cagggtaaat tgcctgatgt tttggatcaa 1320 |
| gagcttcaat acagagtcgc catcacattg ttccaagcat gtttaaggcc attactagac 1380 |
| caagatgccg aaggatcatg gaacaagtct atcgaagcca cagcctacgg catccttatc 1440 |
| ctaactgaag ctaggagagt ttgtttcttc gacagattgt ctgagccatt gaatgaggca 1500 |
| atccgtagag gtatcgcttt cgccgactct atgtctggaa ctgaagctca gttgaactac 1560 |
| atttggatcg aaaaggttag ttacgcacct gcattattga ctaaatccta tttgttagca 1620 |
| gcaagatggg ctgctaagtc tcctttaggc gcttccgtag gctcttcttt gtggactcca 1680 |
| ccaagagaag gattggataa gcatgtcaga ttattccatc aagctgagtt attcagatcc 1740 |
| cttccagaat gggaattaag agcctccatg attgaagcag ctttgttcac accacttcta 1800 |
| agagcacata gactagacgt tttccctaga caagatgtag gtgaagacaa atatcttgat 1860 |
| gtagttccat tcttttggac tgccgctaac aacagagata gaacttacgc ttccactcta 1920 |
| ttcctttacg atatgtgttt tatcgcaatg ttaaacttcc agttagacga attcatggag 1980 |
| gccacagccg gtatcttatt cagagatcat atggatgatt tgaggcaatt gattcatgat 2040 |
| cttttggcag agaaaacttc cccaaagagt tctggtagaa gtagtcaggg cacaaaagat 2100 |
| gctgactcag gtatagagga agacgtgtca atgtccgatt cagcttcaga ttcccaggat 2160 |
| agaagtccag aatacgactt ggttttcagt gcattgagta cctttacaaa acatgtcttg 2220 |
| caacacccat ctatacaaag tgcctctgta tgggatagaa aactacttgc tagagagatg 2280 |
| aaggcttact tacttgctca tatccaacaa gcagaagatt caactccatt gtctgaattg 2340 |
| aaagatgtgc ctcaaaagac tgatgtaaca agagtttcta catctactac taccttcttt 2400 |
| aactgggtta gaacaacttc cgcagaccat atatcctgcc catactcctt ccactttgta 2460 |
| gcatgccatc taggcgcagc attgtcacct aaagggtcta acggtgattg ctatccttca 2520 |
| gctggtgaga agttcttggc agctgcagtc tgcagacatt tggccaccat gtgtagaatg 2580 |
| tacaacgatc ttggatcagc tgaacgtgat tctgatgaag gtaatttgaa ctccttggac 2640 |
| ttccctgaat tcgccgattc cgcaggaaac ggagggatag aaattcagaa ggccgctcta 2700 |
| ttaaggttag ctgagtttga gagagattca tacttagagg ccttccgtcg tttacaagat 2760 |
| gaatccaata gagttcacgg tccagccggt ggtgatgaag ccagattgtc cagaaggaga 2820 |
| atggcaatcc ttgaattctt cgcccagcag gtagatttgt acggtcaagt atacgtcatt 2880 |
| agggatattt ccgctcgtat tcctaaaaac gaggttgaga aaaagagaaa attggatgat 2940 |
| gctttcaatt ga 2952 |
| |
| SEQ ID NO: 54 |
| MEFDEPLVDE ARSLVQRTLQ DYDDRYGFGT MSCAAYDTAW VSLVTKTVDG RKQWLFPECF 60 |
| EFLLETQSDA GGWEIGNSAP IDGILNTAAS LLALKRHVQT EQIIQPQHDH KDLAGRAERA 120 |
| AASLRAQLAA LDVSTTEHVG FEIIVPAMLD PLEAEDPSLV FDFPARKPLM KIHDAKMSRF 180 |
| RPEYLYGKQP MTALHSLEAF IGKIDFDKVR HHRTHGSMMG SPSSTAAYLM HASQWDGDSE 240 |
| AYLRHVIKHA AGQGTGAVPS AFPSTHFESS WILTTLFRAG FSASHLACDE LNKLVEILEG 300 |
| SFEKEGGAIG YAPGFQADVD DTAKTISTLA VLGRDATPRQ MIKVFEANTH FRTYPGERDP 360 |
| SLTANCNALS ALLHQPDAAM YGSQIQKITK FVCDYWWKSD GKIKDKWNTC YLYPSVLLVE 420 |
| VLVDLVSLLE QGKLPDVLDQ ELQYRVAITL FQACLRPLLD QDAEGSWNKS IEATAYGILI 480 |
| LTEARRVCFF DRLSEPLNEA IRRGIAFADS MSGTEAQLNY IWIEKVSYAP ALLTKSYLLA 540 |
| ARWAAKSPLG ASVGSSLWTP PREGLDKHVR LFHQAELFRS LPEWELRASM IEAALFTPLL 600 |
| RAHRLDVFPR QDVGEDKYLD VVPFFWTAAN NRDRTYASTL FLYDMCFIAM LNFQLDEFME 660 |
| ATAGILFRDH MDDLRQLIHD LLAEKTSPKS SGRSSQGTKD ADSGIEEDVS MSDSASDSQD 720 |
| RSPEYDLVFS ALSTFTKHVL QHPSIQSASV WDRKLLAREM KAYLLAHIQQ AEDSTPLSEL 780 |
| KDVPQKTDVT RVSTSTTTFF NWVRTTSADH ISCPYSFHFV ACHLGAALSP KGSNGDCYPS 840 |
| AGEKFLAAAV CRHLATMCRM YNDLGSAERD SDEGNLNSLD FPEFADSAGN GGIEIQKAAL 900 |
| LRLAEFERDS YLEAFRRLQD ESNRVHGPAG GDEARLSRRR MAILEFFAQQ VDLYGQVYVI 960 |
| RDISARIPKN EVEKKRKLDD AFN 983 |
| |
| SEQ ID NO: 55 |
| atggcttcta gtacacttat ccaaaacaga tcatgtggcg tcacatcatc tatgtcaagt 60 |
| tttcaaatct tcagaggtca accactaaga tttcctggca ctagaacccc agctgcagtt 120 |
| caatgcttga aaaagaggag atgccttagg ccaaccgaat ccgtactaga atcatctcct 180 |

TABLE 11-continued

Sequences disclosed herein.

```
ggctctggtt catatagaat agtaactggc ccttctggaa ttaaccctag ttctaacggg   240
cacttgcaag agggttcctt gactcacagg ttaccaatac caatggaaaa atctatcgat   300
aacttccaat ctactctata tgtgtcagat atttggtctg aaacactaca gagaactgaa   360
tgtttgctac aagtaactga aaacgtccag atgaatgagt ggattgagga aattagaatg   420
tactttagaa atatgacttt aggtgaaatt tccatgtccc cttacgacac tgcttgggtg   480
gctagagttc cagcgttgga cggttctcat gggcctcaat tccacagatc tttgcaatgg   540
attatcgaca accaattacc agatggggac tggggcgaac cttctctttt cttgggttac   600
gatagagttt gtaatacttt agcctgtgtg attgcgttga aaacatgggg tgttggggca   660
caaaacgttg aaagaggaat tcagttccta caatctaaca tatacaagat ggaggaagat   720
gacgctaatc atatgccaat aggattcgaa atcgtattcc ctgctatgat ggaagatgcc   780
aaagcattag gtttggattt gccatacgat gctactattt tgcaacagat ttcagccgaa   840
agagagaaaa agatgaaaaa gatcccaatg gcaatggtgt acaaataccc aaccacttta   900
cttcactcct tagaaggctt gcatagagaa gttgattgga ataagttgtt acaattacaa   960
tctgaaaatg gtagttttct ttattcacct gcttcaaccg catgcgcctt aatgtacact  1020
aaggacgtta aatgtttttga ttacttaaac cagttgttga tcaagttcga ccacgcatgc  1080
ccaaatgtat atccagtcga tctattcgaa agattatgga tggttgacag attgcagaga  1140
ttagggatct ccagatactt tgaaagagag attagagatt gtttacaata cgtctacaga  1200
tattggaaag attgtggaat cggatgggct tctaactctt ccgtacaaga tgttgatgat  1260
acagccatgg cgtttagact tttaaggact catggtttcg acgtaaagga agattgcttt  1320
agacagtttt tcaaggacgg agaattcttc tgcttcgcag gccaatcatc tcaagcagtt  1380
acaggcatgt ttaatctttc aagagccagt caaacattgt ttccaggaga atctttattg  1440
aaaaaggcta gaaccttctc tagaaacttc ttgagaacaa agcatgagaa caacgaatgt  1500
ttcgataaat ggatcattac taaagatttg gctggtgaag tcgagtataa cttgaccttc  1560
ccatggtatg cctctttgcc tagattagaa cataggacat acttagatca atatggaatc  1620
gatgatatct ggataggcaa atctttatac aaaatgcctg ctgttaccaa cgaagttttc  1680
ctaaagttgg caaaggcaga ctttaacatg tgtcaagctc tacacaaaaa ggaattggaa  1740
caagtgataa agtggaacgc gtcctgtcaa ttcagagatc ttgaattcgc cagacaaaaa  1800
tcagtagaat gctattttgc tggtgcagcc acaatgttcg aaccagaaat ggttcaagct  1860
agattagtct gggcaagatg ttgtgtattg acaactgtct tagacgatta ctttgaccac  1920
gggacacctg ttgaggaact tagagtgttt gttcaagctg tcagaacatg gaatccagag  1980
ttgatcaacg gtttgccaga gcaagctaaa atcttgttta tgggcttata caaaaacagtt 2040
aacacaattg cagaggaagc attcatggca cagaaaagag acgtccatca tcatttgaaa  2100
cactattggg acaagttgat aacaagtgcc ctaaaggagg ccgaatgggc agagtcaggt  2160
tacgtcccaa catttgatga atacatggaa gtagctgaaa tttctgttgc tctagaacca  2220
attgtctgta gtaccttgtt ctttgcgggt catagactag atgaggatgt tctagatagt  2280
tacgattacc atctagttat gcatttggta aacagagtcg gtagaatctt gaatgatata  2340
caaggcatga agagggaggc ttcacaaggt aagatctcat cagttcaaat ctacatggag  2400
gaacatccat ctgttccatc tgaggccatg gcgatcgctc atcttcaaga gttagttgat  2460
aattcaatgc agcaattgac atacgaagtt cttaggttca ctgcggttcc aaaaagttgt  2520
aagagaatcc acttgaatat ggctaaaatc atgcatgcct tctacaagga tactgatgga  2580
ttctcatccc ttactgcaat gacaggattc gtcaaaaagg ttcttttcga acctgtgcct  2640
gagtaa                                                             2646

SEQ ID NO: 56
MASSTLIQNR SCGVTSSMSS FQIFRGQPLR FPGTRTPAAV QCLKKRRCLR PTESVLESSP    60
GSGSYRIVTG PSGINPSSNG HLQEGSLTHR LPIPMEKSID NFQSTLYVSD IWSETLQRTE   120
CLLQVTENVQ MNEWIEEIRM YFRNMTLGEI SMSPYDTAWV ARVPALDGSH GPQFHRSLQW   180
IIDNQLPDGD WGEPSLFLGY DRVCNTLACV IALKTWGVGA QNVERGIQFL QSNIYKMEED   240
DANHMPIGFE IVFPAMMEDA KALGLDLPYD ATILQQISAE REKKMKKIPM AMVYKYPTTL   300
LHSLEGLHRE VDWNKLLQLQ SENGSFLYSP ASTACALMYT KDVKCFDYLN QLLIKFDHAC   360
PNVYPVDLFE RLWMVDRLQR LGISRYFERE IRDCLQYVYR YWKDCGIGWA SNSSVQDVDD   420
TAMAFRLLRT HGFDVKEDCF RQFFKDGEFF CFAGQSSQAV TGMFNLSRAS QTLFPGESLL   480
KKARTFSRNF LRTKHENNEC FDKWIITKDL AGEVEYNLTF PWYASLPRLE HRTYLDQYGI   540
DDIWIGKSLY KMPAVTNEVF LKLAKADFNM CQALHKKELE QVIKWNASCQ FRDLEFARQK   600
SVECYFAGAA TMFEPEMVQA RLVWARCCVL TTVLDDYFDH GTPVEELRVF VQAVRTWNPE   660
LINGLPEQAK ILFMGLYKTV NTIAEEAFMA QKRDVHHHLK HYWDKLITSA LKEAEWAESG   720
YVPTFDEYME VAEISVALEP IVCSTLFFAG HRLDEDVLDS YDYHLVMHLV NRVGRILNDI   780
QGMKREASQG KISSVQIYME EHPSVPSEAM AIAHLQELVD NSMQQLTYEV LRFTAVPKSC   840
KRIHLNMAKI MHAFYKDTDG FSSLTAMTGF VKKVLFEPVP E                       881

SEQ ID NO: 57
atgcctggta aaattgaaaa tggtacccca aaggacctca agactggaaa tgattttgtt    60
tctgctgcta agagtttact agatcgagct ttcaaaagtc atcattccta ctacggatta   120
tgctcaactt catgtcaagt ttatgataca gcttgggttg caatgattcc aaaaacaaga   180
gataatgtaa aacagtggtt gtttccagaa tgtttccatt acctcttaaa aacacaagcc   240
gcagatggct catggggttc attgcctaca acacagacag cgggtatcct agatacagcc   300
tcagctgtgc tggcattatt gtgccacgca caagagcctt tacaaatatt ggatgtatct   360
ccagatgaaa tggggttgag aatagaacac ggtgtcacat ccttgaaacg tcaattagca   420
gtttggaatg atgtggagga caccaaccat attggcgtcg agtttatcat accagcctta   480
ctttccatgc tagaaaagga attagatgtt ccatcttttg aatttccatg taggtccatc   540
ttagagagaa tgcacgggga gaaattaggt catttcgacc tggaacaagt ttacggcaag   600
ccaagctcat tgttgcactc attggaagca tttctcggta agctagattt tgatcgacta   660
tcacatcacc tataccacgg cagtatgatg gcatctccat cttcaacggc tgcttatctt   720
attggggcta caaaatggga tgacgaagcc gaagattacc taagacatgt aatgcgtaat   780
ggtgcaggac atgggaatgg aggtatttct ggtacatttc caactactca tttcgaatgt   840
agctggatta tagcaacgtt gttaaaggtt ggctttactt tgaagcaaat tgacggcgat   900
ggcttaagag gtttatcaac catcttactt gaggcgcttc gtgatgagaa tggtgtcata   960
ggctttgccc ctagaacagc agatgtagat gacacagcca aagctctatt ggccttgtca  1020
```

TABLE 11-continued

| Sequences disclosed herein. |
|---|
| ttggtaaacc agccagtgtc acctgatatc atgattaagg tctttgaggg caaagaccat 1080 |
| tttaccactt ttggttcaga aagagatcca tcattgactt ccaacctgca cgtcctttta 1140 |
| tctttactta aacaatctaa cttgtctcaa taccatcctc aaatcctcaa aacaacatta 1200 |
| ttcacttgta gatggtggtg gggttccgat cattgtgtca aagacaaatg gaatttgagt 1260 |
| cacctatatc caactatgtt gttggttgaa gccttcactg aagtgctcca tctcattgac 1320 |
| ggtggtgaat tgtctagtct gtttgatgaa tcctttaagt gtaagattgg tcttagcatc 1380 |
| tttcaagcgg tacttagaat aatcctcacc caagacaacg acggctcttg gagaggatac 1440 |
| agagaacaga cgtgttacgc aatattggct ttagttcaag cgagacatgt atgctttttc 1500 |
| actcacatgg ttgacagact gcaatcatgt gttgatcgag gtttctcatg gttgaaatct 1560 |
| tgctcttttc attctcaaga cctgacttgg acctctaaaa cagcttatga agtgggtttc 1620 |
| gtagctgaag catataaact agctgcttta caatctgctt ccctggaggt tcctgctgcc 1680 |
| accattggac attctgtcac gtctgccgtt ccatcaagtg atcttgaaaa atacatgaga 1740 |
| ttggtgagaa aaactgcgtt attctctcca ctggatgagt ggggtctaat ggcttctatc 1800 |
| atcgaatctt catttttcgt accattactg caggcacaaa gagttgaaat ataccctaga 1860 |
| gataatatca aggtggacga agataagtac ttgtctatta tcccattcac atgggtcgga 1920 |
| tgcaataata ggtctagaac tttcgcaagt aacagatggc tatacgatat gatgtacctt 1980 |
| tcattactcg gctatcaaac cgacgagtac atggaagctg tagctgggcc agtgtttggg 2040 |
| gatgtttcct tgttacatca aacaattgat aaggtgattg ataatacaat gggtaacctt 2100 |
| gcgagagcca atggaacagt acacagtggt aatggacatc agcacgaatc tcctaatata 2160 |
| ggtcaagtcg aggacacctt gactcgtttc acaaattcag tcttgaatca caaagacgtc 2220 |
| cttaactcta gctcatctga tcaagatact ttgagaagag agtttagaac attcatgcac 2280 |
| gctcatataa cacaaatcga agataactca cgattcagta agcaagcctc atccgatgcg 2340 |
| ttttcctctc ctgaacaatc ttactttcaa tgggtgaact caactggtgg ctcacatgtc 2400 |
| gcttgcgcct attcatttgc cttctctaat tgcctcatgt ctgcaaattt gttgcagggt 2460 |
| aaagacgcat ttccaagcgg aacgcaaaag tacttaatct cctctgttat gagacatgcc 2520 |
| acaaacatgt gtagaatgta taacgacttt ggctctattg ccagagacaa cgctgagaga 2580 |
| aatgttaata gtattcattt tcctgagttt actctctgta acggaacttc tcaaaaccta 2640 |
| gatgaaagga aggaaagact tctgaaaatc gcaacttacg aacaagggta tttggataga 2700 |
| gcactagagg ccttggaaag acagagtaga gatgatgccg gagacagagc tggatctaaa 2760 |
| gatatgagaa agttgaaaat cgttaagtta ttctgtgatg ttacggactt atacgatcag 2820 |
| ctctacgtta tcaaagattt gtcatcctct atgaagtaa 2859 |
| |
| SEQ ID NO: 58 |
| MPGKIENGTP KDLKTGNDFV SAAKSLLDRA FKSHHSYYGL CSTSCQVYDT AWVAMIPKTR 60 |
| DNVKQWLFPE CFHYLLKTQA ADGSWGSLPT TQTAGILDTA SAVLALLCHA QEPLQILDVS 120 |
| PDEMGLRIEH GVTSLKRQLA VWNDVEDTNH IGVEFIIPAL LSMLEKELDV PSFEFPCRSI 180 |
| LERMHGEKLG HFDLEQVYGK PSSLLHSLEA FLGKLDFDRL SHHLYHGSMM ASPSSTAAYL 240 |
| IGATKWDDEA EDYLRHVMRN GAGHGNGGIS GTFPTTHFEC SWIIATLLKV GFTLKQIDGD 300 |
| GLRGLSTILL EALRDENGVI GFAPRTADVD DTAKALLALS LVNQPVSPDI MIKVFEGKDH 360 |
| FTTFGSERDP SLTSNLHVLL SLLKQSNLSQ YHPQILKTTL FTCRWWWGSD HCVKDKWNLS 420 |
| HLYPTMLLVE AFTEVLHLID GGELSSLFDE SFKCKIGLSI FQAVLRIILT QDNDGSWRGY 480 |
| REQTCYAILA LVQARHVCFF THMVDRLQSC VDRGFSWLKS CSFHSQDLTW TSKTAYEVGF 540 |
| VAEAYKLAAL QSASLEVPAA TIGHSVTSAV PSSDLEKYMR LVRKTALFSP LDEWGLMASI 600 |
| IESSFFVPLL QAQRVEIYPR DNIKVDEDKY LSIIPFTWVG CNNRSRTFAS NRWLYDMMYL 660 |
| SLLGYQTDEY MEAVAGPVFG DVSLLHQTID KVIDNTMGNL ARANGTVHSG NGHQHESPNI 720 |
| GQVEDTLTRF TNSVLNHKDV LNSSSSDQDT LRREFRTFMH AHITQIEDNS RFSKQASSDA 780 |
| FSSPEQSYFQ WVNSTGGSHV ACAYSFAFSN CLMSANLLQG KDAFPSGTQK YLISSVMRHA 840 |
| TNMCRMYNDF GSIARDNAER NVNSIHFPEF TLCNGTSQNL DERKERLLKI ATYEQGYLDR 900 |
| ALEALERQSR DDAGDRAGSK DMRKLKIVKL FCDVTDLYDQ LYVIKDLSSS MK 952 |
| |
| SEQ ID NO: 59 |
| *S. rebaudiana* |
| atggatgctg tgacgggttt gttaactgtc ccagcaaccg ctataactat tggtggaact 60 |
| gctgtagcat tggcggtagc gctaatcttt tggtacctga aatcctacac atcagctaga 120 |
| agatcccaat caaatcatct tccaagagtg cctgaagtcc caggtgttcc attgttagga 180 |
| aatctgttac aattgaagga gaaaaagcca tacatgactt ttacgagatg ggcagcgaca 240 |
| tatggaccta tctatagtat caaaactggg gctacaagta tggttgtggt atcatctaat 300 |
| gagatagcca aggaggcatt ggtgaccaga ttccaatcca tatctacaag gaacttatct 360 |
| aaagccctga aagtacttac agcagataag acaatggtcg caatgtcaga ttatgatgat 420 |
| tatcataaaa cagttaagag acacatactg accgccgtct tgggtcctaa tgcacagaaa 480 |
| aagcatagaa ttcacagaga tatcatgatg gataacatat ctactcaact tcatgaattc 540 |
| gtgaaaaaca acccagaaca ggaagaggta gaccttagaa aaatctttca atctgagtta 600 |
| ttcggcttag ctatgagaca agccttagga aaggatgttg aaagtttgta cgttgaagac 660 |
| ctgaaaatca ctatgaatag agacgaaatc tttcaagtcc ttgttgttga tccaatgatg 720 |
| ggagcaatcg atgttgattg gagagacttc tttccatacc taaagtgggt cccaaacaaa 780 |
| aagttcgaaa atactattca acaaatgtac atcagaagag aagctgttat gaaatcttta 840 |
| atcaaagagc acaaaaagag aatagcgtca ggcgaaaagc taaatagtta tatcgattac 900 |
| cttttatctg aagctcaaac tttaaccgat cagcaactat tgatgtcctt gtgggaacca 960 |
| atcattgaat cttcagatac aacaatggtc acaacagaat gggcaatgta cgaattagct 1020 |
| aaaaacccta aattgcaaga taggttgtac agagacatta agtccgtctg tggatctgaa 1080 |
| aagataaccg aagagcatct atcacagctg ccttacatta cagctatttt ccacgaaaca 1140 |
| ctgagaagac actcaccagt tcctatcatt cctctaagac atgtacatga agataccgtt 1200 |
| ctaggcggct accatgttcc tgctggcaca gaacttgccg ttaacatcta cggttgcaac 1260 |
| atggacaaaa acgtttggga aaatccagag gaatggaacc cagaaagatt catgaaagag 1320 |
| aatgagacaa ttgattttca aaagacgatg gccttcggtg gtggtaagag agtttgtgct 1380 |
| ggttccttgc aagccctttt aactgcatct attgggattg ggagaatggt tcaagagttc 1440 |
| gaatggaaac tgaaggatat gactcaagag gaagtgaaca cgataggcct aactacacaa 1500 |
| atgttaagac cattgagagc tattatcaaa cctaggatct aa 1542 |

TABLE 11-continued

Sequences disclosed herein.

SEQ ID NO: 60
*S. rebaudiana*
MDAVTGLLTV PATAITIGGT AVALAVALIF WYLKSYTSAR RSQSNHLPRV PEVPGVPLLG 60
NLLQLKEKKP YMTFTRWAAT YGPIYSIKTG ATSMVVVSSN EIAKEALVTR FQSISTRNLS 120
KALKVLTADK TMVAMSDYDD YHKTVKRHIL TAVLGPNAQK KHRIHRDIMM DNISTQLHEF 180
VKNNPEQEEV DLRKIFQSEL FGLAMRQALG KDVESLYVED LKITMNRDEI FQVLVVDPMM 240
GAIDVDWRDF FPYLKWVPNK KFENTIQQMY IRREAVMKSL IKEHKKRIAS GEKLNSYIDY 300
LLSEAQTLTD QQLLMSLWEP IIESSDTTMV TTEWAMYELA KNPKLQDRLY RDIKSVCGSE 360
KITEEHLSQL PYITAIFHET LRRHSPVPII PLRHVHEDTV LGGYHVPAGT ELAVNIYGCN 420
MDKNVWENPE EWNPERFMKE NETIDFQKTM AFGGGKRVCA GSLQALLTAS IGIGRMVQEF 480
EWKLKDMTQE EVNTIGLTTQ MLRPLRAIIK PRI 513

SEQ ID NO: 61
aagcttacta gtaaaatgga cggtgtcatc gatatgcaaa ccattccatt gagaaccgct 60
attgctattg gtggtactgc tgttgctttg gttgttgcat tatacttttg gttcttgaga 120
tcctacgctt ccccatctca tcattctaat catttgccac cagtacctga agttccaggt 180
gttccagttt tgggtaattt gttgcaattg aaagaaaaaa agccttacat gaccttcacc 240
aagtgggctg aaatgtatgg tccaatctac tctattagaa ctggtgctac ttccatggtt 300
gttgtctctt ctaacgaaat cgccaaagaa gttgttgtta ccagattccc atctatctct 360
accagaaaat tgtcttacgc cttgaaggtt ttgaccgaag ataagtctat ggttgccatg 420
tctgattatc acgattacca taagaccgtc aagagacata ttttgactgc tgttttgggt 480
ccaaacgccc aaaaaaagtt tagagcacat agagacacca tgatggaaaa cgtttccaat 540
gaattgcatg ccttcttcga aaagaaccca aatcaagaag tcaacttgag aaagatcttc 600
caatcccaat tattcggttt ggctatgaag caagccttgg gtaaagatgt tgaatccatc 660
tacgttaagg atttggaaac caccatgaag agagaagaaa tcttcgaagt tttggttgtc 720
gatccaatga tgggtgctat tgaagttgat tggagagact tttcccata cttgaaatgg 780
gttccaaaca agtccttcga aaacatcatc catagaatgt acactagaag agaagctgtt 840
atgaaggcct tgatccaaga acacaagaaa agaattgcct ccggtgaaaa cttgaactcc 900
tacattgatt acttgttgtc tgaagcccaa accttgaccg ataagcaatt attgatgtct 960
ttgtgggaac ctattatcga atcttctgat accactatgg ttactactga atgggctatg 1020
tacgaattgg ctaagaatcc aaacatgcaa gacagattat acgaagaaat ccaatccgtt 1080
tgcggttccg aaaagattac tgaagaaaac ttgtcccaat tgccatactt gtacgctgtt 1140
ttccaagaaa ctttgagaaa gcactgtcca gttcctatta tgccattgag atatgttcac 1200
gaaaacaccg ttttgggtgg ttatcatgtt ccagctggta ctgaagttgc tattaacatc 1260
tacggttgca acatggataa gaaggtctgg gaaaatccag aagaatggaa tccagaaaga 1320
ttcttgtccg aaaaagaatc catggacttg tacaaaacta tggcttttgg tggtggtaaa 1380
agagtttgcg ctggtcttct acaagccatg gttatttctt gcattggtat cggtagattg 1440
gtccaagatt ttgaatggaa gttgaaggat gatgccgaag aagatgttaa cactttgggt 1500
ttgactaccc aaaagttgca tccattattg gccttgatta acccaagaaa gtaactcgag 1560
ccgcgg 1566

SEQ ID NO: 62
MDGVIDMQTI PLRTAIAIGG TAVALVVALY FWFLRSYASP SHHSNHLPPV PEVPGVPVLG 60
NLLQLKEKKP YMTFTKWAEM YGPIYSIRTG ATSMVVVSSN EIAKEVVVTR FPSISTRKLS 120
YALKVLTEDK SMVAMSDYHD YHKTVKRHIL TAVLGPNAQK KFRAHRDTMM ENVSNELHAF 180
FEKNPNQEVN LRKIFQSQLF GLAMKQALGK DVESIYVKDL ETTMKREEIF EVLVVDPMMG 240
AIEVDWRDFF PYLKWVPNKS FENIIHRMYT RREAVMKALI QEHKKRIASG ENLNSYIDYL 300
LSEAQTLTDK QLLMSLWEPI IESSDTTMVT TEWAMYELAK NPNMQDRLYE EIQSVCGSEK 360
ITEENLSQLP YLYAVFQETL RKHCPVPIMP LRYVHENTVL GGYHVPAGTE VAINIYGCNM 420
DKKVWENPEE WNPERFLSEK ESMDLYKTMA FGGGKRVCAG SLQAMVISCI GIGRLVQDFE 480
WKLKDDAEED VNTLGLTTQK LHPLLALINP RK 512

SEQ ID NO: 63
*R. suavissimus*
atggccaccc tccttgagca tttccaagct atgccctttg ccatccctat tgcactggct 60
gctctgtctt ggctgttcct cttttacatc aaagtttcat tcttttccaa caagagtgct 120
caggctaagc tccctcctgt gccagtggtt cctgggctgc cggtgattgg gaatttactg 180
caactcaagg agaagaaacc ctaccagact tttacaaggt gggctgagga gtatggacca 240
atctattcta tcaggactgg tgcttccacc atggtcgttc tcaataccac ccaagttgca 300
aaagaggcca tggtgaccag atatttatcc atctcaacca gaaagctatc aaacgcacta 360
aagattctta ctgctgataa atgtatggtt gcaataagtg actacaacga ttttcacaag 420
atgataaagc gatacatact ctcaaatgtt cttggaccta gtgctcagaa gcgtcaccgg 480
agcaacagag ataccttgag agctaatgtc tgcagccgat tgcattctca agtaaagaac 540
tctcctcgag aagctgtgaa tttcagaaga gtttttgagt gggaactctt tggaattgca 600
ttgaagcaag cctttggaaa ggacatagaa aagcccattt atgtggagga acttggcact 660
acactgtcaa gagatgagat ctttaaggtt ctagtgcttg acataatgga gggtgcaatt 720
gaggttgatt ggagagattt cttcccttac ctgagatgga ttccgaatac gcgcatggaa 780
acaaaaattc agcgactcta tttccgcagg aaagcagtga tgactgccct gatcaacgag 840
cagaagaagc gaattgcttc aggagaggaa atcaactgtt atatcgactt cttgcttaag 900
gaagggaaga cactgacaat ggaccaaata agtatgttgc tttgggagac ggttattgaa 960
acagcagata ctacaatggt aacgacagaa tgggctatgt atgaagttgc taaagactca 1020
aagcgtcagg atcgtctcta tcaggaaatc caaaaggttt gtggatcgga gatggttaca 1080
gaggaatact tgtcccaact gccgtacctg aatgcagttt tccatgaaac gctaaggaag 1140
cacagtccgg ctgcgttagt tcctttaaga tatgcacatg aagataccca actaggaggt 1200
tactacattc cagctggaac tgagattgct ataaacatat acgggtgtaa catggacaag 1260
catcaatggg aaagccctga ggaatggaaa ccggagagat tttggaccc gaaatttgat 1320
cctatggatt tgtacaagac catggctttt ggggctggaa agagggtatg tgctggttct 1380

TABLE 11-continued

| Sequences disclosed herein. |
| --- |
| cttcaggcaa tgttaatagc gtgcccgacg attggtaggc tggtgcagga gtttgagtgg 1440<br>aagctgagag atggagaaga agaaaatgta gatactgttg ggctcaccac tcacaaacgc 1500<br>tatccaatgc atgcaatcct gaagccaaga agtta 1535 |
| SEQ ID NO: 64<br>*R. suavissimus*<br>atggctacct tgttggaaca ttttcaagct atgccattcg ctattccaat tgctttggct 60<br>gctttgtctt ggttgttttt gttctacatc aaggtttctt tcttctccaa caaatccgct 120<br>caagctaaat tgccaccagt tccagttgtt ccaggtttgc cagttattgg taatttgttg 180<br>caattgaaag aaaagaagcc ataccaaacc ttcactagat gggctgaaga atatggtcca 240<br>atctactcta ttagaactgg tgcttctact atggttgtct tgaacactac tcaagttgcc 300<br>aaagaagcta tggttaccag atacttgtct atctctacca gaaagttgtc caacgccttg 360<br>aaaattttga ccgctgataa gtgcatggtt gccatttctg attacaacga tttccacaag 420<br>atgatcaaga gatatatctt gtctaacgtt ttgggtccat ctgcccaaaa aagacataga 480<br>tctaacagag ataccttgag agccaacgtt tgttctagat tgcattccca agttaagaac 540<br>tctccaagag aagctgtcaa ctttagaaga gttttcgaat gggaattatt cggtatcgct 600<br>ttgaaacaag ccttcggtaa ggatattgaa aagccaatct acgtcgaaga attgggtact 660<br>actttgtcca gagatgaaat cttcaaggtt ttggtcttgg acattatgga aggtgccatt 720<br>gaagttgatt ggagagattt tttcccatac ttgcgttgga ttccaaacac cagaatggaa 780<br>actaagatcc aaagattata ctttagaaga aaggccgtta tgaccgcctt gattaacgaa 840<br>caaaagaaaa gaattgcctc cggtgaagaa atcaactgct acatcgattt cttgttgaaa 900<br>gaaggtaaga ccttgaccat ggaccaaatc tctatgttgt tgtgggaaac cgttattgaa 960<br>actgctgata ccacaatggt tactactgaa tgggctatgt acgaagttgc taaggattct 1020<br>aaaagacaag acagattata ccaagaaatc caaaaggtct gcggttctga aatggttaca 1080<br>gaagaatact tgtcccaatt gccatacttg aatgctgttt tccacgaaac tttgagaaaa 1140<br>cattctccag ctgctttggt tccattgaga tatgctcatg aagatactca attgggtggt 1200<br>tattacattc cagccggtac tgaaattgcc attaacatct acggttgcaa catggacaaa 1260<br>caccaatggg aatctccaga agaatggaag ccagaaagat tttggatcc taagtttgac 1320<br>ccaatggact tgtacaaaac tatggctttt ggtgctggta aaagagtttg cgctggttct 1380<br>ttacaagcta tgttgattgc ttgtccaacc atcggtagat tggttcaaga atttgaatgg 1440<br>aagttgagag atggtgaaga agaaaacgtt gatactgttg gtttgaccac ccataagaga 1500<br>tatccaatgc atgctatttt gaagccaaga tcttaa 1536 |
| SEQ ID NO: 65<br>aagcttacta gtaaaatggc ctccatcacc catttcttac aagattttca agctactcca 60<br>ttcgctactg cttttgctgt tggtggtgtt tctttgttga tattcttctt cttcatccgt 120<br>ggtttccact ctactaagaa aaacgaatat tacaagttgc caccagttcc agttgttcca 180<br>ggtttgccag ttgttggtaa tttgttgcaa ttgaaagaaa agaagccata caagactttc 240<br>ttgagatggg ctgaaattca tggtccaatc tactctatta gaactggtgc ttctaccatg 300<br>gttgttgtta actctactca tgttgccaaa gaagctatgg ttaccagatt ctcttcaatc 360<br>tctaccagaa agttgtccaa ggctttggaa ttattgacct ccaacaaatc tatggttgcc 420<br>acctctgatt acaacgaatt tcacaagatg gtcaagaagt acatcttggc cgaattattg 480<br>ggtgctaatg ctcaaaagag acacagaatt catagagaca ccttgatcga aaacgtcttg 540<br>aacaaattgc atgcccatac caagaattct ccattgcaag ctgttaactt cagaaagatc 600<br>ttcgaatctg aattattcgg tttggctatg aagcaagcct tgggttatga tgttgattcc 660<br>ttgttcgttg aagaattggg tactaccttg tccagagaag aaatctacaa cgtttttggtc 720<br>agtgacatgt tgaagggtgc tattgaagtt gattggagag actttttccc atacttgaaa 780<br>tggatcccaa acaagtcctt cgaaatgaag attcaaagat tggcctctag aagacaagcc 840<br>gttatgaact ctattgtcaa agaacaaaag aagtccattg cctctggtaa gggtgaaaac 900<br>tgttacttga attacttgtt gtccgaagct aagactttga ccgaaaagca aatttccatt 960<br>ttggcctggg aaaccattat tgaaactgct gatacaactg ttgttaccac tgaatgggct 1020<br>atgtacgaat tggctaaaaa cccaaagcaa caagacagat tatacaacga aatccaaaac 1080<br>gtctgcggta ctgataagat taccgaagaa catttgtcca agttgcctta cttgtctgct 1140<br>gtttttcacg aaaccttgag aaagtattct ccatctccat tggttccatt gagatacgct 1200<br>catgaagata ctcaattggg tggttattat gttccagccg gtactgaaat tgctgttaat 1260<br>atctacggtt gcaacatgga caagaatcaa tgggaaactc cagaagaatg gaagccagaa 1320<br>agatttttgg acgaaaagta cgatccaatg gacatgtaca agactatgtc ttttggttcc 1380<br>ggtaaaagag tttgcgctgg ttctttacaa gctagtttga ttgcttgtac ctccatcggt 1440<br>agattggttc aagaatttga atggagattg aaagacggtg aagttgaaaa cgttgatacc 1500<br>ttgggtttga ctacccataa gttgtatcca atgcaagcta tcttgcaacc tagaaactga 1560<br>ctcgagccgc gg 1572 |
| SEQ ID NO: 66<br>MASITHFLQD FQATPFATAF AVGGVSLLIF FFFIRGFHST KKNEYYKLPP VPVVPGLPVV 60<br>GNLLQLKEKK PYKTFLRWAE IHGPIYSIRT GASTMVVVNS THVAKEAMVT RFSSISTRKL 120<br>SKALELLTSN KSMVATSDYN EFHKMVKKYI LAELLGANAQ KRHRIHRDTL IENVLNKLHA 180<br>HTKNSPLQAV NFRKIFESEL FGLAMKQALG YDVDSLFVEE LGTTLSREEI YNVLVSDMLK 240<br>GAIEVDWRDF FPYLKWIPNK SFEMKIQRLA SRRQAVMNSI VKEQKKSIAS GKGENCYLNY 300<br>LLSEAKTLTE KQISILAWET IIETADTTVV TTEWAMYELA KNPKQQDRLY NEIQNVCGTD 360<br>KITEEHLSKL PYLSAVFHET LRKYSPSPLV PLRYAHEDTQ LGGYYVPAGT EIAVNIYGCN 420<br>MDKNQWETPE EWKPERFLDE KYDPMDMYKT MSFGSGKRVC AGSLQASLIA CTSIGRLVQE 480<br>FEWRLKDGEV ENVDTLGLTT HKLYPMQAIL QPRN 514 |
| SEQ ID NO: 67<br>atgatttcct tgttgttggg ttttgttgtc tcctccttct tgtttatctt cttcttgaaa 60<br>aaattgttgt tcttcttcag tcgtcacaaa atgtccgaag tttctagatt gccatctgtt 120<br>ccagttccag gttttccatt gattggtaac ttgttgcaat tgaaagaaaa gaagccacac 180<br>aagactttca ccaagtggtc tgaattatat ggtccaatct actctatcaa gatgggttcc 240 |

TABLE 11-continued

Sequences disclosed herein.

```
tcttctttga tcgtcttgaa ctctattgaa accgccaaag aagctatggt cagtagattc   300
tcttcaatct ctaccagaaa gttgtctaac gctttgactg ttttgacctg caacaaatct   360
atggttgcta cctctgatta cgatgacttt cataagttcg tcaagagatg cttgttgaac   420
ggtttgttgg gtgctaatgc tcaagaaaga aaaagacatt acagagatgc cttgatcgaa   480
aacgttacct ctaaattgca tgcccatacc agaaatcatc cacaagaacc agttaacttc   540
agagccattt tcgaacacga attattcggt gttgctttga aacaagcctt cggtaaagat   600
gtcgaatcca tctatgtaaa agaattgggt gtcaccttgt ccagagatga aattttcaag   660
gttttggtcc acgacatgat ggaaggtgct attgatgttg attggagaga tttcttccca   720
tacttgaaat ggatcccaaa caactctttc gaagccagaa ttcaacaaaa gcacaagaga   780
agattggctg ttatgaacgc cttgatccaa gacagattga atcaaaacga ttccgaatcc   840
gatgatgact gctacttgaa tttcttgatg tctgaagcta agaccttgac catggaacaa   900
attgctattt tggtttggga aaccattatc gaaactgctg ataccacttt ggttactact   960
gaatgggcta tgtacgaatt ggccaaacat caatctgttc aagatagatt attcaaagaa  1020
atccaatccg tctgcggtgg tgaaaagatc aaagaagaac aattgccaag attgccttac  1080
gtcaatggtg tttttcacga aaccttgaga aagtattctc cagctccatt ggttccaatt  1140
agatacgctc atgaagatac ccaaattggt ggttatcata ttccagccgg ttctgaaatt  1200
gccattaaca tctacggttg caacatggat aagaagagat gggaaagacc tgaagaatgg  1260
tggccagaaa gatttttgga agatagatac gaatcctccg acttgcataa gactatggct  1320
tttggtgctg gtaaaagagt ttgtgctggt gctttacaag ctagtttgat ggctggtatt  1380
gctatcggta gattggttca agaattcgaa tggaagttga gagatggtga agaagaaaac  1440
gttgatactt acggtttgac ctcccaaaag ttgtatccat tgatggccat tatcaaccca  1500
agaagatctt aa                                                     1512

SEQ ID NO: 68
MASMISLLLG FVVSSFLFIF FLKKLLFFFS RHKMSEVSRL PSVPVPGFPL IGNLLQLKEK    60
KPHKTFTKWS ELYGPIYSIK MGSSSLIVLN SIETAKEAMV SRFSSISTRK LSNALTVLTC   120
NKSMVATSDY DDFHKFVKRC LLNGLLGANA QERKRHYRDA LIENVTSKLH AHTRNHPQEP   180
VNFRAIFEHE LFGVALKQAF GKDVESIYVK ELGVTLSRDE IFKVLVHDMM EGAIDVDWRD   240
FFPYLKWIPN NSFEARIQQK HKRRLAVMNA LIQDRLNQND SESDDDCYLN FLMSEAKTLT   300
MEQIAILVWE TIIETADTTL VTTEWAMYEL AKHQSVQDRL FKEIQSVCGG EKIKEEQLPR   360
LPYVNGVFHE TLRKYSPAPL VPIRYAHEDT QIGGYHIPAG SEIAINIYGC NMDKKRWERP   420
EEWWPERFLE DRYESSDLHK TMAFGAGKRV CAGALQASLM AGIAIGRLVQ EFEWKLRDGE   480
EENVDTYGLT SQKLYPLMAI INPRRS                                        506

SEQ ID NO: 69
aagcttacta gtaaaatgga catgatgggt attgaagctg ttccatttgc tactgctgtt    60
gttttgggtg gtatttcctt ggttgttttg atcttcatca gaagattcgt ttccaacaga   120
aagagatccg ttgaaggttt gccaccagtt ccagatattc caggtttacc attgattggt   180
aacttgttgc aattgaaaga aaagaagcca cataagacct ttgctagatg ggctgaaact   240
tacggtccaa ttttctctat tagaactggt gcttctacca tgatcgtctt gaattcttct   300
gaagttgcca aagaagctat ggtcactaga ttctcttcaa tctctaccag aaagttgtcc   360
aacgccttga agattttgac cttcgataag tgtatggttg ccacctctga ttacaacgat   420
tttcacaaaa tggtcaaggg tttcatcttg agaaacgttt taggtgctcc agcccaaaaa   480
agacatagat gtcatagaga taccttgatc gaaaacatct ctaagtactt gcatgcccat   540
gttaagactt ctccattgga accagttgtc ttgaagaaga ttttcgaatc cgaaattttc   600
ggtttggctt tgaaacaagc cttgggtaag gatatcgaat ccatctatgt tgaagaattg   660
ggtactacct tgtccagaga agaaattttt gccgttttgg ttgttgatcc aatggctggt   720
gctattgaag ttgattggag agatttttttc ccatacttgt cctggattcc aaacaagtct   780
atggaaatga agatccaaag aatggatttt agaagaggtg ctttgatgaa ggccttgatt   840
ggtgaacaaa agaaaagaat cggttccggt gaagaaaaga actcctacat tgatttcttg   900
ttgtctgaag ctaccacttt gaccgaaaag caaattgcta tgttgatctg ggaaaccatc   960
atcgaaattt ccgatacaac tttggttacc tctgaatggg ctatgtacga attggctaaa  1020
gacccaaata gacaagaaat cttgtacaga gaaatccaca aggtttgcgg ttctaacaag  1080
ttgactgaag aaaacttgtc caagttgcca tacttgaact ctgttttcca cgaaaccttg  1140
agaaagtatt ctccagctcc aatggttcca gttagatatg ctcatgaaga tactcaattg  1200
ggtggttacc atattccagc tggttctcaa attgccatta acatctacgg ttgcaacatg  1260
aacaaaaagc aatgggaaaa tcctgaagaa tggaagccag aaagattctt ggacgaaaag  1320
tatgacttga tggacttgca taagactatg gcttttggtg gtggtaaaag agtttgtgct  1380
ggtgctttac aagcaatgtt gattgcttgc acttccatcg gtagattcgt tcaagaattt  1440
gaatggaagt tgatgggtgg tgaagaagaa aacgttgata ctgttgcttt gacctcccaa  1500
aaattgcatc caatgcaagc cattattaag gccagagaat gactcgagcc gcgg        1554

SEQ ID NO: 70
MDMMGIEAVP FATAVVLGGI SLVVLIFIRR FVSNRKRSVE GLPPVPDIPG LPLIGNLLQL    60
KEKKPHKTFA RWAETYGPIF SIRTGASTMI VLNSSEVAKE AMVTRFSSIS TRKLSNALKI   120
LTFDKCMVAT SDYNDFHKMV KGFILRNVLG APAQKRHRCH RDTLIENISK YLHAHVKTSP   180
LEPVVLKKIF ESEIFGLALK QALGKDIESI YVEELGTTLS REEIFAVLVV DPMAGAIEVD   240
WRDFFPYLSW IPNKSMEMKI QRMDFRRGAL MKALIGEQKK RIGSGEEKNS YIDFLLSEAT   300
TLTEKQIAML IWETIIEISD TTLVTSEWAM YELAKDPNRQ EILYREIHKV CGSNKLTEEN   360
LSKLPYLNSV FHETLRKYSP APMVPVRYAH EDTQLGGYHI PAGSQIAINI YGCNMNKKQW   420
ENPEEWKPER FLDEKYDLMD LHKTMAFGGG KRVCAGALQA MLIACTSIGR FVQEFEWKLM   480
GGEEENVDTV ALTSQKLHPM QAIIKARE                                      508

SEQ ID NO: 71
aagcttaaaa tgagtaagtc taatagtatg aattctacat cacacgaaac ccttttttcaa    60
caattggtct tgggtttgga ccgtatgcca ttgatggatg ttcactggtt gatctacgtt   120
gctttcggcg catggttatg ttcttatgtg atacatgttt tatcatcttc ctctacagta   180
aaagtgccag ttgttggata caggtctgta ttcgaaccta catggttgct tagacttaga   240
```

TABLE 11-continued

| Sequences disclosed herein. |
|---|

```
ttcgtctggg aaggtggctc tatcataggt caagggtaca ataagtttaa agactctatt   300
ttccaagtta ggaaattggg aactgatatt gtcattatac cacctaacta tattgatgaa   360
gtgagaaaat tgtcacagga caagactaga tcagttgaac ctttcattaa tgattttgca   420
ggtcaataca caagaggcat ggttttcttg caatctgact tacaaaaccg tgttatacaa   480
caaagactaa ctccaaaatt ggtttccttg accaaggtca tgaaggaaga gttggattat   540
gctttaacaa aagagatgcc tgatatgaaa aatgacgaat gggtagaagt agatatcagt   600
agtataatgg tgagattgat ttccaggatc tccgccagag tctttctagg gcctgaacac   660
tgtcgtaacc aggaatggtt gactactaca gcagaatatt cagaatcact tttcattaca   720
gggtttatct taagagttgt acctcatatc ttaagaccat tcatcgcccc tctattacct   780
tcatacagga ctctacttag aaacgtttca agtggtagaa gagtcatcgg tgacatcata   840
agatctcagc aaggggatgg taacgaagat atactttcct ggatgagaga tgctgccaca   900
ggagaggaaa agcaaatcga taacattgct cagagaatgt taattctttc tttagcatca   960
atccacacta ctgcgatgac catgacacat gccatgtacg atctatgtgc ttgccctgag  1020
tacattgaac cattaagaga tgaagttaaa tctgttgttg gggcttctgg ctgggacaag  1080
acagcgttaa acagatttca taagttggac tccttcctaa aagagtcaca aagattcaac  1140
ccagtattct tattgacatt caatagaatc taccatcaat ctatgacctt atcagatggc  1200
actaacattc catctggaac acgtattgct gttccatcac acgcaatgtt gcaagattct  1260
gcacatgtcc caggtccaac cccacctact gaatttgatg gattcagata tagtaagata  1320
cgttctgata gtaactacgc acaaaagtac ctattctcca tgaccgattc ttcaaacatg  1380
gctttcggat acggcaagta tgcttgtcca ggtagatttt acgcgtctaa tgagatgaaa  1440
ctaacattag ccattttgtt gctacaattt gagttcaaac taccagatgg taaaggtcgt  1500
cctagaaata tcactatcga ttctgatatg attccagacc caagagctag actttgcgtc  1560
agaaaaagat cacttagaga tgaatgaccg cgg                               1593

SEQ ID NO: 72
MSKSNSMNST SHETLFQQLV LGLDRMPLMD VHWLIYVAFG AWLCSYVIHV LSSSSTVKVP    60
VVGYRSVFEP TWLLRLRFVW EGGSIIGQGY NKFKDSIFQV RKLGTDIVII PPNYIDEVRK   120
LSQDKTRSVE PFINDFAGQY TRGMVFLQSD LQNRVIQQRL TPKLVSLTKV MKEELDYALT   180
KEMPDMKNDE WVEVDISSIM VRLISRISAR VFLGPEHCRN QEWLTTTAEY SESLFITGFI   240
LRVVPHILRP FIAPLLPSYR TLLRNVSSGR RVIGDIIRSQ QGDGNEDILS WMRDAATGEE   300
KQIDNIAQRM LILSLASIHT TAMTMTHAMY DLCACPEYIE PLRDEVKSVV GASGWDKTAL   360
NRFHKLDSFL KESQRFNPVF LLTFNRIYHQ SMTLSDGTNI PSGTRIAVPS HAMLQDSAHV   420
PGPTPPTEFD GFRYSKIRSD SNYAQKYLFS MTDSSNMAFG YGKYACPGRF YASNEMKLTL   480
AILLLQFEFK LPDGKGRPRN ITIDSDMIPD PRARLCVRKR SLRDE                   525

SEQ ID NO: 73
aagcttaaaa tggaagatcc tactgtctta tatgcttgtc ttgccattgc agttgcaact    60
ttcgttgtta gatggtacag agatccattg agatccatcc caacagttgg tggttccgat   120
ttgcctattc tatcttacat cggcgcacta agatggacaa gacgtggcag agagatactt   180
caagagggat atgatggcta cagaggatct acattcaaaa tcgcgatgtt agaccgttgg   240
atcgtgatcg caaatggtcc taaactagct gatgaagtca gacgtagacc agatgaagag   300
ttaaacttta tggacggatt aggagcattc gtccaaacta agtacacctt aggtgaagct   360
attcataacg atccatacca tgtcgatatc ataagagaaa aactaacaag aggccttcca   420
gccgtgcttc ctgatgtcat tgaagagttg acacttgcgg ttagacagta cattccaaca   480
gaaggtgatg aatgggtgtc cgtaaactgt tcaaaggccg caagagatat tgttgctaga   540
gcttctaata gagtctttgt aggtttgcct gcttgcagaa accaaggtta cttagatttg   600
gcaatagact ttacattgtc tgttgtcaag gatagagcca tcatcaatat gtttccagaa   660
ttgttgaagc caatagttgg cagagttgta ggtaacgcca ccagaaatgt tcgtagagct   720
gttccttttg ttgctccatt ggtggaggaa agacgtagac ttatggaaga gtacggtgaa   780
gactggtctg aaaaacctaa tgatatgtta cagtggataa tggatgaagc tgcatccaga   840
gatagttcag tgaaggcaat cgcagagaga ttgttaatgg tgaacttcgc ggctattcat   900
acctcatcaa acactatcac tcatgctttg taccaccttg ccgaaatgcc tgaaactttg   960
caaccactta gagaagagat cgaaccatta gtcaaagagg agggctggac caaggctgct  1020
atgggaaaaa tgtggtggtt agattcattt ctaagagaat ctcaaagata caatggcatt  1080
aacatcgtat ctttaactag aatggctgac aaagatatta cattgagtga tggcacattt  1140
ttgccaaaag gtactctagt ggccgttcca gcgtattcta ctcatagaga tgatgctgtc  1200
tacgctgatg ccttagtatt cgatcctttc agattctcac gtatgagagc gagagaaggt  1260
gaaggtacaa agcaccagtt cgttaatact tcagtcgagt acgttccatt tggtcacgga  1320
aagcatgctt gtccaggaag attcttcgcc gcaaacgaat tgaaagcaat gttggcttac  1380
attgttctaa actatgatgt aaagttgcct ggtgacggta aacgtccatt gaacatgtat  1440
tggggtccaa cagttttgcc tgcaccagca ggccaagtat tgttcagaaa gagacaagtt  1500
agtctataac cgcgg                                                   1515

SEQ ID NO: 74
MEDPTVLYAC LAIAVATFVV RWYRDPLRSI PTVGGSDLPI LSYIGALRWT RRGREILQEG    60
YDGYRGSTFK IAMLDRWIVI ANGPKLADEV RRRPDEELNF MDGLGAFVQT KYTLGEAIHN   120
DPYHVDIIRE KLTRGLPAVL PDVIEELTLA VRQYIPTEGD EWVSVNCSKA ARDIVARASN   180
RVFVGLPACR NQGYLDLAID FTLSVVKDRA IINMFPELLK PIVGRVVGNA TRNVRRAVPF   240
VAPLVEERRR LMEEYGEDWS EKPNDMLQWI MDEAASRDSS VKAIAERLLM VNFAAIHTSS   300
NTITHALYHL AEMPETLQPL REEIEPLVKE EGWTKAAMGK MWWLDSFLRE SQRYNGINIV   360
SLTRMADKDI TLSDGTFLPK GTLVAVPAYS THRDDAVYAD ALVFDPFRFS RMRAREGEGT   420
KHQFVNTSVE YVPFGHGKHA CPGRFFAANE LKAMLAYIVL NYDVKLPGDG KRPLNMYWGP   480
TVLPAPAGQV LFRKRQVSL                                               499

SEQ ID NO: 75
atggcatttt tctctatgat ttcaattttg ttgggatttg ttatttcttc tttcatcttc    60
atctttttct tcaaaaagtt acttagtttt agtaggaaaa acatgtcaga agtttctact   120
ttgccaagtg ttccagtagt gcctggtttt ccagttattg ggaatttgtt gcaactaaag   180
```

TABLE 11-continued

Sequences disclosed herein.

```
gagaaaaagc ctcataaaac tttcactaga tggtcagaga tatatggacc tatctactct   240
ataaagatgg gttcttcatc tcttattgta ttgaacagta cagaaactgc taaggaagca   300
atggtcacta gattttcatc aatatctacc agaaaattgt caaacgccct aacagttcta   360
acctgcgata agtctatggt cgccacttct gattatgatg acttccacaa attagttaag   420
agatgtttgc taaatggact tcttggtgct aatgctcaaa agagaaaaag acactacaga   480
gatgctttga ttgaaaatgt gagttccaag ctacatgcac acgctagaga tcatccacaa   540
gagccagtta actttagagc aattttcgaa cacgaattgt ttggtgtagc attaaagcaa   600
gccttcggta aagacgtaga atccatatac gtcaaggagt taggcgtaac attatcaaaa   660
gatgaaatct ttaaggtgct tgtacatgat atgatggagg gtgcaattga tgtagattgg   720
agagatttct tcccatattt gaaatggatc cctaataagt cttttgaagc taggatacaa   780
caaaagcaca agagaagact agctgttatg aacgcactta tacaggacag attgaagcaa   840
aatgggtctg aatcagatga tgattgttac cttaacttct taatgtctga ggctaaaaca   900
ttgactaagg aacagatcgc aatccttgtc tgggaaacaa tcattgaaac agcagatact   960
accttagtca caactgaatg ggccatatac gagctagcca aacatccatc tgtgcaagat  1020
aggttgtgta aggagatcca gaacgtgtgt ggtggagaga aattcaagga agagcagttg  1080
tcacaagttc cttaccttaa cggcgttttc catgaaacct tgagaaaata ctcacctgca  1140
ccattagttc ctattagata cgcccacgaa gatacacaaa tcggtggcta ccatgttcca  1200
gctgggtccg aaattgctat aaacatctac gggtgcaaca tggacaaaaa gagatgggaa  1260
agaccagaag attggtggcc agaaagattc ttagatgatg gcaaatatga aacatctgat  1320
ttgcataaaa caatggcttt cggagctggc aaaagagtgt gtgccggtgc tctacaagcc  1380
tccctaatgg ctggtatcgc tattggtaga ttggtccaag agttcgaatg gaaacttaga  1440
gatggtgaag aggaaaatgt cgatacttat gggttaacat ctcaaaagtt atacccacta  1500
atggcaatca tcaatcctag aagatcctaa                                   1530
```

SEQ ID NO: 76

```
MAFFSMISIL LGFVISSFIF IFFFKKLLSF SRKNMSEVST LPSVPVVPGF PVIGNLLQLK    60
EKKPHKTFTR WSEIYGPIYS IKMGSSSLIV LNSTETAKEA MVTRFSSIST RKLSNALTVL   120
TCDKSMVATS DYDDFHKLVK RCLLNGLLGA NAQKRKRHYR DALIENVSSK LHAHARDHPQ   180
EPVNFRAIFE HELFGVALKQ AFGKDVESIY VKELGVTLSK DEIFKVLVHD MMEGAIDVDW   240
RDFFPYLKWI PNKSFEARIQ QKHKRRLAVM NALIQDRLKQ NGSESDDDCY LNFLMSEAKT   300
LTKEQIAILV WETIIETADT TLVTTEWAIY ELAKHPSVQD RLCKEIQNVC GGEKFKEEQL   360
SQVPYLNGVF HETLRKYSPA PLVPIRYAHE DTQIGGYHVP AGSEIAINIY GCNMDKKRWE   420
RPEDWWPERF LDDGKYETSD LHKTMAFGAG KRVCAGALQA SLMAGIAIGR LVQEFEWKLR   480
DGEEENVDTY GLTSQKLYPL MAIINPRRS                                     509
```

SEQ ID NO: 77

*S. rebaudiana*

```
atgcaatcag attcagtcaa agtctctcca tttgatttgg tttccgctgc tatgaatggc    60
aaggcaatgg aaaagttgaa cgctagtgaa tctgaagatc caacaacatt gcctgcacta   120
aagatgctag ttgaaaatag agaattgttg acactgttca caacttcctt cgcagttctt   180
attgggtgtc ttgtatttct aatgtggaga cgttcatcct ctaaaaagct ggtacaagat   240
ccagttccac aagttatcgt tgtaaagaag aaagagaagg agtcagaggt tgatgacggg   300
aaaaagaaag tttctatttt ctacggcaca caaacaggaa ctgccgaagg ttttgctaaa   360
gcattagtcg aggaagcaaa agtgagatat gaaaagacct ctttcaaggt tatcgatcta   420
gatgactacg ctgcagatga tgatgaatat gaggaaaaac tgaaaaagga atccttagcc   480
ttcttcttct tggccacata cggtgatggt gaacctactg ataatgctgc taacttctac   540
aagtggttca cagaaggcga cgataaaggt gaatggctga aaaagttaca atacggagta   600
tttggtttag gtaacagaca atatgaacat ttcaacaaga tcgctattgt agttgatgat   660
aaacttactg aaatgggagc caaaagatta gtaccagtag gattagggga tgatgatcag   720
tgtatagaag atgacttcac cgcctggaag gaattggtat ggccagaatt ggatcaactt   780
ttaagggacg aagatgatac ttctgtgact accccataca ctgcagccgt attggagtac   840
agagtggttt accatgataa accagcagac tcatatgctg aagatcaaac ccatacaaac   900
ggtcatgttg ttcatgatgc acagcatcct tcaagatcta atgtggcttt caaaaaggaa   960
ctacacacct ctcaatcaga taggtcttgt actcacttag aattcgatat ttctcacaca  1020
ggactgtctt acgaaactgg cgatcacgtt ggcgtttatt ccgagaactt gtccgaagtt  1080
gtcgatgaag cactaaaact gttagggtta tcaccagaca catacttctc agtccatgct  1140
gataaggagg atgggacacc tatcggtggt gcttcactac caccaccttt tcctccttgc  1200
acattgagag acgctctaac cagatacgca gatgtcttat cctcacctaa aaaggtagct  1260
ttgctggcat tggctgctca tgctagtgat cctagtgaag ccgataggtt aaagttcctg  1320
gcttcaccag ccggaaaaga tgaatatgca caatggatcg tcgccaacca acgttctttg  1380
ctagaagtga tgcaaagttt tccatctgcc aagcctccat taggtgtgtt cttcgcagca  1440
gtagctccac gtttacaacc aagatactac tctatcagtt catctcctaa gatgtctcct  1500
aacagaatac atgttacatg tgctttggtg tacgagacta ctccagcagg cagaattcac  1560
agaggattgt gttcaacctg gatgaaaaat gctgtccctt taacagagtc acctgattgc  1620
tctcaagcat ccattttcgt tagaacatca aatttcagac ttccagtgga tccaaaagtt  1680
ccagtcatta tgataggacc aggcactggt cttgccccat tcaggggctt tcttcaagag  1740
agattggcct tgaaggaatc tggtacagaa ttgggttctt ctatcttttt ctttggttgc  1800
cgtaatagaa aagttgactt tatctacgag gacgagctta acaattttgt tgagacagga  1860
gcattgtcag aattgatcgt cgcattttca agagaaggga ctgccaaaga gtacgttcag  1920
cacaagatga gtcaaaaagc ctccgatata tggaaacttc taagtgaagg tgcctatctt  1980
tatgtctgtg gcgatgcaaa gggcatggcc aaggatgtcc atagaactct gcatacaatt  2040
gttcaggaac aagggagtct ggattcttcc aaggctgaat tgtacgtcaa aaacttacag  2100
atgtctggaa gatacttaag agatgtttgg taa                                2133
```

SEQ ID NO: 78

*S. rebaudiana*

```
MQSDSVKVSP FDLVSAAMNG KAMEKLNASE SEDPTTLPAL KMLVENRELL TLFTTSFAVL    60
IGCLVFLMWR RSSSKKLVQD PVPQVIVVKK KEKESEVDDG KKKVSIFYGT QTGTAEGFAK   120
```

TABLE 11-continued

Sequences disclosed herein.

```
ALVEEAKVRY EKTSFKVIDL DDYAADDDEY EEKLKKESLA FFFLATYGDG EPTDNAANFY   180
KWFTEGDDKG EWLKKLQYGV FGLGNRQYEH FNKIAIVVDD KLTEMGAKRL VPVGLGDDDQ   240
CIEDDFTAWK ELVWPELDQL LRDEDDTSVT TPYTAAVLEY RVVYHDKPAD SYAEDQTHTN   300
GHVVHDAQHP SRSNVAFKKE LHTSQSDRSC THLEFDISHT GLSYETGDHV GVYSENLSEV   360
VDEALKLLGL SPDTYFSVHA DKEDGTPIGG ASLPPPFPPC TLRDALTRYA DVLSSPKKVA   420
LLALAAHASD PSEADRLKFL ASPAGKDEYA QWIVANQRSL LEVMQSFPSA KPPLGVFFAA   480
VAPRLQPRYY SISSSPKMSP NRIHVTCALV YETTPAGRIH RGLCSTWMKN AVPLTESPDC   540
SQASIFVRTS NFRLPVDPKV PVIMIGPGTG LAPFRGFLQE RLALKESGTE LGSSIFFFGC   600
RNRKVDFIYE DELNNFVETG ALSELIVAFS REGTAKEYVQ HKMSQKASDI WKLLSEGAYL   660
YVCGDAKGMA KDVHRTLHTI VQEQGSLDSS KAELYVKNLQ MSGRYLRDVW              710

SEQ ID NO: 79
atgaaggtca gtccattcga attcatgtcc gctattatca agggtagaat ggacccatct    60
aactcctcat ttgaatctac tggtgaagtt gcctccgtta tctttgaaaa cagagaattg   120
gttgccatct tgaccacttc tattgctgtt atgattggtt gcttcgttgt cttgatgtgg   180
agaagagctg gttctagaaa ggttaagaat gtcgaattgc caaagccatt gattgtccat   240
gaaccagaac ctgaagttga agatggtaag aagaaggttt ccatcttctt cggtactcaa   300
actggtactg ctgaaggttt tgctaaggct ttggctgatg aagctaaagc tagatacgaa   360
aaggctacct tcagagttgt tgatttggat gattatgctg ccgatgatga ccaatacgaa   420
gaaaaattga agaacgaatc cttcgccgtt ttcttgttgg ctacttatgg tgatggtgaa   480
cctactgata atgctgctag attttacaag tggttcgccg aaggtaaaga aagaggtgaa   540
tggttgcaaa acttgcacta tgctgttttt ggtttgggta acagacaata cgaacacttc   600
aacaagattg ctaaggttgc cgacgaatta ttggaagctc aaggtggtaa tagattggtt   660
aaggttggtt taggtgatga cgatcaatgc atcgaagatg atttttctgc ttggagagaa   720
tctttgtggc cagaattgga tatgttgttg agagatgaag atgatgctac tactgttact   780
actccatata ctgctgctgt cttggaatac agagttgtct ttcatgattc tgctgatgtt   840
gctgctgaag ataagtcttg gattaacgct aatggtcatg ctgttcatga tgctcaacat   900
ccattcagat ctaacgttgt cgtcagaaaa gaattgcata cttctgcctc tgatagatcc   960
tgttctcatt tggaattcaa catttccggt tccgctttga attacgaaac tggtgatcat  1020
gttggtgtct actgtgaaaa cttgactgaa actgttgatg aagccttgaa cttgttgggt  1080
ttgtctccag aaacttactt ctctatctac accgataacg aagatggtac tccattgggt  1140
ggttcttcat tgccaccacc atttccatca tgtactttga gaactgcttt gaccagatac  1200
gctgatttgt tgaactctcc aaaaaagtct gctttgttgg ctttagctgc tcatgcttct  1260
aatccagttg aagctgatag attgagatac ttggcttctc cagctggtaa agatgaatat  1320
gcccaatctg ttatcggttc ccaaaagtct ttgttggaag ttatggctga attcccatct  1380
gctaaaccac cattaggtgt ttttttgct gctgttgctc caagattgca acctagattc  1440
tactccattt catcctctcc aagaatggct ccatctagaa tccatgttac ttgtgctttg  1500
gtttacgata agatgccaac tggtagaatt cataagggtg tttgttctac ctggatgaag  1560
aattctgttc caatggaaaa gtcccatgaa tgttcttggg ctccaatttt cgttagacaa  1620
tccaatttta agttgccagc cgaatccaag gttccaatta tcatggttgg tccaggtact  1680
ggtttggctc cttttagagg ttttttacaa gaaagattgg ccttgaaaga atccggtgtt  1740
gaattgggtc catccatttt gtttttcggt tgcagaaaca gaagaatgga ttacatctac  1800
gaagatgaat tgaacaactt cgttgaaacc ggtgctttgt ccgaattggt tattgctttt  1860
tctagagaag gtcctaccaa agaatacgtc caacataaga tggctgaaaa ggcttctgat  1920
atctggaact tgatttctga aggtgcttac ttgtacgttt gtggtgatgc taaaggtatg  1980
gctaaggatg ttcatagaac cttgcatacc atcatgcaag aacaaggttc tttggattct  2040
tccaaagctg aatccatggt caagaacttg caaatgaatg gtagatactt aagagatgtt  2100
tggtaa                                                             2106

SEQ ID NO: 80
MKVSPFEFMS AIIKGRMDPS NSSFESTGEV ASVIFENREL VAILTTSIAV MIGCFVVLMW    60
RRAGSRKVKN VELPKPLIVH EPEPEVEDGK KKVSIFFGTQ TGTAEGFAKA LADEAKARYE   120
KATFRVVDLD DYAADDDQYE EKLKNESFAV FLLATYGDGE PTDNAARFYK WFAEGKERGE   180
WLQNLHYAVF GLGNRQYEHF NKIAKVADEL LEAQGGNRLV KVGLGDDDQC IEDDFSAWRE   240
SLWPELDMLL RDEDDATTVT TPYTAAVLEY RVVFHDSADV AAEDKSWINA NGHAVHDAQH   300
PFRSNVVVRK ELHTSASDRS CSHLEFNISG SALNYETGDH VGVYCENLTE TVDEALNLLG   360
LSPETYFSIY TDNEDGTPLG GSSLPPPFPS CTLRTALTRY ADLLNSPKKS ALLALAAHAS   420
NPVEADRLRY LASPAGKDEY AQSVIGSQKS LLEVMAEFPS AKPPLGVFFA AVAPRLQPRF   480
YSISSSPRMA PSRIHVTCAL VYDKMPTGRI HKGVCSTWMK NSVPMEKSHE CSWAPIFVRQ   540
SNFKLPAESK VPIIMVGPGT GLAPFRGFLQ ERLALKESGV ELGPSILFFG CRNRRMDYIY   600
EDELNNFVET GALSELVIAF SREGPTKEYV QHKMAEKASD IWNLISEGAY LYVCGDAKGM   660
AKDVHRTLHT IMQEQGSLDS SKAESMVKNL QMNGRYLRDV W                        701

SEQ ID NO: 81
atggcagaat tagatacact tgatatagta gtattaggtg ttatcttttt gggtactgtg    60
gcatacttta ctaagggtaa attgtggggt gttaccaagg atccatacgc taacggattc   120
gctgcaggtg gtgcttccaa gcctggcaga actagaaaca tcgtcgaagc tatggaggaa   180
tcaggtaaaa actgtgttgt tttctacggc agtcaaacag gtacagcgga ggattacgca   240
tcaagacttg caaaggaagg aaagtccaga ttcggtttga acactatgat cgccgatcta   300
gaagattatg acttcgataa cttagacact gttccatctg ataacatcgt tatgtttgta   360
ttggctactt acggtgaagg cgaaccaaca gataacgccg tggatttcta tgagttcatt   420
actggcgaag atgcctcttt caatgagggc aacgatcctc cactaggtaa cttgaattac   480
gttgcgttcg gtctgggcaa caatacctac gaacactaca actcaatggt caggaacgtt   540
aacaaggctc tagaaaagtt aggagctcat agaattggag aagcaggtga gggtgacgac   600
ggagctggaa ctatggaaga ggacttttta gcttggaaag atccaatgtg ggaagccttg   660
gctaaaaaga tgggcttgga ggaaagagaa gctgtatatg aacctatttt cgctatcaat   720
gagagagatg atttgacccc tgaagcgaat gaggtatact tgggagaacc taataagcta   780
cacttggaag gtacagcgaa aggtccattc aactcccaca acccatatat cgcaccaatt   840
```

TABLE 11-continued

| Sequences disclosed herein. |
|---|

gcagaatcat acgaactttt ctcagctaag gatagaaatt gtctgcatat ggaaattgat 900
atttctggta gtaatctaaa gtatgaaaca ggcgaccata tcgcgatctg gcctaccaac 960
ccaggtgaag aggtcaacaa atttcttgac attctagatc tgtctggtaa gcaacattcc 1020
gtcgtaacag tgaaagcctt agaacctaca gccaaagttc cttttccaaa tccaactacc 1080
tacgatgcta tattgagata ccatctggaa atatgcgctc cagtttctag acagtttgtc 1140
tcaactttag cagcattcgc ccctaatgat gatatcaaag ctgagatgaa ccgtttggga 1200
tcagacaaag attacttcca cgaaaagaca ggaccacatt actacaatat cgctagattt 1260
ttggcctcag tctctaaagg tgaaaaatgg acaaagatac cattttctgc tttcatagaa 1320
ggccttacaa aactacaacc aagatactat tctatctctt cctctagttt agttcagcct 1380
aaaaagatta gtattactgc tgttgtcgaa tctcagcaaa ttccaggtag agatgaccca 1440
ttcagaggtg tagcgactaa ctacttgttc gctttgaagc agaaacaaaa cggtgatcca 1500
aatccagctc cttttggcca atcatacgag ttgacaggac caaggaataa gtatgatggt 1560
atacatgttc cagtccatgt aagacattct aactttaagc taccatctga tccaggcaaa 1620
cctattatca tgatcggtcc aggtaccggt gttgcccctt ttagaggctt cgtccaagag 1680
agggcaaaac aagccagaga tggtgtagaa gttggtaaaa cactgctgtt ctttggatgt 1740
agaaagagta cagaagattt catgtatcaa aaagagtggc aagagtacaa ggaagctctt 1800
ggcgacaaat tcgaaatgat tacagctttt tcaagagaag gatctaaaaa ggtttatgtt 1860
caacacagac tgaaggaaag atcaaaggaa gtttctgatc ttctatccca aaaagcatac 1920
ttctacgttt gcggagacgc cgcacatatg gcacgtgaag tgaacactgt gttagcacag 1980
atcatagcag aaggccgtgg tgtatcagaa gccaagggtg aggaaattgt caaaaacatg 2040
agatcagcaa atcaatacca agtgtgttct gatttcgtaa ctttacactg taaagagaca 2100
acatacgcga attcagaatt gcaagaggat gtctggagtt aa 2142

SEQ ID NO: 82
MAELDTLDIV VLGVIFLGTV AYFTKGKLWG VTKDPYANGF AAGGASKPGR TRNIVEAMEE 60
SGKNCVVFYG SQTGTAEDYA SRLAKEGKSR FGLNTMIADL EDYDFDNLDT VPSDNIVMFV 120
LATYGEGEPT DNAVDFYEFI TGEDASFNEG NDPPLGNLNY VAFGLGNNTY EHYNSMVRNV 180
NKALEKLGAH RIGEAGEGDD GAGTMEEDFL AWKDPMWEAL AKKMGLEERE AVYEPIFAIN 240
ERDDLTPEAN EVYLGEPNKL HLEGTAKGPF NSHNPYIAPI AESYELFSAK DRNCLHMEID 300
ISGSNLKYET GDHIAIWPTN PGEEVNKFLD ILDLSGKQHS VVTVKALEPT AKVPFPNPTT 360
YDAILRYHLE ICAPVSRQFV STLAAFAPND DIKAEMNRLG SDKDYFHEKT GPHYYNIARF 420
LASVSKGEKW TKIPFSAFIE GLTKLQPRYY SISSSSLVQP KKISITAVVE SQQIPGRDDP 480
FRGVATNYLF ALKQKQNGDP NPAPFGQSYE LTGPRNKYDG IHVPVHVRHS NFKLPSDPGK 540
PIIMIGPGTG VAPFRGFVQE RAKQARDGVE VGKTLLFFGC RKSTEDFMYQ KEWQEYKEAL 600
GDKFEMITAF SREGSKKVYV QHRLKERSKE VSDLLSQKAY FYVCGDAAHM AREVNTVLAQ 660
IIAEGRGVSE AKGEEIVKNM RSANQYQVCS DFVTLHCKET TYANSELQED VWS 713

SEQ ID NO: 83
atgcaatcgg aatccgttga agcatcgacg attgatttga tgactgctgt tttgaaggac 60
acagtgatcg atacagcgaa cgcatctgat aacggagact caaagatgcc gccggcgttg 120
gcgatgatgt tcgaaattcg tgatctgttg ctgattttga ctacgtcagt tgctgttttg 180
gtcggatgtt tcgttgtttt ggtgtggaag agatcgtccg ggaagaagtc cggcaaggaa 240
ttggagccgc cgaagatcgt tgtgccgaag aggcggctgg agcaggaggt tgatgatggt 300
aagaagaagg ttacgatttt cttcggaaca caaactggaa cggctgaagg tttcgctaag 360
gcacttttcg aagaagcgaa agcgcgatat gaaaaggcag cgtttaaagt gattgatttg 420
gatgattatg ctgctgattt ggatgagtat gcagagaagc tgaagaagga aacatatgct 480
ttcttcttct tggctacata tggagatggt gagccaactg ataatgctgc caaattttat 540
aaatggttta ctgagggaga cgagaaaggc gtttggcttc aaaaacttca atatggagta 600
tttggtcttg gcaacagaca atatgaacat ttcaacaaga ttggaatagt ggttgatgat 660
ggtctcaccg agcagggtgc aaaacgcatt gttcccgttg gtcttggaga cgacgatcaa 720
tcaattgaag acgattttc ggcatggaaa gagttagtgt ggcccgaatt ggatctattg 780
cttcgcgatg aagatgacaa agctgctgca actccttaca cagctgcaat ccctgaatac 840
cgcgtcgtat ttcatgacaa acccgatgcg ttttctgatg atcatactca aaccaatggt 900
catgctgttc atgatgctca acatccatgc agatccaatg tggctgttaa aaaagagctt 960
catactcctg aatccgatcg ttcatgcaca catcttgaat ttgacatttc tcacactgga 1020
ttatcttatg aaactgggga tcatgttggt gtatactgtg aaaacctaat tgaagtagtg 1080
gaagaagctg ggaaattgtt aggattatca acagatactt atttctcgtt acatattgat 1140
aacgaagatg gttcaccact tggtggacct tcattacaac ctccttttcc tccttgtact 1200
ttaagaaaag cattgactaa ttatgcagat ctgttaagct ctcccaaaaa gtcaactttg 1260
cttgctctag ctgctcatgc ttccgatccc actgaagctg atcgtttaag atttcttgca 1320
tctcgcgagg gcaaggatga atatgctgaa tgggttgttg caaaccaaag aagtcttctt 1380
gaagtcatgg aagctttccc gtcagctaga ccgccacttg gtgttttctt tgcagcggtt 1440
gcaccgcgtt tacagcctcg ttactactct atttcttcct ccccaaagat ggaaccaaac 1500
aggattcatg ttacttgcgc gttggtttat gaaaaaactc ccgcaggtcg tatccacaaa 1560
ggaatctgct caacctggat gaagaacgct gtacctttga ccgaaagtca agattgcagt 1620
tgggcaccga tttttgttag aacatcaaac ttcagacttc caattgaccc gaaagtcccg 1680
gttatcatga ttggtcctgg aaccgggttg gctccattta ggggttttct tcaagaaaga 1740
ttggctctta aagaatccgg aaccgaactc gggtcatcta ttttattctt cggttgtaga 1800
aaccgcaaag tggattacat atatgagaat gaactcaaca actttgttga aaatggtgcg 1860
ctttctgagc ttgatgttgc tttctcccgc gatggcccga cgaaagaata cgtgcaacat 1920
aaaatgaccc aaaaggcttc tgaaatatgg aatatgcttt ctgagggagc atatttatat 1980
gtatgtggtg atgctaaagg catggctaaa gatgtacacc gtacacttca caccattgtg 2040
caagaacagg gaagtttgga ctcgtctaaa gcggagttgt atgtgaagaa tctacaaatg 2100
tcaggaagat acctccgtga tgtttggtaa 2130

SEQ ID NO: 84
MQSESVEAST IDLMTAVLKD TVIDTANASD NGDSKMPPAL AMMFEIRDLL LILTTSVAVL 60
VGCFVVLVWK RSSGKKSGKE LEPPKIVVPK RRLEQEVDDG KKKVTIFFGT QTGTAEGFAK 120

TABLE 11-continued

Sequences disclosed herein.

```
ALFEEAKARY EKAAFKVIDL DDYAADLDEY AEKLKKETYA FFFLATYGDG EPTDNAAKFY   180
KWFTEGDEKG VWLQKLQYGV FGLGNRQYEH FNKIGIVVDD GLTEQGAKRI VPVGLGDDDQ   240
SIEDDFSAWK ELVWPELDLL LRDEDDKAAA TPYTAAIPEY RVVFHDKPDA FSDDHTQTNG   300
HAVHDAQHPC RSNVAVKKEL HTPESDRSCT HLEFDISHTG LSYETGDHVG VYCENLIEVV   360
EEAGKLLGLS TDTYFSLHID NEDGSPLGGP SLQPPFPPCT LRKALTNYAD LLSSPKKSTL   420
LALAAHASDP TEADRLRFLA SREGKDEYAE WVVANQRSLL EVMEAFPSAR PPLGVFFAAV   480
APRLQPRYYS ISSSPKMEPN RIHVTCALVY EKTPAGRIHK GICSTWMKNA VPLTESQDCS   540
WAPIFVRTSN FRLPIDPKVP VIMIGPGTGL APFRGFLQER LALKESGTEL GSSILFFGCR   600
NRKVDYIYEN ELNNFVENGA LSELDVAFSR DGPTKEYVQH KMTQKASEIW NMLSEGAYLY   660
VCGDAKGMAK DVHRTLHTIV QEQGSLDSSK AELYVKNLQM SGRYLRDVW               709
```

SEQ ID NO: 85
*S. rebaudiana*

```
atgcaatcta actccgtgaa gatttcgccg cttgatctgg taactgcgct gtttagcggc    60
aaggttttgg acacatcgaa cgcatcggaa tcgggagaat ctgctatgct gccgactata   120
gcgatgatta tggagaatcg tgagctgttg atgatactca caacgtcggt tgctgtattg   180
atcggatgcg ttgtcgtttt ggtgtggcgg agatcgtcta cgaagaagtc ggcgttggag   240
ccaccggtga ttgtggttcc gaagagagtg caagaggagg aagttgatga tggtaagaag   300
aaagttacgg ttttcttcgg cacccaaact ggaacagctg aaggcttcgc taaggcactt   360
gttgaggaag ctaaagctcg atatgaaaag gctgtcttta aagtaattga tttggatgat   420
tatgctgctg atgacgatga gtatgaggag aaactaaaga aagaatcttt ggcctttttc   480
tttttggcta cgtatggaga tggtgagcca acagataatg ctgccagatt ttataaatgg   540
tttactgagg gagatgcgaa aggagaatgg cttaataagc ttcaatatgg agtatttggt   600
ttgggtaaca gacaatatga acattttaac aagatcgcaa aagtggttga tgatggtctt   660
gtagaacagg gtgcaaagcg tcttgttcct gttggacttg gagatgatga tcaatgtatt   720
gaagatgact tcaccgcatg gaaagagtta gtatggccgg agttggatca attacttcgt   780
gatgaggatg acacaactgt tgctactcca tacacagctg ctgttgcaga atatcgcgtt   840
gtttttcatg aaaaaccaga cgcgctttct gaagattata gttatacaaa tggccatgct   900
gttcatgatg ctcaacatcc atgcagatcc aacgtggctg tcaaaaagga acttcatagt   960
cctgaatctg accggtcttg cactcatctt gaatttgaca tctcgaacac cggactatca  1020
tatgaaactg ggaccatgt tggagtttac tgtgaaaact tgagtgaagt tgtgaatgat  1080
gctgaaagat tagtaggatt accaccagac acttactcct ccatccacac tgatagtgaa  1140
gacgggtcgc cacttggcgg agcctcattg ccgcctcctt tcccgccatg cactttaagg  1200
aaagcattga cgtgttatgc tgatgttttg agttctccca agaagtcggc tttgcttgca  1260
ctagctgctc atgccaccga tcccagtgaa gctgatagat tgaaatttct tgcatccccc  1320
gccggaaagg atgaatattc tcaatggata gttgcaagcc aaagaagtct ccttgaagtc  1380
atggaagcat tcccgtcagc taagccttca cttggtgttt tctttgcatc tgttgccccg  1440
cgcttacaac caagatacta ctctatttct tcctcaccca agatggcacc ggataggatt  1500
catgttacat gtgcattagt ctatgagaaa acacctgcag gccgcatcca caaaggagtt  1560
tgttcaactt ggatgaagaa cgcagtgcct atgaccgaga gtcaagattg cagttgggcc  1620
ccaatatacg tccgaacatc caatttcaga ctaccatctg accctaaggt cccggttatc  1680
atgattggac ctggcactgg tttggctcct tttagaggtt tccttcaaga gcggttagct  1740
ttaaaggaag ccggaactga cctcggttta tccattttat tcttcggatg taggaatcgc  1800
aaagtggatt tcatatatga aaacgagctt aacaactttg tggagactgg tgctctttct  1860
gagcttattg ttgctttctc ccgtgaaggc ccgactaagg aatatgtgca acacaagatg  1920
agtgagaagg cttcggatat ctggaacttg ctttctgaag gagcatattt atacgtatgt  1980
ggtgatgcca aaggcatggc caaagatgta catcgaaccc tccacacaat tgtgcaagaa  2040
cagggatctc ttgactcgtc aaaggcagaa ctctacgtga agaatctaca aatgtcagga  2100
agatacctcc gtgacgtttg gtaa                                         2124
```

SEQ ID NO: 86
*S. rebaudiana*

```
MQSNSVKISP LDLVTALFSG KVLDTSNASE SGESAMLPTI AMIMENRELL MILTTSVAVL    60
IGCVVVLVWR RSSTKKSALE PPVIVVPKRV QEEEVDDGKK KVTVFFGTQT GTAEGFAKAL   120
VEEAKARYEK AVFKVIDLDD YAADDDEYEE KLKKESLAFF FLATYGDGEP TDNAARFYKW   180
FTEGDAKGEW LNKLQYGVFG LGNRQYEHFN KIAKVVDDGL VEQGAKRLVP VGLGDDDQCI   240
EDDFTAWKEL VWPELDQLLR DEDDTTVATP YTAAVAEYRV VFHEKPDALS EDYSYTNGHA   300
VHDAQHPCRS NVAVKKELHS PESDRSCTHL EFDISNTGLS YETGDHVGVY CENLSEVVND   360
AERLVGLPPD TYSSIHTDSE DGSPLGGASL PPPFPPCTLR KALTCYADVL SSPKKSALLA   420
LAAHATDPSE ADRLKFLASP AGKDEYSQWI VASQRSLLEV MEAFPSAKPS LGVFFASVAP   480
RLQPRYYSIS SSPKMAPDRI HVTCALVYEK TPAGRIHKGV CSTWMKNAVP MTESQDCSWA   540
PIYVRTSNFR LPSDPKVPVI MIGPGTGLAP FRGFLQERLA LKEAGTDLGL SILFFGCRNR   600
KVDFIYENEL NNFVETGALS ELIVAFSREG PTKEYVQHKM SEKASDIWNL LSEGAYLYVC   660
GDAKGMAKDV HRTLHTIVQE QGSLDSSKAE LYVKNLQMSG RYLRDVW                 707
```

SEQ ID NO: 87

```
atgtcctcca actccgattt ggtcagaaga ttggaatctg ttttgggtgt ttctttcggt    60
ggttctgtta ctgattccgt tgttgttatt gctaccacct ctattgcttt ggttatcggt   120
gttttggttt tgttgtggag aagatcctct gacagatcta gagaagttaa gcaattggct   180
gttccaaagc cagttactat cgttgaagaa gaagatgaat tcgaagttgc ttctggtaag   240
accagagttt ctattttcta cggtactcaa actggtactg ctgaaggttt tgctaaggct   300
ttggctgaag aaatcaaagc cagatacgaa aaagctgccg ttaaggttat tgatttggat   360
gattacacag ccgaagatga caaatacggt gaaaagttga agaaagaaac tatggccttc   420
ttcatgttgg ctacttatgg tgatggtgaa cctactgata atgctgctag attttacaag   480
tggttcaccg aaggtactga tagaggtgtt tggttggaac atttgagata cggtgtattc   540
ggtttgggta acagacaata cgaacacttc aacaagattg ccaaggttgt tgatgatttg   600
ttggttgaac aaggtgccaa gagattggtt actgttggtt tgggtgatga tgatcaatgc   660
atcgaagatg atttctccgc ttggaaagaa gccttgtggc cagaattgga tcaattattg   720
```

TABLE 11-continued

Sequences disclosed herein.

```
caagatgata ccaacaccgt ttctactcca tacactgctg ttattccaga atacagagtt   780
gttatccacg atccatctgt tacctcttat gaagatccat actctaacat ggctaacggt   840
aatgcctctt acgatattca tcatccatgt agagctaacg ttgccgtcca aaaagaattg   900
cataagccag aatctgacag aagttgcatc catttggaat tcgatatttt cgctactggt   960
ttgacttacg aaaccggtga tcatgttggt gtttacgctg ataattgtga tgatactgta  1020
gaagaagccg ctaagttgtt gggtcaacca ttggatttgt tgttctccat tcataccgat  1080
aacaacgacg gtacttcttt gggttcttct ttgccaccac catttccagg tccatgtact  1140
ttgagaactg ctttggctag atatgccgat ttgttgaatc caccaaaaaa ggctgctttg  1200
attgctttag ctgctcatgc tgatgaacca tctgaagctg aaagattgaa gttcttgtca  1260
tctccacaag gtaaggacga atattctaaa tgggttgtcg gttcccaaag atccttggtt  1320
gaagttatgg ctgaatttcc atctgctaaa ccaccattgg gtgtattttt tgctgctgtt  1380
gttcctagat tgcaacctag atattactcc atctcttcca gtccaagatt tgctccacat  1440
agagttcatg ttacttgcgc tttggtttat ggtccaactc caactggtag aattcacaga  1500
ggtgtatgtt cattctggat gaagaatgtt gtcccattgg aaaagtctca aaactgttct  1560
tgggccccaa ttttcatcag acaatctaat ttcaagttgc cagccgatca ttctgttcca  1620
atagttatgg ttggtccagg tactggttta gctcctttta gaggtttctt acaagaaaga  1680
ttggccttga aagaagaagg tgctcaagtt ggtcctgctt tgttgttttt tggttgcaga  1740
aacagacaaa tggacttcat ctacgaagtc gaattgaaca actttgtcga acaaggtgct  1800
ttgtccgaat tgatcgttgc tttttcaaga gaaggtccat ccaaagaata cgtccaacat  1860
aagatggttg aaaaggcagc ttacatgtgg aacttgattt ctcaaggtgg ttacttctac  1920
gtttgtggtg atgctaaagg tatggctaga gatgttcata gaacattgca taccatcgtc  1980
caacaagaag aaaaggttga ttctaccaag gccgaatcca tcgttaagaa attgcaaatg  2040
gacggtagat acttgagaga tgtttggtga                                   2070

SEQ ID NO: 88
MSSNSDLVRR LESVLGVSFG GSVTDSVVVI ATTSIALVIG VLVLLWRRSS DRSREVKQLA    60
VPKPVTIVEE EDEFEVASGK TRVSIFYGTQ TGTAEGFAKA LAEEIKARYE KAAVKVIDLD   120
DYTAEDDKYG EKLKKETMAF FMLATYGDGE PTDNAARFYK WFTEGTDRGV WLEHLRYGVF   180
GLGNRQYEHF NKIAKVVDDL LVEQGAKRLV TVGLGDDDQC IEDDFSAWKE ALWPELDQLL   240
QDDTNTVSTP YTAVIPEYRV VIHDPSVTSY EDPYSNMANG NASYDIHHPC RANVAVQKEL   300
HKPESDRSCI HLEFDIFATG LTYETGDHVG VYADNCDDTV EEAAKLLGQP LDLLFSIHTD   360
NNDGTSLGSS LPPPFPGPCT LRTALARYAD LLNPPKKAAL IALAAHADEP SEAERLKFLS   420
SPQGKDEYSK WVVGSQRSLV EVMAEFPSAK PPLGVFFAAV VPRLQPRYYS ISSSPRFAPH   480
RVHVTCALVY GPTPTGRIHR GVCSFWMKNV VPLEKSQNCS WAPIFIRQSN FKLPADHSVP   540
IVMVGPGTGL APFRGFLQER LALKEEGAQV GPALLFFGCR NRQMDFIYEV ELNNFVEQGA   600
LSELIVAFSR EGPSKEYVQH KMVEKAAYMW NLISQGGYFY VCGDAKGMAR DVHRTLHTIV   660
QQEEKVDSTK AESIVKKLQM DGRYLRDVW                                     689

SEQ ID NO: 89
atgacttctg cactttatgc ctccgatctt ttcaaacaat tgaaaagtat catgggaacg    60
gattctttgt ccgatgatgt tgtattagtt attgctacaa cttctctggc actggttgct   120
ggtttcgttg tcttattgtg gaaaaagacc acggcagatc gttccggcga gctaaagcca   180
ctaatgatcc ctaagtctct gatggcgaaa gatgaggatg atgacttaga tctaggttct   240
ggaaaaacga gagtctctat cttcttcggc acacaaaccg gaacagccga aggattcgct   300
aaagcacttt cagaagagat caaagcaaga tacgaaaagg cggctgtaaa agtaatcgat   360
ttggatgatt acgctgccga tgatgaccaa tatgaggaaa agttgaaaaa ggaaacattg   420
gctttcttttt gtgtagccac gtatggtgat ggtgaaccaa ccgataacgc cgcaagattc   480
tacaagtggt ttactgaaga gaacgaaaga gatatcaagt tgcagcaact tgcttacggc   540
gtttttgcct taggtaacag acaatacgag cactttaaca agataggtat tgtcttagat   600
gaagagttat gcaaaaaggg tgcgaagaga ttgattgaag tcggtttagg agatgatgat   660
caatctatcg aggatgactt taatgcatgg aaggaatctt tgtggtctga attagataag   720
ttacttaagg acgaagatga taaatccgtt gccactccat acacagccgt cattccagaa   780
tatagagtag ttactcatga tccaagattc acaacacaga aatcaatgga aagtaatgtg   840
gctaatggta atactaccat cgatattcat catccatgta gagtagacgt tgcagttcaa   900
aaggaattgc acactcatga atcagacaga tcttgcatac atcttgaatt tgatatatca   960
cgtactggta tcacttacga aacaggtgat cacgtgggtg tctacgctga aaaccatgtt  1020
gaaattgtag aggaagctgg aaagttgttg ggccatagtt tagatcttgt tttctcaatt  1080
catgccgata aagaggatgg ctcaccacta gaaagtgcag tgcctccacc atttccagga  1140
ccatgcaccc taggtaccgg tttagctcgt tacgcggatc tgttaaatcc tccacgtaaa  1200
tcagctctag tggccttggc tgcgtacgcc acagaacctt ctgaggcaga aaaactgaaa  1260
catctaactt caccagatgg taaggatgaa tactcacaat ggatagtagc tagtcaacgt  1320
tctttactag aagttatggc tgctttccca tccgctaaac ctcctttggg tgttttcttc  1380
gccgcaatag cgcctagact gcaaccaaga tactattcaa tttcatcctc acctagactg  1440
gcaccatcaa gagttcatgt cacatccgct ttagtgtacg gtccaactcc tactggtaga  1500
atccataagg gcgtttgttc aacatggatg aaaaacgcgg ttccagcaga gaagtctcac  1560
gaatgttctg gtgctccaat ctttatcaga gcctccaact tcaaactgcc ttccaatcct  1620
tctactccta ttgtcatggt cggtcctggt acaggtcttg ctccattcag aggtttctta  1680
caagagagaa tggccttaaa ggaggatggt gaagagttgg gatcttcttt gttgtttttc  1740
ggctgtagaa acagacaaat ggatttcatc tacgaagatg aactgaataa ctttgtagat  1800
caaggagtta tttcagagtt gataatggct ttttctagag aaggtgctca gaaggagtac  1860
gtccaacaca aaatgatgga aaaggccgca caagtttggg acttaatcaa agaggaaggc  1920
tatctatatg tctgtggtga tgcaaagggt atggcaagag atgttcacag aacacttcat  1980
actatagtcc aggaacagga aggcgttagt tcttctgaag cggaagcaat tgtgaaaaag  2040
ttacaaacag agggaagata cttgagagat gtgtggtaa                          2079

SEQ ID NO: 90
MTSALYASDL FKQLKSIMGT DSLSDDVVLV IATTSLALVA GFVVLLWKKT TADRSGELKP    60
LMIPKSLMAK DEDDDLDLGS GKTRVSIFFG TQTGTAEGFA KALSEEIKAR YEKAAVKVID   120
```

TABLE 11-continued

| Sequences disclosed herein. |
|---|
| LDDYAADDDQ YEEKLKKETL AFFCVATYGD GEPTDNAARF YKWFTEENER DIKLQQLAYG 180 |
| VFALGNRQYE HFNKIGIVLD EELCKKGAKR LIEVGLGDDD QSIEDDFNAW KESLWSELDK 240 |
| LLKDEDDKSV ATPYTAVIPE YRVVTHDPRF TTQKSMESNV ANGNTTIDIH HPCRVDVAVQ 300 |
| KELHTHESDR SCIHLEFDIS RTGITYETGD HVGVYAENHV EIVEEAGKLL GHSLDLVFSI 360 |
| HADKEDGSPL ESAVPPPFPG PCTLGTGLAR YADLLNPPRK SALVALAAYA TEPSEAEKLK 420 |
| HLTSPDGKDE YSQWIVASQR SLLEVMAAFP SAKPPLGVFF AAIAPRLQPR YYSISSSPRL 480 |
| APSRVHVTSA LVYGPTPTGR IHKGVCSTWM KNAVPAEKSH ECSGAPIFIR ASNFKLPSNP 540 |
| STPIVMVGPG TGLAPFRGFL QERMALKEDG EELGSSLLFF GCRNRQMDFI YEDELNNFVD 600 |
| QGVISELIMA FSREGAQKEY VQHKMMEKAA QVWDLIKEEG YLYVCGDAKG MARDVHRTLH 660 |
| TIVQEQEGVS SSEAEAIVKK LQTEGRYLRD VW 692 |
| |
| SEQ ID NO: 91 |
| *A. thaliana* |
| atgtcttcct cttcctcttc cagtacctct atgattgatt tgatggctgc tattattaaa 60 |
| ggtgaaccag ttatcgtctc cgacccagca aatgcctctg cttatgaatc agttgctgca 120 |
| gaattgtctt caatgttgat cgaaaacaga caattcgcca tgatcgtaac tacatcaatc 180 |
| gctgttttga tcggttgtat tgtcatgttg gtatggagaa gatccggtag tggtaattct 240 |
| aaaagagtcg aacctttgaa accattagta attaagccaa gagaagaaga aatagatgac 300 |
| ggtagaaaga aagttacaat atttttcggt acccaaactg gtacagctga aggttttgca 360 |
| aaagccttag gtgaagaagc taaggcaaga tacgaaaaga ctagattcaa gatagtcgat 420 |
| ttggatgact atgccgctga tgacgatgaa tacgaagaaa agttgaagaa agaagatgtt 480 |
| gcatttttct ttttggcaac ctatggtgac ggtgaaccaa ctgacaatgc agccagattc 540 |
| tacaaatggt ttacagaggg taatgatcgt ggtgaatggt tgaaaaactt aaagtacggt 600 |
| gttttcggtt tgggtaacag acaatacgaa catttcaaca aagttgcaaa ggttgtcgac 660 |
| gatattttgg tcgaacaagg tgctcaaaga ttagtccaag taggtttggg tgacgatgac 720 |
| caatgtatag aagatgactt tactgcctgg agagaagctt tgtggcctga attagacaca 780 |
| atcttgagag aagaaggtga caccgccgtt gctaccccat atactgctgc agtattagaa 840 |
| tacagagttt ccatccatga tagtgaagac gcaaagttta atgatatcac tttggccaat 900 |
| ggtaacggtt atacagtttt cgatgcacaa caccccttaca aagctaacgt tgcagtcaag 960 |
| agagaattac atacaccaga atccgacaga agttgtatac acttggaatt tgatatcgct 1020 |
| ggttccggtt taaccatgaa gttgggtgac catgtaggtg ttttatgcga caatttgtct 1080 |
| gaaactgttg atgaagcatt gagattgttg gatatgtccc ctgacactta ttttagtttg 1140 |
| cacgctgaaa aagaagatgg tacaccaatt tccagttctt taccacctcc attccctcca 1200 |
| tgtaacttaa gaacagcctt gaccagatac gcttgcttgt tatcatcccc taaaaagtcc 1260 |
| gccttggttg ctttagccgc tcatgctagt gatcctactg aagcagaaag attgaaacac 1320 |
| ttagcatctc cagccggtaa agatgaatat tcaaagtggg tagttgaatc tcaaagatca 1380 |
| ttgttagaag ttatggcaga atttccatct gccaagcctc cattaggtgt cttctttgct 1440 |
| ggtgtagcac ctagattgca accaagattc tactcaatca gttcttcacc taagatcgct 1500 |
| gaaactagaa ttcatgttac atgtgcatta gtctacgaaa agatgccaac cggtagaatt 1560 |
| cacaagggtg tatgctctac ttggatgaaa aatgctgttc cttacgaaaa atcagaaaag 1620 |
| ttgttcttag gtagaccaat cttcgtaaga caatcaaact tcaagttgcc ttctgattca 1680 |
| aaggttccaa taatcatgat aggtcctggt acaggtttag ccccattcag aggtttcttg 1740 |
| caagaaagat tggctttagt tgaatctggt gtcgaattag gtccttcagt tttgttcttt 1800 |
| ggttgtagaa acagaagaat ggatttcatc tatgaagaag aattgcaaag attcgtcgaa 1860 |
| tctggtgcat tggccgaatt atctgtagct tttcaagag aaggtccaac taaggaatac 1920 |
| gttcaacata agatgatgga taaggcatcc gacatatgga acatgatcag tcaaggtgct 1980 |
| tatttgtacg tttgcggtga cgcaaagggt atggccagag atgtccatag atctttgcac 2040 |
| acaattgctc aagaacaagg ttccatggat agtaccaaag ctgaaggttt cgtaaagaac 2100 |
| ttacaaactt ccggtagata cttgagagat gtctggtga 2139 |
| |
| SEQ ID NO: 92 |
| *A. thaliana* |
| MSSSSSSSTS MIDLMAAIIK GEPVIVSDPA NASAYESVAA ELSSMLIENR QFAMIVTTSI 60 |
| AVLIGCIVML VWRRSGSGNS KRVEPLKPLV IKPREEEIDD GRKKVTIFFG TQTGTAEGFA 120 |
| KALGEEAKAR YEKTRFKIVD LDDYAADDDE YEEKLKKEDV AFFFLATYGD GEPTDNAARF 180 |
| YKWFTEGNDR GEWLKNLKYG VFGLGNRQYE HFNKVAKVVD DILVEQGAQR LVQVGLGDDD 240 |
| QCIEDDFTAW REALWPELDT ILREEGDTAV ATPYTAAVLE YRVSIHDSED AKFNDITLAN 300 |
| GNGYTVFDAQ HPYKANVAVK RELHTPESDR SCIHLEFDIA GSGLTMKLGD HVGVLCDNLS 360 |
| ETVDEALRLL DMSPDTYFSL HAEKEDGTPI SSSLPPPFPP CNLRTALTRY ACLLSSPKKS 420 |
| ALVALAAHAS DPTEAERLKH LASPAGKDEY SKWVVESQRS LLEVMAEFPS AKPPLGVFFA 480 |
| GVAPRLQPRF YSISSSPKIA ETRIHVTCAL VYEKMPTGRI HKGVCSTWMK NAVPYEKSEK 540 |
| LFLGRPIFVR QSNFKLPSDS KVPIIMIGPG TGLAPFRGFL QERLALVESG VELGPSVLFF 600 |
| GCRNRRMDFI YEEELQRFVE SGALAELSVA FSREGPTKEY VQHKMMDKAS DIWNMISQGA 660 |
| YLYVCGDAKG MARDVHRSLH TIAQEQGSMD STKAEGFVKN LQTSGRYLRD VW 712 |
| |
| SEQ ID NO: 93 |
| *S. rebaudiana* |
| atggaagcct cttacctata catttctatt ttgcttttac tggcatcata cctgttcacc 60 |
| actcaactta gaaggaagag cgctaatcta ccaccaaccg tgtttccatc aataccaatc 120 |
| attggacact tatacttact caaaaagcct ctttatagaa ctttagcaaa aattgccgct 180 |
| aagtacggac caatactgca attacaactc ggctacagac gtgttctggt gatttcctca 240 |
| ccatcagcag cagaagagtg ctttaccaat aacgatgtaa tcttcgcaaa tagacctaag 300 |
| acattgtttg gcaaaatagt gggtggaaca tcccttggca gtttatccta cggcgatcaa 360 |
| tggcgtaatc taaggagagt agcttctatc gaaatcctat cagttcatag gttgaacgaa 420 |
| tttcatgata tcagagtgga tgagaacaga ttgttaatta gaaaacttag aagttcatct 480 |
| tctcctgtta ctcttataac agtcttttat gctctaacat tgaacgtcat tatgagaatg 540 |
| atctctggca aaagatattt cgacagtggg gatagagaat tggaggagga aggtaagaga 600 |
| tttcgagaaa tcttagacga aacgttgctt ctagccggtg cttctaatgt tggcgactac 660 |

TABLE 11-continued

Sequences disclosed herein.

```
ttaccaatat tgaactggtt gggagttaag tctcttgaaa agaaattgat cgctttgcag   720
aaaaagagag atgacttttt ccagggtttg attgaacagg ttagaaaatc tcgtggtgct   780
aaagtaggca aaggtagaaa aacgatgatc gaactcttat tatctttgca agagtcagaa   840
cctgagtact atacagatgc tatgataaga tcttttgtcc taggtctgct ggctgcaggt   900
agtgatactt cagcgggcac tatggaatgg gccatgagct tactggtcaa tcacccacat   960
gtattgaaga aagctcaagc tgaaatcgat agagttatcg gtaataacag attgattgac  1020
gagtcagaca ttggaaatat ccccttacatc gggtgtatta tcaatgaaac tctaagactc  1080
tatccagcag ggccattgtt gttcccacat gaaagttctg ccgactgcgt tatttccggt  1140
tacaatatac ctagaggtac aatgttaatc gtaaaccaat gggcgattca tcacgatcct  1200
aaagtctggg atgatcctga aacctttaaa cctgaaagat ttcaaggatt agaaggaact  1260
agagatggtt tcaaacttat gccattcggt tctgggagaa gaggatgtcc aggtgaaggt  1320
ttggcaataa ggctgttagg gatgacacta ggctcagtga tccaatgttt tgattgggag  1380
agagtaggag atgagatggt tgacatgaca gaaggtttgg gtgtcacact tcctaaggcc  1440
gttccattag ttgccaaatg taagccacgt tccgaaatga ctaatctcct atccgaactt  1500
taa                                                                1503
```

SEQ ID NO: 94

*S. rebaudiana*

```
MEASYLYISI LLLLASYLFT TQLRRKSANL PPTVFPSIPI IGHLYLLKKP LYRTLAKIAA    60
KYGPILQLQL GYRRVLVISS PSAAEECFTN NDVIFANRPK TLFGKIVGGT SLGSLSYGDQ   120
WRNLRRVASI EILSVHRLNE FHDIRVDENR LLIRKLRSSS SPVTLITVFY ALTLNVIMRM   180
ISGKRYFDSG DRELEEEGKR FREILDETLL LAGASNVGDY LPILNWLGVK SLEKKLIALQ   240
KKRDDFFQGL IEQVRKSRGA KVGKGRKTMI ELLLSLQESE PEYYTDAMIR SFVLGLLAAG   300
SDTSAGTMEW AMSLLVNHPH VLKKAQAEID RVIGNNRLID ESDIGNIPYI GCIINETLRL   360
YPAGPLLFPH ESSADCVISG YNIPRGTMLI VNQWAIHHDP KVWDDPETFK PERFQGLEGT   420
RDGFKLMPFG SGRRGCPGEG LAIRLLGMTL GSVIQCFDWE RVGDEMVDMT EGLGVTLPKA   480
VPLVAKCKPR SEMTNLLSEL                                              500
```

SEQ ID NO: 95

```
atggaagtaa cagtagctag tagtgtagcc ctgagcctgg tctttattag catagtagta    60
agatgggcat ggagtgtggt gaattgggtg tggtttaagc cgaagaagct ggaaagattt   120
ttgagggagc aaggccttaa aggcaattcc tacaggtttt tatatggaga catgaaggag   180
aactctatcc tgctcaaaca agcaagatcc aaacccatga acctctccac ctcccatgac   240
atagcacctc aagtcacccc ttttgtcgac caaaccgtga aagcttacgg taagaactct   300
tttaattggg ttggccccat accaagggtg aacataatga atccagaaga tttgaaggac   360
gtcttaacaa aaaatgttga ctttgttaag ccaatatcaa acccacttat caagttgcta   420
gctacaggta ttgcaatcta tgaaggtgag aaatggacta aacacagaag gattatcaac   480
ccaacattcc attcggagag gctaaagcgt atgttacctt catttcacca aagttgtaat   540
gagatggtca aggaatggga gagcttggtg tcaaaagagg gttcatcatg tgagttggat   600
gtctggcctt ttcttgaaaa tatgtcggca gatgtgatct cgagaacagc atttggaact   660
agctacaaaa aaggacagaa aatctttgaa ctcttgagag agcaagtaat atatgtaacg   720
aaaggctttc aaagttttta cattccagga tggaggtttc tcccaactaa gatgaacaag   780
aggatgaatg agattaacga agaaataaaa ggattaatca ggggtattat aattgacaga   840
gagcaaatca ttaaggcagg tgaagaaacc aacgatgact tattaggtgc acttatggag   900
tcaaacttga aggacattcg ggaacatggg aaaaacaaca aaaatgttgg gatgagtatt   960
gaagatgtaa ttcaggagtg taagctgttt tactttgctg ggcaagaaac cacttcagtg  1020
ttgctggctt ggacaatggt tttacttggt caaaatcaga actggcaaga tcgagcaaga  1080
caagaggttt tgcaagtctt tggaagcagc aagccagatt ttgatggtct agctcacctt  1140
aaagtcgtaa ccatgatttt gcttgaagtt cttcgattat acccaccagt cattgaactt  1200
attcgaacca ttcacaagaa aacacaactt gggaagctct cactaccaga aggagttgaa  1260
gtccgcttac caacactgct cattcaccat gacaaggaac tgtggggtga tgatgcaaac  1320
cagttcaatc cagagaggtt ttcggaagga gtttccaaag caacaaagaa ccgactctca  1380
ttcttcccct tcggagccgg tccacgcatt tgcattggac agaacttttc tatgatggaa  1440
gcaaagttgg ccttagcatt gatcttgcaa cacttcacct ttgagctttc tccatctcat  1500
gcacatgctc cttcccatcg tataaccctt caaccacagt atggtgttcg tatcatttta  1560
catcgacgtt ag                                                      1572
```

SEQ ID NO: 96

*R. suavissimus*

```
atggaagtca ctgtcgcctc ttctgtcgct ttatccttag tcttcatttc cattgtcgtc    60
agatgggctt ggtccgttgt caactgggtt tggttcaaac caaagaagtt ggaaagattc   120
ttgagagagc aaggtttgaa gggtaattct tatagattct tgtacggtga catgaaggaa   180
aattctattt tgttgaagca agccagatcc aaaccaatga acttgtctac ctctcatgat   240
attgctccac aagttactcc attcgtcgat caaactgtta aagcctacgg taagaactct   300
ttcaattggg ttggtccaat tcctagagtt aacatcatga acccagaaga tttgaaggat   360
gtcttgacca agaacgttga cttcgttaag ccaatttcca acccattgat taaattgttg   420
gctactggta ttgccattta cgaaggtgaa aagtggacta agcatagaag aatcatcaac   480
cctaccttcc actctgaaag attgaagaga atgttaccat ctttccatca atcctgtaat   540
gaaatggtta aggaatggga atccttggtt tctaaagaag gttcttcttg cgaattggat   600
gtttggccat tcttggaaaa tatgtctgct gatgtcattt ccagaaccgc tttcggtacc   660
tcctacaaga agggtcaaaa gattttcgaa ttgttgagag agcaagttat ttacgttacc   720
aagggtttcc aatccttcta catcccaggt tggagattct tgccaactaa aatgaacaag   780
cgtatgaacg agatcaacga agaaattaaa ggtttgatca gaggtattat tatcgacaga   840
gaacaaatta ttaaagctgg tgaagaaacc aacgatgatt tgttgggtgc tttgatggag   900
tccaacttga aggatattag agaacatggt aagaacaaca agaatgttgg tatgtctatt   960
gaagatgtta ttcaagaatg taagttattc tacttcgctg gtcaagagac cacttctgtt  1020
ttgttagcct ggactatggt cttgttaggt caaaaccaaa attggcaaga tagagctaga  1080
caagaagttt tgcaagtctt cggttcttcc aagccagact ttgatggttt ggcccacttg  1140
```

TABLE 11-continued

Sequences disclosed herein.

```
aaggttgtta ctatgatttt gttagaagtt ttgagattgt acccaccagt cattgagtta  1200
atcagaacca ttcataaaaa gactcaattg ggtaaattat ctttgccaga aggtgttgaa  1260
gtcagattac caaccttgtt gattcaccac gataaggaat tatggggtga cgacgctaat  1320
caatttaatc cagaaagatt ttccgaaggt gtttccaagg ctaccaaaaa ccgtttgtcc  1380
ttcttcccat ttggtgctgg tccacgtatt tgtatcggtc aaaacttttc catgatggaa  1440
gccaagttgg ctttggcttt aatcttgcaa cacttcactt tcgaattgtc tccatcccat  1500
gcccacgctc cttctcatag aatcacttta caaccacaat acggtgtcag aatcatctta  1560
cacagaagat aa                                                      1572
```

SEQ ID NO: 97
*R. suavissimus*

```
MEVTVASSVA LSLVFISIVV RWAWSVVNWV WFKPKKLERF LREQGLKGNS YRFLYGDMKE    60
NSILLKQARS KPMNLSTSHD IAPQVTPFVD QTVKAYGKNS FNWVGPIPRV NIMNPEDLKD   120
VLTKNVDFVK PISNPLIKLL ATGIAIYEGE KWTKHRRIIN PTFHSERLKR MLPSFHQSCN   180
EMVKEWESLV SKEGSSCELD VWPFLENMSA DVISRTAFGT SYKKGQKIFE LLREQVIYVT   240
KGFQSFYIPG WRFLPTKMNK RMNEINEEIK GLIRGIIIDR EQIIKAGEET NDDLLGALME   300
SNLKDIREHG KNNKNVGMSI EDVIQECKLF YFAGQETTSV LLAWTMVLLG QNQNWQDRAR   360
QEVLQVFGSS KPDFDGLAHL KVVTMILLEV LRLYPPVIEL IRTIHKKTQL GKLSLPEGVE   420
VRLPTLLIHH DKELWGDDAN QFNPERFSEG VSKATKNRLS FFPFGAGPRI CIGQNFSMME   480
AKLALALILQ HFTFELSPSH AHAPSHRITL QPQYGVRIIL HRR                     523
```

SEQ ID NO: 98

```
atggaagcat caagggctag ttgtgttgcg ctatgtgttg tttgggtgag catagtaatt    60
acattggcat ggagggtgct gaattgggtg tggttgaggc caaagaaact agaaagatgc   120
ttgagggagc aaggccttac aggcaattct tacaggcttt tgtttggaga caccaaggat   180
ctctcgaaga tgctggaaca aacacaatcc aaacccatca aactctccac ctcccatgat   240
atagcgccac gagtcacccc atttttccat cgaactgtga actctaatgg caagaattct   300
tttgtttgga tgggccctat accaagagtg cacatcatga atccagaaga tttgaaagat   360
gccttcaaca gacatgatga ttttcataag acagtaaaaa atcctatcat gaagtctcca   420
ccaccgggca ttgtaggcat tgaaggtgag caatgggcta aacacagaaa gattatcaac   480
ccagcattcc atttagagaa gctaaagggt atggtaccaa tattttacca aagttgtagc   540
gagatgatta acaaatggga gagcttggtg tccaaagaga gttcatgtga gttggatgtg   600
tggccttatc ttgaaaattt taccagcgat gtgatttccc gagctgcatt tggaagtagc   660
tatgaagagg gaaggaaaat atttcaacta ctaagagagg aagcaaaagt ttattcggta   720
gctctacgaa gtgtttacat tccaggatgg aggtttctac caaccaagca gaacaagaag   780
acgaaggaaa ttcacaatga aattaaaggc ttacttaagg gcattataaa taaaagggaa   840
gaggcgatga aggcagggga agccactaaa gatgacttac taggaatact tatggagtcc   900
aacttcaggg aaattcagga acatgggaac aacaaaaatg ctggaatgag tattgaagat   960
gtaattggag agtgtaagtt gttttacttt gctgggcaag agaccacttc ggtgttgctt  1020
gtttggacaa tgattttact aagccaaaat caggattggc aagctcgtgc aagagaagag  1080
gtcttgaaag tctttggaag caacatccca acctatgaag agctaagtca cctaaaagtt  1140
gtgaccatga ttttacttga agttcttcga ttatacccat cagtcgttgc gcttcctcga  1200
accactcaca agaaaacaca gcttggaaaa ttatcattac cagctggagt ggaagtctcc  1260
ttgcccatac tgcttgttca ccatgacaaa gagttgtggg gtgaggatgc aaatgagttc  1320
aagccagaga ggttttcaga gggagtttca aaggcaacaa agaacaaatt tacatactta  1380
cctttcggag ggggtccaag gatttgcatt ggacaaaact ttgccatggt ggaagctaaa  1440
ttggccttgg ccctgatttt acaacacttt gcctttgagc tttctccatc ctatgctcat  1500
gctccttctg cagttataac ccttcaacct caatttggtg ctcatatcat tttgcataaa  1560
cgttga                                                             1566
```

SEQ ID NO: 99

```
atggaagctt ctagagcatc ttgtgttgct ttgtgtgttg tttgggtttc catcgttatt    60
actttggctt ggagagtttt gaattgggtc tggttaagac caaaaaagtt ggaaagatgc   120
ttgagagaac aaggtttgac tggtaactct tacagattgt tgttcggtga taccaaggac   180
ttgtctaaga tgttggaaca aactcaatcc aagcctatca agttgtctac ctctcatgat   240
attgctccaa gagttactcc attcttccat agaactgtta actccaacgg taagaactct   300
tttgtttgga tgggtccaat tccaagagtc catattatga accctgaaga tttgaaggac   360
gctttcaaca gacatgatga tttccataag accgtcaaga acccaattat gaagtctcca   420
ccaccaggta tagttggtat tgaaggtgaa caatgggcca aacatagaaa gattattaac   480
ccagccttcc acttggaaaa gttgaaaggt atggttccaa tcttctacca atcctgctct   540
gaaatgatta acaagtggga atccttggtt tccaaagaat cttcctgtga attggatgtc   600
tggccatatt tggaaaactt cacctccgat gttatttcca gagctgcttt tggttcttct   660
tacgaagaag gtagaaagat cttccaatta ttgagagaag aagccaaggt ttactccgtt   720
gctttgagat ctgtttacat tccaggttgg agattcttgc caactaagca aaacaaaaag   780
accaaagaaa tccacaacga aatcaagggt ttgttgaagg gtatcatcaa caagagagaa   840
gaagctatga aggctggtga agctacaaaa gatgatttgt tgggtatctt gatggaatcc   900
aacttcagag aaatccaaga acacggtaac aacaagaatg ccggtatgtc tattgaagat   960
gttatcggtg aatgcaagtt gttctacttt gctggtcaag aaactacctc cgttttgttg  1020
gtttggacca tgattttgtt gtcccaaaat caagattggc aagctagagc tagagaagaa  1080
gtcttgaaag ttttcggttc taacatccca acctacgaag aattgtctca cttgaaggtt  1140
gtcactatga tcttgttgga agtattgaga ttatacccat ccgttgttgc attgccaaga  1200
actactcata agaaaactca attgggtaaa ttgtccttgc cagctggtgt tgaagtttct  1260
ttgccaattt tgttagtcca ccacgacaaa gaattgtggg gtgaagatgc taatgaattc  1320
aagccagaaa gattctccga aggtgtttct aaagctacca agaacaagtt cacttacttg  1380
ccatttggtg gtggtccaag aatatgtatt ggtcaaaatt tcgctatggt cgaagctaaa  1440
ttggctttgg ctttgatctt gcaacatttc gctttcgaat tgtcaccatc ttatgctcat  1500
gctccatctg ctgttattac attgcaacca caatttggtg cccatatcat cttgcataag  1560
agataac                                                            1567
```

TABLE 11-continued

| Sequences disclosed herein. |
|---|

SEQ ID NO: 100
MEASRASCVA LCVVWVSIVI TLAWRVLNWV WLRPKKLERC LREQGLTGNS YRLLFGDTKD 60
LSKMLEQTQS KPIKLSTSHD IAPRVTPFFH RTVNSNGKNS FVWMGPIPRV HIMNPEDLKD 120
AFNRHDDFHK TVKNPIMKSP PPGIVGIEGE QWAKHRKIIN PAFHLEKLKG MVPIFYQSCS 180
EMINKWESLV SKESSCELDV WPYLENFTSD VISRAAFGSS YEEGRKIFQL LREEAKVYSV 240
ALRSVYIPGW RFLPTKQNKK TKEIHNEIKG LLKGIINKRE EAMKAGEATK DDLLGILMES 300
NFREIQEHGN NKNAGMSIED VIGECKLFYF AGQETTSVLL VWTMILLSQN QDWQARAREE 360
VLKVFGSNIP TYEELSHLKV VTMILLEVLR LYPSVVALPR TTHKKTQLGK LSLPAGVEVS 420
LPILLVHHDK ELWGEDANEF KPERFSEGVS KATKNKFTYL PFGGGPRICI GQNFAMVEAK 480
LALALILQHF AFELSPSYAH APSAVITLQP QFGAHIILHK R 521

SEQ ID NO: 101
ASWVAVLSVV WVSMVIAWAW RVLNWVWLRP KKLEKCLREQ GLAGNSYRLL FGDTKDLSKM 60
LEQTQSKPIK LSTSHDIAPH VTPFFHQTVN SYGKNSFVWM GPIPRVHIMN PEDLKDTFNR 120
HDDFHKVVKN PIMKSLPQGI VGIEGEQWAK HRKIINPAFH LEKLKGMVPI FYRSCSEMIN 180
KWESLVSKES SCELDVWPYL ENFTSDVISR AAFGSSYEEG RKIFQLLREE AKIYTVAMRS 240
VYIPGWRFLP TKQNKKAKEI HNEIKGLLKG IINKREEAMK AGEATKDDLL GILMESNFRE 300
IQEHGNNKNA GMSIEDVIGE CKLFYFAGQE TTSVLLVWTM VLLSQNQDWQ ARAREEVLQV 360
FGSNIPTYEE LSQLKVVTMI LLEVLRLYPS VVALPRTTHK KTQLGKLSLP AGVEVSLPIL 420
LVHHDKELWG EDANEFKPER FSEGVSKATK NQFTYFPFGG GPRICIGQNF AMMEAKLALS 480
LILRHFALEL SPLYAHAPSV TITLQPQYGA HIILHKR 517

SEQ ID NO: 102
MEASRPSCVA LSVVLVSIVI AWAWRVLNWV WLRPNKLERC LREQGLTGNS YRLLFGDTKE 60
ISMMVEQAQS KPIKLSTTHD IAPRVIPFSH QIVYTYGRNS FVWMGPTPRV TIMNPEDLKD 120
AFNKSDEFQR AISNPIVKSI SQGLSSLEGE KWAKHRKIIN PAFHLEKLKG MLPTFYQSCS 180
EMINKWESLV FKEGSREMDV WPYLENLTSD VISRAAFGSS YEEGRKIFQL LREEAKFYTI 240
AARSVYIPGW RFLPTKQNKR MKEIHKEVRG LLKGIINKRE DAIKAGEAAK GNLLGILMES 300
NFREIQEHGN NKNAGMSIED VIGECKLFYF AGQETTSVLL VWTLVLLSQN QDWQARAREE 360
VLQVFGTNIP TYDQLSHLKV VTMILLEVLR LYPAVVELPR TTYKKTQLGK FLLPAGVEVS 420
LHIMLAHHDK ELWGEDAKEF KPERFSEGVS KATKNQFTYF PFGAGPRICI GQNFAMLEAK 480
LALSLILQHF TFELSPSYAH APSVTITLHP QFGAHFILHK R 521

SEQ ID NO: 103
CVALSVVLVS IVIAWAWRVL NWVWLRPNKL ERCLREQGLT GNSYRLLFGD TKEISMMVEQ 60
AQSKPIKLST THDIAPRVIP FSHQIVYTYG RNSFVWMGPT PRVTIMNPED LKDAFNKSDE 120
FQRAISNPIV KSISQGLSSL EGEKWAKHRK IINPAFHLEK LKGMLPTFYQ SCSEMINKWE 180
SLVFKEGSRE MDVWPYLENL TSDVISRAAF GSSYEEGRKI FQLLREEAKF YTIAARSVYI 240
PGWRFLPTKQ NKRMKEIHKE VRGLLKGIIN KREDAIKAGE AAKGNLLGIL MESNFREIQE 300
HGNNKNAGMS IEDVIGECKL FYFAGQETTS VLLVWTLVLL SQNQDWQARA REEVLQVFGT 360
NIPTYDQLSH LKVVTMILLE VLRLYPAVVE LPRTTYKKTQ LGKFLLPAGV EVSLHIMLAH 420
HDKELWGEDA KEFKPERFSE GVSKATKNQF TYFPFGAGPR ICIGQNFAML EAKLALSLIL 480
QHFTFELSPS YAHAPSVTIT LHPQFGAHFI LHKR 514

SEQ ID NO: 104
MGPIPRVHIM NPEDLKDTFN RHDDFHKVVK NPIMKSLPQG IVGIEGDQWA KHRKIINPAF 60
HLEKLKGMVP IFYQSCSEMI NIWKSLVSKE SSCELDVWPY LENFTSDVIS RAAFGSSYEE 120
GRKIFQLLRE EAKVYTVAVR SVYIPGWRFL PTKQNKKTKE IHNEIKGLLK GIINKREEAM 180
KAGEATKDDL LGILMESNFR EIQEHGNNKN AGMSIEDVIG ECKLFYFAGQ ETTSVLLVWT 240
MVLLSQNQDW QARAREEVLQ VFGSNIPTYE ELSHLKVVTM ILLEVLRLYP SVVALPRTTH 300
KKTQLGKLSL PAGVEVSLPI LLVHHDKELW GEDANEFKPE RFSEGVSKAT KNQFTYFPFG 360
GGPRICIGQN FAMMEAKLAL SLILQHFTFE LSPQYSHAPS VTITLQPQYG AHLILHKR 418

SEQ ID NO: 105
atgggtttgt tcccattaga ggattcctac gcgctggtct ttgaaggact agcaataaca 60
ctggctttgt actatctact gtctttcatc tacaaaacat ctaaaaagac atgtacacct 120
cctaaagcat ctggtgaaat cattccaatt acaggaatca tattgaatct gctatctggc 180
tcaagtggtc tacctattat cttagcactt gcctctttag cagacagatg tggtcctatt 240
ttcaccatta ggctgggtat taggagagtg ctagtagtat caaattggga aatcgctaag 300
gagattttca ctacccacga tttgatagtt tctaatagac caaaatactt agccgctaag 360
attcttggtt tcaattatgt ttcattctct ttcgctccat acggcccata ttgggtcgga 420
atcagaaaga ttattgctac aaaactaatg tcttcttcca gacttcagaa gttgcaattt 480
gtaagagttt ttgaactaga aaactctatg aaatctatca gagaatcatg gaaggagaaa 540
aaggatgaag agggaaaggt attagttgag atgaaaaagt ggttctggga actgaatatg 600
aacatagtgt taaggacagt tgctggtaaa caatacactg gtacagttga tgatgccgat 660
gcaaagcgta tctccgagtt attcagagaa tggtttcact acactggcag atttgtcgtt 720
ggagacgctt ttcctttttct aggttggttg gacctgggcg gatacaaaaa gacaatggaa 780
ttagttgcta gtagattgga ctcaatggtc agtaaatggt tagatgagca tcgtaaaaag 840
caagctaacg atgacaaaaa ggaggatatg gatttcatgg atatcatgat ctccatgaca 900
gaagcaaatt caccacttga aggatacggc actgatacta ttatcaagac cacatgtatg 960
actttgattg tttcaggagt tgatacaacc tcaatcgtac ttacttgggc cttatcactt 1020
ttgttaaaca acagagatac tttgaaaaag gcacaagagg aattagatat gtgcgtaggt 1080
aaaggaagac aagtcaacga gtctgatctt gttaacttga tatacttgga agcagtgctt 1140
aaagaggctt taagacttta cccagcagcg ttcttaggcg gaccaagagc attcttggaa 1200
gattgtactg ttgctggtta tagaattcca aagggcacct gcttgttgat taacatgtgg 1260
aaactgcata gagatccaaa catttggagt gatccttgcg aattcaagcc agaaagattt 1320
ttgacaccta atcaaaagga tgttgatgtg atcggtatgg atttcgaatt gataccattt 1380

TABLE 11-continued

| Sequences disclosed herein. |
| --- |
| ggtgccggca gaagatattg tccaggtact agattggctt tacagatgtt gcatatcgta 1440 |
| ttagcgacat tgctgcaaaa cttcgaaatg tcaacaccaa acgatgcgcc agtcgatatg 1500 |
| actgcttctg ttggcatgac aaatgccaaa gcatcacctt tagaagtctt gctatcacct 1560 |
| cgtgttaaat ggtcctaa 1578 |
| |
| SEQ ID NO: 106 |
| MGLFPLEDSY ALVFEGLAIT LALYYLLSFI YKTSKKTCTP PKASGEHPIT GHLNLLSGSS 60 |
| GLPHLALASL ADRCGPIFTI RLGIRRVLVV SNWEIAKEIF TTHDLIVSNR PKYLAAKILG 120 |
| FNYVSFSFAP YGPYWVGIRK IIATKLMSSS RLQKLQFVRV FELENSMKSI RESWKEKKDE 180 |
| EGKVLVEMKK WFWELNMNIV LRTVAGKQYT GTVDDADAKR ISELFREWFH YTGRFVVGDA 240 |
| FPFLGWLDLG GYKKTMELVA SRLDSMVSKW LDEHRKKQAN DDKKEDMDFM DIMISMTEAN 300 |
| SPLEGYGTDT IIKTTCMTLI VSGVDTTSIV LTWALSLLLN NRDTLKKAQE ELDMCVGKGR 360 |
| QVNESDLVNL IYLEAVLKEA LRLYPAAFLG GPRAFLEDCT VAGYRIPKGT CLLINMWKLH 420 |
| RDPNIWSDPC EFKPERFLTP NQKDVDVIGM DFELIPFGAG RRYCPGTRLA LQMLHIVLAT 480 |
| LLQNFEMSTP NDAPVDMTAS VGMTNAKASP LEVLLSPRVK WS 522 |
| |
| SEQ ID NO: 107 |
| atgatacaag ttttaactcc aattctactc ttcctcatct tcttcgtttt ctggaaagtc 60 |
| tacaaacatc aaaagactaa aatcaatcta ccaccaggtt ccttcggctg gccatttttg 120 |
| ggtgaaacct tagccttact tagagcaggc tgggattctg agccagaaag attcgtaaga 180 |
| gagcgtatca aaaagcatgg atctccactt gttttcaaga catcactatt tggagacaga 240 |
| ttcgctgttc tttgcggtcc agctggtaat aagtttttgt tctgcaacga aaacaaatta 300 |
| gtggcatctt ggtggccagt ccctgtaagg aagttgttcg gtaaaagttt actcacaata 360 |
| agaggagatg aagcaaaatg gatgagaaaa atgctattgt cttacttggg tccagatgca 420 |
| tttgccacac attatgccgt tactatggat gttgtaacac gtagacatat tgatgtccat 480 |
| tggaggggca aggaggaagt taatgtattt caaacagtta agttgtacgc attcgaatta 540 |
| gcttgtagat tattcatgaa cctagatgac ccaaaccaca tcgcgaaact cggtagtctt 600 |
| ttcaacattt tcctcaaagg gatcatcgag cttcctatag acgttcctgg aactagattt 660 |
| tactccagta aaaaggccgc agctgccatt agaattgaat tgaaaaagct cattaaagct 720 |
| agaaaactcg aattgaagga gggtaaggcg tcttcttcac aggacttgct ttctcatcta 780 |
| ttaacatcac ctgatgagaa tgggatgttc ttgacagaag aggaaatagt cgataacatt 840 |
| ctacttttgt tattcgctgg tcacgatacc tctgcactat caataacact tttgatgaaa 900 |
| accttaggtg aacacagtga tgtgtacgac aaggtttgga aggaacaatt agaaatttcc 960 |
| aaaacaaagg aggcttggga atcactaaag tgggaagata tccagaagat gaagtactca 1020 |
| tggtcagtaa tctgtgaagt catgagattg aatcctcctg tcatagggac atacagagag 1080 |
| gcgttggttg atatcgacta tgctggttac actatcccaa aaggatggaa gttgcattgg 1140 |
| tcagctgttt ctactcaaag agacgaagcc aatttcgaag atgtaactag attcgatcca 1200 |
| tccagatttg aaggggcagg ccctactcca ttcacatttg tgcctttcgg tggaggtcct 1260 |
| agaatgtgtt taggcaaaga gtttgccagg ttagaagtgt tagcatttct ccacaacatt 1320 |
| gttaccaact ttaagtggga tcttctaatc cctgatgaga agatcgaata tgatccaatg 1380 |
| gctactccag ctaagggctt gccaattaga cttcatccac accaagtcta a 1431 |
| |
| SEQ ID NO: 108 |
| MIQVLTPILL FLIFFVFWKV YKHQKTKINL PPGSFGWPFL GETLALLRAG WDSEPERFVR 60 |
| ERIKKHGSPL VFKTSLFGDR FAVLCGPAGN KFLFCNENKL VASWWPVPVR KLFGKSLLTI 120 |
| RGDEAKWMRK MLLSYLGPDA FATHYAVTMD VVTRRHIDVH WRGKEEVNVF QTVKLYAFEL 180 |
| ACRLFMNLDD PNHIAKLGSL FNIFLKGIIE LPIDVPGTRF YSSKKAAAAI RIELKKLIKA 240 |
| RKLELKEGKA SSSQDLLSHL LTSPDENGMF LTEEEIVDNI LLLLFAGHDT SALSITLLMK 300 |
| TLGEHSDVYD KVLKEQLEIS KTKEAWESLK WEDIQKMKYS WSVICEVMRL NPPVIGTYRE 360 |
| ALVDIDYAGY TIPKGWKLHW SAVSTQRDEA NFEDVTRFDP SRFEGAGPTP FTFVPFGGGP 420 |
| RMCLGKEFAR LEVLAFLHNI VTNFKWDLLI PDEKIEYDPM ATPAKGLPIR LHPHQV 476 |
| |
| SEQ ID NO: 109 |
| atggagtctt tagtggttca tacagtaaat gctatctggt gtattgtaat cgtcgggatt 60 |
| ttctcagttg gttatcacgt ttacggtaga gctgtggtcg aacaatggag aatgagaaga 120 |
| tcactgaagc tacaaggtgt taaaggccca ccaccatcca tcttcaatgg taacgtctca 180 |
| gaaatgcaac gtatccaatc cgaagctaaa cactgctctg gcgataacat tatctcacat 240 |
| gattattctt cttcattatt cccacacttc gatcactgga gaaaacagta cggcagaatc 300 |
| tacacatact ctactggatt aaagcaacac ttgtacatca atcatccaga aatggtgaag 360 |
| gagctatctc agactaacac attgaacttg ggtagaatca cccatataac caaaagattg 420 |
| aatcctatct taggtaacgg aatcataacc tctaatggtc ctcattgggc ccatcagcgt 480 |
| agaattatcg cctacgagtt tactcatgat aagatcaagg gtatggttgg tttgatggtt 540 |
| gagtctgcta tgcctatgtt gaataagtgg gaggagatgg taaagagagg cggagaaatg 600 |
| ggatgcgaca taagagttga tgaggacttg aaagatgttt cagcagatgt gattgcaaaa 660 |
| gcctgtttcg gatcctcatt ttctaaaggt aaggctattt tctctatgat aagagatttg 720 |
| cttacagcta tcacaaagag aagtgttcta ttcagattca acggattcac tgatatggtc 780 |
| tttgggagta aaaagcatgg tgacgttgat atagacgctt tagaaatgga attggaatca 840 |
| tccatttggg aaactgtcaa ggaacgtgaa atagaatgta aagatactca caaaaaggat 900 |
| ctgatgcaat tgattttgga aggggcaatg cgttcatgtg acggtaacct ttgggataaa 960 |
| tcagcatata gaagatttgt tgtagataat tgtaaatcta tctacttcgc agggcatgat 1020 |
| agtacagctg tctcagtgtc atggtgtttg atgttactgg ccctaaaccc atcatggcaa 1080 |
| gttaagatcc gtgatgaaat tctgtcttct tgcaaaaatg gtattccaga tgccgaaagt 1140 |
| atcccaaacc ttaaaacagt gactatggtt attcaagaga caatgagatt ataccctcca 1200 |
| gcaccaatcg tcgggagaga agcctctaaa gatatcagat tgggcgatct agttgttcct 1260 |
| aaaggcgtct gtatatggac actaatacca gctttacaca gagatcctga gatttgggga 1320 |
| ccagatgcaa acgatttcaa accagaaaga ttttctgaag gaatttcaaa ggcttgtaag 1380 |
| tatcctcaaa gttacattcc atttggtctg ggtcctagaa catgcgttgg taaaaacttt 1440 |
| ggcatgatgg aagtaaaggt tcttgtttcc ctgattgtct ccaagttctc tttcactcta 1500 |

TABLE 11-continued

Sequences disclosed herein.

```
tctcctacct accaacatag tcctagtcac aaacttttag tagaaccaca acatggggtg  1560
gtaattagag tggtttaa                                                 1578

SEQ ID NO: 110
MESLVVHTVN AIWCIVIVGI FSVGYHVYGR AVVEQWRMRR SLKLQGVKGP PPSIFNGNVS    60
EMQRIQSEAK HCSGDNIISH DYSSSLFPHF DHWRKQYGRI YTYSTGLKQH LYINHPEMVK   120
ELSQTNTLNL GRITHITKRL NPILGNGIIT SNGPHWAHQR RIIAYEFTHD KIKGMVGLMV   180
ESAMPMLNKW EEMVKRGGEM GCDIRVDEDL KDVSADVIAK ACFGSSFSKG KAIFSMIRDL   240
LTAITKRSVL FRFNGFTDMV FGSKKHGDVD IDALEMELES SIWETVKERE IECKDTHKKD   300
LMQLILEGAM RSCDGNLWDK SAYRRFVVDN CKSIYFAGHD STAVSVSWCL MLLALNPSWQ   360
VKIRDEILSS CKNGIPDAES IPNLKTVTMV IQETMRLYPP APIVGREASK DIRLGDLVVP   420
KGVCIWTLIP ALHRDPEIWG PDANDFKPER FSEGISKACK YPQSYIPFGL GPRTCVGKNF   480
GMMEVKVLVS LIVSKFSFTL SPTYQHSPSH KLLVEPQHGV VIRVV                   525

SEQ ID NO: 111
atgtacttcc tactacaata cctcaacatc acaaccgttg gtgtctttgc cacattgttt    60
ctctcttatt gtttacttct ctggagaagt agagcgggta acaaaaagat tgccccagaa   120
gctgccgctg catggcctat tatcggccac ctccacttac ttgcaggtgg atcccatcaa   180
ctaccacata ttacattggg taacatggca gataagtacg gtcctgtatt cacaatcaga   240
ataggcttgc atagagctgt agttgtctca tcttgggaaa tggcaaagga atgttcaaca   300
gctaatgatc aagtgtcttc ttcaagacct gaactattag cttctaagtt gttgggttat   360
aactacgcca tgtttggttt ttcaccatac ggttcatact ggagagaaat gagaaagatc   420
atctctctcg aattactatc taattccaga ttggaactat tgaaagatgt tagagcctca   480
gaagttgtca catctattaa ggaactatac aaattgtggg cggaaaagaa gaatgagtca   540
ggattggttt ctgtcgagat gaaacaatgg ttcggagatt tgactttaaa cgtgatcttg   600
agaatggtgg ctggtaaaag atacttctcc gcgagtgacg cttcagaaaa caaacaggcc   660
cagcgttgta gaagagtctt cagagaattc ttccatctct ccggcttgtt tgtggttgct   720
gatgctatac cttttcttgg atggctcgat tggggaagac acgagaagac cttgaaaaag   780
accgccatag aaatggattc catcgcccag gagtggcttg aggaacatag acgtagaaaa   840
gattctggag atgataattc tacccaagat ttcatggacg ttatgcaatc tgtgctagat   900
ggcaaaaatc taggcggata cgatgctgat acgattaaca aggctacatg cttaactctt   960
atatcaggtg gcagtgatac tactgtagtt tctttgacat gggctcttag tcttgtgtta  1020
aacaatagag atactttgaa aaaggcacag gaagagttag acatccaagt cggtaaggaa  1080
agattggtta acgagcaaga catcagtaag ttagtttact tgcaagcaat agtaaaagag  1140
acactcagac tttatccacc aggtcctttg ggtggtttga gacaattcac tgaagattgt  1200
acactaggtg gctatcacgt ttcaaaagga actagattaa tcatgaactt atccaagatt  1260
caaaaagatc cacgtatttg gtctgatcct actgaattcc aaccagagag attccttacg  1320
actcataaag atgtcgatcc acgtggtaaa cactttgaat tcattccatt cggtgcagga  1380
agacgtgcat gtcctggtat cacattcgga ttacaagtac tacatctaac attggcatct  1440
ttcttgcatg cgtttgaatt ttcaacacca tcaaatgagc aggttaacat gagagaatca  1500
ttaggtctta cgaatatgaa atctacccca ttagaagttt tgatttctcc aagactatcc  1560
cttaattgct tcaaccttat gaaaatttga                                    1590

SEQ ID NO: 112
MYFLLQYLNI TTVGVFATLF LSYCLLLWRS RAGNKKIAPE AAAAWPIIGH LHLLAGGSHQ    60
LPHITLGNMA DKYGPVFTIR IGLHRAVVVS SWEMAKECST ANDQVSSSRP ELLASKLLGY   120
NYAMFGFSPY GSYWREMRKI ISLELLSNSR LELLKDVRAS EVVTSIKELY KLWAEKKNES   180
GLVSVEMKQW FGDLTLNVIL RMVAGKRYFS ASDASENKQA QRCRRVFREF FHLSGLFVVA   240
DAIPFLGWLD WGRHEKTLKK TAIEMDSIAQ EWLEEHRRRK DSGDDNSTQD FMDVMQSVLD   300
GKNLGGYDAD TINKATCLTL ISGGSDTTVV SLTWALSLVL NNRDTLKKAQ EELDIQVGKE   360
RLVNEQDISK LVYLQAIVKE TLRLYPPGPL GGLRQFTEDC TLGGYHVSKG TRLIMNLSKI   420
QKDPRIWSDP TEFQPERFLT THKDVDPRGK HFEFIPFGAG RRACPGITFG LQVLHLTLAS   480
FLHAFEFSTP SNEQVNMRES LGLTNMKSTP LEVLISPRLS SCSLYN                  526

SEQ ID NO: 113
atggaaccta actttactt gtcattacta ttgttgttcg tgaccttcat ttctttaagt    60
ctgtttttca tcttttacaa acaaaagtcc ccattgaatt tgccaccagg gaaaatgggt   120
taccctatca taggtgaaag tttagaattc ctatccacag gctggaaggg acatcctgaa   180
aagttcatat ttgatagaat gcgtaagtac agtagtgagt tattcaagac ttctattgta   240
ggcgaatcca cagttgtttg ctgtggggca gctagtaaca aattcctatt ctctaacgaa   300
aacaaactgg taactgcctg gtggccagat tctgttaaca aaatcttccc aacaacttca   360
ctggattcta atttgaagga ggaatctata aagatgagaa agttgctgcc acagttcttc   420
aaaccagaag cacttcaaag atacgtcggc gttatggatg taatcgcaca aagacatttt   480
gtcactcact gggacaacaa aaatgagatc acagtttatc cacttgctaa aagatacact   540
ttcttgcttg cgtgtagact gttcatgtct gttgaggatg aaaatcatgt ggcgaaattc   600
tcagacccat tccaactaat cgctgcaggc atcatttcac ttcctatcga tcttcctggt   660
actccattca acaaggccat aaaggcttca aatttcatta gaaaagagct gataaagatt   720
atcaaacaaa gacgtgttga tctggcagag ggtacagcat ctccaaccca ggatatcttg   780
tcacatatgc tattaacatc tgatgaaaac ggtaaatcta tgaacgagtt gaacattgcc   840
gacaagattc ttggactatt gataggaggc cacgatacag cttcagtagc ttgcacattt   900
ctagtgaagt acttaggaga attaccacat atctacgata aagtctacca agagcaaatg   960
gaaattgcca agtccaaacc tgctggggaa ttgttgaatt gggatgactt gaaaaagatg  1020
aagtattcat ggaatgtggc atgtgaggta atgagattgt caccaccttt acaaggtggt  1080
tttagagagg ctataactga ctttatgttt aacggtttct ctattccaaa agggtggaag  1140
ttatactggt ccgccaactc tacacacaaa aatgcagaat gtttcccaat gcctgagaaa  1200
```

TABLE 11-continued

Sequences disclosed herein.

```
ttcgatccta ccagatttga aggtaatggt ccagcgcctt atacatttgt accattcggt  1260
ggaggcccta gaatgtgtcc tggaaaggaa tacgctagat tagaaatctt ggttttcatg  1320
cataatctgg tcaaacgttt taagtgggaa aaggttattc cagacgaaaa gattattgtc  1380
gatccattcc caatcccagc taaagatctt ccaatccgtt tgtatcctca caaagcttaa  1440

SEQ ID NO: 114
MEPNFYLSLL LLFVTFISLS LFFIFYKQKS PLNLPPGKMG YPIIGESLEF LSTGWKGHPE    60
KFIFDRMRKY SSELFKTSIV GESTVVCCGA ASNKFLFSNE NKLVTAWWPD SVNKIFPTTS   120
LDSNLKEESI KMRKLLPQFF KPEALQRYVG VMDVIAQRHF VTHWDNKNEI TVYPLAKRYT   180
FLLACRLFMS VEDENHVAKF SDPFQLIAAG IISLPIDLPG TPFNKAIKAS NFIRKELIKI   240
IKQRRVDLAE GTASPTQDIL SHMLLTSDEN GKSMNELNIA DKILGLLIGG HDTASVACTF   300
LVKYLGELPH IYDKVYQEQM EIAKSKPAGE LLNWDDLKKM KYSWNVACEV MRLSPPLQGG   360
FREAITDFMF NGFSIPKGWK LYWSANSTHK NAECFPMPEK FDPTRFEGNG PAPYTFVPFG   420
GGPRMCPGKE YARLEILVFM HNLVKRFKWE KVIPDEKIIV DPFPIPAKDL PIRLYPHKA    479

SEQ ID NO: 115
atggcctctg ttactttggg ttcctggatc gtcgtccacc accataacca tcaccatcca    60
tcatctatcc taactaaatc tcgttcaaga tcctgtccta ttacactaac caaaccaatc   120
tcttttcgtt caaagagaac agtttcctct agtagttcta tcgtgtcctc tagtgtcgtc   180
actaaggaag acaatctgag acagtctgaa ccttcttcct ttgatttcat gtcatatatc   240
attactaagg cagaactagt gaataaggct cttgattcag cagttccatt aagagagcca   300
ttgaaaatcc atgaagcaat gagatactct cttctagctg gcgggaagag agtcagacct   360
gtactctgca tagcagcgtg cgaattagtt ggtggcgagg aatcaaccgc tatgcctgcc   420
gcttgtgctg tagaaatgat tcatacaatg tcactgatac acgatgattt gccatgtatg   480
gataacgatg atctgagaag gggtaagcca actaaccata aggttttcgg cgaagatgtt   540
gccgtcttag ctggtgatgc tttgttatct ttcgcgttcg aacatttggc atccgcaaca   600
tcaagtgatg ttgtgtcacc agtaagagta gttagagcag ttggagaact ggctaaagct   660
attggaactg agggtttagt tgcaggtcaa gtcgtcgata tctcttccga aggtcttgat   720
ttgaatgatg taggtcttga acatctcgaa ttcatccatc ttcacaagac agctgcactt   780
ttagaagcca gtgcggttct cggcgcaatt gttggcggag ggagtgatga cgaaattgag   840
agattgagga agtttgctag atgtatagga ttactgttcc aagtagtaga cgatatacta   900
gatgtgacaa agtcttccaa agagttggga aaaacagctg gtaaagattt gattgccgac   960
aaattgacct accctaagat tatggggcta gaaaaatcaa gagaatttgc cgagaaactc  1020
aatagagagg cgcgtgatca actgttgggt ttcgattctg ataaagttgc accactctta  1080
gccttagcca actacatcgc ttacagacaa aactaa                            1116

SEQ ID NO: 116
MASVTLGSWI VVHHHNHHHP SSILTKSRSR SCPITLTKPI SFRSKRTVSS SSSIVSSSVV    60
TKEDNLRQSE PSSFDFMSYI ITKAELVNKA LDSAVPLREP LKIHEAMRYS LLAGGKRVRP   120
VLCIAACELV GGEESTAMPA ACAVEMIHTM SLIHDDLPCM DNDDLRRGKP TNHKVFGEDV   180
AVLAGDALLS FAFEHLASAT SSDVVSPVRV VRAVGELAKA IGTEGLVAGQ VVDISSEGLD   240
LNDVGLEHLE FIHLHKTAAL LEASAVLGAI VGGGSDDEIE RLRKFARCIG LLFQVVDDIL   300
DVTKSSKELG KTAGKDLIAD KLTYPKIMGL EKSREFAEKL NREARDQLLG FDSDKVAPLL   360
ALANYIAYRQ N                                                        371
```

SEQ ID NO: 117
*R. suavissimus*

```
MATLLEHFQA MPFAIPIALA ALSWLFLFYI KVSFFSNKSA QAKLPPVPVV PGLPVIGNLL    60
QLKEKKPYQT FTRWAEEYGP IYSIRTGAST MVVLNTTQVA KEAMVTRYLS ISTRKLSNAL   120
KILTADKCMV AISDYNDFHK MIKRYILSNV LGPSAQKRHR SNRDTLRANV CSRLHSQVKN   180
SPREAVNFRR VFEWELFGIA LKQAFGKDIE KPIYVEELGT TLSRDEIFKV LVLDIMEGAI   240
EVDWRDFFPY LRWIPNTRME TKIQRLYFRR KAVMTALINE QKKRIASGEE INCYIDFLLK   300
EGKTLTMDQI SMLLWETVIE TADTTMVTTE WAMYEVAKDS KRQDRLYQEI QKVCGSEMVT   360
EEYLSQLPYL NAVFHETLRK HSPAALVPLR YAHEDTQLGG YYIPAGTEIA INIYGCNMDK   420
HQWESPEEWK PERFLDPKFD PMDLYKTMAF GAGKRVCAGS LQAMLIACPT IGRLVQEFEW   480
KLRDGEEENV DTVGLTTHKR YPMHAILKPR S                                  511
```

SEQ ID NO: 118
*S. cerevisiae*

```
atgtcatttc aaattgaaac ggttcccacc aaaccatatg aagaccaaaa gcctggtacc    60
tctggtttgc gtaagaagac aaaggtgttt aaagacgaac ctaactacac agaaaatttc   120
attcaatcga tcatggaagc tattccagag ggttctaaag gtgccactct tgttgtcggt   180
ggtgatgggc gttactacaa tgatgtcatt cttcataaga ttgccgctat cggtgctgcc   240
aacggtatta aaaagttagt tattggccag catggtcttc tgtctacgcc agccgcttct   300
cacatcatga gaacctacga ggaaaaatgt actggtggta ttatcttaac cgcctcacat   360
aatccaggtg gtccagaaaa tgacatggat attaagtata acttatccaa tgggggtcct   420
gctcctgaat ccgtcacaaa tgctatttgg gagatttcca aaaagcttac cagctataag   480
attatcaaag acttcccaga actagacttg ggtacgatag gcaagaacaa gaaatacggt   540
ccattactcg ttgacattat cgatattaca aaagattatg tcaacttctt gaaggaaatc   600
ttcgatttcg acttaatcaa gaaattcatc gataatcaac gttctactaa gaattggaag   660
ttactgtttg acagtatgaa cggtgtaact ggaccatacg gtaaggctat tttcgttgat   720
gaatttggtt taccggcgga tgaggtttta caaaactggc atccttctcc ggattttggt   780
ggtatgcatc cagatccaaa cttaacttat gccagttcgt tagtgaaaag agtagatcgt   840
gaaaagattg agtttggtgc tgcatccgat ggtgatggtg atagaaatat gatttacggt   900
tacggcccat ctttcgtttc tccaggtgac tccgtcgcaa ttattgccga atatgcagct   960
gaaatcccat atttcgccaa gcaaggtata tatggtctgg cccgttcatt ccctacctca  1020
ggagccatag accgtgttgc caaggcccat ggtctaaact gttatgaggt cccaactggc  1080
tggaaatttt tctgtgcttt gttcgacgct aaaaaattat ctatttgtgg tgaagaatcg  1140
```

TABLE 11-continued

| Sequences disclosed herein. |
| --- |

```
tttggtactg gttccaacca cgtaagggaa aaggacggtg tttgggccat tatggcgtgg  1200
ttgaacatct tggccattta caacaagcat catccggaga acgaagcttc tattaagacg  1260
atacagaatg aattctgggc aaagtacggc cgtactttct tcactcgtta tgattttgaa  1320
aaagttgaaa cagaaaaagc taacaagatt gtcgatcaat tgagagcata tgttaccaaa  1380
tcgggtgttg ttaattccgc cttcccagcc gatgagtctc ttaaggtcac cgattgtggt  1440
gatttttcat acacagattt ggacggttct gtttctgacc atcaaggttt atatgtcaag  1500
ctttccaatg gtgcaagatt cgttctaaga ttgtcaggta caggttcttc aggtgctacc  1560
attagattgt acattgaaaa atactgcgat gataaatcac aataccaaaa gacagctgaa  1620
gaatacttga agccaattat taactcggtc atcaagttct tgaactttaa acaagtttta  1680
ggaactgaag aaccaacggt tcgtacttaa                                   1710
```

SEQ ID NO: 119
*S. cerevisiae*

```
MSFQIETVPT KPYEDQKPGT SGLRKKTKVF KDEPNYTENF IQSIMEAIPE GSKGATLVVG    60
GDGRYYNDVI LHKIAAIGAA NGIKKLVIGQ HGLLSTPAAS HIMRTYEEKC TGGIILTASH   120
NPGGPENDMG IKYNLSNGGP APESVTNAIW EISKKLTSYK IIKDFPELDL GTIGKNKKYG   180
PLLVDIIDIT KDYVNFLKEI FDFDLIKKFI DNQRSTKNWK LLFDSMNGVT GPYGKAIFVD   240
EFGLPADEVL QNWHPSPDFG GMHPDPNLTY ASSLVKRVDR EKIEFGAASD GDGDRNMIYG   300
YGPSFVSPGD SVAIIAEYAA EIPYFAKQGI YGLARSFPTS GAIDRVAKAH GLNCYEVPTG   360
WKFFCALFDA KKLSICGEES FGTGSNHVRE KDGVWAIMAW LNILAIYNKH HPENEASIKT   420
IQNEFWAKYG RTFFTRYDFE KVETEKANKI VDQLRAYVTK SGVVNSAFPA DESLKVTDCG   480
DFSYTDLDGS VSDHQGLYVK LSNGARFVLR LSGTGSSGAT IRLYIEKYCD DKSQYQKTAE   540
EYLKPIINSV IKFLNFKQVL GTEEPTVRT                                     569
```

SEQ ID NO: 120
*S. cerevisiae*

```
atgtccacta agaagcacac caaaacacat tccacttatg cattcgagag caacacaaac    60
agcgttgctg cctcacaaat gagaaacgcc ttaaacaagt tggcggactc tagtaaactt   120
gacgatgctg ctcgcgctaa gtttgagaac gaactggatt cgtttttcac gcttttcagg   180
agatatttgg tagagaagtc ttctagaacc accttggaat gggacaagat caagtctccc   240
aacccggatg aagtggttaa gtatgaaatt atttctcagc agcccgagaa tgtctcaaac   300
ctttccaaat tggctgtttt gaagttgaac ggtgggctgg gtacctccat gggctgcgtt   360
ggccctaaat ctgttattga agtgagagag ggaaacacct tttggattt gtctgttcgt    420
caaattgaat acttgaacag acagtacgat agcgacgtgc cattgttatt gatgaattct   480
ttcaacactg acaaggatac ggaacacttg attaagaagt attccgctaa cagaatcaga   540
atcagatctt tcaatcaatc caggttccca agagtctaca aggattcttt attgcctgtc   600
cccaccgaat acgattctcc actggatgct tggtatccac caggtcacgg tgatttgttt   660
gaatctttac acgtatctgg tgaactggat gccttaattg cccaaggaag agaaatatta   720
tttgtttcta acggtgacaa cttgggtgct accgtcgact taaaaatttt aaaccacatg   780
atcgagactg gtgccgaata tataatggaa ttgactgata agaccagagc cgatgttaaa   840
ggtggtactt tgatttctta cgatggtcaa gtccgtttat tggaagtcgc ccaagttcca   900
aaagaacaca ttgacgaatt caaaaatatc agaaagttta ccaacttcaa cacgaataac   960
ttatggatca atctgaaagc agtaaagagg ttgatcgaat cgagcaattt ggagatggaa  1020
atcattccaa accaaaaaac tataacaaga gacggtcatg aaattaatgt cttacaatta  1080
gaaaccgctt gtggtgctgc tatcaggcat tttgatggtg ctcacggtgt tgtcgttcca  1140
agatcaagat tcttgcctgt caagacctgt tccgatttgt tgctggttaa atcagatcta  1200
ttccgtctgg aacacggttc tttgaagtta gacccatccc gttttggtcc aaacccatta  1260
atcaagttgg gctcgcattt caaaaaggtt tctggtttta acgcaagaat ccctcacatc  1320
ccaaaaatcg tcgagctaga tcatttgacc atcactggta acgtcttttt aggtaaagat  1380
gtcactttga ggggtactgt catcatcgtt tgctccgacg gtcataaaat cgatattcca  1440
aacggctcca tattggaaaa tgttgtcgtt actggtaatt tgcaaatctt ggaacattga  1500
```

SEQ ID NO: 121
*S. cerevisiae*

```
MSTKKHTKTH STYAFESNTN SVAASQMRNA LNKLADSSKL DDAARAKFEN ELDSFFTLFR    60
RYLVEKSSRT TLEWDKIKSP NPDEVVKYEI ISQQPENVSN LSKLAVLKLN GGLGTSMGCV   120
GPKSVIEVRE GNTFLDLSVR QIEYLNRQYD SDVPLLLMNS FNTDKDTEHL IKKYSANRIR   180
IRSFNQSRFP RVYKDSLLPV PTEYDSPLDA WYPPGHGDLF ESLHVSGELD ALIAQGREIL   240
FVSNGDNLGA TVDLKILNHM IETGAEYIME LTDKTRADVK GGTLISYDGQ VRLLEVAQVP   300
KEHIDEFKNI RKFTNFNTNN LWINLKAVKR LIESSNLEME IIPNQKTITR DGHEINVLQL   360
ETACGAAIRH FDGAHGVVVP RSRFLPVKTC SDLLLVKSDL FRLEHGSLKL DPSRFGPNPL   420
IKLGSHFKKV SGFNARIPHI PKIVELDHLT ITGNVFLGKD VTLRGTVIIV CSDGHKIDIP   480
NGSILENVVV TGNLQILEH                                                499
```

SEQ ID NO: 122
*S. cerevisiae*

```
atgtctagtc aaacagaaag aacttttatt gcggtaaaac cagatggtgt ccagaggggc    60
ttagtatctc aaattctatc tcgttttgaa aaaaaaggtt acaaactagt tgctattaaa   120
ttagttaaag cggatgataa attactagag caacattacg cagagcatgt tggtaaacca   180
tttttcccaa agatggtatc ctttatgaag tctggtccca ttttggccac ggtctgggag   240
ggaaaagatg tggttagaca aggaagaact attcttggtg ctactaatcc tttgggcagt   300
gcaccaggta ccattagagg tgatttcggt attgacctag gcagaaacgt ctgtcacggc   360
agtgattctg ttgatagcgc tgaacgtgaa atcaatttgt ggtttaagaa ggaagagtta   420
gttgattggg aatctaatca agctaagtgg atttatgaat ga                      462
```

TABLE 11-continued

Sequences disclosed herein.

SEQ ID NO: 123
*S. cerevisiae*
MSSQTERTFI AVKPDGVQRG LVSQILSRFE KKGYKLVAIK LVKADDKLLE QHYAEHVGKP 60
FFPKMVSFMK SGPILATVWE GKDVVRQGRT ILGATNPLGS APGTIRGDFG IDLGRNVCHG 120
SDSVDSAERE INLWFKKEEL VDWESNQAEW IYE 153

SEQ ID NO: 124
*S. rebaudiana*
atggctgctg ctgatactga aaagttgaac aatttgagat ccgccgtttc tggtttgacc 60
caaatttctg ataacgaaaa gtccggtttc atcaacttgg tcagtagata tttgtctggt 120
gaagctcaac acgttgaatg gtctaaaatt caaactccaa ccgataagat cgttgttcca 180
tacgatactt tgtctgctgt tccagaagat gctgctcaaa caaaatcttt gttggataag 240
ttggtcgtct tgaagttgaa cggtggtttg ggtactacta tgggttgtac tggtccaaag 300
tctgttatcg aagttagaaa cggtttgacc ttcttggatt tgatcgtcat ccaaatcgaa 360
tccttgaaca agaagtacgg ttgttctgtt cctttgttgt tgatgaactc tttcaacacc 420
catgaagata cccaaaagat cgtcgaaaag tactccggtt ctaacattga agttcacacc 480
ttcaatcaat cccaataccc aagattggtt gtcgatgaat tttgccatt gccatctaaa 540
ggtgaaactg gtaaagatgg ttggtatcca ccaggtcatg gtgatgtttt tccatccttg 600
atgaattccg gtaagttgga tgctttgttg tcccaaggta aagaatacgt tttcgttgcc 660
aactctgata acttgggtgc agttgttgat ttgaagatct tgaaccactt gatccaaaac 720
aagaacgaat actgcatgga agttactcca aagactttgg ctgatgttaa gggtggtact 780
ttgatttctt acgatggtaa ggttcaatta ttggaaatcg cccaagttcc agatgaacac 840
gttaatgaat tcaagtccat cgaaaagttt aagatcttta acactaacaa cttgtgggtc 900
aacttgaacg ccattaagag attggttcaa gctgatgctt tgaagatgga aattattcca 960
aatccaaaag aagtcaacgg tgtcaaggta ttgcaattgg aaactgctgc tggtgctgct 1020
attaagtttt tcgataatgc catcggtatc aacgtcccaa gatctagatt tttgcctgtt 1080
aaggcttcct ctgacttgtt gttagttcaa tcagacttgt acaccgaaaa ggatggttac 1140
gttattagaa acccagctag aaaggatcca gctaacccat ctattgaatt gggtccagaa 1200
ttcaaaaagg tcggtgattt cttgaagaga ttcaagtcta tcccatccat catcgaattg 1260
gactcattga aagtttctgg tgatgtctgg tttggttcca acgttgtttt gaaaggtaag 1320
gttgttgttg ctgccaaatc cggtgaaaaa ttggaaattc cagatggtgc cttgattgaa 1380
aacaaagaag ttcatggtgc ctccgacatt tga 1413

SEQ ID NO: 125
*S. rebaudiana*
MAAADTEKLN NLRSAVSGLT QISDNEKSGF INLVSRYLSG EAQHVEWSKI QTPTDKIVVP 60
YDTLSAVPED AAQTKSLLDK LVVLKLNGGL GTTMGCTGPK SVIEVRNGLT FLDLIVIQIE 120
SLNKKYGCSV PLLLMNSFNT HEDTQKIVEK YSGSNIEVHT FNQSQYPRLV VDEFLPLPSK 180
GETGKDGWYP PGHGDVFPSL MNSGKLDALL SQGKEYVFVA NSDNLGAVVD LKILNHLIQN 240
KNEYCMEVTP KTLADVKGGT LISYDGKVQL LEIAQVPDEH VNEFKSIEKF KIFNTNNLWV 300
NLNAIKRLVQ ADALKMEIIP NPKEVNGVKV LQLETAAGAA IKFFDNAIGI NVPRSRFLPV 360
KASSDLLLVQ SDLYTEKDGY VIRNPARKDP ANPSIELGPE FKKVGDFLKR FKSIPSIIEL 420
DSLKVSGDVW FGSNVVLKGK VVVAAKSGEK LEIPDGALIE NKEVHGASDI 470

SEQ ID NO: 126
*A. pullulans*
atgtcctctg aaatggctac tcatttgaaa cctaatggtg gtgccgaatt cgaaaaaaga 60
catcatggta agacccaatc ccatgttgct tttgaaaaca cttctacatc tgttgctgcc 120
tcccaaatga gaaatgcttt gaatactttg tgcgattccg ttactgatcc agctgaaaag 180
caaagattcg aaaccgaaat ggataacttc ttcgccttgt ttagaagata cttgaacgat 240
aaggctaagg gtaacgaaat cgaatggtct agaattgctc caccaaaacc agaacaagtt 300
gttgcttatc aagacttgcc tgaacaagaa tccgttgaat tcttgaacaa attggccgtc 360
ttgaagttga atggtggttt gggtacttct atgggttgtg ttggtccaaa gtctgttatc 420
gaagttagag atggtatgtc cttcttggat ttgtccgtta gacaaatcga atacttgaat 480
agaacctacg gtgttaacgt tccattcgtc ttgatgaatt ctttcaacac tgatgctgat 540
accgccaaca ttatcaaaaa gtacgaaggt cacaacatcg acatcatgac cttcaatcaa 600
tctagatacc caagaatctt gaaggattct ttgttgccag ctccaaaatc tgccaactct 660
caaatttctg attggtatcc accaggtcat ggtgacgttt ttgaatcctt gtacaactct 720
ggtatcttgg ataagttgtt ggaaagaggt gtcgaaatcg ttttcttgtc caatgctgat 780
aatttgggtg ccgttgttga tttgaagatc ttgcaacata tggttgatac caaggccgaa 840
tatatcatgg aattgactga taagactaag gccgatgtta agggtggtac tattattgac 900
tatgaaggtc aagccagatt attggaaatt gcccaagttc caaaagaaca cgtcaacgaa 960
ttcaagtcca tcaagaagtt taagtacttc aacaccaaca acatctggat gaacttgaga 1020
gctgttaaga gaatcgtcga aaacaacgaa ttggccatgg aaattatccc aaacggtaaa 1080
tctattccag ccgacaaaaa aggtgaagcc gatgtttcta tagttcaatt ggaaactgct 1140
gttggtgctg ccattagaca ttttaacaat gctcatggtg tcaacgtccc aagaagaaga 1200
tttttgccag ttaagacctg ctccgatttg atgttggtta agtctgactt gtacactttg 1260
aagcacggtc aattgattat ggacccaaat agatttggtc cagcccatt gattaagttg 1320
ggtggtgatt ttaagaaggt ttcctcattc caatccagaa tcccatccat tcctaaaatc 1380
ttggaattgg atcatttgac cattaccggt ccagttaact tgggtagagg tgttactttt 1440
aagggtactg ttattatcgt tgcctccgaa ggtcaaacca ttgatattcc acctggttcc 1500
attttggaaa acgttgttgt tcaaggttcc ttgagattat tagaacatta a 1551

SEQ ID NO: 127
*A. pullulans*
MSSEMATHLK PNGGAEFEKR HHGKTQSHVA FENTSTSVAA SQMRNALNTL CDSVTDPAEK 60
QRFETEMDNF FALFRRYLND KAKGNEIEWS RIAPPKPEQV VAYQDLPEQE SVEFLNKLAV 120
LKLNGGLGTS MGCVGPKSVI EVRDGMSFLD LSVRQIEYLN RTYGVNVPFV LMNSFNTDAD 180

TABLE 11-continued

Sequences disclosed herein.

```
TANIIKKYEG HNIDIMTFNQ SRYPRILKDS LLPAPKSANS QISDWYPPGH GDVFESLYNS   240
GILDKLLERG VEIVFLSNAD NLGAVVDLKI LQHMVDTKAE YIMELTDKTK ADVKGGTIID   300
YEGQARLLEI AQVPKEHVNE FKSIKKFKYF NTNNIWMNLR AVKRIVENNE LAMEIIPNGK   360
SIPADKKGEA DVSIVQLETA VGAAIRHFNN AHGVNVPRRR FLPVKTCSDL MLVKSDLYTL   420
KHGQLIMDPN RFGPAPLIKL GGDFKKVSSF QSRIPSIPKI LELDHLTITG PVNLGRGVTF   480
KGTVIIVASE GQTIDIPPGS ILENVVVQGS LRLLEH                             516
```

SEQ ID NO: 128
*A. thaliana*

```
atggctgcta ctactgaaaa cttgccacaa ttgaaatctg ccgttgatgg tttgactgaa     60
atgtccgaat ctgaaaagtc cggtttcatc tctttggtca gtagatattt gtctggtgaa    120
gcccaacata tcgaatggtc taaaattcaa actccaaccg acgaaatcgt tgtcccatac    180
gaaaaaatga ctccagtttc tcaagatgtc gccgaaacta agaatttgtt ggataagttg    240
gtcgtcttga agttgaatgg tggtttgggt actactatgg gttgtactgg tccaaagtct    300
gttatcgaag ttagagatgg tttaaccttc ttggacttga tcgtcatcca aatcgaaaac    360
ttgaacaaca agtacggttg caaggttcca ttggtcttga tgaattcttt caacacccat    420
gatgataccc acaagatcgt tgaaaagtac accaactcca acgttgatat ccacaccttc    480
aatcaatcta agtacccaag agttgttgcc gatgaatttg ttccatggcc atctaaaggt    540
aagactgaca aagaaggttg gtatccacca ggtcatggtg atgtttttcc agctttaatg    600
aactccggta agttggatac tttcttgtcc caaggtaaag aatacgtttt cgttgccaac    660
tctgataact tgggtgctat agttgatttg accatcttga agcacttgat ccaaaacaag    720
aacgaatact gcatggaagt tactccaaag actttggctg atgttaaggg tggtactttg    780
atttcttacg aaggtaaggt tcaattattg gaaatcgccc aagttccaga tgaacacgtt    840
aatgaattca agtccatcga aaagttcaag atcttcaaca ccaacaactt gtgggttaac    900
ttgaaggcca tcaagaaatt ggttgaagct gatgctttga agatggaaat tatcccaaac    960
ccaaaagaag ttgacggtgt taaggtattg caattggaaa ctgctgctgg tgctgctatt   1020
agatttttcg ataatgccat cggtgttaac gtcccaagat ctagattttt gccagttaag   1080
gcttcctccg atttgttgtt ggttcaatct gacttgtaca ccttggttga cggttttgtt   1140
acaagaaaca aggctagaac taacccatcc aacccatcta ttgaattggg tccagaattc   1200
aaaaaggttg ccacattctt gtccagattc aagtctattc catccatcgt cgaattggac   1260
tcattgaaag tttctggtga tgtctggttt ggttcctcta tagttttgaa gggtaaggtt   1320
actgttgctg ctaaatctgg tgttaagttg gaaattccag atagagccgt tgtcgaaaac   1380
aaaaacatta acggtcctga agatttgtga                                    1410
```

SEQ ID NO: 129
*A. thaliana*

```
MAATTENLPQ LKSAVDGLTE MSESEKSGFI SLVSRYLSGE AQHIEWSKIQ TPTDEIVVPY    60
EKMTPVSQDV AETKNLLDKL VVLKLNGGLG TTMGCTGPKS VIEVRDGLTF LDLIVIQIEN   120
LNNKYGCKVP LVLMNSFNTH DDTHKIVEKY TNSNVDIHTF NQSKYPRVVA DEFVPWPSKG   180
KTDKEGWYPP GHGDVFPALM NSGKLDTFLS QGKEYVFVAN SDNLGAIVDL TILKHLIQNK   240
NEYCMEVTPK TLADVKGGTL ISYEGKVQLL EIAQVPDEHV NEFKSIEKFK IFNTNNLWVN   300
LKAIKKLVEA DALKMEIIPN PKEVDGVKVL QLETAAGAAI RFFDNAIGVN VPRSRFLPVK   360
ASSDLLLVQS DLYTLVDGFV TRNKARTNPS NPSIELGPEF KKVATFLSRF KSIPSIVELD   420
SLKVSGDVWF GSSIVLKGKV TVAAKSGVKL EIPDRAVVEN KNINGPEDL              469
```

SEQ ID NO: 130
*E. coli*

```
atggctgcta ttaacaccaa ggttaagaag gctgttattc cagttgctgg tttgggtact     60
agaatgttgc cagctacaaa agccattcca aaagaaatgt taccattggt cgataagcca    120
ttgatccaat acgttgtcaa cgaatgtatt gctgctggta ttaccgaaat cgttttggtt    180
actcactcct ccaagaactc cattgaaaat catttcgaca cctcattcga attggaagcc    240
atgttggaaa agagagtcaa gagacaatta ttggacgaag tccaatctat ttgcccacca    300
catgttacta tcatgcaagt tagacaaggt ttggctaaag gtttgggtca tgctgttttg    360
tgtgctcatc cagttgttgg tgatgaacca gttgcagtta ttttgccaga tgttatcttg    420
gacgaatacg aatccgattt gtctcaagat aacttggctg aaatgatcag aagattcgac    480
gaaactggtc actcccaaat tatggttgaa cctgttgctg atgttactgc ttatggtgtt    540
gttgattgca agggtgttga attggctcca ggtgaatctg ttccaatggt tggtgttgta    600
gaaaagccaa aagctgatgt tgctccatct aatttggcta tcgttggtag atatgttttg    660
tccgctgata tttggccttt gttggctaaa actccaccag gtgctggtga cgaaattcaa    720
ttgactgatg ctatcgacat gttgatcgaa aaagaaaccg ttgaagccta ccacatgaag    780
ggtaaatctc atgattgtgg taacaagttg ggttacatgc aagcttttgt tgaatacggt    840
atcagacata acaccttagg tactgaattc aaggcttggt tggaagaaga aatgggtatc    900
aagaagtaa                                                            909
```

SEQ ID NO: 131
*E. coli*

```
MAAINTKVKK AVIPVAGLGT RMLPATKAIP KEMLPLVDKP LIQYVVNECI AAGITEIVLV    60
THSSKNSIEN HFDTSFELEA MLEKRVKRQL LDEVQSICPP HVTIMQVRQG LAKGLGHAVL   120
CAHPVVGDEP VAVILPDVIL DEYESDLSQD NLAEMIRRFD ETGHSQIMVE PVADVTAYGV   180
VDCKGVELAP GESVPMVGVV EKPKADVAPS NLAIVGRYVL SADIWPLLAK TPPGAGDEIQ   240
LTDAIDMLIE KETVEAYHMK GKSHDCGNKL GYMQAFVEYG IRHNTLGTEF KAWLEEEMGI   300
KK                                                                  302
```

SEQ ID NO: 132
*R. suavissimus*

```
atggctgctg ttgctactga taagatctct aagttgaagt ctgaagttgc tgccttgtcc     60
caaatttctg aaaacgaaaa gtccggtttc atcaacttgg tcagtagata tttgtctggt    120
actgaagcta ctcacgttga atggtctaaa attcaaactc caaccgatga agttgttgtt    180
```

TABLE 11-continued

Sequences disclosed herein.

```
ccatatgata ctttggctcc aactccagaa gatccagctg aaactaagaa gttgttagat   240
aagttggtcg tcttgaagtt gaacggtggt ttgggtacta ctatgggttg tactggtcca   300
aagtctgtta tcgaagttag aaacggtttg accttcttgg atttgatcgt cattcaaatc   360
gaaaccttga acaacaagta cggttgtaac gttcctttgt tgttgatgaa ctctttcaac   420
acccatgatg acaccttcaa gatcgttgaa agatacacca agtccaacgt tcaaatccat   480
accttcaatc aatcccaata cccaagattg gttgtcgaag ataattctcc attgccatct   540
aagggtcaaa ctggtaaaga tggttggtat ccaccaggtc atggtgatgt tttccatct   600
ttgagaaact ccggtaagtt ggatttgttg ttatcccaag gtaaagaata cgttttcatc   660
tccaactctg ataacttggg tgcagttgtt gatttgaaga tcttgtccca tttggtccaa   720
aaaaagaacg aatactgcat ggaagttacc ccaaaaactt tggctgatgt taagggtggt   780
actttgattt cttacgaagg tagaacccaa ttattggaaa ttgcccaagt tccagatcaa   840
cacgttaacg aattcaagtc catcgaaaag ttcaagatct ttaacaccaa caatttgtgg   900
gtcaacttga acgccattaa gagattagtt gaagctgatg ccttgaaaat ggaaatcatc   960
ccaaatccaa aagaagtcga cggtattaag gtcttgcaat tggaaactgc tgctggtgct  1020
gctattagat tttcaatca tgccatcggt atcaacgtcc caagatctag atttttgcca  1080
gttaaggcta cctccgattt gttattggtt caatctgact tgtacaccgt cgaagatggt  1140
ttcgttatta gaaacactgc tagaaagaat ccagccaacc catctgttga attgggtcca  1200
gaattcaaaa aggttgccaa cttcttgtcc agattcaagt ctattccatc catcatcgaa  1260
ttggactcat tgaaggttgt tggtgatgta tggtttggtg ctggtgttgt tttgaaaggt  1320
aaggttacta ttactgctaa gccaggtgtt aagttggaaa ttccagataa ggctgtcttg  1380
gaaaacaagg atattaacgg tcctgaagat ttgtga                            1416
```

SEQ ID NO: 133
*R. suavissimus*

```
MAAVATDKIS KLKSEVAALS QISENEKSGF INLVSRYLSG TEATHVEWSK IQTPTDEVVV    60
PYDTLAPTPE DPAETKKLLD KLVVLKLNGG LGTTMGCTGP KSVIEVRNGL TFLDLIVIQI   120
ETLNNKYGCN VPLLLMNSFN THDDTFKIVE RYTKSNVQIH TFNQSQYPRL VVEDNSPLPS   180
KGQTGKDGWY PPGHGDVFPS LRNSGKLDLL LSQGKEYVFI SNSDNLGAVV DLKILSHLVQ   240
KKNEYCMEVT PKTLADVKGG TLISYEGRTQ LLEIAQVPDQ HVNEFKSIEK FKIFNTNNLW   300
VNLNAIKRLV EADALKMEII PNPKEVDGIK VLQLETAAGA AIRFFNHAIG INVPRSRFLP   360
VKATSDLLLV QSDLYTVEDG FVIRNTARKN PANPSVELGP EFKKVANFLS RFKSIPSIIE   420
LDSLKVVGDV WFGAGVVLKG KVTITAKPGV KLEIPDKAVL ENKDINGPED L           471
```

SEQ ID NO: 134
*H. vulgare*

```
atggctgctg ctgcagttgc tgctgattct aaaattgatg gtttgagaga tgctgttgcc    60
aagttgggtg aaatttctga aaacgaaaag gccggtttca tctccttggt ttctagatat   120
ttgtctggtg aagccgaaca aatcgaatgg tctaaaattc aaactccaac cgatgaagtt   180
gttgttccat atgatacttt ggctccacca cctgaagatt tggatgctat gaaggctttg   240
ttggataagt tggttgtctt gaagttgaat ggtggtttgg gtactactat gggttgtact   300
ggtccaaagt ctgttatcga agttagaaac ggtttcacct tcttggattt gatcgttatc   360
caaattgaat ccttgaacaa gaagtacggt tgctctgttc ctttgttgtt gatgaactct   420
ttcaacaccc atgatgacac ccaaaagatc gttgaaaagt actccaactc caacatcgaa   480
atccacacct tcaatcaatc tcaataccca agaatcgtca ccgaagattt tttgccattg   540
ccatctaaag gtcaaactgg taaagatggt tggtatccac caggtcatgg tgatgttttt   600
ccatctttga acaactccgg taagttggat accttgttgt ctcaaggtaa agaatacgtt   660
ttcgttgcca actctgataa cttgggtgct atcgttgata ttaagatctt gaaccacttg   720
atccacaatc aaaacgaata ctgcatggaa gttactccaa agactttggc tgatgttaag   780
ggtggtactt tgatttctta cgaaggtaga gttcaattat tggaaatcgc ccaagttcca   840
gatgaacacg ttgatgaatt caagtccatc gaaaagttca aaatcttcaa caccaacaac   900
ttgtgggtta acttgaaggc cattaagaga ttggttgatg ctgaagcttt gaaaatggaa   960
atcatcccaa accctaaaga agttgacggt gttaaggtat tgcaattgga aactgctgct  1020
ggtgctgcta ttagattctt tgaaaaagcc atcggtatca acgtcccaag atctagattt  1080
ttgccagtta aggctacctc tgacttgttg ttggttcaat cagacttgta caccttggtt  1140
gacggttacg ttattagaaa tccagctaga gttaagccat ccaacccatc tattgaattg  1200
ggtccagaat tcaagaaggt cgctaatttc ttggctagat tcaagtctat cccatccatc  1260
gttgaattgg actcattgaa agtttctggt gatgtctctt ttggttccgg tgttgttttg  1320
aagggtaatg ttactattgc tgctaaggct ggtgttaagt tggaaattcc agatggtgct  1380
gttttggaaa acaaggatat taacggtcca gaagatattt ga                     1422
```

SEQ ID NO: 135
*H. vulgare*

```
MAAAAVAADS KIDGLRDAVA KLGEISENEK AGFISLVSRY LSGEAEQIEW SKIQTPTDEV    60
VVPYDTLAPP PEDLDAMKAL LDKLVVLKLN GGLGTTMGCT GPKSVIEVRN GFTFLDLIVI   120
QIESLNKKYG CSVPLLLMNS FNTHDDTQKI VEKYSNSNIE IHTFNQSQYP RIVTEDFLPL   180
PSKGQTGKDG WYPPGHGDVF PSLNNSGKLD TLLSQGKEYV FVANSDNLGA IVDIKILNHL   240
IHNQNEYCME VTPKTLADVK GGTLISYEGR VQLLEIAQVP DEHVDEFKSI EKFKIFNTNN   300
LWVNLKAIKR LVDAEALKME IIPNPKEVDG VKVLQLETAA GAAIRFFEKA IGINVPRSRF   360
LPVKATSDLL LVQSDLYTLV DGYVIRNPAR VKPSNPSIEL GPEFKKVANF LARFKSIPSI   420
VELDSLKVSG DVSFGSGVVL KGNVTIAAKA GVKLEIPDGA VLENKDINGP EDI          473
```

SEQ ID NO: 136
*O. sativa*

```
atggctgacg aaaaattggc caaattgaga gaagctgttg ctggtttgtc tcaaatctct    60
gataacgaaa agtccggttt catttccttg gttgctagat atttgtccgg tgaagaagaa   120
catgttgaat gggctaaaat tcatacccca accgatgaag ttgttgttcc atatgatact   180
ttggaagctc caccagaaga tttggaagaa acaaaaaagt tgttgaacaa gttggccgtc   240
ttgaagttga atggtggttt gggtactact atgggttgta ctggtccaaa gtctgttatc   300
```

TABLE 11-continued

| Sequences disclosed herein. |
|---|
| gaagttagaa acggtttcac cttcttggat ttgatcgtca tccaaatcga atccttgaac 360 |
| aaaaagtacg gttccaacgt tcctttgttg ttgatgaact ctttcaacac ccatgaagat 420 |
| accttgaaga tcgttgaaaa gtacaccaac tccaacatcg aagttcacac cttcaatcaa 480 |
| tctcaatacc caagagttgt tgccgatgaa tttttgccat ggccatctaa aggtaagact 540 |
| tgtaaagatg gttggtatcc accaggtcat ggtgatattt ttccatcctt gatgaacagt 600 |
| ggtaagttgg acttgttgtt gtcccaaggt aaagaatacg ttttcattgc caactccgat 660 |
| aacttgggtg ctatagttga tatgaagatt ttgaaccact tgatccacaa gcaaaacgaa 720 |
| tactgtatgg aagttactcc aaagactttg gctgatgtta agggtggtac tttgatctct 780 |
| tacgaagata aggttcaatt attggaaatc gcccaagttc cagatgctca tgttaatgaa 840 |
| ttcaagtcca tcgaaaagtt caagatcttt aacaccaaca acttgtgggt taacttgaag 900 |
| gccattaaga gattagttga agctgacgct ttgaagatgg aaattatccc aaacccaaaa 960 |
| gaagttgacg gtgttaaggt attgcaattg gaaactgctg ctggtgctgc tattagattt 1020 |
| ttcgatcatg ctatcggtat caacgtccca agatctagat tttaccagt taaggctacc 1080 |
| tccgacttgc aattagttca atctgacttg tacaccttgg ttgatggttt cgttactaga 1140 |
| aatccagcta gaactaatcc atccaaccca tctattgaat tgggtccaga attcaagaag 1200 |
| gttggttgtt ttttgggtag attcaagtct atcccatcca tcgttgaatt ggacactttg 1260 |
| aaagtttctg gtgatgtttg gttcggttcc tccattacat tgaaaggtaa ggttactatt 1320 |
| accgctcaac caggtgttaa gttggaaatt ccagatggtg ctgtcatcga aaacaaggat 1380 |
| attaacggtc ctgaagattt gtga 1404 |
| |
| SEQ ID NO: 137 |
| *O. sativa* |
| MADEKLAKLR EAVAGLSQIS DNEKSGFISL VARYLSGEEE HVEWAKIHTP TDEVVVPYDT 60 |
| LEAPPEDLEE TKKLLNKLAV LKLNGGLGTT MGCTGPKSVI EVRNGFTFLD LIVIQIESLN 120 |
| KKYGSNVPLL LMNSFNTHED TLKIVEKYTN SNIEVHTFNQ SQYPRVVADE FLPWPSKGKT 180 |
| CKDGWYPPGH GDIFPSLMNS GKLDLLLSQG KEYVFIANSD NLGAIVDMKI LNHLIHKQNE 240 |
| YCMEVTPKTL ADVKGGTLIS YEDKVQLLEI AQVPDAHVNE FKSIEKFKIF NTNNLWVNLK 300 |
| AIKRLVEADA LKMEIIPNPK EVDGVKVLQL ETAAGAAIRF FDHAIGINVP RSRFLPVKAT 360 |
| SDLQLVQSDL YTLVDGFVTR NPARTNPSNP SIELGPEFKK VGCFLGRFKS IPSIVELDTL 420 |
| KVSGDVWFGS SITLKGKVTI TAQPGVKLEI PDGAVIENKD INGPEDL 467 |
| |
| SEQ ID NO: 138 |
| *S. tuberosum* |
| atggctactg ctactacttt gtctccagct gatgctgaaa agttgaacaa tttgaaatct 60 |
| gctgtcgccg gtttgaatca aatctctgaa aacgaaaagt ccggtttcat caacttggtt 120 |
| ggtagatatt tgtctggtga agcccaacat attgactggt ctaaaattca aactccaacc 180 |
| gatgaagttg ttgtcccata tgataagttg gctccattgt ctgaagatcc agctgaaaca 240 |
| aaaaagttgt tggacaagtt ggtcgtcttg aagttgaatg gtggtttggg tactactatg 300 |
| ggttgtactg gtccaaagtc tgttatcgaa gttagaaacg gtttgacctt cttggatttg 360 |
| atcgtcaagc aaattgaagc tttgaacgct aagttcggtt gttctgttcc tttgttgttg 420 |
| atgaactctt tcaacaccca tgatgacacc ttgaagatcg ttgaaaagta cgccaactcc 480 |
| aacattgata tccacacctt caatcaatcc caatacccaa gattggttac cgaagatttt 540 |
| gctccattgc catgtaaagg taactctggt aaagatggtt ggtatccacc aggtcatggt 600 |
| gatgtttttc catccttgat gaattccggt aagttggatg ctttgttggc taagggtaaa 660 |
| gaatacgttt tcgttgccaa ctctgataac ttgggtgcta tcgttgattt gaaaatcttg 720 |
| aaccacttga tcttgaacaa gaacgaatac tgcatggaag ttactccaaa gactttggct 780 |
| gatgttaagg gtggtacttt gatttcttac gaaggtaagg ttcaattatt ggaaatcgcc 840 |
| caagttccag atgaacacgt taatgaattc aagtccatcg aaaagtttaa gatcttcaac 900 |
| actaacaact tgtgggtcaa cttgtctgcc attaagagat tggttgaagc tgatgccttg 960 |
| aaaatggaaa ttattccaaa cccaaaagaa gtcgatggtg tcaaagtatt gcaattggaa 1020 |
| actgctgctg gtgctgctat taagtttttc gatagagcta ttggtgccaa cgttccaaga 1080 |
| tctagatttt tgccagttaa ggctacctct gacttgttgt tggttcaatc agacttgtac 1140 |
| actttgactg atgaaggtta cgttattaga aacccagcta gatccaatcc atccaaccca 1200 |
| tctattgaat tgggtccaga attcaagaag gtagccaatt ttttgggtag attcaagtct 1260 |
| atcccatcca tcatcgattt ggattctttg aaagttactg gtgatgtctg gtttggttct 1320 |
| ggtgttactt tgaaaggtaa agttaccgtt gctgctaagt caggtgttaa gttggaaatt 1380 |
| ccagatggtg ctgttattgc caacaaggat attaacggtc cagaagatat ctaa 1434 |
| |
| SEQ ID NO: 139 |
| *S. tuberosum* |
| MATATTLSPA DAEKLNNLKS AVAGLNQISE NEKSGFINLV GRYLSGEAQH IDWSKIQTPT 60 |
| DEVVVPYDKL APLSEDPAET KKLLDKLVVL KLNGGLGTTM GCTGPKSVIE VRNGLTFLDL 120 |
| IVKQIEALNA KFGCSVPLLL MNSFNTHDDT LKIVEKYANS NIDIHTFNQS QYPRLVTEDF 180 |
| APLPCKGNSG KDGWYPPGHG DVFPSLMNSG KLDALLAKGK EYVFVANSDN LGAIVDLKIL 240 |
| NHLILNKNEY CMEVTPKTLA DVKGGTLISY EGKVQLLEIA QVPDEHVNEF KSIEKFKIFN 300 |
| TNNLWVNLSA IKRLVEADAL KMEIIPNPKE VDGVKVLQLE TAAGAAIKFF DRAIGANVPR 360 |
| SRFLPVKATS DLLLVQSDLY TLTDEGYVIR NPARSNPSNP SIELGPEFKK VANFLGRFKS 420 |
| IPSIIDLDSL KVTGDVWFGS GVTLKGKVTV AAKSGVKLEI PDGAVIANKD INGPEDI 477 |
| |
| SEQ ID NO: 140 |
| atgttcttgt tggttacctc ttgcttcttg ccagattctg gttcttctgt taaggtcagt 60 |
| ttgttcatct tcggtgtctc attggtttct acctctccaa ttgatggtca aaaaccaggt 120 |
| acttctggtt tgagaaagaa ggtcaaggtt ttcaagcaac ctaactactt ggaaaacttc 180 |
| gttcaagcta ctttcaacgc tttgactacc gaaaaagtta agggtgctac tttggttgtt 240 |
| tctggtgatg gtagatatta ctccgaacaa gccattcaaa tcatcgttaa gatggctgct 300 |
| gctaacggtg ttagaagagt ttgggttggt caaaactctt tgttgtctac tccagctgtt 360 |
| tccgccatta ttagagaaag agttggtgct gatggttcta aagctactgg tgctttcatt 420 |
| ttgactgctt ctcataatcc aggtggtcca actgaagatt tcggtattaa gtacaacatg 480 |

TABLE 11-continued

Sequences disclosed herein.

```
gaaaatggtg gtccagcccc agaatctatt actgataaga tatacgaaaa caccaagacc   540
atcaaagaat acccaattgc agaagatttg ccaagagttg atatctctac tatcggtatc   600
acttctttcg aaggtcctga aggtaaattc gacgttgaag tttttgattc cgctgatgat   660
tacgtcaagt tgatgaagtc catcttcgac ttcgaatcca tcaagaagtt gttgtcttac   720
ccaaagttca ccttttgtta cgatgcattg catggtgttg ctggtgctta tgctcataga   780
attttcgttg aagaattggg tgctccagaa tcctctttat tgaactgtgt tccaaaagaa   840
gattttggtg gtggtcatcc agatccaaat ttgacttatg ccaaagaatt ggttgccaga   900
atgggtttgt ctaagactga tgatgctggt ggtgaaccac ctgaatttgg tgctgctgca   960
gatggtgatg ctgatagaaa tatgatcttg ggtaaaagat tcttcgtcac cccatctgat  1020
tccgttgcta ttattgctgc taatgctgtt ggtgctattc catacttttc atccggtttg  1080
aaaggtgttg ctagatctat gccaacttct gctgctttgg atgttgttgc taagaatttg  1140
ggtttgaagt tcttcgaagt tccaactggt tggaaattct tcggtaattt gatggatgca  1200
ggtatgtgtt ctgtttgcgg tgaagaatca tttggtactg gttccgatca tatcagagaa  1260
aaggatggta tttgggctgt tttggcttgg ttgtctattt tggctcacaa gaacaaagaa  1320
accttggatg gtaatgccaa gttggttact gttgaagata tcgttagaca acattgggct  1380
acttacggta gacattacta cactagatac gactacgaaa acgttgatgc tacagctgct  1440
aaagaattga tgggtttatt ggtcaagttg caatcctcat tgccagaagt taacaagatc  1500
atcaagggta tccatcctga agttgctaat gttgcttctg ctgatgaatt cgaatacaag  1560
gatccagttg atggttccgt ttctaaacat caaggtatca gatacttgtt tgaagatggt  1620
tccagattgg ttttcagatt gtctggtaca ggttctgaag gtgctactat tagattgtac  1680
atcgaacaat acgaaaagga cgcctctaag attggtagag attctcaaga tgctttgggt  1740
ccattggttg atgttgcttt gaagttgtcc aagatgcaag aattcactgg tagatcttct  1800
ccaaccgtta ttacctga                                                1818

SEQ ID NO: 141
MFLLVTSCFL PDSGSSVKVS LFIFGVSLVS TSPIDGQKPG TSGLRKKVKV FKQPNYLENF    60
VQATFNALTT EKVKGATLVV SGDGRYYSEQ AIQIIVKMAA ANGVRRVWVG QNSLLSTPAV   120
SAIIRERVGA DGSKATGAFI LTASHNPGGP TEDFGIKYNM ENGGPAPESI TDKIYENTKT   180
IKEYPIAEDL PRVDISTIGI TSFEGPEGKF DVEVFDSADD YVKLMKSIFD FESIKKLLSY   240
PKFTFCYDAL HGVAGAYAHR IFVEELGAPE SSLLNCVPKE DFGGGHPDPN LTYAKELVAR   300
MGLSKTDDAG GEPPEFGAAA DGDADRNMIL GKRFFVTPSD SVAIIAANAV GAIPYFSSGL   360
KGVARSMPTS AALDVVAKNL GLKFFEVPTG WKFFGNLMDA GMCSVCGEES FGTGSDHIRE   420
KDGIWAVLAW LSILAHKNKE TLDGNAKLVT VEDIVRQHWA TYGRHYYTRY DYENVDATAA   480
KELMGLLVKL QSSLPEVNKI IKGIHPEVAN VASADEFEYK DPVDGSVSKH QGIRYLFEDG   540
SRLVFRLSGT GSEGATIRLY IEQYEKDASK IGRDSQDALG PLVDVALKLS KMQEFTGRSS   600
PTVIT                                                               605

SEQ ID NO: 142
atggccattc ataatagagc tggtcaacca gcacaacaat ccgatttgat taacgttgct    60
caattgaccg cccaatatta cgttttgaaa cctgaagctg gtaacgctga acatgctgtt   120
aagtttggta cttctggtca tagaggttct gctgctagac attcttttaa cgaaccacat   180
attttggcta tcgctcaagc tattgctgaa gaaagagcta agaacggtat tactggtcca   240
tgttacgttg gtaaagatac ccatgctttg tctgaaccag ctttcatttc tgttttggaa   300
gttttggctg ctaacggtgt tgatgttatc gttcaagaaa acaacggttt cactccaact   360
ccagctgttt ctaatgctat tttggttcac aacaaaaagg gtggtccatt ggctgatggt   420
atagttatta ctccatctca taacccacct gaagatggtg gtattaagta caatccacca   480
aatggtggtc cagctgatac aaatgttact aaggttgttg aagatagagc caacgctttg   540
ttagctgatg gtttgaaagg tgtcaagaga atctctttgg atgaagctat ggcttcaggt   600
catgtcaaag aacaagattt ggttcaacca ttcgttgaag gtttggctga tatagttgat   660
atggctgcta ttcaaaaggc tggtttgact ttgggtgttg atccattggg tggttctggt   720
attgaatact ggaaaagaat cggtgaatat tacaacttga acttgaccat cgtcaacgat   780
caagttgacc aaactttcag attcatgcac ttggataagg atggtgctat tagaatggac   840
tgttcttctg aatgtgctat ggctggttta ttggctttga gagataagtt cgatttggct   900
tttgctaacg atccagatta cgatagacat ggtatcgtta ctccagcagg tttgatgaat   960
ccaaatcatt acttggctgt tgccatcaac tacttgtttc aacatagacc acaatggggt  1020
aaggatgttg ctgttggtaa aactttggtt tcctccgcta tgatcgatag agttgttaac  1080
gatttgggta gaaagttggt tgaagttcca gttggtttca agtggtttgt tgacggtttg  1140
tttgatggtt cttttggttt tggtggtgaa gaatctgctg gtgcttcatt tttgagattt  1200
gatggtactc catggtccac tgacaaagat ggtattatca tgtgtttgtt ggctgctgaa  1260
attactgctg ttactggtaa gaatccacaa gaacactaca acgaattggc taagagattt  1320
ggtgctccat cttacaatag attgcaagct gctgctactt ctgctcaaaa agctgcttta  1380
tctaagttgt ccccagaaat ggtttctgct tctactttag ctggtgatcc aattacagct  1440
agattgactg ctgctccagg taatggtgct tctattggtg gtttaaaggt tatgactgat  1500
aacggttggt ttgctgcaag accatctggt actgaagatg cttacaaaat ctactgcgaa  1560
tccttcttgg gtgaagaaca tagaaagcaa attgaaaaag aagccgtcga aatcgtcagt  1620
gaagttttga agaatgccta a                                            1641

SEQ ID NO: 143
MAIHNRAGQP AQQSDLINVA QLTAQYYVLK PEAGNAEHAV KFGTSGHRGS AARHSFNEPH    60
ILAIAQAIAE ERAKNGITGP CYVGKDTHAL SEPAFISVLE VLAANGVDVI VQENNGFTPT   120
PAVSNAILVH NKKGGPLADG IVITPSHNPP EDGGIKYNPP NGGPADTNVT KVVEDRANAL   180
LADGLKGVKR ISLDEAMASG HVKEQDLVQP FVEGLADIVD MAAIQKAGLT LGVDPLGGSG   240
IEYWKRIGEY YNLNLTIVND QVDQTFRFMH LDKDGAIRMD CSSECAMAGL LALRDKFDLA   300
FANDPDYDRH GIVTPAGLMN PNHYLAVAIN YLFQHRPQWG KDVAVGKTLV SSAMIDRVVN   360
DLGRKLVEVP VGFKWFVDGL FDGSFGFGGE ESAGASFLRF DGTPWSTDKD GIIMCLLAAE   420
ITAVTGKNPQ EHYNELAKRF GAPSYNRLQA AATSAQKAAL SKLSPEMVSA STLAGDPITA   480
RLTAAPGNGA SIGGLKVMTD NGWFAARPSG TEDAYKIYCE SFLGEEHRKQ IEKEAVEIVS   540
EVLKNA                                                              546
```

TABLE 11-continued

| Sequences disclosed herein. |
| --- |

SEQ ID NO: 144
*R. suavissimus*
```
atgtcctccg gtaagattaa gagagttcaa actactccat tcgacggtca aaaaccaggt    60
acttctggtt tgagaaagaa ggttaaggtt ttcacccaac ctaactactt gcaaaacttc   120
gttcaatcta ccttcaacgc tttgccatct gataaggtaa aggtgctag attggttgtt    180
tctggtgatg gtagatactt ctccaaagaa gccattcaaa tcatcattaa gatggctgct   240
ggtaacggtg ttaagtctgt ttgggttggt caaaatggtt tgttgtctac tccagctgtt   300
tctgctgttg ttagagaaag agttggtgct gatggttgta aagcttctgg tgctttcatt   360
ttgactgctt ctcataatcc aggtggtcca aatgaagatt tcggtatcaa gtacaacatg   420
gaaaatggtg gtccagctcc agaatctatt accaacaaaa tctacgaaaa caccacccaa   480
atcaaagaat acttgaccgt tgatttgcca gaagttgata ttactaagcc aggtgttact   540
accttcgaag ttgaaggtgg tactttcact gttgatgttt tcgattctgc ttccgattac   600
gtcaagttga tgaagtccat tttcgacttc gaatccatca gaaagttgtt gtcctctcca   660
aagttcacct tttgttttga tgcattgcat ggtgttggtg gtgcttacgc taaaagaatt   720
ttcgttgaag aattgggtgc caaagaatcc tctttgttga actgtgttcc taaagaagat   780
tttggtggtg gtcatccaga tccaaatttg acatatgcta aagaattggt cgccagaatg   840
ggtttgtcta agtctaatac tcaaaacgaa ccaccagaat ttggtgctgc tgcagatggt   900
gatgctgata gaaatatggt tttgggtaag agattcttcg ttaccccatc tgattccgtt   960
gctattattg ctgctaatgc tgttgaagct atcccatact tttctactgg tttgaaaggt  1020
gttgctagat ctatgccaac ttctgctgct ttggatgttg ttgctaaaca cttgaacttg  1080
aagttcttcg aagtaccaac tggttggaag tttttcggta atttgatgga tgctggtttg  1140
tgttctgttt gcggtgaaga atcttttggt actggttccg atcatatcag agaaaaggat  1200
ggtatttggg ctgttttggc ttggttgtca attattgcca tcaagaacaa ggataacatc  1260
ggtggtgata agttggttac cgttgaagat atcgttagaa aacattgggc tacttacggt  1320
agacattact acactagata cgattacgaa aacgttgatg ctggtaaggc taaagatttg  1380
atggcatcat tggtcaactt gcaatcatct ttgcctgaag ttaacaagat cgttaagggt  1440
atctgttccg atgttgcaaa tgttgttggt gccgatgaat tcgaatacaa ggattctgtt  1500
gatggttcca tctccaaaca tcaaggtatc agatacttgt tcgaagatgg ttcaagattg  1560
gttttcagat tgtctggtac aggttctgaa ggtgctacta ttagattgta catcgaacaa  1620
tacgaaaatg acccatccaa gatctccaga gaatcttctg aagctttggc tccattggtt  1680
gaagttgctt tgaaattgtc caagatgcaa gaattcactg gtagatcagc tccaactgtt  1740
attacctga                                                          1749
```

SEQ ID NO: 145
R. suavissimus
```
MSSGKIKRVQ TTPFDGQKPG TSGLRKKVKV FTQPNYLQNF VQSTFNALPS DKVKGARLVV    60
SGDGRYFSKE AIQIIIKMAA GNGVKSVWVG QNGLLSTPAV SAVVRERVGA DGCKASGAFI   120
LTASHNPGGP NEDFGIKYNM ENGGPAPESI TNKIYENTTQ IKEYLTVDLP EVDITKPGVT   180
TFEVEGGTFT VDVFDSASDY VKLMKSIFDF ESIRKLLSSP KFTFCFDALH GVGGAYAKRI   240
FVEELGAKES SLLNCVPKED FGGGHPDPNL TYAKELVARM GLSKSNTQNE PPEFGAAADG   300
DADRNMVLGK RFFVTPSDSV AIIAANAVEA IPYFSTGLKG VARSMPTSAA LDVVAKHLNL   360
KFFEVPTGWK FFGNLMDAGL CSVCGEESFG TGSDHIREKD GIWAVLAWLS IIAIKNKDNI   420
GGDKLVTVED IVRKHWATYG RHYYTRYDYE NVDAGKAKDL MASLVNLQSS LPEVNKIVKG   480
ICSDVANVVG ADEFEYKDSV DGSISKHQGI RYLFEDGSRL VFRLSGTGSE GATIRLYIEQ   540
YENDPSKISR ESSEALAPLV EVALKLSKMQ EFTGRSAPTV IT                      582
```

SEQ ID NO: 146
```
atggcctctt tcaaggttaa cagagttgaa tcctctccaa tcgaaggtca aaaaccaggt    60
acttctggtt tgagaaagaa ggttaaggtt ttcacccaac cacattactt gcacaacttc   120
gttcaatcta ctttcaacgc tttgtctgcc gaaaaagtta agggtctac tttggttgtt    180
tccggtgatg gtagatatta ctccaaggat gccattcaaa tcatcattaa gatggctgct   240
gctaacggtg ttagaagagt ttgggttggt caaaatggtt tgttgtctac tccagctgtt   300
tctgctgttg ttagagaaag agttggtgct gatggttcta aatctaacgg tgctttcatt   360
ttgactgcct ctcataatcc aggtggtcca aatgaagatt tcggtatcaa gtacaacatg   420
gaaaatggtg gtccagctcc agaaggtatt actgataaga tttttgaaaa caccaagacc   480
atcaaagaat acttcattgc tgaaggtttg ccagacgttg atatttccgc tattggtatc   540
tcttcattct ctggtccaga tggtcaattc gatgttgatg ttttcgattc ctcttccgac   600
tacgtcaaat tgatgaagtc catcttcgac ttccaatcca tcaagaagtt gattacctcc   660
ccacaatttt ctttctgtta cgatgcttta catggtgttg gtggtgctta tgctaagcca   720
atttttgttg atgaattggg tgccaaagaa tcctctttgt tgaactgtgt tcctaaagaa   780
gattttggtg gtggtcatcc agatccaaat ttgacttacg ctaaagaatt ggtttccaga   840
atgggtttgg gtaagaatcc agattctaat ccaccagaat ttggtgctgc tgcagatggt   900
gatgctgata gaaatatgat cttgggtaaa agattcttcg tcaccccatc tgattccgtt   960
gctattattg ctgctaatgc cgttcaatca atcccatact tttcatccgg tttgaaaggt  1020
gttgctagat ctatgccaac ttctgctgct ttggatgttg ttgctaagtc tttgaacttg  1080
aagttcttcg aagttccaac tggttggaag tttttcggta atttgatgga tgctggtttg  1140
tgttctgttt gcggtgaaga atcatttggt actggttccg atcatatcag agaaaaggat  1200
ggtatttggg ctgttttggc ttggttgtct attttggctc ataagaacaa ggacaacttg  1260
aacggtggta acttggttac tgttgaagat atcgttaagc aacattgggc tacttacggt  1320
agacattact acactagata cgactacgaa aacgttgatg ctggtgctgc aaaagaattg  1380
atggctcatt tggttaagtt gcaatcctcc atctctgatg ttaacacctt cattaagggt  1440
atcagatccg atgttgctaa tgttgcatct gctgatgaat tcgaatacaa ggatccagtt  1500
gacggttcta tttccaaaca tcaaggtatt agatacttgt ttgaagatgg ttccagattg  1560
gttttcagat tgtctggtac aggttctgaa ggtgctacta ttagattgta catcgaacaa  1620
tacgaaaagg attcctctaa gaccggtaga gattctcaag aagctttggc tccattagtt  1680
gaagttgcct tgaaattgtc caagatgcaa gaattcactg gtagatctgc tccaactgtt  1740
attacctga                                                          1749
```

TABLE 11-continued

Sequences disclosed herein.

SEQ ID NO: 147
MASFKVNRVE SSPIEGQKPG TSGLRKKVKV FTQPHYLHNF VQSTFNALSA EKVKGSTLVV 60
SGDGRYYSKD AIQIIIKMAA ANGVRRVWVG QNGLLSTPAV SAVVRERVGA DGSKSNGAFI 120
LTASHNPGGP NEDFGIKYNM ENGGPAPEGI TDKIFENTKT IKEYFIAEGL PDVDISAIGI 180
SSFSGPDGQF DVDVFDSSSD YVKLMKSIFD FQSIKKLITS PQFSFCYDAL HGVGGAYAKP 240
IFVDELGAKE SSLLNCVPKE DFGGGHPDPN LTYAKELVSR MGLGKNPDSN PPEFGAAADG 300
DADRNMILGK RFFVTPSDSV AIIAANAVQS IPYFSSGLKG VARSMPTSAA LDVVAKSLNL 360
KFFEVPTGWK FFGNLMDAGL CSVCGEESFG TGSDHIREKD GIWAVLAWLS ILAHKNKDNL 420
NGGNLVTVED IVKQHWATYG RHYYTRYDYE NVDAGAAKEL MAHLVKLQSS ISDVNTFIKG 480
IRSDVANVAS ADEFEYKDPV DGSISKHQGI RYLFEDGSRL VFRLSGTGSE GATIRLYIEQ 540
YEKDSSKTGR DSQEALAPLV EVALKLSKMQ EFTGRSAPTV IT 582

SEQ ID NO: 148
gcacacacca tagcttcaaa atgtttctac tcctttttta ctcttccaga ttttctcgga 60
ctccgcgcat cgccgtacca cttcaaaaca cccaagcaca gcatactaaa tttcccctct 120
ttcttcctct agggtgtcgt taattacccg tactaaaggt ttggaaaaga aaaaagagac 180
cgcctcgttt ctttttcttc gtcgaaaaag gcaataaaaa tttttatcac gtttcttttt 240
cttgaaaatt tttttttttg atttttttct ctttcgatga cctcccattg atatttaagt 300
taataaacgg tcttcaattt ctcaagtttc agtttcattt ttcttgttct attacaactt 360
tttttacttc ttgctcatta gaaagaaagc atagcaatct aatctaagtt ttaattacaa 420
ggatcc 426

SEQ ID NO: 149
ggaagtacct tcaaagaatg gggtcttatc ttgttttgca agtaccactg agcaggataa 60
taatagaaat gataaatatac tatagtagag ataacgtcga tgacttccca tactgtaatt 120
gcttttagtt gtgtattttt agtgtgcaag tttctgtaaa tcgattaatt ttttttttctt 180
tcctcttttt attaacctta atttttattt tagattcctg acttcaactc aagacgcaca 240
gatattataa catctgcata ataggcattt gcaagaatta ctcgtgagta aggaaagagt 300
gaggaactat cgcatacctg catttaaaga tgccgatttg ggcgcgaatc ctttattttg 360
gcttcaccct catactatta tcagggccag aaaaaggaag tgtttccctc cttcttgaat 420
tgatgttacc ctcataaagc acgtggcctc ttatcgagaa agaaattacc gtcgctcgtg 480
atttgtttgc aaaaagaaca aaactgaaaa aacccagaca cgctcgactt cctgtcttcc 540
tattgattgc agcttccaat ttcgtcacac aacaaggtcc tagcgacggc tcacaggttt 600
tgtaacaagc aatcgaaggt tctggaatgg cgggaaaggg tttagtacca catgctatga 660
tgcccactgt gatctccaga gcaaagttcg ttcgatcgta ctgttactct ctctctttca 720
aacagaattg tccgaatcgt gtgacaacaa cagcctgttc tcacacactc ttttcttcta 780
accaaggggg tggtttagtt tagtagaacc tcgtgaaact tacatttaca tatatataaa 840
cttgcataaa ttggtcaatg caagaaatac atatttggtc ttttctaatt cgtagttttt 900
caagttctta gatgctttct ttttctcttt tttacagatc atcaaggaag taattatcta 960
ctttttacaa caaatataaa acaa 984

SEQ ID NO: 150
cattatcaat actgccattt caaagaatac gtaaataatt aatagtagtg attttcctaa 60
ctttatttag tcaaaaaatt agccttttaa ttctgctgta acccgtacat gcccaaaata 120
gggggcgggt tacacagaat atataacatc gtaggtgtct gggtgaacag tttattcctg 180
gcatccacta aatataatgg agcccgcttt ttaagctggc atccagaaaa aaaaagaatc 240
ccagcaccaa aatattgttt tcttcaccaa ccatcagttc ataggtccat tctcttagcg 300
caactacaga gaacaggggc acaaacaggc aaaaaacggg cacaacctca atggagtgat 360
gcaacctgcc tggagtaaat gatgacacaa ggcaattgac ccacgcatgt atctatctca 420
ttttcttaca ccttctatta ccttctgctc tctctgattt ggaaaaagct gaaaaaaaag 480
gttgaaacca gttccctgaa attattcccc tacttgacta ataagtatat aaagacggta 540
ggtattgatt gtaattctgt aaatctattt cttaaacttc ttaaattcta cttttatagt 600
tagtcttttt tttagtttta aaacaccaag aacttagttt cgaataaaca cacataaaca 660
aacaaa 666

SEQ ID NO: 151
gatctgggcc gtatacttac atatagtaga tgtcaagcgt aggcgcttcc cctgccggct 60
gtgagggcgc cataaccaag gtatctatag accgccaatc agcaaactac ctccgtacat 120
tcatgttgca cccacacatt tatacaccca gaccgcgaca aattacccat aaggttgttt 180
gtgacggcgt cgtacaagag aacgtgggaa ctttttaggc tcaccaaaaa agaaagaaaa 240
aatacgagtt gctgacagaa gcctcaagaa aaaaaaaatt cttcttcgac tatgctggag 300
gcagagatga tcgagccggt agttaactat atatagctaa attggttcca tcaccttctt 360
ttctggtgtc gctccttcta gtgctatttc tggcttttcc tatttttttt tttccatttt 420
tctttctctc tttctaatat ataaattctc ttgcattttc tatttttctc tctatctatt 480
ctacttgttt attcccttca aggttttttt ttaaggagta cttgttttta gaatatacgg 540
tcaacgaact ataattaact aaaca 565

SEQ ID NO: 152
agttataata atcctacgtt agtgtgagcg ggatttaaac tgtgaggacc ttaatacatt 60
cagacacttc tgcggtatca ccctacttat tcccttcgag attatatcta ggaacccatc 120
aggttggtgg aagattaccc gttctaagac ttttcagctt cctctattga tgttacacct 180
ggacacccct tttctggcat ccagttttta atcttcagtg gcatgtgaga ttctccgaaa 240
ttaattaaag caatcacaca attctctcgg ataccacctc ggttgaaact gacaggtggt 300
ttgttacgca tgctaatgca aaggagccta tatacctttg gctcggctgc tgtaacaggg 360
aatataaagg gcagcataat ttaggagttt agtgaacttg caacatttac tattttccct 420
tcttacgtaa atatttttct ttttaattct aaatcaatct ttttcaattt tttgtttgta 480
ttcttttctt gcttaaatct ataactacaa aaaacacata cataaactaa aa 532

TABLE 11-continued

Sequences disclosed herein.

SEQ ID NO: 153
gatctatgcg actgggtgag catatgttcc gctgatgtga tgtgcaagat aaacaagcaa 60
ggcagaaact aacttcttct tcatgtaata aacacacccc gcgtttattt acctatctct 120
aaacttcaac accttatatc ataactaata tttcttgaga taagcacact gcacccatac 180
cttccttaaa aacgtagctt ccagtttttg gtggttccgg cttccttccc gattccgccc 240
gctaaacgca tatttttgtt gcctggtggc atttgcaaaa tgcataacct atgcatttaa 300
aagattatgt atgctcttct gacttttcgt gtgatgaggc tcgtggaaaa aatgaataat 360
ttatgaattt gagaacaatt ttgtgttgtt acggtatttt actatggaat aatcaatcaa 420
ttgaggattt tatgcaaata tcgtttgaat atttttccga ccctttgagt acttttcttc 480
ataattgcat aatattgtcc gctgcccctt tttctgttag acggtgtctt gatctacttg 540
ctatcgttca acaccacctt attttctaac tatttttttt ttagctcatt tgaatcagct 600
tatggtgatg gcacattttt gcataaacct agctgtcctc gttgaacata ggaaaaaaaa 660
atatataaac aaggctcttt cactctcctt gcaatcagat ttgggtttgt tccctttatt 720
ttcatatttc ttgtcatatt cctttctcaa ttattatttt ctactcataa cctcacgcaa 780
aataacacag tcaaatctat caaaa 805

SEQ ID NO: 154
atccgctcta accgaaaagg aaggagttag acaacctgaa gtctaggtcc ctatttattt 60
tttttaatag ttatgttagt attaagaacg ttatttatat ttcaaatttt tctttttttt 120
ctgtacaaac gcgtgtacgc atgtaacatt atactgaaaa ccttgcttga gaaggttttg 180
ggacgctcga ag 192

SEQ ID NO: 155
gtagatacgt tgttgacact tctaaataag cgaatttctt atgatttatg atttttatta 60
ttaaataagt tataaaaaaa ataagtgtat acaaatttta aagtgactct taggttttaa 120
aacgaaaatt cttattcttg agtaactctt tcctgtaggt caggttgctt tctcaggtat 180
agcatgaggt cgctc 195

What is claimed is:

1. A method of producing one or more steviol glycosides or a steviol glycoside composition in a cell culture, comprising culturing a recombinant host cell comprising:

(a) a recombinant gene encoding a polypeptide capable of synthesizing uridine 5'-triphosphate (UTP) from uridine diphosphate (UDP);
  wherein the polypeptide comprises a polypeptide having at least 90% sequence identity to the amino acid sequence set forth in SEQ ID NO:123;

(b) a recombinant gene encoding a polypeptide capable of converting glucose-6-phosphate to glucose-1-phosphate;
  wherein the polypeptide comprises a polypeptide having at least 90% sequence identity to the amino acid sequence set forth in any one of SEQ ID NOs:2, 119, 141, 143, 145, or 147; and/or (c) a recombinant gene encoding a polypeptide capable of synthesizing uridine diphosphate glucose (UDP-glucose) from UTP and glucose-1 phosphate;
  wherein the polypeptide comprises a polypeptide having at least 90% sequence identity to the amino acid sequence set forth in any one of SEQ ID NOs:121, 125, 127, 129, 131, 133, 135, 137, or 139, in the cell culture, under conditions in which the recombinant genes are expressed, and wherein the one or more steviol glycosides or the steviol glycoside composition is produced by the recombinant host cell.

2. The method of claim 1, wherein the recombinant genes are constitutively expressed and/or expression of the genes is induced.

3. The method of claim 1, wherein the amount of UDP-glucose accumulated by the cell is increased by at least by at least about 10% relative to a corresponding host lacking the one or more recombinant genes.

4. The method of claim 1, wherein the amount of RebA, RebB, RebD, and/or RebM produced by the cell is increased by at least about 5% relative to a corresponding host lacking the one or more recombinant genes.

5. The method of claim 1, wherein the amount of RebB, RebD, and/or 13-SMG accumulated by the cell is decreased by at least about 5% relative to a corresponding host lacking the one or more recombinant genes.

6. The method of claim 1, wherein the amount of total steviol glycosides produced by the cell is decreased by less than about 5% relative to a corresponding host lacking the one or more recombinant genes.

7. The method of claim 1, wherein the amount of total steviol glycosides produced by the cell is increased by at least about 5% relative to a corresponding host lacking the one or more recombinant genes.

8. The method of any claim 1, wherein the recombinant host cell is grown in a fermentor at a temperature for a period of time, wherein the temperature and period of time facilitate the production of the one or more steviol glycosides or the steviol glycoside composition.

9. The method of claim 8, wherein the amount of UDP-glucose present in the cell culture is increased by at least about 10% at any point throughout the period of time.

10. The method of claim 1, further comprising isolating the produced one or more steviol glycosides or the steviol glycoside composition from the cell culture;

wherein the isolating step comprises separating a liquid phase of the cell culture from a solid phase of the cell culture to obtain a supernatant comprising the produced one or more steviol glycosides or the steviol glycoside composition, and:

(a) contacting the supernatant with one or more adsorbent resins in order to obtain at least a portion of the produced one or more steviol glycosides or the steviol glycoside composition; or (b) contacting the supernatant with one or more ion exchange or reversed-phase chromatography columns in order to obtain at least a portion of the produced one or more steviol glycosides or the steviol glycoside composition; or (c) crystallizing or extracting the produced one or more steviol glycosides or the steviol glycoside composition;

thereby isolating the produced one or more steviol glycosides or the steviol glycoside composition.

11. The method of claim 1, further comprising recovering the one or more steviol glycosides alone or as a composition comprising the one or more steviol glycosides from the cell culture.

12. The method of claim 11, wherein the recovered composition is enriched for the one or more steviol glycosides or glycosides of the steviol precursor relative to a steviol glycoside composition of *Stevia* plant and has a reduced level of *Stevia* plant-derived components relative to a steviol glycoside composition obtained from a plant-derived *Stevia* extract.

13. A method for producing one or more steviol glycosides or a steviol glycoside composition, comprising whole-cell bioconversion of plant-derived or synthetic steviol and/or steviol glycosides in a cell culture medium of a recombinant host cell using:

(a) a recombinant gene encoding a polypeptide capable of synthesizing uridine 5'-triphosphate (UTP) from uridine diphosphate (UDP);

wherein the polypeptide comprises a polypeptide having at least 90% sequence identity to the amino acid sequence set forth in SEQ ID NO:123;

(b) a recombinant gene encoding a polypeptide capable of converting glucose-6-phosphate to glucose-1-phosphate;

wherein the polypeptide comprises a polypeptide having at least 90% sequence identity to the amino acid sequence set forth in any one of SEQ ID NOs:2, 119, 141, 143, 145, or 147; and/or (c) a recombinant gene encoding a polypeptide capable of synthesizing uridine diphosphate glucose (UDP-glucose) from UTP and glucose-1 phosphate;

wherein the polypeptide comprises a polypeptide having at least 90% sequence identity to the amino acid sequence set forth in any one of SEQ ID NOs:121, 125, 127, 129, 131, 133, 135, 137, or 139, and one or more of:

(d) a gene encoding a polypeptide capable of glycosylating steviol or a steviol glycoside at its C-13 hydroxyl group thereof;

wherein the polypeptide comprises a polypeptide having at least 90% sequence identity to the amino acid sequence set forth in SEQ ID NO:7;

(e) a gene encoding a polypeptide capable of beta 1,3 glycosylation of the C3' of the 13-O-glucose, 19-O-glucose, or both 13-O-glucose and 19-O-glucose of a steviol glycoside;

wherein the polypeptide comprises a polypeptide having at least 90% sequence identity to the amino acid sequence set forth in SEQ ID NO:9;

(f) a gene encoding a polypeptide capable of glycosylating steviol or a steviol glycoside at its C-19 carboxyl group thereof;

wherein the polypeptide comprises a polypeptide having at least 90% sequence identity to the amino acid sequence set forth in SEQ ID NO:4; and/or (g) a gene encoding a polypeptide capable of beta 1,2 glycosylation of the C2' of the 13-O-glucose, 19-O-glucose, or both 13-O-glucose and 19-O-glucose of a steviol glycoside;

wherein the polypeptide comprises a polypeptide having at least 90% sequence identity to the amino acid sequence set forth in any one of SEQ ID NO:11, 13, or 16;

wherein at least one of the polypeptides is a recombinant polypeptide expressed in the recombinant host cell; and producing the one or more steviol glycosides or the steviol glycoside composition thereby.

14. The method of claim 1, wherein the recombinant host cell is a plant cell, a fungal cell, an algal cell, or a bacterial cell.

15. The method of claim 1, wherein the one or more steviol glycosides is, or the steviol glycoside composition comprises, steviol-13-O-glucoside (13-SMG), steviol-1,2-Bioside, steviol-1,3-Bioside, steviol-19-O-glucoside (19-SMG), 1,2-stevioside, 1,3-stevioside (RebG), rubusoside, rebaudioside A (RebA), rebaudioside B (RebB), rebaudioside C (RebC), rebaudioside D (RebD), rebaudioside E (RebE), rebaudioside F (RebF), rebaudioside M (RebM), rebaudioside Q (RebQ), rebaudioside I (RebI), dulcoside A, and/or an isomer thereof.

16. The method of claim 1, wherein the recombinant host cell further comprises:

(a) a gene encoding a polypeptide capable of glycosylating steviol or a steviol glycoside at its C-13 hydroxyl group thereof;

wherein the polypeptide comprises a polypeptide having at least 90% sequence identity to the amino acid sequence set forth in SEQ ID NO:7;

(b) a gene encoding a polypeptide capable of beta 1,3 glycosylation of the C3' of the 13-O-glucose, 19-O-glucose, or both 13-O-glucose and 19-O-glucose of a steviol glycoside;

wherein the polypeptide comprises a polypeptide having at least 90% sequence identity to the amino acid sequence set forth in SEQ ID NO:9;

(c) a gene encoding a polypeptide capable of glycosylating steviol or a steviol glycoside at its C-19 carboxyl group thereof;

wherein the polypeptide comprises a polypeptide having at least 90% sequence identity to the amino acid sequence set forth in SEQ ID NO:4; and/or (d) a gene encoding a polypeptide capable of beta 1,2 glycosylation of the C2' of the 13-O-glucose, 19-O-glucose, or both 13-O-glucose and 19-O-glucose of a steviol glycoside;

wherein the polypeptide comprises a polypeptide having at least 90% sequence identity to the amino acid sequence set forth in any one of SEQ ID NO:11, 13, or 16;

wherein at least one of the genes in items (a)-(d) is a recombinant gene.

17. The method of claim 16, wherein the recombinant host cell further comprises:

(e) a gene encoding a polypeptide capable of synthesizing geranylgeranyl pyrophosphate (GGPP) from farnesyl diphosphate (FPP) and isopentenyl diphosphate (IPP);

wherein the polypeptide comprises a polypeptide having at least 90% sequence identity to the amino acid sequence set forth in any one of SEQ ID NOs:20, 22, 24, 26, 28, 30, 32, or 116;

(f) a gene encoding a polypeptide capable of synthesizing ent-copalyl diphosphate from GGPP;

wherein the polypeptide comprises a polypeptide having at least 90% sequence identity to the amino acid sequence set forth in any one of SEQ ID NOs:34, 36, 38, 40, 42, or 120;

(g) a gene encoding an a polypeptide capable of synthesizing ent-kaurene from ent-copalyl diphosphate;

wherein the polypeptide comprises a polypeptide having at least 90% sequence identity to the amino acid sequence set forth in any one of SEQ ID NOs:44, 46, 48, 50, or 52;

(h) a gene encoding a polypeptide capable of synthesizing ent-kaurenoic acid from ent-kaurene;

wherein the polypeptide comprises a polypeptide having at least 90% sequence identity to the amino acid sequence set forth in any one of SEQ ID NOs:60, 62, 66, 68, 70, 72, 74, 76 or 117;

(i) a gene encoding a polypeptide capable of reducing cytochrome P450 complex;

wherein the polypeptide comprises a polypeptide having at least 90% sequence identity to the amino acid sequence set forth in any one of SEQ ID NOs:78, 80, 82, 84, 86, 88, 90, or 92; and/or (j) a gene encoding a polypeptide capable of synthesizing steviol from ent-kaurenoic acid;

wherein the polypeptide comprises a polypeptide having at least 90% sequence identity to the amino acid sequence set forth in any one of SEQ ID NOs:94, 97, 100-104, 106, 108, 110, 112, or 114;

wherein at least one of the genes in items (e)-(j) is a recombinant gene.

18. The method of claim 1, wherein the recombinant host cell comprises:

(a) the recombinant gene encoding a polypeptide capable of synthesizing uridine 5'-triphosphate (UTP) from uridine diphosphate (UDP) having at least 90% sequence identity to the amino acid sequence set forth in SEQ ID NO:123;

(b) one or more recombinant genes encoding a polypeptide capable of converting glucose-6-phosphate to glucose-1-phosphate, each having at least 90% sequence identity to the amino acid sequence set forth in SEQ ID NO:2 and/or SEQ ID NO:119; and (c) the recombinant gene encoding a polypeptide capable of synthesizing UDP-glucose from UTP and glucose-1-phosphate having at least 90% sequence identity to the amino acid sequence set forth in SEQ ID NO:121.

19. The method of claim 1, wherein the recombinant host cell comprises:

(a) a recombinant gene encoding a polypeptide capable of synthesizing uridine 5'-triphosphate (UTP) from uridine diphosphate (UDP);

(b) a recombinant gene encoding a polypeptide capable of converting glucose-6-phosphate to glucose-1-phosphate; and (c) the recombinant gene encoding a polypeptide capable of synthesizing UDP-glucose from UTP and glucose-1-phosphate having at least 90% sequence identity to the amino acid sequence set forth in any one of SEQ ID NOs:121, 125, 127, 129, 131, 133, 135, 137, or 139; and one or more of:

(d) a gene encoding a polypeptide capable of glycosylating steviol or a steviol glycoside at its C-13 hydroxyl group thereof;

wherein the polypeptide comprises a polypeptide having at least 90% sequence identity to the amino acid sequence set forth in SEQ ID NO:7;

(e) a gene encoding a polypeptide capable of beta 1,3 glycosylation of the C3' of the 13-O-glucose, 19-O-glucose, or both 13-O-glucose and 19-O-glucose of a steviol glycoside;

wherein the polypeptide comprises a polypeptide having at least 90% sequence identity to the amino acid sequence set forth in SEQ ID NO:9;

(f) a gene encoding a polypeptide capable of glycosylating steviol or a steviol glycoside at its C-19 carboxyl group thereof;

wherein the polypeptide comprises a polypeptide having at least 90% sequence identity to the amino acid sequence set forth in SEQ ID NO:4; and/or (g) a gene encoding a polypeptide capable of beta 1,2 glycosylation of the C2' of the 13-O-glucose, 19-O-glucose, or both 13-O-glucose and 19-O-glucose of a steviol glycoside;

wherein the polypeptide comprises a polypeptide having at least 90% sequence identity to the amino acid sequence set forth in any one of SEQ ID NO:11, 13, or 16.

20. The method of claim 1, wherein the recombinant host cell comprises:

(a) the recombinant gene encoding a polypeptide capable of synthesizing uridine 5'-triphosphate (UTP) from uridine diphosphate (UDP) having at least 90% sequence identity to the amino acid sequence set forth in SEQ ID NO:123;

(b) one or more recombinant genes encoding a polypeptide capable of converting glucose-6-phosphate to glucose-1-phosphate, each having at least 90% sequence identity to the amino acid sequence set forth in SEQ ID NO:2 and/or SEQ ID NO:119; and/or (c) the recombinant gene encoding a polypeptide capable of synthesizing UDP-glucose from UTP and glucose-1-phosphate having at least 90% sequence identity to the amino acid sequence set forth in SEQ ID NO:121;

wherein the gene encoding a polypeptide capable of synthesizing uridine 5'-triphosphate (UTP) from uridine diphosphate (UDP), the one or more genes encoding a polypeptide capable of converting glucose-6-phosphate to glucose-1-phosphate, and/or the gene encoding a polypeptide capable of synthesizing UDP-glucose from UTP and glucose-1-phosphate are overexpressed relative to a corresponding host cell lacking the one or more recombinant genes.

21. The method of claim 20, wherein the gene encoding the polypeptide capable of synthesizing uridine 5'-triphosphate (UTP) from uridine diphosphate (UDP), the one or more genes encoding a polypeptide capable of converting glucose-6-phosphate to glucose-1-phosphate, and/or the gene encoding a polypeptide capable of synthesizing UDP-glucose from UTP and glucose-1-phosphate are overexpressed by at least 10% relative to a corresponding host cell lacking the one or more recombinant genes.

22. The method of claim 20, wherein the amount of the one or more steviol glycosides produced by the cell is increased by at least about 5% relative to a corresponding host lacking the one or more recombinant genes.

* * * * *

SEQUENCE LISTING

<160> NUMBER OF SEQ ID NOS: 155

<210> SEQ ID NO 1
<211> LENGTH: 1713
<212> TYPE: DNA
<213> ORGANISM: Saccharomyces cerevisiae

<400> SEQUENCE: 1
atgtcacttc taatagattc tgtaccaaca gttgcttata aggaccaaaa accgggtact 60
tcaggtttac gtaagaagac caaggttttc atggatgagc ctcattatac tgagaacttc 120
attcaagcaa caatgcaatc tatccctaat ggctcagagg gaaccacttt agttgttgga 180
ggagatggtc gtttctacaa cgatgttatc atgaacaaga ttgccgcagt aggtgctgca 240
aacggtgtca gaaagttagt cattggtcaa ggcggtttac tttcaacacc agctgcttct 300
catataatta gaacatacga ggaaaagtgt accggtggtg gtatcatatt aactgcctca 360
cacaacccag gcggtccaga gaatgattta ggtatcaagt ataatttacc taatggtggg 420
ccagctccag agagtgtcac taacgctatc tgggaagcgt ctaaaaaatt aactcactat 480
aaaattataa agaacttccc caagttgaat ttgaacaagc ttggtaaaaa ccaaaaatat 540
ggcccattgt tagtggacat aattgatcct gccaaagcat acgttcaatt tctgaaggaa 600
atttttgatt ttgacttaat taaaagcttc ttagcgaaac agcgcaaaga caaagggtgg 660
aagttgttgt ttgactcctt aaatggtatt acaggaccat atggtaaggc tatatttgtt 720
gatgaatttg gtttaccggc agaggaagtt cttcaaaatt ggcacccttt acctgatttc 780
ggcggtttac atcccgatcc gaatctaacc tatgcacgaa ctcttgttga cagggttgac 840
cgcgaaaaaa ttgcctttgg agcagcctcc gatggtgatg gtgataggaa tatgatttac 900
ggttatggcc ctgctttcgt ttcgccaggt gattctgttg ccattattgc cgaatatgca 960
cccgaaattc catacttcgc caaacaaggt atttatggct tggcacgttc atttcctaca 1020

```
tcctcagcca ttgatcgtgt tgcagcaaaa aagggattaa gatgttacga agttccaacc   1080

ggctggaaat tcttctgtgc cttatttgat gctaaaaagc tatcaatctg tggtgaagaa   1140

tccttcggta caggttccaa tcatatcaga gaaaaggacg gtctatgggc cattattgct   1200

tggttaaata tcttggctat ctaccatagg cgtaaccctg aaaaggaagc ttcgatcaaa   1260

actattcagg acgaattttg gaacgagtat ggccgtactt tcttcacaag atacgattac   1320

gaacatatcg aatgcgagca ggccgaaaaa gttgtagctc ttttgagtga atttgtatca   1380

aggccaaacg tttgtggctc ccacttccca gctgatgagt ctttaaccgt tatcgattgt   1440

ggtgattttt cgtatagaga tctagatggc tccatctctg aaaatcaagg cctttttcgta  1500

aagttttcga atgggactaa atttgttttg aggttatccg gcacaggcag ttctggtgca   1560

acaataagat tatacgtaga aaagtatact gataaaaagg agaactatgg ccaaacagct   1620

gacgtcttct tgaaacccgt catcaactcc attgtaaaat tcttaagatt taaagaaatt   1680

ttaggaacag acgaaccaac agtccgcaca tag                                1713
```

<210> SEQ ID NO 2
<211> LENGTH: 570
<212> TYPE: PRT
<213> ORGANISM: Saccharomyces cerevisiae

<400> SEQUENCE: 2

```
Met Ser Leu Leu Ile Asp Ser Val Pro Thr Val Ala Tyr Lys Asp Gln
1               5                   10                  15

Lys Pro Gly Thr Ser Gly Leu Arg Lys Lys Thr Lys Val Phe Met Asp
            20                  25                  30

Glu Pro His Tyr Thr Glu Asn Phe Ile Gln Ala Thr Met Gln Ser Ile
        35                  40                  45

Pro Asn Gly Ser Glu Gly Thr Thr Leu Val Val Gly Gly Asp Gly Arg
    50                  55                  60

Phe Tyr Asn Asp Val Ile Met Asn Lys Ile Ala Ala Val Gly Ala Ala
65                  70                  75                  80

Asn Gly Val Arg Lys Leu Val Ile Gly Gln Gly Gly Leu Leu Ser Thr
                85                  90                  95

Pro Ala Ala Ser His Ile Ile Arg Thr Tyr Glu Glu Lys Cys Thr Gly
            100                 105                 110

Gly Gly Ile Ile Leu Thr Ala Ser His Asn Pro Gly Gly Pro Glu Asn
        115                 120                 125

Asp Leu Gly Ile Lys Tyr Asn Leu Pro Asn Gly Gly Pro Ala Pro Glu
    130                 135                 140

Ser Val Thr Asn Ala Ile Trp Glu Ala Ser Lys Lys Leu Thr His Tyr
145                 150                 155                 160

Lys Ile Ile Lys Asn Phe Pro Lys Leu Asn Leu Asn Lys Leu Gly Lys
                165                 170                 175

Asn Gln Lys Tyr Gly Pro Leu Leu Val Asp Ile Ile Asp Pro Ala Lys
            180                 185                 190

Ala Tyr Val Gln Phe Leu Lys Glu Ile Phe Asp Phe Asp Leu Ile Lys
        195                 200                 205

Ser Phe Leu Ala Lys Gln Arg Lys Asp Lys Gly Trp Lys Leu Leu Phe
    210                 215                 220

Asp Ser Leu Asn Gly Ile Thr Gly Pro Tyr Gly Lys Ala Ile Phe Val
225                 230                 235                 240

Asp Glu Phe Gly Leu Pro Ala Glu Glu Val Leu Gln Asn Trp His Pro
```

-continued

```
                245                 250                 255

Leu Pro Asp Phe Gly Gly Leu His Pro Asp Pro Asn Leu Thr Tyr Ala
            260                 265                 270

Arg Thr Leu Val Asp Arg Val Asp Arg Glu Lys Ile Ala Phe Gly Ala
        275                 280                 285

Ala Ser Asp Gly Asp Gly Asp Arg Asn Met Ile Tyr Gly Tyr Gly Pro
    290                 295                 300

Ala Phe Val Ser Pro Gly Asp Ser Val Ala Ile Ile Ala Glu Tyr Ala
305                 310                 315                 320

Pro Glu Ile Pro Tyr Phe Ala Lys Gln Gly Ile Tyr Gly Leu Ala Arg
                325                 330                 335

Ser Phe Pro Thr Ser Ser Ala Ile Asp Arg Val Ala Ala Lys Lys Gly
            340                 345                 350

Leu Arg Cys Tyr Glu Val Pro Thr Gly Trp Lys Phe Phe Cys Ala Leu
        355                 360                 365

Phe Asp Ala Lys Lys Leu Ser Ile Cys Gly Glu Glu Ser Phe Gly Thr
    370                 375                 380

Gly Ser Asn His Ile Arg Glu Lys Asp Gly Leu Trp Ala Ile Ile Ala
385                 390                 395                 400

Trp Leu Asn Ile Leu Ala Ile Tyr His Arg Arg Asn Pro Glu Lys Glu
                405                 410                 415

Ala Ser Ile Lys Thr Ile Gln Asp Glu Phe Trp Asn Glu Tyr Gly Arg
            420                 425                 430

Thr Phe Phe Thr Arg Tyr Asp Tyr Glu His Ile Glu Cys Glu Gln Ala
        435                 440                 445

Glu Lys Val Val Ala Leu Leu Ser Glu Phe Val Ser Arg Pro Asn Val
    450                 455                 460

Cys Gly Ser His Phe Pro Ala Asp Glu Ser Leu Thr Val Ile Asp Cys
465                 470                 475                 480

Gly Asp Phe Ser Tyr Arg Asp Leu Asp Gly Ser Ile Ser Glu Asn Gln
                485                 490                 495

Gly Leu Phe Val Lys Phe Ser Asn Gly Thr Lys Phe Val Leu Arg Leu
            500                 505                 510

Ser Gly Thr Gly Ser Ser Gly Ala Thr Ile Arg Leu Tyr Val Glu Lys
        515                 520                 525

Tyr Thr Asp Lys Lys Glu Asn Tyr Gly Gln Thr Ala Asp Val Phe Leu
    530                 535                 540

Lys Pro Val Ile Asn Ser Ile Val Lys Phe Leu Arg Phe Lys Glu Ile
545                 550                 555                 560

Leu Gly Thr Asp Glu Pro Thr Val Arg Thr
                565                 570
```

<210> SEQ ID NO 3
<211> LENGTH: 1383
<212> TYPE: DNA
<213> ORGANISM: Stevia rebaudiana

<400> SEQUENCE: 3

```
atggcagagc aacaaaagat caaaaagtca cctcacgtct tacttattcc atttcctctg      60

caaggacata tcaacccatt catacaattt gggaaaagat tgattagtaa gggtgtaaag     120

acaacactgg taaccactat ccacactttg aattctactc tgaaccactc aaatactact     180

actacaagta tagaaattca agctatatca gacggatgcg atgagggtgg ctttatgtct     240

gccggtgaat cttacttgga aacattcaag caagtgggat ccaagtctct ggccgatcta     300
```

-continued

```
atcaaaaagt tacagagtga aggcaccaca attgacgcca taatctacga ttctatgaca    360

gagtgggttt tagacgttgc tatcgaattt ggtattgatg gaggttcctt tttcacacaa    420

gcatgtgttg tgaattctct atactaccat gtgcataaag ggttaatctc tttaccattg    480

ggtgaaactg tttcagttcc aggttttcca gtgttacaac gttgggaaac cccattgatc    540

ttacaaaatc atgaacaaat acaatcacct tggtcccaga tgttgtttgg tcaattcgct    600

aacatcgatc aagcaagatg ggtctttact aattcattct ataagttaga ggaagaggta    660

attgaatgga ctaggaagat ctggaatttg aaagtcattg gtccaacatt gccatcaatg    720

tatttggaca aaagacttga tgatgataaa gataatggtt tcaatttgta caaggctaat    780

catcacgaat gtatgaattg gctggatgac aaaccaaagg aatcagttgt atatgttgct    840

ttcggctctc ttgttaaaca tggtccagaa caagttgagg agattacaag agcacttata    900

gactctgacg taaacttttt gtgggtcatt aagcacaaag aggaggggaa actgccagaa    960

aacctttctg aagtgataaa gaccggaaaa ggtctaatcg ttgcttggtg taaacaattg   1020

gatgttttag ctcatgaatc tgtaggctgt tttgtaacac attgcggatt caactctaca   1080

ctagaagcca tttccttagg cgtacctgtc gttgcaatgc ctcagttctc cgatcagaca   1140

accaacgcta aacttttgga cgaaatacta ggggtgggtg tcagagttaa agcagacgag   1200

aatggtatcg tcagaagagg gaacctagct tcatgtatca aaatgatcat ggaagaggaa   1260

agaggagtta tcataaggaa aaacgcagtt aagtggaagg atcttgcaaa ggttgccgtc   1320

catgaaggcg gctcttcaga taatgatatt gttgaatttg tgtccgaact aatcaaagcc   1380

taa                                                                 1383
```

<210> SEQ ID NO 4
<211> LENGTH: 460
<212> TYPE: PRT
<213> ORGANISM: Stevia rebaudiana

<400> SEQUENCE: 4

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175
```

```
Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
    450                 455                 460


<210> SEQ ID NO 5
<211> LENGTH: 1586
<212> TYPE: DNA
<213> ORGANISM: Stevia rebaudiana

<400> SEQUENCE: 5

atggatgcaa tggctacaac tgagaagaaa ccacacgtca tcttcatacc atttccagca     60

caaagccaca ttaaagccat gctcaaacta gcacaacttc tccaccacaa aggactccag    120

ataaccttcg tcaacaccga cttcatccac aaccagtttc ttgaatcatc gggcccacat    180

tgtctagacg gtgcaccggg tttccggttc gaaaccattc cggatggtgt ttctcacagt    240

ccggaagcga gcatcccaat cagagaatca ctcttgagat ccattgaaac caacttcttg    300

gatcgtttca ttgatcttgt aaccaaactt ccggatcctc cgacttgtat tatctcagat    360

gggttcttgt cggttttcac aattgacgct gcaaaaaagc ttggaattcc ggtcatgatg    420

tattggacac ttgctgcctg tgggttcatg ggtttttacc atattcattc tctcattgag    480
```

-continued

```
aaaggatttg caccacttaa agatgcaagt tacttgacaa atgggtattt ggacaccgtc    540

attgattggg ttccgggaat ggaaggcatc cgtctcaagg atttcccgct ggactggagc    600

actgacctca atgacaaagt tttgatgttc actacggaag ctcctcaaag gtcacacaag    660

gtttcacatc atattttcca cacgttcgat gagttggagc ctagtattat aaaaactttg    720

tcattgaggt ataatcacat ttacaccatc ggcccactgc aattacttct tgatcaaata    780

cccgaagaga aaaagcaaac tggaattacg agtctccatg gatacagttt agtaaaagaa    840

gaaccagagt gtttccagtg gcttcagtct aaagaaccaa attccgtcgt ttatgtaaat    900

tttggaagta ctacagtaat gtctttagaa gacatgacgg aatttggttg ggacttgct    960

aatagcaacc attatttcct ttggatcatc cgatcaaact tggtgatagg ggaaaatgca   1020

gttttgcccc ctgaacttga ggaacatata aagaaaagag gctttattgc tagctggtgt   1080

tcacaagaaa aggtcttgaa gcacccttcg gttggagggt tcttgactca ttgtgggtgg   1140

ggatcgacca tcgagagctt gtctgctggg gtgccaatga tatgctggcc ttattcgtgg   1200

gaccagctga ccaactgtag gtatatatgc aaagaatggg aggttgggct cgagatggga   1260

accaaagtga aacgagatga agtcaagagg cttgtacaag agttgatggg agaaggaggt   1320

cacaaaatga ggaacaaggc taaagattgg aaagaaaagg ctcgcattgc aatagctcct   1380

aacggttcat cttctttgaa catagacaaa atggtcaagg aaatcaccgt gctagcaaga   1440

aactagttac aaagttgttt cacattgtgc tttctattta agatgtaact ttgttctaat   1500

ttaatattgt ctagatgtat tgaaccataa gtttagttgg tctcaggaat tgatttttaa   1560

tgaaataatg gtcattaggg gtgagt                                         1586
```

<210> SEQ ID NO 6
<211> LENGTH: 1446
<212> TYPE: DNA
<213> ORGANISM: Artificial Sequence
<220> FEATURE:
<223> OTHER INFORMATION: Codon-optimized UGT85C2

<400> SEQUENCE: 6

```
atggatgcaa tggcaactac tgagaaaaag cctcatgtga tcttcattcc atttcctgca     60

caatctcaca taaaggcaat gctaaagtta gcacaactat tacaccataa gggattacag    120

ataactttcg tgaataccga cttcatccat aatcaatttc tggaatctag tggccctcat    180

tgtttggacg gagccccagg gtttagattc gaaacaattc ctgacggtgt ttcacattcc    240

ccagaggcct ccatcccaat aagagagagt ttactgaggt caatagaaac caactttttg    300

gatcgtttca ttgacttggt cacaaaactt ccagacccac caacttgcat aatctctgat    360

ggctttctgt cagtgtttac tatcgacgct gccaaaaagt tgggtatccc agttatgatg    420

tactggactc ttgctgcatg cggtttcatg ggtttctatc acatccattc tcttatcgaa    480

aagggttttg ctccactgaa agatgcatca tacttaacca acggctacct ggatactgtt    540

attgactggg taccaggtat ggaaggtata agacttaaag attttccttt ggattggtct    600

acagacctta atgataaagt attgatgttt actacagaag ctccacaaag atctcataag    660

gtttcacatc atatctttca cacctttgat gaattggaac catcaatcat caaaaccttg    720

tctctaagat acaatcatat ctacactatt ggtccattac aattacttct agatcaaatt    780

cctgaagaga aaaagcaaac tggtattaca tccttacacg gctactcttt agtgaaagag    840

gaaccagaat gttttcaatg gctacaaagt aaagagccta attctgtggt ctacgtcaac    900

ttcggaagta caacagtcat gtccttggaa gatatgactg aatttggttg ggccttgct    960
```

```
aattcaaatc attactttct atggattatc aggtccaatt tggtaatagg ggaaaacgcc   1020

gtattacctc cagaattgga ggaacacatc aaaaagagag gtttcattgc ttcctggtgt   1080

tctcaggaaa aggtattgaa acatccttct gttggtggtt tccttactca ttgcggttgg   1140

ggctctacaa tcgaatcact aagtgcagga gttccaatga tttgttggcc atattcatgg   1200

gaccaactta caaattgtag gtatatctgt aaagagtggg aagttggatt agaaatggga   1260

acaaaggtta aacgtgatga agtgaaaaga ttggttcagg agttgatggg ggaaggtggc   1320

cacaagatga gaaacaaggc caaagattgg aaggaaaaag ccagaattgc tattgctcct   1380

aacgggtcat cctctctaaa cattgataag atggtcaaag agattacagt cttagccaga   1440

aactaa                                                              1446
```

<210> SEQ ID NO 7
<211> LENGTH: 481
<212> TYPE: PRT
<213> ORGANISM: Stevia rebaudiana

<400> SEQUENCE: 7

```
Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
```

```
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn


<210> SEQ ID NO 8
<211> LENGTH: 1377
<212> TYPE: DNA
<213> ORGANISM: Artificial Sequence
<220> FEATURE:
<223> OTHER INFORMATION: Codon-optimized UGT76G1

<400> SEQUENCE: 8

atggaaaaca agaccgaaac aacagttaga cgtaggcgta gaatcattct gtttccagta     60

ccttttcaag ggcacatcaa tccaatacta caactagcca acgttttgta ctctaaaggt    120

ttttctatta caatctttca caccaatttc aacaaaccaa aaacatccaa ttacccacat    180

ttcacattca gattcatact tgataatgat ccacaagatg aacgtatttc aaacttacct    240

acccacggtc ctttagctgg aatgagaatt ccaatcatca atgaacatgg tgccgatgag    300

cttagaagag aattagagtt acttatgttg gcatccgaag aggacgagga agtctcttgt    360

ctgattactg acgctctatg gtactttgcc caatctgtgg ctgatagttt gaatttgagg    420

agattggtac taatgacatc cagtctgttt aactttcacg ctcatgttag tttaccacaa    480

tttgacgaat tgggatactt ggaccctgat gacaagacta ggttagagga acaggcctct    540

ggttttccta tgttgaaagt caaagatatc aagtctgcct attctaattg gcaaatcttg    600

aaagagatct taggaaagat gatcaaacag acaaaggctt catctggagt gatttggaac    660

agtttcaaag agttagaaga gtctgaattg gagactgtaa tcagagaaat tccagcacct    720

tcattcctga taccattacc aaaacatttg actgcttcct cttcctcttt gttggatcat    780

gacagaacag tttttcaatg gttggaccaa caaccaccta gttctgtttt gtacgtgtca    840

tttggtagta cttctgaagt cgatgaaaag gacttccttg aaatcgcaag aggcttagtc    900
```

```
gatagtaagc agtcattcct ttgggtcgtg cgtccaggtt tcgtgaaagg ctcaacatgg    960

gtcgaaccac ttccagatgg ttttctaggc gaaagaggta gaatagtcaa atgggttcct   1020

caacaggaag ttttagctca tggcgctatt ggggcattct ggactcattc cggatggaat   1080

tcaactttag aatcagtatg cgaaggggta cctatgatct tttcagattt tggtcttgat   1140

caaccactga acgcaagata catgtctgat gttttgaaag tgggtgtata tctagaaaat   1200

ggctgggaaa ggggtgaaat agctaatgca ataagacgtg ttatggttga tgaagagggg   1260

gagtatatca gacaaaacgc aagagtgctg aagcaaaagg ccgacgtttc tctaatgaag   1320

ggaggctctt catacgaatc cttagaatct cttgtttcct acatttcatc actgtaa      1377


<210> SEQ ID NO 9
<211> LENGTH: 458
<212> TYPE: PRT
<213> ORGANISM: Stevia rebaudiana

<400> SEQUENCE: 9

Met Glu Asn Lys Thr Glu Thr Thr Val Arg Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285
```

-continued

```
Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455
```

<210> SEQ ID NO 10
<211> LENGTH: 1422
<212> TYPE: DNA
<213> ORGANISM: Artificial Sequence
<220> FEATURE:
<223> OTHER INFORMATION: Codon-optimized UGT91D2e

<400> SEQUENCE: 10

```
atggctacat ctgattctat tgttgatgac aggaagcagt tgcatgtggc tactttccct     60

tggcttgctt tcggtcatat actgccttac ctacaactat caaaactgat agctgaaaaa    120

ggacataaag tgtcattcct ttcaacaact agaaacattc aaagattatc ttcccacata    180

tcaccattga ttaacgtcgt tcaattgaca cttccaagag tacaggaatt accagaagat    240

gctgaagcta caacagatgt gcatcctgaa gatatccctt acttgaaaaa ggcatccgat    300

ggattacagc ctgaggtcac tagattcctt gagcaacaca gtccagattg gatcatatac    360

gactacactc actattggtt gccttcaatt gcagcatcac taggcatttc tagggcacat    420

ttcagtgtaa ccacaccttg ggccattgct tacatgggtc catccgctga tgctatgatt    480

aacggcagtg atggtagaac taccgttgaa gatttgacaa ccccaccaaa gtggtttcca    540

tttccaacta aagtctgttg gagaaaacac gacttagcaa gactggttcc atacaaggca    600

ccaggaatct cagacggcta tagaatgggt ttagtcctta aagggtctga ctgcctattg    660

tctaagtgtt accatgagtt tggacacaa tggctaccac ttttggaaac attacaccaa    720

gttcctgtcg taccagttgg tctattacct ccagaaatcc ctggtgatga gaaggacgag    780

acttgggttt caatcaaaaa gtggttagac gggaagcaaa aaggctcagt ggtatatgtg    840

gcactgggtt ccgaagtttt agtatctcaa acagaagttg tggaacttgc cttaggtttg    900

gaactatctg gattgccatt tgtctgggcc tacagaaaac caaaaggccc tgcaaagtcc    960

gattcagttg aattgccaga cggctttgtc gagagaacta gagatagagg gttggtatgg   1020

acttcatggg ctccacaatt gagaatcctg agtcacgaat ctgtgtgcgg tttcctaaca   1080
```

-continued cattgtggtt ctggttctat agttgaagga ctgatgtttg gtcatccact tatcatgttg 1140
ccaatctttg gtgaccagcc tttgaatgca cgtctgttag aagataaaca agttggaatt 1200
gaaatcccac gtaatgagga agatggatgt ttaaccaagg agtctgtggc cagatcatta 1260
cgttccgttg tcgttgaaaa ggaaggcgaa atctacaagg ccaatgcccg tgaactttca 1320
aagatctaca atgacacaaa agtagagaag gaatatgttt ctcaatttgt agattaccta 1380
gagaaaaacg ctagagccgt agctattgat catgaatcct aa 1422

<210> SEQ ID NO 11
<211> LENGTH: 473
<212> TYPE: PRT
<213> ORGANISM: Stevia rebaudiana

<400> SEQUENCE: 11

Met Ala Thr Ser Asp Ser Ile Val Asp Asp Arg Lys Gln Leu His Val
1 5 10 15

Ala Thr Phe Pro Trp Leu Ala Phe Gly His Ile Leu Pro Tyr Leu Gln
20 25 30

Leu Ser Lys Leu Ile Ala Glu Lys Gly His Lys Val Ser Phe Leu Ser
35 40 45

Thr Thr Arg Asn Ile Gln Arg Leu Ser Ser His Ile Ser Pro Leu Ile
50 55 60

Asn Val Val Gln Leu Thr Leu Pro Arg Val Gln Glu Leu Pro Glu Asp
65 70 75 80

Ala Glu Ala Thr Thr Asp Val His Pro Glu Asp Ile Pro Tyr Leu Lys
85 90 95

Lys Ala Ser Asp Gly Leu Gln Pro Glu Val Thr Arg Phe Leu Glu Gln
100 105 110

His Ser Pro Asp Trp Ile Ile Tyr Asp Tyr Thr His Tyr Trp Leu Pro
115 120 125

Ser Ile Ala Ala Ser Leu Gly Ile Ser Arg Ala His Phe Ser Val Thr
130 135 140

Thr Pro Trp Ala Ile Ala Tyr Met Gly Pro Ser Ala Asp Ala Met Ile
145 150 155 160

Asn Gly Ser Asp Gly Arg Thr Thr Val Glu Asp Leu Thr Thr Pro Pro
165 170 175

Lys Trp Phe Pro Phe Pro Thr Lys Val Cys Trp Arg Lys His Asp Leu
180 185 190

Ala Arg Leu Val Pro Tyr Lys Ala Pro Gly Ile Ser Asp Gly Tyr Arg
195 200 205

Met Gly Leu Val Leu Lys Gly Ser Asp Cys Leu Leu Ser Lys Cys Tyr
210 215 220

His Glu Phe Gly Thr Gln Trp Leu Pro Leu Leu Glu Thr Leu His Gln
225 230 235 240

Val Pro Val Val Pro Val Gly Leu Leu Pro Pro Glu Ile Pro Gly Asp
245 250 255

Glu Lys Asp Glu Thr Trp Val Ser Ile Lys Lys Trp Leu Asp Gly Lys
260 265 270

Gln Lys Gly Ser Val Val Tyr Val Ala Leu Gly Ser Glu Val Leu Val
275 280 285

Ser Gln Thr Glu Val Val Glu Leu Ala Leu Gly Leu Glu Leu Ser Gly
290 295 300

Leu Pro Phe Val Trp Ala Tyr Arg Lys Pro Lys Gly Pro Ala Lys Ser
305 310 315 320

```
Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470
```

<210> SEQ ID NO 12
<211> LENGTH: 1422
<212> TYPE: DNA
<213> ORGANISM: Artificial Sequence
<220> FEATURE:
<223> OTHER INFORMATION: Codon-optimized UGT91D2e-b

<400> SEQUENCE: 12

```
atggctactt ctgattccat cgttgacgat agaaagcaat tgcatgttgc tacttttcca     60

tggttggctt tcggtcatat tttgccatac ttgcaattgt ccaagttgat tgctgaaaag    120

ggtcacaagg tttcattctt gtctaccacc agaaacatcc aaagattgtc ctctcatatc    180

tccccattga tcaacgttgt tcaattgact ttgccaagag tccaagaatt gccagaagat    240

gctgaagcta ctactgatgt tcatccagaa gatatccctt acttgaaaaa ggcttccgat    300

ggtttacaac cagaagttac tagattcttg gaacaacatt ccccagattg gatcatctac    360

gattatactc attactggtt gccatccatt gctgcttcat tgggtatttc tagagcccat    420

ttctctgtta ctactccatg ggctattgct tatatgggtc catctgctga tgctatgatt    480

aacggttctg atggtagaac taccgttgaa gatttgacta ctccaccaaa gtggtttcca    540

tttccaacaa aagtctgttg gagaaaacac gatttggcta gattggttcc atacaaagct    600

ccaggtattt ctgatggtta cagaatgggt atggttttga aaggttccga ttgcttgttg    660

tctaagtgct atcatgaatt cggtactcaa tggttgcctt tgttggaaac attgcatcaa    720

gttccagttg ttccagtagg tttgttgcca ccagaaattc caggtgacga aaaagacgaa    780

acttgggttt ccatcaaaaa gtggttggat ggtaagcaaa agggttctgt tgtttatgtt    840

gctttgggtt ccgaagcttt ggtttctcaa accgaagttg ttgaattggc tttgggtttg    900

gaattgtctg gtttgccatt tgtttgggct tacagaaaac ctaaaggtcc agctaagtct    960

gattctgttg aattgccaga tggtttcgtt gaaagaacta gagatagagg tttggtttgg   1020

acttcttggg ctccacaatt gagaattttg tctcatgaat ccgtctgtgg tttcttgact   1080

cattgtggtt ctggttctat cgttgaaggt ttgatgtttg gtcacccatt gattatgttg   1140
```

-continued

```
ccaatctttg gtgaccaacc attgaacgct agattattgg aagataagca agtcggtatc   1200

gaaatcccaa gaaatgaaga agatggttgc ttgaccaaag aatctgttgc tagatctttg   1260

agatccgttg tcgttgaaaa agaaggtgaa atctacaagg ctaacgctag agaattgtcc   1320

aagatctaca acgataccaa ggtcgaaaaa gaatacgttt cccaattcgt tgactacttg   1380

gaaaagaatg ctagagctgt tgccattgat catgaatctt ga                      1422


<210> SEQ ID NO 13
<211> LENGTH: 473
<212> TYPE: PRT
<213> ORGANISM: Artificial Sequence
<220> FEATURE:
<223> OTHER INFORMATION: UGT91D2e-b

<400> SEQUENCE: 13

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320
```

```
Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470
```

<210> SEQ ID NO 14
<211> LENGTH: 1389
<212> TYPE: DNA
<213> ORGANISM: Oryza sativa

<400> SEQUENCE: 14

```
atggactccg gctactcctc ctcctacgcc gccgccgccg ggatgcacgt cgtgatctgc     60

ccgtggctcg ccttcggcca cctgctcccg tgcctcgacc tcgcccagcg cctcgcgtcg    120

cggggccacc gcgtgtcgtt cgtctccacg ccgcggaaca tatcccgcct cccgccggtg    180

cgccccgcgc tcgcgccgct cgtcgccttc gtggcgctgc cgctcccgcg cgtcgagggg    240

ctccccgacg gcgccgagtc caccaacgac gtcccccacg acaggccgga catggtcgag    300

ctccaccgga gggccttcga cgggctcgcc gcgcccttct cggagttctt gggcaccgcg    360

tgcgccgact gggtcatcgt cgacgtcttc caccactggg ccgcagccgc cgctctcgag    420

cacaaggtgc catgtgcaat gatgttgttg ggctctgcac atatgatcgc ttccatagca    480

gacagacggc tcgagcgcgc ggagacagag tcgcctgcgg ctgccgggca gggacgccca    540

gcggcggcgc caacgttcga ggtggcgagg atgaagttga tacgaaccaa aggctcatcg    600

ggaatgtccc tcgccgagcg cttctccttg acgctctcga ggagcagcct cgtcgtcggg    660

cggagctgcg tggagttcga gccggagacc gtcccgctcc tgtcgacgct ccgcggtaag    720

cctattacct tccttggcct tatgccgccg ttgcatgaag gccgccgcga ggacggcgag    780

gatgccaccg tccgctggct cgacgcgcag ccggccaagt ccgtcgtgta cgtcgcgcta    840

ggcagcgagg tgccactggg agtggagaag gtccacgagc tcgcgctcgg gctggagctc    900

gccgggacgc gcttcctctg ggctcttagg aagcccactg gcgtctccga cgccgacctc    960

ctccccgccg gcttcgagga gcgcacgcgc ggccgcggcg tcgtggcgac gagatgggtt   1020

cctcagatga gcatactggc gcacgccgcc gtgggcgcgt tcctgaccca ctgcggctgg   1080

aactcgacca tcgaggggct catgttcggc cacccgctta tcatgctgcc gatcttcggc   1140

gaccagggac cgaacgcgcg gctaatcgag gcgaagaacg ccggattgca ggtggcaaga   1200
```

-continued

```
aacgacggcg atggatcgtt cgaccgagaa ggcgtcgcgg cggcgattcg tgcagtcgcg   1260

gtggaggaag aaagcagcaa agtgtttcaa gccaaagcca agaagctgca ggagatcgtc   1320

gcggacatgg cctgccatga gaggtacatc gacggattca ttcagcaatt gagatcttac   1380

aaggattga                                                           1389
```

```
<210> SEQ ID NO 15
<211> LENGTH: 1389
<212> TYPE: DNA
<213> ORGANISM: Artificial Sequence
<220> FEATURE:
<223> OTHER INFORMATION: Codon-optimized EUGT11

<400> SEQUENCE: 15

atggatagtg gctactcctc atcttatgct gctgccgctg gtatgcacgt tgtgatctgc     60

ccttggttgg cctttggtca cctgttacca tgtctggatt tagcccaaag actggcctca    120

agaggccata gagtatcatt tgtgtctact cctagaaata tctctcgttt accaccagtc    180

agacctgctc tagctcctct agttgcattc gttgctcttc cacttccaag agtagaagga    240

ttgccagacg gcgctgaatc tactaatgac gtaccacatg atagacctga catggtcgaa    300

ttgcatagaa gagcctttga tggattggca gctccatttt ctgagttcct gggcacagca    360

tgtgcagact gggttatagt cgatgtattt catcactggg ctgctgcagc cgcattggaa    420

cataaggtgc cttgtgctat gatgttgtta gggtcagcac acatgatcgc atccatagct    480

gatagaagat tggaaagagc tgaaacagaa tccccagccg cagcaggaca aggtaggcca    540

gctgccgccc caacctttga agtggctaga atgaaattga ttcgtactaa aggtagttca    600

gggatgagtc ttgctgaaag gttttctctg acattatcta gatcatcatt agttgtaggt    660

agatcctgcg tcgagttcga acctgaaaca gtacctttac tatctacttt gagaggcaaa    720

cctattactt tccttggtct aatgcctcca ttacatgaag gaaggagaga agatggtgaa    780

gatgctactg ttaggtggtt agatgcccaa cctgctaagt ctgttgttta cgttgcattg    840

ggttctgagg taccactagg ggtggaaaag gtgcatgaat tagcattagg acttgagctg    900

gccggaacaa gattcctttg ggctttgaga aaaccaaccg gtgtttctga cgccgacttg    960

ctaccagctg ggttcgaaga gagaacaaga ggccgtggtg tcgttgctac tagatgggtc   1020

ccacaaatga gtattctagc tcatgcagct gtaggggcct ttctaaccca ttgcggttgg   1080

aactcaacaa tagaaggact gatgtttggt catccactta ttatgttacc aatctttggc   1140

gatcagggac ctaacgcaag attgattgag gcaaagaacg caggtctgca ggttgcacgt   1200

aatgatggtg atggttcctt tgatagagaa ggcgttgcag ctgccatcag agcagtcgcc   1260

gttgaggaag agtcatctaa agttttccaa gctaaggcca aaaaattaca agagattgtg   1320

gctgacatgg cttgtcacga aagatacatc gatggtttca tccaacaatt gagaagttat   1380

aaagactaa                                                           1389
```

```
<210> SEQ ID NO 16
<211> LENGTH: 462
<212> TYPE: PRT
<213> ORGANISM: Oryza sativa

<400> SEQUENCE: 16

Met Asp Ser Gly Tyr Ser Ser Ser Tyr Ala Ala Ala Ala Gly Met His
1               5                   10                  15

Val Val Ile Cys Pro Trp Leu Ala Phe Gly His Leu Leu Pro Cys Leu
            20                  25                  30
```

-continued

```
Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
        275                 280                 285

Glu Lys Val His Glu Leu Ala Leu Gly Leu Glu Leu Ala Gly Thr Arg
    290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
        355                 360                 365

Phe Gly His Pro Leu Ile Met Leu Pro Ile Phe Gly Asp Gln Gly Pro
    370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
        435                 440                 445
```

```
Tyr Ile Asp Gly Phe Ile Gln Gln Leu Arg Ser Tyr Lys Asp
    450                 455                 460


<210> SEQ ID NO 17
<211> LENGTH: 465
<212> TYPE: PRT
<213> ORGANISM: Artificial Sequence
<220> FEATURE:
<223> OTHER INFORMATION: UGT91D2e-b-EUGT11 chimera 3

<400> SEQUENCE: 17

Met Asp Ser Gly Tyr Ser Ser Ser Tyr Ala Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Leu Pro Pro Glu Ile Pro Gly Asp Glu
                245                 250                 255

Lys Asp Glu Thr Trp Val Ser Ile Lys Lys Trp Leu Asp Gly Lys Gln
            260                 265                 270

Lys Gly Ser Val Val Tyr Val Ala Leu Gly Ser Glu Ala Leu Val Ser
        275                 280                 285

Gln Thr Glu Val Val Glu Leu Ala Leu Gly Leu Glu Leu Ser Gly Leu
    290                 295                 300

Pro Phe Val Trp Ala Tyr Arg Lys Pro Lys Gly Pro Ala Lys Ser Asp
305                 310                 315                 320

Ser Val Glu Leu Pro Asp Gly Phe Val Glu Arg Thr Arg Asp Arg Gly
                325                 330                 335

Leu Val Trp Thr Ser Trp Ala Pro Gln Leu Arg Ile Leu Ser His Glu
            340                 345                 350
```

```
Ser Val Cys Gly Phe Leu Thr His Cys Gly Ser Gly Ser Ile Val Glu
        355                 360                 365

Gly Leu Met Phe Gly His Pro Leu Ile Met Leu Pro Ile Phe Gly Asp
    370                 375                 380

Gln Pro Leu Asn Ala Arg Leu Leu Glu Asp Lys Gln Val Gly Ile Glu
385                 390                 395                 400

Ile Ala Arg Asn Asp Gly Asp Gly Ser Phe Asp Arg Glu Gly Val Ala
                405                 410                 415

Ala Ala Ile Arg Ala Val Ala Val Glu Glu Glu Ser Ser Lys Val Phe
            420                 425                 430

Gln Ala Lys Ala Lys Lys Leu Gln Glu Ile Val Ala Asp Met Ala Cys
        435                 440                 445

His Glu Arg Tyr Ile Asp Gly Phe Ile Gln Gln Leu Arg Ser Tyr Lys
    450                 455                 460

Asp
465


<210> SEQ ID NO 18
<211> LENGTH: 470
<212> TYPE: PRT
<213> ORGANISM: Artificial Sequence
<220> FEATURE:
<223> OTHER INFORMATION: UGT91D2e-b-EUGT11 chimera 7

<400> SEQUENCE: 18

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240
```

-continued

```
Val Pro Val Val Pro Val Gly Leu Met Pro Pro Leu His Glu Gly Arg
                245                 250                 255

Arg Glu Asp Gly Glu Asp Ala Thr Val Arg Trp Leu Asp Ala Gln Pro
            260                 265                 270

Ala Lys Ser Val Val Tyr Val Ala Leu Gly Ser Glu Val Pro Leu Gly
        275                 280                 285

Val Glu Lys Val His Glu Leu Ala Leu Gly Leu Glu Leu Ala Gly Thr
    290                 295                 300

Arg Phe Leu Trp Ala Leu Arg Lys Pro Thr Gly Val Ser Asp Ala Asp
305                 310                 315                 320

Leu Leu Pro Ala Gly Phe Glu Glu Arg Thr Arg Gly Arg Gly Val Val
                325                 330                 335

Ala Thr Arg Trp Val Pro Gln Met Ser Ile Leu Ala His Ala Ala Val
            340                 345                 350

Gly Ala Phe Leu Thr His Cys Gly Trp Asn Ser Thr Ile Glu Gly Leu
        355                 360                 365

Met Phe Gly His Pro Leu Ile Met Leu Pro Ile Phe Gly Asp Gln Gly
    370                 375                 380

Pro Asn Ala Arg Leu Ile Glu Ala Lys Asn Ala Gly Leu Gln Val Pro
385                 390                 395                 400

Arg Asn Glu Glu Asp Gly Cys Leu Thr Lys Glu Ser Val Ala Arg Ser
                405                 410                 415

Leu Arg Ser Val Val Val Glu Lys Glu Gly Glu Ile Tyr Lys Ala Asn
            420                 425                 430

Ala Arg Glu Leu Ser Lys Ile Tyr Asn Asp Thr Lys Val Glu Lys Glu
        435                 440                 445

Tyr Val Ser Gln Phe Val Asp Tyr Leu Glu Lys Asn Ala Arg Ala Val
    450                 455                 460

Ala Ile Asp His Glu Ser
465                 470
```

<210> SEQ ID NO 19
<211> LENGTH: 1086
<212> TYPE: DNA
<213> ORGANISM: Artificial Sequence
<220> FEATURE:
<223> OTHER INFORMATION: Codon-optimized GGPPS

<400> SEQUENCE: 19

```
atggctttgg taaacccaac cgctcttttc tatggtacct ctatcagaac aagacctaca     60

aacttactaa atccaactca aaagctaaga ccagtttcat catcttcctt accttctttc    120

tcatcagtta gtgcgattct tactgaaaaa catcaatcta atccttctga gaacaacaat    180

ttgcaaactc atctagaaac tcctttcaac tttgatagtt atatgttgga aaaagtcaac    240

atggttaacg aggcgcttga tgcatctgtc ccactaaaag acccaatcaa aatccatgaa    300

tccatgagat actctttatt ggcaggcggt aagagaatca gaccaatgat gtgtattgca    360

gcctgcgaaa tagtcggagg taatatcctt aacgccatgc cagccgcatg tgccgtggaa    420

atgattcata ctatgtcttt ggtgcatgac gatcttccat gtatggataa tgatgacttc    480

agaagaggta aacctatttc acacaaggtc tacggggagg aaatggcagt attgaccggc    540

gatgctttac taagtttatc tttcgaacat atagctactg ctacaaaggg tgtatcaaag    600

gatagaatcg tcagagctat aggggagttg gcccgttcag ttggctccga aggtttagtg    660

gctggacaag ttgtagatat cttgtcagag ggtgctgatg ttggattaga tcacctagaa    720
```

```
tacattcaca tccacaaaac agcaatgttg cttgagtcct cagtagttat tggcgctatc    780

atgggaggag gatctgatca gcagatcgaa aagttgagaa aattcgctag atctattggt    840

ctactattcc aagttgtgga tgacattttg gatgttacaa aatctaccga agagttgggg    900

aaaacagctg gtaaggattt gttgacagat aagacaactt acccaaagtt gttaggtata    960

gaaaagtcca gagaatttgc cgaaaaactt aacaaggaag cacaagagca attaagtggc   1020

tttgatagac gtaaggcagc tcctttgatc gcgttagcca actacaatgc gtaccgtcaa   1080

aattga                                                              1086


<210> SEQ ID NO 20
<211> LENGTH: 361
<212> TYPE: PRT
<213> ORGANISM: Stevia rebaudiana

<400> SEQUENCE: 20

Met Ala Leu Val Asn Pro Thr Ala Leu Phe Tyr Gly Thr Ser Ile Arg
1               5                   10                  15

Thr Arg Pro Thr Asn Leu Leu Asn Pro Thr Gln Lys Leu Arg Pro Val
            20                  25                  30

Ser Ser Ser Ser Leu Pro Ser Phe Ser Ser Val Ser Ala Ile Leu Thr
        35                  40                  45

Glu Lys His Gln Ser Asn Pro Ser Glu Asn Asn Asn Leu Gln Thr His
    50                  55                  60

Leu Glu Thr Pro Phe Asn Phe Asp Ser Tyr Met Leu Glu Lys Val Asn
65                  70                  75                  80

Met Val Asn Glu Ala Leu Asp Ala Ser Val Pro Leu Lys Asp Pro Ile
                85                  90                  95

Lys Ile His Glu Ser Met Arg Tyr Ser Leu Leu Ala Gly Gly Lys Arg
            100                 105                 110

Ile Arg Pro Met Met Cys Ile Ala Ala Cys Glu Ile Val Gly Gly Asn
        115                 120                 125

Ile Leu Asn Ala Met Pro Ala Ala Cys Ala Val Glu Met Ile His Thr
    130                 135                 140

Met Ser Leu Val His Asp Asp Leu Pro Cys Met Asp Asn Asp Asp Phe
145                 150                 155                 160

Arg Arg Gly Lys Pro Ile Ser His Lys Val Tyr Gly Glu Glu Met Ala
                165                 170                 175

Val Leu Thr Gly Asp Ala Leu Leu Ser Leu Ser Phe Glu His Ile Ala
            180                 185                 190

Thr Ala Thr Lys Gly Val Ser Lys Asp Arg Ile Val Arg Ala Ile Gly
        195                 200                 205

Glu Leu Ala Arg Ser Val Gly Ser Glu Gly Leu Val Ala Gly Gln Val
    210                 215                 220

Val Asp Ile Leu Ser Glu Gly Ala Asp Val Gly Leu Asp His Leu Glu
225                 230                 235                 240

Tyr Ile His Ile His Lys Thr Ala Met Leu Leu Glu Ser Ser Val Val
                245                 250                 255

Ile Gly Ala Ile Met Gly Gly Gly Ser Asp Gln Gln Ile Glu Lys Leu
            260                 265                 270

Arg Lys Phe Ala Arg Ser Ile Gly Leu Leu Phe Gln Val Val Asp Asp
        275                 280                 285

Ile Leu Asp Val Thr Lys Ser Thr Glu Glu Leu Gly Lys Thr Ala Gly
    290                 295                 300
```

```
Lys Asp Leu Leu Thr Asp Lys Thr Thr Tyr Pro Lys Leu Leu Gly Ile
305                 310                 315                 320

Glu Lys Ser Arg Glu Phe Ala Glu Lys Leu Asn Lys Glu Ala Gln Glu
                325                 330                 335

Gln Leu Ser Gly Phe Asp Arg Arg Lys Ala Ala Pro Leu Ile Ala Leu
            340                 345                 350

Ala Asn Tyr Asn Ala Tyr Arg Gln Asn
        355                 360


<210> SEQ ID NO 21
<211> LENGTH: 1029
<212> TYPE: DNA
<213> ORGANISM: Artificial Sequence
<220> FEATURE:
<223> OTHER INFORMATION: Codon-optimized GGPPS

<400> SEQUENCE: 21

atggctgagc aacaaatatc taacttgctg tctatgtttg atgcttcaca tgctagtcag     60

aaattagaaa ttactgtcca aatgatggac acataccatt acagagaaac gcctccagat    120

tcctcatctt ctgaaggcgg ttcattgtct agatacgacg agagaagagt ctctttgcct    180

ctcagtcata atgctgcctc tccagatatt gtatcacaac tatgtttttc cactgcaatg    240

tcttcagagt tgaatcacag atggaaatct caaagattaa aggtggccga ttctccttac    300

aactatatcc taacattacc atcaaaagga attagaggtg cctttatcga ttccctgaac    360

gtatggttgg aggttccaga ggatgaaaca tcagtcatca aggaagttat tggtatgctc    420

cacaactctt cattaatcat tgatgacttc caagataatt ctccacttag aagaggaaag    480

ccatctaccc atacagtctt cggccctgcc caggctatca atactgctac ttacgttata    540

gttaaagcaa tcgaaaagat acaagacata gtgggacacg atgcattggc agatgttacg    600

ggtactatta caactatttt ccaaggtcag gccatggact tgtggtggac agcaaatgca    660

atcgttccat caatacagga atacttactt atggtaaacg ataaaaccgg tgctctcttt    720

agactgagtt tggagttgtt agctctgaat tccgaagcca gtatttctga ctctgcttta    780

gaaagtttat ctagtgctgt ttccttgcta ggtcaatact tccaaatcag agacgactat    840

atgaacttga tcgataacaa gtatacagat cagaaaggct tctgcgaaga tcttgatgaa    900

ggcaagtact cactaacact tattcatgcc ctccaaactg attcatccga tctactgacc    960

aacatccttt caatgagaag agtgcaagga aagttaacgg cacaaaagag atgttggttc   1020

tggaaatga                                                           1029


<210> SEQ ID NO 22
<211> LENGTH: 342
<212> TYPE: PRT
<213> ORGANISM: Gibberella fujikuroi

<400> SEQUENCE: 22

Met Ala Glu Gln Gln Ile Ser Asn Leu Leu Ser Met Phe Asp Ala Ser
1               5                   10                  15

His Ala Ser Gln Lys Leu Glu Ile Thr Val Gln Met Met Asp Thr Tyr
            20                  25                  30

His Tyr Arg Glu Thr Pro Pro Asp Ser Ser Ser Ser Glu Gly Gly Ser
        35                  40                  45

Leu Ser Arg Tyr Asp Glu Arg Arg Val Ser Leu Pro Leu Ser His Asn
    50                  55                  60

Ala Ala Ser Pro Asp Ile Val Ser Gln Leu Cys Phe Ser Thr Ala Met
```

```
65                  70                  75                  80

Ser Ser Glu Leu Asn His Arg Trp Lys Ser Gln Arg Leu Lys Val Ala
                85                  90                  95

Asp Ser Pro Tyr Asn Tyr Ile Leu Thr Leu Pro Ser Lys Gly Ile Arg
            100                 105                 110

Gly Ala Phe Ile Asp Ser Leu Asn Val Trp Leu Glu Val Pro Glu Asp
        115                 120                 125

Glu Thr Ser Val Ile Lys Glu Val Ile Gly Met Leu His Asn Ser Ser
    130                 135                 140

Leu Ile Ile Asp Asp Phe Gln Asp Asn Ser Pro Leu Arg Arg Gly Lys
145                 150                 155                 160

Pro Ser Thr His Thr Val Phe Gly Pro Ala Gln Ala Ile Asn Thr Ala
                165                 170                 175

Thr Tyr Val Ile Val Lys Ala Ile Glu Lys Ile Gln Asp Ile Val Gly
            180                 185                 190

His Asp Ala Leu Ala Asp Val Thr Gly Thr Ile Thr Thr Ile Phe Gln
        195                 200                 205

Gly Gln Ala Met Asp Leu Trp Trp Thr Ala Asn Ala Ile Val Pro Ser
    210                 215                 220

Ile Gln Glu Tyr Leu Leu Met Val Asn Asp Lys Thr Gly Ala Leu Phe
225                 230                 235                 240

Arg Leu Ser Leu Glu Leu Leu Ala Leu Asn Ser Glu Ala Ser Ile Ser
                245                 250                 255

Asp Ser Ala Leu Glu Ser Leu Ser Ser Ala Val Ser Leu Leu Gly Gln
            260                 265                 270

Tyr Phe Gln Ile Arg Asp Asp Tyr Met Asn Leu Ile Asp Asn Lys Tyr
        275                 280                 285

Thr Asp Gln Lys Gly Phe Cys Glu Asp Leu Asp Glu Gly Lys Tyr Ser
    290                 295                 300

Leu Thr Leu Ile His Ala Leu Gln Thr Asp Ser Ser Asp Leu Leu Thr
305                 310                 315                 320

Asn Ile Leu Ser Met Arg Arg Val Gln Gly Lys Leu Thr Ala Gln Lys
                325                 330                 335

Arg Cys Trp Phe Trp Lys
            340


<210> SEQ ID NO 23
<211> LENGTH: 903
<212> TYPE: DNA
<213> ORGANISM: Artificial Sequence
<220> FEATURE:
<223> OTHER INFORMATION: Codon-optimized GGPPS

<400> SEQUENCE: 23

atggaaaaga ctaaggagaa agcagaacgt atcttgctgg agccatacag atacttatta      60

caactaccag gaaagcaagt ccgttctaaa ctatcacaag cgttcaatca ctggttaaaa     120

gttcctgaag ataagttaca aatcattatt gaagtcacag aaatgctaca caatgcttct     180

ttactgatcg atgatataga ggattcttcc aaactgagaa gaggttttcc tgtcgctcat     240

tccatatacg ggtaccaag tgtaatcaac tcagctaatt acgtctactt cttgggattg      300

gaaaaagtat tgacattaga tcatccagac gctgtaaagc tattcaccag acaacttctt     360

gaattgcatc aaggtcaagg tttggatatc tattggagag acacttatac ttgcccaaca     420

gaagaggagt acaaagcaat ggttctacaa aagactggcg gtttgttcgg acttgccgtt     480
```

```
ggtctgatgc aacttttctc tgattacaag gaggacttaa agcctctgtt ggataccttg    540

ggcttgtttt tccagattag agatgactac gctaacttac attcaaagga atattcagaa    600

aacaaatcat tctgtgaaga tttgactgaa gggaagttta gttttccaac aatccacgcc    660

atttggtcaa gaccagaatc tactcaagtg caaaacattc tgcgtcagag aacagagaat    720

attgacatca aaaagtattg tgttcagtac ttggaagatg ttggttcttt tgcttacaca    780

agacatacac ttagagaatt agaggcaaaa gcatacaagc aaatagaagc ctgtggaggc    840

aatccttctc tagtggcatt ggttaaacat ttgtccaaaa tgttcaccga ggaaaacaag    900

taa                                                                  903
```

```
<210> SEQ ID NO 24
<211> LENGTH: 300
<212> TYPE: PRT
<213> ORGANISM: Mus musculus

<400> SEQUENCE: 24

Met Glu Lys Thr Lys Glu Lys Ala Glu Arg Ile Leu Leu Glu Pro Tyr
1               5                   10                  15

Arg Tyr Leu Leu Gln Leu Pro Gly Lys Gln Val Arg Ser Lys Leu Ser
            20                  25                  30

Gln Ala Phe Asn His Trp Leu Lys Val Pro Glu Asp Lys Leu Gln Ile
        35                  40                  45

Ile Ile Glu Val Thr Glu Met Leu His Asn Ala Ser Leu Leu Ile Asp
    50                  55                  60

Asp Ile Glu Asp Ser Ser Lys Leu Arg Arg Gly Phe Pro Val Ala His
65                  70                  75                  80

Ser Ile Tyr Gly Val Pro Ser Val Ile Asn Ser Ala Asn Tyr Val Tyr
                85                  90                  95

Phe Leu Gly Leu Glu Lys Val Leu Thr Leu Asp His Pro Asp Ala Val
            100                 105                 110

Lys Leu Phe Thr Arg Gln Leu Leu Glu Leu His Gln Gly Gln Gly Leu
        115                 120                 125

Asp Ile Tyr Trp Arg Asp Thr Tyr Thr Cys Pro Thr Glu Glu Glu Tyr
    130                 135                 140

Lys Ala Met Val Leu Gln Lys Thr Gly Gly Leu Phe Gly Leu Ala Val
145                 150                 155                 160

Gly Leu Met Gln Leu Phe Ser Asp Tyr Lys Glu Asp Leu Lys Pro Leu
                165                 170                 175

Leu Asp Thr Leu Gly Leu Phe Phe Gln Ile Arg Asp Asp Tyr Ala Asn
            180                 185                 190

Leu His Ser Lys Glu Tyr Ser Glu Asn Lys Ser Phe Cys Glu Asp Leu
        195                 200                 205

Thr Glu Gly Lys Phe Ser Phe Pro Thr Ile His Ala Ile Trp Ser Arg
    210                 215                 220

Pro Glu Ser Thr Gln Val Gln Asn Ile Leu Arg Gln Arg Thr Glu Asn
225                 230                 235                 240

Ile Asp Ile Lys Lys Tyr Cys Val Gln Tyr Leu Glu Asp Val Gly Ser
                245                 250                 255

Phe Ala Tyr Thr Arg His Thr Leu Arg Glu Leu Glu Ala Lys Ala Tyr
            260                 265                 270

Lys Gln Ile Glu Ala Cys Gly Gly Asn Pro Ser Leu Val Ala Leu Val
        275                 280                 285

Lys His Leu Ser Lys Met Phe Thr Glu Glu Asn Lys
```

290 295 300

<210> SEQ ID NO 25
<211> LENGTH: 1020
<212> TYPE: DNA
<213> ORGANISM: Artificial Sequence
<220> FEATURE:
<223> OTHER INFORMATION: Codon-optimized GGPPS

<400> SEQUENCE: 25
atggcaagat tctattttct taacgcacta ttgatggtta tctcattaca atcaactaca 60
gccttcactc cagctaaact tgcttatcca acaacaacaa cagctctaaa tgtcgcctcc 120
gccgaaactt ctttcagtct agatgaatac ttggcctcta agataggacc tatagagtct 180
gccttggaag catcagtcaa atccagaatt ccacagaccg ataagatctg cgaatctatg 240
gcctactctt tgatggcagg aggcaagaga attagaccag tgttgtgtat cgctgcatgt 300
gagatgttcg gtggatccca agatgtcgct atgcctactg ctgtggcatt agaaatgata 360
cacacaatgt ctttgattca tgatgatttg ccatccatgg ataacgatga cttgagaaga 420
ggtaaaccaa caaaccatgt cgttttcggc gaagatgtag ctattcttgc aggtgactct 480
ttattgtcaa cttccttcga gcacgtcgct agagaaacaa aaggagtgtc agcagaaaag 540
atcgtggatg ttatcgctag attaggcaaa tctgttggtg ccgagggcct tgctggcggt 600
caagttatgg acttagaatg tgaagctaaa ccaggtacca cattagacga cttgaaatgg 660
attcatatcc ataaaaccgc tacattgtta caagttgctg tagcttctgg tgcagttcta 720
ggtggtgcaa ctcctgaaga ggttgctgca tgcgagttgt ttgctatgaa tataggtctt 780
gcctttcaag ttgccgacga tatccttgat gtaaccgctt catcagaaga tttgggtaaa 840
actgcaggca aagatgaagc tactgataag acaacttacc caaagttatt aggattagaa 900
gagagtaagg catacgcaag acaactaatc gatgaagcca aggaaagttt ggctcctttt 960
ggagatagag ctgccccttt attggccatt gcagatttca ttattgatag aaagaattga 1020

<210> SEQ ID NO 26
<211> LENGTH: 339
<212> TYPE: PRT
<213> ORGANISM: Thalassiosira pseudonana

<400> SEQUENCE: 26

Met Ala Arg Phe Tyr Phe Leu Asn Ala Leu Leu Met Val Ile Ser Leu
1 5 10 15

Gln Ser Thr Thr Ala Phe Thr Pro Ala Lys Leu Ala Tyr Pro Thr Thr
20 25 30

Thr Thr Ala Leu Asn Val Ala Ser Ala Glu Thr Ser Phe Ser Leu Asp
35 40 45

Glu Tyr Leu Ala Ser Lys Ile Gly Pro Ile Glu Ser Ala Leu Glu Ala
50 55 60

Ser Val Lys Ser Arg Ile Pro Gln Thr Asp Lys Ile Cys Glu Ser Met
65 70 75 80

Ala Tyr Ser Leu Met Ala Gly Gly Lys Arg Ile Arg Pro Val Leu Cys
85 90 95

Ile Ala Ala Cys Glu Met Phe Gly Gly Ser Gln Asp Val Ala Met Pro
100 105 110

Thr Ala Val Ala Leu Glu Met Ile His Thr Met Ser Leu Ile His Asp
115 120 125

Asp Leu Pro Ser Met Asp Asn Asp Asp Leu Arg Arg Gly Lys Pro Thr

-continued

```
    130                 135                 140

Asn His Val Val Phe Gly Glu Asp Val Ala Ile Leu Ala Gly Asp Ser
145                 150                 155                 160

Leu Leu Ser Thr Ser Phe Glu His Val Ala Arg Glu Thr Lys Gly Val
                165                 170                 175

Ser Ala Glu Lys Ile Val Asp Val Ile Ala Arg Leu Gly Lys Ser Val
            180                 185                 190

Gly Ala Glu Gly Leu Ala Gly Gly Gln Val Met Asp Leu Glu Cys Glu
        195                 200                 205

Ala Lys Pro Gly Thr Thr Leu Asp Asp Leu Lys Trp Ile His Ile His
    210                 215                 220

Lys Thr Ala Thr Leu Leu Gln Val Ala Val Ala Ser Gly Ala Val Leu
225                 230                 235                 240

Gly Gly Ala Thr Pro Glu Glu Val Ala Ala Cys Glu Leu Phe Ala Met
                245                 250                 255

Asn Ile Gly Leu Ala Phe Gln Val Ala Asp Asp Ile Leu Asp Val Thr
            260                 265                 270

Ala Ser Ser Glu Asp Leu Gly Lys Thr Ala Gly Lys Asp Glu Ala Thr
        275                 280                 285

Asp Lys Thr Thr Tyr Pro Lys Leu Leu Gly Leu Glu Glu Ser Lys Ala
    290                 295                 300

Tyr Ala Arg Gln Leu Ile Asp Glu Ala Lys Glu Ser Leu Ala Pro Phe
305                 310                 315                 320

Gly Asp Arg Ala Ala Pro Leu Leu Ala Ile Ala Asp Phe Ile Ile Asp
                325                 330                 335

Arg Lys Asn


<210> SEQ ID NO 27
<211> LENGTH: 1068
<212> TYPE: DNA
<213> ORGANISM: Artificial Sequence
<220> FEATURE:
<223> OTHER INFORMATION: Codon-optimized GGPPS

<400> SEQUENCE: 27

atgcacttag caccacgtag agtccctaga ggtagaagat caccacctga cagagttcct     60

gaaagacaag gtgccttggg tagaagacgt ggagctggct ctactggctg tgcccgtgct    120

gctgctggtg ttcaccgtag aagaggagga ggcgaggctg atccatcagc tgctgtgcat    180

agaggctggc aagccggtgg tggcaccggt ttgcctgatg aggtggtgtc taccgcagcc    240

gccttagaaa tgtttcatgc ttttgcttta atccatgatg atatcatgga tgatagtgca    300

actagaagag gctccccaac tgttcacaga gccctagctg atcgtttagg cgctgctctg    360

gacccagatc aggccggtca actaggagtt tctactgcta tcttggttgg agatctggct    420

ttgacatggt ccgatgaatt gttatacgct ccattgactc cacatagact ggcagcagta    480

ctaccattgg taacagctat gagagctgaa accgttcatg gccaatatct tgatataact    540

agtgctagaa gacctgggac cgatacttct cttgcattga gaatagccag atataagaca    600

gcagcttaca caatggaacg tccactgcac attggtgcag ccctggctgg ggcaagacca    660

gaactattag cagggctttc agcatacgcc ttgccagctg gagaagcctt ccaattggca    720

gatgacctgc taggcgtctt cggtgatcca agacgtacag ggaaacctga cctagatgat    780

cttagaggtg gaaagcatac tgtcttagtc gccttggcaa gagaacatgc cactccagaa    840

cagagacaca cattggatac attattgggt acaccaggtc ttgatagaca aggcgcttca    900
```

agactaagat gcgtattggt agcaactggt gcaagagccg aagccgaaag acttattaca 960
gagagaagag atcaagcatt aactgcattg aacgcattaa cactgccacc tcctttagct 1020
gaggcattag caagattgac attagggtct acagctcatc ctgcctaa 1068

<210> SEQ ID NO 28
<211> LENGTH: 355
<212> TYPE: PRT
<213> ORGANISM: Streptomyces clavuligerus

<400> SEQUENCE: 28

```
Met His Leu Ala Pro Arg Arg Val Pro Arg Gly Arg Arg Ser Pro Pro
1               5                   10                  15

Asp Arg Val Pro Glu Arg Gln Gly Ala Leu Gly Arg Arg Arg Gly Ala
            20                  25                  30

Gly Ser Thr Gly Cys Ala Arg Ala Ala Ala Gly Val His Arg Arg Arg
        35                  40                  45

Gly Gly Gly Glu Ala Asp Pro Ser Ala Ala Val His Arg Gly Trp Gln
    50                  55                  60

Ala Gly Gly Gly Thr Gly Leu Pro Asp Glu Val Val Ser Thr Ala Ala
65                  70                  75                  80

Ala Leu Glu Met Phe His Ala Phe Ala Leu Ile His Asp Asp Ile Met
                85                  90                  95

Asp Asp Ser Ala Thr Arg Arg Gly Ser Pro Thr Val His Arg Ala Leu
            100                 105                 110

Ala Asp Arg Leu Gly Ala Ala Leu Asp Pro Asp Gln Ala Gly Gln Leu
        115                 120                 125

Gly Val Ser Thr Ala Ile Leu Val Gly Asp Leu Ala Leu Thr Trp Ser
    130                 135                 140

Asp Glu Leu Leu Tyr Ala Pro Leu Thr Pro His Arg Leu Ala Ala Val
145                 150                 155                 160

Leu Pro Leu Val Thr Ala Met Arg Ala Glu Thr Val His Gly Gln Tyr
                165                 170                 175

Leu Asp Ile Thr Ser Ala Arg Arg Pro Gly Thr Asp Thr Ser Leu Ala
            180                 185                 190

Leu Arg Ile Ala Arg Tyr Lys Thr Ala Ala Tyr Thr Met Glu Arg Pro
        195                 200                 205

Leu His Ile Gly Ala Ala Leu Ala Gly Ala Arg Pro Glu Leu Leu Ala
    210                 215                 220

Gly Leu Ser Ala Tyr Ala Leu Pro Ala Gly Glu Ala Phe Gln Leu Ala
225                 230                 235                 240

Asp Asp Leu Leu Gly Val Phe Gly Asp Pro Arg Arg Thr Gly Lys Pro
                245                 250                 255

Asp Leu Asp Asp Leu Arg Gly Gly Lys His Thr Val Leu Val Ala Leu
            260                 265                 270

Ala Arg Glu His Ala Thr Pro Glu Gln Arg His Thr Leu Asp Thr Leu
        275                 280                 285

Leu Gly Thr Pro Gly Leu Asp Arg Gln Gly Ala Ser Arg Leu Arg Cys
    290                 295                 300

Val Leu Val Ala Thr Gly Ala Arg Ala Glu Ala Glu Arg Leu Ile Thr
305                 310                 315                 320

Glu Arg Arg Asp Gln Ala Leu Thr Ala Leu Asn Ala Leu Thr Leu Pro
                325                 330                 335

Pro Pro Leu Ala Glu Ala Leu Ala Arg Leu Thr Leu Gly Ser Thr Ala
```

-continued 340 345 350

His Pro Ala
355

<210> SEQ ID NO 29
<211> LENGTH: 993
<212> TYPE: DNA
<213> ORGANISM: Artificial Sequence
<220> FEATURE:
<223> OTHER INFORMATION: Codon-optimized GGPPS

<400> SEQUENCE: 29
atgtcatatt tcgataacta cttcaatgag atagttaatt ccgtgaacga catcattaag 60
tcttacatct ctggcgacgt accaaaacta tacgaagcct cctaccattt gtttacatca 120
ggaggaaaga gactaagacc attgatcctt acaatttctt ctgatctttt cggtggacag 180
agagaaagag catactatgc tggcgcagca atcgaagttt tgcacacatt cactttggtt 240
cacgatgata tcatggatca agataacatt cgtagaggtc ttcctactgt acatgtcaag 300
tatggcctac ctttggccat tttagctggt gacttattgc atgcaaaagc ctttcaattg 360
ttgactcagg cattgagagg tctaccatct gaaactatca tcaaggcgtt tgatatcttt 420
acaagatcta tcattatcat atcagaaggt caagctgtcg atatggaatt cgaagataga 480
attgatatca aggaacaaga gtatttggat atgatatctc gtaaaaccgc tgccttattc 540
tcagcttctt cttccattgg ggcgttgata gctggagcta atgataacga tgtgagatta 600
atgtccgatt tcggtacaaa tcttgggatc gcatttcaaa ttgtagatga tatacttggt 660
ttaacagctg atgaaaaaga gctaggaaaa cctgttttca gtgatatcag agaaggtaaa 720
aagaccatat tagtcattaa gactttagaa ttgtgtaagg aagacgagaa aaagattgtg 780
ttaaaagcgc taggcaacaa gtcagcatca aaggaagagt tgatgagttc tgctgacata 840
atcaaaaagt actcattgga ttacgcctac aacttagctg agaaatacta caaaaacgcc 900
atcgattctc taaatcaagt ttcaagtaaa agtgatattc cagggaaggc attgaaatat 960
cttgctgaat tcaccatcag aagacgtaag taa 993

<210> SEQ ID NO 30
<211> LENGTH: 330
<212> TYPE: PRT
<213> ORGANISM: Sulfolobus acidocaldarius

<400> SEQUENCE: 30

Met Ser Tyr Phe Asp Asn Tyr Phe Asn Glu Ile Val Asn Ser Val Asn
1 5 10 15

Asp Ile Ile Lys Ser Tyr Ile Ser Gly Asp Val Pro Lys Leu Tyr Glu
20 25 30

Ala Ser Tyr His Leu Phe Thr Ser Gly Gly Lys Arg Leu Arg Pro Leu
35 40 45

Ile Leu Thr Ile Ser Ser Asp Leu Phe Gly Gly Gln Arg Glu Arg Ala
50 55 60

Tyr Tyr Ala Gly Ala Ala Ile Glu Val Leu His Thr Phe Thr Leu Val
65 70 75 80

His Asp Asp Ile Met Asp Gln Asp Asn Ile Arg Arg Gly Leu Pro Thr
85 90 95

Val His Val Lys Tyr Gly Leu Pro Leu Ala Ile Leu Ala Gly Asp Leu
100 105 110

Leu His Ala Lys Ala Phe Gln Leu Leu Thr Gln Ala Leu Arg Gly Leu

```
        115                 120                 125

Pro Ser Glu Thr Ile Ile Lys Ala Phe Asp Ile Phe Thr Arg Ser Ile
    130                 135                 140

Ile Ile Ile Ser Glu Gly Gln Ala Val Asp Met Glu Phe Glu Asp Arg
145                 150                 155                 160

Ile Asp Ile Lys Glu Gln Glu Tyr Leu Asp Met Ile Ser Arg Lys Thr
                165                 170                 175

Ala Ala Leu Phe Ser Ala Ser Ser Ser Ile Gly Ala Leu Ile Ala Gly
            180                 185                 190

Ala Asn Asp Asn Asp Val Arg Leu Met Ser Asp Phe Gly Thr Asn Leu
        195                 200                 205

Gly Ile Ala Phe Gln Ile Val Asp Asp Ile Leu Gly Leu Thr Ala Asp
    210                 215                 220

Glu Lys Glu Leu Gly Lys Pro Val Phe Ser Asp Ile Arg Glu Gly Lys
225                 230                 235                 240

Lys Thr Ile Leu Val Ile Lys Thr Leu Glu Leu Cys Lys Glu Asp Glu
                245                 250                 255

Lys Lys Ile Val Leu Lys Ala Leu Gly Asn Lys Ser Ala Ser Lys Glu
            260                 265                 270

Glu Leu Met Ser Ser Ala Asp Ile Ile Lys Lys Tyr Ser Leu Asp Tyr
        275                 280                 285

Ala Tyr Asn Leu Ala Glu Lys Tyr Tyr Lys Asn Ala Ile Asp Ser Leu
    290                 295                 300

Asn Gln Val Ser Ser Lys Ser Asp Ile Pro Gly Lys Ala Leu Lys Tyr
305                 310                 315                 320

Leu Ala Glu Phe Thr Ile Arg Arg Arg Lys
                325                 330


<210> SEQ ID NO 31
<211> LENGTH: 894
<212> TYPE: DNA
<213> ORGANISM: Artificial Sequence
<220> FEATURE:
<223> OTHER INFORMATION: Codon-optimized GGPPS

<400> SEQUENCE: 31

atggtcgcac aaactttcaa cctggatacc tacttatccc aaagacaaca acaagttgaa     60

gaggccctaa gtgctgctct tgtgccagct tatcctgaga gaatatacga agctatgaga    120

tactccctcc tggcaggtgg caaaagatta agacctatct tatgtttagc tgcttgcgaa    180

ttggcaggtg gttctgttga acaagccatg ccaactgcgt gtgcacttga aatgatccat    240

acaatgtcac taattcatga tgacctgcca gccatggata acgatgattt cagaagagga    300

aagccaacta atcacaaggt gttcggggaa gatatagcca tcttagcggg tgatgcgctt    360

ttagcttacg cttttgaaca tattgcttct caaacaagag gagtaccacc tcaattggtg    420

ctacaagtta ttgctagaat cggacacgcc gttgctgcaa caggcctcgt tggaggccaa    480

gtcgtagacc ttgaatctga aggtaaagct atttccttag aaacattgga gtatattcac    540

tcacataaga ctggagcctt gctggaagca tcagttgtct caggcggtat tctcgcaggg    600

gcagatgaag agcttttggc cagattgtct cattacgcta gagatatagg cttggctttt    660

caaatcgtcg atgatatcct ggatgttact gctacatctg aacagttggg gaaaaccgct    720

ggtaaagacc aggcagccgc aaaggcaact tatccaagtc tattgggttt agaagcctct    780

agacagaaag cggaagagtt gattcaatct gctaaggaag ccttaagacc ttacggttca    840
```

-continued caagcagagc cactcctagc gctggcagac ttcatcacac gtcgtcagca ttaa 894

<210> SEQ ID NO 32
<211> LENGTH: 297
<212> TYPE: PRT
<213> ORGANISM: Synechococcus sp.

<400> SEQUENCE: 32

Met Val Ala Gln Thr Phe Asn Leu Asp Thr Tyr Leu Ser Gln Arg Gln
1 5 10 15

Gln Gln Val Glu Glu Ala Leu Ser Ala Ala Leu Val Pro Ala Tyr Pro
20 25 30

Glu Arg Ile Tyr Glu Ala Met Arg Tyr Ser Leu Leu Ala Gly Gly Lys
35 40 45

Arg Leu Arg Pro Ile Leu Cys Leu Ala Ala Cys Glu Leu Ala Gly Gly
50 55 60

Ser Val Glu Gln Ala Met Pro Thr Ala Cys Ala Leu Glu Met Ile His
65 70 75 80

Thr Met Ser Leu Ile His Asp Asp Leu Pro Ala Met Asp Asn Asp Asp
85 90 95

Phe Arg Arg Gly Lys Pro Thr Asn His Lys Val Phe Gly Glu Asp Ile
100 105 110

Ala Ile Leu Ala Gly Asp Ala Leu Leu Ala Tyr Ala Phe Glu His Ile
115 120 125

Ala Ser Gln Thr Arg Gly Val Pro Pro Gln Leu Val Leu Gln Val Ile
130 135 140

Ala Arg Ile Gly His Ala Val Ala Ala Thr Gly Leu Val Gly Gly Gln
145 150 155 160

Val Val Asp Leu Glu Ser Glu Gly Lys Ala Ile Ser Leu Glu Thr Leu
165 170 175

Glu Tyr Ile His Ser His Lys Thr Gly Ala Leu Leu Glu Ala Ser Val
180 185 190

Val Ser Gly Gly Ile Leu Ala Gly Ala Asp Glu Glu Leu Leu Ala Arg
195 200 205

Leu Ser His Tyr Ala Arg Asp Ile Gly Leu Ala Phe Gln Ile Val Asp
210 215 220

Asp Ile Leu Asp Val Thr Ala Thr Ser Glu Gln Leu Gly Lys Thr Ala
225 230 235 240

Gly Lys Asp Gln Ala Ala Ala Lys Ala Thr Tyr Pro Ser Leu Leu Gly
245 250 255

Leu Glu Ala Ser Arg Gln Lys Ala Glu Glu Leu Ile Gln Ser Ala Lys
260 265 270

Glu Ala Leu Arg Pro Tyr Gly Ser Gln Ala Glu Pro Leu Leu Ala Leu
275 280 285

Ala Asp Phe Ile Thr Arg Arg Gln His
290 295

<210> SEQ ID NO 33
<211> LENGTH: 1680
<212> TYPE: DNA
<213> ORGANISM: Artificial Sequence
<220> FEATURE:
<223> OTHER INFORMATION: Codon-optimized CDPS

<400> SEQUENCE: 33
atgaaaaccg ggtttatctc accagcaaca gtatttcatc acagaatctc accagcgacc 60

-continued

```
actttcagac atcacttatc acctgctact acaaactcta caggcattgt cgccttaaga    120

gacatcaact tcagatgtaa agcagtttct aaagagtact ctgatctgtt gcagaaagat    180

gaggcttctt tcacaaaatg ggacgatgac aaggtgaaag atcatcttga taccaacaaa    240

aacttatacc caaatgatga gattaaggaa tttgttgaat cagtaaaggc tatgttcggt    300

agtatgaatg acggggagat aaacgtctct gcatacgata ctgcatgggt tgctttggtt    360

caagatgtcg atggatcagg tagtcctcag ttcccttctt ctttagaatg gattgccaac    420

aatcaattgt cagatggatc atggggagat catttgctgt tctcagctca cgatagaatc    480

atcaacacat tagcatgcgt tattgcactt acaagttgga atgttcatcc ttctaagtgt    540

gaaaaaggtt tgaattttct gagagaaaac atttgcaaat tagaagatga aaacgcagaa    600

catatgccaa ttggttttga agtaacattc ccatcactaa ttgatatcgc gaaaaagttg    660

aacattgaag tacctgagga tactccagca cttaaagaga tctacgcacg tagagatatc    720

aagttaacta agatcccaat ggaagttctt cacaaggtac ctactacttt gttacattct    780

ttggaaggaa tgcctgattt ggagtgggaa aaactgttaa agctacaatg taaagatggt    840

agtttcttgt tttccccatc tagtaccgca ttcgccctaa tgcaaacaaa agatgagaaa    900

tgcttacagt atctaacaaa tatcgtcact aagttcaacg gtggcgtgcc taatgtgtac    960

ccagtcgatt tgtttgaaca tatttgggtt gttgatagac tgcagagatt ggggattgcc   1020

agatacttca aatcagagat aaaagattgt gtagagtata tcaataagta ctggaccaaa   1080

aatggaattt gttgggctag aaatactcac gttcaagata tcgatgatac agccatggga   1140

ttcagagtgt tgagagcgca cggttatgac gtcactccag atgtttttag acaatttgaa   1200

aaagatggta aattcgtttg ctttgcaggg caatcaacac aagccgtgac aggaatgttt   1260

aacgtttaca gagcctctca aatgttgttc ccaggggaga gaattttgga agatgccaaa   1320

aagttctctt acaattactt aaaggaaaag caaagtacca acgaattgct ggataaatgg   1380

ataatcgcta aagatctacc tggtgaagtt ggttatgctc tggatatccc atggtatgct   1440

tccttaccaa gattggaaac tcgttattac cttgaacaat acggcggtga agatgatgtc   1500

tggataggca agacattata cagaatgggt tacgtgtcca ataacacata tctagaaatg   1560

gcaaagctgg attacaataa ctatgttgca gtccttcaat tagaatggta cacaatacaa   1620

caatggtacg tcgatattgg tatagagaag ttcgaatctg acaacatcaa gtcagtcctg   1680
```

```
<210> SEQ ID NO 34
<211> LENGTH: 787
<212> TYPE: PRT
<213> ORGANISM: Stevia rebaudiana

<400> SEQUENCE: 34

Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
            20                  25                  30

Ser Thr Gly Ile Val Ala Leu Arg Asp Ile Asn Phe Arg Cys Lys Ala
        35                  40                  45

Val Ser Lys Glu Tyr Ser Asp Leu Leu Gln Lys Asp Glu Ala Ser Phe
    50                  55                  60

Thr Lys Trp Asp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
                85                  90                  95
```

-continued

```
Ala Met Phe Gly Ser Met Asn Asp Gly Glu Ile Asn Val Ser Ala Tyr
            100                 105                 110

Asp Thr Ala Trp Val Ala Leu Val Gln Asp Val Asp Gly Ser Gly Ser
        115                 120                 125

Pro Gln Phe Pro Ser Ser Leu Glu Trp Ile Ala Asn Asn Gln Leu Ser
    130                 135                 140

Asp Gly Ser Trp Gly Asp His Leu Leu Phe Ser Ala His Asp Arg Ile
145                 150                 155                 160

Ile Asn Thr Leu Ala Cys Val Ile Ala Leu Thr Ser Trp Asn Val His
                165                 170                 175

Pro Ser Lys Cys Glu Lys Gly Leu Asn Phe Leu Arg Glu Asn Ile Cys
            180                 185                 190

Lys Leu Glu Asp Glu Asn Ala Glu His Met Pro Ile Gly Phe Glu Val
        195                 200                 205

Thr Phe Pro Ser Leu Ile Asp Ile Ala Lys Lys Leu Asn Ile Glu Val
    210                 215                 220

Pro Glu Asp Thr Pro Ala Leu Lys Glu Ile Tyr Ala Arg Arg Asp Ile
225                 230                 235                 240

Lys Leu Thr Lys Ile Pro Met Glu Val Leu His Lys Val Pro Thr Thr
                245                 250                 255

Leu Leu His Ser Leu Glu Gly Met Pro Asp Leu Glu Trp Glu Lys Leu
            260                 265                 270

Leu Lys Leu Gln Cys Lys Asp Gly Ser Phe Leu Phe Ser Pro Ser Ser
        275                 280                 285

Thr Ala Phe Ala Leu Met Gln Thr Lys Asp Glu Lys Cys Leu Gln Tyr
    290                 295                 300

Leu Thr Asn Ile Val Thr Lys Phe Asn Gly Gly Val Pro Asn Val Tyr
305                 310                 315                 320

Pro Val Asp Leu Phe Glu His Ile Trp Val Val Asp Arg Leu Gln Arg
                325                 330                 335

Leu Gly Ile Ala Arg Tyr Phe Lys Ser Glu Ile Lys Asp Cys Val Glu
            340                 345                 350

Tyr Ile Asn Lys Tyr Trp Thr Lys Asn Gly Ile Cys Trp Ala Arg Asn
        355                 360                 365

Thr His Val Gln Asp Ile Asp Asp Thr Ala Met Gly Phe Arg Val Leu
    370                 375                 380

Arg Ala His Gly Tyr Asp Val Thr Pro Asp Val Phe Arg Gln Phe Glu
385                 390                 395                 400

Lys Asp Gly Lys Phe Val Cys Phe Ala Gly Gln Ser Thr Gln Ala Val
                405                 410                 415

Thr Gly Met Phe Asn Val Tyr Arg Ala Ser Gln Met Leu Phe Pro Gly
            420                 425                 430

Glu Arg Ile Leu Glu Asp Ala Lys Lys Phe Ser Tyr Asn Tyr Leu Lys
        435                 440                 445

Glu Lys Gln Ser Thr Asn Glu Leu Leu Asp Lys Trp Ile Ile Ala Lys
    450                 455                 460

Asp Leu Pro Gly Glu Val Gly Tyr Ala Leu Asp Ile Pro Trp Tyr Ala
465                 470                 475                 480

Ser Leu Pro Arg Leu Glu Thr Arg Tyr Tyr Leu Glu Gln Tyr Gly Gly
                485                 490                 495

Glu Asp Asp Val Trp Ile Gly Lys Thr Leu Tyr Arg Met Gly Tyr Val
            500                 505                 510
```

```
Ser Asn Asn Thr Tyr Leu Glu Met Ala Lys Leu Asp Tyr Asn Asn Tyr
        515                 520                 525

Val Ala Val Leu Gln Leu Glu Trp Tyr Thr Ile Gln Gln Trp Tyr Val
    530                 535                 540

Asp Ile Gly Ile Glu Lys Phe Glu Ser Asp Asn Ile Lys Ser Val Leu
545                 550                 555                 560

Val Ser Tyr Tyr Leu Ala Ala Ala Ser Ile Phe Glu Pro Glu Arg Ser
                565                 570                 575

Lys Glu Arg Ile Ala Trp Ala Lys Thr Thr Ile Leu Val Asp Lys Ile
            580                 585                 590

Thr Ser Ile Phe Asp Ser Ser Gln Ser Ser Lys Glu Asp Ile Thr Ala
        595                 600                 605

Phe Ile Asp Lys Phe Arg Asn Lys Ser Ser Ser Lys Lys His Ser Ile
    610                 615                 620

Asn Gly Glu Pro Trp His Glu Val Met Val Ala Leu Lys Lys Thr Leu
625                 630                 635                 640

His Gly Phe Ala Leu Asp Ala Leu Met Thr His Ser Gln Asp Ile His
                645                 650                 655

Pro Gln Leu His Gln Ala Trp Glu Met Trp Leu Thr Lys Leu Gln Asp
            660                 665                 670

Gly Val Asp Val Thr Ala Glu Leu Met Val Gln Met Ile Asn Met Thr
        675                 680                 685

Ala Gly Arg Trp Val Ser Lys Glu Leu Leu Thr His Pro Gln Tyr Gln
    690                 695                 700

Arg Leu Ser Thr Val Thr Asn Ser Val Cys His Asp Ile Thr Lys Leu
705                 710                 715                 720

His Asn Phe Lys Glu Asn Ser Thr Thr Val Asp Ser Lys Val Gln Glu
                725                 730                 735

Leu Val Gln Leu Val Phe Ser Asp Thr Pro Asp Asp Leu Asp Gln Asp
            740                 745                 750

Met Lys Gln Thr Phe Leu Thr Val Met Lys Thr Phe Tyr Tyr Lys Ala
        755                 760                 765

Trp Cys Asp Pro Asn Thr Ile Asn Asp His Ile Ser Lys Val Phe Glu
    770                 775                 780

Ile Val Ile
785
```

<210> SEQ ID NO 35
<211> LENGTH: 1584
<212> TYPE: DNA
<213> ORGANISM: Artificial Sequence
<220> FEATURE:
<223> OTHER INFORMATION: Codon-optimized CDPS

<400> SEQUENCE: 35

```
atgcctgatg cacacgatgc tccacctcca caaataagac agagaacact agtagatgag      60

gctacccaac tgctaactga gtccgcagaa gatgcatggg gtgaagtcag tgtgtcagaa     120

tacgaaacag caaggctagt tgcccatgct acatggttag gtggacacgc cacaagagtg     180

gccttccttc tggagagaca acacgaagac gggtcatggg gtccaccagg tggatatagg     240

ttagtcccta cattatctgc tgttcacgca ttattgacat gtcttgcctc tcctgctcag     300

gatcatggcg ttccacatga tagactttta agagctgttg acgcaggctt gactgccttg     360

agaagattgg ggacatctga ctccccacct gatactatag cagttgagct ggttatccca     420

tctttgctag agggcattca acacttactg gaccctgctc atcctcatag tagaccagcc     480
```

-continued

```
ttctctcaac atagaggctc tcttgtttgt cctggtggac tagatgggag aactctagga    540
gctttgagat cacacgccgc agcaggtaca ccagtaccag gaaaagtctg gcacgcttcc    600
gagactttgg gcttgagtac cgaagctgct tctcacttgc aaccagccca aggtataatc    660
ggtggctctg ctgctgccac agcaacatgg ctaaccaggg ttgcaccatc tcaacagtca    720
gattctgcca gaagatacct tgaggaatta caacacagat actctggccc agttccttcc    780
attaccccta tcacatactt cgaaagagca tggttattga acaattttgc agcagccggt    840
gttccttgtg aggctccagc tgctttgttg gattccttag aagcagcact tacaccacaa    900
ggtgctcctg ctggagcagg attgcctcca gatgctgatg atacagccgc tgtgttgctt    960
gcattggcaa cacatgggag aggtagaaga ccagaagtac tgatggatta caggactgac   1020
gggtatttcc aatgctttat tggggaaagg actccatcaa tttcaacaaa cgctcacgta   1080
ttggaaacat tagggcatca tgtggcccaa catccacaag atagagccag atacggatca   1140
gccatggata ccgcatcagc ttggctgctg gcagctcaaa agcaagatgg ctcttggtta   1200
gataaatggc atgcctcacc atactacgct actgtttgtt gcacacaagc cctagccgct   1260
catgcaagtc ctgcaactgc accagctaga cagagagctg tcagatgggt tttagccaca   1320
caaagatccg atggcggttg ggtctatgg cattcaactg ttgaagagac tgcttatgcc    1380
ttacagatct tggccccacc ttctggtggt ggcaatatcc cagtccaaca agcacttact   1440
agaggcagag caagattgtg tggagccttg ccactgactc ctttatggca tgataaggat   1500
ttgtatactc cagtaagagt agtcagagct gccagagctg ctgctctgta cactaccaga   1560
gatctattgt taccaccatt gtaa                                          1584
```

<210> SEQ ID NO 36
<211> LENGTH: 527
<212> TYPE: PRT
<213> ORGANISM: Streptomyces clavuligerus

<400> SEQUENCE: 36

```
Met Pro Asp Ala His Asp Ala Pro Pro Pro Gln Ile Arg Gln Arg Thr
1               5                   10                  15

Leu Val Asp Glu Ala Thr Gln Leu Leu Thr Glu Ser Ala Glu Asp Ala
            20                  25                  30

Trp Gly Glu Val Ser Val Ser Glu Tyr Glu Thr Ala Arg Leu Val Ala
        35                  40                  45

His Ala Thr Trp Leu Gly Gly His Ala Thr Arg Val Ala Phe Leu Leu
    50                  55                  60

Glu Arg Gln His Glu Asp Gly Ser Trp Gly Pro Pro Gly Gly Tyr Arg
65                  70                  75                  80

Leu Val Pro Thr Leu Ser Ala Val His Ala Leu Leu Thr Cys Leu Ala
                85                  90                  95

Ser Pro Ala Gln Asp His Gly Val Pro His Asp Arg Leu Leu Arg Ala
            100                 105                 110

Val Asp Ala Gly Leu Thr Ala Leu Arg Arg Leu Gly Thr Ser Asp Ser
        115                 120                 125

Pro Pro Asp Thr Ile Ala Val Glu Leu Val Ile Pro Ser Leu Leu Glu
    130                 135                 140

Gly Ile Gln His Leu Leu Asp Pro Ala His Pro His Ser Arg Pro Ala
145                 150                 155                 160

Phe Ser Gln His Arg Gly Ser Leu Val Cys Pro Gly Gly Leu Asp Gly
                165                 170                 175
```

-continued

Arg Thr Leu Gly Ala Leu Arg Ser His Ala Ala Ala Gly Thr Pro Val
180 185 190

Pro Gly Lys Val Trp His Ala Ser Glu Thr Leu Gly Leu Ser Thr Glu
195 200 205

Ala Ala Ser His Leu Gln Pro Ala Gln Gly Ile Ile Gly Gly Ser Ala
210 215 220

Ala Ala Thr Ala Thr Trp Leu Thr Arg Val Ala Pro Ser Gln Gln Ser
225 230 235 240

Asp Ser Ala Arg Arg Tyr Leu Glu Glu Leu Gln His Arg Tyr Ser Gly
245 250 255

Pro Val Pro Ser Ile Thr Pro Ile Thr Tyr Phe Glu Arg Ala Trp Leu
260 265 270

Leu Asn Asn Phe Ala Ala Ala Gly Val Pro Cys Glu Ala Pro Ala Ala
275 280 285

Leu Leu Asp Ser Leu Glu Ala Ala Leu Thr Pro Gln Gly Ala Pro Ala
290 295 300

Gly Ala Gly Leu Pro Pro Asp Ala Asp Asp Thr Ala Ala Val Leu Leu
305 310 315 320

Ala Leu Ala Thr His Gly Arg Gly Arg Arg Pro Glu Val Leu Met Asp
325 330 335

Tyr Arg Thr Asp Gly Tyr Phe Gln Cys Phe Ile Gly Glu Arg Thr Pro
340 345 350

Ser Ile Ser Thr Asn Ala His Val Leu Glu Thr Leu Gly His His Val
355 360 365

Ala Gln His Pro Gln Asp Arg Ala Arg Tyr Gly Ser Ala Met Asp Thr
370 375 380

Ala Ser Ala Trp Leu Leu Ala Ala Gln Lys Gln Asp Gly Ser Trp Leu
385 390 395 400

Asp Lys Trp His Ala Ser Pro Tyr Tyr Ala Thr Val Cys Cys Thr Gln
405 410 415

Ala Leu Ala Ala His Ala Ser Pro Ala Thr Ala Pro Ala Arg Gln Arg
420 425 430

Ala Val Arg Trp Val Leu Ala Thr Gln Arg Ser Asp Gly Gly Trp Gly
435 440 445

Leu Trp His Ser Thr Val Glu Glu Thr Ala Tyr Ala Leu Gln Ile Leu
450 455 460

Ala Pro Pro Ser Gly Gly Gly Asn Ile Pro Val Gln Gln Ala Leu Thr
465 470 475 480

Arg Gly Arg Ala Arg Leu Cys Gly Ala Leu Pro Leu Thr Pro Leu Trp
485 490 495

His Asp Lys Asp Leu Tyr Thr Pro Val Arg Val Val Arg Ala Ala Arg
500 505 510

Ala Ala Ala Leu Tyr Thr Thr Arg Asp Leu Leu Leu Pro Pro Leu
515 520 525

<210> SEQ ID NO 37
<211> LENGTH: 1551
<212> TYPE: DNA
<213> ORGANISM: Artificial Sequence
<220> FEATURE:
<223> OTHER INFORMATION: Codon-optimized CDPS

<400> SEQUENCE: 37
atgaacgccc tatccgaaca cattttgtct gaattgagaa gattattgtc tgaaatgagt 60

```
gatggcggat ctgttggtcc atctgtgtat gatacggccc aggccctaag attccacggt    120

aacgtaacag gtagacaaga tgcatatgct tggttgatcg cccagcaaca agcagatgga    180

ggttggggct ctgccgactt tccactcttt agacatgctc caacatgggc tgcacttctc    240

gcattacaaa gagctgatcc acttcctggc gcagcagacg cagttcagac cgcaacaaga    300

ttcttgcaaa gacaaccaga tccatacgct catgccgttc ctgaggatgc ccctattggt    360

gctgaactga tcttgcctca gttttgtgga gaggctgctt ggttgttggg aggtgtggcc    420

ttccctagac acccagccct attaccatta agacaggctt gtttagtcaa actgggtgca    480

gtcgccatgt tgccttcagg acacccattg ctccactcct gggaggcatg ggtacttct     540

ccaacaacag cctgtccaga cgatgatggt tctataggta tctcaccagc agctacagcc    600

gcctggagag cccaggctgt gaccagaggc tcaactcctc aagtgggcag agctgacgca    660

tacttacaaa tggcttcaag agcaacgaga tcaggcatag aaggagtctt ccctaatgtt    720

tggcctataa acgtattcga accatgctgg tcactgtaca ctctccatct tgccggtctg    780

ttcgcccatc cagcactggc tgaggctgta agagttatcg ttgctcaact tgaagcaaga    840

ttgggagtgc atggcctcgg accagcttta cattttgctg ccgacgctga tgatactgca    900

gttgccttat gcgttctgca tttggctggc agagatcctg cagttgacgc attgagacat    960

tttgaaattg gtgagctctt tgttacattc ccaggagaga gaaatgctag tgtctctacg   1020

aacattcacg ctcttcatgc tttgagattg ttaggtaaac cagctgccgg agcaagtgca   1080

tacgtcgaag caaatagaaa tccacatggt ttgtgggaca acgaaaaatg gcacgtttca   1140

tggctttatc caactgcaca cgccgttgca gctctagctc aaggcaagcc tcaatggaga   1200

gatgaaagag cactagccgc tctactacaa gctcaaagag atgatggtgg ttggggagct   1260

ggtagaggat ccactttcga ggaaaccgcc tacgctcttt tcgctttaca cgttatggac   1320

ggatctgagg aagccacagg cagaagaaga atcgctcaag tcgtcgcaag agccttagaa   1380

tggatgctag ctagacatgc cgcacatgga ttaccacaaa caccactctg gattggtaag   1440

gaattgtact gtcctactag agtcgtaaga gtagctgagc tagctggcct gtggttagca   1500

ttaagatggg gtagaagagt attagctgaa ggtgctggtg ctgcacctta a             1551
```

<210> SEQ ID NO 38
<211> LENGTH: 516
<212> TYPE: PRT
<213> ORGANISM: Bradyrhizobium japonicum

<400> SEQUENCE: 38

```
Met Asn Ala Leu Ser Glu His Ile Leu Ser Glu Leu Arg Arg Leu Leu
1               5                   10                  15

Ser Glu Met Ser Asp Gly Gly Ser Val Gly Pro Ser Val Tyr Asp Thr
            20                  25                  30

Ala Gln Ala Leu Arg Phe His Gly Asn Val Thr Gly Arg Gln Asp Ala
        35                  40                  45

Tyr Ala Trp Leu Ile Ala Gln Gln Gln Ala Asp Gly Gly Trp Gly Ser
    50                  55                  60

Ala Asp Phe Pro Leu Phe Arg His Ala Pro Thr Trp Ala Ala Leu Leu
65                  70                  75                  80

Ala Leu Gln Arg Ala Asp Pro Leu Pro Gly Ala Ala Asp Ala Val Gln
                85                  90                  95

Thr Ala Thr Arg Phe Leu Gln Arg Gln Pro Asp Pro Tyr Ala His Ala
            100                 105                 110
```

-continued

```
Val Pro Glu Asp Ala Pro Ile Gly Ala Glu Leu Ile Leu Pro Gln Phe
        115                 120                 125

Cys Gly Glu Ala Ala Trp Leu Leu Gly Gly Val Ala Phe Pro Arg His
    130                 135                 140

Pro Ala Leu Leu Pro Leu Arg Gln Ala Cys Leu Val Lys Leu Gly Ala
145                 150                 155                 160

Val Ala Met Leu Pro Ser Gly His Pro Leu Leu His Ser Trp Glu Ala
                165                 170                 175

Trp Gly Thr Ser Pro Thr Thr Ala Cys Pro Asp Asp Asp Gly Ser Ile
            180                 185                 190

Gly Ile Ser Pro Ala Ala Thr Ala Ala Trp Arg Ala Gln Ala Val Thr
        195                 200                 205

Arg Gly Ser Thr Pro Gln Val Gly Arg Ala Asp Ala Tyr Leu Gln Met
    210                 215                 220

Ala Ser Arg Ala Thr Arg Ser Gly Ile Glu Gly Val Phe Pro Asn Val
225                 230                 235                 240

Trp Pro Ile Asn Val Phe Glu Pro Cys Trp Ser Leu Tyr Thr Leu His
                245                 250                 255

Leu Ala Gly Leu Phe Ala His Pro Ala Leu Ala Glu Ala Val Arg Val
            260                 265                 270

Ile Val Ala Gln Leu Glu Ala Arg Leu Gly Val His Gly Leu Gly Pro
        275                 280                 285

Ala Leu His Phe Ala Ala Asp Ala Asp Asp Thr Ala Val Ala Leu Cys
    290                 295                 300

Val Leu His Leu Ala Gly Arg Asp Pro Ala Val Asp Ala Leu Arg His
305                 310                 315                 320

Phe Glu Ile Gly Glu Leu Phe Val Thr Phe Pro Gly Glu Arg Asn Ala
                325                 330                 335

Ser Val Ser Thr Asn Ile His Ala Leu His Ala Leu Arg Leu Leu Gly
            340                 345                 350

Lys Pro Ala Ala Gly Ala Ser Ala Tyr Val Glu Ala Asn Arg Asn Pro
        355                 360                 365

His Gly Leu Trp Asp Asn Glu Lys Trp His Val Ser Trp Leu Tyr Pro
    370                 375                 380

Thr Ala His Ala Val Ala Ala Leu Ala Gln Gly Lys Pro Gln Trp Arg
385                 390                 395                 400

Asp Glu Arg Ala Leu Ala Ala Leu Leu Gln Ala Gln Arg Asp Asp Gly
                405                 410                 415

Gly Trp Gly Ala Gly Arg Gly Ser Thr Phe Glu Glu Thr Ala Tyr Ala
            420                 425                 430

Leu Phe Ala Leu His Val Met Asp Gly Ser Glu Glu Ala Thr Gly Arg
        435                 440                 445

Arg Arg Ile Ala Gln Val Val Ala Arg Ala Leu Glu Trp Met Leu Ala
    450                 455                 460

Arg His Ala Ala His Gly Leu Pro Gln Thr Pro Leu Trp Ile Gly Lys
465                 470                 475                 480

Glu Leu Tyr Cys Pro Thr Arg Val Val Arg Val Ala Glu Leu Ala Gly
                485                 490                 495

Leu Trp Leu Ala Leu Arg Trp Gly Arg Arg Val Leu Ala Glu Gly Ala
            500                 505                 510

Gly Ala Ala Pro
        515
```

<210> SEQ ID NO 39
<211> LENGTH: 2490
<212> TYPE: DNA
<213> ORGANISM: Artificial Sequence
<220> FEATURE:
<223> OTHER INFORMATION: Codon-optimized CDPS

<400> SEQUENCE: 39

```
atggttttgt cttcttcttg tactacagta ccacacttat cttcattagc tgtcgtgcaa     60
cttggtcctt ggagcagtag gattaaaaag aaaaccgata ctgttgcagt accagccgct    120
gcaggaaggt ggagaagggc cttggctaga gcacagcaca catcagaatc cgcagctgtc    180
gcaaagggca gcagtttgac ccctatagtg agaactgacg ctgagtcaag gagaacaaga    240
tggccaaccg atgacgatga cgccgaacct ttagtggatg agatcagggc aatgcttact    300
tccatgtctg atggtgacat ttccgtgagc gcatacgata cagcctgggt cggattggtt    360
ccaagattag acggcggtga aggtcctcaa tttccagcag ctgtgagatg gataagaaat    420
aaccagttgc ctgacggaag ttggggcgat gccgcattat tctctgccta tgacaggctt    480
atcaataccc ttgcctgcgt tgtaactttg acaaggtggt ccctagaacc agagatgaga    540
ggtagaggac tatctttttt gggtaggaac atgtggaaat tagcaactga agatgaagag    600
tcaatgccta ttggcttcga attagcattt ccatctttga tagagcttgc taagagccta    660
ggtgtccatg acttccctta tgatcaccag gccctacaag gaatctactc ttcaagagag    720
atcaaaatga agaggattcc aaaagaagtg atgcataccg ttccaacatc aatattgcac    780
agtttggagg gtatgcctgg cctagattgg gctaaactac ttaaactaca gagcagcgac    840
ggaagttttt tgttctcacc agctgccact gcatatgctt taatgaatac cggagatgac    900
aggtgtttta gctacatcga tagaacagta aagaaattca acggcggcgt ccctaatgtt    960
tatccagtgg atctatttga acatatttgg gccgttgata gacttgaaag attaggaatc   1020
tccaggtact tccaaaagga gatcgaacaa tgcatggatt atgtaaacag gcattggact   1080
gaggacggta tttgttgggc aaggaactct gatgtcaaag aggtggacga cacagctatg   1140
gcctttagac ttcttaggtt gcacggctac agcgtcagtc ctgatgtgtt taaaaacttc   1200
gaaaaggacg gtgaattttt cgcatttgtc ggacagtcta atcaagctgt taccggtatg   1260
tacaacttaa acagagcaag ccagatatcc ttcccaggcg aggatgtgct tcatagagct   1320
ggtgccttct catatgagtt cttgaggaga aaagaagcag agggagcttt gagggacaag   1380
tggatcattt ctaaagatct acctggtgaa gttgtgtata ctttggattt tccatggtac   1440
ggcaacttac ctagagtcga ggccagagac tacctagagc aatacggagg tggtgatgac   1500
gtttggattg gcaagacatt gtataggatg ccacttgtaa acaatgatgt atatttggaa   1560
ttggcaagaa tggatttcaa ccactgccag gctttgcatc agttagagtg gcaaggacta   1620
aaaagatggt atactgaaaa taggttgatg gactttggtg tcgcccaaga agatgccctt   1680
agagcttatt ttcttgcagc cgcatctgtt tacgagcctt gtagagctgc cgagaggctt   1740
gcatgggcta gagccgcaat actagctaac gccgtgagca cccacttaag aaatagccca   1800
tcattcagag aaaggttaga gcattctctt aggtgtagac ctagtgaaga gacagatggc   1860
tcctggttta actcctcaag tggctctgat gcagttttag taaaggctgt cttaagactt   1920
actgattcat tagccaggga agcacagcca atccatggag gtgacccaga agatattata   1980
cacaagttgt taagatctgc ttgggccgag tgggttaggg aaaaggcaga cgctgccgat   2040
agcgtgtgca atggtagttc tgcagtagaa caagagggat caagaatggt ccatgataaa   2100
```

```
cagacctgtc tattattggc tagaatgatc gaaatttctg ccggtagggc agctggtgaa   2160

gcagccagtg aggacggcga tagaagaata attcaattaa caggctccat ctgcgacagt   2220

cttaagcaaa aaatgctagt ttcacaggac cctgaaaaaa atgaagagat gatgtctcac   2280

gtggatgacg aattgaagtt gaggattaga gagttcgttc aatatttgct tagactaggt   2340

gaaaaaaaga ctggatctag cgaaaccagg caaacatttt taagtatagt gaaatcatgt   2400

tactatgctg ctcattgccc acctcatgtc gttgatagac acattagtag agtgattttc   2460

gagccagtaa gtgccgcaaa gtaaccgcgg                                    2490
```

<210> SEQ ID NO 40
<211> LENGTH: 827
<212> TYPE: PRT
<213> ORGANISM: Zea mays

<400> SEQUENCE: 40

```
Met Val Leu Ser Ser Ser Cys Thr Thr Val Pro His Leu Ser Ser Leu
1               5                   10                  15

Ala Val Val Gln Leu Gly Pro Trp Ser Ser Arg Ile Lys Lys Lys Thr
            20                  25                  30

Asp Thr Val Ala Val Pro Ala Ala Ala Gly Arg Trp Arg Arg Ala Leu
        35                  40                  45

Ala Arg Ala Gln His Thr Ser Glu Ser Ala Ala Val Ala Lys Gly Ser
    50                  55                  60

Ser Leu Thr Pro Ile Val Arg Thr Asp Ala Glu Ser Arg Arg Thr Arg
65                  70                  75                  80

Trp Pro Thr Asp Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr
            100                 105                 110

Asp Thr Ala Trp Val Gly Leu Val Pro Arg Leu Asp Gly Gly Glu Gly
        115                 120                 125

Pro Gln Phe Pro Ala Ala Val Arg Trp Ile Arg Asn Asn Gln Leu Pro
    130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175

Pro Glu Met Arg Gly Arg Gly Leu Ser Phe Leu Gly Arg Asn Met Trp
            180                 185                 190

Lys Leu Ala Thr Glu Asp Glu Glu Ser Met Pro Ile Gly Phe Glu Leu
        195                 200                 205

Ala Phe Pro Ser Leu Ile Glu Leu Ala Lys Ser Leu Gly Val His Asp
    210                 215                 220

Phe Pro Tyr Asp His Gln Ala Leu Gln Gly Ile Tyr Ser Ser Arg Glu
225                 230                 235                 240

Ile Lys Met Lys Arg Ile Pro Lys Glu Val Met His Thr Val Pro Thr
                245                 250                 255

Ser Ile Leu His Ser Leu Glu Gly Met Pro Gly Leu Asp Trp Ala Lys
            260                 265                 270

Leu Leu Lys Leu Gln Ser Ser Asp Gly Ser Phe Leu Phe Ser Pro Ala
        275                 280                 285

Ala Thr Ala Tyr Ala Leu Met Asn Thr Gly Asp Asp Arg Cys Phe Ser
    290                 295                 300
```

Tyr Ile Asp Arg Thr Val Lys Lys Phe Asn Gly Gly Val Pro Asn Val
305 310 315 320

Tyr Pro Val Asp Leu Phe Glu His Ile Trp Ala Val Asp Arg Leu Glu
325 330 335

Arg Leu Gly Ile Ser Arg Tyr Phe Gln Lys Glu Ile Glu Gln Cys Met
340 345 350

Asp Tyr Val Asn Arg His Trp Thr Glu Asp Gly Ile Cys Trp Ala Arg
355 360 365

Asn Ser Asp Val Lys Glu Val Asp Asp Thr Ala Met Ala Phe Arg Leu
370 375 380

Leu Arg Leu His Gly Tyr Ser Val Ser Pro Asp Val Phe Lys Asn Phe
385 390 395 400

Glu Lys Asp Gly Glu Phe Phe Ala Phe Val Gly Gln Ser Asn Gln Ala
405 410 415

Val Thr Gly Met Tyr Asn Leu Asn Arg Ala Ser Gln Ile Ser Phe Pro
420 425 430

Gly Glu Asp Val Leu His Arg Ala Gly Ala Phe Ser Tyr Glu Phe Leu
435 440 445

Arg Arg Lys Glu Ala Glu Gly Ala Leu Arg Asp Lys Trp Ile Ile Ser
450 455 460

Lys Asp Leu Pro Gly Glu Val Val Tyr Thr Leu Asp Phe Pro Trp Tyr
465 470 475 480

Gly Asn Leu Pro Arg Val Glu Ala Arg Asp Tyr Leu Glu Gln Tyr Gly
485 490 495

Gly Gly Asp Asp Val Trp Ile Gly Lys Thr Leu Tyr Arg Met Pro Leu
500 505 510

Val Asn Asn Asp Val Tyr Leu Glu Leu Ala Arg Met Asp Phe Asn His
515 520 525

Cys Gln Ala Leu His Gln Leu Glu Trp Gln Gly Leu Lys Arg Trp Tyr
530 535 540

Thr Glu Asn Arg Leu Met Asp Phe Gly Val Ala Gln Glu Asp Ala Leu
545 550 555 560

Arg Ala Tyr Phe Leu Ala Ala Ala Ser Val Tyr Glu Pro Cys Arg Ala
565 570 575

Ala Glu Arg Leu Ala Trp Ala Arg Ala Ala Ile Leu Ala Asn Ala Val
580 585 590

Ser Thr His Leu Arg Asn Ser Pro Ser Phe Arg Glu Arg Leu Glu His
595 600 605

Ser Leu Arg Cys Arg Pro Ser Glu Glu Thr Asp Gly Ser Trp Phe Asn
610 615 620

Ser Ser Ser Gly Ser Asp Ala Val Leu Val Lys Ala Val Leu Arg Leu
625 630 635 640

Thr Asp Ser Leu Ala Arg Glu Ala Gln Pro Ile His Gly Gly Asp Pro
645 650 655

Glu Asp Ile Ile His Lys Leu Leu Arg Ser Ala Trp Ala Glu Trp Val
660 665 670

Arg Glu Lys Ala Asp Ala Ala Asp Ser Val Cys Asn Gly Ser Ser Ala
675 680 685

Val Glu Gln Glu Gly Ser Arg Met Val His Asp Lys Gln Thr Cys Leu
690 695 700

Leu Leu Ala Arg Met Ile Glu Ile Ser Ala Gly Arg Ala Ala Gly Glu
705 710 715 720

Ala Ala Ser Glu Asp Gly Asp Arg Arg Ile Ile Gln Leu Thr Gly Ser

```
                725                 730                 735

Ile Cys Asp Ser Leu Lys Gln Lys Met Leu Val Ser Gln Asp Pro Glu
            740                 745                 750

Lys Asn Glu Glu Met Met Ser His Val Asp Asp Glu Leu Lys Leu Arg
        755                 760                 765

Ile Arg Glu Phe Val Gln Tyr Leu Leu Arg Leu Gly Glu Lys Lys Thr
    770                 775                 780

Gly Ser Ser Glu Thr Arg Gln Thr Phe Leu Ser Ile Val Lys Ser Cys
785                 790                 795                 800

Tyr Tyr Ala Ala His Cys Pro Pro His Val Val Asp Arg His Ile Ser
                805                 810                 815

Arg Val Ile Phe Glu Pro Val Ser Ala Ala Lys
            820                 825


<210> SEQ ID NO 41
<211> LENGTH: 2570
<212> TYPE: DNA
<213> ORGANISM: Artificial Sequence
<220> FEATURE:
<223> OTHER INFORMATION: Codon-optimized CDPS

<400> SEQUENCE: 41

cttcttcact aaatacttag acagagaaaa cagagctttt taaagccatg tctcttcagt     60

atcatgttct aaactccatt ccaagtacaa cctttctcag ttctactaaa acaacaatat    120

cttcttcttt ccttaccatc tcaggatctc ctctcaatgt cgctagagac aaatccagaa    180

gcggttccat acattgttca aagcttcgaa ctcaagaata cattaattct caagaggttc    240

aacatgattt gcctctaata catgagtggc aacagcttca aggagaagat gctcctcaga    300

ttagtgttgg aagtaatagt aatgcattca aagaagcagt gaagagtgtg aaaacgatct    360

tgagaaacct aacggacggg gaaattacga tatcggctta cgatacagct tgggttgcat    420

tgatcgatgc cggagataaa actccggcgt ttccctccgc cgtgaaatgg atcgccgaga    480

accaactttc cgatggttct tggggagatg cgtatctctt ctcttatcat gatcgtctca    540

tcaataccct tgcatgcgtc gttgctctaa gatcatggaa tctctttcct catcaatgca    600

acaaaggaat cacgtttttc cgggaaaata ttgggaagct agaagacgaa aatgatgagc    660

atatgccaat cggattcgaa gtagcattcc catcgttgct tgagatagct cgaggaataa    720

acattgatgt accgtacgat tctccggtct taaaagatat atacgccaag aaagagctaa    780

agcttacaag gataccaaaa gagataatgc acaagatacc aacaacattg ttgcatagtt    840

tggaggggat gcgtgattta gattgggaaa agctcttgaa acttcaatct caagacggat    900

ctttcctctt ctctccttcc tctaccgctt ttgcattcat gcagacccga gacagtaact    960

gcctcgagta tttgcgaaat gccgtcaaac gtttcaatgg aggagttccc aatgtctttc   1020

ccgtggatct tttcgagcac atatggatag tggatcggtt acaacgttta gggatatcga   1080

gatactttga agaagagatt aaagagtgtc ttgactatgt ccacagatat tggaccgaca   1140

atggcatatg ttgggctaga tgttcccatg tccaagacat cgatgataca gccatggcat   1200

ttaggctctt aagacaacat ggataccaag tgtccgcaga tgtattcaag aactttgaga   1260

aagagggaga gtttttctgc tttgtggggc aatcaaacca agcagtaacc ggtatgttca   1320

acctataccg ggcatcacaa ttggcgtttc caagggaaga gatattgaaa aacgccaaag   1380

agttttctta taattatctg ctagaaaaac gggagagaga ggagttgatt gataagtgga   1440

ttataatgaa agacttacct ggcgagattg ggtttgcgtt agagattcca tggtacgcaa   1500
```

```
gcttgcctcg agtagagacg agattctata ttgatcaata tggtggagaa aacgacgttt   1560

ggattggcaa gactctttat aggatgccat acgtgaacaa taatggatat ctggaattag   1620

caaaacaaga ttacaacaat tgccaagctc agcatcagct cgaatgggac atattccaaa   1680

agtggtatga agaaaatagg ttaagtgagt ggggtgtgcg cagaagtgag cttctcgagt   1740

gttactactt agcggctgca actatatttg aatcagaaag gtcacatgag agaatggttt   1800

gggctaagtc aagtgtattg gttaaagcca tttcttcttc ttttggggaa tcctctgact   1860

ccagaagaag cttctccgat cagtttcatg aatacattgc caatgctcga cgaagtgatc   1920

atcactttaa tgacaggaac atgagattgg accgaccagg atcggttcag gccagtcggc   1980

ttgccggagt gttaatcggg actttgaatc aaatgtcttt tgaccttttc atgtctcatg   2040

gccgtgacgt taacaatctc ctctatctat cgtggggaga ttggatggaa aaatggaaac   2100

tatatggaga tgaaggagaa ggagagctca tggtgaagat gataattcta atgaagaaca   2160

atgacctaac taacttcttc acccacactc acttcgttcg tctcgcggaa atcatcaatc   2220

gaatctgtct tcctcgccaa tacttaaagg caaggagaaa cgatgagaag gagaagacaa   2280

taaagagtat ggagaaggag atggggaaaa tggttgagtt agcattgtcg gagagtgaca   2340

catttcgtga cgtcagcatc acgtttcttg atgtagcaaa agcattttac tactttgctt   2400

tatgtggcga tcatctccaa actcacatct ccaaagtctt gtttcaaaaa gtctagtaac   2460

ctcatcatca tcatcgatcc attaacaatc agtggatcga tgtatccata gatgcgtgaa   2520

taatatttca tgtagagaag gagaacaaat tagatcatgt agggttatca              2570
```

<210> SEQ ID NO 42
<211> LENGTH: 802
<212> TYPE: PRT
<213> ORGANISM: Arabidopsis thaliana

<400> SEQUENCE: 42

```
Met Ser Leu Gln Tyr His Val Leu Asn Ser Ile Pro Ser Thr Thr Phe
1               5                   10                  15

Leu Ser Ser Thr Lys Thr Thr Ile Ser Ser Ser Phe Leu Thr Ile Ser
            20                  25                  30

Gly Ser Pro Leu Asn Val Ala Arg Asp Lys Ser Arg Ser Gly Ser Ile
        35                  40                  45

His Cys Ser Lys Leu Arg Thr Gln Glu Tyr Ile Asn Ser Gln Glu Val
    50                  55                  60

Gln His Asp Leu Pro Leu Ile His Glu Trp Gln Gln Leu Gln Gly Glu
65                  70                  75                  80

Asp Ala Pro Gln Ile Ser Val Gly Ser Asn Ser Asn Ala Phe Lys Glu
                85                  90                  95

Ala Val Lys Ser Val Lys Thr Ile Leu Arg Asn Leu Thr Asp Gly Glu
            100                 105                 110

Ile Thr Ile Ser Ala Tyr Asp Thr Ala Trp Val Ala Leu Ile Asp Ala
        115                 120                 125

Gly Asp Lys Thr Pro Ala Phe Pro Ser Ala Val Lys Trp Ile Ala Glu
    130                 135                 140

Asn Gln Leu Ser Asp Gly Ser Trp Gly Asp Ala Tyr Leu Phe Ser Tyr
145                 150                 155                 160

His Asp Arg Leu Ile Asn Thr Leu Ala Cys Val Val Ala Leu Arg Ser
                165                 170                 175

Trp Asn Leu Phe Pro His Gln Cys Asn Lys Gly Ile Thr Phe Phe Arg
```

```
            180                 185                 190

Glu Asn Ile Gly Lys Leu Glu Asp Glu Asn Asp Glu His Met Pro Ile
        195                 200                 205

Gly Phe Glu Val Ala Phe Pro Ser Leu Leu Glu Ile Ala Arg Gly Ile
    210                 215                 220

Asn Ile Asp Val Pro Tyr Asp Ser Pro Val Leu Lys Asp Ile Tyr Ala
225                 230                 235                 240

Lys Lys Glu Leu Lys Leu Thr Arg Ile Pro Lys Glu Ile Met His Lys
                245                 250                 255

Ile Pro Thr Thr Leu Leu His Ser Leu Glu Gly Met Arg Asp Leu Asp
            260                 265                 270

Trp Glu Lys Leu Leu Lys Leu Gln Ser Gln Asp Gly Ser Phe Leu Phe
        275                 280                 285

Ser Pro Ser Ser Thr Ala Phe Ala Phe Met Gln Thr Arg Asp Ser Asn
    290                 295                 300

Cys Leu Glu Tyr Leu Arg Asn Ala Val Lys Arg Phe Asn Gly Gly Val
305                 310                 315                 320

Pro Asn Val Phe Pro Val Asp Leu Phe Glu His Ile Trp Ile Val Asp
                325                 330                 335

Arg Leu Gln Arg Leu Gly Ile Ser Arg Tyr Phe Glu Glu Glu Ile Lys
            340                 345                 350

Glu Cys Leu Asp Tyr Val His Arg Tyr Trp Thr Asp Asn Gly Ile Cys
        355                 360                 365

Trp Ala Arg Cys Ser His Val Gln Asp Ile Asp Asp Thr Ala Met Ala
    370                 375                 380

Phe Arg Leu Leu Arg Gln His Gly Tyr Gln Val Ser Ala Asp Val Phe
385                 390                 395                 400

Lys Asn Phe Glu Lys Glu Gly Glu Phe Phe Cys Phe Val Gly Gln Ser
                405                 410                 415

Asn Gln Ala Val Thr Gly Met Phe Asn Leu Tyr Arg Ala Ser Gln Leu
            420                 425                 430

Ala Phe Pro Arg Glu Glu Ile Leu Lys Asn Ala Lys Glu Phe Ser Tyr
        435                 440                 445

Asn Tyr Leu Leu Glu Lys Arg Glu Arg Glu Glu Leu Ile Asp Lys Trp
    450                 455                 460

Ile Ile Met Lys Asp Leu Pro Gly Glu Ile Gly Phe Ala Leu Glu Ile
465                 470                 475                 480

Pro Trp Tyr Ala Ser Leu Pro Arg Val Glu Thr Arg Phe Tyr Ile Asp
                485                 490                 495

Gln Tyr Gly Gly Glu Asn Asp Val Trp Ile Gly Lys Thr Leu Tyr Arg
            500                 505                 510

Met Pro Tyr Val Asn Asn Asn Gly Tyr Leu Glu Leu Ala Lys Gln Asp
        515                 520                 525

Tyr Asn Asn Cys Gln Ala Gln His Gln Leu Glu Trp Asp Ile Phe Gln
    530                 535                 540

Lys Trp Tyr Glu Glu Asn Arg Leu Ser Glu Trp Gly Val Arg Arg Ser
545                 550                 555                 560

Glu Leu Leu Glu Cys Tyr Tyr Leu Ala Ala Ala Thr Ile Phe Glu Ser
                565                 570                 575

Glu Arg Ser His Glu Arg Met Val Trp Ala Lys Ser Ser Val Leu Val
            580                 585                 590

Lys Ala Ile Ser Ser Ser Phe Gly Glu Ser Ser Asp Ser Arg Arg Ser
        595                 600                 605
```

-continued

```
Phe Ser Asp Gln Phe His Glu Tyr Ile Ala Asn Ala Arg Arg Ser Asp
    610                 615                 620

His His Phe Asn Asp Arg Asn Met Arg Leu Asp Arg Pro Gly Ser Val
625                 630                 635                 640

Gln Ala Ser Arg Leu Ala Gly Val Leu Ile Gly Thr Leu Asn Gln Met
                645                 650                 655

Ser Phe Asp Leu Phe Met Ser His Gly Arg Asp Val Asn Asn Leu Leu
            660                 665                 670

Tyr Leu Ser Trp Gly Asp Trp Met Glu Lys Trp Lys Leu Tyr Gly Asp
        675                 680                 685

Glu Gly Glu Gly Glu Leu Met Val Lys Met Ile Ile Leu Met Lys Asn
    690                 695                 700

Asn Asp Leu Thr Asn Phe Phe Thr His Thr His Phe Val Arg Leu Ala
705                 710                 715                 720

Glu Ile Ile Asn Arg Ile Cys Leu Pro Arg Gln Tyr Leu Lys Ala Arg
                725                 730                 735

Arg Asn Asp Glu Lys Glu Lys Thr Ile Lys Ser Met Glu Lys Glu Met
            740                 745                 750

Gly Lys Met Val Glu Leu Ala Leu Ser Glu Ser Asp Thr Phe Arg Asp
        755                 760                 765

Val Ser Ile Thr Phe Leu Asp Val Ala Lys Ala Phe Tyr Tyr Phe Ala
    770                 775                 780

Leu Cys Gly Asp His Leu Gln Thr His Ile Ser Lys Val Leu Phe Gln
785                 790                 795                 800

Lys Val


<210> SEQ ID NO 43
<211> LENGTH: 2355
<212> TYPE: DNA
<213> ORGANISM: Artificial Sequence
<220> FEATURE:
<223> OTHER INFORMATION: Codon-optimized KS

<400> SEQUENCE: 43

atgaatttga gtttgtgtat agcatctcca ctattgacca aatctaatag accagctgct      60

ttatcagcaa ttcatacagc tagtacatcc catggtggcc aaaccaaccc tacgaatctg     120

ataatcgata cgaccaagga gagaatacaa aaacaattca aaaatgttga aatttcagtt     180

tcttcttatg atactgcgtg ggttgccatg gttccatcac ctaattctcc aaagtctcca     240

tgtttcccag aatgtttgaa ttggctgatt aacaaccagt tgaatgatgg atcttggggt     300

ttagtcaatc acacgcacaa tcacaaccat ccacttttga aagattcttt atcctcaact     360

ttggcttgca tcgtggccct aaagagatgg aacgtaggtg aggatcagat taacaagggg     420

cttagtttca ttgaatctaa cttggcttcc gcgactgaaa aatctcaacc atctccaata     480

ggattcgata tcatctttcc aggtctgtta gagtacgcca aaaatctaga tatcaactta     540

ctgtctaagc aaactgattt ctcactaatg ttacacaaga gagaattaga acaaaagaga     600

tgtcattcaa acgaaatgga tggttaccta gcttatatct ctgaaggtct tggtaatctt     660

tacgattgga atatggtgaa aaagtaccag atgaaaaatg gctcagtttt caattcccct     720

tctgcaactg cggcagcatt cattaaccat caaaatccag gatgcctgaa ctatttgaat     780

tcactactag acaaattcgg caacgcagtt ccaactgtat accctcacga tttgtttatc     840

agattgagta tggtggatac aattgaaaga cttggtatat cccaccactt tagagtcgag     900
```

```
atcaaaaatg ttttggatga gacataccgt tgttgggtgg agagagatga acaaatcttt    960

atggatgttg tgacgtgcgc gttggccttt agattgttgc gtattaacgg ttacgaagtt   1020

agtccagatc cacttgccga aattacaaac gaattagctt taaaggatga atacgccgct   1080

cttgaaacat atcatgcgtc acatatcctt taccaagagg acttatcatc tggaaaacaa   1140

attcttaaat ctgctgattt cctgaaggaa atcatatcca ctgatagtaa tagactgtcc   1200

aaactgatcc ataaagaggt tgaaaatgca cttaagttcc ctattaacac cggcttagaa   1260

cgtattaaca caagacgtaa catccagctt tacaacgtag acaatactag aatcttgaaa   1320

accacttacc attcttccaa catatcaaac actgattacc taagattagc tgttgaagat   1380

ttctacacat gtcagtctat ctatagagaa gagctgaaag gattagagag atgggtcgtt   1440

gagaataagc tagatcaatt gaaatttgcc agacaaaaga cagcttattg ttacttctca   1500

gttgccgcca ctttatcaag tccagaattg tcagatgcac gtatttcttg ggctaaaaac   1560

ggaattttga caactgttgt tgatgatttc tttgatattg gcgggacaat cgacgaattg   1620

acaaacctga ttcaatgcgt tgaaaagtgg aatgtcgatg tcgataaaga ctgttgctca   1680

gaacatgtta gaatactgtt cttggctctg aaagatgcta tctgttggat cggggatgag   1740

gctttcaaat ggcaagctag agatgtgacg tctcacgtca ttcaaacctg gctagaactg   1800

atgaactcta tgttgagaga agcaatttgg actagagatg catacgttcc tacattaaac   1860

gagtatatgg aaaacgctta tgtctccttt gctttgggtc ctatcgttaa gcctgccata   1920

tactttgtag gaccaaagct atccgaggaa atcgtcgaat catcagaata ccataacttg   1980

ttcaagttaa tgtccacaca aggcagatta cttaatgata ttcattcttt caaaagagag   2040

tttaaggaag gaaagttaaa tgctgttgct ctgcatcttt ctaatggcga aagtggtaaa   2100

gtcgaagagg aagtagttga ggaaatgatg atgatgatca aaaacaagag aaaggagttg   2160

atgaaactaa tcttcgaaga gaacggttca attgttccta gagcatgtaa ggatgcattt   2220

tggaacatgt gtcatgtgct aaactttttc tacgcaaacg acgatggttt tactgggaac   2280

acaatactag atacagtaaa agacatcata tacaaccctt tggtcttagt aaacgaaaac   2340

gaggagcaaa gataa                                                    2355


<210> SEQ ID NO 44
<211> LENGTH: 784
<212> TYPE: PRT
<213> ORGANISM: Stevia rebaudiana

<400> SEQUENCE: 44

Met Asn Leu Ser Leu Cys Ile Ala Ser Pro Leu Leu Thr Lys Ser Asn
1               5                   10                  15

Arg Pro Ala Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Gln Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110
```

```
Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Glu Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Met Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270

Val Tyr Pro His Asp Leu Phe Ile Arg Leu Ser Met Val Asp Thr Ile
        275                 280                 285

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile Asn
                325                 330                 335

Gly Tyr Glu Val Ser Pro Asp Pro Leu Ala Glu Ile Thr Asn Glu Leu
            340                 345                 350

Ala Leu Lys Asp Glu Tyr Ala Ala Leu Glu Thr Tyr His Ala Ser His
        355                 360                 365

Ile Leu Tyr Gln Glu Asp Leu Ser Ser Gly Lys Gln Ile Leu Lys Ser
    370                 375                 380

Ala Asp Phe Leu Lys Glu Ile Ile Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Asp Tyr Leu Arg Leu Ala Val Glu Asp Phe Tyr Thr Cys
    450                 455                 460

Gln Ser Ile Tyr Arg Glu Glu Leu Lys Gly Leu Glu Arg Trp Val Val
465                 470                 475                 480

Glu Asn Lys Leu Asp Gln Leu Lys Phe Ala Arg Gln Lys Thr Ala Tyr
                485                 490                 495

Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
```

```
    530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
    610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
        675                 680                 685

Val Ala Leu His Leu Ser Asn Gly Glu Ser Gly Lys Val Glu Glu Glu
    690                 695                 700

Val Val Glu Glu Met Met Met Met Ile Lys Asn Lys Arg Lys Glu Leu
705                 710                 715                 720

Met Lys Leu Ile Phe Glu Glu Asn Gly Ser Ile Val Pro Arg Ala Cys
                725                 730                 735

Lys Asp Ala Phe Trp Asn Met Cys His Val Leu Asn Phe Phe Tyr Ala
            740                 745                 750

Asn Asp Asp Gly Phe Thr Gly Asn Thr Ile Leu Asp Thr Val Lys Asp
        755                 760                 765

Ile Ile Tyr Asn Pro Leu Val Leu Val Asn Glu Asn Glu Glu Gln Arg
    770                 775                 780


<210> SEQ ID NO 45
<211> LENGTH: 2355
<212> TYPE: DNA
<213> ORGANISM: Artificial Sequence
<220> FEATURE:
<223> OTHER INFORMATION: Codon-optimized KS

<400> SEQUENCE: 45

atgaatctgt ccctttgtat agctagtcca ctgttgacaa aatcttctag accaactgct      60

ctttctgcaa ttcatactgc cagtactagt catggaggtc aaacaaaccc aacaaatttg     120

ataatcgata ctactaagga gagaatccaa aagctattca aaaatgttga aatctcagta     180

tcatcttatg acaccgcatg ggttgcaatg gtgccatcac ctaattcccc aaaaagtcca     240

tgttttccag agtgcttgaa ttggttaatc aataatcagt taaacgatgg ttcttggggt     300

ttagtcaacc acactcataa ccacaatcat ccattattga aggactcttt atcatcaaca     360

ttagcctgta ttgttgcatt gaaaagatgg aatgtaggtg aagatcaaat caacaagggt     420

ttatcattca tagaatccaa tctagcttct gctaccgaca aatcacaacc atctccaatc     480

gggttcgaca taatcttccc tggtttgctg gagtatgcca aaaaccttga tatcaactta     540

ctgtctaaac aaacagattt ctctttgatg ctacacaaaa gagagttaga gcagaaaaga     600

tgccattcta acgaaattga cgggtactta gcatatatct cagaaggttt gggtaatttg     660
```

-continued

```
tatgactgga acatggtcaa aaagtatcag atgaaaaatg gatccgtatt caattctcct    720

tctgcaactg ccgcagcatt cattaatcat caaaaccctg ggtgtcttaa ctacttgaac    780

tcactattag ataagtttgg aaatgcagtt ccaacagtct atcctttgga cttgtacatc    840

agattatcta tggttgacac tatagagaga ttaggtattt ctcatcattt cagagttgag    900

atcaaaaatg ttttggacga gacatacaga tgttgggtcg aaagagatga gcaaatcttt    960

atggatgtcg tgacctgcgc tctggctttt agattgctaa ggatacacgg atacaaagta   1020

tctcctgatc aactggctga gattacaaac gaactggctt tcaaagacga atacgccgca   1080

ttagaaacat accatgcatc ccaaatactt taccaggaag acctaagttc aggaaaacaa   1140

atcttgaagt ctgcagattt cctgaaaggc attctgtcta cagatagtaa taggttgtct   1200

aaattgatac acaaggaagt agaaaacgca ctaaagtttc ctattaacac tggtttagag   1260

agaatcaata ctaggagaaa cattcagctg tacaacgtag ataatacaag gattcttaag   1320

accacctacc atagttcaaa catttccaac acctattact taagattagc tgtcgaagac   1380

ttttacactt gtcaatcaat ctacagagag gagttaaagg gcctagaaag atgggtagtt   1440

caaaacaagt tggatcaact gaagtttgct agacagaaga cagcatactg ttatttctct   1500

gttgctgcta ccctttcatc cccagaattg tctgatgcca gaataagttg ggccaaaaat   1560

ggtattctta caactgtagt cgatgatttc tttgatattg gaggtactat tgatgaactg   1620

acaaatctta ttcaatgtgt tgaaaagtgg aacgtggatg tagataagga ttgctgcagt   1680

gaacatgtga gaatactttt cctggctcta aaagatgcaa tatgttggat tggcgacgag   1740

gccttcaagt ggcaagctag agatgttaca tctcatgtca tccaaacttg gcttgaactg   1800

atgaactcaa tgctaagaga agcaatctgg acaagagatg catacgttcc aacattgaac   1860

gaatacatgg aaaacgctta cgtctcattt gccttgggtc ctattgttaa gccagccata   1920

tactttgttg ggccaaagtt atccgaagag attgttgagt cttccgaata tcataaccta   1980

ttcaagttaa tgtcaacaca aggcagactt ctgaacgata tccactcctt caaaagagaa   2040

ttcaaggaag gtaagctaaa cgctgttgct ttgcacttgt ctaatggtga atctggcaaa   2100

gtggaagagg aagtcgttga ggaaatgatg atgatgatca aaaacaagag aaaggaattg   2160

atgaaattga ttttcgagga aaatggttca atcgtaccta gagcttgtaa agatgctttt   2220

tggaatatgt gccatgttct taacttcttt tacgctaatg atgatggctt cactggaaat   2280

acaatattgg atacagttaa agatatcatc tacaacccac ttgttttggt caatgagaac   2340

gaggaacaaa gataa                                                    2355


<210> SEQ ID NO 46
<211> LENGTH: 784
<212> TYPE: PRT
<213> ORGANISM: Stevia rebaudiana

<400> SEQUENCE: 46

Met Asn Leu Ser Leu Cys Ile Ala Ser Pro Leu Leu Thr Lys Ser Ser
1               5                   10                  15

Arg Pro Thr Ala Leu Ser Ala Ile His Thr Ala Ser Thr Ser His Gly
            20                  25                  30

Gly Gln Thr Asn Pro Thr Asn Leu Ile Ile Asp Thr Thr Lys Glu Arg
        35                  40                  45

Ile Gln Lys Leu Phe Lys Asn Val Glu Ile Ser Val Ser Ser Tyr Asp
    50                  55                  60

Thr Ala Trp Val Ala Met Val Pro Ser Pro Asn Ser Pro Lys Ser Pro
```

-continued

```
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Asp Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Ile Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
            260                 265                 270

Val Tyr Pro Leu Asp Leu Tyr Ile Arg Leu Ser Met Val Asp Thr Ile
        275                 280                 285

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile His
                325                 330                 335

Gly Tyr Lys Val Ser Pro Asp Gln Leu Ala Glu Ile Thr Asn Glu Leu
            340                 345                 350

Ala Phe Lys Asp Glu Tyr Ala Ala Leu Glu Thr Tyr His Ala Ser Gln
        355                 360                 365

Ile Leu Tyr Gln Glu Asp Leu Ser Ser Gly Lys Gln Ile Leu Lys Ser
    370                 375                 380

Ala Asp Phe Leu Lys Gly Ile Leu Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
            420                 425                 430

Val Asp Asn Thr Arg Ile Leu Lys Thr Thr Tyr His Ser Ser Asn Ile
        435                 440                 445

Ser Asn Thr Tyr Tyr Leu Arg Leu Ala Val Glu Asp Phe Tyr Thr Cys
    450                 455                 460

Gln Ser Ile Tyr Arg Glu Glu Leu Lys Gly Leu Glu Arg Trp Val Val
465                 470                 475                 480

Gln Asn Lys Leu Asp Gln Leu Lys Phe Ala Arg Gln Lys Thr Ala Tyr
                485                 490                 495
```

```
Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
        515                 520                 525

Asp Phe Phe Asp Ile Gly Gly Thr Ile Asp Glu Leu Thr Asn Leu Ile
    530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
        595                 600                 605

Ile Trp Thr Arg Asp Ala Tyr Val Pro Thr Leu Asn Glu Tyr Met Glu
    610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
        675                 680                 685

Val Ala Leu His Leu Ser Asn Gly Glu Ser Gly Lys Val Glu Glu Glu
    690                 695                 700

Val Val Glu Glu Met Met Met Met Ile Lys Asn Lys Arg Lys Glu Leu
705                 710                 715                 720

Met Lys Leu Ile Phe Glu Glu Asn Gly Ser Ile Val Pro Arg Ala Cys
                725                 730                 735

Lys Asp Ala Phe Trp Asn Met Cys His Val Leu Asn Phe Phe Tyr Ala
            740                 745                 750

Asn Asp Asp Gly Phe Thr Gly Asn Thr Ile Leu Asp Thr Val Lys Asp
        755                 760                 765

Ile Ile Tyr Asn Pro Leu Val Leu Val Asn Glu Asn Glu Glu Gln Arg
    770                 775                 780
```

<210> SEQ ID NO 47
<211> LENGTH: 1773
<212> TYPE: DNA
<213> ORGANISM: Artificial Sequence
<220> FEATURE:
<223> OTHER INFORMATION: Codon-optimized KS

<400> SEQUENCE: 47

```
atggctatgc cagtgaagct aacacctgcg tcattatcct taaaagctgt gtgctgcaga      60

ttctcatccg gtggccatgc tttgagattc gggagtagtc tgccatgttg gagaaggacc     120

cctacccaaa gatctacttc ttcctctact actagaccag ctgccgaagt gtcatcaggt     180

aagagtaaac aacatgatca ggaagctagt gaagcgacta tcagacaaca attacaactt     240

gtggatgtcc tggagaatat gggaatatcc agacattttg ctgcagagat aaagtgcata     300

ctagacagaa cttacagatc ttggttacaa agacacgagg aaatcatgct ggacactatg     360

acatgtgcta tggcttttag aatcctaaga ttgaacggat acaacgtttc atcagatgaa     420
```

```
ctataccacg ttgtagaggc atctggtctg cataattctt tgggtgggta tcttaacgat    480

accagaacac tacttgaatt acacaaggct tcaacagtta gtatctctga ggatgaatct    540

atcttagatt caattggctc tagatccaga acattgctta gagaacaatt ggagtctggt    600

ggcgcactga gaaagccttc tttattcaaa gaggttgaac atgcactgga tggacctttt    660

tacaccacac ttgatagact tcatcatagg tggaatattg aaaacttcaa cattattgag    720

caacacatgt tggagactcc atacttatct aaccagcata catcaaggga tatcctagca    780

ttgtcaatta gagatttttc ctcctcacaa ttcacttatc aacaagagct acagcatctg    840

gagagttggg ttaaggaatg tagattagat caactacagt tcgcaagaca gaaattagcg    900

tacttttacc tatcagccgc aggcaccatg ttttctcctg agctttctga tgcgagaaca    960

ttatgggcca aaaacggggt gttgacaact attgttgatg atttctttga tgttgccggt   1020

tctaaagagg aattggaaaa cttagtcatg ctggtcgaaa tgtgggatga acatcacaaa   1080

gttgaattct attctgagca ggtcgaaatc atcttctctt ccatctacga ttctgtcaac   1140

caattgggtg agaaggcctc tttggttcaa gacagatcaa ttacaaaaca ccttgttgaa   1200

atatggttag acttgttaaa gtccatgatg acggaagttg aatggagact gtcaaaatac   1260

gtgcctacag aaaaggaata catgattaat gcctctctta tcttcggcct aggtccaatc   1320

gttttaccag ctttgtattt cgttggtcca aagatttcag aaagtatagt aaaggaccca   1380

gaatatgatg aattgttcaa actaatgtca acatgtggta gattgttgaa tgacgtgcaa   1440

acgttcgaaa gagaatacaa tgagggtaaa ctgaattctg tcagtctatt ggttcttcac   1500

ggaggcccaa tgtctatttc agacgcaaag aggaaattac aaaagcctat tgatacgtgt   1560

agaagagatc ttctttcttt ggtccttaga gaagagtctg tagtaccaag accatgtaag   1620

gaactattct ggaaaatgtg taaagtgtgc tatttctttt actcaacaac tgatgggttt   1680

tctagtcaag tcgaaagagc aaaagaggta gacgctgtca taaatgagcc actgaagttg   1740

caaggttctc atacactggt atctgatgtt taa                                1773
```

<210> SEQ ID NO 48
<211> LENGTH: 590
<212> TYPE: PRT
<213> ORGANISM: Zea mays

<400> SEQUENCE: 48

```
Met Ala Met Pro Val Lys Leu Thr Pro Ala Ser Leu Ser Leu Lys Ala
1               5                   10                  15

Val Cys Cys Arg Phe Ser Ser Gly Gly His Ala Leu Arg Phe Gly Ser
            20                  25                  30

Ser Leu Pro Cys Trp Arg Arg Thr Pro Thr Gln Arg Ser Thr Ser Ser
        35                  40                  45

Ser Thr Thr Arg Pro Ala Ala Glu Val Ser Ser Gly Lys Ser Lys Gln
    50                  55                  60

His Asp Gln Glu Ala Ser Glu Ala Thr Ile Arg Gln Gln Leu Gln Leu
65                  70                  75                  80

Val Asp Val Leu Glu Asn Met Gly Ile Ser Arg His Phe Ala Ala Glu
                85                  90                  95

Ile Lys Cys Ile Leu Asp Arg Thr Tyr Arg Ser Trp Leu Gln Arg His
            100                 105                 110

Glu Glu Ile Met Leu Asp Thr Met Thr Cys Ala Met Ala Phe Arg Ile
        115                 120                 125

Leu Arg Leu Asn Gly Tyr Asn Val Ser Ser Asp Glu Leu Tyr His Val
```

-continued

```
    130                 135                 140

Val Glu Ala Ser Gly Leu His Asn Ser Leu Gly Gly Tyr Leu Asn Asp
145                 150                 155                 160

Thr Arg Thr Leu Leu Glu Leu His Lys Ala Ser Thr Val Ser Ile Ser
                165                 170                 175

Glu Asp Glu Ser Ile Leu Asp Ser Ile Gly Ser Arg Ser Arg Thr Leu
            180                 185                 190

Leu Arg Glu Gln Leu Glu Ser Gly Gly Ala Leu Arg Lys Pro Ser Leu
        195                 200                 205

Phe Lys Glu Val Glu His Ala Leu Asp Gly Pro Phe Tyr Thr Thr Leu
    210                 215                 220

Asp Arg Leu His His Arg Trp Asn Ile Glu Asn Phe Asn Ile Ile Glu
225                 230                 235                 240

Gln His Met Leu Glu Thr Pro Tyr Leu Ser Asn Gln His Thr Ser Arg
                245                 250                 255

Asp Ile Leu Ala Leu Ser Ile Arg Asp Phe Ser Ser Ser Gln Phe Thr
            260                 265                 270

Tyr Gln Gln Glu Leu Gln His Leu Glu Ser Trp Val Lys Glu Cys Arg
        275                 280                 285

Leu Asp Gln Leu Gln Phe Ala Arg Gln Lys Leu Ala Tyr Phe Tyr Leu
    290                 295                 300

Ser Ala Ala Gly Thr Met Phe Ser Pro Glu Leu Ser Asp Ala Arg Thr
305                 310                 315                 320

Leu Trp Ala Lys Asn Gly Val Leu Thr Thr Ile Val Asp Asp Phe Phe
                325                 330                 335

Asp Val Ala Gly Ser Lys Glu Glu Leu Glu Asn Leu Val Met Leu Val
            340                 345                 350

Glu Met Trp Asp Glu His His Lys Val Glu Phe Tyr Ser Glu Gln Val
        355                 360                 365

Glu Ile Ile Phe Ser Ser Ile Tyr Asp Ser Val Asn Gln Leu Gly Glu
    370                 375                 380

Lys Ala Ser Leu Val Gln Asp Arg Ser Ile Thr Lys His Leu Val Glu
385                 390                 395                 400

Ile Trp Leu Asp Leu Leu Lys Ser Met Met Thr Glu Val Glu Trp Arg
                405                 410                 415

Leu Ser Lys Tyr Val Pro Thr Glu Lys Glu Tyr Met Ile Asn Ala Ser
            420                 425                 430

Leu Ile Phe Gly Leu Gly Pro Ile Val Leu Pro Ala Leu Tyr Phe Val
        435                 440                 445

Gly Pro Lys Ile Ser Glu Ser Ile Val Lys Asp Pro Glu Tyr Asp Glu
    450                 455                 460

Leu Phe Lys Leu Met Ser Thr Cys Gly Arg Leu Leu Asn Asp Val Gln
465                 470                 475                 480

Thr Phe Glu Arg Glu Tyr Asn Glu Gly Lys Leu Asn Ser Val Ser Leu
                485                 490                 495

Leu Val Leu His Gly Gly Pro Met Ser Ile Ser Asp Ala Lys Arg Lys
            500                 505                 510

Leu Gln Lys Pro Ile Asp Thr Cys Arg Arg Asp Leu Leu Ser Leu Val
        515                 520                 525

Leu Arg Glu Glu Ser Val Val Pro Arg Pro Cys Lys Glu Leu Phe Trp
    530                 535                 540

Lys Met Cys Lys Val Cys Tyr Phe Phe Tyr Ser Thr Thr Asp Gly Phe
545                 550                 555                 560
```

```
Ser Ser Gln Val Glu Arg Ala Lys Glu Val Asp Ala Val Ile Asn Glu
                565                 570                 575

Pro Leu Lys Leu Gln Gly Ser His Thr Leu Val Ser Asp Val
            580                 585                 590


<210> SEQ ID NO 49
<211> LENGTH: 2232
<212> TYPE: DNA
<213> ORGANISM: Artificial Sequence
<220> FEATURE:
<223> OTHER INFORMATION: Codon-optimized KS

<400> SEQUENCE: 49

atgcagaact tccatggtac aaaggaaagg atcaaaaaga tgtttgacaa gattgaattg      60

tccgtttctt cttatgatac agcctgggtt gcaatggtcc catcccctga ttgcccagaa     120

acaccttgtt ttccagaatg tactaaatgg atcctagaaa atcagttggg tgatggtagt     180

tggtcacttc ctcatggcaa tccacttcta gttaaagatg cattatcttc cactcttgct     240

tgtattctgg ctcttaaaag atggggaatc ggtgaggaac agattaacaa aggactgaga     300

ttcatagaac tcaactctgc tagtgtaacc gataacgaac aacacaaacc aattggattt     360

gacattatct ttccaggtat gattgaatac gctatagact tagacctgaa tctaccacta     420

aaaccaactg acattaactc catgttgcat cgtagagccc ttgaattgac atcaggtgga     480

ggcaaaaatc tagaaggtag aagagcttac ttggcctacg tctctgaagg aatcggtaag     540

ctgcaagatt gggaaatggc tatgaaatac caacgtaaaa acggatctct gttcaatagt     600

ccatcaacaa ctgcagctgc attcatccat atacaagatg ctgaatgcct ccactatatt     660

cgttctcttc tccagaaatt tggaaacgca gtccctacaa tataccctct cgatatctat     720

gccagacttt caatggtaga tgccctggaa cgtcttggta ttgatagaca tttcagaaag     780

gagagaaagt tcgttctgga tgaaacatac agattttggt tgcaaggaga agaggagatt     840

ttctccgata acgcaacctg tgctttggcc ttcagaatat tgagacttaa tggttacgat     900

gtctctcttg aagatcactt ctctaactct ctgggcggtt acttaaagga ctcaggagca     960

gctttagaac tgtacagagc cctccaattg tcttacccag acgagtccct cctggaaaag    1020

caaaattcta gaacttctta cttcttaaaa caaggtttat ccaatgtctc cctctgtggt    1080

gacagattgc gtaaaaacat aattggagag gtgcatgatg ctttaaactt ttccgaccac    1140

gctaacttac aaagattagc tattcgtaga aggattaagc attacgctac tgacgataca    1200

aggattctaa aaacttccta cagatgctca acaatcggta accaagattt tctaaaactt    1260

gcagtggaag atttcaatat ctgtcaatca atacaaagag aggaattcaa gcatattgaa    1320

agatgggtcg ttgaaagacg tctagacaag ttaaagttcg ctagacaaaa agaggcctat    1380

tgctatttct cagccgcagc aacattgttt gcccctgaat tgtctgatgc tagaatgtct    1440

tgggccaaaa atggtgtatt gacaactgtg gttgatgatt tcttcgatgt cggaggctct    1500

gaagaggaat tagttaactt gatagaattg atcgagcgtt gggatgtgaa tggcagtgca    1560

gatttttgta gtgaggaagt tgagattatc tattctgcta tccactcaac tatctctgaa    1620

ataggtgata agtcatttgg ctggcaaggt agagatgtaa agtctcaagt tatcaagatc    1680

tggctggact tattgaaatc aatgttaact gaagctcaat ggtcttcaaa caagtctgtt    1740

cctaccctag atgagtatat gacaaccgcc catgtttcat tcgcacttgg tccaattgta    1800

cttccagcct tatacttcgt tggcccaaag ttgtcagaag aggttgcagg tcatcctgaa    1860
```

-continued

```
ctactaaacc tctacaaagt cacatctact tgtggcagac tactgaatga ttggagaagt   1920

tttaagagag aatccgagga aggtaagctc aacgctatta gtttatacat gatccactcc   1980

ggtggtgctt ctacagaaga ggaaacaatc gaacatttca aaggtttgat tgattctcag   2040

agaaggcaac tgttacaatt ggtgttgcaa gagaaggata gtatcatacc tagaccatgt   2100

aaagatctat tttggaatat gattaagtta ttacacactt tctacatgaa agatgatggc   2160

ttcacctcaa atgagatgag gaatgtagtt aaggcaatca ttaacgaacc aatctcactg   2220

gatgaattat ga                                                       2232
```

```
<210> SEQ ID NO 50
<211> LENGTH: 775
<212> TYPE: PRT
<213> ORGANISM: Populus trichocarpa

<400> SEQUENCE: 50

Met Ser Cys Ile Arg Pro Trp Phe Cys Pro Ser Ser Ile Ser Ala Thr
1               5                   10                  15

Leu Thr Asp Pro Ala Ser Lys Leu Val Thr Gly Glu Phe Lys Thr Thr
            20                  25                  30

Ser Leu Asn Phe His Gly Thr Lys Glu Arg Ile Lys Lys Met Phe Asp
        35                  40                  45

Lys Ile Glu Leu Ser Val Ser Ser Tyr Asp Thr Ala Trp Val Ala Met
    50                  55                  60

Val Pro Ser Pro Asp Cys Pro Glu Thr Pro Cys Phe Pro Glu Cys Thr
65                  70                  75                  80

Lys Trp Ile Leu Glu Asn Gln Leu Gly Asp Gly Ser Trp Ser Leu Pro
                85                  90                  95

His Gly Asn Pro Leu Leu Val Lys Asp Ala Leu Ser Ser Thr Leu Ala
            100                 105                 110

Cys Ile Leu Ala Leu Lys Arg Trp Gly Ile Gly Glu Glu Gln Ile Asn
        115                 120                 125

Lys Gly Leu Arg Phe Ile Glu Leu Asn Ser Ala Ser Val Thr Asp Asn
    130                 135                 140

Glu Gln His Lys Pro Ile Gly Phe Asp Ile Ile Phe Pro Gly Met Ile
145                 150                 155                 160

Glu Tyr Ala Lys Asp Leu Asp Leu Asn Leu Pro Leu Lys Pro Thr Asp
                165                 170                 175

Ile Asn Ser Met Leu His Arg Arg Ala Leu Glu Leu Thr Ser Gly Gly
            180                 185                 190

Gly Lys Asn Leu Glu Gly Arg Arg Ala Tyr Leu Ala Tyr Val Ser Glu
        195                 200                 205

Gly Ile Gly Lys Leu Gln Asp Trp Glu Met Ala Met Lys Tyr Gln Arg
    210                 215                 220

Lys Asn Gly Ser Leu Phe Asn Ser Pro Ser Thr Thr Ala Ala Ala Phe
225                 230                 235                 240

Ile His Ile Gln Asp Ala Glu Cys Leu His Tyr Ile Arg Ser Leu Leu
                245                 250                 255

Gln Lys Phe Gly Asn Ala Val Pro Thr Ile Tyr Pro Leu Asp Ile Tyr
            260                 265                 270

Ala Arg Leu Ser Met Val Asp Ala Leu Glu Arg Leu Gly Ile Asp Arg
        275                 280                 285

His Phe Arg Lys Glu Arg Lys Phe Val Leu Asp Glu Thr Tyr Arg Phe
    290                 295                 300
```

-continued

```
Trp Leu Gln Gly Glu Glu Glu Ile Phe Ser Asp Asn Ala Thr Cys Ala
305                 310                 315                 320

Leu Ala Phe Arg Ile Leu Arg Leu Asn Gly Tyr Asp Val Ser Leu Glu
                325                 330                 335

Asp His Phe Ser Asn Ser Leu Gly Gly Tyr Leu Lys Asp Ser Gly Ala
            340                 345                 350

Ala Leu Glu Leu Tyr Arg Ala Leu Gln Leu Ser Tyr Pro Asp Glu Ser
        355                 360                 365

Leu Leu Glu Lys Gln Asn Ser Arg Thr Ser Tyr Phe Leu Lys Gln Gly
    370                 375                 380

Leu Ser Asn Val Ser Leu Cys Gly Asp Arg Leu Arg Lys Asn Ile Ile
385                 390                 395                 400

Gly Glu Val His Asp Ala Leu Asn Phe Pro Asp His Ala Asn Leu Gln
                405                 410                 415

Arg Leu Ala Ile Arg Arg Arg Ile Lys His Tyr Ala Thr Asp Asp Thr
            420                 425                 430

Arg Ile Leu Lys Thr Ser Tyr Arg Cys Ser Thr Ile Gly Asn Gln Asp
        435                 440                 445

Phe Leu Lys Leu Ala Val Glu Asp Phe Asn Ile Cys Gln Ser Ile Gln
    450                 455                 460

Arg Glu Glu Phe Lys His Ile Glu Arg Trp Val Val Glu Arg Arg Leu
465                 470                 475                 480

Asp Lys Leu Lys Phe Ala Arg Gln Lys Glu Ala Tyr Cys Tyr Phe Ser
                485                 490                 495

Ala Ala Ala Thr Leu Phe Ala Pro Glu Leu Ser Asp Ala Arg Met Ser
            500                 505                 510

Trp Ala Lys Asn Gly Val Leu Thr Thr Val Val Asp Asp Phe Phe Asp
        515                 520                 525

Val Gly Gly Ser Glu Glu Glu Leu Val Asn Leu Ile Glu Leu Ile Glu
    530                 535                 540

Arg Trp Asp Val Asn Gly Ser Ala Asp Phe Cys Ser Glu Glu Val Glu
545                 550                 555                 560

Ile Ile Tyr Ser Ala Ile His Ser Thr Ile Ser Glu Ile Gly Asp Lys
                565                 570                 575

Ser Phe Gly Trp Gln Gly Arg Asp Val Lys Ser His Val Ile Lys Ile
            580                 585                 590

Trp Leu Asp Leu Leu Lys Ser Met Leu Thr Glu Ala Gln Trp Ser Ser
        595                 600                 605

Asn Lys Ser Val Pro Thr Leu Asp Glu Tyr Met Thr Thr Ala His Val
    610                 615                 620

Ser Phe Ala Leu Gly Pro Ile Val Leu Pro Ala Leu Tyr Phe Val Gly
625                 630                 635                 640

Pro Lys Leu Ser Glu Glu Val Ala Gly His Pro Glu Leu Leu Asn Leu
                645                 650                 655

Tyr Lys Val Met Ser Thr Cys Gly Arg Leu Leu Asn Asp Trp Arg Ser
            660                 665                 670

Phe Lys Arg Glu Ser Glu Glu Gly Lys Leu Asn Ala Ile Ser Leu Tyr
        675                 680                 685

Met Ile His Ser Gly Gly Ala Ser Thr Glu Glu Glu Thr Ile Glu His
    690                 695                 700

Phe Lys Gly Leu Ile Asp Ser Gln Arg Arg Gln Leu Leu Gln Leu Val
705                 710                 715                 720

Leu Gln Glu Lys Asp Ser Ile Ile Pro Arg Pro Cys Lys Asp Leu Phe
```

```
                725                 730                 735

Trp Asn Met Ile Lys Leu Leu His Thr Phe Tyr Met Lys Asp Asp Gly
            740                 745                 750

Phe Thr Ser Asn Glu Met Arg Asn Val Val Lys Ala Ile Ile Asn Glu
        755                 760                 765

Pro Ile Ser Leu Asp Glu Leu
    770                 775


<210> SEQ ID NO 51
<211> LENGTH: 2358
<212> TYPE: DNA
<213> ORGANISM: Artificial Sequence
<220> FEATURE:
<223> OTHER INFORMATION: Codon-optimized KS

<400> SEQUENCE: 51

atgtctatca accttcgctc ctccggttgt tcgtctccga tctcagctac tttggaacga     60

ggattggact cagaagtaca gacaagagct aacaatgtga gctttgagca aacaaaggag    120

aagattagga agatgttgga gaaagtggag ctttctgttt cggcctacga tactagttgg    180

gtagcaatgg ttccatcacc gagctcccaa aatgctccac ttttcccaca gtgtgtgaaa    240

tggttattgg ataatcaaca tgaagatgga tcttggggac ttgataacca tgaccatcaa    300

tctcttaaga aggatgtgtt atcatctaca ctggctagta tcctcgcgtt aaagaagtgg    360

ggaattggtg aaagacaaat aaacaagggt ctccagttta ttgagctgaa ttctgcatta    420

gtcactgatg aaaccataca gaaaccaaca gggtttgata ttatatttcc tgggatgatt    480

aaatatgcta gagatttgaa tctgacgatt ccattgggct cagaagtggt ggatgacatg    540

atacgaaaaa gagatctgga tcttaaatgt gatagtgaaa agttttcaaa gggaagagaa    600

gcatatctgg cctatgtttt agaggggaca agaaacctaa aagattggga tttgatagtc    660

aaatatcaaa ggaaaaatgg gtcactgttt gattctccag ccacaacagc agctgctttt    720

actcagtttg ggaatgatgg ttgtctccgt tatctctgtt ctctccttca gaaattcgag    780

gctgcagttc cttcagttta tccatttgat caatatgcac gccttagtat aattgtcact    840

cttgaaagct taggaattga tagagatttc aaaaccgaaa tcaaaagcat attggatgaa    900

acctatagat attggcttcg tggggatgaa gaaatatgtt tggacttggc cacttgtgct    960

ttggctttcc gattattgct tgctcatggc tatgatgtgt cttacgatcc gctaaaacca   1020

tttgcagaag aatctggttt ctctgatact ttggaaggat atgttaagaa tacgttttct   1080

gtgttagaat tatttaaggc tgctcaaagt tatccacatg aatcagcttt gaagaagcag   1140

tgttgttgga ctaaacaata tctggagatg gaattgtcca gctgggttaa gacctctgtt   1200

cgagataaat acctcaagaa agaggtcgag gatgctcttg cttttccctc ctatgcaagc   1260

ctagaaagat cagatcacag gagaaaaata ctcaatggtt ctgctgtgga aaacaccaga   1320

gttacaaaaa cctcatatcg tttgcacaat atttgcacct ctgatatcct gaagttagct   1380

gtggatgact tcaatttctg ccagtccata caccgtgaag aaatggaacg tcttgatagg   1440

tggattgtgg agaatagatt gcaggaactg aaatttgcca gacagaagct ggcttactgt   1500

tatttctctg ggctgcaac tttattttct ccagaactat ctgatgctcg tatatcgtgg    1560

gccaaaggtg gagtacttac aacggttgta gacgacttct ttgatgttgg agggtccaaa   1620

gaagaactgg aaaacctcat acacttggtc gaaaagtggg atttgaacgg tgttcctgag   1680

tacagctcag aacatgttga gatcatattc tcagttctaa gggacaccat tctcgaaaca   1740
```

ggagacaaag cattcaccta tcaaggacgc aatgtgacac accacattgt gaaaatttgg 1800
ttggatctgc tcaagtctat gttgagagaa gccgagtggt ccagtgacaa gtcaacacca 1860
agcttggagg attacatgga aaatgcgtac atatcatttg cattaggacc aattgtcctc 1920
ccagctacct atctgatcgg acctccactt ccagagaaga cagtcgatag ccaccaatat 1980
aatcagctct acaagctcgt gagcactatg ggtcgtcttc taaatgacat acaaggtttt 2040
aagagagaaa gcgcggaagg gaagctgaat gcggtttcat tgcacatgaa acacgagaga 2100
gacaatcgca gcaaagaagt gatcatagaa tcgatgaaag gtttagcaga gagaaagagg 2160
gaagaattgc ataagctagt tttggaggag aaaggaagtg tggttccaag ggaatgcaaa 2220
gaagcgttct tgaaaatgag caaagtgttg aacttatttt acaggaagga cgatggattc 2280
acatcaaatg atctgatgag tcttgttaaa tcagtgatct acgagcctgt tagcttacag 2340
aaagaatctt taacttga 2358

<210> SEQ ID NO 52
<211> LENGTH: 785
<212> TYPE: PRT
<213> ORGANISM: Arabidopsis thaliana

<400> SEQUENCE: 52

Met Ser Ile Asn Leu Arg Ser Ser Gly Cys Ser Ser Pro Ile Ser Ala
1 5 10 15

Thr Leu Glu Arg Gly Leu Asp Ser Glu Val Gln Thr Arg Ala Asn Asn
20 25 30

Val Ser Phe Glu Gln Thr Lys Glu Lys Ile Arg Lys Met Leu Glu Lys
35 40 45

Val Glu Leu Ser Val Ser Ala Tyr Asp Thr Ser Trp Val Ala Met Val
50 55 60

Pro Ser Pro Ser Ser Gln Asn Ala Pro Leu Phe Pro Gln Cys Val Lys
65 70 75 80

Trp Leu Leu Asp Asn Gln His Glu Asp Gly Ser Trp Gly Leu Asp Asn
85 90 95

His Asp His Gln Ser Leu Lys Lys Asp Val Leu Ser Ser Thr Leu Ala
100 105 110

Ser Ile Leu Ala Leu Lys Lys Trp Gly Ile Gly Glu Arg Gln Ile Asn
115 120 125

Lys Gly Leu Gln Phe Ile Glu Leu Asn Ser Ala Leu Val Thr Asp Glu
130 135 140

Thr Ile Gln Lys Pro Thr Gly Phe Asp Ile Ile Phe Pro Gly Met Ile
145 150 155 160

Lys Tyr Ala Arg Asp Leu Asn Leu Thr Ile Pro Leu Gly Ser Glu Val
165 170 175

Val Asp Asp Met Ile Arg Lys Arg Asp Leu Asp Leu Lys Cys Asp Ser
180 185 190

Glu Lys Phe Ser Lys Gly Arg Glu Ala Tyr Leu Ala Tyr Val Leu Glu
195 200 205

Gly Thr Arg Asn Leu Lys Asp Trp Asp Leu Ile Val Lys Tyr Gln Arg
210 215 220

Lys Asn Gly Ser Leu Phe Asp Ser Pro Ala Thr Thr Ala Ala Ala Phe
225 230 235 240

Thr Gln Phe Gly Asn Asp Gly Cys Leu Arg Tyr Leu Cys Ser Leu Leu
245 250 255

Gln Lys Phe Glu Ala Ala Val Pro Ser Val Tyr Pro Phe Asp Gln Tyr

-continued

```
            260                 265                 270

Ala Arg Leu Ser Ile Ile Val Thr Leu Glu Ser Leu Gly Ile Asp Arg
        275                 280                 285

Asp Phe Lys Thr Glu Ile Lys Ser Ile Leu Asp Glu Thr Tyr Arg Tyr
    290                 295                 300

Trp Leu Arg Gly Asp Glu Glu Ile Cys Leu Asp Leu Ala Thr Cys Ala
305                 310                 315                 320

Leu Ala Phe Arg Leu Leu Leu Ala His Gly Tyr Asp Val Ser Tyr Asp
                325                 330                 335

Pro Leu Lys Pro Phe Ala Glu Glu Ser Gly Phe Ser Asp Thr Leu Glu
            340                 345                 350

Gly Tyr Val Lys Asn Thr Phe Ser Val Leu Glu Leu Phe Lys Ala Ala
        355                 360                 365

Gln Ser Tyr Pro His Glu Ser Ala Leu Lys Lys Gln Cys Cys Trp Thr
    370                 375                 380

Lys Gln Tyr Leu Glu Met Glu Leu Ser Ser Trp Val Lys Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Arg Lys Ile Leu Asn
            420                 425                 430

Gly Ser Ala Val Glu Asn Thr Arg Val Thr Lys Thr Ser Tyr Arg Leu
        435                 440                 445

His Asn Ile Cys Thr Ser Asp Ile Leu Lys Leu Ala Val Asp Asp Phe
    450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
                485                 490                 495

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Gly Val Leu Thr Thr
        515                 520                 525

Val Val Asp Asp Phe Phe Asp Val Gly Gly Ser Lys Glu Glu Leu Glu
    530                 535                 540

Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
                565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
        595                 600                 605

Arg Glu Ala Glu Trp Ser Ser Asp Lys Ser Thr Pro Ser Leu Glu Asp
    610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
                645                 650                 655

Ser His Gln Tyr Asn Gln Leu Tyr Lys Leu Val Ser Thr Met Gly Arg
            660                 665                 670

Leu Leu Asn Asp Ile Gln Gly Phe Lys Arg Glu Ser Ala Glu Gly Lys
        675                 680                 685
```

```
Leu Asn Ala Val Ser Leu His Met Lys His Glu Arg Asp Asn Arg Ser
    690                 695                 700

Lys Glu Val Ile Ile Glu Ser Met Lys Gly Leu Ala Glu Arg Lys Arg
705                 710                 715                 720

Glu Glu Leu His Lys Leu Val Leu Glu Glu Lys Gly Ser Val Val Pro
                725                 730                 735

Arg Glu Cys Lys Glu Ala Phe Leu Lys Met Ser Lys Val Leu Asn Leu
            740                 745                 750

Phe Tyr Arg Lys Asp Asp Gly Phe Thr Ser Asn Asp Leu Met Ser Leu
        755                 760                 765

Val Lys Ser Val Ile Tyr Glu Pro Val Ser Leu Gln Lys Glu Ser Leu
    770                 775                 780

Thr
785


<210> SEQ ID NO 53
<211> LENGTH: 2952
<212> TYPE: DNA
<213> ORGANISM: Artificial Sequence
<220> FEATURE:
<223> OTHER INFORMATION: Codon-optimized CDPS-KS

<400> SEQUENCE: 53

atggaatttg atgaaccatt ggttgacgaa gcaagatctt tagtgcagcg tactttacaa     60

gattatgatg acagatacgg cttcggtact atgtcatgtg ctgcttatga tacagcctgg    120

gtgtctttag ttacaaaaac agtcgatggg agaaaacaat ggcttttccc agagtgtttt    180

gaatttctac tagaaacaca atctgatgcc ggaggatggg aaatcgggaa ttcagcacca    240

atcgacggta tattgaatac agctgcatcc ttacttgctc taaaacgtca cgttcaaact    300

gagcaaatca tccaacctca acatgaccat aaggatctag caggtagagc tgaacgtgcc    360

gctgcatctt tgagagcaca attggctgca ttggatgtgt ctacaactga acacgtcggt    420

tttgagataa ttgttcctgc aatgctagac ccattagaag ccgaagatcc atctctagtt    480

ttcgattttc cagctaggaa acctttgatg aagattcatg atgctaagat gagtagattc    540

aggccagaat acttgtatgg caaacaacca atgaccgcct tacattcatt agaggctttc    600

ataggcaaaa tcgacttcga taaggtaaga caccaccgta cccatgggtc tatgatgggt    660

tctccttcat ctaccgcagc ctacttaatg cacgcttcac aatgggatgg tgactcagag    720

gcttacctta gacacgtgat taaacacgca gcagggcagg gaactggtgc tgtaccatct    780

gctttcccat caacacattt tgagtcatct tggattctta ccacattgtt tagagctgga    840

ttttcagctt ctcatcttgc ctgtgatgag ttgaacaagt tggtcgagat acttgagggc    900

tcattcgaga aggaaggtgg ggcaatcggt tacgctccag ggtttcaagc agatgttgat    960

gatactgcta aaacaataag tacattagca gtccttggaa gagatgctac accaagacaa   1020

atgatcaagg tatttgaagc taatacacat tttagaacat accctggtga aagagatcct   1080

tctttgacag ctaattgtaa tgctctatca gccttactac accaaccaga tgcagcaatg   1140

tatggatctc aaattcaaaa gattaccaaa tttgtctgtg actattggtg gaagtctgat   1200

ggtaagatta aagataagtg gaacacttgc tacttgtacc catctgtctt attagttgag   1260

gttttggttg atcttgttag tttattggag cagggtaaat tgcctgatgt tttggatcaa   1320

gagcttcaat acagagtcgc catcacattg ttccaagcat gtttaaggcc attactagac   1380

caagatgccg aaggatcatg gaacaagtct atcgaagcca cagcctacgg catccttatc   1440
```

```
ctaactgaag ctaggagagt ttgtttcttc gacagattgt ctgagccatt gaatgaggca   1500

atccgtagag gtatcgcttt cgccgactct atgtctggaa ctgaagctca gttgaactac   1560

atttggatcg aaaaggttag ttacgcacct gcattattga ctaaatccta tttgttagca   1620

gcaagatggg ctgctaagtc tcctttaggc gcttccgtag gctcttcttt gtggactcca   1680

ccaagagaag gattggataa gcatgtcaga ttattccatc aagctgagtt attcagatcc   1740

cttccagaat gggaattaag agcctccatg attgaagcag ctttgttcac accacttcta   1800

agagcacata gactagacgt tttccctaga caagatgtag gtgaagacaa atatcttgat   1860

gtagttccat tcttttggac tgccgctaac aacagagata gaacttacgc ttccactcta   1920

ttcctttacg atatgtgttt tatcgcaatg ttaaacttcc agttagacga attcatggag   1980

gccacagccg gtatcttatt cagagatcat atggatgatt tgaggcaatt gattcatgat   2040

cttttggcag agaaaacttc cccaaagagt tctggtagaa gtagtcaggg cacaaaagat   2100

gctgactcag gtatagagga agacgtgtca atgtccgatt cagcttcaga ttcccaggat   2160

agaagtccag aatacgactt ggttttcagt gcattgagta cctttacaaa acatgtcttg   2220

caacacccat ctatacaaag tgcctctgta tgggatagaa aactacttgc tagagagatg   2280

aaggcttact tacttgctca tatccaacaa gcagaagatt caactccatt gtctgaattg   2340

aaagatgtgc ctcaaaagac tgatgtaaca agagtttcta catctactac taccttcttt   2400

aactgggtta gaacaacttc cgcagaccat atatcctgcc catactcctt ccactttgta   2460

gcatgccatc taggcgcagc attgtcacct aaagggtcta acggtgattg ctatccttca   2520

gctggtgaga agttcttggc agctgcagtc tgcagacatt tggccaccat gtgtagaatg   2580

tacaacgatc ttggatcagc tgaacgtgat tctgatgaag gtaatttgaa ctccttggac   2640

ttccctgaat tcgccgattc cgcaggaaac ggagggatag aaattcagaa ggccgctcta   2700

ttaaggttag ctgagtttga gagagattca tacttagagg ccttccgtcg tttacaagat   2760

gaatccaata gagttcacgg tccagccggt ggtgatgaag ccagattgtc cagaaggaga   2820

atggcaatcc ttgaattctt cgcccagcag gtagatttgt acggtcaagt atacgtcatt   2880

agggatattt ccgctcgtat tcctaaaaac gaggttgaga aaaagagaaa attggatgat   2940

gctttcaatt ga                                                      2952
```

<210> SEQ ID NO 54
<211> LENGTH: 983
<212> TYPE: PRT
<213> ORGANISM: Phomopsis amygdali

<400> SEQUENCE: 54

```
Met Glu Phe Asp Glu Pro Leu Val Asp Glu Ala Arg Ser Leu Val Gln
1               5                   10                  15

Arg Thr Leu Gln Asp Tyr Asp Asp Arg Tyr Gly Phe Gly Thr Met Ser
            20                  25                  30

Cys Ala Ala Tyr Asp Thr Ala Trp Val Ser Leu Val Thr Lys Thr Val
        35                  40                  45

Asp Gly Arg Lys Gln Trp Leu Phe Pro Glu Cys Phe Glu Phe Leu Leu
    50                  55                  60

Glu Thr Gln Ser Asp Ala Gly Gly Trp Glu Ile Gly Asn Ser Ala Pro
65                  70                  75                  80

Ile Asp Gly Ile Leu Asn Thr Ala Ala Ser Leu Leu Ala Leu Lys Arg
                85                  90                  95
```

```
His Val Gln Thr Glu Gln Ile Ile Gln Pro Gln His Asp His Lys Asp
            100                 105                 110

Leu Ala Gly Arg Ala Glu Arg Ala Ala Ala Ser Leu Arg Ala Gln Leu
        115                 120                 125

Ala Ala Leu Asp Val Ser Thr Thr Glu His Val Gly Phe Glu Ile Ile
    130                 135                 140

Val Pro Ala Met Leu Asp Pro Leu Glu Ala Glu Asp Pro Ser Leu Val
145                 150                 155                 160

Phe Asp Phe Pro Ala Arg Lys Pro Leu Met Lys Ile His Asp Ala Lys
                165                 170                 175

Met Ser Arg Phe Arg Pro Glu Tyr Leu Tyr Gly Lys Gln Pro Met Thr
            180                 185                 190

Ala Leu His Ser Leu Glu Ala Phe Ile Gly Lys Ile Asp Phe Asp Lys
        195                 200                 205

Val Arg His His Arg Thr His Gly Ser Met Met Gly Ser Pro Ser Ser
    210                 215                 220

Thr Ala Ala Tyr Leu Met His Ala Ser Gln Trp Asp Gly Asp Ser Glu
225                 230                 235                 240

Ala Tyr Leu Arg His Val Ile Lys His Ala Ala Gly Gln Gly Thr Gly
                245                 250                 255

Ala Val Pro Ser Ala Phe Pro Ser Thr His Phe Glu Ser Ser Trp Ile
            260                 265                 270

Leu Thr Thr Leu Phe Arg Ala Gly Phe Ser Ala Ser His Leu Ala Cys
        275                 280                 285

Asp Glu Leu Asn Lys Leu Val Glu Ile Leu Glu Gly Ser Phe Glu Lys
    290                 295                 300

Glu Gly Gly Ala Ile Gly Tyr Ala Pro Gly Phe Gln Ala Asp Val Asp
305                 310                 315                 320

Asp Thr Ala Lys Thr Ile Ser Thr Leu Ala Val Leu Gly Arg Asp Ala
                325                 330                 335

Thr Pro Arg Gln Met Ile Lys Val Phe Glu Ala Asn Thr His Phe Arg
            340                 345                 350

Thr Tyr Pro Gly Glu Arg Asp Pro Ser Leu Thr Ala Asn Cys Asn Ala
        355                 360                 365

Leu Ser Ala Leu Leu His Gln Pro Asp Ala Ala Met Tyr Gly Ser Gln
    370                 375                 380

Ile Gln Lys Ile Thr Lys Phe Val Cys Asp Tyr Trp Trp Lys Ser Asp
385                 390                 395                 400

Gly Lys Ile Lys Asp Lys Trp Asn Thr Cys Tyr Leu Tyr Pro Ser Val
                405                 410                 415

Leu Leu Val Glu Val Leu Val Asp Leu Val Ser Leu Leu Glu Gln Gly
            420                 425                 430

Lys Leu Pro Asp Val Leu Asp Gln Glu Leu Gln Tyr Arg Val Ala Ile
        435                 440                 445

Thr Leu Phe Gln Ala Cys Leu Arg Pro Leu Leu Asp Gln Asp Ala Glu
    450                 455                 460

Gly Ser Trp Asn Lys Ser Ile Glu Ala Thr Ala Tyr Gly Ile Leu Ile
465                 470                 475                 480

Leu Thr Glu Ala Arg Arg Val Cys Phe Phe Asp Arg Leu Ser Glu Pro
                485                 490                 495

Leu Asn Glu Ala Ile Arg Arg Gly Ile Ala Phe Ala Asp Ser Met Ser
            500                 505                 510

Gly Thr Glu Ala Gln Leu Asn Tyr Ile Trp Ile Glu Lys Val Ser Tyr
```

```
        515                 520                 525

Ala Pro Ala Leu Leu Thr Lys Ser Tyr Leu Leu Ala Ala Arg Trp Ala
    530                 535                 540

Ala Lys Ser Pro Leu Gly Ala Ser Val Gly Ser Ser Leu Trp Thr Pro
545                 550                 555                 560

Pro Arg Glu Gly Leu Asp Lys His Val Arg Leu Phe His Gln Ala Glu
                565                 570                 575

Leu Phe Arg Ser Leu Pro Glu Trp Glu Leu Arg Ala Ser Met Ile Glu
            580                 585                 590

Ala Ala Leu Phe Thr Pro Leu Leu Arg Ala His Arg Leu Asp Val Phe
        595                 600                 605

Pro Arg Gln Asp Val Gly Glu Asp Lys Tyr Leu Asp Val Val Pro Phe
    610                 615                 620

Phe Trp Thr Ala Ala Asn Asn Arg Asp Arg Thr Tyr Ala Ser Thr Leu
625                 630                 635                 640

Phe Leu Tyr Asp Met Cys Phe Ile Ala Met Leu Asn Phe Gln Leu Asp
                645                 650                 655

Glu Phe Met Glu Ala Thr Ala Gly Ile Leu Phe Arg Asp His Met Asp
            660                 665                 670

Asp Leu Arg Gln Leu Ile His Asp Leu Leu Ala Glu Lys Thr Ser Pro
        675                 680                 685

Lys Ser Ser Gly Arg Ser Ser Gln Gly Thr Lys Asp Ala Asp Ser Gly
    690                 695                 700

Ile Glu Glu Asp Val Ser Met Ser Asp Ser Ala Ser Asp Ser Gln Asp
705                 710                 715                 720

Arg Ser Pro Glu Tyr Asp Leu Val Phe Ser Ala Leu Ser Thr Phe Thr
                725                 730                 735

Lys His Val Leu Gln His Pro Ser Ile Gln Ser Ala Ser Val Trp Asp
            740                 745                 750

Arg Lys Leu Leu Ala Arg Glu Met Lys Ala Tyr Leu Leu Ala His Ile
        755                 760                 765

Gln Gln Ala Glu Asp Ser Thr Pro Leu Ser Glu Leu Lys Asp Val Pro
    770                 775                 780

Gln Lys Thr Asp Val Thr Arg Val Ser Thr Ser Thr Thr Thr Phe Phe
785                 790                 795                 800

Asn Trp Val Arg Thr Thr Ser Ala Asp His Ile Ser Cys Pro Tyr Ser
                805                 810                 815

Phe His Phe Val Ala Cys His Leu Gly Ala Ala Leu Ser Pro Lys Gly
            820                 825                 830

Ser Asn Gly Asp Cys Tyr Pro Ser Ala Gly Glu Lys Phe Leu Ala Ala
        835                 840                 845

Ala Val Cys Arg His Leu Ala Thr Met Cys Arg Met Tyr Asn Asp Leu
    850                 855                 860

Gly Ser Ala Glu Arg Asp Ser Asp Glu Gly Asn Leu Asn Ser Leu Asp
865                 870                 875                 880

Phe Pro Glu Phe Ala Asp Ser Ala Gly Asn Gly Gly Ile Glu Ile Gln
                885                 890                 895

Lys Ala Ala Leu Leu Arg Leu Ala Glu Phe Glu Arg Asp Ser Tyr Leu
            900                 905                 910

Glu Ala Phe Arg Arg Leu Gln Asp Glu Ser Asn Arg Val His Gly Pro
        915                 920                 925

Ala Gly Gly Asp Glu Ala Arg Leu Ser Arg Arg Arg Met Ala Ile Leu
    930                 935                 940
```

Glu Phe Phe Ala Gln Gln Val Asp Leu Tyr Gly Gln Val Tyr Val Ile
945 950 955 960

Arg Asp Ile Ser Ala Arg Ile Pro Lys Asn Glu Val Glu Lys Lys Arg
965 970 975

Lys Leu Asp Asp Ala Phe Asn
980

<210> SEQ ID NO 55
<211> LENGTH: 2646
<212> TYPE: DNA
<213> ORGANISM: Artificial Sequence
<220> FEATURE:
<223> OTHER INFORMATION: Codon-optimized CDPS-KS

<400> SEQUENCE: 55
atggcttcta gtacacttat ccaaaacaga tcatgtggcg tcacatcatc tatgtcaagt 60
tttcaaatct tcagaggtca accactaaga tttcctggca ctagaacccc agctgcagtt 120
caatgcttga aaaagaggag atgccttagg ccaaccgaat ccgtactaga atcatctcct 180
ggctctggtt catatagaat agtaactggc ccttctggaa ttaaccctag ttctaacggg 240
cacttgcaag agggttcctt gactcacagg ttaccaatac caatggaaaa atctatcgat 300
aacttccaat ctactctata tgtgtcagat atttggtctg aaacactaca gagaactgaa 360
tgtttgctac aagtaactga aaacgtccag atgaatgagt ggattgagga aattagaatg 420
tactttagaa atatgacttt aggtgaaatt tccatgtccc cttacgacac tgcttgggtg 480
gctagagttc cagcgttgga cggttctcat gggcctcaat tccacagatc tttgcaatgg 540
attatcgaca accaattacc agatggggac tggggcgaac cttctctttt cttgggttac 600
gatagagttt gtaatacttt agcctgtgtg attgcgttga aaacatgggg tgttggggca 660
caaaacgttg aaagaggaat tcagttccta caatctaaca tatacaagat ggaggaagat 720
gacgctaatc atatgccaat aggattcgaa atcgtattcc ctgctatgat ggaagatgcc 780
aaagcattag gtttggattt gccatacgat gctactattt tgcaacagat ttcagccgaa 840
agagagaaaa agatgaaaaa gatcccaatg gcaatggtgt acaaataccc aaccacttta 900
cttcactcct tagaaggctt gcatagagaa gttgattgga ataagttgtt acaattacaa 960
tctgaaaatg gtagttttct ttattcacct gcttcaaccg catgcgcctt aatgtacact 1020
aaggacgtta aatgttttga ttacttaaac cagttgttga tcaagttcga ccacgcatgc 1080
ccaaatgtat atccagtcga tctattcgaa agattatgga tggttgacag attgcagaga 1140
ttagggatct ccagatactt tgaaagagag attagagatt gtttacaata cgtctacaga 1200
tattggaaag attgtggaat cggatgggct tctaactctt ccgtacaaga tgttgatgat 1260
acagccatgg cgtttagact tttaaggact catggtttcg acgtaaagga agattgcttt 1320
agacagtttt tcaaggacgg agaattcttc tgcttcgcag gccaatcatc tcaagcagtt 1380
acaggcatgt ttaatctttc aagagccagt caaacattgt ttccaggaga atctttattg 1440
aaaaaggcta gaaccttctc tagaaacttc ttgagaacaa agcatgagaa caacgaatgt 1500
ttcgataaat ggatcattac taaagatttg gctggtgaag tcgagtataa cttgaccttc 1560
ccatggtatg cctctttgcc tagattagaa cataggacat acttagatca atatggaatc 1620
gatgatatct ggataggcaa atctttatac aaaatgcctg ctgttaccaa cgaagttttc 1680
ctaaagttgg caaaggcaga ctttaacatg tgtcaagctc tacacaaaaa ggaattggaa 1740
caagtgataa agtggaacgc gtcctgtcaa ttcagagatc ttgaattcgc cagacaaaaa 1800

```
tcagtagaat gctattttgc tggtgcagcc acaatgttcg aaccagaaat ggttcaagct   1860

agattagtct gggcaagatg ttgtgtattg acaactgtct tagacgatta ctttgaccac   1920

gggacacctg ttgaggaact tagagtgttt gttcaagctg tcagaacatg gaatccagag   1980

ttgatcaacg gtttgccaga gcaagctaaa atcttgttta tgggcttata caaaaacagtt  2040

aacacaattg cagaggaagc attcatggca cagaaaagag acgtccatca tcatttgaaa   2100

cactattggg acaagttgat aacaagtgcc ctaaaggagg ccgaatgggc agagtcaggt   2160

tacgtcccaa catttgatga atacatggaa gtagctgaaa tttctgttgc tctagaacca   2220

attgtctgta gtaccttgtt ctttgcgggt catagactag atgaggatgt tctagatagt   2280

tacgattacc atctagttat gcatttggta aacagagtcg gtagaatctt gaatgatata   2340

caaggcatga agagggaggc ttcacaaggt aagatctcat cagttcaaat ctacatggag   2400

gaacatccat ctgttccatc tgaggccatg gcgatcgctc atcttcaaga gttagttgat   2460

aattcaatgc agcaattgac atacgaagtt cttaggttca ctgcggttcc aaaaagttgt   2520

aagagaatcc acttgaatat ggctaaaatc atgcatgcct tctacaagga tactgatgga   2580

ttctcatccc ttactgcaat gacaggattc gtcaaaaagg ttcttttcga acctgtgcct   2640

gagtaa                                                              2646
```

<210> SEQ ID NO 56
<211> LENGTH: 881
<212> TYPE: PRT
<213> ORGANISM: Physcomitrella patens

<400> SEQUENCE: 56

```
Met Ala Ser Ser Thr Leu Ile Gln Asn Arg Ser Cys Gly Val Thr Ser
1               5                   10                  15

Ser Met Ser Ser Phe Gln Ile Phe Arg Gly Gln Pro Leu Arg Phe Pro
            20                  25                  30

Gly Thr Arg Thr Pro Ala Ala Val Gln Cys Leu Lys Lys Arg Arg Cys
        35                  40                  45

Leu Arg Pro Thr Glu Ser Val Leu Glu Ser Ser Pro Gly Ser Gly Ser
    50                  55                  60

Tyr Arg Ile Val Thr Gly Pro Ser Gly Ile Asn Pro Ser Ser Asn Gly
65                  70                  75                  80

His Leu Gln Glu Gly Ser Leu Thr His Arg Leu Pro Ile Pro Met Glu
                85                  90                  95

Lys Ser Ile Asp Asn Phe Gln Ser Thr Leu Tyr Val Ser Asp Ile Trp
            100                 105                 110

Ser Glu Thr Leu Gln Arg Thr Glu Cys Leu Leu Gln Val Thr Glu Asn
        115                 120                 125

Val Gln Met Asn Glu Trp Ile Glu Glu Ile Arg Met Tyr Phe Arg Asn
    130                 135                 140

Met Thr Leu Gly Glu Ile Ser Met Ser Pro Tyr Asp Thr Ala Trp Val
145                 150                 155                 160

Ala Arg Val Pro Ala Leu Asp Gly Ser His Gly Pro Gln Phe His Arg
                165                 170                 175

Ser Leu Gln Trp Ile Ile Asp Asn Gln Leu Pro Asp Gly Asp Trp Gly
            180                 185                 190

Glu Pro Ser Leu Phe Leu Gly Tyr Asp Arg Val Cys Asn Thr Leu Ala
        195                 200                 205

Cys Val Ile Ala Leu Lys Thr Trp Gly Val Gly Ala Gln Asn Val Glu
```

-continued

```
    210                 215                 220

Arg Gly Ile Gln Phe Leu Gln Ser Asn Ile Tyr Lys Met Glu Glu Asp
225                 230                 235                 240

Asp Ala Asn His Met Pro Ile Gly Phe Glu Ile Val Phe Pro Ala Met
                245                 250                 255

Met Glu Asp Ala Lys Ala Leu Gly Leu Asp Leu Pro Tyr Asp Ala Thr
            260                 265                 270

Ile Leu Gln Gln Ile Ser Ala Glu Arg Glu Lys Lys Met Lys Lys Ile
        275                 280                 285

Pro Met Ala Met Val Tyr Lys Tyr Pro Thr Thr Leu Leu His Ser Leu
    290                 295                 300

Glu Gly Leu His Arg Glu Val Asp Trp Asn Lys Leu Leu Gln Leu Gln
305                 310                 315                 320

Ser Glu Asn Gly Ser Phe Leu Tyr Ser Pro Ala Ser Thr Ala Cys Ala
                325                 330                 335

Leu Met Tyr Thr Lys Asp Val Lys Cys Phe Asp Tyr Leu Asn Gln Leu
            340                 345                 350

Leu Ile Lys Phe Asp His Ala Cys Pro Asn Val Tyr Pro Val Asp Leu
        355                 360                 365

Phe Glu Arg Leu Trp Met Val Asp Arg Leu Gln Arg Leu Gly Ile Ser
    370                 375                 380

Arg Tyr Phe Glu Arg Glu Ile Arg Asp Cys Leu Gln Tyr Val Tyr Arg
385                 390                 395                 400

Tyr Trp Lys Asp Cys Gly Ile Gly Trp Ala Ser Asn Ser Ser Val Gln
                405                 410                 415

Asp Val Asp Asp Thr Ala Met Ala Phe Arg Leu Leu Arg Thr His Gly
            420                 425                 430

Phe Asp Val Lys Glu Asp Cys Phe Arg Gln Phe Phe Lys Asp Gly Glu
        435                 440                 445

Phe Phe Cys Phe Ala Gly Gln Ser Ser Gln Ala Val Thr Gly Met Phe
    450                 455                 460

Asn Leu Ser Arg Ala Ser Gln Thr Leu Phe Pro Gly Glu Ser Leu Leu
465                 470                 475                 480

Lys Lys Ala Arg Thr Phe Ser Arg Asn Phe Leu Arg Thr Lys His Glu
                485                 490                 495

Asn Asn Glu Cys Phe Asp Lys Trp Ile Ile Thr Lys Asp Leu Ala Gly
            500                 505                 510

Glu Val Glu Tyr Asn Leu Thr Phe Pro Trp Tyr Ala Ser Leu Pro Arg
        515                 520                 525

Leu Glu His Arg Thr Tyr Leu Asp Gln Tyr Gly Ile Asp Asp Ile Trp
    530                 535                 540

Ile Gly Lys Ser Leu Tyr Lys Met Pro Ala Val Thr Asn Glu Val Phe
545                 550                 555                 560

Leu Lys Leu Ala Lys Ala Asp Phe Asn Met Cys Gln Ala Leu His Lys
                565                 570                 575

Lys Glu Leu Glu Gln Val Ile Lys Trp Asn Ala Ser Cys Gln Phe Arg
            580                 585                 590

Asp Leu Glu Phe Ala Arg Gln Lys Ser Val Glu Cys Tyr Phe Ala Gly
        595                 600                 605

Ala Ala Thr Met Phe Glu Pro Glu Met Val Gln Ala Arg Leu Val Trp
    610                 615                 620

Ala Arg Cys Cys Val Leu Thr Thr Val Leu Asp Asp Tyr Phe Asp His
625                 630                 635                 640
```

Gly Thr Pro Val Glu Glu Leu Arg Val Phe Val Gln Ala Val Arg Thr
645 650 655

Trp Asn Pro Glu Leu Ile Asn Gly Leu Pro Glu Gln Ala Lys Ile Leu
660 665 670

Phe Met Gly Leu Tyr Lys Thr Val Asn Thr Ile Ala Glu Glu Ala Phe
675 680 685

Met Ala Gln Lys Arg Asp Val His His His Leu Lys His Tyr Trp Asp
690 695 700

Lys Leu Ile Thr Ser Ala Leu Lys Glu Ala Glu Trp Ala Glu Ser Gly
705 710 715 720

Tyr Val Pro Thr Phe Asp Glu Tyr Met Glu Val Ala Glu Ile Ser Val
725 730 735

Ala Leu Glu Pro Ile Val Cys Ser Thr Leu Phe Phe Ala Gly His Arg
740 745 750

Leu Asp Glu Asp Val Leu Asp Ser Tyr Asp Tyr His Leu Val Met His
755 760 765

Leu Val Asn Arg Val Gly Arg Ile Leu Asn Asp Ile Gln Gly Met Lys
770 775 780

Arg Glu Ala Ser Gln Gly Lys Ile Ser Ser Val Gln Ile Tyr Met Glu
785 790 795 800

Glu His Pro Ser Val Pro Ser Glu Ala Met Ala Ile Ala His Leu Gln
805 810 815

Glu Leu Val Asp Asn Ser Met Gln Gln Leu Thr Tyr Glu Val Leu Arg
820 825 830

Phe Thr Ala Val Pro Lys Ser Cys Lys Arg Ile His Leu Asn Met Ala
835 840 845

Lys Ile Met His Ala Phe Tyr Lys Asp Thr Asp Gly Phe Ser Ser Leu
850 855 860

Thr Ala Met Thr Gly Phe Val Lys Lys Val Leu Phe Glu Pro Val Pro
865 870 875 880

Glu

<210> SEQ ID NO 57
<211> LENGTH: 2859
<212> TYPE: DNA
<213> ORGANISM: Artificial Sequence
<220> FEATURE:
<223> OTHER INFORMATION: Codon-optimized CDPS-KS

<400> SEQUENCE: 57
atgcctggta aaattgaaaa tggtacccca aaggacctca agactggaaa tgattttgtt 60
tctgctgcta agagtttact agatcgagct ttcaaaagtc atcattccta ctacggatta 120
tgctcaactt catgtcaagt ttatgataca gcttgggttg caatgattcc aaaaacaaga 180
gataatgtaa aacagtggtt gtttccagaa tgtttccatt acctcttaaa aacacaagcc 240
gcagatggct catggggttc attgcctaca acacagacag cgggtatcct agatacagcc 300
tcagctgtgc tggcattatt gtgccacgca caagagcctt tacaaatatt ggatgtatct 360
ccagatgaaa tggggttgag aatagaacac ggtgtcacat ccttgaaacg tcaattagca 420
gtttggaatg atgtggagga caccaaccat attggcgtcg agtttatcat accagcctta 480
ctttccatgc tagaaaagga attagatgtt ccatcttttg aatttccatg taggtccatc 540
ttagagagaa tgcacgggga gaaattaggt catttcgacc tggaacaagt ttacggcaag 600
ccaagctcat tgttgcactc attggaagca tttctcggta agctagattt tgatcgacta 660

```
tcacatcacc tataccacgg cagtatgatg gcatctccat cttcaacggc tgcttatctt    720
attggggcta caaaatggga tgacgaagcc gaagattacc taagacatgt aatgcgtaat    780
ggtgcaggac atgggaatgg aggtatttct ggtacatttc caactactca tttcgaatgt    840
agctggatta tagcaacgtt gttaaaggtt ggctttactt tgaagcaaat tgacggcgat    900
ggcttaagag gtttatcaac catcttactt gaggcgcttc gtgatgagaa tggtgtcata    960
ggctttgccc ctagaacagc agatgtagat gacacagcca aagctctatt ggccttgtca   1020
ttggtaaacc agccagtgtc acctgatatc atgattaagg tctttgaggg caaagaccat   1080
tttaccactt ttggttcaga aagagatcca tcattgactt ccaacctgca cgtccttta    1140
tctttactta aacaatctaa cttgtctcaa taccatcctc aaatcctcaa aacaacatta   1200
ttcacttgta gatggtggtg gggttccgat cattgtgtca aagacaaatg gaatttgagt   1260
cacctatatc caactatgtt gttggttgaa gccttcactg aagtgctcca tctcattgac   1320
ggtggtgaat tgtctagtct gtttgatgaa tcctttaagt gtaagattgg tcttagcatc   1380
tttcaagcgg tacttagaat aatcctcacc caagacaacg acggctcttg gagaggatac   1440
agagaacaga cgtgttacgc aatattggct ttagttcaag cgagacatgt atgcttttc    1500
actcacatgg ttgacagact gcaatcatgt gttgatcgag gtttctcatg gttgaaatct   1560
tgctcttttc attctcaaga cctgacttgg acctctaaaa cagcttatga agtgggtttc   1620
gtagctgaag catataaact agctgcttta caatctgctt ccctggaggt tcctgctgcc   1680
accattggac attctgtcac gtctgccgtt ccatcaagtg atcttgaaaa atacatgaga   1740
ttggtgagaa aaactgcgtt attctctcca ctggatgagt ggggtctaat ggcttctatc   1800
atcgaatctt catttttcgt accattactg caggcacaaa gagttgaaat ataccctaga   1860
gataatatca aggtggacga agataagtac ttgtctatta tcccattcac atgggtcgga   1920
tgcaataata ggtctagaac tttcgcaagt aacagatggc tatacgatat gatgtacctt   1980
tcattactcg gctatcaaac cgacgagtac atggaagctg tagctgggcc agtgtttggg   2040
gatgtttcct tgttacatca aacaattgat aaggtgattg ataatacaat gggtaacctt   2100
gcgagagcca atggaacagt acacagtggt aatggacatc agcacgaatc tcctaatata   2160
ggtcaagtcg aggacacctt gactcgtttc acaaattcag tcttgaatca caaagacgtc   2220
cttaactcta gctcatctga tcaagatact ttgagaagag agtttagaac attcatgcac   2280
gctcatataa cacaaatcga agataactca cgattcagta agcaagcctc atccgatgcg   2340
ttttcctctc ctgaacaatc ttactttcaa tgggtgaact caactggtgg ctcacatgtc   2400
gcttgcgcct attcatttgc cttctctaat tgcctcatgt ctgcaaattt gttgcagggt   2460
aaagacgcat ttccaagcgg aacgcaaaag tacttaatct cctctgttat gagacatgcc   2520
acaaacatgt gtagaatgta taacgacttt ggctctattg ccagagacaa cgctgagaga   2580
aatgttaata gtattcattt tcctgagttt actctctgta acggaacttc tcaaaaccta   2640
gatgaaagga aggaaagact tctgaaaatc gcaacttacg aacaagggta tttggataga   2700
gcactagagg ccttggaaag acagagtaga gatgatgccg gagacagagc tggatctaaa   2760
gatatgagaa agttgaaaat cgttaagtta ttctgtgatg ttacggactt atacgatcag   2820
ctctacgtta tcaaagattt gtcatcctct atgaagtaa                          2859
```

<210> SEQ ID NO 58
<211> LENGTH: 952
<212> TYPE: PRT

<213> ORGANISM: Gibberella fujikuroi

<400> SEQUENCE: 58

```
Met Pro Gly Lys Ile Glu Asn Gly Thr Pro Lys Asp Leu Lys Thr Gly
1               5                   10                  15

Asn Asp Phe Val Ser Ala Ala Lys Ser Leu Leu Asp Arg Ala Phe Lys
            20                  25                  30

Ser His His Ser Tyr Tyr Gly Leu Cys Ser Thr Ser Cys Gln Val Tyr
        35                  40                  45

Asp Thr Ala Trp Val Ala Met Ile Pro Lys Thr Arg Asp Asn Val Lys
    50                  55                  60

Gln Trp Leu Phe Pro Glu Cys Phe His Tyr Leu Leu Lys Thr Gln Ala
65                  70                  75                  80

Ala Asp Gly Ser Trp Gly Ser Leu Pro Thr Thr Gln Thr Ala Gly Ile
                85                  90                  95

Leu Asp Thr Ala Ser Ala Val Leu Ala Leu Leu Cys His Ala Gln Glu
            100                 105                 110

Pro Leu Gln Ile Leu Asp Val Ser Pro Asp Glu Met Gly Leu Arg Ile
        115                 120                 125

Glu His Gly Val Thr Ser Leu Lys Arg Gln Leu Ala Val Trp Asn Asp
    130                 135                 140

Val Glu Asp Thr Asn His Ile Gly Val Glu Phe Ile Ile Pro Ala Leu
145                 150                 155                 160

Leu Ser Met Leu Glu Lys Glu Leu Asp Val Pro Ser Phe Glu Phe Pro
                165                 170                 175

Cys Arg Ser Ile Leu Glu Arg Met His Gly Glu Lys Leu Gly His Phe
            180                 185                 190

Asp Leu Glu Gln Val Tyr Gly Lys Pro Ser Ser Leu Leu His Ser Leu
        195                 200                 205

Glu Ala Phe Leu Gly Lys Leu Asp Phe Asp Arg Leu Ser His His Leu
    210                 215                 220

Tyr His Gly Ser Met Met Ala Ser Pro Ser Ser Thr Ala Ala Tyr Leu
225                 230                 235                 240

Ile Gly Ala Thr Lys Trp Asp Asp Glu Ala Glu Asp Tyr Leu Arg His
                245                 250                 255

Val Met Arg Asn Gly Ala Gly His Gly Asn Gly Gly Ile Ser Gly Thr
            260                 265                 270

Phe Pro Thr Thr His Phe Glu Cys Ser Trp Ile Ile Ala Thr Leu Leu
        275                 280                 285

Lys Val Gly Phe Thr Leu Lys Gln Ile Asp Gly Asp Gly Leu Arg Gly
    290                 295                 300

Leu Ser Thr Ile Leu Leu Glu Ala Leu Arg Asp Glu Asn Gly Val Ile
305                 310                 315                 320

Gly Phe Ala Pro Arg Thr Ala Asp Val Asp Asp Thr Ala Lys Ala Leu
                325                 330                 335

Leu Ala Leu Ser Leu Val Asn Gln Pro Val Ser Pro Asp Ile Met Ile
            340                 345                 350

Lys Val Phe Glu Gly Lys Asp His Phe Thr Thr Phe Gly Ser Glu Arg
        355                 360                 365

Asp Pro Ser Leu Thr Ser Asn Leu His Val Leu Leu Ser Leu Leu Lys
    370                 375                 380

Gln Ser Asn Leu Ser Gln Tyr His Pro Gln Ile Leu Lys Thr Thr Leu
385                 390                 395                 400
```

```
Phe Thr Cys Arg Trp Trp Trp Gly Ser Asp His Cys Val Lys Asp Lys
                405                 410                 415

Trp Asn Leu Ser His Leu Tyr Pro Thr Met Leu Leu Val Glu Ala Phe
            420                 425                 430

Thr Glu Val Leu His Leu Ile Asp Gly Gly Glu Leu Ser Ser Leu Phe
        435                 440                 445

Asp Glu Ser Phe Lys Cys Lys Ile Gly Leu Ser Ile Phe Gln Ala Val
    450                 455                 460

Leu Arg Ile Ile Leu Thr Gln Asp Asn Asp Gly Ser Trp Arg Gly Tyr
465                 470                 475                 480

Arg Glu Gln Thr Cys Tyr Ala Ile Leu Ala Leu Val Gln Ala Arg His
                485                 490                 495

Val Cys Phe Phe Thr His Met Val Asp Arg Leu Gln Ser Cys Val Asp
            500                 505                 510

Arg Gly Phe Ser Trp Leu Lys Ser Cys Ser Phe His Ser Gln Asp Leu
        515                 520                 525

Thr Trp Thr Ser Lys Thr Ala Tyr Glu Val Gly Phe Val Ala Glu Ala
    530                 535                 540

Tyr Lys Leu Ala Ala Leu Gln Ser Ala Ser Leu Glu Val Pro Ala Ala
545                 550                 555                 560

Thr Ile Gly His Ser Val Thr Ser Ala Val Pro Ser Ser Asp Leu Glu
                565                 570                 575

Lys Tyr Met Arg Leu Val Arg Lys Thr Ala Leu Phe Ser Pro Leu Asp
            580                 585                 590

Glu Trp Gly Leu Met Ala Ser Ile Ile Glu Ser Ser Phe Phe Val Pro
        595                 600                 605

Leu Leu Gln Ala Gln Arg Val Glu Ile Tyr Pro Arg Asp Asn Ile Lys
    610                 615                 620

Val Asp Glu Asp Lys Tyr Leu Ser Ile Ile Pro Phe Thr Trp Val Gly
625                 630                 635                 640

Cys Asn Asn Arg Ser Arg Thr Phe Ala Ser Asn Arg Trp Leu Tyr Asp
                645                 650                 655

Met Met Tyr Leu Ser Leu Leu Gly Tyr Gln Thr Asp Glu Tyr Met Glu
            660                 665                 670

Ala Val Ala Gly Pro Val Phe Gly Asp Val Ser Leu Leu His Gln Thr
        675                 680                 685

Ile Asp Lys Val Ile Asp Asn Thr Met Gly Asn Leu Ala Arg Ala Asn
    690                 695                 700

Gly Thr Val His Ser Gly Asn Gly His Gln His Glu Ser Pro Asn Ile
705                 710                 715                 720

Gly Gln Val Glu Asp Thr Leu Thr Arg Phe Thr Asn Ser Val Leu Asn
                725                 730                 735

His Lys Asp Val Leu Asn Ser Ser Ser Ser Asp Gln Asp Thr Leu Arg
            740                 745                 750

Arg Glu Phe Arg Thr Phe Met His Ala His Ile Thr Gln Ile Glu Asp
        755                 760                 765

Asn Ser Arg Phe Ser Lys Gln Ala Ser Ser Asp Ala Phe Ser Ser Pro
    770                 775                 780

Glu Gln Ser Tyr Phe Gln Trp Val Asn Ser Thr Gly Gly Ser His Val
785                 790                 795                 800

Ala Cys Ala Tyr Ser Phe Ala Phe Ser Asn Cys Leu Met Ser Ala Asn
                805                 810                 815

Leu Leu Gln Gly Lys Asp Ala Phe Pro Ser Gly Thr Gln Lys Tyr Leu
```

820 825 830

Ile Ser Ser Val Met Arg His Ala Thr Asn Met Cys Arg Met Tyr Asn
835 840 845

Asp Phe Gly Ser Ile Ala Arg Asp Asn Ala Glu Arg Asn Val Asn Ser
850 855 860

Ile His Phe Pro Glu Phe Thr Leu Cys Asn Gly Thr Ser Gln Asn Leu
865 870 875 880

Asp Glu Arg Lys Glu Arg Leu Leu Lys Ile Ala Thr Tyr Glu Gln Gly
885 890 895

Tyr Leu Asp Arg Ala Leu Glu Ala Leu Glu Arg Gln Ser Arg Asp Asp
900 905 910

Ala Gly Asp Arg Ala Gly Ser Lys Asp Met Arg Lys Leu Lys Ile Val
915 920 925

Lys Leu Phe Cys Asp Val Thr Asp Leu Tyr Asp Gln Leu Tyr Val Ile
930 935 940

Lys Asp Leu Ser Ser Ser Met Lys
945 950

<210> SEQ ID NO 59
<211> LENGTH: 1542
<212> TYPE: DNA
<213> ORGANISM: Artificial Sequence
<220> FEATURE:
<223> OTHER INFORMATION: Codon-optimized KO

<400> SEQUENCE: 59
atggatgctg tgacgggttt gttaactgtc ccagcaaccg ctataactat tggtggaact 60
gctgtagcat tggcggtagc gctaatcttt tggtacctga aatcctacac atcagctaga 120
agatcccaat caaatcatct tccaagagtg cctgaagtcc caggtgttcc attgttagga 180
aatctgttac aattgaagga gaaaaagcca tacatgactt ttacgagatg ggcagcgaca 240
tatggaccta tctatagtat caaaactggg gctacaagta tggttgtggt atcatctaat 300
gagatagcca aggaggcatt ggtgaccaga ttccaatcca tatctacaag gaacttatct 360
aaagccctga aagtacttac agcagataag acaatggtcg caatgtcaga ttatgatgat 420
tatcataaaa cagttaagag acacatactg accgccgtct tgggtcctaa tgcacagaaa 480
aagcatagaa ttcacagaga tatcatgatg gataacatat ctactcaact tcatgaattc 540
gtgaaaaaca acccagaaca ggaagaggta gaccttagaa aaatctttca atctgagtta 600
ttcggcttag ctatgagaca agccttagga aaggatgttg aaagtttgta cgttgaagac 660
ctgaaaatca ctatgaatag agacgaaatc tttcaagtcc ttgttgttga tccaatgatg 720
ggagcaatcg atgttgattg gagagacttc tttccatacc taaagtgggt cccaaacaaa 780
aagttcgaaa atactattca acaaatgtac atcagaagag aagctgttat gaaatcttta 840
atcaaagagc acaaaaagag aatagcgtca ggcgaaaagc taaatagtta tatcgattac 900
cttttatctg aagctcaaac tttaaccgat cagcaactat tgatgtcctt gtgggaacca 960
atcattgaat cttcagatac aacaatggtc acaacagaat gggcaatgta cgaattagct 1020
aaaaacccta aattgcaaga taggttgtac agagacatta agtccgtctg tggatctgaa 1080
aagataaccg aagagcatct atcacagctg ccttacatta cagctatttt ccacgaaaca 1140
ctgagaagac actcaccagt tcctatcatt cctctaagac atgtacatga agataccgtt 1200
ctaggcggct accatgttcc tgctggcaca gaacttgccg ttaacatcta cggttgcaac 1260
atggacaaaa acgtttggga aaatccagag gaatggaacc cagaaagatt catgaaagag 1320

```
aatgagacaa ttgattttca aaagacgatg gccttcggtg gtggtaagag agtttgtgct   1380

ggttccttgc aagccctttt aactgcatct attgggattg ggagaatggt tcaagagttc   1440

gaatggaaac tgaaggatat gactcaagag gaagtgaaca cgataggcct aactacacaa   1500

atgttaagac cattgagagc tattatcaaa cctaggatct aa                      1542


<210> SEQ ID NO 60
<211> LENGTH: 513
<212> TYPE: PRT
<213> ORGANISM: Stevia rebaudiana

<400> SEQUENCE: 60

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335
```

```
Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
            500                 505                 510

Ile
```

<210> SEQ ID NO 61
<211> LENGTH: 1566
<212> TYPE: DNA
<213> ORGANISM: Artificial Sequence
<220> FEATURE:
<223> OTHER INFORMATION: Codon-optimized KO

<400> SEQUENCE: 61

```
aagcttacta gtaaaatgga cggtgtcatc gatatgcaaa ccattccatt gagaaccgct      60

attgctattg gtggtactgc tgttgctttg gttgttgcat tatacttttg gttcttgaga     120

tcctacgctt ccccatctca tcattctaat catttgccac cagtacctga agttccaggt     180

gttccagttt tgggtaattt gttgcaattg aaagaaaaaa agccttacat gaccttcacc     240

aagtgggctg aaatgtatgg tccaatctac tctattagaa ctggtgctac ttccatggtt     300

gttgtctctt ctaacgaaat cgccaaagaa gttgttgtta ccagattccc atctatctct     360

accagaaaat tgtcttacgc cttgaaggtt ttgaccgaag ataagtctat ggttgccatg     420

tctgattatc acgattacca taagaccgtc aagagacata ttttgactgc tgttttgggt     480

ccaaacgccc aaaaaaagtt tagagcacat agagacacca tgatggaaaa cgtttccaat     540

gaattgcatg ccttcttcga aaagaaccca aatcaagaag tcaacttgag aaagatcttc     600

caatcccaat tattcggttt ggctatgaag caagccttgg gtaaagatgt tgaatccatc     660

tacgttaagg atttggaaac caccatgaag agagaagaaa tcttcgaagt tttggttgtc     720

gatccaatga tgggtgctat tgaagttgat tggagagact tttcccata cttgaaatgg      780

gttccaaaca agtccttcga aaacatcatc catagaatgt acactagaag agaagctgtt     840

atgaaggcct tgatccaaga acacaagaaa agaattgcct ccggtgaaaa cttgaactcc     900

tacattgatt acttgttgtc tgaagcccaa accttgaccg ataagcaatt attgatgtct     960

ttgtgggaac ctattatcga atcttctgat accactatgg ttactactga atgggctatg    1020
```

```
tacgaattgg ctaagaatcc aaacatgcaa gacagattat acgaagaaat ccaatccgtt   1080

tgcggttccg aaaagattac tgaagaaaac ttgtcccaat tgccatactt gtacgctgtt   1140

ttccaagaaa ctttgagaaa gcactgtcca gttcctatta tgccattgag atatgttcac   1200

gaaaacaccg ttttgggtgg ttatcatgtt ccagctggta ctgaagttgc tattaacatc   1260

tacggttgca acatggataa gaaggtctgg gaaaatccag aagaatggaa tccagaaaga   1320

ttcttgtccg aaaaagaatc catggacttg tacaaaacta tggcttttgg tggtggtaaa   1380

agagtttgcg ctggttcttt acaagccatg gttatttctt gcattggtat cggtagattg   1440

gtccaagatt ttgaatggaa gttgaaggat gatgccgaag aagatgttaa cactttgggt   1500

ttgactaccc aaaagttgca tccattattg gccttgatta acccaagaaa gtaactcgag   1560

ccgcgg                                                              1566


<210> SEQ ID NO 62
<211> LENGTH: 512
<212> TYPE: PRT
<213> ORGANISM: Lactuca sativa

<400> SEQUENCE: 62

Met Asp Gly Val Ile Asp Met Gln Thr Ile Pro Leu Arg Thr Ala Ile
1               5                   10                  15

Ala Ile Gly Gly Thr Ala Val Ala Leu Val Val Ala Leu Tyr Phe Trp
            20                  25                  30

Phe Leu Arg Ser Tyr Ala Ser Pro Ser His His Ser Asn His Leu Pro
        35                  40                  45

Pro Val Pro Glu Val Pro Gly Val Pro Val Leu Gly Asn Leu Leu Gln
    50                  55                  60

Leu Lys Glu Lys Lys Pro Tyr Met Thr Phe Thr Lys Trp Ala Glu Met
65                  70                  75                  80

Tyr Gly Pro Ile Tyr Ser Ile Arg Thr Gly Ala Thr Ser Met Val Val
                85                  90                  95

Val Ser Ser Asn Glu Ile Ala Lys Glu Val Val Val Thr Arg Phe Pro
            100                 105                 110

Ser Ile Ser Thr Arg Lys Leu Ser Tyr Ala Leu Lys Val Leu Thr Glu
        115                 120                 125

Asp Lys Ser Met Val Ala Met Ser Asp Tyr His Asp Tyr His Lys Thr
    130                 135                 140

Val Lys Arg His Ile Leu Thr Ala Val Leu Gly Pro Asn Ala Gln Lys
145                 150                 155                 160

Lys Phe Arg Ala His Arg Asp Thr Met Met Glu Asn Val Ser Asn Glu
                165                 170                 175

Leu His Ala Phe Phe Glu Lys Asn Pro Asn Gln Glu Val Asn Leu Arg
            180                 185                 190

Lys Ile Phe Gln Ser Gln Leu Phe Gly Leu Ala Met Lys Gln Ala Leu
        195                 200                 205

Gly Lys Asp Val Glu Ser Ile Tyr Val Lys Asp Leu Glu Thr Thr Met
    210                 215                 220

Lys Arg Glu Glu Ile Phe Glu Val Leu Val Val Asp Pro Met Met Gly
225                 230                 235                 240

Ala Ile Glu Val Asp Trp Arg Asp Phe Phe Pro Tyr Leu Lys Trp Val
                245                 250                 255

Pro Asn Lys Ser Phe Glu Asn Ile Ile His Arg Met Tyr Thr Arg Arg
            260                 265                 270
```

```
Glu Ala Val Met Lys Ala Leu Ile Gln Glu His Lys Lys Arg Ile Ala
        275                 280                 285

Ser Gly Glu Asn Leu Asn Ser Tyr Ile Asp Tyr Leu Leu Ser Glu Ala
    290                 295                 300

Gln Thr Leu Thr Asp Lys Gln Leu Leu Met Ser Leu Trp Glu Pro Ile
305                 310                 315                 320

Ile Glu Ser Ser Asp Thr Thr Met Val Thr Thr Glu Trp Ala Met Tyr
                325                 330                 335

Glu Leu Ala Lys Asn Pro Asn Met Gln Asp Arg Leu Tyr Glu Glu Ile
            340                 345                 350

Gln Ser Val Cys Gly Ser Glu Lys Ile Thr Glu Glu Asn Leu Ser Gln
        355                 360                 365

Leu Pro Tyr Leu Tyr Ala Val Phe Gln Glu Thr Leu Arg Lys His Cys
    370                 375                 380

Pro Val Pro Ile Met Pro Leu Arg Tyr Val His Glu Asn Thr Val Leu
385                 390                 395                 400

Gly Gly Tyr His Val Pro Ala Gly Thr Glu Val Ala Ile Asn Ile Tyr
                405                 410                 415

Gly Cys Asn Met Asp Lys Lys Val Trp Glu Asn Pro Glu Glu Trp Asn
            420                 425                 430

Pro Glu Arg Phe Leu Ser Glu Lys Glu Ser Met Asp Leu Tyr Lys Thr
        435                 440                 445

Met Ala Phe Gly Gly Gly Lys Arg Val Cys Ala Gly Ser Leu Gln Ala
    450                 455                 460

Met Val Ile Ser Cys Ile Gly Ile Gly Arg Leu Val Gln Asp Phe Glu
465                 470                 475                 480

Trp Lys Leu Lys Asp Asp Ala Glu Glu Asp Val Asn Thr Leu Gly Leu
                485                 490                 495

Thr Thr Gln Lys Leu His Pro Leu Leu Ala Leu Ile Asn Pro Arg Lys
            500                 505                 510


<210> SEQ ID NO 63
<211> LENGTH: 1535
<212> TYPE: DNA
<213> ORGANISM: Rubus suavissimus

<400> SEQUENCE: 63

atggccaccc tccttgagca tttccaagct atgccctttg ccatccctat tgcactggct      60

gctctgtctt ggctgttcct cttttacatc aaagtttcat tcttttccaa caagagtgct     120

caggctaagc tccctcctgt gccagtggtt cctgggctgc cggtgattgg gaatttactg     180

caactcaagg agaagaaacc ctaccagact tttacaaggt gggctgagga gtatggacca     240

atctattcta tcaggactgg tgcttccacc atggtcgttc tcaataccac ccaagttgca     300

aaagaggcca tggtgaccag atatttatcc atctcaacca gaaagctatc aaacgcacta     360

aagattctta ctgctgataa atgtatggtt gcaataagtg actacaacga ttttcacaag     420

atgataaagc gatacatact ctcaaatgtt cttggaccta gtgctcagaa gcgtcaccgg     480

agcaacagag ataccttgag agctaatgtc tgcagccgat tgcattctca agtaaagaac     540

tctcctcgag aagctgtgaa tttcagaaga gtttttgagt gggaactctt tggaattgca     600

ttgaagcaag cctttggaaa ggacatagaa aagcccattt atgtggagga acttggcact     660

acactgtcaa gagatgagat ctttaaggtt ctagtgcttg acataatgga gggtgcaatt     720

gaggttgatt ggagagattt cttcccttac ctgagatgga ttccgaatac gcgcatggaa     780
```

acaaaaattc agcgactcta tttccgcagg aaagcagtga tgactgccct gatcaacgag 840
cagaagaagc gaattgcttc aggagaggaa atcaactgtt atatcgactt cttgcttaag 900
gaagggaaga cactgacaat ggaccaaata agtatgttgc tttgggagac ggttattgaa 960
acagcagata ctacaatggt aacgacagaa tgggctatgt atgaagttgc taaagactca 1020
aagcgtcagg atcgtctcta tcaggaaatc caaaaggttt gtggatcgga gatggttaca 1080
gaggaatact tgtcccaact gccgtacctg aatgcagttt tccatgaaac gctaaggaag 1140
cacagtccgg ctgcgttagt tcctttaaga tatgcacatg aagataccca actaggaggt 1200
tactacattc cagctggaac tgagattgct ataaacatat acgggtgtaa catggacaag 1260
catcaatggg aaagccctga ggaatggaaa ccggagagat tttggaccc gaaatttgat 1320 cctatggatt tgtacaagac catggctttt ggggctggaa agagggtatg tgctggttct 1380
cttcaggcaa tgttaatagc gtgcccgacg attggtaggc tggtgcagga gtttgagtgg 1440
aagctgagag atggagaaga agaaaatgta gatactgttg ggctcaccac tcacaaacgc 1500
tatccaatgc atgcaatcct gaagccaaga agtta 1535

<210> SEQ ID NO 64
<211> LENGTH: 1536
<212> TYPE: DNA
<213> ORGANISM: Artificial Sequence
<220> FEATURE:
<223> OTHER INFORMATION: Codon-optimized KO

<400> SEQUENCE: 64
atggctacct tgttggaaca ttttcaagct atgccattcg ctattccaat tgctttggct 60
gctttgtctt ggttgttttt gttctacatc aaggtttctt tcttctccaa caaatccgct 120
caagctaaat tgccaccagt tccagttgtt ccaggtttgc cagttattgg taatttgttg 180
caattgaaag aaaagaagcc ataccaaacc ttcactagat gggctgaaga atatggtcca 240
atctactcta ttagaactgg tgcttctact atggttgtct tgaacactac tcaagttgcc 300
aaagaagcta tggttaccag atacttgtct atctctacca gaaagttgtc caacgccttg 360
aaaattttga ccgctgataa gtgcatggtt gccatttctg attacaacga tttccacaag 420
atgatcaaga gatatatctt gtctaacgtt ttgggtccat ctgcccaaaa aagacataga 480
tctaacagag ataccttgag agccaacgtt tgttctagat tgcattccca agttaagaac 540
tctccaagag aagctgtcaa ctttagaaga gttttcgaat gggaattatt cggtatcgct 600
ttgaaacaag ccttcggtaa ggatattgaa aagccaatct acgtcgaaga attgggtact 660
actttgtcca gagatgaaat cttcaaggtt ttggtcttgg acattatgga aggtgccatt 720
gaagttgatt ggagagattt tttcccatac ttgcgttgga ttccaaacac cagaatggaa 780
actaagatcc aaagattata ctttagaaga aaggccgtta tgaccgcctt gattaacgaa 840
caaaagaaaa gaattgcctc cggtgaagaa atcaactgct acatcgattt cttgttgaaa 900
gaaggtaaga ccttgaccat ggaccaaatc tctatgttgt tgtgggaaac cgttattgaa 960
actgctgata ccacaatggt tactactgaa tgggctatgt acgaagttgc taaggattct 1020
aaaagacaag acagattata ccaagaaatc caaaaggtct gcggttctga aatggttaca 1080
gaagaatact tgtcccaatt gccatacttg aatgctgttt tccacgaaac tttgagaaaa 1140
cattctccag ctgctttggt tccattgaga tatgctcatg aagatactca attgggtggt 1200
tattacattc cagccggtac tgaaattgcc attaacatct acggttgcaa catggacaaa 1260

-continued

```
caccaatggg aatctccaga agaatggaag ccagaaagat ttttggatcc taagtttgac   1320

ccaatggact tgtacaaaac tatggctttt ggtgctggta aaagagtttg cgctggttct   1380

ttacaagcta tgttgattgc ttgtccaacc atcggtagat tggttcaaga atttgaatgg   1440

aagttgagag atggtgaaga agaaaacgtt gatactgttg gtttgaccac ccataagaga   1500

tatccaatgc atgctatttt gaagccaaga tcttaa                              1536
```

```
<210> SEQ ID NO 65
<211> LENGTH: 1572
<212> TYPE: DNA
<213> ORGANISM: Artificial Sequence
<220> FEATURE:
<223> OTHER INFORMATION: Codon-optimized KO

<400> SEQUENCE: 65

aagcttacta gtaaaatggc ctccatcacc catttcttac aagattttca agctactcca     60

ttcgctactg cttttgctgt tggtggtgtt tctttgttga tattcttctt cttcatccgt    120

ggtttccact ctactaagaa aaacgaatat tacaagttgc caccagttcc agttgttcca    180

ggtttgccag ttgttggtaa tttgttgcaa ttgaaagaaa agaagccata caagactttc    240

ttgagatggg ctgaaattca tggtccaatc tactctatta gaactggtgc ttctaccatg    300

gttgttgtta actctactca tgttgccaaa gaagctatgg ttaccagatt ctcttcaatc    360

tctaccagaa agttgtccaa ggctttggaa ttattgacct ccaacaaatc tatggttgcc    420

acctctgatt acaacgaatt tcacaagatg gtcaagaagt acatcttggc cgaattattg    480

ggtgctaatg ctcaaaagag acacagaatt catagagaca ccttgatcga aaacgtcttg    540

aacaaattgc atgcccatac caagaattct ccattgcaag ctgttaactt cagaaagatc    600

ttcgaatctg aattattcgg tttggctatg aagcaagcct tgggttatga tgttgattcc    660

ttgttcgttg aagaattggg tactaccttg tccagagaag aaatctacaa cgttttggtc    720

agtgacatgt tgaagggtgc tattgaagtt gattggagag actttttccc atacttgaaa    780

tggatcccaa acaagtcctt cgaaatgaag attcaaagat tggcctctag aagacaagcc    840

gttatgaact ctattgtcaa agaacaaaag aagtccattg cctctggtaa gggtgaaaac    900

tgttacttga attacttgtt gtccgaagct aagactttga ccgaaaagca aatttccatt    960

ttggcctggg aaaccattat tgaaactgct gatacaactg ttgttaccac tgaatgggct   1020

atgtacgaat tggctaaaaa cccaaagcaa caagacagat tatacaacga aatccaaaac   1080

gtctgcggta ctgataagat taccgaagaa catttgtcca agttgcctta cttgtctgct   1140

gtttttcacg aaaccttgag aaagtattct ccatctccat tggttccatt gagatacgct   1200

catgaagata ctcaattggg tggttattat gttccagccg gtactgaaat tgctgttaat   1260

atctacggtt gcaacatgga caagaatcaa tgggaaactc cagaagaatg gaagccagaa   1320

agatttttgg acgaaaagta cgatccaatg gacatgtaca agactatgtc ttttggttcc   1380

ggtaaaagag tttgcgctgg ttctttacaa gctagtttga ttgcttgtac ctccatcggt   1440

agattggttc aagaatttga atggagattg aaagacggtg aagttgaaaa cgttgatacc   1500

ttgggtttga ctacccataa gttgtatcca atgcaagcta tcttgcaacc tagaaactga   1560

ctcgagccgc gg                                                        1572
```

```
<210> SEQ ID NO 66
<211> LENGTH: 514
<212> TYPE: PRT
<213> ORGANISM: Castanea mollissima
```

<400> SEQUENCE: 66

Met Ala Ser Ile Thr His Phe Leu Gln Asp Phe Gln Ala Thr Pro Phe
1 5 10 15

Ala Thr Ala Phe Ala Val Gly Gly Val Ser Leu Leu Ile Phe Phe Phe
20 25 30

Phe Ile Arg Gly Phe His Ser Thr Lys Lys Asn Glu Tyr Tyr Lys Leu
35 40 45

Pro Pro Val Pro Val Val Pro Gly Leu Pro Val Val Gly Asn Leu Leu
50 55 60

Gln Leu Lys Glu Lys Lys Pro Tyr Lys Thr Phe Leu Arg Trp Ala Glu
65 70 75 80

Ile His Gly Pro Ile Tyr Ser Ile Arg Thr Gly Ala Ser Thr Met Val
85 90 95

Val Val Asn Ser Thr His Val Ala Lys Glu Ala Met Val Thr Arg Phe
100 105 110

Ser Ser Ile Ser Thr Arg Lys Leu Ser Lys Ala Leu Glu Leu Leu Thr
115 120 125

Ser Asn Lys Ser Met Val Ala Thr Ser Asp Tyr Asn Glu Phe His Lys
130 135 140

Met Val Lys Lys Tyr Ile Leu Ala Glu Leu Leu Gly Ala Asn Ala Gln
145 150 155 160

Lys Arg His Arg Ile His Arg Asp Thr Leu Ile Glu Asn Val Leu Asn
165 170 175

Lys Leu His Ala His Thr Lys Asn Ser Pro Leu Gln Ala Val Asn Phe
180 185 190

Arg Lys Ile Phe Glu Ser Glu Leu Phe Gly Leu Ala Met Lys Gln Ala
195 200 205

Leu Gly Tyr Asp Val Asp Ser Leu Phe Val Glu Glu Leu Gly Thr Thr
210 215 220

Leu Ser Arg Glu Glu Ile Tyr Asn Val Leu Val Ser Asp Met Leu Lys
225 230 235 240

Gly Ala Ile Glu Val Asp Trp Arg Asp Phe Phe Pro Tyr Leu Lys Trp
245 250 255

Ile Pro Asn Lys Ser Phe Glu Met Lys Ile Gln Arg Leu Ala Ser Arg
260 265 270

Arg Gln Ala Val Met Asn Ser Ile Val Lys Glu Gln Lys Lys Ser Ile
275 280 285

Ala Ser Gly Lys Gly Glu Asn Cys Tyr Leu Asn Tyr Leu Leu Ser Glu
290 295 300

Ala Lys Thr Leu Thr Glu Lys Gln Ile Ser Ile Leu Ala Trp Glu Thr
305 310 315 320

Ile Ile Glu Thr Ala Asp Thr Thr Val Val Thr Thr Glu Trp Ala Met
325 330 335

Tyr Glu Leu Ala Lys Asn Pro Lys Gln Gln Asp Arg Leu Tyr Asn Glu
340 345 350

Ile Gln Asn Val Cys Gly Thr Asp Lys Ile Thr Glu Glu His Leu Ser
355 360 365

Lys Leu Pro Tyr Leu Ser Ala Val Phe His Glu Thr Leu Arg Lys Tyr
370 375 380

Ser Pro Ser Pro Leu Val Pro Leu Arg Tyr Ala His Glu Asp Thr Gln
385 390 395 400

Leu Gly Gly Tyr Tyr Val Pro Ala Gly Thr Glu Ile Ala Val Asn Ile

-continued

```
                405                 410                 415

Tyr Gly Cys Asn Met Asp Lys Asn Gln Trp Glu Thr Pro Glu Glu Trp
            420                 425                 430

Lys Pro Glu Arg Phe Leu Asp Glu Lys Tyr Asp Pro Met Asp Met Tyr
        435                 440                 445

Lys Thr Met Ser Phe Gly Ser Gly Lys Arg Val Cys Ala Gly Ser Leu
    450                 455                 460

Gln Ala Ser Leu Ile Ala Cys Thr Ser Ile Gly Arg Leu Val Gln Glu
465                 470                 475                 480

Phe Glu Trp Arg Leu Lys Asp Gly Glu Val Glu Asn Val Asp Thr Leu
                485                 490                 495

Gly Leu Thr Thr His Lys Leu Tyr Pro Met Gln Ala Ile Leu Gln Pro
            500                 505                 510

Arg Asn


<210> SEQ ID NO 67
<211> LENGTH: 1512
<212> TYPE: DNA
<213> ORGANISM: Artificial Sequence
<220> FEATURE:
<223> OTHER INFORMATION: Codon-optimized KO

<400> SEQUENCE: 67

atgatttcct tgttgttggg ttttgttgtc tcctccttct tgtttatctt cttcttgaaa     60

aaattgttgt tcttcttcag tcgtcacaaa atgtccgaag tttctagatt gccatctgtt    120

ccagttccag gttttccatt gattggtaac ttgttgcaat tgaaagaaaa gaagccacac    180

aagactttca ccaagtggtc tgaattatat ggtccaatct actctatcaa gatgggttcc    240

tcttctttga tcgtcttgaa ctctattgaa accgccaaag aagctatggt cagtagattc    300

tcttcaatct ctaccagaaa gttgtctaac gctttgactg ttttgacctg caacaaatct    360

atggttgcta cctctgatta cgatgacttt cataagttcg tcaagagatg cttgttgaac    420

ggtttgttgg gtgctaatgc tcaagaaaga aaaagacatt acagagatgc cttgatcgaa    480

aacgttacct ctaaattgca tgcccatacc agaaatcatc cacaagaacc agttaacttc    540

agagccattt tcgaacacga attattcggt gttgctttga aacaagcctt cggtaaagat    600

gtcgaatcca tctatgtaaa agaattgggt gtcaccttgt ccagagatga aattttcaag    660

gttttggtcc acgacatgat ggaaggtgct attgatgttg attggagaga tttcttccca    720

tacttgaaat ggatcccaaa caactctttc gaagccagaa ttcaacaaaa gcacaagaga    780

agattggctg ttatgaacgc cttgatccaa gacagattga atcaaaacga ttccgaatcc    840

gatgatgact gctacttgaa tttcttgatg tctgaagcta agaccttgac catggaacaa    900

attgctattt tggtttggga aaccattatc gaaactgctg ataccacttt ggttactact    960

gaatgggcta tgtacgaatt ggccaaacat caatctgttc aagatagatt attcaaagaa   1020

atccaatccg tctgcggtgg tgaaaagatc aaagaagaac aattgccaag attgccttac   1080

gtcaatggtg tttttcacga aaccttgaga aagtattctc cagctccatt ggttccaatt   1140

agatacgctc atgaagatac ccaaattggt ggttatcata ttccagccgg ttctgaaatt   1200

gccattaaca tctacggttg caacatggat aagaagagat gggaaagacc tgaagaatgg   1260

tggccagaaa gatttttgga agatagatac gaatcctccg acttgcataa gactatggct   1320

tttggtgctg gtaaaagagt ttgtgctggt gctttacaag ctagtttgat ggctggtatt   1380

gctatcggta gattggttca agaattcgaa tggaagttga gagatggtga agaagaaaac   1440
```

```
gttgatactt acggtttgac ctcccaaaag ttgtatccat tgatggccat tatcaaccca   1500

agaagatctt aa                                                       1512


<210> SEQ ID NO 68
<211> LENGTH: 506
<212> TYPE: PRT
<213> ORGANISM: Thellungiella halophila

<400> SEQUENCE: 68

Met Ala Ser Met Ile Ser Leu Leu Leu Gly Phe Val Val Ser Ser Phe
1               5                   10                  15

Leu Phe Ile Phe Phe Leu Lys Lys Leu Leu Phe Phe Phe Ser Arg His
            20                  25                  30

Lys Met Ser Glu Val Ser Arg Leu Pro Ser Val Pro Val Pro Gly Phe
        35                  40                  45

Pro Leu Ile Gly Asn Leu Leu Gln Leu Lys Glu Lys Lys Pro His Lys
    50                  55                  60

Thr Phe Thr Lys Trp Ser Glu Leu Tyr Gly Pro Ile Tyr Ser Ile Lys
65                  70                  75                  80

Met Gly Ser Ser Ser Leu Ile Val Leu Asn Ser Ile Glu Thr Ala Lys
                85                  90                  95

Glu Ala Met Val Ser Arg Phe Ser Ser Ile Ser Thr Arg Lys Leu Ser
            100                 105                 110

Asn Ala Leu Thr Val Leu Thr Cys Asn Lys Ser Met Val Ala Thr Ser
        115                 120                 125

Asp Tyr Asp Asp Phe His Lys Phe Val Lys Arg Cys Leu Leu Asn Gly
    130                 135                 140

Leu Leu Gly Ala Asn Ala Gln Glu Arg Lys Arg His Tyr Arg Asp Ala
145                 150                 155                 160

Leu Ile Glu Asn Val Thr Ser Lys Leu His Ala His Thr Arg Asn His
                165                 170                 175

Pro Gln Glu Pro Val Asn Phe Arg Ala Ile Phe Glu His Glu Leu Phe
            180                 185                 190

Gly Val Ala Leu Lys Gln Ala Phe Gly Lys Asp Val Glu Ser Ile Tyr
        195                 200                 205

Val Lys Glu Leu Gly Val Thr Leu Ser Arg Asp Glu Ile Phe Lys Val
    210                 215                 220

Leu Val His Asp Met Met Glu Gly Ala Ile Asp Val Asp Trp Arg Asp
225                 230                 235                 240

Phe Phe Pro Tyr Leu Lys Trp Ile Pro Asn Asn Ser Phe Glu Ala Arg
                245                 250                 255

Ile Gln Gln Lys His Lys Arg Arg Leu Ala Val Met Asn Ala Leu Ile
            260                 265                 270

Gln Asp Arg Leu Asn Gln Asn Asp Ser Glu Ser Asp Asp Asp Cys Tyr
        275                 280                 285

Leu Asn Phe Leu Met Ser Glu Ala Lys Thr Leu Thr Met Glu Gln Ile
    290                 295                 300

Ala Ile Leu Val Trp Glu Thr Ile Ile Glu Thr Ala Asp Thr Thr Leu
305                 310                 315                 320

Val Thr Thr Glu Trp Ala Met Tyr Glu Leu Ala Lys His Gln Ser Val
                325                 330                 335

Gln Asp Arg Leu Phe Lys Glu Ile Gln Ser Val Cys Gly Gly Glu Lys
            340                 345                 350
```

```
Ile Lys Glu Glu Gln Leu Pro Arg Leu Pro Tyr Val Asn Gly Val Phe
        355                 360                 365

His Glu Thr Leu Arg Lys Tyr Ser Pro Ala Pro Leu Val Pro Ile Arg
    370                 375                 380

Tyr Ala His Glu Asp Thr Gln Ile Gly Gly Tyr His Ile Pro Ala Gly
385                 390                 395                 400

Ser Glu Ile Ala Ile Asn Ile Tyr Gly Cys Asn Met Asp Lys Lys Arg
                405                 410                 415

Trp Glu Arg Pro Glu Glu Trp Trp Pro Glu Arg Phe Leu Glu Asp Arg
            420                 425                 430

Tyr Glu Ser Ser Asp Leu His Lys Thr Met Ala Phe Gly Ala Gly Lys
        435                 440                 445

Arg Val Cys Ala Gly Ala Leu Gln Ala Ser Leu Met Ala Gly Ile Ala
    450                 455                 460

Ile Gly Arg Leu Val Gln Glu Phe Glu Trp Lys Leu Arg Asp Gly Glu
465                 470                 475                 480

Glu Glu Asn Val Asp Thr Tyr Gly Leu Thr Ser Gln Lys Leu Tyr Pro
                485                 490                 495

Leu Met Ala Ile Ile Asn Pro Arg Arg Ser
            500                 505


<210> SEQ ID NO 69
<211> LENGTH: 1554
<212> TYPE: DNA
<213> ORGANISM: Artificial Sequence
<220> FEATURE:
<223> OTHER INFORMATION: Codon-optimized KO

<400> SEQUENCE: 69

aagcttacta gtaaaatgga catgatgggt attgaagctg ttccatttgc tactgctgtt      60

gttttgggtg gtatttcctt ggttgttttg atcttcatca gaagattcgt ttccaacaga     120

aagagatccg ttgaaggttt gccaccagtt ccagatattc caggtttacc attgattggt     180

aacttgttgc aattgaaaga aaagaagcca cataagacct ttgctagatg ggctgaaact     240

tacggtccaa ttttctctat tagaactggt gcttctacca tgatcgtctt gaattcttct     300

gaagttgcca aagaagctat ggtcactaga ttctcttcaa tctctaccag aaagttgtcc     360

aacgccttga agattttgac cttcgataag tgtatggttg ccacctctga ttacaacgat     420

tttcacaaaa tggtcaaggg tttcatcttg agaaacgttt taggtgctcc agcccaaaaa     480

agacatagat gtcatagaga taccttgatc gaaaacatct ctaagtactt gcatgcccat     540

gttaagactt ctccattgga accagttgtc ttgaagaaga ttttcgaatc cgaaattttc     600

ggtttggctt tgaaacaagc cttgggtaag gatatcgaat ccatctatgt tgaagaattg     660

ggtactacct tgtccagaga agaaattttt gccgttttgg ttgttgatcc aatggctggt     720

gctattgaag ttgattggag agattttttc ccatacttgt cctggattcc aaacaagtct     780

atggaaatga agatccaaag aatggatttt agaagaggtg ctttgatgaa ggccttgatt     840

ggtgaacaaa agaaaagaat cggttccggt gaagaaaaga actcctacat tgatttcttg     900

ttgtctgaag ctaccacttt gaccgaaaag caaattgcta tgttgatctg ggaaaccatc     960

atcgaaattt ccgatacaac tttggttacc tctgaatggg ctatgtacga attggctaaa    1020

gacccaaata gacaagaaat cttgtacaga gaaatccaca aggtttgcgg ttctaacaag    1080

ttgactgaag aaaacttgtc caagttgcca tacttgaact ctgttttcca cgaaaccttg    1140

agaaagtatt ctccagctcc aatggttcca gttagatatg ctcatgaaga tactcaattg    1200
```

```
ggtggttacc atattccagc tggttctcaa attgccatta acatctacgg ttgcaacatg   1260

aacaaaaagc aatgggaaaa tcctgaagaa tggaagccag aaagattctt ggacgaaaag   1320

tatgacttga tggacttgca taagactatg gcttttggtg gtggtaaaag agtttgtgct   1380

ggtgctttac aagcaatgtt gattgcttgc acttccatcg gtagattcgt tcaagaattt   1440

gaatggaagt tgatgggtgg tgaagaagaa aacgttgata ctgttgcttt gacctcccaa   1500

aaattgcatc caatgcaagc cattattaag gccagagaat gactcgagcc gcgg         1554
```

<210> SEQ ID NO 70
<211> LENGTH: 508
<212> TYPE: PRT
<213> ORGANISM: Vitis vinifera

<400> SEQUENCE: 70

```
Met Asp Met Met Gly Ile Glu Ala Val Pro Phe Ala Thr Ala Val Val
1               5                   10                  15

Leu Gly Gly Ile Ser Leu Val Val Leu Ile Phe Ile Arg Arg Phe Val
            20                  25                  30

Ser Asn Arg Lys Arg Ser Val Glu Gly Leu Pro Pro Val Pro Asp Ile
        35                  40                  45

Pro Gly Leu Pro Leu Ile Gly Asn Leu Leu Gln Leu Lys Glu Lys Lys
    50                  55                  60

Pro His Lys Thr Phe Ala Arg Trp Ala Glu Thr Tyr Gly Pro Ile Phe
65                  70                  75                  80

Ser Ile Arg Thr Gly Ala Ser Thr Met Ile Val Leu Asn Ser Ser Glu
                85                  90                  95

Val Ala Lys Glu Ala Met Val Thr Arg Phe Ser Ser Ile Ser Thr Arg
            100                 105                 110

Lys Leu Ser Asn Ala Leu Lys Ile Leu Thr Phe Asp Lys Cys Met Val
        115                 120                 125

Ala Thr Ser Asp Tyr Asn Asp Phe His Lys Met Val Lys Gly Phe Ile
    130                 135                 140

Leu Arg Asn Val Leu Gly Ala Pro Ala Gln Lys Arg His Arg Cys His
145                 150                 155                 160

Arg Asp Thr Leu Ile Glu Asn Ile Ser Lys Tyr Leu His Ala His Val
                165                 170                 175

Lys Thr Ser Pro Leu Glu Pro Val Val Leu Lys Lys Ile Phe Glu Ser
            180                 185                 190

Glu Ile Phe Gly Leu Ala Leu Lys Gln Ala Leu Gly Lys Asp Ile Glu
        195                 200                 205

Ser Ile Tyr Val Glu Glu Leu Gly Thr Thr Leu Ser Arg Glu Glu Ile
    210                 215                 220

Phe Ala Val Leu Val Val Asp Pro Met Ala Gly Ala Ile Glu Val Asp
225                 230                 235                 240

Trp Arg Asp Phe Phe Pro Tyr Leu Ser Trp Ile Pro Asn Lys Ser Met
                245                 250                 255

Glu Met Lys Ile Gln Arg Met Asp Phe Arg Arg Gly Ala Leu Met Lys
            260                 265                 270

Ala Leu Ile Gly Glu Gln Lys Lys Arg Ile Gly Ser Gly Glu Glu Lys
        275                 280                 285

Asn Ser Tyr Ile Asp Phe Leu Leu Ser Glu Ala Thr Thr Leu Thr Glu
    290                 295                 300

Lys Gln Ile Ala Met Leu Ile Trp Glu Thr Ile Ile Glu Ile Ser Asp
```

```
305                 310                 315                 320

Thr Thr Leu Val Thr Ser Glu Trp Ala Met Tyr Glu Leu Ala Lys Asp
                325                 330                 335

Pro Asn Arg Gln Glu Ile Leu Tyr Arg Glu Ile His Lys Val Cys Gly
            340                 345                 350

Ser Asn Lys Leu Thr Glu Glu Asn Leu Ser Lys Leu Pro Tyr Leu Asn
        355                 360                 365

Ser Val Phe His Glu Thr Leu Arg Lys Tyr Ser Pro Ala Pro Met Val
    370                 375                 380

Pro Val Arg Tyr Ala His Glu Asp Thr Gln Leu Gly Gly Tyr His Ile
385                 390                 395                 400

Pro Ala Gly Ser Gln Ile Ala Ile Asn Ile Tyr Gly Cys Asn Met Asn
                405                 410                 415

Lys Lys Gln Trp Glu Asn Pro Glu Glu Trp Lys Pro Glu Arg Phe Leu
            420                 425                 430

Asp Glu Lys Tyr Asp Leu Met Asp Leu His Lys Thr Met Ala Phe Gly
        435                 440                 445

Gly Gly Lys Arg Val Cys Ala Gly Ala Leu Gln Ala Met Leu Ile Ala
    450                 455                 460

Cys Thr Ser Ile Gly Arg Phe Val Gln Glu Phe Glu Trp Lys Leu Met
465                 470                 475                 480

Gly Gly Glu Glu Glu Asn Val Asp Thr Val Ala Leu Thr Ser Gln Lys
                485                 490                 495

Leu His Pro Met Gln Ala Ile Ile Lys Ala Arg Glu
            500                 505
```

<210> SEQ ID NO 71
<211> LENGTH: 1593
<212> TYPE: DNA
<213> ORGANISM: Artificial Sequence
<220> FEATURE:
<223> OTHER INFORMATION: Codon-optimized KO

<400> SEQUENCE: 71

```
aagcttaaaa tgagtaagtc taatagtatg aattctacat cacacgaaac ccttttttcaa     60

caattggtct tgggtttgga ccgtatgcca ttgatggatg ttcactggtt gatctacgtt    120

gctttcggcg catggttatg ttcttatgtg atacatgttt tatcatcttc ctctacagta    180

aaagtgccag ttgttggata caggtctgta ttcgaaccta catggttgct tagacttaga    240

ttcgtctggg aaggtggctc tatcataggt caagggtaca ataagtttaa agactctatt    300

ttccaagtta ggaaattggg aactgatatt gtcattatac cacctaacta tattgatgaa    360

gtgagaaaat tgtcacagga caagactaga tcagttgaac ctttcattaa tgattttgca    420

ggtcaataca caagaggcat ggttttcttg caatctgact tacaaaaccg tgttatacaa    480

caaagactaa ctccaaaatt ggtttccttg accaaggtca tgaaggaaga gttggattat    540

gctttaacaa aagagatgcc tgatatgaaa aatgacgaat gggtagaagt agatatcagt    600

agtataatgg tgagattgat ttccaggatc tccgccagag tctttctagg gcctgaacac    660

tgtcgtaacc aggaatggtt gactactaca gcagaatatt cagaatcact tttcattaca    720

gggtttatct taagagttgt acctcatatc ttaagaccat tcatcgcccc tctattacct    780

tcatacagga ctctacttag aaacgtttca agtggtagaa gagtcatcgg tgacatcata    840

agatctcagc aaggggatgg taacgaagat atactttcct ggatgagaga tgctgccaca    900

ggagaggaaa agcaaatcga taacattgct cagagaatgt taattctttc tttagcatca    960
```

-continued

```
atccacacta ctgcgatgac catgacacat gccatgtacg atctatgtgc ttgccctgag   1020

tacattgaac cattaagaga tgaagttaaa tctgttgttg gggcttctgg ctgggacaag   1080

acagcgttaa acagatttca taagttggac tccttcctaa aagagtcaca aagattcaac   1140

ccagtattct tattgacatt caatagaatc taccatcaat ctatgacctt atcagatggc   1200

actaacattc catctggaac acgtattgct gttccatcac acgcaatgtt gcaagattct   1260

gcacatgtcc caggtccaac cccacctact gaatttgatg gattcagata tagtaagata   1320

cgttctgata gtaactacgc acaaaagtac ctattctcca tgaccgattc ttcaaacatg   1380

gctttcggat acggcaagta tgcttgtcca ggtagatttt acgcgtctaa tgagatgaaa   1440

ctaacattag ccattttgtt gctacaattt gagttcaaac taccagatgg taaaggtcgt   1500

cctagaaata tcactatcga ttctgatatg attccagacc caagagctag actttgcgtc   1560

agaaaaagat cacttagaga tgaatgaccg cgg                                 1593
```

<210> SEQ ID NO 72
<211> LENGTH: 525
<212> TYPE: PRT
<213> ORGANISM: Gibberella fujikuroi

<400> SEQUENCE: 72

```
Met Ser Lys Ser Asn Ser Met Asn Ser Thr Ser His Glu Thr Leu Phe
1               5                   10                  15

Gln Gln Leu Val Leu Gly Leu Asp Arg Met Pro Leu Met Asp Val His
            20                  25                  30

Trp Leu Ile Tyr Val Ala Phe Gly Ala Trp Leu Cys Ser Tyr Val Ile
        35                  40                  45

His Val Leu Ser Ser Ser Ser Thr Val Lys Val Pro Val Val Gly Tyr
    50                  55                  60

Arg Ser Val Phe Glu Pro Thr Trp Leu Leu Arg Leu Arg Phe Val Trp
65                  70                  75                  80

Glu Gly Gly Ser Ile Ile Gly Gln Gly Tyr Asn Lys Phe Lys Asp Ser
                85                  90                  95

Ile Phe Gln Val Arg Lys Leu Gly Thr Asp Ile Val Ile Ile Pro Pro
            100                 105                 110

Asn Tyr Ile Asp Glu Val Arg Lys Leu Ser Gln Asp Lys Thr Arg Ser
        115                 120                 125

Val Glu Pro Phe Ile Asn Asp Phe Ala Gly Gln Tyr Thr Arg Gly Met
    130                 135                 140

Val Phe Leu Gln Ser Asp Leu Gln Asn Arg Val Ile Gln Gln Arg Leu
145                 150                 155                 160

Thr Pro Lys Leu Val Ser Leu Thr Lys Val Met Lys Glu Glu Leu Asp
                165                 170                 175

Tyr Ala Leu Thr Lys Glu Met Pro Asp Met Lys Asn Asp Glu Trp Val
            180                 185                 190

Glu Val Asp Ile Ser Ser Ile Met Val Arg Leu Ile Ser Arg Ile Ser
        195                 200                 205

Ala Arg Val Phe Leu Gly Pro Glu His Cys Arg Asn Gln Glu Trp Leu
    210                 215                 220

Thr Thr Thr Ala Glu Tyr Ser Glu Ser Leu Phe Ile Thr Gly Phe Ile
225                 230                 235                 240

Leu Arg Val Val Pro His Ile Leu Arg Pro Phe Ile Ala Pro Leu Leu
                245                 250                 255
```

```
Pro Ser Tyr Arg Thr Leu Leu Arg Asn Val Ser Ser Gly Arg Arg Val
            260                 265                 270

Ile Gly Asp Ile Ile Arg Ser Gln Gln Gly Asp Gly Asn Glu Asp Ile
        275                 280                 285

Leu Ser Trp Met Arg Asp Ala Ala Thr Gly Glu Glu Lys Gln Ile Asp
    290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Cys Pro
                325                 330                 335

Glu Tyr Ile Glu Pro Leu Arg Asp Glu Val Lys Ser Val Val Gly Ala
            340                 345                 350

Ser Gly Trp Asp Lys Thr Ala Leu Asn Arg Phe His Lys Leu Asp Ser
        355                 360                 365

Phe Leu Lys Glu Ser Gln Arg Phe Asn Pro Val Phe Leu Leu Thr Phe
    370                 375                 380

Asn Arg Ile Tyr His Gln Ser Met Thr Leu Ser Asp Gly Thr Asn Ile
385                 390                 395                 400

Pro Ser Gly Thr Arg Ile Ala Val Pro Ser His Ala Met Leu Gln Asp
                405                 410                 415

Ser Ala His Val Pro Gly Pro Thr Pro Pro Thr Glu Phe Asp Gly Phe
            420                 425                 430

Arg Tyr Ser Lys Ile Arg Ser Asp Ser Asn Tyr Ala Gln Lys Tyr Leu
        435                 440                 445

Phe Ser Met Thr Asp Ser Ser Asn Met Ala Phe Gly Tyr Gly Lys Tyr
    450                 455                 460

Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
                485                 490                 495

Arg Pro Arg Asn Ile Thr Ile Asp Ser Asp Met Ile Pro Asp Pro Arg
            500                 505                 510

Ala Arg Leu Cys Val Arg Lys Arg Ser Leu Arg Asp Glu
        515                 520                 525
```

<210> SEQ ID NO 73
<211> LENGTH: 1515
<212> TYPE: DNA
<213> ORGANISM: Artificial Sequence
<220> FEATURE:
<223> OTHER INFORMATION: Codon-optimized KO

<400> SEQUENCE: 73

```
aagcttaaaa tggaagatcc tactgtctta tatgcttgtc ttgccattgc agttgcaact     60

ttcgttgtta gatggtacag agatccattg agatccatcc caacagttgg tggttccgat    120

ttgcctattc tatcttacat cggcgcacta agatggacaa gacgtggcag agagatactt    180

caagagggat atgatggcta cagaggatct acattcaaaa tcgcgatgtt agaccgttgg    240

atcgtgatcg caaatggtcc taaactagct gatgaagtca gacgtagacc agatgaagag    300

ttaaacttta tggacggatt aggagcattc gtccaaacta agtacacctt aggtgaagct    360

attcataacg atccatacca tgtcgatatc ataagagaaa aactaacaag aggccttcca    420

gccgtgcttc ctgatgtcat tgaagagttg acacttgcgg ttagacagta cattccaaca    480

gaaggtgatg aatgggtgtc cgtaaactgt tcaaaggccg caagagatat tgttgctaga    540
```

```
gcttctaata gagtctttgt aggtttgcct gcttgcagaa accaaggtta cttagatttg    600

gcaatagact ttacattgtc tgttgtcaag gatagagcca tcatcaatat gtttccagaa    660

ttgttgaagc caatagttgg cagagttgta ggtaacgcca ccagaaatgt tcgtagagct    720

gttccttttg ttgctccatt ggtggaggaa agacgtagac ttatggaaga gtacggtgaa    780

gactggtctg aaaaacctaa tgatatgtta cagtggataa tggatgaagc tgcatccaga    840

gatagttcag tgaaggcaat cgcagagaga ttgttaatgg tgaacttcgc ggctattcat    900

acctcatcaa acactatcac tcatgctttg taccaccttg ccgaaatgcc tgaaactttg    960

caaccactta gagaagagat cgaaccatta gtcaaagagg agggctggac caaggctgct   1020

atgggaaaaa tgtggtggtt agattcattt ctaagagaat ctcaaagata caatggcatt   1080

aacatcgtat ctttaactag aatggctgac aaagatatta cattgagtga tggcacattt   1140

ttgccaaaag gtactctagt ggccgttcca gcgtattcta ctcatagaga tgatgctgtc   1200

tacgctgatg ccttagtatt cgatcctttc agattctcac gtatgagagc gagagaaggt   1260

gaaggtacaa agcaccagtt cgttaatact tcagtcgagt acgttccatt tggtcacgga   1320

aagcatgctt gtccaggaag attcttcgcc gcaaacgaat tgaaagcaat gttggcttac   1380

attgttctaa actatgatgt aaagttgcct ggtgacggta aacgtccatt gaacatgtat   1440

tggggtccaa cagttttgcc tgcaccagca ggccaagtat tgttcagaaa gagacaagtt   1500

agtctataac cgcgg                                                    1515
```

<210> SEQ ID NO 74
<211> LENGTH: 499
<212> TYPE: PRT
<213> ORGANISM: Trametes versicolor

<400> SEQUENCE: 74

```
Met Glu Asp Pro Thr Val Leu Tyr Ala Cys Leu Ala Ile Ala Val Ala
1               5                   10                  15

Thr Phe Val Val Arg Trp Tyr Arg Asp Pro Leu Arg Ser Ile Pro Thr
            20                  25                  30

Val Gly Gly Ser Asp Leu Pro Ile Leu Ser Tyr Ile Gly Ala Leu Arg
        35                  40                  45

Trp Thr Arg Arg Gly Arg Glu Ile Leu Gln Glu Gly Tyr Asp Gly Tyr
    50                  55                  60

Arg Gly Ser Thr Phe Lys Ile Ala Met Leu Asp Arg Trp Ile Val Ile
65                  70                  75                  80

Ala Asn Gly Pro Lys Leu Ala Asp Glu Val Arg Arg Arg Pro Asp Glu
                85                  90                  95

Glu Leu Asn Phe Met Asp Gly Leu Gly Ala Phe Val Gln Thr Lys Tyr
            100                 105                 110

Thr Leu Gly Glu Ala Ile His Asn Asp Pro Tyr His Val Asp Ile Ile
        115                 120                 125

Arg Glu Lys Leu Thr Arg Gly Leu Pro Ala Val Leu Pro Asp Val Ile
    130                 135                 140

Glu Glu Leu Thr Leu Ala Val Arg Gln Tyr Ile Pro Thr Glu Gly Asp
145                 150                 155                 160

Glu Trp Val Ser Val Asn Cys Ser Lys Ala Ala Arg Asp Ile Val Ala
                165                 170                 175

Arg Ala Ser Asn Arg Val Phe Val Gly Leu Pro Ala Cys Arg Asn Gln
            180                 185                 190

Gly Tyr Leu Asp Leu Ala Ile Asp Phe Thr Leu Ser Val Val Lys Asp
```

-continued

```
        195                 200                 205

Arg Ala Ile Ile Asn Met Phe Pro Glu Leu Leu Lys Pro Ile Val Gly
    210                 215                 220

Arg Val Val Gly Asn Ala Thr Arg Asn Val Arg Arg Ala Val Pro Phe
225                 230                 235                 240

Val Ala Pro Leu Val Glu Glu Arg Arg Arg Leu Met Glu Glu Tyr Gly
                245                 250                 255

Glu Asp Trp Ser Glu Lys Pro Asn Asp Met Leu Gln Trp Ile Met Asp
            260                 265                 270

Glu Ala Ala Ser Arg Asp Ser Ser Val Lys Ala Ile Ala Glu Arg Leu
        275                 280                 285

Leu Met Val Asn Phe Ala Ala Ile His Thr Ser Ser Asn Thr Ile Thr
    290                 295                 300

His Ala Leu Tyr His Leu Ala Glu Met Pro Glu Thr Leu Gln Pro Leu
305                 310                 315                 320

Arg Glu Glu Ile Glu Pro Leu Val Lys Glu Glu Gly Trp Thr Lys Ala
                325                 330                 335

Ala Met Gly Lys Met Trp Trp Leu Asp Ser Phe Leu Arg Glu Ser Gln
            340                 345                 350

Arg Tyr Asn Gly Ile Asn Ile Val Ser Leu Thr Arg Met Ala Asp Lys
        355                 360                 365

Asp Ile Thr Leu Ser Asp Gly Thr Phe Leu Pro Lys Gly Thr Leu Val
    370                 375                 380

Ala Val Pro Ala Tyr Ser Thr His Arg Asp Asp Ala Val Tyr Ala Asp
385                 390                 395                 400

Ala Leu Val Phe Asp Pro Phe Arg Phe Ser Arg Met Arg Ala Arg Glu
                405                 410                 415

Gly Glu Gly Thr Lys His Gln Phe Val Asn Thr Ser Val Glu Tyr Val
            420                 425                 430

Pro Phe Gly His Gly Lys His Ala Cys Pro Gly Arg Phe Phe Ala Ala
        435                 440                 445

Asn Glu Leu Lys Ala Met Leu Ala Tyr Ile Val Leu Asn Tyr Asp Val
    450                 455                 460

Lys Leu Pro Gly Asp Gly Lys Arg Pro Leu Asn Met Tyr Trp Gly Pro
465                 470                 475                 480

Thr Val Leu Pro Ala Pro Ala Gly Gln Val Leu Phe Arg Lys Arg Gln
                485                 490                 495

Val Ser Leu
```

<210> SEQ ID NO 75
<211> LENGTH: 1530
<212> TYPE: DNA
<213> ORGANISM: Artificial Sequence
<220> FEATURE:
<223> OTHER INFORMATION: Codon-optimized KO

<400> SEQUENCE: 75

```
atggcatttt tctctatgat ttcaattttg ttgggatttg ttatttcttc tttcatcttc      60

atctttttct tcaaaaagtt acttagtttt agtaggaaaa acatgtcaga agtttctact     120

ttgccaagtg ttccagtagt gcctggtttt ccagttattg ggaatttgtt gcaactaaag     180

gagaaaaagc ctcataaaac tttcactaga tggtcagaga tatatggacc tatctactct     240

ataaagatgg gttcttcatc tcttattgta ttgaacagta cagaaactgc taaggaagca     300

atggtcacta gattttcatc aatatctacc agaaaattgt caaacgccct aacagttcta     360
```

```
acctgcgata agtctatggt cgccacttct gattatgatg acttccacaa attagttaag    420

agatgtttgc taaatggact tcttggtgct aatgctcaaa agagaaaaag acactacaga    480

gatgctttga ttgaaaatgt gagttccaag ctacatgcac acgctagaga tcatccacaa    540

gagccagtta actttagagc aattttcgaa cacgaattgt ttggtgtagc attaaagcaa    600

gccttcggta aagacgtaga atccatatac gtcaaggagt taggcgtaac attatcaaaa    660

gatgaaatct ttaaggtgct tgtacatgat atgatggagg gtgcaattga tgtagattgg    720

agagatttct tcccatattt gaaatggatc cctaataagt cttttgaagc taggatacaa    780

caaaagcaca agagaagact agctgttatg aacgcactta tacaggacag attgaagcaa    840

aatgggtctg aatcagatga tgattgttac cttaacttct taatgtctga ggctaaaaca    900

ttgactaagg aacagatcgc aatccttgtc tgggaaacaa tcattgaaac agcagatact    960

accttagtca caactgaatg ggccatatac gagctagcca aacatccatc tgtgcaagat   1020

aggttgtgta aggagatcca gaacgtgtgt ggtggagaga aattcaagga agagcagttg   1080

tcacaagttc cttaccttaa cggcgttttc catgaaacct tgagaaaata ctcacctgca   1140

ccattagttc ctattagata cgcccacgaa gatacacaaa tcggtggcta ccatgttcca   1200

gctgggtccg aaattgctat aaacatctac gggtgcaaca tggacaaaaa gagatgggaa   1260

agaccagaag attggtggcc agaaagattc ttagatgatg gcaaatatga aacatctgat   1320

ttgcataaaa caatggcttt cggagctggc aaaagagtgt gtgccggtgc tctacaagcc   1380

tccctaatgg ctggtatcgc tattggtaga ttggtccaag agttcgaatg gaaacttaga   1440

gatggtgaag aggaaaatgt cgatacttat gggttaacat ctcaaaagtt atacccacta   1500

atggcaatca tcaatcctag aagatcctaa                                    1530
```

```
<210> SEQ ID NO 76
<211> LENGTH: 509
<212> TYPE: PRT
<213> ORGANISM: Arabidopsis thaliana

<400> SEQUENCE: 76

Met Ala Phe Phe Ser Met Ile Ser Ile Leu Leu Gly Phe Val Ile Ser
1               5                   10                  15

Ser Phe Ile Phe Ile Phe Phe Phe Lys Lys Leu Leu Ser Phe Ser Arg
            20                  25                  30

Lys Asn Met Ser Glu Val Ser Thr Leu Pro Ser Val Pro Val Val Pro
        35                  40                  45

Gly Phe Pro Val Ile Gly Asn Leu Leu Gln Leu Lys Glu Lys Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Arg Lys Arg His Tyr Arg
145                 150                 155                 160
```

```
Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
    290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Pro Ala Pro Leu Val Pro
    370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
        435                 440                 445

Ala Gly Lys Arg Val Cys Ala Gly Ala Leu Gln Ala Ser Leu Met Ala
    450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
            500                 505
```

<210> SEQ ID NO 77
<211> LENGTH: 2133
<212> TYPE: DNA
<213> ORGANISM: Artificial Sequence
<220> FEATURE:
<223> OTHER INFORMATION: Codon-optimized CPR

<400> SEQUENCE: 77

```
atgcaatcag attcagtcaa agtctctcca tttgatttgg tttccgctgc tatgaatggc      60

aaggcaatgg aaaagttgaa cgctagtgaa tctgaagatc caacaacatt gcctgcacta     120
```

```
aagatgctag ttgaaaatag agaattgttg acactgttca caacttcctt cgcagttctt    180
attgggtgtc ttgtatttct aatgtggaga cgttcatcct ctaaaaagct ggtacaagat    240
ccagttccac aagttatcgt tgtaaagaag aaagagaagg agtcagaggt tgatgacggg    300
aaaaagaaag tttctatttt ctacggcaca caaacaggaa ctgccgaagg ttttgctaaa    360
gcattagtcg aggaagcaaa agtgagatat gaaaagacct ctttcaaggt tatcgatcta    420
gatgactacg ctgcagatga tgatgaatat gaggaaaaac tgaaaaagga atccttagcc    480
ttcttcttct tggccacata cggtgatggt gaacctactg ataatgctgc taacttctac    540
aagtggttca cagaaggcga cgataaaggt gaatggctga aaaagttaca atacggagta    600
tttggtttag gtaacagaca atatgaacat ttcaacaaga tcgctattgt agttgatgat    660
aaacttactg aaatgggagc caaaagatta gtaccagtag gattagggga tgatgatcag    720
tgtatagaag atgacttcac cgcctggaag gaattggtat ggccagaatt ggatcaactt    780
ttaagggacg aagatgatac ttctgtgact accccataca ctgcagccgt attggagtac    840
agagtggttt accatgataa accagcagac tcatatgctg aagatcaaac ccatacaaac    900
ggtcatgttg ttcatgatgc acagcatcct tcaagatcta atgtggcttt caaaaaggaa    960
ctacacacct ctcaatcaga taggtcttgt actcacttag aattcgatat ttctcacaca   1020
ggactgtctt acgaaactgg cgatcacgtt ggcgtttatt ccgagaactt gtccgaagtt   1080
gtcgatgaag cactaaaact gttagggtta tcaccagaca catacttctc agtccatgct   1140
gataaggagg atgggacacc tatcggtggt gcttcactac caccaccttt tcctccttgc   1200
acattgagag acgctctaac cagatacgca gatgtcttat cctcacctaa aaaggtagct   1260
ttgctggcat tggctgctca tgctagtgat cctagtgaag ccgataggtt aaagttcctg   1320
gcttcaccag ccggaaaaga tgaatatgca caatggatcg tcgccaacca acgttctttg   1380
ctagaagtga tgcaaagttt tccatctgcc aagcctccat taggtgtgtt cttcgcagca   1440
gtagctccac gtttacaacc aagatactac tctatcagtt catctcctaa gatgtctcct   1500
aacagaatac atgttacatg tgctttggtg tacgagacta ctccagcagg cagaattcac   1560
agaggattgt gttcaacctg gatgaaaaat gctgtccctt taacagagtc acctgattgc   1620
tctcaagcat ccattttcgt tagaacatca aatttcagac ttccagtgga tccaaaagtt   1680
ccagtcatta tgataggacc aggcactggt cttgccccat tcaggggctt tcttcaagag   1740
agattggcct tgaaggaatc tggtacagaa ttgggttctt ctatcttttt ctttggttgc   1800
cgtaatagaa aagttgactt tatctacgag gacgagctta acaattttgt tgagacagga   1860
gcattgtcag aattgatcgt cgcattttca agagaaggga ctgccaaaga gtacgttcag   1920
cacaagatga gtcaaaaagc ctccgatata tggaaacttc taagtgaagg tgcctatctt   1980
tatgtctgtg gcgatgcaaa gggcatggcc aaggatgtcc atagaactct gcatacaatt   2040
gttcaggaac aagggagtct ggattcttcc aaggctgaat tgtacgtcaa aaacttacag   2100
atgtctggaa gatacttaag agatgtttgg taa                                2133
```

<210> SEQ ID NO 78
<211> LENGTH: 710
<212> TYPE: PRT
<213> ORGANISM: Stevia rebaudiana

<400> SEQUENCE: 78

```
Met Gln Ser Asp Ser Val Lys Val Ser Pro Phe Asp Leu Val Ser Ala
1               5                   10                  15
```

```
Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Ser Lys Lys Leu Val Gln Asp
65                  70                  75                  80

Pro Val Pro Gln Val Ile Val Val Lys Lys Lys Glu Lys Glu Ser Glu
                85                  90                  95

Val Asp Asp Gly Lys Lys Lys Val Ser Ile Phe Tyr Gly Thr Gln Thr
            100                 105                 110

Gly Thr Ala Glu Gly Phe Ala Lys Ala Leu Val Glu Glu Ala Lys Val
        115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
            180                 185                 190

Leu Lys Lys Leu Gln Tyr Gly Val Phe Gly Leu Gly Asn Arg Gln Tyr
        195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Asp Thr Ser Val Thr Thr Pro
            260                 265                 270

Tyr Thr Ala Ala Val Leu Glu Tyr Arg Val Val Tyr His Asp Lys Pro
        275                 280                 285

Ala Asp Ser Tyr Ala Glu Asp Gln Thr His Thr Asn Gly His Val Val
    290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
            340                 345                 350

Tyr Ser Glu Asn Leu Ser Glu Val Val Asp Glu Ala Leu Lys Leu Leu
        355                 360                 365

Gly Leu Ser Pro Asp Thr Tyr Phe Ser Val His Ala Asp Lys Glu Asp
    370                 375                 380

Gly Thr Pro Ile Gly Gly Ala Ser Leu Pro Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
            420                 425                 430
```

```
Glu Ala Asp Arg Leu Lys Phe Leu Ala Ser Pro Ala Gly Lys Asp Glu
        435                 440                 445

Tyr Ala Gln Trp Ile Val Ala Asn Gln Arg Ser Leu Leu Glu Val Met
    450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
    530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Phe Gly Cys Arg Asn Arg Lys Val Asp Phe Ile
        595                 600                 605

Tyr Glu Asp Glu Leu Asn Asn Phe Val Glu Thr Gly Ala Leu Ser Glu
    610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685

Ser Ser Lys Ala Glu Leu Tyr Val Lys Asn Leu Gln Met Ser Gly Arg
    690                 695                 700

Tyr Leu Arg Asp Val Trp
705                 710
```

<210> SEQ ID NO 79
<211> LENGTH: 2106
<212> TYPE: DNA
<213> ORGANISM: Siraitia grosvenorii

<400> SEQUENCE: 79

```
atgaaggtca gtccattcga attcatgtcc gctattatca agggtagaat ggacccatct      60

aactcctcat ttgaatctac tggtgaagtt gcctccgtta tctttgaaaa cagagaattg     120

gttgccatct tgaccacttc tattgctgtt atgattggtt gcttcgttgt cttgatgtgg     180

agaagagctg gttctagaaa ggttaagaat gtcgaattgc caaagccatt gattgtccat     240

gaaccagaac ctgaagttga agatggtaag aagaaggttt ccatcttctt cggtactcaa     300

actggtactg ctgaaggttt tgctaaggct ttggctgatg aagctaaagc tagatacgaa     360

aaggctacct tcagagttgt tgatttggat gattatgctg ccgatgatga ccaatacgaa     420

gaaaaattga agaacgaatc cttcgccgtt ttcttgttgg ctacttatgg tgatggtgaa     480

cctactgata atgctgctag attttacaag tggttcgccg aaggtaaaga aagaggtgaa     540
```

```
tggttgcaaa acttgcacta tgctgttttt ggtttgggta acagacaata cgaacacttc    600

aacaagattg ctaaggttgc cgacgaatta ttggaagctc aaggtggtaa tagattggtt    660

aaggttggtt taggtgatga cgatcaatgc atcgaagatg atttttctgc ttggagagaa    720

tctttgtggc cagaattgga tatgttgttg agagatgaag atgatgctac tactgttact    780

actccatata ctgctgctgt cttggaatac agagttgtct ttcatgattc tgctgatgtt    840

gctgctgaag ataagtcttg gattaacgct aatggtcatg ctgttcatga tgctcaacat    900

ccattcagat ctaacgttgt cgtcagaaaa gaattgcata cttctgcctc tgatagatcc    960

tgttctcatt tggaattcaa catttccggt tccgctttga attacgaaac tggtgatcat   1020

gttggtgtct actgtgaaaa cttgactgaa actgttgatg aagccttgaa cttgttgggt   1080

ttgtctccag aaacttactt ctctatctac accgataacg aagatggtac tccattgggt   1140

ggttcttcat tgccaccacc atttccatca tgtactttga gaactgcttt gaccagatac   1200

gctgatttgt tgaactctcc aaaaaagtct gctttgttgg ctttagctgc tcatgcttct   1260

aatccagttg aagctgatag attgagatac ttggcttctc cagctggtaa agatgaatat   1320

gcccaatctg ttatcggttc ccaaaagtct ttgttggaag ttatggctga attcccatct   1380

gctaaaccac cattaggtgt ttttttttgct gctgttgctc caagattgca acctagattc   1440

tactccattt catcctctcc aagaatggct ccatctagaa tccatgttac ttgtgctttg   1500

gtttacgata agatgccaac tggtagaatt cataagggtg tttgttctac ctggatgaag   1560

aattctgttc caatggaaaa gtcccatgaa tgttcttggg ctccaatttt cgttagacaa   1620

tccaatttta agttgccagc cgaatccaag gttccaatta tcatggttgg tccaggtact   1680

ggtttggctc cttttagagg ttttttacaa gaaagattgg ccttgaaaga atccggtgtt   1740

gaattgggtc catccatttt gtttttcggt tgcagaaaca gaagaatgga ttacatctac   1800

gaagatgaat tgaacaactt cgttgaaacc ggtgctttgt ccgaattggt tattgctttt   1860

tctagagaag gtcctaccaa agaatacgtc caacataaga tggctgaaaa ggcttctgat   1920

atctggaact tgatttctga aggtgcttac ttgtacgttt gtggtgatgc taaaggtatg   1980

gctaaggatg ttcatagaac cttgcatacc atcatgcaag aacaaggttc tttggattct   2040

tccaaagctg aatccatggt caagaacttg caaatgaatg gtagatactt aagagatgtt   2100

tggtaa                                                              2106
```

<210> SEQ ID NO 80
<211> LENGTH: 701
<212> TYPE: PRT
<213> ORGANISM: Siraitia grosvenorii

<400> SEQUENCE: 80

```
Met Lys Val Ser Pro Phe Glu Phe Met Ser Ala Ile Ile Lys Gly Arg
1               5                   10                  15

Met Asp Pro Ser Asn Ser Ser Phe Glu Ser Thr Gly Glu Val Ala Ser
            20                  25                  30

Val Ile Phe Glu Asn Arg Glu Leu Val Ala Ile Leu Thr Thr Ser Ile
        35                  40                  45

Ala Val Met Ile Gly Cys Phe Val Val Leu Met Trp Arg Arg Ala Gly
    50                  55                  60

Ser Arg Lys Val Lys Asn Val Glu Leu Pro Lys Pro Leu Ile Val His
65                  70                  75                  80

Glu Pro Glu Pro Glu Val Glu Asp Gly Lys Lys Lys Val Ser Ile Phe
```

-continued

```
                85                  90                  95

Phe Gly Thr Gln Thr Gly Thr Ala Glu Gly Phe Ala Lys Ala Leu Ala
            100                 105                 110

Asp Glu Ala Lys Ala Arg Tyr Glu Lys Ala Thr Phe Arg Val Val Asp
        115                 120                 125

Leu Asp Asp Tyr Ala Ala Asp Asp Asp Gln Tyr Glu Glu Lys Leu Lys
    130                 135                 140

Asn Glu Ser Phe Ala Val Phe Leu Leu Ala Thr Tyr Gly Asp Gly Glu
145                 150                 155                 160

Pro Thr Asp Asn Ala Ala Arg Phe Tyr Lys Trp Phe Ala Glu Gly Lys
                165                 170                 175

Glu Arg Gly Glu Trp Leu Gln Asn Leu His Tyr Ala Val Phe Gly Leu
            180                 185                 190

Gly Asn Arg Gln Tyr Glu His Phe Asn Lys Ile Ala Lys Val Ala Asp
        195                 200                 205

Glu Leu Leu Glu Ala Gln Gly Gly Asn Arg Leu Val Lys Val Gly Leu
    210                 215                 220

Gly Asp Asp Asp Gln Cys Ile Glu Asp Asp Phe Ser Ala Trp Arg Glu
225                 230                 235                 240

Ser Leu Trp Pro Glu Leu Asp Met Leu Leu Arg Asp Glu Asp Asp Ala
                245                 250                 255

Thr Thr Val Thr Thr Pro Tyr Thr Ala Ala Val Leu Glu Tyr Arg Val
            260                 265                 270

Val Phe His Asp Ser Ala Asp Val Ala Ala Glu Asp Lys Ser Trp Ile
        275                 280                 285

Asn Ala Asn Gly His Ala Val His Asp Ala Gln His Pro Phe Arg Ser
    290                 295                 300

Asn Val Val Val Arg Lys Glu Leu His Thr Ser Ala Ser Asp Arg Ser
305                 310                 315                 320

Cys Ser His Leu Glu Phe Asn Ile Ser Gly Ser Ala Leu Asn Tyr Glu
                325                 330                 335

Thr Gly Asp His Val Gly Val Tyr Cys Glu Asn Leu Thr Glu Thr Val
            340                 345                 350

Asp Glu Ala Leu Asn Leu Leu Gly Leu Ser Pro Glu Thr Tyr Phe Ser
        355                 360                 365

Ile Tyr Thr Asp Asn Glu Asp Gly Thr Pro Leu Gly Gly Ser Ser Leu
    370                 375                 380

Pro Pro Pro Phe Pro Ser Cys Thr Leu Arg Thr Ala Leu Thr Arg Tyr
385                 390                 395                 400

Ala Asp Leu Leu Asn Ser Pro Lys Lys Ser Ala Leu Leu Ala Leu Ala
                405                 410                 415

Ala His Ala Ser Asn Pro Val Glu Ala Asp Arg Leu Arg Tyr Leu Ala
            420                 425                 430

Ser Pro Ala Gly Lys Asp Glu Tyr Ala Gln Ser Val Ile Gly Ser Gln
        435                 440                 445

Lys Ser Leu Leu Glu Val Met Ala Glu Phe Pro Ser Ala Lys Pro Pro
    450                 455                 460

Leu Gly Val Phe Phe Ala Ala Val Ala Pro Arg Leu Gln Pro Arg Phe
465                 470                 475                 480

Tyr Ser Ile Ser Ser Ser Pro Arg Met Ala Pro Ser Arg Ile His Val
                485                 490                 495

Thr Cys Ala Leu Val Tyr Asp Lys Met Pro Thr Gly Arg Ile His Lys
            500                 505                 510
```

```
Gly Val Cys Ser Thr Trp Met Lys Asn Ser Val Pro Met Glu Lys Ser
        515                 520                 525

His Glu Cys Ser Trp Ala Pro Ile Phe Val Arg Gln Ser Asn Phe Lys
    530                 535                 540

Leu Pro Ala Glu Ser Lys Val Pro Ile Ile Met Val Gly Pro Gly Thr
545                 550                 555                 560

Gly Leu Ala Pro Phe Arg Gly Phe Leu Gln Glu Arg Leu Ala Leu Lys
                565                 570                 575

Glu Ser Gly Val Glu Leu Gly Pro Ser Ile Leu Phe Phe Gly Cys Arg
            580                 585                 590

Asn Arg Arg Met Asp Tyr Ile Tyr Glu Asp Glu Leu Asn Asn Phe Val
        595                 600                 605

Glu Thr Gly Ala Leu Ser Glu Leu Val Ile Ala Phe Ser Arg Glu Gly
    610                 615                 620

Pro Thr Lys Glu Tyr Val Gln His Lys Met Ala Glu Lys Ala Ser Asp
625                 630                 635                 640

Ile Trp Asn Leu Ile Ser Glu Gly Ala Tyr Leu Tyr Val Cys Gly Asp
                645                 650                 655

Ala Lys Gly Met Ala Lys Asp Val His Arg Thr Leu His Thr Ile Met
            660                 665                 670

Gln Glu Gln Gly Ser Leu Asp Ser Ser Lys Ala Glu Ser Met Val Lys
        675                 680                 685

Asn Leu Gln Met Asn Gly Arg Tyr Leu Arg Asp Val Trp
    690                 695                 700


<210> SEQ ID NO 81
<211> LENGTH: 2142
<212> TYPE: DNA
<213> ORGANISM: Artificial Sequence
<220> FEATURE:
<223> OTHER INFORMATION: Codon-optimized CPR

<400> SEQUENCE: 81

atggcagaat tagatacact tgatatagta gtattaggtg ttatcttttt gggtactgtg      60

gcatacttta ctaagggtaa attgtggggt gttaccaagg atccatacgc taacggattc     120

gctgcaggtg gtgcttccaa gcctggcaga actagaaaca tcgtcgaagc tatggaggaa     180

tcaggtaaaa actgtgttgt tttctacggc agtcaaacag gtacagcgga ggattacgca     240

tcaagacttg caaaggaagg aaagtccaga ttcggtttga acactatgat cgccgatcta     300

gaagattatg acttcgataa cttagacact gttccatctg ataacatcgt tatgtttgta     360

ttggctactt acggtgaagg cgaaccaaca gataacgccg tggatttcta tgagttcatt     420

actggcgaag atgcctcttt caatgagggc aacgatcctc cactaggtaa cttgaattac     480

gttgcgttcg gtctgggcaa caatacctac gaacactaca actcaatggt caggaacgtt     540

aacaaggctc tagaaaagtt aggagctcat agaattggag aagcaggtga gggtgacgac     600

ggagctggaa ctatggaaga ggactttta gcttggaaag atccaatgtg ggaagccttg     660

gctaaaaaga tgggcttgga ggaaagagaa gctgtatatg aacctatttt cgctatcaat     720

gagagagatg atttgacccc tgaagcgaat gaggtatact tgggagaacc taataagcta     780

cacttggaag gtacagcgaa aggtccattc aactcccaca acccatatat cgcaccaatt     840

gcagaatcat acgaactttt ctcagctaag gatagaaatt gtctgcatat ggaaattgat     900

atttctggta gtaatctaaa gtatgaaaca ggcgaccata tcgcgatctg gcctaccaac     960
```

```
ccaggtgaag aggtcaacaa atttcttgac attctagatc tgtctggtaa gcaacattcc   1020

gtcgtaacag tgaaagcctt agaacctaca gccaaagttc cttttccaaa tccaactacc   1080

tacgatgcta tattgagata ccatctggaa atatgcgctc cagtttctag acagtttgtc   1140

tcaactttag cagcattcgc ccctaatgat gatatcaaag ctgagatgaa ccgtttggga   1200

tcagacaaag attacttcca cgaaaagaca ggaccacatt actacaatat cgctagattt   1260

ttggcctcag tctctaaagg tgaaaaatgg acaaagatac cattttctgc tttcatagaa   1320

ggccttacaa aactacaacc aagatactat tctatctctt cctctagttt agttcagcct   1380

aaaaagatta gtattactgc tgttgtcgaa tctcagcaaa ttccaggtag agatgaccca   1440

ttcagaggtg tagcgactaa ctacttgttc gctttgaagc agaaacaaaa cggtgatcca   1500

aatccagctc cttttggcca atcatacgag ttgacaggac caaggaataa gtatgatggt   1560

atacatgttc cagtccatgt aagacattct aactttaagc taccatctga tccaggcaaa   1620

cctattatca tgatcggtcc aggtaccggt gttgcccctt ttagaggctt cgtccaagag   1680

agggcaaaac aagccagaga tggtgtagaa gttggtaaaa cactgctgtt ctttggatgt   1740

agaaagagta cagaagattt catgtatcaa aaagagtggc aagagtacaa ggaagctctt   1800

ggcgacaaat tcgaaatgat tacagctttt tcaagagaag gatctaaaaa ggtttatgtt   1860

caacacagac tgaaggaaag atcaaaggaa gtttctgatc ttctatccca aaaagcatac   1920

ttctacgttt gcggagacgc cgcacatatg gcacgtgaag tgaacactgt gttagcacag   1980

atcatagcag aaggccgtgg tgtatcagaa gccaagggtg aggaaattgt caaaaacatg   2040

agatcagcaa atcaatacca agtgtgttct gatttcgtaa ctttacactg taaagagaca   2100

acatacgcga attcagaatt gcaagaggat gtctggagtt aa                      2142
```

<210> SEQ ID NO 82
<211> LENGTH: 713
<212> TYPE: PRT
<213> ORGANISM: Gibberella fujikuroi

<400> SEQUENCE: 82

```
Met Ala Glu Leu Asp Thr Leu Asp Ile Val Val Leu Gly Val Ile Phe
1               5                   10                  15

Leu Gly Thr Val Ala Tyr Phe Thr Lys Gly Lys Leu Trp Gly Val Thr
            20                  25                  30

Lys Asp Pro Tyr Ala Asn Gly Phe Ala Ala Gly Gly Ala Ser Lys Pro
        35                  40                  45

Gly Arg Thr Arg Asn Ile Val Glu Ala Met Glu Glu Ser Gly Lys Asn
    50                  55                  60

Cys Val Val Phe Tyr Gly Ser Gln Thr Gly Thr Ala Glu Asp Tyr Ala
65                  70                  75                  80

Ser Arg Leu Ala Lys Glu Gly Lys Ser Arg Phe Gly Leu Asn Thr Met
                85                  90                  95

Ile Ala Asp Leu Glu Asp Tyr Asp Phe Asp Asn Leu Asp Thr Val Pro
            100                 105                 110

Ser Asp Asn Ile Val Met Phe Val Leu Ala Thr Tyr Gly Glu Gly Glu
        115                 120                 125

Pro Thr Asp Asn Ala Val Asp Phe Tyr Glu Phe Ile Thr Gly Glu Asp
    130                 135                 140

Ala Ser Phe Asn Glu Gly Asn Asp Pro Pro Leu Gly Asn Leu Asn Tyr
145                 150                 155                 160

Val Ala Phe Gly Leu Gly Asn Asn Thr Tyr Glu His Tyr Asn Ser Met
```

```
                165                 170                 175

Val Arg Asn Val Asn Lys Ala Leu Glu Lys Leu Gly Ala His Arg Ile
            180                 185                 190

Gly Glu Ala Gly Glu Gly Asp Asp Gly Ala Gly Thr Met Glu Glu Asp
        195                 200                 205

Phe Leu Ala Trp Lys Asp Pro Met Trp Glu Ala Leu Ala Lys Lys Met
    210                 215                 220

Gly Leu Glu Glu Arg Glu Ala Val Tyr Glu Pro Ile Phe Ala Ile Asn
225                 230                 235                 240

Glu Arg Asp Asp Leu Thr Pro Glu Ala Asn Glu Val Tyr Leu Gly Glu
                245                 250                 255

Pro Asn Lys Leu His Leu Glu Gly Thr Ala Lys Gly Pro Phe Asn Ser
            260                 265                 270

His Asn Pro Tyr Ile Ala Pro Ile Ala Glu Ser Tyr Glu Leu Phe Ser
        275                 280                 285

Ala Lys Asp Arg Asn Cys Leu His Met Glu Ile Asp Ile Ser Gly Ser
    290                 295                 300

Asn Leu Lys Tyr Glu Thr Gly Asp His Ile Ala Ile Trp Pro Thr Asn
305                 310                 315                 320

Pro Gly Glu Glu Val Asn Lys Phe Leu Asp Ile Leu Asp Leu Ser Gly
                325                 330                 335

Lys Gln His Ser Val Val Thr Val Lys Ala Leu Glu Pro Thr Ala Lys
            340                 345                 350

Val Pro Phe Pro Asn Pro Thr Thr Tyr Asp Ala Ile Leu Arg Tyr His
        355                 360                 365

Leu Glu Ile Cys Ala Pro Val Ser Arg Gln Phe Val Ser Thr Leu Ala
    370                 375                 380

Ala Phe Ala Pro Asn Asp Asp Ile Lys Ala Glu Met Asn Arg Leu Gly
385                 390                 395                 400

Ser Asp Lys Asp Tyr Phe His Glu Lys Thr Gly Pro His Tyr Tyr Asn
                405                 410                 415

Ile Ala Arg Phe Leu Ala Ser Val Ser Lys Gly Glu Lys Trp Thr Lys
            420                 425                 430

Ile Pro Phe Ser Ala Phe Ile Glu Gly Leu Thr Lys Leu Gln Pro Arg
        435                 440                 445

Tyr Tyr Ser Ile Ser Ser Ser Ser Leu Val Gln Pro Lys Lys Ile Ser
    450                 455                 460

Ile Thr Ala Val Val Glu Ser Gln Gln Ile Pro Gly Arg Asp Asp Pro
465                 470                 475                 480

Phe Arg Gly Val Ala Thr Asn Tyr Leu Phe Ala Leu Lys Gln Lys Gln
                485                 490                 495

Asn Gly Asp Pro Asn Pro Ala Pro Phe Gly Gln Ser Tyr Glu Leu Thr
            500                 505                 510

Gly Pro Arg Asn Lys Tyr Asp Gly Ile His Val Pro Val His Val Arg
        515                 520                 525

His Ser Asn Phe Lys Leu Pro Ser Asp Pro Gly Lys Pro Ile Ile Met
    530                 535                 540

Ile Gly Pro Gly Thr Gly Val Ala Pro Phe Arg Gly Phe Val Gln Glu
545                 550                 555                 560

Arg Ala Lys Gln Ala Arg Asp Gly Val Glu Val Gly Lys Thr Leu Leu
                565                 570                 575

Phe Phe Gly Cys Arg Lys Ser Thr Glu Asp Phe Met Tyr Gln Lys Glu
            580                 585                 590
```

Trp Gln Glu Tyr Lys Glu Ala Leu Gly Asp Lys Phe Glu Met Ile Thr
595 600 605

Ala Phe Ser Arg Glu Gly Ser Lys Lys Val Tyr Val Gln His Arg Leu
610 615 620

Lys Glu Arg Ser Lys Glu Val Ser Asp Leu Leu Ser Gln Lys Ala Tyr
625 630 635 640

Phe Tyr Val Cys Gly Asp Ala Ala His Met Ala Arg Glu Val Asn Thr
645 650 655

Val Leu Ala Gln Ile Ile Ala Glu Gly Arg Gly Val Ser Glu Ala Lys
660 665 670

Gly Glu Glu Ile Val Lys Asn Met Arg Ser Ala Asn Gln Tyr Gln Val
675 680 685

Cys Ser Asp Phe Val Thr Leu His Cys Lys Glu Thr Thr Tyr Ala Asn
690 695 700

Ser Glu Leu Gln Glu Asp Val Trp Ser
705 710

<210> SEQ ID NO 83
<211> LENGTH: 2130
<212> TYPE: DNA
<213> ORGANISM: Stevia rebaudiana

<400> SEQUENCE: 83
atgcaatcgg aatccgttga agcatcgacg attgatttga tgactgctgt tttgaaggac 60
acagtgatcg atacagcgaa cgcatctgat aacggagact caaagatgcc gccggcgttg 120
gcgatgatgt tcgaaattcg tgatctgttg ctgattttga ctacgtcagt tgctgttttg 180
gtcggatgtt tcgttgtttt ggtgtggaag agatcgtccg ggaagaagtc cggcaaggaa 240
ttggagccgc cgaagatcgt tgtgccgaag aggcggctgg agcaggaggt tgatgatggt 300
aagaagaagg ttacgatttt cttcggaaca caaactggaa cggctgaagg tttcgctaag 360
gcacttttcg aagaagcgaa agcgcgatat gaaaaggcag cgtttaaagt gattgatttg 420
gatgattatg ctgctgattt ggatgagtat gcagagaagc tgaagaagga aacatatgct 480
ttcttcttct tggctacata tggagatggt gagccaactg ataatgctgc caaattttat 540
aaatggttta ctgagggaga cgagaaaggc gtttggcttc aaaaacttca atatggagta 600
tttggtcttg gcaacagaca atatgaacat ttcaacaaga ttggaatagt ggttgatgat 660
ggtctcaccg agcagggtgc aaaacgcatt gttcccgttg gtcttggaga cgacgatcaa 720
tcaattgaag acgatttttc ggcatggaaa gagttagtgt ggcccgaatt ggatctattg 780
cttcgcgatg aagatgacaa agctgctgca actccttaca cagctgcaat ccctgaatac 840
cgcgtcgtat ttcatgacaa acccgatgcg ttttctgatg atcatactca aaccaatggt 900
catgctgttc atgatgctca acatccatgc agatccaatg tggctgttaa aaaagagctt 960
catactcctg aatccgatcg ttcatgcaca catcttgaat ttgacatttc tcacactgga 1020
ttatcttatg aaactgggga tcatgttggt gtatactgtg aaaacctaat tgaagtagtg 1080
gaagaagctg ggaaattgtt aggattatca acagatactt atttctcgtt acatattgat 1140
aacgaagatg gttcaccact tggtggacct tcattacaac ctccttttcc tccttgtact 1200
ttaagaaaag cattgactaa ttatgcagat ctgttaagct ctcccaaaaa gtcaactttg 1260
cttgctctag ctgctcatgc ttccgatccc actgaagctg atcgtttaag atttcttgca 1320
tctcgcgagg gcaaggatga atatgctgaa tgggttgttg caaaccaaag aagtcttctt 1380
gaagtcatgg aagctttccc gtcagctaga ccgccacttg gtgttttctt tgcagcggtt 1440
gcaccgcgtt tacagcctcg ttactactct atttcttcct ccccaaagat ggaaccaaac 1500
aggattcatg ttacttgcgc gttggtttat gaaaaaactc ccgcaggtcg tatccacaaa 1560
ggaatctgct caacctggat gaagaacgct gtacctttga ccgaaagtca agattgcagt 1620
tgggcaccga tttttgttag aacatcaaac ttcagacttc caattgaccc gaaagtcccg 1680
gttatcatga ttggtcctgg aaccgggttg gctccattta ggggttttct tcaagaaaga 1740
ttggctctta aagaatccgg aaccgaactc gggtcatcta ttttattctt cggttgtaga 1800
aaccgcaaag tggattacat atatgagaat gaactcaaca actttgttga aaatggtgcg 1860
ctttctgagc ttgatgttgc tttctcccgc gatggcccga cgaaagaata cgtgcaacat 1920
aaaatgaccc aaaaggcttc tgaaatatgg aatatgcttt ctgagggagc atatttatat 1980
gtatgtggtg atgctaaagg catggctaaa gatgtacacc gtacacttca caccattgtg 2040
caagaacagg gaagtttgga ctcgtctaaa gcggagttgt atgtgaagaa tctacaaatg 2100
tcaggaagat acctccgtga tgtttggtaa 2130

<210> SEQ ID NO 84
<211> LENGTH: 709
<212> TYPE: PRT
<213> ORGANISM: Stevia rebaudiana

<400> SEQUENCE: 84

Met Gln Ser Glu Ser Val Glu Ala Ser Thr Ile Asp Leu Met Thr Ala
1 5 10 15

Val Leu Lys Asp Thr Val Ile Asp Thr Ala Asn Ala Ser Asp Asn Gly
20 25 30

Asp Ser Lys Met Pro Pro Ala Leu Ala Met Met Phe Glu Ile Arg Asp
35 40 45

Leu Leu Leu Ile Leu Thr Thr Ser Val Ala Val Leu Val Gly Cys Phe
50 55 60

Val Val Leu Val Trp Lys Arg Ser Ser Gly Lys Lys Ser Gly Lys Glu
65 70 75 80

Leu Glu Pro Pro Lys Ile Val Val Pro Lys Arg Arg Leu Glu Gln Glu
85 90 95

Val Asp Asp Gly Lys Lys Lys Val Thr Ile Phe Phe Gly Thr Gln Thr
100 105 110

Gly Thr Ala Glu Gly Phe Ala Lys Ala Leu Phe Glu Glu Ala Lys Ala
115 120 125

Arg Tyr Glu Lys Ala Ala Phe Lys Val Ile Asp Leu Asp Asp Tyr Ala
130 135 140

Ala Asp Leu Asp Glu Tyr Ala Glu Lys Leu Lys Lys Glu Thr Tyr Ala
145 150 155 160

Phe Phe Phe Leu Ala Thr Tyr Gly Asp Gly Glu Pro Thr Asp Asn Ala
165 170 175

Ala Lys Phe Tyr Lys Trp Phe Thr Glu Gly Asp Glu Lys Gly Val Trp
180 185 190

Leu Gln Lys Leu Gln Tyr Gly Val Phe Gly Leu Gly Asn Arg Gln Tyr
195 200 205

Glu His Phe Asn Lys Ile Gly Ile Val Val Asp Asp Gly Leu Thr Glu
210 215 220

Gln Gly Ala Lys Arg Ile Val Pro Val Gly Leu Gly Asp Asp Asp Gln
225 230 235 240

```
Ser Ile Glu Asp Asp Phe Ser Ala Trp Lys Glu Leu Val Trp Pro Glu
                245                 250                 255

Leu Asp Leu Leu Leu Arg Asp Glu Asp Asp Lys Ala Ala Ala Thr Pro
            260                 265                 270

Tyr Thr Ala Ala Ile Pro Glu Tyr Arg Val Val Phe His Asp Lys Pro
        275                 280                 285

Asp Ala Phe Ser Asp Asp His Thr Gln Thr Asn Gly His Ala Val His
    290                 295                 300

Asp Ala Gln His Pro Cys Arg Ser Asn Val Ala Val Lys Lys Glu Leu
305                 310                 315                 320

His Thr Pro Glu Ser Asp Arg Ser Cys Thr His Leu Glu Phe Asp Ile
                325                 330                 335

Ser His Thr Gly Leu Ser Tyr Glu Thr Gly Asp His Val Gly Val Tyr
            340                 345                 350

Cys Glu Asn Leu Ile Glu Val Val Glu Glu Ala Gly Lys Leu Leu Gly
        355                 360                 365

Leu Ser Thr Asp Thr Tyr Phe Ser Leu His Ile Asp Asn Glu Asp Gly
    370                 375                 380

Ser Pro Leu Gly Gly Pro Ser Leu Gln Pro Pro Phe Pro Pro Cys Thr
385                 390                 395                 400

Leu Arg Lys Ala Leu Thr Asn Tyr Ala Asp Leu Leu Ser Ser Pro Lys
                405                 410                 415

Lys Ser Thr Leu Leu Ala Leu Ala Ala His Ala Ser Asp Pro Thr Glu
            420                 425                 430

Ala Asp Arg Leu Arg Phe Leu Ala Ser Arg Glu Gly Lys Asp Glu Tyr
        435                 440                 445

Ala Glu Trp Val Val Ala Asn Gln Arg Ser Leu Leu Glu Val Met Glu
    450                 455                 460

Ala Phe Pro Ser Ala Arg Pro Pro Leu Gly Val Phe Phe Ala Ala Val
465                 470                 475                 480

Ala Pro Arg Leu Gln Pro Arg Tyr Tyr Ser Ile Ser Ser Ser Pro Lys
                485                 490                 495

Met Glu Pro Asn Arg Ile His Val Thr Cys Ala Leu Val Tyr Glu Lys
            500                 505                 510

Thr Pro Ala Gly Arg Ile His Lys Gly Ile Cys Ser Thr Trp Met Lys
        515                 520                 525

Asn Ala Val Pro Leu Thr Glu Ser Gln Asp Cys Ser Trp Ala Pro Ile
    530                 535                 540

Phe Val Arg Thr Ser Asn Phe Arg Leu Pro Ile Asp Pro Lys Val Pro
545                 550                 555                 560

Val Ile Met Ile Gly Pro Gly Thr Gly Leu Ala Pro Phe Arg Gly Phe
                565                 570                 575

Leu Gln Glu Arg Leu Ala Leu Lys Glu Ser Gly Thr Glu Leu Gly Ser
            580                 585                 590

Ser Ile Leu Phe Phe Gly Cys Arg Asn Arg Lys Val Asp Tyr Ile Tyr
        595                 600                 605

Glu Asn Glu Leu Asn Asn Phe Val Glu Asn Gly Ala Leu Ser Glu Leu
    610                 615                 620

Asp Val Ala Phe Ser Arg Asp Gly Pro Thr Lys Glu Tyr Val Gln His
625                 630                 635                 640

Lys Met Thr Gln Lys Ala Ser Glu Ile Trp Asn Met Leu Ser Glu Gly
                645                 650                 655

Ala Tyr Leu Tyr Val Cys Gly Asp Ala Lys Gly Met Ala Lys Asp Val
```

-continued

```
            660                 665                 670

His Arg Thr Leu His Thr Ile Val Gln Glu Gln Gly Ser Leu Asp Ser
        675                 680                 685

Ser Lys Ala Glu Leu Tyr Val Lys Asn Leu Gln Met Ser Gly Arg Tyr
    690                 695                 700

Leu Arg Asp Val Trp
705


<210> SEQ ID NO 85
<211> LENGTH: 2124
<212> TYPE: DNA
<213> ORGANISM: Artificial Sequence
<220> FEATURE:
<223> OTHER INFORMATION: Codon-optimized CPR

<400> SEQUENCE: 85

atgcaatcta actccgtgaa gatttcgccg cttgatctgg taactgcgct gtttagcggc      60

aaggttttgg acacatcgaa cgcatcggaa tcgggagaat ctgctatgct gccgactata     120

gcgatgatta tggagaatcg tgagctgttg atgatactca caacgtcggt tgctgtattg     180

atcggatgcg ttgtcgtttt ggtgtggcgg agatcgtcta cgaagaagtc ggcgttggag     240

ccaccggtga ttgtggttcc gaagagagtg caagaggagg aagttgatga tggtaagaag     300

aaagttacgg ttttcttcgg cacccaaact ggaacagctg aaggcttcgc taaggcactt     360

gttgaggaag ctaaagctcg atatgaaaag gctgtcttta aagtaattga tttggatgat     420

tatgctgctg atgacgatga gtatgaggag aaactaaaga aagaatcttt ggcctttttc     480

tttttggcta cgtatggaga tggtgagcca acagataatg ctgccagatt ttataaatgg     540

tttactgagg gagatgcgaa aggagaatgg cttaataagc ttcaatatgg agtatttggt     600

ttgggtaaca gacaatatga acattttaac aagatcgcaa aagtggttga tgatggtctt     660

gtagaacagg gtgcaaagcg tcttgttcct gttggacttg gagatgatga tcaatgtatt     720

gaagatgact tcaccgcatg gaaagagtta gtatggccgg agttggatca attacttcgt     780

gatgaggatg acacaactgt tgctactcca tacacagctg ctgttgcaga atatcgcgtt     840

gtttttcatg aaaaaccaga cgcgctttct gaagattata gttatacaaa tggccatgct     900

gttcatgatg ctcaacatcc atgcagatcc aacgtggctg tcaaaaagga acttcatagt     960

cctgaatctg accggtcttg cactcatctt gaatttgaca tctcgaacac cggactatca    1020

tatgaaactg gggaccatgt tggagtttac tgtgaaaact tgagtgaagt tgtgaatgat    1080

gctgaaagat tagtaggatt accaccagac acttactcct ccatccacac tgatagtgaa    1140

gacgggtcgc cacttggcgg agcctcattg ccgcctcctt tcccgccatg cactttaagg    1200

aaagcattga cgtgttatgc tgatgttttg agttctccca agaagtcggc tttgcttgca    1260

ctagctgctc atgccaccga tcccagtgaa gctgatagat tgaaatttct tgcatccccc    1320

gccggaaagg atgaatattc tcaatggata gttgcaagcc aaagaagtct ccttgaagtc    1380

atggaagcat tcccgtcagc taagccttca cttggtgttt tctttgcatc tgttgccccg    1440

cgcttacaac caagatacta ctctatttct tcctcaccca agatggcacc ggataggatt    1500

catgttacat gtgcattagt ctatgagaaa acacctgcag gccgcatcca caaaggagtt    1560

tgttcaactt ggatgaagaa cgcagtgcct atgaccgaga gtcaagattg cagttgggcc    1620

ccaatatacg tccgaacatc caatttcaga ctaccatctg accctaaggt cccggttatc    1680

atgattggac ctggcactgg tttggctcct tttagaggtt tccttcaaga gcggttagct    1740
```

-continued

```
ttaaaggaag ccggaactga cctcggttta tccattttat tcttcggatg taggaatcgc   1800

aaagtggatt tcatatatga aaacgagctt aacaactttg tggagactgg tgctctttct   1860

gagcttattg ttgctttctc ccgtgaaggc ccgactaagg aatatgtgca acacaagatg   1920

agtgagaagg cttcggatat ctggaacttg ctttctgaag gagcatattt atacgtatgt   1980

ggtgatgcca aaggcatggc caaagatgta catcgaaccc tccacacaat tgtgcaagaa   2040

cagggatctc ttgactcgtc aaaggcagaa ctctacgtga agaatctaca aatgtcagga   2100

agatacctcc gtgacgtttg gtaa                                          2124
```

<210> SEQ ID NO 86
<211> LENGTH: 707
<212> TYPE: PRT
<213> ORGANISM: Stevia rebaudiana

<400> SEQUENCE: 86

```
Met Gln Ser Asn Ser Val Lys Ile Ser Pro Leu Asp Leu Val Thr Ala
1               5                   10                  15

Leu Phe Ser Gly Lys Val Leu Asp Thr Ser Asn Ala Ser Glu Ser Gly
            20                  25                  30

Glu Ser Ala Met Leu Pro Thr Ile Ala Met Ile Met Glu Asn Arg Glu
        35                  40                  45

Leu Leu Met Ile Leu Thr Thr Ser Val Ala Val Leu Ile Gly Cys Val
    50                  55                  60

Val Val Leu Val Trp Arg Arg Ser Ser Thr Lys Lys Ser Ala Leu Glu
65                  70                  75                  80

Pro Pro Val Ile Val Val Pro Lys Arg Val Gln Glu Glu Glu Val Asp
                85                  90                  95

Asp Gly Lys Lys Lys Val Thr Val Phe Phe Gly Thr Gln Thr Gly Thr
            100                 105                 110

Ala Glu Gly Phe Ala Lys Ala Leu Val Glu Glu Ala Lys Ala Arg Tyr
        115                 120                 125

Glu Lys Ala Val Phe Lys Val Ile Asp Leu Asp Asp Tyr Ala Ala Asp
    130                 135                 140

Asp Asp Glu Tyr Glu Glu Lys Leu Lys Lys Glu Ser Leu Ala Phe Phe
145                 150                 155                 160

Phe Leu Ala Thr Tyr Gly Asp Gly Glu Pro Thr Asp Asn Ala Ala Arg
                165                 170                 175

Phe Tyr Lys Trp Phe Thr Glu Gly Asp Ala Lys Gly Glu Trp Leu Asn
            180                 185                 190

Lys Leu Gln Tyr Gly Val Phe Gly Leu Gly Asn Arg Gln Tyr Glu His
        195                 200                 205

Phe Asn Lys Ile Ala Lys Val Val Asp Asp Gly Leu Val Glu Gln Gly
    210                 215                 220

Ala Lys Arg Leu Val Pro Val Gly Leu Gly Asp Asp Asp Gln Cys Ile
225                 230                 235                 240

Glu Asp Asp Phe Thr Ala Trp Lys Glu Leu Val Trp Pro Glu Leu Asp
                245                 250                 255

Gln Leu Leu Arg Asp Glu Asp Asp Thr Thr Val Ala Thr Pro Tyr Thr
            260                 265                 270

Ala Ala Val Ala Glu Tyr Arg Val Val Phe His Glu Lys Pro Asp Ala
        275                 280                 285

Leu Ser Glu Asp Tyr Ser Tyr Thr Asn Gly His Ala Val His Asp Ala
    290                 295                 300
```

-continued

```
Gln His Pro Cys Arg Ser Asn Val Ala Val Lys Lys Glu Leu His Ser
305                 310                 315                 320

Pro Glu Ser Asp Arg Ser Cys Thr His Leu Glu Phe Asp Ile Ser Asn
                325                 330                 335

Thr Gly Leu Ser Tyr Glu Thr Gly Asp His Val Gly Val Tyr Cys Glu
            340                 345                 350

Asn Leu Ser Glu Val Val Asn Asp Ala Glu Arg Leu Val Gly Leu Pro
        355                 360                 365

Pro Asp Thr Tyr Ser Ser Ile His Thr Asp Ser Glu Asp Gly Ser Pro
    370                 375                 380

Leu Gly Gly Ala Ser Leu Pro Pro Pro Phe Pro Pro Cys Thr Leu Arg
385                 390                 395                 400

Lys Ala Leu Thr Cys Tyr Ala Asp Val Leu Ser Ser Pro Lys Lys Ser
                405                 410                 415

Ala Leu Leu Ala Leu Ala Ala His Ala Thr Asp Pro Ser Glu Ala Asp
            420                 425                 430

Arg Leu Lys Phe Leu Ala Ser Pro Ala Gly Lys Asp Glu Tyr Ser Gln
        435                 440                 445

Trp Ile Val Ala Ser Gln Arg Ser Leu Leu Glu Val Met Glu Ala Phe
    450                 455                 460

Pro Ser Ala Lys Pro Ser Leu Gly Val Phe Phe Ala Ser Val Ala Pro
465                 470                 475                 480

Arg Leu Gln Pro Arg Tyr Tyr Ser Ile Ser Ser Ser Pro Lys Met Ala
                485                 490                 495

Pro Asp Arg Ile His Val Thr Cys Ala Leu Val Tyr Glu Lys Thr Pro
            500                 505                 510

Ala Gly Arg Ile His Lys Gly Val Cys Ser Thr Trp Met Lys Asn Ala
        515                 520                 525

Val Pro Met Thr Glu Ser Gln Asp Cys Ser Trp Ala Pro Ile Tyr Val
    530                 535                 540

Arg Thr Ser Asn Phe Arg Leu Pro Ser Asp Pro Lys Val Pro Val Ile
545                 550                 555                 560

Met Ile Gly Pro Gly Thr Gly Leu Ala Pro Phe Arg Gly Phe Leu Gln
                565                 570                 575

Glu Arg Leu Ala Leu Lys Glu Ala Gly Thr Asp Leu Gly Leu Ser Ile
            580                 585                 590

Leu Phe Phe Gly Cys Arg Asn Arg Lys Val Asp Phe Ile Tyr Glu Asn
        595                 600                 605

Glu Leu Asn Asn Phe Val Glu Thr Gly Ala Leu Ser Glu Leu Ile Val
    610                 615                 620

Ala Phe Ser Arg Glu Gly Pro Thr Lys Glu Tyr Val Gln His Lys Met
625                 630                 635                 640

Ser Glu Lys Ala Ser Asp Ile Trp Asn Leu Leu Ser Glu Gly Ala Tyr
                645                 650                 655

Leu Tyr Val Cys Gly Asp Ala Lys Gly Met Ala Lys Asp Val His Arg
            660                 665                 670

Thr Leu His Thr Ile Val Gln Glu Gln Gly Ser Leu Asp Ser Ser Lys
        675                 680                 685

Ala Glu Leu Tyr Val Lys Asn Leu Gln Met Ser Gly Arg Tyr Leu Arg
    690                 695                 700

Asp Val Trp
705
```

<210> SEQ ID NO 87
<211> LENGTH: 2070
<212> TYPE: DNA
<213> ORGANISM: Artificial Sequence
<220> FEATURE:
<223> OTHER INFORMATION: Codon-optimized CPR

<400> SEQUENCE: 87

```
atgtcctcca actccgattt ggtcagaaga ttggaatctg ttttgggtgt ttctttcggt     60
ggttctgtta ctgattccgt tgttgttatt gctaccacct ctattgcttt ggttatcggt    120
gttttggttt tgttgtggag aagatcctct gacagatcta gagaagttaa gcaattggct    180
gttccaaagc cagttactat cgttgaagaa gaagatgaat tcgaagttgc ttctggtaag    240
accagagttt ctattttcta cggtactcaa actggtactg ctgaaggttt tgctaaggct    300
ttggctgaag aaatcaaagc cagatacgaa aaagctgccg ttaaggttat tgatttggat    360
gattacacag ccgaagatga caaatacggt gaaaagttga agaaagaaac tatggccttc    420
ttcatgttgg ctacttatgg tgatggtgaa cctactgata atgctgctag attttacaag    480
tggttcaccg aaggtactga tagaggtgtt tggttggaac atttgagata cggtgtattc    540
ggtttgggta acagacaata cgaacacttc aacaagattg ccaaggttgt tgatgatttg    600
ttggttgaac aaggtgccaa gagattggtt actgttggtt tgggtgatga tgatcaatgc    660
atcgaagatg atttctccgc ttggaaagaa gccttgtggc cagaattgga tcaattattg    720
caagatgata ccaacaccgt ttctactcca tacactgctg ttattccaga atacagagtt    780
gttatccacg atccatctgt tacctcttat gaagatccat actctaacat ggctaacggt    840
aatgcctctt acgatattca tcatccatgt agagctaacg ttgccgtcca aaaagaattg    900
cataagccag aatctgacag aagttgcatc catttggaat tcgatatttt cgctactggt    960
ttgacttacg aaaccggtga tcatgttggt gtttacgctg ataattgtga tgatactgta   1020
gaagaagccg ctaagttgtt gggtcaacca ttggatttgt tgttctccat tcataccgat   1080
aacaacgacg gtacttcttt gggttcttct ttgccaccac catttccagg tccatgtact   1140
ttgagaactg ctttggctag atatgccgat ttgttgaatc caccaaaaaa ggctgctttg   1200
attgctttag ctgctcatgc tgatgaacca tctgaagctg aaagattgaa gttcttgtca   1260
tctccacaag gtaaggacga atattctaaa tgggttgtcg gttcccaaag atccttggtt   1320
gaagttatgg ctgaatttcc atctgctaaa ccaccattgg gtgtattttt tgctgctgtt   1380
gttcctagat tgcaacctag atattactcc atctcttcca gtccaagatt tgctccacat   1440
agagttcatg ttacttgcgc tttggtttat ggtccaactc caactggtag aattcacaga   1500
ggtgtatgtt cattctggat gaagaatgtt gtcccattgg aaaagtctca aaactgttct   1560
tgggccccaa ttttcatcag acaatctaat ttcaagttgc cagccgatca ttctgttcca   1620
atagttatgg ttggtccagg tactggttta gctcctttta gaggtttctt acaagaaaga   1680
ttggccttga aagaagaagg tgctcaagtt ggtcctgctt tgttgttttt tggttgcaga   1740
aacagacaaa tggacttcat ctacgaagtc gaattgaaca actttgtcga acaaggtgct   1800
ttgtccgaat tgatcgttgc tttttcaaga gaaggtccat ccaaagaata cgtccaacat   1860
aagatggttg aaaaggcagc ttacatgtgg aacttgattt ctcaaggtgg ttacttctac   1920
gtttgtggtg atgctaaagg tatggctaga gatgttcata gaacattgca taccatcgtc   1980
caacaagaag aaaaggttga ttctaccaag gccgaatcca tcgttaagaa attgcaaatg   2040
gacggtagat acttgagaga tgtttggtga                                    2070
```

<210> SEQ ID NO 88
<211> LENGTH: 689
<212> TYPE: PRT
<213> ORGANISM: Rubus suavissimus

<400> SEQUENCE: 88

```
Met Ser Ser Asn Ser Asp Leu Val Arg Arg Leu Glu Ser Val Leu Gly
1               5                   10                  15

Val Ser Phe Gly Gly Ser Val Thr Asp Ser Val Val Val Ile Ala Thr
            20                  25                  30

Thr Ser Ile Ala Leu Val Ile Gly Val Leu Val Leu Leu Trp Arg Arg
        35                  40                  45

Ser Ser Asp Arg Ser Arg Glu Val Lys Gln Leu Ala Val Pro Lys Pro
    50                  55                  60

Val Thr Ile Val Glu Glu Glu Asp Glu Phe Glu Val Ala Ser Gly Lys
65                  70                  75                  80

Thr Arg Val Ser Ile Phe Tyr Gly Thr Gln Thr Gly Thr Ala Glu Gly
                85                  90                  95

Phe Ala Lys Ala Leu Ala Glu Glu Ile Lys Ala Arg Tyr Glu Lys Ala
            100                 105                 110

Ala Val Lys Val Ile Asp Leu Asp Asp Tyr Thr Ala Glu Asp Asp Lys
        115                 120                 125

Tyr Gly Glu Lys Leu Lys Lys Glu Thr Met Ala Phe Phe Met Leu Ala
    130                 135                 140

Thr Tyr Gly Asp Gly Glu Pro Thr Asp Asn Ala Ala Arg Phe Tyr Lys
145                 150                 155                 160

Trp Phe Thr Glu Gly Thr Asp Arg Gly Val Trp Leu Glu His Leu Arg
                165                 170                 175

Tyr Gly Val Phe Gly Leu Gly Asn Arg Gln Tyr Glu His Phe Asn Lys
            180                 185                 190

Ile Ala Lys Val Val Asp Asp Leu Leu Val Glu Gln Gly Ala Lys Arg
        195                 200                 205

Leu Val Thr Val Gly Leu Gly Asp Asp Asp Gln Cys Ile Glu Asp Asp
    210                 215                 220

Phe Ser Ala Trp Lys Glu Ala Leu Trp Pro Glu Leu Asp Gln Leu Leu
225                 230                 235                 240

Gln Asp Asp Thr Asn Thr Val Ser Thr Pro Tyr Thr Ala Val Ile Pro
                245                 250                 255

Glu Tyr Arg Val Val Ile His Asp Pro Ser Val Thr Ser Tyr Glu Asp
            260                 265                 270

Pro Tyr Ser Asn Met Ala Asn Gly Asn Ala Ser Tyr Asp Ile His His
        275                 280                 285

Pro Cys Arg Ala Asn Val Ala Val Gln Lys Glu Leu His Lys Pro Glu
    290                 295                 300

Ser Asp Arg Ser Cys Ile His Leu Glu Phe Asp Ile Phe Ala Thr Gly
305                 310                 315                 320

Leu Thr Tyr Glu Thr Gly Asp His Val Gly Val Tyr Ala Asp Asn Cys
                325                 330                 335

Asp Asp Thr Val Glu Glu Ala Ala Lys Leu Leu Gly Gln Pro Leu Asp
            340                 345                 350

Leu Leu Phe Ser Ile His Thr Asp Asn Asn Asp Gly Thr Ser Leu Gly
        355                 360                 365

Ser Ser Leu Pro Pro Pro Phe Pro Gly Pro Cys Thr Leu Arg Thr Ala
    370                 375                 380
```

```
Leu Ala Arg Tyr Ala Asp Leu Leu Asn Pro Pro Lys Lys Ala Ala Leu
385                 390                 395                 400

Ile Ala Leu Ala Ala His Ala Asp Glu Pro Ser Glu Ala Glu Arg Leu
                405                 410                 415

Lys Phe Leu Ser Ser Pro Gln Gly Lys Asp Glu Tyr Ser Lys Trp Val
            420                 425                 430

Val Gly Ser Gln Arg Ser Leu Val Glu Val Met Ala Glu Phe Pro Ser
        435                 440                 445

Ala Lys Pro Pro Leu Gly Val Phe Phe Ala Ala Val Val Pro Arg Leu
    450                 455                 460

Gln Pro Arg Tyr Tyr Ser Ile Ser Ser Ser Pro Arg Phe Ala Pro His
465                 470                 475                 480

Arg Val His Val Thr Cys Ala Leu Val Tyr Gly Pro Thr Pro Thr Gly
                485                 490                 495

Arg Ile His Arg Gly Val Cys Ser Phe Trp Met Lys Asn Val Val Pro
            500                 505                 510

Leu Glu Lys Ser Gln Asn Cys Ser Trp Ala Pro Ile Phe Ile Arg Gln
        515                 520                 525

Ser Asn Phe Lys Leu Pro Ala Asp His Ser Val Pro Ile Val Met Val
    530                 535                 540

Gly Pro Gly Thr Gly Leu Ala Pro Phe Arg Gly Phe Leu Gln Glu Arg
545                 550                 555                 560

Leu Ala Leu Lys Glu Glu Gly Ala Gln Val Gly Pro Ala Leu Leu Phe
                565                 570                 575

Phe Gly Cys Arg Asn Arg Gln Met Asp Phe Ile Tyr Glu Val Glu Leu
            580                 585                 590

Asn Asn Phe Val Glu Gln Gly Ala Leu Ser Glu Leu Ile Val Ala Phe
        595                 600                 605

Ser Arg Glu Gly Pro Ser Lys Glu Tyr Val Gln His Lys Met Val Glu
    610                 615                 620

Lys Ala Ala Tyr Met Trp Asn Leu Ile Ser Gln Gly Gly Tyr Phe Tyr
625                 630                 635                 640

Val Cys Gly Asp Ala Lys Gly Met Ala Arg Asp Val His Arg Thr Leu
                645                 650                 655

His Thr Ile Val Gln Gln Glu Glu Lys Val Asp Ser Thr Lys Ala Glu
            660                 665                 670

Ser Ile Val Lys Lys Leu Gln Met Asp Gly Arg Tyr Leu Arg Asp Val
        675                 680                 685

Trp
```

<210> SEQ ID NO 89
<211> LENGTH: 2079
<212> TYPE: DNA
<213> ORGANISM: Artificial Sequence
<220> FEATURE:
<223> OTHER INFORMATION: Codon-optimized CPR

<400> SEQUENCE: 89

```
atgacttctg cactttatgc ctccgatctt ttcaaacaat tgaaaagtat catgggaacg      60

gattctttgt ccgatgatgt tgtattagtt attgctacaa cttctctggc actggttgct     120

ggtttcgttg tcttattgtg gaaaaagacc acggcagatc gttccggcga gctaaagcca     180

ctaatgatcc ctaagtctct gatggcgaaa gatgaggatg atgacttaga tctaggttct     240

ggaaaaacga gagtctctat cttcttcggc acacaaaccg gaacagccga aggattcgct     300
```

```
aaagcacttt cagaagagat caaagcaaga tacgaaaagg cggctgtaaa agtaatcgat    360

ttggatgatt acgctgccga tgatgaccaa tatgaggaaa agttgaaaaa ggaaacattg    420

gctttctttt gtgtagccac gtatggtgat ggtgaaccaa ccgataacgc cgcaagattc    480

tacaagtggt ttactgaaga gaacgaaaga gatatcaagt tgcagcaact tgcttacggc    540

gtttttgcct taggtaacag acaatacgag cactttaaca agataggtat tgtcttagat    600

gaagagttat gcaaaaaggg tgcgaagaga ttgattgaag tcggtttagg agatgatgat    660

caatctatcg aggatgactt taatgcatgg aaggaatctt tgtggtctga attagataag    720

ttacttaagg acgaagatga taaatccgtt gccactccat acacagccgt cattccagaa    780

tatagagtag ttactcatga tccaagattc acaacacaga aatcaatgga aagtaatgtg    840

gctaatggta atactaccat cgatattcat catccatgta gagtagacgt tgcagttcaa    900

aaggaattgc acactcatga atcagacaga tcttgcatac atcttgaatt tgatatatca    960

cgtactggta tcacttacga aacaggtgat cacgtgggtg tctacgctga aaaccatgtt   1020

gaaattgtag aggaagctgg aaagttgttg ggccatagtt tagatcttgt tttctcaatt   1080

catgccgata aagaggatgg ctcaccacta gaaagtgcag tgcctccacc atttccagga   1140

ccatgcaccc taggtaccgg tttagctcgt tacgcggatc tgttaaatcc tccacgtaaa   1200

tcagctctag tggccttggc tgcgtacgcc acagaacctt ctgaggcaga aaaactgaaa   1260

catctaactt caccagatgg taaggatgaa tactcacaat ggatagtagc tagtcaacgt   1320

tctttactag aagttatggc tgctttccca tccgctaaac ctcctttggg tgttttcttc   1380

gccgcaatag cgcctagact gcaaccaaga tactattcaa tttcatcctc acctagactg   1440

gcaccatcaa gagttcatgt cacatccgct ttagtgtacg gtccaactcc tactggtaga   1500

atccataagg gcgtttgttc aacatggatg aaaaacgcgg ttccagcaga gaagtctcac   1560

gaatgttctg gtgctccaat ctttatcaga gcctccaact tcaaactgcc ttccaatcct   1620

tctactccta ttgtcatggt cggtcctggt acaggtcttg ctccattcag aggtttctta   1680

caagagagaa tggccttaaa ggaggatggt gaagagttgg gatcttcttt gttgtttttc   1740

ggctgtagaa acagacaaat ggatttcatc tacgaagatg aactgaataa ctttgtagat   1800

caaggagtta tttcagagtt gataatggct ttttctagag aaggtgctca gaaggagtac   1860

gtccaacaca aaatgatgga aaaggccgca caagtttggg acttaatcaa agaggaaggc   1920

tatctatatg tctgtggtga tgcaaagggt atggcaagag atgttcacag aacacttcat   1980

actatagtcc aggaacagga aggcgttagt tcttctgaag cggaagcaat tgtgaaaaag   2040

ttacaaacag agggaagata cttgagagat gtgtggtaa                          2079
```

<210> SEQ ID NO 90
<211> LENGTH: 692
<212> TYPE: PRT
<213> ORGANISM: Arabidopsis thaliana

<400> SEQUENCE: 90

```
Met Thr Ser Ala Leu Tyr Ala Ser Asp Leu Phe Lys Gln Leu Lys Ser
1               5                   10                  15

Ile Met Gly Thr Asp Ser Leu Ser Asp Asp Val Val Leu Val Ile Ala
            20                  25                  30

Thr Thr Ser Leu Ala Leu Val Ala Gly Phe Val Val Leu Leu Trp Lys
        35                  40                  45

Lys Thr Thr Ala Asp Arg Ser Gly Glu Leu Lys Pro Leu Met Ile Pro
```

```
    50                  55                  60

Lys Ser Leu Met Ala Lys Asp Glu Asp Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
    130                 135                 140

Val Ala Thr Tyr Gly Asp Gly Glu Pro Thr Asp Asn Ala Ala Arg Phe
145                 150                 155                 160

Tyr Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Asp Gln Ser Ile Glu
    210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
    290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350

Ser Leu Asp Leu Val Phe Ser Ile His Ala Asp Lys Glu Asp Gly Ser
        355                 360                 365

Pro Leu Glu Ser Ala Val Pro Pro Pro Phe Pro Gly Pro Cys Thr Leu
    370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
        435                 440                 445

Phe Pro Ser Ala Lys Pro Pro Leu Gly Val Phe Phe Ala Ala Ile Ala
    450                 455                 460

Pro Arg Leu Gln Pro Arg Tyr Tyr Ser Ile Ser Ser Ser Pro Arg Leu
465                 470                 475                 480
```

```
Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
    530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
    610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690
```

<210> SEQ ID NO 91
<211> LENGTH: 2139
<212> TYPE: DNA
<213> ORGANISM: Artificial Sequence
<220> FEATURE:
<223> OTHER INFORMATION: Codon-optimized CPR

<400> SEQUENCE: 91

```
atgtcttcct cttcctcttc cagtacctct atgattgatt tgatggctgc tattattaaa      60

ggtgaaccag ttatcgtctc cgacccagca aatgcctctg cttatgaatc agttgctgca     120

gaattgtctt caatgttgat cgaaaacaga caattcgcca tgatcgtaac tacatcaatc     180

gctgttttga tcggttgtat tgtcatgttg gtatggagaa gatccggtag tggtaattct     240

aaaagagtcg aacctttgaa accattagta attaagccaa gagaagaaga aatagatgac     300

ggtagaaaga aagttacaat atttttcggt acccaaactg gtacagctga aggttttgca     360

aaagccttag gtgaagaagc taaggcaaga tacgaaaaga ctagattcaa gatagtcgat     420

ttggatgact atgccgctga tgacgatgaa tacgaagaaa agttgaagaa agaagatgtt     480

gcatttttct tttggcaac ctatggtgac ggtgaaccaa ctgacaatgc agccagattc     540

tacaaatggt ttacagaggg taatgatcgt ggtgaatggt tgaaaaactt aaagtacggt     600

gttttcggtt tgggtaacag acaatacgaa catttcaaca aagttgcaaa ggttgtcgac     660

gatattttgg tcgaacaagg tgctcaaaga ttagtccaag taggtttggg tgacgatgac     720

caatgtatag aagatgactt tactgcctgg agagaagctt tgtggcctga attagacaca     780
```

-continued

```
atcttgagag aagaaggtga caccgccgtt gctaccccat atactgctgc agtattagaa    840

tacagagttt ccatccatga tagtgaagac gcaaagttta atgatatcac tttggccaat    900

ggtaacggtt atacagtttt cgatgcacaa caccccttaca aagctaacgt tgcagtcaag    960

agagaattac atacaccaga atccgacaga agttgtatac acttggaatt tgatatcgct   1020

ggttccggtt taaccatgaa gttgggtgac catgtaggtg ttttatgcga caatttgtct   1080

gaaactgttg atgaagcatt gagattgttg gatatgtccc ctgacactta ttttagtttg   1140

cacgctgaaa aagaagatgg tacaccaatt tccagttctt taccacctcc attccctcca   1200

tgtaacttaa gaacagcctt gaccagatac gcttgcttgt tatcatcccc taaaaagtcc   1260

gccttggttg ctttagccgc tcatgctagt gatcctactg aagcagaaag attgaaacac   1320

ttagcatctc cagccggtaa agatgaatat tcaaagtggg tagttgaatc tcaaagatca   1380

ttgttagaag ttatggcaga atttccatct gccaagcctc cattaggtgt cttctttgct   1440

ggtgtagcac ctagattgca accaagattc tactcaatca gttcttcacc taagatcgct   1500

gaaactagaa ttcatgttac atgtgcatta gtctacgaaa agatgccaac cggtagaatt   1560

cacaagggtg tatgctctac ttggatgaaa aatgctgttc cttacgaaaa atcagaaaag   1620

ttgttcttag gtagaccaat cttcgtaaga caatcaaact tcaagttgcc ttctgattca   1680

aaggttccaa taatcatgat aggtcctggt acaggtttag ccccattcag aggtttcttg   1740

caagaaagat tggctttagt tgaatctggt gtcgaattag gtccttcagt tttgttcttt   1800

ggttgtagaa acagaagaat ggatttcatc tatgaagaag aattgcaaag attcgtcgaa   1860

tctggtgcat tggccgaatt atctgtagct tttcaagag aaggtccaac taaggaatac   1920

gttcaacata agatgatgga taaggcatcc gacatatgga acatgatcag tcaaggtgct   1980

tatttgtacg tttgcggtga cgcaaagggt atggccagag atgtccatag atctttgcac   2040

acaattgctc aagaacaagg ttccatggat agtaccaaag ctgaaggttt cgtaaagaac   2100

ttacaaactt ccggtagata cttgagagat gtctggtga                          2139
```

<210> SEQ ID NO 92
<211> LENGTH: 712
<212> TYPE: PRT
<213> ORGANISM: Arabidopsis thaliana

<400> SEQUENCE: 92

```
Met Ser Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
```

```
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Thr Leu Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Met Lys Leu Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
    370                 375                 380

Glu Asp Gly Thr Pro Ile Ser Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Asp
        435                 440                 445

Glu Tyr Ser Lys Trp Val Val Glu Ser Gln Arg Ser Leu Leu Glu Val
    450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525

Met Lys Asn Ala Val Pro Tyr Glu Lys Ser Glu Lys Leu Phe Leu Gly
    530                 535                 540

Arg Pro Ile Phe Val Arg Gln Ser Asn Phe Lys Leu Pro Ser Asp Ser
545                 550                 555                 560
```

```
Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
    610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
    690                 695                 700

Gly Arg Tyr Leu Arg Asp Val Trp
705                 710
```

<210> SEQ ID NO 93
<211> LENGTH: 1503
<212> TYPE: DNA
<213> ORGANISM: Artificial Sequence
<220> FEATURE:
<223> OTHER INFORMATION: Codon-optimized KAH

<400> SEQUENCE: 93

```
atggaagcct cttacctata catttctatt ttgcttttac tggcatcata cctgttcacc     60

actcaactta gaaggaagag cgctaatcta ccaccaaccg tgtttccatc aataccaatc    120

attggacact tatacttact caaaaagcct ctttatagaa ctttagcaaa aattgccgct    180

aagtacggac caatactgca attacaactc ggctacagac gtgttctggt gatttcctca    240

ccatcagcag cagaagagtg ctttaccaat aacgatgtaa tcttcgcaaa tagacctaag    300

acattgtttg gcaaaatagt gggtggaaca tcccttggca gtttatccta cggcgatcaa    360

tggcgtaatc taaggagagt agcttctatc gaaatcctat cagttcatag gttgaacgaa    420

tttcatgata tcagagtgga tgagaacaga ttgttaatta gaaaacttag aagttcatct    480

tctcctgtta ctcttataac agtcttttat gctctaacat tgaacgtcat tatgagaatg    540

atctctggca aaagatattt cgacagtggg gatagagaat tggaggagga aggtaagaga    600

tttcgagaaa tcttagacga aacgttgctt ctagccggtg cttctaatgt tggcgactac    660

ttaccaatat tgaactggtt gggagttaag tctcttgaaa agaaattgat cgctttgcag    720

aaaaagagag atgacttttt ccagggtttg attgaacagg ttagaaaatc tcgtggtgct    780

aaagtaggca aaggtagaaa aacgatgatc gaactcttat tatctttgca agagtcagaa    840

cctgagtact atacagatgc tatgataaga tcttttgtcc taggtctgct ggctgcaggt    900

agtgatactt cagcgggcac tatggaatgg gccatgagct tactggtcaa tcacccacat    960

gtattgaaga aagctcaagc tgaaatcgat agagttatcg gtaataacag attgattgac   1020

gagtcagaca ttggaaatat cccttacatc gggtgtatta tcaatgaaac tctaagactc   1080

tatccagcag ggccattgtt gttcccacat gaaagttctg ccgactgcgt tatttccggt   1140
```

```
tacaatatac ctagaggtac aatgttaatc gtaaaccaat gggcgattca tcacgatcct   1200

aaagtctggg atgatcctga aacctttaaa cctgaaagat ttcaaggatt agaaggaact   1260

agagatggtt tcaaacttat gccattcggt tctgggagaa gaggatgtcc aggtgaaggt   1320

ttggcaataa ggctgttagg gatgacacta ggctcagtga tccaatgttt tgattgggag   1380

agagtaggag atgagatggt tgacatgaca gaaggtttgg gtgtcacact tcctaaggcc   1440

gttccattag ttgccaaatg taagccacgt tccgaaatga ctaatctcct atccgaactt   1500

taa                                                                  1503
```

<210> SEQ ID NO 94
<211> LENGTH: 500
<212> TYPE: PRT
<213> ORGANISM: Stevia rebaudiana

<400> SEQUENCE: 94

```
Met Glu Ala Ser Tyr Leu Tyr Ile Ser Ile Leu Leu Leu Leu Ala Ser
1               5                   10                  15

Tyr Leu Phe Thr Thr Gln Leu Arg Arg Lys Ser Ala Asn Leu Pro Pro
            20                  25                  30

Thr Val Phe Pro Ser Ile Pro Ile Ile Gly His Leu Tyr Leu Leu Lys
        35                  40                  45

Lys Pro Leu Tyr Arg Thr Leu Ala Lys Ile Ala Ala Lys Tyr Gly Pro
    50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95

Asn Arg Pro Lys Thr Leu Phe Gly Lys Ile Val Gly Gly Thr Ser Leu
            100                 105                 110

Gly Ser Leu Ser Tyr Gly Asp Gln Trp Arg Asn Leu Arg Arg Val Ala
        115                 120                 125

Ser Ile Glu Ile Leu Ser Val His Arg Leu Asn Glu Phe His Asp Ile
    130                 135                 140

Arg Val Asp Glu Asn Arg Leu Leu Ile Arg Lys Leu Arg Ser Ser Ser
145                 150                 155                 160

Ser Pro Val Thr Leu Ile Thr Val Phe Tyr Ala Leu Thr Leu Asn Val
                165                 170                 175

Ile Met Arg Met Ile Ser Gly Lys Arg Tyr Phe Asp Ser Gly Asp Arg
            180                 185                 190

Glu Leu Glu Glu Glu Gly Lys Arg Phe Arg Glu Ile Leu Asp Glu Thr
        195                 200                 205

Leu Leu Leu Ala Gly Ala Ser Asn Val Gly Asp Tyr Leu Pro Ile Leu
    210                 215                 220

Asn Trp Leu Gly Val Lys Ser Leu Glu Lys Lys Leu Ile Ala Leu Gln
225                 230                 235                 240

Lys Lys Arg Asp Asp Phe Phe Gln Gly Leu Ile Glu Gln Val Arg Lys
                245                 250                 255

Ser Arg Gly Ala Lys Val Gly Lys Gly Arg Lys Thr Met Ile Glu Leu
            260                 265                 270

Leu Leu Ser Leu Gln Glu Ser Glu Pro Glu Tyr Tyr Thr Asp Ala Met
        275                 280                 285

Ile Arg Ser Phe Val Leu Gly Leu Leu Ala Ala Gly Ser Asp Thr Ser
    290                 295                 300
```

-continued

```
Ala Gly Thr Met Glu Trp Ala Met Ser Leu Leu Val Asn His Pro His
305                 310                 315                 320

Val Leu Lys Lys Ala Gln Ala Glu Ile Asp Arg Val Ile Gly Asn Asn
                325                 330                 335

Arg Leu Ile Asp Glu Ser Asp Ile Gly Asn Ile Pro Tyr Ile Gly Cys
            340                 345                 350

Ile Ile Asn Glu Thr Leu Arg Leu Tyr Pro Ala Gly Pro Leu Leu Phe
        355                 360                 365

Pro His Glu Ser Ser Ala Asp Cys Val Ile Ser Gly Tyr Asn Ile Pro
    370                 375                 380

Arg Gly Thr Met Leu Ile Val Asn Gln Trp Ala Ile His His Asp Pro
385                 390                 395                 400

Lys Val Trp Asp Asp Pro Glu Thr Phe Lys Pro Glu Arg Phe Gln Gly
                405                 410                 415

Leu Glu Gly Thr Arg Asp Gly Phe Lys Leu Met Pro Phe Gly Ser Gly
            420                 425                 430

Arg Arg Gly Cys Pro Gly Glu Gly Leu Ala Ile Arg Leu Leu Gly Met
        435                 440                 445

Thr Leu Gly Ser Val Ile Gln Cys Phe Asp Trp Glu Arg Val Gly Asp
    450                 455                 460

Glu Met Val Asp Met Thr Glu Gly Leu Gly Val Thr Leu Pro Lys Ala
465                 470                 475                 480

Val Pro Leu Val Ala Lys Cys Lys Pro Arg Ser Glu Met Thr Asn Leu
                485                 490                 495

Leu Ser Glu Leu
            500
```

<210> SEQ ID NO 95
<211> LENGTH: 1572
<212> TYPE: DNA
<213> ORGANISM: Rubus suavissimus

<400> SEQUENCE: 95

```
atggaagtaa cagtagctag tagtgtagcc ctgagcctgg tctttattag catagtagta      60

agatgggcat ggagtgtggt gaattgggtg tggtttaagc cgaagaagct ggaaagattt     120

ttgagggagc aaggccttaa aggcaattcc tacaggtttt tatatggaga catgaaggag     180

aactctatcc tgctcaaaca agcaagatcc aaacccatga acctctccac ctcccatgac     240

atagcacctc aagtcacccc ttttgtcgac caaaccgtga aagcttacgg taagaactct     300

tttaattggg ttggccccat accaagggtg aacataatga atccagaaga tttgaaggac     360

gtcttaacaa aaaatgttga ctttgttaag ccaatatcaa acccacttat caagttgcta     420

gctacaggta ttgcaatcta tgaaggtgag aaatggacta aacacagaag gattatcaac     480

ccaacattcc attcggagag gctaaagcgt atgttacctt catttcacca aagttgtaat     540

gagatggtca aggaatggga gagcttggtg tcaaaagagg gttcatcatg tgagttggat     600

gtctggcctt ttcttgaaaa tatgtcggca gatgtgatct cgagaacagc atttggaact     660

agctacaaaa aaggacagaa aatctttgaa ctcttgagag agcaagtaat atatgtaacg     720

aaaggctttc aaagttttta cattccagga tggaggtttc tcccaactaa gatgaacaag     780

aggatgaatg agattaacga agaaataaaa ggattaatca ggggtattat aattgacaga     840

gagcaaatca ttaaggcagg tgaagaaacc aacgatgact tattaggtgc acttatggag     900

tcaaacttga aggacattcg ggaacatggg aaaaacaaca aaaatgttgg gatgagtatt     960
```

```
gaagatgtaa ttcaggagtg taagctgttt tactttgctg ggcaagaaac cacttcagtg   1020
ttgctggctt ggacaatggt tttacttggt caaaatcaga actggcaaga tcgagcaaga   1080
caagaggttt tgcaagtctt tggaagcagc aagccagatt ttgatggtct agctcacctt   1140
aaagtcgtaa ccatgatttt gcttgaagtt cttcgattat acccaccagt cattgaactt   1200
attcgaacca ttcacaagaa aacacaactt gggaagctct cactaccaga aggagttgaa   1260
gtccgcttac caacactgct cattcaccat gacaaggaac tgtggggtga tgatgcaaac   1320
cagttcaatc cagagaggtt ttcggaagga gtttccaaag caacaaagaa ccgactctca   1380
ttcttcccct tcggagccgg tccacgcatt tgcattggac agaacttttc tatgatggaa   1440
gcaaagttgg ccttagcatt gatcttgcaa cacttcacct ttgagctttc tccatctcat   1500
gcacatgctc cttcccatcg tataaccctt caaccacagt atggtgttcg tatcatttta   1560
catcgacgtt ag                                                       1572
```

<210> SEQ ID NO 96
<211> LENGTH: 1572
<212> TYPE: DNA
<213> ORGANISM: Artificial Sequence
<220> FEATURE:
<223> OTHER INFORMATION: Codon-optimized KAH

<400> SEQUENCE: 96

```
atggaagtca ctgtcgcctc ttctgtcgct ttatccttag tcttcatttc cattgtcgtc     60
agatgggctt ggtccgttgt caactgggtt tggttcaaac caaagaagtt ggaaagattc    120
ttgagagagc aaggtttgaa gggtaattct tatagattct tgtacggtga catgaaggaa    180
aattctattt tgttgaagca agccagatcc aaaccaatga acttgtctac ctctcatgat    240
attgctccac aagttactcc attcgtcgat caaactgtta aagcctacgg taagaactct    300
ttcaattggg ttggtccaat tcctagagtt aacatcatga acccagaaga tttgaaggat    360
gtcttgacca agaacgttga cttcgttaag ccaatttcca acccattgat taaattgttg    420
gctactggta ttgccattta cgaaggtgaa aagtggacta agcatagaag aatcatcaac    480
cctaccttcc actctgaaag attgaagaga atgttaccat ctttccatca atcctgtaat    540
gaaatggtta aggaatggga atccttggtt tctaaagaag gttcttcttg cgaattggat    600
gtttggccat tcttggaaaa tatgtctgct gatgtcattt ccagaaccgc tttcggtacc    660
tcctacaaga agggtcaaaa gattttcgaa ttgttgagag agcaagttat ttacgttacc    720
aagggtttcc aatccttcta catcccaggt tggagattct tgccaactaa aatgaacaag    780
cgtatgaacg agatcaacga agaaattaaa ggtttgatca gaggtattat tatcgacaga    840
gaacaaatta ttaaagctgg tgaagaaacc aacgatgatt tgttgggtgc tttgatggag    900
tccaacttga aggatattag agaacatggt aagaacaaca agaatgttgg tatgtctatt    960
gaagatgtta ttcaagaatg taagttattc tacttcgctg gtcaagagac cacttctgtt   1020
ttgttagcct ggactatggt cttgttaggt caaaaccaaa attggcaaga tagagctaga   1080
caagaagttt tgcaagtctt cggttcttcc aagccagact ttgatggttt ggcccacttg   1140
aaggttgtta ctatgatttt gttagaagtt ttgagattgt acccaccagt cattgagtta   1200
atcagaacca ttcataaaaa gactcaattg ggtaaattat ctttgccaga aggtgttgaa   1260
gtcagattac caaccttgtt gattcaccac gataaggaat tatggggtga cgacgctaat   1320
caatttaatc cagaaagatt ttccgaaggt gtttccaagg ctaccaaaaa ccgtttgtcc   1380
ttcttcccat ttggtgctgg tccacgtatt tgtatcggtc aaaacttttc catgatggaa   1440
```

gccaagttgg ctttggcttt aatcttgcaa cacttcactt tcgaattgtc tccatcccat 1500
gcccacgctc cttctcatag aatcacttta caaccacaat acggtgtcag aatcatctta 1560
cacagaagat aa 1572

<210> SEQ ID NO 97
<211> LENGTH: 523
<212> TYPE: PRT
<213> ORGANISM: Rubus suavissimus

<400> SEQUENCE: 97

Met Glu Val Thr Val Ala Ser Ser Val Ala Leu Ser Leu Val Phe Ile
1 5 10 15

Ser Ile Val Val Arg Trp Ala Trp Ser Val Val Asn Trp Val Trp Phe
20 25 30

Lys Pro Lys Lys Leu Glu Arg Phe Leu Arg Glu Gln Gly Leu Lys Gly
35 40 45

Asn Ser Tyr Arg Phe Leu Tyr Gly Asp Met Lys Glu Asn Ser Ile Leu
50 55 60

Leu Lys Gln Ala Arg Ser Lys Pro Met Asn Leu Ser Thr Ser His Asp
65 70 75 80

Ile Ala Pro Gln Val Thr Pro Phe Val Asp Gln Thr Val Lys Ala Tyr
85 90 95

Gly Lys Asn Ser Phe Asn Trp Val Gly Pro Ile Pro Arg Val Asn Ile
100 105 110

Met Asn Pro Glu Asp Leu Lys Asp Val Leu Thr Lys Asn Val Asp Phe
115 120 125

Val Lys Pro Ile Ser Asn Pro Leu Ile Lys Leu Leu Ala Thr Gly Ile
130 135 140

Ala Ile Tyr Glu Gly Glu Lys Trp Thr Lys His Arg Arg Ile Ile Asn
145 150 155 160

Pro Thr Phe His Ser Glu Arg Leu Lys Arg Met Leu Pro Ser Phe His
165 170 175

Gln Ser Cys Asn Glu Met Val Lys Glu Trp Glu Ser Leu Val Ser Lys
180 185 190

Glu Gly Ser Ser Cys Glu Leu Asp Val Trp Pro Phe Leu Glu Asn Met
195 200 205

Ser Ala Asp Val Ile Ser Arg Thr Ala Phe Gly Thr Ser Tyr Lys Lys
210 215 220

Gly Gln Lys Ile Phe Glu Leu Leu Arg Glu Gln Val Ile Tyr Val Thr
225 230 235 240

Lys Gly Phe Gln Ser Phe Tyr Ile Pro Gly Trp Arg Phe Leu Pro Thr
245 250 255

Lys Met Asn Lys Arg Met Asn Glu Ile Asn Glu Glu Ile Lys Gly Leu
260 265 270

Ile Arg Gly Ile Ile Ile Asp Arg Glu Gln Ile Ile Lys Ala Gly Glu
275 280 285

Glu Thr Asn Asp Asp Leu Leu Gly Ala Leu Met Glu Ser Asn Leu Lys
290 295 300

Asp Ile Arg Glu His Gly Lys Asn Asn Lys Asn Val Gly Met Ser Ile
305 310 315 320

Glu Asp Val Ile Gln Glu Cys Lys Leu Phe Tyr Phe Ala Gly Gln Glu
325 330 335

Thr Thr Ser Val Leu Leu Ala Trp Thr Met Val Leu Leu Gly Gln Asn

-continued

```
            340                 345                 350

Gln Asn Trp Gln Asp Arg Ala Arg Gln Glu Val Leu Gln Val Phe Gly
        355                 360                 365

Ser Ser Lys Pro Asp Phe Asp Gly Leu Ala His Leu Lys Val Val Thr
    370                 375                 380

Met Ile Leu Leu Glu Val Leu Arg Leu Tyr Pro Pro Val Ile Glu Leu
385                 390                 395                 400

Ile Arg Thr Ile His Lys Lys Thr Gln Leu Gly Lys Leu Ser Leu Pro
                405                 410                 415

Glu Gly Val Glu Val Arg Leu Pro Thr Leu Leu Ile His His Asp Lys
            420                 425                 430

Glu Leu Trp Gly Asp Asp Ala Asn Gln Phe Asn Pro Glu Arg Phe Ser
        435                 440                 445

Glu Gly Val Ser Lys Ala Thr Lys Asn Arg Leu Ser Phe Phe Pro Phe
    450                 455                 460

Gly Ala Gly Pro Arg Ile Cys Ile Gly Gln Asn Phe Ser Met Met Glu
465                 470                 475                 480

Ala Lys Leu Ala Leu Ala Leu Ile Leu Gln His Phe Thr Phe Glu Leu
                485                 490                 495

Ser Pro Ser His Ala His Ala Pro Ser His Arg Ile Thr Leu Gln Pro
            500                 505                 510

Gln Tyr Gly Val Arg Ile Ile Leu His Arg Arg
        515                 520


<210> SEQ ID NO 98
<211> LENGTH: 1566
<212> TYPE: DNA
<213> ORGANISM: Prunus avium

<400> SEQUENCE: 98

atggaagcat caagggctag ttgtgttgcg ctatgtgttg tttgggtgag catagtaatt      60

acattggcat ggagggtgct gaattgggtg tggttgaggc caaagaaact agaaagatgc     120

ttgagggagc aaggccttac aggcaattct tacaggcttt tgtttggaga caccaaggat     180

ctctcgaaga tgctggaaca aacacaatcc aaacccatca aactctccac ctcccatgat     240

atagcgccac gagtcacccc atttttccat cgaactgtga actctaatgg caagaattct     300

tttgtttgga tgggccctat accaagagtg cacatcatga atccagaaga tttgaaagat     360

gccttcaaca gacatgatga ttttcataag acagtaaaaa atcctatcat gaagtctcca     420

ccaccgggca ttgtaggcat tgaaggtgag caatgggcta aacacagaaa gattatcaac     480

ccagcattcc atttagagaa gctaaagggt atggtaccaa tattttacca aagttgtagc     540

gagatgatta acaaatggga gagcttggtg tccaaagaga gttcatgtga gttggatgtg     600

tggccttatc ttgaaaattt taccagcgat gtgatttccc gagctgcatt tggaagtagc     660

tatgaagagg gaaggaaaat atttcaacta ctaagagagg aagcaaaagt ttattcggta     720

gctctacgaa gtgtttacat tccaggatgg aggtttctac caaccaagca gaacaagaag     780

acgaaggaaa ttcacaatga aattaaaggc ttacttaagg gcattataaa taaaagggaa     840

gaggcgatga aggcagggga agccactaaa gatgacttac taggaatact tatggagtcc     900

aacttcaggg aaattcagga acatgggaac aacaaaaatg ctggaatgag tattgaagat     960

gtaattggag agtgtaagtt gttttacttt gctgggcaag agaccacttc ggtgttgctt    1020

gtttggacaa tgattttact aagccaaaat caggattggc aagctcgtgc aagagaagag    1080
```

gtcttgaaag tctttggaag caacatccca acctatgaag agctaagtca cctaaaagtt 1140
gtgaccatga ttttacttga agttcttcga ttatacccat cagtcgttgc gcttcctcga 1200
accactcaca agaaaacaca gcttggaaaa ttatcattac cagctggagt ggaagtctcc 1260
ttgcccatac tgcttgttca ccatgacaaa gagttgtggg gtgaggatgc aaatgagttc 1320
aagccagaga ggttttcaga gggagtttca aaggcaacaa agaacaaatt tacatactta 1380
cctttcggag gggtccaag gatttgcatt ggacaaaact ttgccatggt ggaagctaaa 1440
ttggccttgg ccctgatttt acaacacttt gcctttgagc tttctccatc ctatgctcat 1500
gctccttctg cagttataac ccttcaacct caatttggtg ctcatatcat tttgcataaa 1560
cgttga 1566

<210> SEQ ID NO 99
<211> LENGTH: 1567
<212> TYPE: DNA
<213> ORGANISM: Artificial Sequence
<220> FEATURE:
<223> OTHER INFORMATION: Codon-optimized KAH

<400> SEQUENCE: 99
atggaagctt ctagagcatc ttgtgttgct ttgtgtgttg tttgggtttc catcgttatt 60
actttggctt ggagagtttt gaattgggtc tggttaagac caaaaaagtt ggaaagatgc 120
ttgagagaac aaggtttgac tggtaactct tacagattgt tgttcggtga taccaaggac 180
ttgtctaaga tgttggaaca aactcaatcc aagcctatca agttgtctac ctctcatgat 240
attgctccaa gagttactcc attcttccat agaactgtta actccaacgg taagaactct 300
tttgtttgga tgggtccaat tccaagagtc catattatga accctgaaga tttgaaggac 360
gctttcaaca gacatgatga tttccataag accgtcaaga acccaattat gaagtctcca 420
ccaccaggta tagttggtat tgaaggtgaa caatgggcca aacatagaaa gattattaac 480
ccagccttcc acttggaaaa gttgaaaggt atggttccaa tcttctacca atcctgctct 540
gaaatgatta acaagtggga atccttggtt tccaaagaat cttcctgtga attggatgtc 600
tggccatatt tggaaaactt cacctccgat gttatttcca gagctgcttt tggttcttct 660
tacgaagaag gtagaaagat cttccaatta ttgagagaag aagccaaggt ttactccgtt 720
gctttgagat ctgtttacat tccaggttgg agattcttgc caactaagca aaacaaaaag 780
accaaagaaa tccacaacga aatcaagggt ttgttgaagg gtatcatcaa caagagagaa 840
gaagctatga aggctggtga agctacaaaa gatgatttgt tgggtatctt gatggaatcc 900
aacttcagag aaatccaaga acacggtaac aacaagaatg ccggtatgtc tattgaagat 960
gttatcggtg aatgcaagtt gttctacttt gctggtcaag aaactacctc cgttttgttg 1020
gtttggacca tgattttgtt gtcccaaaat caagattggc aagctagagc tagagaagaa 1080
gtcttgaaag ttttcggttc taacatccca acctacgaag aattgtctca cttgaaggtt 1140
gtcactatga tcttgttgga agtattgaga ttatacccat ccgttgttgc attgccaaga 1200
actactcata agaaaactca attgggtaaa ttgtccttgc cagctggtgt tgaagtttct 1260
ttgccaattt tgttagtcca ccacgacaaa gaattgtggg gtgaagatgc taatgaattc 1320
aagccagaaa gattctccga aggtgtttct aaagctacca agaacaagtt cacttacttg 1380
ccatttggtg gtggtccaag aatatgtatt ggtcaaaatt tcgctatggt cgaagctaaa 1440
ttggctttgg ctttgatctt gcaacatttc gctttcgaat tgtcaccatc ttatgctcat 1500
gctccatctg ctgttattac attgcaacca caatttggtg cccatatcat cttgcataag 1560
agataac 1567

<210> SEQ ID NO 100
<211> LENGTH: 521
<212> TYPE: PRT
<213> ORGANISM: Prunus avium

<400> SEQUENCE: 100

Met Glu Ala Ser Arg Ala Ser Cys Val Ala Leu Cys Val Val Trp Val
1 5 10 15

Ser Ile Val Ile Thr Leu Ala Trp Arg Val Leu Asn Trp Val Trp Leu
20 25 30

Arg Pro Lys Lys Leu Glu Arg Cys Leu Arg Glu Gln Gly Leu Thr Gly
35 40 45

Asn Ser Tyr Arg Leu Leu Phe Gly Asp Thr Lys Asp Leu Ser Lys Met
50 55 60

Leu Glu Gln Thr Gln Ser Lys Pro Ile Lys Leu Ser Thr Ser His Asp
65 70 75 80

Ile Ala Pro Arg Val Thr Pro Phe Phe His Arg Thr Val Asn Ser Asn
85 90 95

Gly Lys Asn Ser Phe Val Trp Met Gly Pro Ile Pro Arg Val His Ile
100 105 110

Met Asn Pro Glu Asp Leu Lys Asp Ala Phe Asn Arg His Asp Asp Phe
115 120 125

His Lys Thr Val Lys Asn Pro Ile Met Lys Ser Pro Pro Pro Gly Ile
130 135 140

Val Gly Ile Glu Gly Glu Gln Trp Ala Lys His Arg Lys Ile Ile Asn
145 150 155 160

Pro Ala Phe His Leu Glu Lys Leu Lys Gly Met Val Pro Ile Phe Tyr
165 170 175

Gln Ser Cys Ser Glu Met Ile Asn Lys Trp Glu Ser Leu Val Ser Lys
180 185 190

Glu Ser Ser Cys Glu Leu Asp Val Trp Pro Tyr Leu Glu Asn Phe Thr
195 200 205

Ser Asp Val Ile Ser Arg Ala Ala Phe Gly Ser Ser Tyr Glu Glu Gly
210 215 220

Arg Lys Ile Phe Gln Leu Leu Arg Glu Glu Ala Lys Val Tyr Ser Val
225 230 235 240

Ala Leu Arg Ser Val Tyr Ile Pro Gly Trp Arg Phe Leu Pro Thr Lys
245 250 255

Gln Asn Lys Lys Thr Lys Glu Ile His Asn Glu Ile Lys Gly Leu Leu
260 265 270

Lys Gly Ile Ile Asn Lys Arg Glu Glu Ala Met Lys Ala Gly Glu Ala
275 280 285

Thr Lys Asp Asp Leu Leu Gly Ile Leu Met Glu Ser Asn Phe Arg Glu
290 295 300

Ile Gln Glu His Gly Asn Asn Lys Asn Ala Gly Met Ser Ile Glu Asp
305 310 315 320

Val Ile Gly Glu Cys Lys Leu Phe Tyr Phe Ala Gly Gln Glu Thr Thr
325 330 335

Ser Val Leu Leu Val Trp Thr Met Ile Leu Leu Ser Gln Asn Gln Asp
340 345 350

Trp Gln Ala Arg Ala Arg Glu Glu Val Leu Lys Val Phe Gly Ser Asn
355 360 365

```
Ile Pro Thr Tyr Glu Glu Leu Ser His Leu Lys Val Val Thr Met Ile
    370                 375                 380

Leu Leu Glu Val Leu Arg Leu Tyr Pro Ser Val Val Ala Leu Pro Arg
385                 390                 395                 400

Thr Thr His Lys Lys Thr Gln Leu Gly Lys Leu Ser Leu Pro Ala Gly
                405                 410                 415

Val Glu Val Ser Leu Pro Ile Leu Leu Val His His Asp Lys Glu Leu
            420                 425                 430

Trp Gly Glu Asp Ala Asn Glu Phe Lys Pro Glu Arg Phe Ser Glu Gly
        435                 440                 445

Val Ser Lys Ala Thr Lys Asn Lys Phe Thr Tyr Leu Pro Phe Gly Gly
    450                 455                 460

Gly Pro Arg Ile Cys Ile Gly Gln Asn Phe Ala Met Val Glu Ala Lys
465                 470                 475                 480

Leu Ala Leu Ala Leu Ile Leu Gln His Phe Ala Phe Glu Leu Ser Pro
                485                 490                 495

Ser Tyr Ala His Ala Pro Ser Ala Val Ile Thr Leu Gln Pro Gln Phe
            500                 505                 510

Gly Ala His Ile Ile Leu His Lys Arg
        515                 520


<210> SEQ ID NO 101
<211> LENGTH: 517
<212> TYPE: PRT
<213> ORGANISM: Prunus mume

<400> SEQUENCE: 101

Ala Ser Trp Val Ala Val Leu Ser Val Val Trp Val Ser Met Val Ile
1               5                   10                  15

Ala Trp Ala Trp Arg Val Leu Asn Trp Val Trp Leu Arg Pro Lys Lys
            20                  25                  30

Leu Glu Lys Cys Leu Arg Glu Gln Gly Leu Ala Gly Asn Ser Tyr Arg
        35                  40                  45

Leu Leu Phe Gly Asp Thr Lys Asp Leu Ser Lys Met Leu Glu Gln Thr
    50                  55                  60

Gln Ser Lys Pro Ile Lys Leu Ser Thr Ser His Asp Ile Ala Pro His
65                  70                  75                  80

Val Thr Pro Phe Phe His Gln Thr Val Asn Ser Tyr Gly Lys Asn Ser
                85                  90                  95

Phe Val Trp Met Gly Pro Ile Pro Arg Val His Ile Met Asn Pro Glu
            100                 105                 110

Asp Leu Lys Asp Thr Phe Asn Arg His Asp Asp Phe His Lys Val Val
        115                 120                 125

Lys Asn Pro Ile Met Lys Ser Leu Pro Gln Gly Ile Val Gly Ile Glu
    130                 135                 140

Gly Glu Gln Trp Ala Lys His Arg Lys Ile Ile Asn Pro Ala Phe His
145                 150                 155                 160

Leu Glu Lys Leu Lys Gly Met Val Pro Ile Phe Tyr Arg Ser Cys Ser
                165                 170                 175

Glu Met Ile Asn Lys Trp Glu Ser Leu Val Ser Lys Glu Ser Ser Cys
            180                 185                 190

Glu Leu Asp Val Trp Pro Tyr Leu Glu Asn Phe Thr Ser Asp Val Ile
        195                 200                 205

Ser Arg Ala Ala Phe Gly Ser Ser Tyr Glu Glu Gly Arg Lys Ile Phe
```

```
    210                 215                 220

Gln Leu Leu Arg Glu Glu Ala Lys Ile Tyr Thr Val Ala Met Arg Ser
225                 230                 235                 240

Val Tyr Ile Pro Gly Trp Arg Phe Leu Pro Thr Lys Gln Asn Lys Lys
                245                 250                 255

Ala Lys Glu Ile His Asn Glu Ile Lys Gly Leu Leu Lys Gly Ile Ile
            260                 265                 270

Asn Lys Arg Glu Glu Ala Met Lys Ala Gly Glu Ala Thr Lys Asp Asp
        275                 280                 285

Leu Leu Gly Ile Leu Met Glu Ser Asn Phe Arg Glu Ile Gln Glu His
    290                 295                 300

Gly Asn Asn Lys Asn Ala Gly Met Ser Ile Glu Asp Val Ile Gly Glu
305                 310                 315                 320

Cys Lys Leu Phe Tyr Phe Ala Gly Gln Glu Thr Thr Ser Val Leu Leu
                325                 330                 335

Val Trp Thr Met Val Leu Leu Ser Gln Asn Gln Asp Trp Gln Ala Arg
            340                 345                 350

Ala Arg Glu Glu Val Leu Gln Val Phe Gly Ser Asn Ile Pro Thr Tyr
        355                 360                 365

Glu Glu Leu Ser Gln Leu Lys Val Val Thr Met Ile Leu Leu Glu Val
    370                 375                 380

Leu Arg Leu Tyr Pro Ser Val Val Ala Leu Pro Arg Thr Thr His Lys
385                 390                 395                 400

Lys Thr Gln Leu Gly Lys Leu Ser Leu Pro Ala Gly Val Glu Val Ser
                405                 410                 415

Leu Pro Ile Leu Leu Val His His Asp Lys Glu Leu Trp Gly Glu Asp
            420                 425                 430

Ala Asn Glu Phe Lys Pro Glu Arg Phe Ser Glu Gly Val Ser Lys Ala
        435                 440                 445

Thr Lys Asn Gln Phe Thr Tyr Phe Pro Phe Gly Gly Gly Pro Arg Ile
    450                 455                 460

Cys Ile Gly Gln Asn Phe Ala Met Met Glu Ala Lys Leu Ala Leu Ser
465                 470                 475                 480

Leu Ile Leu Arg His Phe Ala Leu Glu Leu Ser Pro Leu Tyr Ala His
                485                 490                 495

Ala Pro Ser Val Thr Ile Thr Leu Gln Pro Gln Tyr Gly Ala His Ile
            500                 505                 510

Ile Leu His Lys Arg
        515


<210> SEQ ID NO 102
<211> LENGTH: 521
<212> TYPE: PRT
<213> ORGANISM: Prunus mume

<400> SEQUENCE: 102

Met Glu Ala Ser Arg Pro Ser Cys Val Ala Leu Ser Val Val Leu Val
1               5                   10                  15

Ser Ile Val Ile Ala Trp Ala Trp Arg Val Leu Asn Trp Val Trp Leu
            20                  25                  30

Arg Pro Asn Lys Leu Glu Arg Cys Leu Arg Glu Gln Gly Leu Thr Gly
        35                  40                  45

Asn Ser Tyr Arg Leu Leu Phe Gly Asp Thr Lys Glu Ile Ser Met Met
    50                  55                  60
```

```
Val Glu Gln Ala Gln Ser Lys Pro Ile Lys Leu Ser Thr Thr His Asp
65                  70                  75                  80

Ile Ala Pro Arg Val Ile Pro Phe Ser His Gln Ile Val Tyr Thr Tyr
                85                  90                  95

Gly Arg Asn Ser Phe Val Trp Met Gly Pro Thr Pro Arg Val Thr Ile
            100                 105                 110

Met Asn Pro Glu Asp Leu Lys Asp Ala Phe Asn Lys Ser Asp Glu Phe
        115                 120                 125

Gln Arg Ala Ile Ser Asn Pro Ile Val Lys Ser Ile Ser Gln Gly Leu
    130                 135                 140

Ser Ser Leu Glu Gly Glu Lys Trp Ala Lys His Arg Lys Ile Ile Asn
145                 150                 155                 160

Pro Ala Phe His Leu Glu Lys Leu Lys Gly Met Leu Pro Thr Phe Tyr
                165                 170                 175

Gln Ser Cys Ser Glu Met Ile Asn Lys Trp Glu Ser Leu Val Phe Lys
            180                 185                 190

Glu Gly Ser Arg Glu Met Asp Val Trp Pro Tyr Leu Glu Asn Leu Thr
        195                 200                 205

Ser Asp Val Ile Ser Arg Ala Ala Phe Gly Ser Ser Tyr Glu Glu Gly
    210                 215                 220

Arg Lys Ile Phe Gln Leu Leu Arg Glu Glu Ala Lys Phe Tyr Thr Ile
225                 230                 235                 240

Ala Ala Arg Ser Val Tyr Ile Pro Gly Trp Arg Phe Leu Pro Thr Lys
                245                 250                 255

Gln Asn Lys Arg Met Lys Glu Ile His Lys Glu Val Arg Gly Leu Leu
            260                 265                 270

Lys Gly Ile Ile Asn Lys Arg Glu Asp Ala Ile Lys Ala Gly Glu Ala
        275                 280                 285

Ala Lys Gly Asn Leu Leu Gly Ile Leu Met Glu Ser Asn Phe Arg Glu
    290                 295                 300

Ile Gln Glu His Gly Asn Asn Lys Asn Ala Gly Met Ser Ile Glu Asp
305                 310                 315                 320

Val Ile Gly Glu Cys Lys Leu Phe Tyr Phe Ala Gly Gln Glu Thr Thr
                325                 330                 335

Ser Val Leu Leu Val Trp Thr Leu Val Leu Leu Ser Gln Asn Gln Asp
            340                 345                 350

Trp Gln Ala Arg Ala Arg Glu Glu Val Leu Gln Val Phe Gly Thr Asn
        355                 360                 365

Ile Pro Thr Tyr Asp Gln Leu Ser His Leu Lys Val Val Thr Met Ile
    370                 375                 380

Leu Leu Glu Val Leu Arg Leu Tyr Pro Ala Val Val Glu Leu Pro Arg
385                 390                 395                 400

Thr Thr Tyr Lys Lys Thr Gln Leu Gly Lys Phe Leu Leu Pro Ala Gly
                405                 410                 415

Val Glu Val Ser Leu His Ile Met Leu Ala His His Asp Lys Glu Leu
            420                 425                 430

Trp Gly Glu Asp Ala Lys Glu Phe Lys Pro Glu Arg Phe Ser Glu Gly
        435                 440                 445

Val Ser Lys Ala Thr Lys Asn Gln Phe Thr Tyr Phe Pro Phe Gly Ala
    450                 455                 460

Gly Pro Arg Ile Cys Ile Gly Gln Asn Phe Ala Met Leu Glu Ala Lys
465                 470                 475                 480

Leu Ala Leu Ser Leu Ile Leu Gln His Phe Thr Phe Glu Leu Ser Pro
```

```
                485                 490                 495

Ser Tyr Ala His Ala Pro Ser Val Thr Ile Thr Leu His Pro Gln Phe
            500                 505                 510

Gly Ala His Phe Ile Leu His Lys Arg
        515                 520


<210> SEQ ID NO 103
<211> LENGTH: 514
<212> TYPE: PRT
<213> ORGANISM: Prunus mume

<400> SEQUENCE: 103

Cys Val Ala Leu Ser Val Val Leu Val Ser Ile Val Ile Ala Trp Ala
1               5                   10                  15

Trp Arg Val Leu Asn Trp Val Trp Leu Arg Pro Asn Lys Leu Glu Arg
            20                  25                  30

Cys Leu Arg Glu Gln Gly Leu Thr Gly Asn Ser Tyr Arg Leu Leu Phe
        35                  40                  45

Gly Asp Thr Lys Glu Ile Ser Met Met Val Glu Gln Ala Gln Ser Lys
    50                  55                  60

Pro Ile Lys Leu Ser Thr Thr His Asp Ile Ala Pro Arg Val Ile Pro
65                  70                  75                  80

Phe Ser His Gln Ile Val Tyr Thr Tyr Gly Arg Asn Ser Phe Val Trp
                85                  90                  95

Met Gly Pro Thr Pro Arg Val Thr Ile Met Asn Pro Glu Asp Leu Lys
            100                 105                 110

Asp Ala Phe Asn Lys Ser Asp Glu Phe Gln Arg Ala Ile Ser Asn Pro
        115                 120                 125

Ile Val Lys Ser Ile Ser Gln Gly Leu Ser Ser Leu Glu Gly Glu Lys
    130                 135                 140

Trp Ala Lys His Arg Lys Ile Ile Asn Pro Ala Phe His Leu Glu Lys
145                 150                 155                 160

Leu Lys Gly Met Leu Pro Thr Phe Tyr Gln Ser Cys Ser Glu Met Ile
                165                 170                 175

Asn Lys Trp Glu Ser Leu Val Phe Lys Glu Gly Ser Arg Glu Met Asp
            180                 185                 190

Val Trp Pro Tyr Leu Glu Asn Leu Thr Ser Asp Val Ile Ser Arg Ala
        195                 200                 205

Ala Phe Gly Ser Ser Tyr Glu Glu Gly Arg Lys Ile Phe Gln Leu Leu
    210                 215                 220

Arg Glu Glu Ala Lys Phe Tyr Thr Ile Ala Ala Arg Ser Val Tyr Ile
225                 230                 235                 240

Pro Gly Trp Arg Phe Leu Pro Thr Lys Gln Asn Lys Arg Met Lys Glu
                245                 250                 255

Ile His Lys Glu Val Arg Gly Leu Leu Lys Gly Ile Ile Asn Lys Arg
            260                 265                 270

Glu Asp Ala Ile Lys Ala Gly Glu Ala Ala Lys Gly Asn Leu Leu Gly
        275                 280                 285

Ile Leu Met Glu Ser Asn Phe Arg Glu Ile Gln Glu His Gly Asn Asn
    290                 295                 300

Lys Asn Ala Gly Met Ser Ile Glu Asp Val Ile Gly Glu Cys Lys Leu
305                 310                 315                 320

Phe Tyr Phe Ala Gly Gln Glu Thr Thr Ser Val Leu Leu Val Trp Thr
                325                 330                 335
```

```
Leu Val Leu Leu Ser Gln Asn Gln Asp Trp Gln Ala Arg Ala Arg Glu
            340                 345                 350

Glu Val Leu Gln Val Phe Gly Thr Asn Ile Pro Thr Tyr Asp Gln Leu
        355                 360                 365

Ser His Leu Lys Val Val Thr Met Ile Leu Leu Glu Val Leu Arg Leu
    370                 375                 380

Tyr Pro Ala Val Val Glu Leu Pro Arg Thr Thr Tyr Lys Lys Thr Gln
385                 390                 395                 400

Leu Gly Lys Phe Leu Leu Pro Ala Gly Val Glu Val Ser Leu His Ile
                405                 410                 415

Met Leu Ala His His Asp Lys Glu Leu Trp Gly Glu Asp Ala Lys Glu
            420                 425                 430

Phe Lys Pro Glu Arg Phe Ser Glu Gly Val Ser Lys Ala Thr Lys Asn
        435                 440                 445

Gln Phe Thr Tyr Phe Pro Phe Gly Ala Gly Pro Arg Ile Cys Ile Gly
    450                 455                 460

Gln Asn Phe Ala Met Leu Glu Ala Lys Leu Ala Leu Ser Leu Ile Leu
465                 470                 475                 480

Gln His Phe Thr Phe Glu Leu Ser Pro Ser Tyr Ala His Ala Pro Ser
                485                 490                 495

Val Thr Ile Thr Leu His Pro Gln Phe Gly Ala His Phe Ile Leu His
            500                 505                 510

Lys Arg


<210> SEQ ID NO 104
<211> LENGTH: 418
<212> TYPE: PRT
<213> ORGANISM: Prunus persica

<400> SEQUENCE: 104

Met Gly Pro Ile Pro Arg Val His Ile Met Asn Pro Glu Asp Leu Lys
1               5                   10                  15

Asp Thr Phe Asn Arg His Asp Asp Phe His Lys Val Val Lys Asn Pro
            20                  25                  30

Ile Met Lys Ser Leu Pro Gln Gly Ile Val Gly Ile Glu Gly Asp Gln
        35                  40                  45

Trp Ala Lys His Arg Lys Ile Ile Asn Pro Ala Phe His Leu Glu Lys
    50                  55                  60

Leu Lys Gly Met Val Pro Ile Phe Tyr Gln Ser Cys Ser Glu Met Ile
65                  70                  75                  80

Asn Ile Trp Lys Ser Leu Val Ser Lys Glu Ser Ser Cys Glu Leu Asp
                85                  90                  95

Val Trp Pro Tyr Leu Glu Asn Phe Thr Ser Asp Val Ile Ser Arg Ala
            100                 105                 110

Ala Phe Gly Ser Ser Tyr Glu Glu Gly Arg Lys Ile Phe Gln Leu Leu
        115                 120                 125

Arg Glu Glu Ala Lys Val Tyr Thr Val Ala Val Arg Ser Val Tyr Ile
    130                 135                 140

Pro Gly Trp Arg Phe Leu Pro Thr Lys Gln Asn Lys Lys Thr Lys Glu
145                 150                 155                 160

Ile His Asn Glu Ile Lys Gly Leu Leu Lys Gly Ile Ile Asn Lys Arg
                165                 170                 175

Glu Glu Ala Met Lys Ala Gly Glu Ala Thr Lys Asp Asp Leu Leu Gly
            180                 185                 190
```

-continued

```
Ile Leu Met Glu Ser Asn Phe Arg Glu Ile Gln Glu His Gly Asn Asn
        195                 200                 205

Lys Asn Ala Gly Met Ser Ile Glu Asp Val Ile Gly Glu Cys Lys Leu
    210                 215                 220

Phe Tyr Phe Ala Gly Gln Glu Thr Thr Ser Val Leu Leu Val Trp Thr
225                 230                 235                 240

Met Val Leu Leu Ser Gln Asn Gln Asp Trp Gln Ala Arg Ala Arg Glu
                245                 250                 255

Glu Val Leu Gln Val Phe Gly Ser Asn Ile Pro Thr Tyr Glu Glu Leu
            260                 265                 270

Ser His Leu Lys Val Val Thr Met Ile Leu Leu Glu Val Leu Arg Leu
        275                 280                 285

Tyr Pro Ser Val Val Ala Leu Pro Arg Thr Thr His Lys Lys Thr Gln
    290                 295                 300

Leu Gly Lys Leu Ser Leu Pro Ala Gly Val Glu Val Ser Leu Pro Ile
305                 310                 315                 320

Leu Leu Val His His Asp Lys Glu Leu Trp Gly Glu Asp Ala Asn Glu
                325                 330                 335

Phe Lys Pro Glu Arg Phe Ser Glu Gly Val Ser Lys Ala Thr Lys Asn
            340                 345                 350

Gln Phe Thr Tyr Phe Pro Phe Gly Gly Gly Pro Arg Ile Cys Ile Gly
        355                 360                 365

Gln Asn Phe Ala Met Met Glu Ala Lys Leu Ala Leu Ser Leu Ile Leu
    370                 375                 380

Gln His Phe Thr Phe Glu Leu Ser Pro Gln Tyr Ser His Ala Pro Ser
385                 390                 395                 400

Val Thr Ile Thr Leu Gln Pro Gln Tyr Gly Ala His Leu Ile Leu His
                405                 410                 415

Lys Arg
```

<210> SEQ ID NO 105
<211> LENGTH: 1578
<212> TYPE: DNA
<213> ORGANISM: Artificial Sequence
<220> FEATURE:
<223> OTHER INFORMATION: Codon-optimized KAH

<400> SEQUENCE: 105

```
atgggtttgt tcccattaga ggattcctac gcgctggtct ttgaaggact agcaataaca     60

ctggctttgt actatctact gtctttcatc tacaaaacat ctaaaaagac atgtacacct    120

cctaaagcat ctggtgaaat cattccaatt acaggaatca tattgaatct gctatctggc    180

tcaagtggtc tacctattat cttagcactt gcctctttag cagacagatg tggtcctatt    240

ttcaccatta ggctgggtat taggagagtg ctagtagtat caaattggga aatcgctaag    300

gagattttca ctacccacga tttgatagtt tctaatagac caaaatactt agccgctaag    360

attcttggtt tcaattatgt ttcattctct ttcgctccat acggcccata ttgggtcgga    420

atcagaaaga ttattgctac aaaactaatg tcttcttcca gacttcagaa gttgcaattt    480

gtaagagttt ttgaactaga aaactctatg aaatctatca gagaatcatg gaaggagaaa    540

aaggatgaag agggaaaggt attagttgag atgaaaaagt ggttctggga actgaatatg    600

aacatagtgt taaggacagt tgctggtaaa caatacactg gtacagttga tgatgccgat    660

gcaaagcgta tctccgagtt attcagagaa tggtttcact acactggcag atttgtcgtt    720

ggagacgctt ttcctttttct aggttggttg gacctgggcg gatacaaaaa gacaatggaa    780
```

ttagttgcta gtagattgga ctcaatggtc agtaaatggt tagatgagca tcgtaaaaag 840
caagctaacg atgacaaaaa ggaggatatg gatttcatgg atatcatgat ctccatgaca 900
gaagcaaatt caccacttga aggatacggc actgatacta ttatcaagac cacatgtatg 960
actttgattg tttcaggagt tgatacaacc tcaatcgtac ttacttgggc cttatcactt 1020
ttgttaaaca acagagatac tttgaaaaag gcacaagagg aattagatat gtgcgtaggt 1080
aaaggaagac aagtcaacga gtctgatctt gttaacttga tatacttgga agcagtgctt 1140
aaagaggctt taagacttta cccagcagcg ttcttaggcg gaccaagagc attcttggaa 1200
gattgtactg ttgctggtta tagaattcca aagggcacct gcttgttgat taacatgtgg 1260
aaactgcata gagatccaaa catttggagt gatccttgcg aattcaagcc agaaagattt 1320
ttgacaccta atcaaaagga tgttgatgtg atcggtatgg atttcgaatt gataccattt 1380
ggtgccggca gaagatattg tccaggtact agattggctt tacagatgtt gcatatcgta 1440
ttagcgacat tgctgcaaaa cttcgaaatg tcaacaccaa acgatgcgcc agtcgatatg 1500
actgcttctg ttggcatgac aaatgccaaa gcatcacctt tagaagtctt gctatcacct 1560
cgtgttaaat ggtcctaa 1578

<210> SEQ ID NO 106
<211> LENGTH: 522
<212> TYPE: PRT
<213> ORGANISM: Stevia rebaudiana

<400> SEQUENCE: 106

Met Gly Leu Phe Pro Leu Glu Asp Ser Tyr Ala Leu Val Phe Glu Gly
1 5 10 15

Leu Ala Ile Thr Leu Ala Leu Tyr Tyr Leu Leu Ser Phe Ile Tyr Lys
20 25 30

Thr Ser Lys Lys Thr Cys Thr Pro Pro Lys Ala Ser Gly Glu His Pro
35 40 45

Ile Thr Gly His Leu Asn Leu Leu Ser Gly Ser Ser Gly Leu Pro His
50 55 60

Leu Ala Leu Ala Ser Leu Ala Asp Arg Cys Gly Pro Ile Phe Thr Ile
65 70 75 80

Arg Leu Gly Ile Arg Arg Val Leu Val Val Ser Asn Trp Glu Ile Ala
85 90 95

Lys Glu Ile Phe Thr Thr His Asp Leu Ile Val Ser Asn Arg Pro Lys
100 105 110

Tyr Leu Ala Ala Lys Ile Leu Gly Phe Asn Tyr Val Ser Phe Ser Phe
115 120 125

Ala Pro Tyr Gly Pro Tyr Trp Val Gly Ile Arg Lys Ile Ile Ala Thr
130 135 140

Lys Leu Met Ser Ser Ser Arg Leu Gln Lys Leu Gln Phe Val Arg Val
145 150 155 160

Phe Glu Leu Glu Asn Ser Met Lys Ser Ile Arg Glu Ser Trp Lys Glu
165 170 175

Lys Lys Asp Glu Glu Gly Lys Val Leu Val Glu Met Lys Lys Trp Phe
180 185 190

Trp Glu Leu Asn Met Asn Ile Val Leu Arg Thr Val Ala Gly Lys Gln
195 200 205

Tyr Thr Gly Thr Val Asp Asp Ala Asp Ala Lys Arg Ile Ser Glu Leu
210 215 220

-continued

```
Phe Arg Glu Trp Phe His Tyr Thr Gly Arg Phe Val Val Gly Asp Ala
225                 230                 235                 240

Phe Pro Phe Leu Gly Trp Leu Asp Leu Gly Gly Tyr Lys Lys Thr Met
                245                 250                 255

Glu Leu Val Ala Ser Arg Leu Asp Ser Met Val Ser Lys Trp Leu Asp
            260                 265                 270

Glu His Arg Lys Lys Gln Ala Asn Asp Asp Lys Lys Glu Asp Met Asp
        275                 280                 285

Phe Met Asp Ile Met Ile Ser Met Thr Glu Ala Asn Ser Pro Leu Glu
    290                 295                 300

Gly Tyr Gly Thr Asp Thr Ile Ile Lys Thr Thr Cys Met Thr Leu Ile
305                 310                 315                 320

Val Ser Gly Val Asp Thr Thr Ser Ile Val Leu Thr Trp Ala Leu Ser
                325                 330                 335

Leu Leu Leu Asn Asn Arg Asp Thr Leu Lys Lys Ala Gln Glu Glu Leu
            340                 345                 350

Asp Met Cys Val Gly Lys Gly Arg Gln Val Asn Glu Ser Asp Leu Val
        355                 360                 365

Asn Leu Ile Tyr Leu Glu Ala Val Leu Lys Glu Ala Leu Arg Leu Tyr
    370                 375                 380

Pro Ala Ala Phe Leu Gly Gly Pro Arg Ala Phe Leu Glu Asp Cys Thr
385                 390                 395                 400

Val Ala Gly Tyr Arg Ile Pro Lys Gly Thr Cys Leu Leu Ile Asn Met
                405                 410                 415

Trp Lys Leu His Arg Asp Pro Asn Ile Trp Ser Asp Pro Cys Glu Phe
            420                 425                 430

Lys Pro Glu Arg Phe Leu Thr Pro Asn Gln Lys Asp Val Asp Val Ile
        435                 440                 445

Gly Met Asp Phe Glu Leu Ile Pro Phe Gly Ala Gly Arg Arg Tyr Cys
    450                 455                 460

Pro Gly Thr Arg Leu Ala Leu Gln Met Leu His Ile Val Leu Ala Thr
465                 470                 475                 480

Leu Leu Gln Asn Phe Glu Met Ser Thr Pro Asn Asp Ala Pro Val Asp
                485                 490                 495

Met Thr Ala Ser Val Gly Met Thr Asn Ala Lys Ala Ser Pro Leu Glu
            500                 505                 510

Val Leu Leu Ser Pro Arg Val Lys Trp Ser
        515                 520
```

<210> SEQ ID NO 107
<211> LENGTH: 1431
<212> TYPE: DNA
<213> ORGANISM: Artificial Sequence
<220> FEATURE:
<223> OTHER INFORMATION: Codon-optimized KAH

<400> SEQUENCE: 107

```
atgatacaag ttttaactcc aattctactc ttcctcatct tcttcgtttt ctggaaagtc     60

tacaaacatc aaaagactaa aatcaatcta ccaccaggtt ccttcggctg gccatttttg    120

ggtgaaacct tagccttact tagagcaggc tgggattctg agccagaaag attcgtaaga    180

gagcgtatca aaaagcatgg atctccactt gttttcaaga catcactatt tggagacaga    240

ttcgctgttc tttgcggtcc agctggtaat aagtttttgt tctgcaacga aaacaaatta    300

gtggcatctt ggtggccagt ccctgtaagg aagttgttcg gtaaaagttt actcacaata    360
```

-continued

```
agaggagatg aagcaaaatg gatgagaaaa atgctattgt cttacttggg tccagatgca    420

tttgccacac attatgccgt tactatggat gttgtaacac gtagacatat tgatgtccat    480

tggaggggca aggaggaagt taatgtattt caaacagtta agttgtacgc attcgaatta    540

gcttgtagat tattcatgaa cctagatgac ccaaaccaca tcgcgaaact cggtagtctt    600

ttcaacattt tcctcaaagg gatcatcgag cttcctatag acgttcctgg aactagattt    660

tactccagta aaaaggccgc agctgccatt agaattgaat tgaaaaagct cattaaagct    720

agaaaactcg aattgaagga gggtaaggcg tcttcttcac aggacttgct ttctcatcta    780

ttaacatcac ctgatgagaa tgggatgttc ttgacagaag aggaaatagt cgataacatt    840

ctacttttgt tattcgctgg tcacgatacc tctgcactat caataacact tttgatgaaa    900

accttaggtg aacacagtga tgtgtacgac aaggttttga aggaacaatt agaaatttcc    960

aaaacaaagg aggcttggga atcactaaag tgggaagata tccagaagat gaagtactca   1020

tggtcagtaa tctgtgaagt catgagattg aatcctcctg tcatagggac atacagagag   1080

gcgttggttg atatcgacta tgctggttac actatcccaa aaggatggaa gttgcattgg   1140

tcagctgttt ctactcaaag agacgaagcc aatttcgaag atgtaactag attcgatcca   1200

tccagatttg aaggggcagg ccctactcca ttcacatttg tgcctttcgg tggaggtcct   1260

agaatgtgtt taggcaaaga gtttgccagg ttagaagtgt tagcatttct ccacaacatt   1320

gttaccaact ttaagtggga tcttctaatc cctgatgaga agatcgaata tgatccaatg   1380

gctactccag ctaagggctt gccaattaga cttcatccac accaagtcta a            1431
```

<210> SEQ ID NO 108
<211> LENGTH: 476
<212> TYPE: PRT
<213> ORGANISM: Stevia rebaudiana

<400> SEQUENCE: 108

```
Met Ile Gln Val Leu Thr Pro Ile Leu Leu Phe Leu Ile Phe Phe Val
1               5                   10                  15

Phe Trp Lys Val Tyr Lys His Gln Lys Thr Lys Ile Asn Leu Pro Pro
            20                  25                  30

Gly Ser Phe Gly Trp Pro Phe Leu Gly Glu Thr Leu Ala Leu Leu Arg
        35                  40                  45

Ala Gly Trp Asp Ser Glu Pro Glu Arg Phe Val Arg Glu Arg Ile Lys
    50                  55                  60

Lys His Gly Ser Pro Leu Val Phe Lys Thr Ser Leu Phe Gly Asp Arg
65                  70                  75                  80

Phe Ala Val Leu Cys Gly Pro Ala Gly Asn Lys Phe Leu Phe Cys Asn
                85                  90                  95

Glu Asn Lys Leu Val Ala Ser Trp Trp Pro Val Pro Val Arg Lys Leu
            100                 105                 110

Phe Gly Lys Ser Leu Leu Thr Ile Arg Gly Asp Glu Ala Lys Trp Met
        115                 120                 125

Arg Lys Met Leu Leu Ser Tyr Leu Gly Pro Asp Ala Phe Ala Thr His
    130                 135                 140

Tyr Ala Val Thr Met Asp Val Val Thr Arg Arg His Ile Asp Val His
145                 150                 155                 160

Trp Arg Gly Lys Glu Glu Val Asn Val Phe Gln Thr Val Lys Leu Tyr
                165                 170                 175

Ala Phe Glu Leu Ala Cys Arg Leu Phe Met Asn Leu Asp Asp Pro Asn
            180                 185                 190
```

His Ile Ala Lys Leu Gly Ser Leu Phe Asn Ile Phe Leu Lys Gly Ile
195 200 205

Ile Glu Leu Pro Ile Asp Val Pro Gly Thr Arg Phe Tyr Ser Ser Lys
210 215 220

Lys Ala Ala Ala Ala Ile Arg Ile Glu Leu Lys Lys Leu Ile Lys Ala
225 230 235 240

Arg Lys Leu Glu Leu Lys Glu Gly Lys Ala Ser Ser Ser Gln Asp Leu
245 250 255

Leu Ser His Leu Leu Thr Ser Pro Asp Glu Asn Gly Met Phe Leu Thr
260 265 270

Glu Glu Glu Ile Val Asp Asn Ile Leu Leu Leu Leu Phe Ala Gly His
275 280 285

Asp Thr Ser Ala Leu Ser Ile Thr Leu Leu Met Lys Thr Leu Gly Glu
290 295 300

His Ser Asp Val Tyr Asp Lys Val Leu Lys Glu Gln Leu Glu Ile Ser
305 310 315 320

Lys Thr Lys Glu Ala Trp Glu Ser Leu Lys Trp Glu Asp Ile Gln Lys
325 330 335

Met Lys Tyr Ser Trp Ser Val Ile Cys Glu Val Met Arg Leu Asn Pro
340 345 350

Pro Val Ile Gly Thr Tyr Arg Glu Ala Leu Val Asp Ile Asp Tyr Ala
355 360 365

Gly Tyr Thr Ile Pro Lys Gly Trp Lys Leu His Trp Ser Ala Val Ser
370 375 380

Thr Gln Arg Asp Glu Ala Asn Phe Glu Asp Val Thr Arg Phe Asp Pro
385 390 395 400

Ser Arg Phe Glu Gly Ala Gly Pro Thr Pro Phe Thr Phe Val Pro Phe
405 410 415

Gly Gly Gly Pro Arg Met Cys Leu Gly Lys Glu Phe Ala Arg Leu Glu
420 425 430

Val Leu Ala Phe Leu His Asn Ile Val Thr Asn Phe Lys Trp Asp Leu
435 440 445

Leu Ile Pro Asp Glu Lys Ile Glu Tyr Asp Pro Met Ala Thr Pro Ala
450 455 460

Lys Gly Leu Pro Ile Arg Leu His Pro His Gln Val
465 470 475

<210> SEQ ID NO 109
<211> LENGTH: 1578
<212> TYPE: DNA
<213> ORGANISM: Artificial Sequence
<220> FEATURE:
<223> OTHER INFORMATION: Codon-optimized KAH

<400> SEQUENCE: 109
atggagtctt tagtggttca tacagtaaat gctatctggt gtattgtaat cgtcgggatt 60
ttctcagttg gttatcacgt ttacggtaga gctgtggtcg aacaatggag aatgagaaga 120
tcactgaagc tacaaggtgt taaaggccca ccaccatcca tcttcaatgg taacgtctca 180
gaaatgcaac gtatccaatc cgaagctaaa cactgctctg gcgataacat tatctcacat 240
gattattctt cttcattatt cccacacttc gatcactgga gaaaacagta cggcagaatc 300
tacacatact ctactggatt aaagcaacac ttgtacatca atcatccaga aatggtgaag 360
gagctatctc agactaacac attgaacttg ggtagaatca cccatataac caaaagattg 420

```
aatcctatct taggtaacgg aatcataacc tctaatggtc ctcattgggc ccatcagcgt    480

agaattatcg cctacgagtt tactcatgat aagatcaagg gtatggttgg tttgatggtt    540

gagtctgcta tgcctatgtt gaataagtgg gaggagatgg taaagagagg cggagaaatg    600

ggatgcgaca taagagttga tgaggacttg aaagatgttt cagcagatgt gattgcaaaa    660

gcctgtttcg gatcctcatt ttctaaaggt aaggctattt tctctatgat aagagatttg    720

cttacagcta tcacaaagag aagtgttcta ttcagattca acggattcac tgatatggtc    780

tttgggagta aaaagcatgg tgacgttgat atagacgctt tagaaatgga attggaatca    840

tccatttggg aaactgtcaa ggaacgtgaa atagaatgta aagatactca caaaaaggat    900

ctgatgcaat tgattttgga aggggcaatg cgttcatgtg acggtaacct ttgggataaa    960

tcagcatata gaagatttgt tgtagataat tgtaaatcta tctacttcgc agggcatgat   1020

agtacagctg tctcagtgtc atggtgtttg atgttactgg ccctaaaccc atcatggcaa   1080

gttaagatcc gtgatgaaat tctgtcttct tgcaaaaatg gtattccaga tgccgaaagt   1140

atcccaaacc ttaaaacagt gactatggtt attcaagaga caatgagatt ataccctcca   1200

gcaccaatcg tcgggagaga agcctctaaa gatatcagat tgggcgatct agttgttcct   1260

aaaggcgtct gtatatggac actaatacca gctttacaca gagatcctga gatttgggga   1320

ccagatgcaa acgatttcaa accagaaaga ttttctgaag gaatttcaaa ggcttgtaag   1380

tatcctcaaa gttacattcc atttggtctg ggtcctagaa catgcgttgg taaaaacttt   1440

ggcatgatgg aagtaaaggt tcttgtttcc ctgattgtct ccaagttctc tttcactcta   1500

tctcctacct accaacatag tcctagtcac aaacttttag tagaaccaca acatggggtg   1560

gtaattagag tggtttaa                                                 1578
```

<210> SEQ ID NO 110
<211> LENGTH: 525
<212> TYPE: PRT
<213> ORGANISM: Arabidopsis thaliana

<400> SEQUENCE: 110

```
Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
            20                  25                  30

Val Glu Gln Trp Arg Met Arg Arg Ser Leu Lys Leu Gln Gly Val Lys
        35                  40                  45

Gly Pro Pro Pro Ser Ile Phe Asn Gly Asn Val Ser Glu Met Gln Arg
    50                  55                  60

Ile Gln Ser Glu Ala Lys His Cys Ser Gly Asp Asn Ile Ile Ser His
65                  70                  75                  80

Asp Tyr Ser Ser Ser Leu Phe Pro His Phe Asp His Trp Arg Lys Gln
                85                  90                  95

Tyr Gly Arg Ile Tyr Thr Tyr Ser Thr Gly Leu Lys Gln His Leu Tyr
            100                 105                 110

Ile Asn His Pro Glu Met Val Lys Glu Leu Ser Gln Thr Asn Thr Leu
        115                 120                 125

Asn Leu Gly Arg Ile Thr His Ile Thr Lys Arg Leu Asn Pro Ile Leu
    130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
```

```
                165                 170                 175

Gly Leu Met Val Glu Ser Ala Met Pro Met Leu Asn Lys Trp Glu Glu
            180                 185                 190

Met Val Lys Arg Gly Gly Glu Met Gly Cys Asp Ile Arg Val Asp Glu
        195                 200                 205

Asp Leu Lys Asp Val Ser Ala Asp Val Ile Ala Lys Ala Cys Phe Gly
    210                 215                 220

Ser Ser Phe Ser Lys Gly Lys Ala Ile Phe Ser Met Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
        275                 280                 285

Arg Glu Ile Glu Cys Lys Asp Thr His Lys Lys Asp Leu Met Gln Leu
    290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Val Lys Ile Arg Asp Glu Ile Leu
        355                 360                 365

Ser Ser Cys Lys Asn Gly Ile Pro Asp Ala Glu Ser Ile Pro Asn Leu
    370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
            420                 425                 430

His Arg Asp Pro Glu Ile Trp Gly Pro Asp Ala Asn Asp Phe Lys Pro
        435                 440                 445

Glu Arg Phe Ser Glu Gly Ile Ser Lys Ala Cys Lys Tyr Pro Gln Ser
    450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
            500                 505                 510

Leu Val Glu Pro Gln His Gly Val Val Ile Arg Val Val
        515                 520                 525
```

<210> SEQ ID NO 111
<211> LENGTH: 1590
<212> TYPE: DNA
<213> ORGANISM: Artificial Sequence
<220> FEATURE:
<223> OTHER INFORMATION: Codon-optimized KAH

<400> SEQUENCE: 111

```
atgtacttcc tactacaata cctcaacatc acaaccgttg gtgtctttgc cacattgttt      60
```

ctctcttatt gtttacttct ctggagaagt agagcgggta acaaaaagat tgccccagaa 120
gctgccgctg catggcctat tatcggccac ctccacttac ttgcaggtgg atcccatcaa 180
ctaccacata ttacattggg taacatggca gataagtacg gtcctgtatt cacaatcaga 240
ataggcttgc atagagctgt agttgtctca tcttgggaaa tggcaaagga atgttcaaca 300
gctaatgatc aagtgtcttc ttcaagacct gaactattag cttctaagtt gttgggttat 360
aactacgcca tgtttggttt ttcaccatac ggttcatact ggagagaaat gagaaagatc 420
atctctctcg aattactatc taattccaga ttggaactat tgaaagatgt tagagcctca 480
gaagttgtca catctattaa ggaactatac aaattgtggg cggaaaagaa gaatgagtca 540
ggattggttt ctgtcgagat gaaacaatgg ttcggagatt tgactttaaa cgtgatcttg 600
agaatggtgg ctggtaaaag atacttctcc gcgagtgacg cttcagaaaa caaacaggcc 660
cagcgttgta gaagagtctt cagagaattc ttccatctct ccggcttgtt tgtggttgct 720
gatgctatac cttttcttgg atggctcgat tggggaagac acgagaagac cttgaaaaag 780
accgccatag aaatggattc catcgcccag gagtggcttg aggaacatag acgtagaaaa 840
gattctggag atgataattc tacccaagat ttcatggacg ttatgcaatc tgtgctagat 900
ggcaaaaatc taggcggata cgatgctgat acgattaaca aggctacatg cttaactctt 960
atatcaggtg gcagtgatac tactgtagtt tctttgacat gggctcttag tcttgtgtta 1020
aacaatagag atactttgaa aaaggcacag gaagagttag acatccaagt cggtaaggaa 1080
agattggtta acgagcaaga catcagtaag ttagtttact tgcaagcaat agtaaaagag 1140
acactcagac tttatccacc aggtcctttg ggtggtttga gacaattcac tgaagattgt 1200
acactaggtg gctatcacgt ttcaaaagga actagattaa tcatgaactt atccaagatt 1260
caaaaagatc cacgtatttg gtctgatcct actgaattcc aaccagagag attccttacg 1320
actcataaag atgtcgatcc acgtggtaaa cactttgaat tcattccatt cggtgcagga 1380
agacgtgcat gtcctggtat cacattcgga ttacaagtac tacatctaac attggcatct 1440
ttcttgcatg cgtttgaatt ttcaacacca tcaaatgagc aggttaacat gagagaatca 1500
ttaggtctta cgaatatgaa atctacccca ttagaagttt tgatttctcc aagactatcc 1560
cttaattgct tcaaccttat gaaaatttga 1590

<210> SEQ ID NO 112
<211> LENGTH: 526
<212> TYPE: PRT
<213> ORGANISM: Vitis vinifera

<400> SEQUENCE: 112

Met Tyr Phe Leu Leu Gln Tyr Leu Asn Ile Thr Thr Val Gly Val Phe
1 5 10 15

Ala Thr Leu Phe Leu Ser Tyr Cys Leu Leu Leu Trp Arg Ser Arg Ala
20 25 30

Gly Asn Lys Lys Ile Ala Pro Glu Ala Ala Ala Ala Trp Pro Ile Ile
35 40 45

Gly His Leu His Leu Leu Ala Gly Gly Ser His Gln Leu Pro His Ile
50 55 60

Thr Leu Gly Asn Met Ala Asp Lys Tyr Gly Pro Val Phe Thr Ile Arg
65 70 75 80

Ile Gly Leu His Arg Ala Val Val Val Ser Ser Trp Glu Met Ala Lys
85 90 95

-continued

```
Glu Cys Ser Thr Ala Asn Asp Gln Val Ser Ser Ser Arg Pro Glu Leu
            100                 105                 110

Leu Ala Ser Lys Leu Leu Gly Tyr Asn Tyr Ala Met Phe Gly Phe Ser
        115                 120                 125

Pro Tyr Gly Ser Tyr Trp Arg Glu Met Arg Lys Ile Ile Ser Leu Glu
    130                 135                 140

Leu Leu Ser Asn Ser Arg Leu Glu Leu Leu Lys Asp Val Arg Ala Ser
145                 150                 155                 160

Glu Val Val Thr Ser Ile Lys Glu Leu Tyr Lys Leu Trp Ala Glu Lys
                165                 170                 175

Lys Asn Glu Ser Gly Leu Val Ser Val Glu Met Lys Gln Trp Phe Gly
            180                 185                 190

Asp Leu Thr Leu Asn Val Ile Leu Arg Met Val Ala Gly Lys Arg Tyr
        195                 200                 205

Phe Ser Ala Ser Asp Ala Ser Glu Asn Lys Gln Ala Gln Arg Cys Arg
    210                 215                 220

Arg Val Phe Arg Glu Phe Phe His Leu Ser Gly Leu Phe Val Val Ala
225                 230                 235                 240

Asp Ala Ile Pro Phe Leu Gly Trp Leu Asp Trp Gly Arg His Glu Lys
                245                 250                 255

Thr Leu Lys Lys Thr Ala Ile Glu Met Asp Ser Ile Ala Gln Glu Trp
            260                 265                 270

Leu Glu Glu His Arg Arg Arg Lys Asp Ser Gly Asp Asp Asn Ser Thr
        275                 280                 285

Gln Asp Phe Met Asp Val Met Gln Ser Val Leu Asp Gly Lys Asn Leu
    290                 295                 300

Gly Gly Tyr Asp Ala Asp Thr Ile Asn Lys Ala Thr Cys Leu Thr Leu
305                 310                 315                 320

Ile Ser Gly Gly Ser Asp Thr Thr Val Val Ser Leu Thr Trp Ala Leu
                325                 330                 335

Ser Leu Val Leu Asn Asn Arg Asp Thr Leu Lys Lys Ala Gln Glu Glu
            340                 345                 350

Leu Asp Ile Gln Val Gly Lys Glu Arg Leu Val Asn Glu Gln Asp Ile
        355                 360                 365

Ser Lys Leu Val Tyr Leu Gln Ala Ile Val Lys Glu Thr Leu Arg Leu
    370                 375                 380

Tyr Pro Pro Gly Pro Leu Gly Gly Leu Arg Gln Phe Thr Glu Asp Cys
385                 390                 395                 400

Thr Leu Gly Gly Tyr His Val Ser Lys Gly Thr Arg Leu Ile Met Asn
                405                 410                 415

Leu Ser Lys Ile Gln Lys Asp Pro Arg Ile Trp Ser Asp Pro Thr Glu
            420                 425                 430

Phe Gln Pro Glu Arg Phe Leu Thr Thr His Lys Asp Val Asp Pro Arg
        435                 440                 445

Gly Lys His Phe Glu Phe Ile Pro Phe Gly Ala Gly Arg Arg Ala Cys
    450                 455                 460

Pro Gly Ile Thr Phe Gly Leu Gln Val Leu His Leu Thr Leu Ala Ser
465                 470                 475                 480

Phe Leu His Ala Phe Glu Phe Ser Thr Pro Ser Asn Glu Gln Val Asn
                485                 490                 495

Met Arg Glu Ser Leu Gly Leu Thr Asn Met Lys Ser Thr Pro Leu Glu
            500                 505                 510

Val Leu Ile Ser Pro Arg Leu Ser Ser Cys Ser Leu Tyr Asn
```

515 520 525

<210> SEQ ID NO 113
<211> LENGTH: 1440
<212> TYPE: DNA
<213> ORGANISM: Artificial Sequence
<220> FEATURE:
<223> OTHER INFORMATION: Codon-optimized KAH

<400> SEQUENCE: 113
atggaaccta acttttactt gtcattacta ttgttgttcg tgaccttcat ttctttaagt 60
ctgtttttca tcttttacaa acaaaagtcc ccattgaatt tgccaccagg gaaaatgggt 120
taccctatca taggtgaaag tttagaattc ctatccacag gctggaaggg acatcctgaa 180
aagttcatat ttgatagaat gcgtaagtac agtagtgagt tattcaagac ttctattgta 240
ggcgaatcca cagttgtttg ctgtggggca gctagtaaca aattcctatt ctctaacgaa 300
aacaaactgg taactgcctg gtggccagat tctgttaaca aaatcttccc aacaacttca 360
ctggattcta atttgaagga ggaatctata aagatgagaa agttgctgcc acagttcttc 420
aaaccagaag cacttcaaag atacgtcggc gttatggatg taatcgcaca aagacatttt 480
gtcactcact gggacaacaa aaatgagatc acagtttatc cacttgctaa aagatacact 540
ttcttgcttg cgtgtagact gttcatgtct gttgaggatg aaaatcatgt ggcgaaattc 600
tcagacccat tccaactaat cgctgcaggc atcatttcac ttcctatcga tcttcctggt 660
actccattca acaaggccat aaaggcttca aatttcatta gaaaagagct gataaagatt 720
atcaaacaaa gacgtgttga tctggcagag ggtacagcat ctccaaccca ggatatcttg 780
tcacatatgc tattaacatc tgatgaaaac ggtaaatcta tgaacgagtt gaacattgcc 840
gacaagattc ttggactatt gataggaggc cacgatacag cttcagtagc ttgcacattt 900
ctagtgaagt acttaggaga attaccacat atctacgata aagtctacca agagcaaatg 960
gaaattgcca agtccaaacc tgctggggaa ttgttgaatt gggatgactt gaaaaagatg 1020
aagtattcat ggaatgtggc atgtgaggta atgagattgt caccaccttt acaaggtggt 1080
tttagagagg ctataactga ctttatgttt aacggtttct ctattccaaa agggtggaag 1140
ttatactggt ccgccaactc tacacacaaa aatgcagaat gtttcccaat gcctgagaaa 1200
ttcgatccta ccagatttga aggtaatggt ccagcgcctt atacatttgt accattcggt 1260
ggaggcccta gaatgtgtcc tggaaaggaa tacgctagat tagaaatctt ggttttcatg 1320
cataatctgg tcaaacgttt taagtgggaa aaggttattc cagacgaaaa gattattgtc 1380
gatccattcc caatcccagc taaagatctt ccaatccgtt tgtatcctca caaagcttaa 1440

<210> SEQ ID NO 114
<211> LENGTH: 479
<212> TYPE: PRT
<213> ORGANISM: Medicago truncatula

<400> SEQUENCE: 114

Met Glu Pro Asn Phe Tyr Leu Ser Leu Leu Leu Leu Phe Val Thr Phe
1 5 10 15

Ile Ser Leu Ser Leu Phe Phe Ile Phe Tyr Lys Gln Lys Ser Pro Leu
20 25 30

Asn Leu Pro Pro Gly Lys Met Gly Tyr Pro Ile Ile Gly Glu Ser Leu
35 40 45

Glu Phe Leu Ser Thr Gly Trp Lys Gly His Pro Glu Lys Phe Ile Phe
50 55 60

-continued

```
Asp Arg Met Arg Lys Tyr Ser Ser Glu Leu Phe Lys Thr Ser Ile Val
65                  70                  75                  80

Gly Glu Ser Thr Val Val Cys Cys Gly Ala Ala Ser Asn Lys Phe Leu
                85                  90                  95

Phe Ser Asn Glu Asn Lys Leu Val Thr Ala Trp Trp Pro Asp Ser Val
            100                 105                 110

Asn Lys Ile Phe Pro Thr Thr Ser Leu Asp Ser Asn Leu Lys Glu Glu
        115                 120                 125

Ser Ile Lys Met Arg Lys Leu Leu Pro Gln Phe Phe Lys Pro Glu Ala
    130                 135                 140

Leu Gln Arg Tyr Val Gly Val Met Asp Val Ile Ala Gln Arg His Phe
145                 150                 155                 160

Val Thr His Trp Asp Asn Lys Asn Glu Ile Thr Val Tyr Pro Leu Ala
                165                 170                 175

Lys Arg Tyr Thr Phe Leu Leu Ala Cys Arg Leu Phe Met Ser Val Glu
            180                 185                 190

Asp Glu Asn His Val Ala Lys Phe Ser Asp Pro Phe Gln Leu Ile Ala
        195                 200                 205

Ala Gly Ile Ile Ser Leu Pro Ile Asp Leu Pro Gly Thr Pro Phe Asn
    210                 215                 220

Lys Ala Ile Lys Ala Ser Asn Phe Ile Arg Lys Glu Leu Ile Lys Ile
225                 230                 235                 240

Ile Lys Gln Arg Arg Val Asp Leu Ala Glu Gly Thr Ala Ser Pro Thr
                245                 250                 255

Gln Asp Ile Leu Ser His Met Leu Leu Thr Ser Asp Glu Asn Gly Lys
            260                 265                 270

Ser Met Asn Glu Leu Asn Ile Ala Asp Lys Ile Leu Gly Leu Leu Ile
        275                 280                 285

Gly Gly His Asp Thr Ala Ser Val Ala Cys Thr Phe Leu Val Lys Tyr
    290                 295                 300

Leu Gly Glu Leu Pro His Ile Tyr Asp Lys Val Tyr Gln Glu Gln Met
305                 310                 315                 320

Glu Ile Ala Lys Ser Lys Pro Ala Gly Glu Leu Leu Asn Trp Asp Asp
                325                 330                 335

Leu Lys Lys Met Lys Tyr Ser Trp Asn Val Ala Cys Glu Val Met Arg
            340                 345                 350

Leu Ser Pro Pro Leu Gln Gly Gly Phe Arg Glu Ala Ile Thr Asp Phe
        355                 360                 365

Met Phe Asn Gly Phe Ser Ile Pro Lys Gly Trp Lys Leu Tyr Trp Ser
    370                 375                 380

Ala Asn Ser Thr His Lys Asn Ala Glu Cys Phe Pro Met Pro Glu Lys
385                 390                 395                 400

Phe Asp Pro Thr Arg Phe Glu Gly Asn Gly Pro Ala Pro Tyr Thr Phe
                405                 410                 415

Val Pro Phe Gly Gly Gly Pro Arg Met Cys Pro Gly Lys Glu Tyr Ala
            420                 425                 430

Arg Leu Glu Ile Leu Val Phe Met His Asn Leu Val Lys Arg Phe Lys
        435                 440                 445

Trp Glu Lys Val Ile Pro Asp Glu Lys Ile Ile Val Asp Pro Phe Pro
    450                 455                 460

Ile Pro Ala Lys Asp Leu Pro Ile Arg Leu Tyr Pro His Lys Ala
465                 470                 475
```

<210> SEQ ID NO 115
<211> LENGTH: 1116
<212> TYPE: DNA
<213> ORGANISM: Artificial Sequence
<220> FEATURE:
<223> OTHER INFORMATION: Codon-optimized GGPPS

<400> SEQUENCE: 115
atggcctctg ttactttggg ttcctggatc gtcgtccacc accataacca tcaccatcca 60
tcatctatcc taactaaatc tcgttcaaga tcctgtccta ttacactaac caaaccaatc 120
tcttttcgtt caaagagaac agtttcctct agtagttcta tcgtgtcctc tagtgtcgtc 180
actaaggaag acaatctgag acagtctgaa ccttcttcct ttgatttcat gtcatatatc 240
attactaagg cagaactagt gaataaggct cttgattcag cagttccatt aagagagcca 300
ttgaaaatcc atgaagcaat gagatactct cttctagctg gcgggaagag agtcagacct 360
gtactctgca tagcagcgtg cgaattagtt ggtggcgagg aatcaaccgc tatgcctgcc 420
gcttgtgctg tagaaatgat tcatacaatg tcactgatac acgatgattt gccatgtatg 480
gataacgatg atctgagaag ggtaagccca actaaccata aggttttcgg cgaagatgtt 540
gccgtcttag ctggtgatgc tttgttatct ttcgcgttcg aacatttggc atccgcaaca 600
tcaagtgatg ttgtgtcacc agtaagagta gttagagcag ttggagaact ggctaaagct 660
attggaactg agggtttagt tgcaggtcaa gtcgtcgata tctcttccga aggtcttgat 720
ttgaatgatg taggtcttga acatctcgaa ttcatccatc ttcacaagac agctgcactt 780
ttagaagcca gtgcggttct cggcgcaatt gttggcggag ggagtgatga cgaaattgag 840
agattgagga agtttgctag atgtatagga ttactgttcc aagtagtaga cgatatacta 900
gatgtgacaa agtcttccaa agagttggga aaaacagctg gtaaagattt gattgccgac 960
aaattgacct accctaagat tatggggcta gaaaaatcaa gagaatttgc cgagaaactc 1020
aatagagagg cgcgtgatca actgttgggt ttcgattctg ataaagttgc accactctta 1080
gccttagcca actacatcgc ttacagacaa aactaa 1116

<210> SEQ ID NO 116
<211> LENGTH: 371
<212> TYPE: PRT
<213> ORGANISM: Arabidopsis thaliana

<400> SEQUENCE: 116

Met Ala Ser Val Thr Leu Gly Ser Trp Ile Val Val His His His Asn
1 5 10 15

His His His Pro Ser Ser Ile Leu Thr Lys Ser Arg Ser Arg Ser Cys
20 25 30

Pro Ile Thr Leu Thr Lys Pro Ile Ser Phe Arg Ser Lys Arg Thr Val
35 40 45

Ser Ser Ser Ser Ser Ile Val Ser Ser Ser Val Val Thr Lys Glu Asp
50 55 60

Asn Leu Arg Gln Ser Glu Pro Ser Ser Phe Asp Phe Met Ser Tyr Ile
65 70 75 80

Ile Thr Lys Ala Glu Leu Val Asn Lys Ala Leu Asp Ser Ala Val Pro
85 90 95

Leu Arg Glu Pro Leu Lys Ile His Glu Ala Met Arg Tyr Ser Leu Leu
100 105 110

Ala Gly Gly Lys Arg Val Arg Pro Val Leu Cys Ile Ala Ala Cys Glu
115 120 125

```
Leu Val Gly Gly Glu Glu Ser Thr Ala Met Pro Ala Ala Cys Ala Val
    130                 135                 140

Glu Met Ile His Thr Met Ser Leu Ile His Asp Asp Leu Pro Cys Met
145                 150                 155                 160

Asp Asn Asp Asp Leu Arg Arg Gly Lys Pro Thr Asn His Lys Val Phe
                165                 170                 175

Gly Glu Asp Val Ala Val Leu Ala Gly Asp Ala Leu Leu Ser Phe Ala
            180                 185                 190

Phe Glu His Leu Ala Ser Ala Thr Ser Ser Asp Val Val Ser Pro Val
        195                 200                 205

Arg Val Val Arg Ala Val Gly Glu Leu Ala Lys Ala Ile Gly Thr Glu
    210                 215                 220

Gly Leu Val Ala Gly Gln Val Val Asp Ile Ser Ser Glu Gly Leu Asp
225                 230                 235                 240

Leu Asn Asp Val Gly Leu Glu His Leu Glu Phe Ile His Leu His Lys
                245                 250                 255

Thr Ala Ala Leu Leu Glu Ala Ser Ala Val Leu Gly Ala Ile Val Gly
            260                 265                 270

Gly Gly Ser Asp Asp Glu Ile Glu Arg Leu Arg Lys Phe Ala Arg Cys
        275                 280                 285

Ile Gly Leu Leu Phe Gln Val Val Asp Asp Ile Leu Asp Val Thr Lys
    290                 295                 300

Ser Ser Lys Glu Leu Gly Lys Thr Ala Gly Lys Asp Leu Ile Ala Asp
305                 310                 315                 320

Lys Leu Thr Tyr Pro Lys Ile Met Gly Leu Glu Lys Ser Arg Glu Phe
                325                 330                 335

Ala Glu Lys Leu Asn Arg Glu Ala Arg Asp Gln Leu Leu Gly Phe Asp
            340                 345                 350

Ser Asp Lys Val Ala Pro Leu Leu Ala Leu Ala Asn Tyr Ile Ala Tyr
        355                 360                 365

Arg Gln Asn
    370
```

<210> SEQ ID NO 117
<211> LENGTH: 511
<212> TYPE: PRT
<213> ORGANISM: Rubus suavissimus

<400> SEQUENCE: 117

```
Met Ala Thr Leu Leu Glu His Phe Gln Ala Met Pro Phe Ala Ile Pro
1               5                   10                  15

Ile Ala Leu Ala Ala Leu Ser Trp Leu Phe Leu Phe Tyr Ile Lys Val
            20                  25                  30

Ser Phe Phe Ser Asn Lys Ser Ala Gln Ala Lys Leu Pro Pro Val Pro
        35                  40                  45

Val Val Pro Gly Leu Pro Val Ile Gly Asn Leu Leu Gln Leu Lys Glu
    50                  55                  60

Lys Lys Pro Tyr Gln Thr Phe Thr Arg Trp Ala Glu Glu Tyr Gly Pro
65                  70                  75                  80

Ile Tyr Ser Ile Arg Thr Gly Ala Ser Thr Met Val Val Leu Asn Thr
                85                  90                  95

Thr Gln Val Ala Lys Glu Ala Met Val Thr Arg Tyr Leu Ser Ile Ser
            100                 105                 110

Thr Arg Lys Leu Ser Asn Ala Leu Lys Ile Leu Thr Ala Asp Lys Cys
```

```
        115                 120                 125

Met Val Ala Ile Ser Asp Tyr Asn Asp Phe His Lys Met Ile Lys Arg
    130                 135                 140

Tyr Ile Leu Ser Asn Val Leu Gly Pro Ser Ala Gln Lys Arg His Arg
145                 150                 155                 160

Ser Asn Arg Asp Thr Leu Arg Ala Asn Val Cys Ser Arg Leu His Ser
                165                 170                 175

Gln Val Lys Asn Ser Pro Arg Glu Ala Val Asn Phe Arg Arg Val Phe
            180                 185                 190

Glu Trp Glu Leu Phe Gly Ile Ala Leu Lys Gln Ala Phe Gly Lys Asp
        195                 200                 205

Ile Glu Lys Pro Ile Tyr Val Glu Glu Leu Gly Thr Thr Leu Ser Arg
    210                 215                 220

Asp Glu Ile Phe Lys Val Leu Val Leu Asp Ile Met Glu Gly Ala Ile
225                 230                 235                 240

Glu Val Asp Trp Arg Asp Phe Phe Pro Tyr Leu Arg Trp Ile Pro Asn
                245                 250                 255

Thr Arg Met Glu Thr Lys Ile Gln Arg Leu Tyr Phe Arg Arg Lys Ala
            260                 265                 270

Val Met Thr Ala Leu Ile Asn Glu Gln Lys Lys Arg Ile Ala Ser Gly
        275                 280                 285

Glu Glu Ile Asn Cys Tyr Ile Asp Phe Leu Leu Lys Glu Gly Lys Thr
    290                 295                 300

Leu Thr Met Asp Gln Ile Ser Met Leu Leu Trp Glu Thr Val Ile Glu
305                 310                 315                 320

Thr Ala Asp Thr Thr Met Val Thr Thr Glu Trp Ala Met Tyr Glu Val
                325                 330                 335

Ala Lys Asp Ser Lys Arg Gln Asp Arg Leu Tyr Gln Glu Ile Gln Lys
            340                 345                 350

Val Cys Gly Ser Glu Met Val Thr Glu Glu Tyr Leu Ser Gln Leu Pro
        355                 360                 365

Tyr Leu Asn Ala Val Phe His Glu Thr Leu Arg Lys His Ser Pro Ala
    370                 375                 380

Ala Leu Val Pro Leu Arg Tyr Ala His Glu Asp Thr Gln Leu Gly Gly
385                 390                 395                 400

Tyr Tyr Ile Pro Ala Gly Thr Glu Ile Ala Ile Asn Ile Tyr Gly Cys
                405                 410                 415

Asn Met Asp Lys His Gln Trp Glu Ser Pro Glu Glu Trp Lys Pro Glu
            420                 425                 430

Arg Phe Leu Asp Pro Lys Phe Asp Pro Met Asp Leu Tyr Lys Thr Met
        435                 440                 445

Ala Phe Gly Ala Gly Lys Arg Val Cys Ala Gly Ser Leu Gln Ala Met
    450                 455                 460

Leu Ile Ala Cys Pro Thr Ile Gly Arg Leu Val Gln Glu Phe Glu Trp
465                 470                 475                 480

Lys Leu Arg Asp Gly Glu Glu Glu Asn Val Asp Thr Val Gly Leu Thr
                485                 490                 495

Thr His Lys Arg Tyr Pro Met His Ala Ile Leu Lys Pro Arg Ser
            500                 505                 510
```

<210> SEQ ID NO 118
<211> LENGTH: 1710
<212> TYPE: DNA
<213> ORGANISM: Saccharomyces cerevisiae

<400> SEQUENCE: 118
atgtcatttc aaattgaaac ggttcccacc aaaccatatg aagaccaaaa gcctggtacc 60
tctggtttgc gtaagaagac aaaggtgttt aaagacgaac ctaactacac agaaaatttc 120
attcaatcga tcatggaagc tattccagag ggttctaaag gtgccactct tgttgtcggt 180
ggtgatgggc gttactacaa tgatgtcatt cttcataaga ttgccgctat cggtgctgcc 240
aacggtatta aaaagttagt tattggccag catggtcttc tgtctacgcc agccgcttct 300
cacatcatga gaacctacga ggaaaaatgt actggtggta ttatcttaac cgcctcacat 360
aatccaggtg gtccagaaaa tgacatgggt attaagtata acttatccaa tgggggtcct 420
gctcctgaat ccgtcacaaa tgctatttgg gagatttcca aaaagcttac cagctataag 480
attatcaaag acttcccaga actagacttg ggtacgatag gcaagaacaa gaaatacggt 540
ccattactcg ttgacattat cgatattaca aaagattatg tcaacttctt gaaggaaatc 600
ttcgatttcg acttaatcaa gaaattcatc gataatcaac gttctactaa gaattggaag 660
ttactgtttg acagtatgaa cggtgtaact ggaccatacg gtaaggctat tttcgttgat 720
gaatttggtt taccggcgga tgaggtttta caaaactggc atccttctcc ggattttggt 780
ggtatgcatc cagatccaaa cttaacttat gccagttcgt tagtgaaaag agtagatcgt 840
gaaaagattg agtttggtgc tgcatccgat ggtgatggtg atagaaatat gatttacggt 900
tacggcccat ctttcgtttc tccaggtgac tccgtcgcaa ttattgccga atatgcagct 960
gaaatcccat atttcgccaa gcaaggtata tatggtctgg cccgttcatt ccctacctca 1020
ggagccatag accgtgttgc caaggcccat ggtctaaact gttatgaggt cccaactggc 1080
tggaaatttt tctgtgcttt gttcgacgct aaaaaattat ctatttgtgg tgaagaatcg 1140
tttggtactg gttccaacca cgtaagggaa aaggacggtg tttgggccat tatggcgtgg 1200
ttgaacatct tggccattta caacaagcat catccggaga acgaagcttc tattaagacg 1260
atacagaatg aattctgggc aaagtacggc cgtactttct tcactcgtta tgattttgaa 1320
aaagttgaaa cagaaaaagc taacaagatt gtcgatcaat tgagagcata tgttaccaaa 1380
tcgggtgttg ttaattccgc cttcccagcc gatgagtctc ttaaggtcac cgattgtggt 1440
gatttttcat acacagattt ggacggttct gtttctgacc atcaaggttt atatgtcaag 1500
ctttccaatg gtgcaagatt cgttctaaga ttgtcaggta caggttcttc aggtgctacc 1560
attagattgt acattgaaaa atactgcgat gataaatcac aataccaaaa gacagctgaa 1620
gaatacttga agccaattat taactcggtc atcaagttct tgaactttaa acaagtttta 1680
ggaactgaag aaccaacggt tcgtacttaa 1710

<210> SEQ ID NO 119
<211> LENGTH: 569
<212> TYPE: PRT
<213> ORGANISM: Saccharomyces cerevisiae

<400> SEQUENCE: 119

Met Ser Phe Gln Ile Glu Thr Val Pro Thr Lys Pro Tyr Glu Asp Gln
1               5                   10                  15

Lys Pro Gly Thr Ser Gly Leu Arg Lys Lys Thr Lys Val Phe Lys Asp
            20                  25                  30

Glu Pro Asn Tyr Thr Glu Asn Phe Ile Gln Ser Ile Met Glu Ala Ile
        35                  40                  45

Pro Glu Gly Ser Lys Gly Ala Thr Leu Val Val Gly Gly Asp Gly Arg

-continued

```
    50                  55                  60

Tyr Tyr Asn Asp Val Ile Leu His Lys Ile Ala Ala Ile Gly Ala Ala
65                  70                  75                  80

Asn Gly Ile Lys Lys Leu Val Ile Gly Gln His Gly Leu Leu Ser Thr
                85                  90                  95

Pro Ala Ala Ser His Ile Met Arg Thr Tyr Glu Glu Lys Cys Thr Gly
            100                 105                 110

Gly Ile Ile Leu Thr Ala Ser His Asn Pro Gly Gly Pro Glu Asn Asp
        115                 120                 125

Met Gly Ile Lys Tyr Asn Leu Ser Asn Gly Gly Pro Ala Pro Glu Ser
    130                 135                 140

Val Thr Asn Ala Ile Trp Glu Ile Ser Lys Lys Leu Thr Ser Tyr Lys
145                 150                 155                 160

Ile Ile Lys Asp Phe Pro Glu Leu Asp Leu Gly Thr Ile Gly Lys Asn
                165                 170                 175

Lys Lys Tyr Gly Pro Leu Leu Val Asp Ile Ile Asp Ile Thr Lys Asp
            180                 185                 190

Tyr Val Asn Phe Leu Lys Glu Ile Phe Asp Phe Asp Leu Ile Lys Lys
        195                 200                 205

Phe Ile Asp Asn Gln Arg Ser Thr Lys Asn Trp Lys Leu Leu Phe Asp
    210                 215                 220

Ser Met Asn Gly Val Thr Gly Pro Tyr Gly Lys Ala Ile Phe Val Asp
225                 230                 235                 240

Glu Phe Gly Leu Pro Ala Asp Glu Val Leu Gln Asn Trp His Pro Ser
                245                 250                 255

Pro Asp Phe Gly Gly Met His Pro Asp Pro Asn Leu Thr Tyr Ala Ser
            260                 265                 270

Ser Leu Val Lys Arg Val Asp Arg Glu Lys Ile Glu Phe Gly Ala Ala
        275                 280                 285

Ser Asp Gly Asp Gly Asp Arg Asn Met Ile Tyr Gly Tyr Gly Pro Ser
    290                 295                 300

Phe Val Ser Pro Gly Asp Ser Val Ala Ile Ile Ala Glu Tyr Ala Ala
305                 310                 315                 320

Glu Ile Pro Tyr Phe Ala Lys Gln Gly Ile Tyr Gly Leu Ala Arg Ser
                325                 330                 335

Phe Pro Thr Ser Gly Ala Ile Asp Arg Val Ala Lys Ala His Gly Leu
            340                 345                 350

Asn Cys Tyr Glu Val Pro Thr Gly Trp Lys Phe Phe Cys Ala Leu Phe
        355                 360                 365

Asp Ala Lys Lys Leu Ser Ile Cys Gly Glu Glu Ser Phe Gly Thr Gly
    370                 375                 380

Ser Asn His Val Arg Glu Lys Asp Gly Val Trp Ala Ile Met Ala Trp
385                 390                 395                 400

Leu Asn Ile Leu Ala Ile Tyr Asn Lys His His Pro Glu Asn Glu Ala
                405                 410                 415

Ser Ile Lys Thr Ile Gln Asn Glu Phe Trp Ala Lys Tyr Gly Arg Thr
            420                 425                 430

Phe Phe Thr Arg Tyr Asp Phe Glu Lys Val Glu Thr Glu Lys Ala Asn
        435                 440                 445

Lys Ile Val Asp Gln Leu Arg Ala Tyr Val Thr Lys Ser Gly Val Val
    450                 455                 460

Asn Ser Ala Phe Pro Ala Asp Glu Ser Leu Lys Val Thr Asp Cys Gly
465                 470                 475                 480
```

```
Asp Phe Ser Tyr Thr Asp Leu Asp Gly Ser Val Ser Asp His Gln Gly
                485                 490                 495

Leu Tyr Val Lys Leu Ser Asn Gly Ala Arg Phe Val Leu Arg Leu Ser
            500                 505                 510

Gly Thr Gly Ser Ser Gly Ala Thr Ile Arg Leu Tyr Ile Glu Lys Tyr
        515                 520                 525

Cys Asp Asp Lys Ser Gln Tyr Gln Lys Thr Ala Glu Glu Tyr Leu Lys
    530                 535                 540

Pro Ile Ile Asn Ser Val Ile Lys Phe Leu Asn Phe Lys Gln Val Leu
545                 550                 555                 560

Gly Thr Glu Glu Pro Thr Val Arg Thr
                565
```

<210> SEQ ID NO 120
<211> LENGTH: 1500
<212> TYPE: DNA
<213> ORGANISM: Saccharomyces cerevisiae

<400> SEQUENCE: 120

```
atgtccacta agaagcacac caaaacacat tccacttatg cattcgagag caacacaaac     60

agcgttgctg cctcacaaat gagaaacgcc ttaaacaagt tggcggactc tagtaaactt    120

gacgatgctg ctcgcgctaa gtttgagaac gaactggatt cgtttttcac gcttttcagg    180

agatatttgg tagagaagtc ttctagaacc accttggaat gggacaagat caagtctccc    240

aacccggatg aagtggttaa gtatgaaatt atttctcagc agcccgagaa tgtctcaaac    300

ctttccaaat tggctgtttt gaagttgaac ggtgggctgg gtacctccat gggctgcgtt    360

ggccctaaat ctgttattga agtgagagag ggaaacacct tttggattt gtctgttcgt     420

caaattgaat acttgaacag acagtacgat agcgacgtgc cattgttatt gatgaattct    480

ttcaacactg acaaggatac ggaacacttg attaagaagt attccgctaa cagaatcaga    540

atcagatctt tcaatcaatc caggttccca agagtctaca aggattcttt attgcctgtc    600

cccaccgaat acgattctcc actggatgct tggtatccac caggtcacgg tgatttgttt    660

gaatctttac acgtatctgg tgaactggat gccttaattg cccaaggaag agaaatatta    720

tttgtttcta acggtgacaa cttgggtgct accgtcgact taaaaatttt aaaccacatg    780

atcgagactg gtgccgaata tataatggaa ttgactgata agaccagagc cgatgttaaa    840

ggtggtactt tgatttctta cgatggtcaa gtccgtttat tggaagtcgc ccaagttcca    900

aaagaacaca ttgacgaatt caaaaatatc agaaagttta ccaacttcaa cacgaataac    960

ttatggatca atctgaaagc agtaaagagg ttgatcgaat cgagcaattt ggagatggaa   1020

atcattccaa accaaaaaac tataacaaga gacggtcatg aaattaatgt cttacaatta   1080

gaaaccgctt gtggtgctgc tatcaggcat tttgatggtg ctcacggtgt tgtcgttcca   1140

agatcaagat tcttgcctgt caagacctgt tccgatttgt tgctggttaa atcagatcta   1200

ttccgtctgg aacacggttc tttgaagtta gacccatccc gttttggtcc aaacccatta   1260

atcaagttgg gctcgcattt caaaaaggtt tctggtttta acgcaagaat ccctcacatc   1320

ccaaaaatcg tcgagctaga tcatttgacc atcactggta acgtcttttt aggtaaagat   1380

gtcactttga ggggtactgt catcatcgtt tgctccgacg gtcataaaat cgatattcca   1440

aacggctcca tattggaaaa tgttgtcgtt actggtaatt tgcaaatctt ggaacattga   1500
```

<210> SEQ ID NO 121

<211> LENGTH: 499
<212> TYPE: PRT
<213> ORGANISM: Saccharomyces cerevisiae

<400> SEQUENCE: 121

```
Met Ser Thr Lys Lys His Thr Lys Thr His Ser Thr Tyr Ala Phe Glu
1               5                   10                  15

Ser Asn Thr Asn Ser Val Ala Ala Ser Gln Met Arg Asn Ala Leu Asn
            20                  25                  30

Lys Leu Ala Asp Ser Ser Lys Leu Asp Asp Ala Ala Arg Ala Lys Phe
        35                  40                  45

Glu Asn Glu Leu Asp Ser Phe Phe Thr Leu Phe Arg Arg Tyr Leu Val
    50                  55                  60

Glu Lys Ser Ser Arg Thr Thr Leu Glu Trp Asp Lys Ile Lys Ser Pro
65                  70                  75                  80

Asn Pro Asp Glu Val Val Lys Tyr Glu Ile Ile Ser Gln Gln Pro Glu
                85                  90                  95

Asn Val Ser Asn Leu Ser Lys Leu Ala Val Leu Lys Leu Asn Gly Gly
            100                 105                 110

Leu Gly Thr Ser Met Gly Cys Val Gly Pro Lys Ser Val Ile Glu Val
        115                 120                 125

Arg Glu Gly Asn Thr Phe Leu Asp Leu Ser Val Arg Gln Ile Glu Tyr
    130                 135                 140

Leu Asn Arg Gln Tyr Asp Ser Asp Val Pro Leu Leu Leu Met Asn Ser
145                 150                 155                 160

Phe Asn Thr Asp Lys Asp Thr Glu His Leu Ile Lys Lys Tyr Ser Ala
                165                 170                 175

Asn Arg Ile Arg Ile Arg Ser Phe Asn Gln Ser Arg Phe Pro Arg Val
            180                 185                 190

Tyr Lys Asp Ser Leu Leu Pro Val Pro Thr Glu Tyr Asp Ser Pro Leu
        195                 200                 205

Asp Ala Trp Tyr Pro Pro Gly His Gly Asp Leu Phe Glu Ser Leu His
    210                 215                 220

Val Ser Gly Glu Leu Asp Ala Leu Ile Ala Gln Gly Arg Glu Ile Leu
225                 230                 235                 240

Phe Val Ser Asn Gly Asp Asn Leu Gly Ala Thr Val Asp Leu Lys Ile
                245                 250                 255

Leu Asn His Met Ile Glu Thr Gly Ala Glu Tyr Ile Met Glu Leu Thr
            260                 265                 270

Asp Lys Thr Arg Ala Asp Val Lys Gly Gly Thr Leu Ile Ser Tyr Asp
        275                 280                 285

Gly Gln Val Arg Leu Leu Glu Val Ala Gln Val Pro Lys Glu His Ile
    290                 295                 300

Asp Glu Phe Lys Asn Ile Arg Lys Phe Thr Asn Phe Asn Thr Asn Asn
305                 310                 315                 320

Leu Trp Ile Asn Leu Lys Ala Val Lys Arg Leu Ile Glu Ser Ser Asn
                325                 330                 335

Leu Glu Met Glu Ile Ile Pro Asn Gln Lys Thr Ile Thr Arg Asp Gly
            340                 345                 350

His Glu Ile Asn Val Leu Gln Leu Glu Thr Ala Cys Gly Ala Ala Ile
        355                 360                 365

Arg His Phe Asp Gly Ala His Gly Val Val Val Pro Arg Ser Arg Phe
    370                 375                 380

Leu Pro Val Lys Thr Cys Ser Asp Leu Leu Leu Val Lys Ser Asp Leu
```

-continued

```
385                 390                 395                 400

Phe Arg Leu Glu His Gly Ser Leu Lys Leu Asp Pro Ser Arg Phe Gly
                405                 410                 415

Pro Asn Pro Leu Ile Lys Leu Gly Ser His Phe Lys Lys Val Ser Gly
            420                 425                 430

Phe Asn Ala Arg Ile Pro His Ile Pro Lys Ile Val Glu Leu Asp His
        435                 440                 445

Leu Thr Ile Thr Gly Asn Val Phe Leu Gly Lys Asp Val Thr Leu Arg
    450                 455                 460

Gly Thr Val Ile Ile Val Cys Ser Asp Gly His Lys Ile Asp Ile Pro
465                 470                 475                 480

Asn Gly Ser Ile Leu Glu Asn Val Val Val Thr Gly Asn Leu Gln Ile
                485                 490                 495

Leu Glu His


<210> SEQ ID NO 122
<211> LENGTH: 462
<212> TYPE: DNA
<213> ORGANISM: Saccharomyces cerevisiae

<400> SEQUENCE: 122

atgtctagtc aaacagaaag aacttttatt gcggtaaaac cagatggtgt ccagaggggc     60

ttagtatctc aaattctatc tcgttttgaa aaaaaaggtt acaaactagt tgctattaaa    120

ttagttaaag cggatgataa attactagag caacattacg cagagcatgt tggtaaacca    180

tttttcccaa agatggtatc ctttatgaag tctggtccca ttttggccac ggtctgggag    240

ggaaaagatg tggttagaca aggaagaact attcttggtg ctactaatcc tttgggcagt    300

gcaccaggta ccattagagg tgatttcggt attgacctag gcagaaacgt ctgtcacggc    360

agtgattctg ttgatagcgc tgaacgtgaa atcaatttgt ggtttaagaa ggaagagtta    420

gttgattggg aatctaatca agctaagtgg atttatgaat ga                       462


<210> SEQ ID NO 123
<211> LENGTH: 153
<212> TYPE: PRT
<213> ORGANISM: Saccharomyces cerevisiae

<400> SEQUENCE: 123

Met Ser Ser Gln Thr Glu Arg Thr Phe Ile Ala Val Lys Pro Asp Gly
1               5                   10                  15

Val Gln Arg Gly Leu Val Ser Gln Ile Leu Ser Arg Phe Glu Lys Lys
            20                  25                  30

Gly Tyr Lys Leu Val Ala Ile Lys Leu Val Lys Ala Asp Asp Lys Leu
        35                  40                  45

Leu Glu Gln His Tyr Ala Glu His Val Gly Lys Pro Phe Phe Pro Lys
    50                  55                  60

Met Val Ser Phe Met Lys Ser Gly Pro Ile Leu Ala Thr Val Trp Glu
65                  70                  75                  80

Gly Lys Asp Val Val Arg Gln Gly Arg Thr Ile Leu Gly Ala Thr Asn
                85                  90                  95

Pro Leu Gly Ser Ala Pro Gly Thr Ile Arg Gly Asp Phe Gly Ile Asp
            100                 105                 110

Leu Gly Arg Asn Val Cys His Gly Ser Asp Ser Val Asp Ser Ala Glu
        115                 120                 125

Arg Glu Ile Asn Leu Trp Phe Lys Lys Glu Glu Leu Val Asp Trp Glu
```

130 135 140

Ser Asn Gln Ala Lys Trp Ile Tyr Glu
145 150

<210> SEQ ID NO 124
<211> LENGTH: 1413
<212> TYPE: DNA
<213> ORGANISM: Stevia rebaudiana

<400> SEQUENCE: 124
atggctgctg ctgatactga aaagttgaac aatttgagat ccgccgtttc tggtttgacc 60
caaatttctg ataacgaaaa gtccggtttc atcaacttgg tcagtagata tttgtctggt 120
gaagctcaac acgttgaatg gtctaaaatt caaactccaa ccgataagat cgttgttcca 180
tacgatactt tgtctgctgt tccagaagat gctgctcaaa caaaatcttt gttggataag 240
ttggtcgtct tgaagttgaa cggtggtttg ggtactacta tgggttgtac tggtccaaag 300
tctgttatcg aagttagaaa cggtttgacc ttcttggatt tgatcgtcat ccaaatcgaa 360
tccttgaaca agaagtacgg ttgttctgtt cctttgttgt tgatgaactc tttcaacacc 420
catgaagata cccaaaagat cgtcgaaaag tactccggtt ctaacattga agttcacacc 480
ttcaatcaat cccaataccc aagattggtt gtcgatgaat tttgccatt gccatctaaa 540 ggtgaaactg gtaaagatgg ttggtatcca ccaggtcatg gtgatgtttt tccatccttg 600
atgaattccg gtaagttgga tgctttgttg tcccaaggta aagaatacgt tttcgttgcc 660
aactctgata acttgggtgc agttgttgat ttgaagatct tgaaccactt gatccaaaac 720
aagaacgaat actgcatgga agttactcca aagactttgg ctgatgttaa gggtggtact 780
ttgatttctt acgatggtaa ggttcaatta ttggaaatcg cccaagttcc agatgaacac 840
gttaatgaat tcaagtccat cgaaaagttt aagatcttta acactaacaa cttgtgggtc 900
aacttgaacg ccattaagag attggttcaa gctgatgctt tgaagatgga aattattcca 960
aatccaaaag aagtcaacgg tgtcaaggta ttgcaattgg aaactgctgc tggtgctgct 1020
attaagtttt tcgataatgc catcggtatc aacgtcccaa gatctagatt tttgcctgtt 1080
aaggcttcct ctgacttgtt gttagttcaa tcagacttgt acaccgaaaa ggatggttac 1140
gttattagaa acccagctag aaaggatcca gctaacccat ctattgaatt gggtccagaa 1200
ttcaaaaagg tcggtgattt cttgaagaga ttcaagtcta tcccatccat catcgaattg 1260
gactcattga aagtttctgg tgatgtctgg tttggttcca acgttgtttt gaaaggtaag 1320
gttgttgttg ctgccaaatc cggtgaaaaa ttggaaattc cagatggtgc cttgattgaa 1380
aacaaagaag ttcatggtgc ctccgacatt tga 1413

<210> SEQ ID NO 125
<211> LENGTH: 470
<212> TYPE: PRT
<213> ORGANISM: Stevia rebaudiana

<400> SEQUENCE: 125

Met Ala Ala Ala Asp Thr Glu Lys Leu Asn Asn Leu Arg Ser Ala Val
1 5 10 15

Ser Gly Leu Thr Gln Ile Ser Asp Asn Glu Lys Ser Gly Phe Ile Asn
20 25 30

Leu Val Ser Arg Tyr Leu Ser Gly Glu Ala Gln His Val Glu Trp Ser
35 40 45

Lys Ile Gln Thr Pro Thr Asp Lys Ile Val Val Pro Tyr Asp Thr Leu

-continued

```
    50                  55                  60

Ser Ala Val Pro Glu Asp Ala Ala Gln Thr Lys Ser Leu Leu Asp Lys
65                  70                  75                  80

Leu Val Val Leu Lys Leu Asn Gly Gly Leu Gly Thr Thr Met Gly Cys
                85                  90                  95

Thr Gly Pro Lys Ser Val Ile Glu Val Arg Asn Gly Leu Thr Phe Leu
            100                 105                 110

Asp Leu Ile Val Ile Gln Ile Glu Ser Leu Asn Lys Lys Tyr Gly Cys
        115                 120                 125

Ser Val Pro Leu Leu Leu Met Asn Ser Phe Asn Thr His Glu Asp Thr
    130                 135                 140

Gln Lys Ile Val Glu Lys Tyr Ser Gly Ser Asn Ile Glu Val His Thr
145                 150                 155                 160

Phe Asn Gln Ser Gln Tyr Pro Arg Leu Val Val Asp Glu Phe Leu Pro
                165                 170                 175

Leu Pro Ser Lys Gly Glu Thr Gly Lys Asp Gly Trp Tyr Pro Pro Gly
            180                 185                 190

His Gly Asp Val Phe Pro Ser Leu Met Asn Ser Gly Lys Leu Asp Ala
        195                 200                 205

Leu Leu Ser Gln Gly Lys Glu Tyr Val Phe Val Ala Asn Ser Asp Asn
    210                 215                 220

Leu Gly Ala Val Val Asp Leu Lys Ile Leu Asn His Leu Ile Gln Asn
225                 230                 235                 240

Lys Asn Glu Tyr Cys Met Glu Val Thr Pro Lys Thr Leu Ala Asp Val
                245                 250                 255

Lys Gly Gly Thr Leu Ile Ser Tyr Asp Gly Lys Val Gln Leu Leu Glu
            260                 265                 270

Ile Ala Gln Val Pro Asp Glu His Val Asn Glu Phe Lys Ser Ile Glu
        275                 280                 285

Lys Phe Lys Ile Phe Asn Thr Asn Asn Leu Trp Val Asn Leu Asn Ala
    290                 295                 300

Ile Lys Arg Leu Val Gln Ala Asp Ala Leu Lys Met Glu Ile Ile Pro
305                 310                 315                 320

Asn Pro Lys Glu Val Asn Gly Val Lys Val Leu Gln Leu Glu Thr Ala
                325                 330                 335

Ala Gly Ala Ala Ile Lys Phe Phe Asp Asn Ala Ile Gly Ile Asn Val
            340                 345                 350

Pro Arg Ser Arg Phe Leu Pro Val Lys Ala Ser Ser Asp Leu Leu Leu
        355                 360                 365

Val Gln Ser Asp Leu Tyr Thr Glu Lys Asp Gly Tyr Val Ile Arg Asn
    370                 375                 380

Pro Ala Arg Lys Asp Pro Ala Asn Pro Ser Ile Glu Leu Gly Pro Glu
385                 390                 395                 400

Phe Lys Lys Val Gly Asp Phe Leu Lys Arg Phe Lys Ser Ile Pro Ser
                405                 410                 415

Ile Ile Glu Leu Asp Ser Leu Lys Val Ser Gly Asp Val Trp Phe Gly
            420                 425                 430

Ser Asn Val Val Leu Lys Gly Lys Val Val Val Ala Ala Lys Ser Gly
        435                 440                 445

Glu Lys Leu Glu Ile Pro Asp Gly Ala Leu Ile Glu Asn Lys Glu Val
    450                 455                 460

His Gly Ala Ser Asp Ile
465                 470
```

<210> SEQ ID NO 126
<211> LENGTH: 1551
<212> TYPE: DNA
<213> ORGANISM: Aureobasidium pullulans

<400> SEQUENCE: 126

```
atgtcctctg aaatggctac tcatttgaaa cctaatggtg gtgccgaatt cgaaaaaaga      60
catcatggta agacccaatc ccatgttgct tttgaaaaca cttctacatc tgttgctgcc     120
tcccaaatga gaaatgcttt gaatactttg tgcgattccg ttactgatcc agctgaaaag     180
caaagattcg aaaccgaaat ggataacttc ttcgccttgt ttagaagata cttgaacgat     240
aaggctaagg gtaacgaaat cgaatggtct agaattgctc caccaaaacc agaacaagtt     300
gttgcttatc aagacttgcc tgaacaagaa tccgttgaat tcttgaacaa attggccgtc     360
ttgaagttga atggtggttt gggtacttct atgggttgtg ttggtccaaa gtctgttatc     420
gaagttagag atggtatgtc cttcttggat ttgtccgtta gacaaatcga atacttgaat     480
agaacctacg gtgttaacgt tccattcgtc ttgatgaatt ctttcaacac tgatgctgat     540
accgccaaca ttatcaaaaa gtacgaaggt cacaacatcg acatcatgac cttcaatcaa     600
tctagatacc caagaatctt gaaggattct ttgttgccag ctccaaaatc tgccaactct     660
caaatttctg attggtatcc accaggtcat ggtgacgttt ttgaatcctt gtacaactct     720
ggtatcttgg ataagttgtt ggaaagaggt gtcgaaatcg ttttcttgtc caatgctgat     780
aatttgggtg ccgttgttga tttgaagatc ttgcaacata tggttgatac caaggccgaa     840
tatatcatgg aattgactga taagactaag gccgatgtta agggtggtac tattattgac     900
tatgaaggtc aagccagatt attggaaatt gcccaagttc caaaagaaca cgtcaacgaa     960
ttcaagtcca tcaagaagtt taagtacttc aacaccaaca acatctggat gaacttgaga    1020
gctgttaaga gaatcgtcga aaacaacgaa ttggccatgg aaattatccc aaacggtaaa    1080
tctattccag ccgacaaaaa aggtgaagcc gatgtttcta tagttcaatt ggaaactgct    1140
gttggtgctg ccattagaca ttttaacaat gctcatggtg tcaacgtccc aagaagaaga    1200
tttttgccag ttaagacctg ctccgatttg atgttggtta agtctgactt gtacactttg    1260
aagcacggtc aattgattat ggacccaaat agatttggtc cagccccatt gattaagttg    1320
ggtggtgatt ttaagaaggt ttcctcattc caatccagaa tcccatccat tcctaaaatc    1380
ttggaattgg atcatttgac cattaccggt ccagttaact tgggtagagg tgttactttt    1440
aagggtactg ttattatcgt tgcctccgaa ggtcaaacca ttgatattcc acctggttcc    1500
attttggaaa acgttgttgt tcaaggttcc ttgagattat tagaacatta a             1551
```

<210> SEQ ID NO 127
<211> LENGTH: 516
<212> TYPE: PRT
<213> ORGANISM: Aureobasidium pullulans

<400> SEQUENCE: 127

```
Met Ser Ser Glu Met Ala Thr His Leu Lys Pro Asn Gly Gly Ala Glu
1               5                   10                  15

Phe Glu Lys Arg His His Gly Lys Thr Gln Ser His Val Ala Phe Glu
            20                  25                  30

Asn Thr Ser Thr Ser Val Ala Ala Ser Gln Met Arg Asn Ala Leu Asn
        35                  40                  45

Thr Leu Cys Asp Ser Val Thr Asp Pro Ala Glu Lys Gln Arg Phe Glu
```

```
    50                  55                  60

Thr Glu Met Asp Asn Phe Phe Ala Leu Phe Arg Arg Tyr Leu Asn Asp
65                  70                  75                  80

Lys Ala Lys Gly Asn Glu Ile Glu Trp Ser Arg Ile Ala Pro Pro Lys
                85                  90                  95

Pro Glu Gln Val Val Ala Tyr Gln Asp Leu Pro Glu Gln Glu Ser Val
            100                 105                 110

Glu Phe Leu Asn Lys Leu Ala Val Leu Lys Leu Asn Gly Gly Leu Gly
        115                 120                 125

Thr Ser Met Gly Cys Val Gly Pro Lys Ser Val Ile Glu Val Arg Asp
    130                 135                 140

Gly Met Ser Phe Leu Asp Leu Ser Val Arg Gln Ile Glu Tyr Leu Asn
145                 150                 155                 160

Arg Thr Tyr Gly Val Asn Val Pro Phe Val Leu Met Asn Ser Phe Asn
                165                 170                 175

Thr Asp Ala Asp Thr Ala Asn Ile Ile Lys Lys Tyr Glu Gly His Asn
            180                 185                 190

Ile Asp Ile Met Thr Phe Asn Gln Ser Arg Tyr Pro Arg Ile Leu Lys
        195                 200                 205

Asp Ser Leu Leu Pro Ala Pro Lys Ser Ala Asn Ser Gln Ile Ser Asp
    210                 215                 220

Trp Tyr Pro Pro Gly His Gly Asp Val Phe Glu Ser Leu Tyr Asn Ser
225                 230                 235                 240

Gly Ile Leu Asp Lys Leu Leu Glu Arg Gly Val Glu Ile Val Phe Leu
                245                 250                 255

Ser Asn Ala Asp Asn Leu Gly Ala Val Val Asp Leu Lys Ile Leu Gln
            260                 265                 270

His Met Val Asp Thr Lys Ala Glu Tyr Ile Met Glu Leu Thr Asp Lys
        275                 280                 285

Thr Lys Ala Asp Val Lys Gly Gly Thr Ile Ile Asp Tyr Glu Gly Gln
    290                 295                 300

Ala Arg Leu Leu Glu Ile Ala Gln Val Pro Lys Glu His Val Asn Glu
305                 310                 315                 320

Phe Lys Ser Ile Lys Lys Phe Lys Tyr Phe Asn Thr Asn Asn Ile Trp
                325                 330                 335

Met Asn Leu Arg Ala Val Lys Arg Ile Val Glu Asn Asn Glu Leu Ala
            340                 345                 350

Met Glu Ile Ile Pro Asn Gly Lys Ser Ile Pro Ala Asp Lys Lys Gly
        355                 360                 365

Glu Ala Asp Val Ser Ile Val Gln Leu Glu Thr Ala Val Gly Ala Ala
    370                 375                 380

Ile Arg His Phe Asn Asn Ala His Gly Val Asn Val Pro Arg Arg Arg
385                 390                 395                 400

Phe Leu Pro Val Lys Thr Cys Ser Asp Leu Met Leu Val Lys Ser Asp
                405                 410                 415

Leu Tyr Thr Leu Lys His Gly Gln Leu Ile Met Asp Pro Asn Arg Phe
            420                 425                 430

Gly Pro Ala Pro Leu Ile Lys Leu Gly Gly Asp Phe Lys Lys Val Ser
        435                 440                 445

Ser Phe Gln Ser Arg Ile Pro Ser Ile Pro Lys Ile Leu Glu Leu Asp
    450                 455                 460

His Leu Thr Ile Thr Gly Pro Val Asn Leu Gly Arg Gly Val Thr Phe
465                 470                 475                 480
```

```
Lys Gly Thr Val Ile Ile Val Ala Ser Glu Gly Gln Thr Ile Asp Ile
                485                 490                 495

Pro Pro Gly Ser Ile Leu Glu Asn Val Val Val Gln Gly Ser Leu Arg
            500                 505                 510

Leu Leu Glu His
        515


<210> SEQ ID NO 128
<211> LENGTH: 1410
<212> TYPE: DNA
<213> ORGANISM: Arabidopsis thaliana

<400> SEQUENCE: 128

atggctgcta ctactgaaaa cttgccacaa ttgaaatctg ccgttgatgg tttgactgaa     60

atgtccgaat ctgaaaagtc cggtttcatc tctttggtca gtagatattt gtctggtgaa    120

gcccaacata tcgaatggtc taaaattcaa actccaaccg acgaaatcgt tgtcccatac    180

gaaaaaatga ctccagtttc tcaagatgtc gccgaaacta agaatttgtt ggataagttg    240

gtcgtcttga agttgaatgg tggtttgggt actactatgg gttgtactgg tccaaagtct    300

gttatcgaag ttagagatgg tttaaccttc ttggacttga tcgtcatcca aatcgaaaac    360

ttgaacaaca agtacggttg caaggttcca ttggtcttga tgaattcttt caacacccat    420

gatgataccc acaagatcgt tgaaaagtac accaactcca acgttgatat ccacaccttc    480

aatcaatcta agtacccaag agttgttgcc gatgaatttg ttccatggcc atctaaaggt    540

aagactgaca aagaaggttg gtatccacca ggtcatggtg atgtttttcc agctttaatg    600

aactccggta agttggatac tttcttgtcc caaggtaaag aatacgtttt cgttgccaac    660

tctgataact tgggtgctat agttgatttg accatcttga agcacttgat ccaaaacaag    720

aacgaatact gcatggaagt tactccaaag actttggctg atgttaaggg tggtactttg    780

atttcttacg aaggtaaggt tcaattattg gaaatcgccc aagttccaga tgaacacgtt    840

aatgaattca agtccatcga aaagttcaag atcttcaaca ccaacaactt gtgggttaac    900

ttgaaggcca tcaagaaatt ggttgaagct gatgctttga agatggaaat tatcccaaac    960

ccaaaagaag ttgacggtgt taaggtattg caattggaaa ctgctgctgg tgctgctatt   1020

agatttttcg ataatgccat cggtgttaac gtcccaagat ctagattttt gccagttaag   1080

gcttcctccg atttgttgtt ggttcaatct gacttgtaca ccttggttga cggttttgtt   1140

acaagaaaca aggctagaac taacccatcc aacccatcta ttgaattggg tccagaattc   1200

aaaaaggttg ccacattctt gtccagattc aagtctattc catccatcgt cgaattggac   1260

tcattgaaag tttctggtga tgtctggttt ggttcctcta tagttttgaa gggtaaggtt   1320

actgttgctg ctaaatctgg tgttaagttg gaaattccag atagagccgt tgtcgaaaac   1380

aaaaacatta acggtcctga agatttgtga                                    1410


<210> SEQ ID NO 129
<211> LENGTH: 469
<212> TYPE: PRT
<213> ORGANISM: Arabidopsis thaliana

<400> SEQUENCE: 129

Met Ala Ala Thr Thr Glu Asn Leu Pro Gln Leu Lys Ser Ala Val Asp
1               5                   10                  15

Gly Leu Thr Glu Met Ser Glu Ser Glu Lys Ser Gly Phe Ile Ser Leu
            20                  25                  30
```

-continued

```
Val Ser Arg Tyr Leu Ser Gly Glu Ala Gln His Ile Glu Trp Ser Lys
        35                  40                  45

Ile Gln Thr Pro Thr Asp Glu Ile Val Val Pro Tyr Glu Lys Met Thr
    50                  55                  60

Pro Val Ser Gln Asp Val Ala Glu Thr Lys Asn Leu Leu Asp Lys Leu
65                  70                  75                  80

Val Val Leu Lys Leu Asn Gly Gly Leu Gly Thr Thr Met Gly Cys Thr
                85                  90                  95

Gly Pro Lys Ser Val Ile Glu Val Arg Asp Gly Leu Thr Phe Leu Asp
            100                 105                 110

Leu Ile Val Ile Gln Ile Glu Asn Leu Asn Asn Lys Tyr Gly Cys Lys
        115                 120                 125

Val Pro Leu Val Leu Met Asn Ser Phe Asn Thr His Asp Asp Thr His
    130                 135                 140

Lys Ile Val Glu Lys Tyr Thr Asn Ser Asn Val Asp Ile His Thr Phe
145                 150                 155                 160

Asn Gln Ser Lys Tyr Pro Arg Val Val Ala Asp Glu Phe Val Pro Trp
                165                 170                 175

Pro Ser Lys Gly Lys Thr Asp Lys Glu Gly Trp Tyr Pro Pro Gly His
            180                 185                 190

Gly Asp Val Phe Pro Ala Leu Met Asn Ser Gly Lys Leu Asp Thr Phe
        195                 200                 205

Leu Ser Gln Gly Lys Glu Tyr Val Phe Val Ala Asn Ser Asp Asn Leu
    210                 215                 220

Gly Ala Ile Val Asp Leu Thr Ile Leu Lys His Leu Ile Gln Asn Lys
225                 230                 235                 240

Asn Glu Tyr Cys Met Glu Val Thr Pro Lys Thr Leu Ala Asp Val Lys
                245                 250                 255

Gly Gly Thr Leu Ile Ser Tyr Glu Gly Lys Val Gln Leu Leu Glu Ile
            260                 265                 270

Ala Gln Val Pro Asp Glu His Val Asn Glu Phe Lys Ser Ile Glu Lys
        275                 280                 285

Phe Lys Ile Phe Asn Thr Asn Asn Leu Trp Val Asn Leu Lys Ala Ile
    290                 295                 300

Lys Lys Leu Val Glu Ala Asp Ala Leu Lys Met Glu Ile Ile Pro Asn
305                 310                 315                 320

Pro Lys Glu Val Asp Gly Val Lys Val Leu Gln Leu Glu Thr Ala Ala
                325                 330                 335

Gly Ala Ala Ile Arg Phe Phe Asp Asn Ala Ile Gly Val Asn Val Pro
            340                 345                 350

Arg Ser Arg Phe Leu Pro Val Lys Ala Ser Ser Asp Leu Leu Leu Val
        355                 360                 365

Gln Ser Asp Leu Tyr Thr Leu Val Asp Gly Phe Val Thr Arg Asn Lys
    370                 375                 380

Ala Arg Thr Asn Pro Ser Asn Pro Ser Ile Glu Leu Gly Pro Glu Phe
385                 390                 395                 400

Lys Lys Val Ala Thr Phe Leu Ser Arg Phe Lys Ser Ile Pro Ser Ile
                405                 410                 415

Val Glu Leu Asp Ser Leu Lys Val Ser Gly Asp Val Trp Phe Gly Ser
            420                 425                 430

Ser Ile Val Leu Lys Gly Lys Val Thr Val Ala Ala Lys Ser Gly Val
        435                 440                 445
```

```
Lys Leu Glu Ile Pro Asp Arg Ala Val Val Glu Asn Lys Asn Ile Asn
    450                 455                 460

Gly Pro Glu Asp Leu
465
```

<210> SEQ ID NO 130
<211> LENGTH: 909
<212> TYPE: DNA
<213> ORGANISM: Escherichia coli

<400> SEQUENCE: 130

```
atggctgcta ttaacaccaa ggttaagaag gctgttattc cagttgctgg tttgggtact      60

agaatgttgc cagctacaaa agccattcca aaagaaatgt taccattggt cgataagcca     120

ttgatccaat acgttgtcaa cgaatgtatt gctgctggta ttaccgaaat cgttttggtt     180

actcactcct ccaagaactc cattgaaaat catttcgaca cctcattcga attggaagcc     240

atgttggaaa agagagtcaa gagacaatta ttggacgaag tccaatctat ttgcccacca     300

catgttacta tcatgcaagt tagacaaggt ttggctaaag gtttgggtca tgctgttttg     360

tgtgctcatc cagttgttgg tgatgaacca gttgcagtta ttttgccaga tgttatcttg     420

gacgaatacg aatccgattt gtctcaagat aacttggctg aaatgatcag aagattcgac     480

gaaactggtc actcccaaat tatggttgaa cctgttgctg atgttactgc ttatggtgtt     540

gttgattgca agggtgttga attggctcca ggtgaatctg ttccaatggt tggtgttgta     600

gaaaagccaa aagctgatgt tgctccatct aatttggcta tcgttggtag atatgttttg     660

tccgctgata tttggccttt gttggctaaa actccaccag gtgctggtga cgaaattcaa     720

ttgactgatg ctatcgacat gttgatcgaa aaagaaaccg ttgaagccta ccacatgaag     780

ggtaaatctc atgattgtgg taacaagttg ggttacatgc aagcttttgt tgaatacggt     840

atcagacata acaccttagg tactgaattc aaggcttggt tggaagaaga aatgggtatc     900

aagaagtaa                                                             909
```

<210> SEQ ID NO 131
<211> LENGTH: 302
<212> TYPE: PRT
<213> ORGANISM: Escherichia coli

<400> SEQUENCE: 131

```
Met Ala Ala Ile Asn Thr Lys Val Lys Lys Ala Val Ile Pro Val Ala
1               5                   10                  15

Gly Leu Gly Thr Arg Met Leu Pro Ala Thr Lys Ala Ile Pro Lys Glu
            20                  25                  30

Met Leu Pro Leu Val Asp Lys Pro Leu Ile Gln Tyr Val Val Asn Glu
        35                  40                  45

Cys Ile Ala Ala Gly Ile Thr Glu Ile Val Leu Val Thr His Ser Ser
    50                  55                  60

Lys Asn Ser Ile Glu Asn His Phe Asp Thr Ser Phe Glu Leu Glu Ala
65                  70                  75                  80

Met Leu Glu Lys Arg Val Lys Arg Gln Leu Leu Asp Glu Val Gln Ser
                85                  90                  95

Ile Cys Pro Pro His Val Thr Ile Met Gln Val Arg Gln Gly Leu Ala
            100                 105                 110

Lys Gly Leu Gly His Ala Val Leu Cys Ala His Pro Val Val Gly Asp
        115                 120                 125

Glu Pro Val Ala Val Ile Leu Pro Asp Val Ile Leu Asp Glu Tyr Glu
```

```
    130                 135                 140

Ser Asp Leu Ser Gln Asp Asn Leu Ala Glu Met Ile Arg Arg Phe Asp
145                 150                 155                 160

Glu Thr Gly His Ser Gln Ile Met Val Glu Pro Val Ala Asp Val Thr
                165                 170                 175

Ala Tyr Gly Val Val Asp Cys Lys Gly Val Glu Leu Ala Pro Gly Glu
            180                 185                 190

Ser Val Pro Met Val Gly Val Val Glu Lys Pro Lys Ala Asp Val Ala
        195                 200                 205

Pro Ser Asn Leu Ala Ile Val Gly Arg Tyr Val Leu Ser Ala Asp Ile
    210                 215                 220

Trp Pro Leu Leu Ala Lys Thr Pro Pro Gly Ala Gly Asp Glu Ile Gln
225                 230                 235                 240

Leu Thr Asp Ala Ile Asp Met Leu Ile Glu Lys Glu Thr Val Glu Ala
                245                 250                 255

Tyr His Met Lys Gly Lys Ser His Asp Cys Gly Asn Lys Leu Gly Tyr
            260                 265                 270

Met Gln Ala Phe Val Glu Tyr Gly Ile Arg His Asn Thr Leu Gly Thr
        275                 280                 285

Glu Phe Lys Ala Trp Leu Glu Glu Glu Met Gly Ile Lys Lys
    290                 295                 300
```

<210> SEQ ID NO 132
<211> LENGTH: 1416
<212> TYPE: DNA
<213> ORGANISM: Rubus suavissimus

<400> SEQUENCE: 132

```
atggctgctg ttgctactga taagatctct aagttgaagt ctgaagttgc tgccttgtcc     60

caaatttctg aaaacgaaaa gtccggtttc atcaacttgg tcagtagata tttgtctggt    120

actgaagcta ctcacgttga atggtctaaa attcaaactc caaccgatga agttgttgtt    180

ccatatgata ctttggctcc aactccagaa gatccagctg aaactaagaa gttgttagat    240

aagttggtcg tcttgaagtt gaacggtggt ttgggtacta ctatgggttg tactggtcca    300

aagtctgtta tcgaagttag aaacggtttg accttcttgg atttgatcgt cattcaaatc    360

gaaaccttga acaacaagta cggttgtaac gttcctttgt tgttgatgaa ctctttcaac    420

acccatgatg acaccttcaa gatcgttgaa agatacacca agtccaacgt tcaaatccat    480

accttcaatc aatcccaata cccaagattg gttgtcgaag ataattctcc attgccatct    540

aagggtcaaa ctggtaaaga tggttggtat ccaccaggtc atggtgatgt ttttccatct    600

ttgagaaact ccggtaagtt ggatttgttg ttatcccaag gtaaagaata cgttttcatc    660

tccaactctg ataacttggg tgcagttgtt gatttgaaga tcttgtccca tttggtccaa    720

aaaaagaacg aatactgcat ggaagttacc ccaaaaactt tggctgatgt taagggtggt    780

actttgattt cttacgaagg tagaacccaa ttattggaaa ttgcccaagt tccagatcaa    840

cacgttaacg aattcaagtc catcgaaaag ttcaagatct ttaacaccaa caatttgtgg    900

gtcaacttga acgccattaa gagattagtt gaagctgatg ccttgaaaat ggaaatcatc    960

ccaaatccaa aagaagtcga cggtattaag gtcttgcaat tggaaactgc tgctggtgct   1020

gctattagat tttcaatca tgccatcggt atcaacgtcc caagatctag atttttgcca   1080

gttaaggcta cctccgattt gttattggtt caatctgact tgtacaccgt cgaagatggt   1140

ttcgttatta gaaacactgc tagaaagaat ccagccaacc catctgttga attgggtcca   1200
```

```
gaattcaaaa aggttgccaa cttcttgtcc agattcaagt ctattccatc catcatcgaa   1260

ttggactcat tgaaggttgt tggtgatgta tggtttggtg ctggtgttgt tttgaaaggt   1320

aaggttacta ttactgctaa gccaggtgtt aagttggaaa ttccagataa ggctgtcttg   1380

gaaaacaagg atattaacgg tcctgaagat ttgtga                             1416
```

<210> SEQ ID NO 133
<211> LENGTH: 471
<212> TYPE: PRT
<213> ORGANISM: Rubus suavissimus

<400> SEQUENCE: 133

```
Met Ala Ala Val Ala Thr Asp Lys Ile Ser Lys Leu Lys Ser Glu Val
1               5                   10                  15

Ala Ala Leu Ser Gln Ile Ser Glu Asn Glu Lys Ser Gly Phe Ile Asn
            20                  25                  30

Leu Val Ser Arg Tyr Leu Ser Gly Thr Glu Ala Thr His Val Glu Trp
        35                  40                  45

Ser Lys Ile Gln Thr Pro Thr Asp Glu Val Val Val Pro Tyr Asp Thr
    50                  55                  60

Leu Ala Pro Thr Pro Glu Asp Pro Ala Glu Thr Lys Lys Leu Leu Asp
65                  70                  75                  80

Lys Leu Val Val Leu Lys Leu Asn Gly Gly Leu Gly Thr Thr Met Gly
                85                  90                  95

Cys Thr Gly Pro Lys Ser Val Ile Glu Val Arg Asn Gly Leu Thr Phe
            100                 105                 110

Leu Asp Leu Ile Val Ile Gln Ile Glu Thr Leu Asn Asn Lys Tyr Gly
        115                 120                 125

Cys Asn Val Pro Leu Leu Leu Met Asn Ser Phe Asn Thr His Asp Asp
    130                 135                 140

Thr Phe Lys Ile Val Glu Arg Tyr Thr Lys Ser Asn Val Gln Ile His
145                 150                 155                 160

Thr Phe Asn Gln Ser Gln Tyr Pro Arg Leu Val Val Glu Asp Asn Ser
                165                 170                 175

Pro Leu Pro Ser Lys Gly Gln Thr Gly Lys Asp Gly Trp Tyr Pro Pro
            180                 185                 190

Gly His Gly Asp Val Phe Pro Ser Leu Arg Asn Ser Gly Lys Leu Asp
        195                 200                 205

Leu Leu Leu Ser Gln Gly Lys Glu Tyr Val Phe Ile Ser Asn Ser Asp
    210                 215                 220

Asn Leu Gly Ala Val Val Asp Leu Lys Ile Leu Ser His Leu Val Gln
225                 230                 235                 240

Lys Lys Asn Glu Tyr Cys Met Glu Val Thr Pro Lys Thr Leu Ala Asp
                245                 250                 255

Val Lys Gly Gly Thr Leu Ile Ser Tyr Glu Gly Arg Thr Gln Leu Leu
            260                 265                 270

Glu Ile Ala Gln Val Pro Asp Gln His Val Asn Glu Phe Lys Ser Ile
        275                 280                 285

Glu Lys Phe Lys Ile Phe Asn Thr Asn Asn Leu Trp Val Asn Leu Asn
    290                 295                 300

Ala Ile Lys Arg Leu Val Glu Ala Asp Ala Leu Lys Met Glu Ile Ile
305                 310                 315                 320

Pro Asn Pro Lys Glu Val Asp Gly Ile Lys Val Leu Gln Leu Glu Thr
                325                 330                 335
```

```
Ala Ala Gly Ala Ala Ile Arg Phe Phe Asn His Ala Ile Gly Ile Asn
            340                 345                 350

Val Pro Arg Ser Arg Phe Leu Pro Val Lys Ala Thr Ser Asp Leu Leu
        355                 360                 365

Leu Val Gln Ser Asp Leu Tyr Thr Val Glu Asp Gly Phe Val Ile Arg
    370                 375                 380

Asn Thr Ala Arg Lys Asn Pro Ala Asn Pro Ser Val Glu Leu Gly Pro
385                 390                 395                 400

Glu Phe Lys Lys Val Ala Asn Phe Leu Ser Arg Phe Lys Ser Ile Pro
                405                 410                 415

Ser Ile Ile Glu Leu Asp Ser Leu Lys Val Val Gly Asp Val Trp Phe
            420                 425                 430

Gly Ala Gly Val Val Leu Lys Gly Lys Val Thr Ile Thr Ala Lys Pro
        435                 440                 445

Gly Val Lys Leu Glu Ile Pro Asp Lys Ala Val Leu Glu Asn Lys Asp
    450                 455                 460

Ile Asn Gly Pro Glu Asp Leu
465                 470
```

<210> SEQ ID NO 134
<211> LENGTH: 1422
<212> TYPE: DNA
<213> ORGANISM: Hordeum vulgare

<400> SEQUENCE: 134

```
atggctgctg ctgcagttgc tgctgattct aaaattgatg gtttgagaga tgctgttgcc     60
aagttgggtg aaatttctga aaacgaaaag gccggtttca tctccttggt ttctagatat    120
ttgtctggtg aagccgaaca aatcgaatgg tctaaaattc aaactccaac cgatgaagtt    180
gttgttccat atgatacttt ggctccacca cctgaagatt tggatgctat gaaggctttg    240
ttggataagt tggttgtctt gaagttgaat ggtggtttgg gtactactat gggttgtact    300
ggtccaaagt ctgttatcga agttagaaac ggtttcacct tcttggattt gatcgttatc    360
caaattgaat ccttgaacaa gaagtacggt tgctctgttc ctttgttgtt gatgaactct    420
ttcaacaccc atgatgacac ccaaaagatc gttgaaaagt actccaactc caacatcgaa    480
atccacacct tcaatcaatc tcaataccca agaatcgtca ccgaagattt tttgccattg    540
ccatctaaag gtcaaactgg taaagatggt tggtatccac caggtcatgg tgatgttttt    600
ccatctttga acaactccgg taagttggat accttgttgt ctcaaggtaa agaatacgtt    660
ttcgttgcca actctgataa cttgggtgct atcgttgata ttaagatctt gaaccacttg    720
atccacaatc aaaacgaata ctgcatggaa gttactccaa agactttggc tgatgttaag    780
ggtggtactt tgatttctta cgaaggtaga gttcaattat tggaaatcgc ccaagttcca    840
gatgaacacg ttgatgaatt caagtccatc gaaaagttca aatcttcaa caccaacaac    900
ttgtgggtta acttgaaggc cattaagaga ttggttgatg ctgaagcttt gaaaatggaa    960
atcatcccaa accctaaaga agttgacggt gttaaggtat tgcaattgga aactgctgct   1020
ggtgctgcta ttagattctt tgaaaaagcc atcggtatca acgtcccaag atctagattt   1080
ttgccagtta aggctacctc tgacttgttg ttggttcaat cagacttgta caccttggtt   1140
gacggttacg ttattagaaa tccagctaga gttaagccat ccaacccatc tattgaattg   1200
ggtccagaat tcaagaaggt cgctaatttc ttggctagat tcaagtctat cccatccatc   1260
gttgaattgg actcattgaa agtttctggt gatgtctctt ttggttccgg tgttgttttg   1320
```

```
aagggtaatg ttactattgc tgctaaggct ggtgttaagt tggaaattcc agatggtgct   1380

gttttggaaa acaaggatat taacggtcca gaagatattt ga                      1422


<210> SEQ ID NO 135
<211> LENGTH: 473
<212> TYPE: PRT
<213> ORGANISM: Hordeum vulgare

<400> SEQUENCE: 135

Met Ala Ala Ala Ala Val Ala Ala Asp Ser Lys Ile Asp Gly Leu Arg
1               5                   10                  15

Asp Ala Val Ala Lys Leu Gly Glu Ile Ser Glu Asn Glu Lys Ala Gly
            20                  25                  30

Phe Ile Ser Leu Val Ser Arg Tyr Leu Ser Gly Glu Ala Glu Gln Ile
        35                  40                  45

Glu Trp Ser Lys Ile Gln Thr Pro Thr Asp Glu Val Val Val Pro Tyr
    50                  55                  60

Asp Thr Leu Ala Pro Pro Pro Glu Asp Leu Asp Ala Met Lys Ala Leu
65                  70                  75                  80

Leu Asp Lys Leu Val Val Leu Lys Leu Asn Gly Gly Leu Gly Thr Thr
                85                  90                  95

Met Gly Cys Thr Gly Pro Lys Ser Val Ile Glu Val Arg Asn Gly Phe
            100                 105                 110

Thr Phe Leu Asp Leu Ile Val Ile Gln Ile Glu Ser Leu Asn Lys Lys
        115                 120                 125

Tyr Gly Cys Ser Val Pro Leu Leu Leu Met Asn Ser Phe Asn Thr His
    130                 135                 140

Asp Asp Thr Gln Lys Ile Val Glu Lys Tyr Ser Asn Ser Asn Ile Glu
145                 150                 155                 160

Ile His Thr Phe Asn Gln Ser Gln Tyr Pro Arg Ile Val Thr Glu Asp
                165                 170                 175

Phe Leu Pro Leu Pro Ser Lys Gly Gln Thr Gly Lys Asp Gly Trp Tyr
            180                 185                 190

Pro Pro Gly His Gly Asp Val Phe Pro Ser Leu Asn Asn Ser Gly Lys
        195                 200                 205

Leu Asp Thr Leu Leu Ser Gln Gly Lys Glu Tyr Val Phe Val Ala Asn
    210                 215                 220

Ser Asp Asn Leu Gly Ala Ile Val Asp Ile Lys Ile Leu Asn His Leu
225                 230                 235                 240

Ile His Asn Gln Asn Glu Tyr Cys Met Glu Val Thr Pro Lys Thr Leu
                245                 250                 255

Ala Asp Val Lys Gly Gly Thr Leu Ile Ser Tyr Glu Gly Arg Val Gln
            260                 265                 270

Leu Leu Glu Ile Ala Gln Val Pro Asp Glu His Val Asp Glu Phe Lys
        275                 280                 285

Ser Ile Glu Lys Phe Lys Ile Phe Asn Thr Asn Asn Leu Trp Val Asn
    290                 295                 300

Leu Lys Ala Ile Lys Arg Leu Val Asp Ala Glu Ala Leu Lys Met Glu
305                 310                 315                 320

Ile Ile Pro Asn Pro Lys Glu Val Asp Gly Val Lys Val Leu Gln Leu
                325                 330                 335

Glu Thr Ala Ala Gly Ala Ala Ile Arg Phe Phe Glu Lys Ala Ile Gly
            340                 345                 350
```

```
Ile Asn Val Pro Arg Ser Arg Phe Leu Pro Val Lys Ala Thr Ser Asp
        355                 360                 365

Leu Leu Leu Val Gln Ser Asp Leu Tyr Thr Leu Val Asp Gly Tyr Val
    370                 375                 380

Ile Arg Asn Pro Ala Arg Val Lys Pro Ser Asn Pro Ser Ile Glu Leu
385                 390                 395                 400

Gly Pro Glu Phe Lys Lys Val Ala Asn Phe Leu Ala Arg Phe Lys Ser
                405                 410                 415

Ile Pro Ser Ile Val Glu Leu Asp Ser Leu Lys Val Ser Gly Asp Val
            420                 425                 430

Ser Phe Gly Ser Gly Val Val Leu Lys Gly Asn Val Thr Ile Ala Ala
        435                 440                 445

Lys Ala Gly Val Lys Leu Glu Ile Pro Asp Gly Ala Val Leu Glu Asn
    450                 455                 460

Lys Asp Ile Asn Gly Pro Glu Asp Ile
465                 470


<210> SEQ ID NO 136
<211> LENGTH: 1404
<212> TYPE: DNA
<213> ORGANISM: Oryza sativa

<400> SEQUENCE: 136

atggctgacg aaaaattggc caaattgaga gaagctgttg ctggtttgtc tcaaatctct      60

gataacgaaa agtccggttt catttccttg gttgctagat atttgtccgg tgaagaagaa     120

catgttgaat gggctaaaat tcatacccca accgatgaag ttgttgttcc atatgatact     180

ttggaagctc caccagaaga tttggaagaa acaaaaaagt tgttgaacaa gttggccgtc     240

ttgaagttga atggtggttt gggtactact atgggttgta ctggtccaaa gtctgttatc     300

gaagttagaa acggtttcac cttcttggat ttgatcgtca tccaaatcga atccttgaac     360

aaaaagtacg gttccaacgt tcctttgttg ttgatgaact ctttcaacac ccatgaagat     420

accttgaaga tcgttgaaaa gtacaccaac tccaacatcg aagttcacac cttcaatcaa     480

tctcaatacc caagagttgt tgccgatgaa tttttgccat ggccatctaa aggtaagact     540

tgtaaagatg gttggtatcc accaggtcat ggtgatattt ttccatcctt gatgaacagt     600

ggtaagttgg acttgttgtt gtcccaaggt aaagaatacg ttttcattgc caactccgat     660

aacttgggtg ctatagttga tatgaagatt ttgaaccact tgatccacaa gcaaaacgaa     720

tactgtatgg aagttactcc aaagactttg gctgatgtta agggtggtac tttgatctct     780

tacgaagata aggttcaatt attggaaatc gcccaagttc cagatgctca tgttaatgaa     840

ttcaagtcca tcgaaaagtt caagatcttt aacaccaaca acttgtgggt taacttgaag     900

gccattaaga gattagttga agctgacgct ttgaagatgg aaattatccc aaacccaaaa     960

gaagttgacg gtgttaaggt attgcaattg gaaactgctg ctggtgctgc tattagattt    1020

ttcgatcatg ctatcggtat caacgtccca agatctagat tttaccagt taaggctacc    1080

tccgacttgc aattagttca atctgacttg tacaccttgg ttgatggttt cgttactaga    1140

aatccagcta gaactaatcc atccaaccca tctattgaat tgggtccaga attcaagaag    1200

gttggttgtt ttttgggtag attcaagtct atcccatcca tcgttgaatt ggacactttg    1260

aaagtttctg gtgatgtttg gttcggttcc tccattacat tgaaaggtaa ggttactatt    1320

accgctcaac caggtgttaa gttggaaatt ccagatggtg ctgtcatcga aaacaaggat    1380

attaacggtc ctgaagattt gtga                                           1404
```

<210> SEQ ID NO 137
<211> LENGTH: 467
<212> TYPE: PRT
<213> ORGANISM: Oryza sativa

<400> SEQUENCE: 137

```
Met Ala Asp Glu Lys Leu Ala Lys Leu Arg Glu Ala Val Ala Gly Leu
1               5                   10                  15

Ser Gln Ile Ser Asp Asn Glu Lys Ser Gly Phe Ile Ser Leu Val Ala
            20                  25                  30

Arg Tyr Leu Ser Gly Glu Glu Glu His Val Glu Trp Ala Lys Ile His
        35                  40                  45

Thr Pro Thr Asp Glu Val Val Val Pro Tyr Asp Thr Leu Glu Ala Pro
    50                  55                  60

Pro Glu Asp Leu Glu Glu Thr Lys Lys Leu Leu Asn Lys Leu Ala Val
65                  70                  75                  80

Leu Lys Leu Asn Gly Gly Leu Gly Thr Thr Met Gly Cys Thr Gly Pro
                85                  90                  95

Lys Ser Val Ile Glu Val Arg Asn Gly Phe Thr Phe Leu Asp Leu Ile
            100                 105                 110

Val Ile Gln Ile Glu Ser Leu Asn Lys Lys Tyr Gly Ser Asn Val Pro
        115                 120                 125

Leu Leu Leu Met Asn Ser Phe Asn Thr His Glu Asp Thr Leu Lys Ile
    130                 135                 140

Val Glu Lys Tyr Thr Asn Ser Asn Ile Glu Val His Thr Phe Asn Gln
145                 150                 155                 160

Ser Gln Tyr Pro Arg Val Val Ala Asp Glu Phe Leu Pro Trp Pro Ser
                165                 170                 175

Lys Gly Lys Thr Cys Lys Asp Gly Trp Tyr Pro Pro Gly His Gly Asp
            180                 185                 190

Ile Phe Pro Ser Leu Met Asn Ser Gly Lys Leu Asp Leu Leu Leu Ser
        195                 200                 205

Gln Gly Lys Glu Tyr Val Phe Ile Ala Asn Ser Asp Asn Leu Gly Ala
    210                 215                 220

Ile Val Asp Met Lys Ile Leu Asn His Leu Ile His Lys Gln Asn Glu
225                 230                 235                 240

Tyr Cys Met Glu Val Thr Pro Lys Thr Leu Ala Asp Val Lys Gly Gly
                245                 250                 255

Thr Leu Ile Ser Tyr Glu Asp Lys Val Gln Leu Leu Glu Ile Ala Gln
            260                 265                 270

Val Pro Asp Ala His Val Asn Glu Phe Lys Ser Ile Glu Lys Phe Lys
        275                 280                 285

Ile Phe Asn Thr Asn Asn Leu Trp Val Asn Leu Lys Ala Ile Lys Arg
    290                 295                 300

Leu Val Glu Ala Asp Ala Leu Lys Met Glu Ile Ile Pro Asn Pro Lys
305                 310                 315                 320

Glu Val Asp Gly Val Lys Val Leu Gln Leu Glu Thr Ala Ala Gly Ala
                325                 330                 335

Ala Ile Arg Phe Phe Asp His Ala Ile Gly Ile Asn Val Pro Arg Ser
            340                 345                 350

Arg Phe Leu Pro Val Lys Ala Thr Ser Asp Leu Gln Leu Val Gln Ser
        355                 360                 365

Asp Leu Tyr Thr Leu Val Asp Gly Phe Val Thr Arg Asn Pro Ala Arg
```

-continued

```
    370                 375                 380

Thr Asn Pro Ser Asn Pro Ser Ile Glu Leu Gly Pro Glu Phe Lys Lys
385                 390                 395                 400

Val Gly Cys Phe Leu Gly Arg Phe Lys Ser Ile Pro Ser Ile Val Glu
                405                 410                 415

Leu Asp Thr Leu Lys Val Ser Gly Asp Val Trp Phe Gly Ser Ser Ile
            420                 425                 430

Thr Leu Lys Gly Lys Val Thr Ile Thr Ala Gln Pro Gly Val Lys Leu
        435                 440                 445

Glu Ile Pro Asp Gly Ala Val Ile Glu Asn Lys Asp Ile Asn Gly Pro
    450                 455                 460

Glu Asp Leu
465


<210> SEQ ID NO 138
<211> LENGTH: 1434
<212> TYPE: DNA
<213> ORGANISM: Solanum tuberosum

<400> SEQUENCE: 138

atggctactg ctactacttt gtctccagct gatgctgaaa agttgaacaa tttgaaatct      60

gctgtcgccg gtttgaatca aatctctgaa aacgaaaagt ccggtttcat caacttggtt     120

ggtagatatt tgtctggtga agcccaacat attgactggt ctaaaattca aactccaacc     180

gatgaagttg ttgtcccata tgataagttg gctccattgt ctgaagatcc agctgaaaca     240

aaaaagttgt tggacaagtt ggtcgtcttg aagttgaatg gtggtttggg tactactatg     300

ggttgtactg gtccaaagtc tgttatcgaa gttagaaacg gtttgacctt cttggatttg     360

atcgtcaagc aaattgaagc tttgaacgct aagttcggtt gttctgttcc tttgttgttg     420

atgaactctt tcaacaccca tgatgacacc ttgaagatcg ttgaaaagta cgccaactcc     480

aacattgata tccacacctt caatcaatcc caatacccaa gattggttac cgaagatttt     540

gctccattgc catgtaaagg taactctggt aaagatggtt ggtatccacc aggtcatggt     600

gatgtttttc catccttgat gaattccggt aagttggatg ctttgttggc taagggtaaa     660

gaatacgttt tcgttgccaa ctctgataac ttgggtgcta tcgttgattt gaaaatcttg     720

aaccacttga tcttgaacaa gaacgaatac tgcatggaag ttactccaaa gactttggct     780

gatgttaagg gtggtacttt gatttcttac gaaggtaagg ttcaattatt ggaaatcgcc     840

caagttccag atgaacacgt taatgaattc aagtccatcg aaaagtttaa gatcttcaac     900

actaacaact tgtgggtcaa cttgtctgcc attaagagat tggttgaagc tgatgccttg     960

aaaatggaaa ttattccaaa cccaaaagaa gtcgatggtg tcaaagtatt gcaattggaa    1020

actgctgctg gtgctgctat taagtttttc gatagagcta ttggtgccaa cgttccaaga    1080

tctagatttt tgccagttaa ggctacctct gacttgttgt tggttcaatc agacttgtac    1140

actttgactg atgaaggtta cgttattaga aacccagcta gatccaatcc atccaaccca    1200

tctattgaat tgggtccaga attcaagaag gtagccaatt ttttgggtag attcaagtct    1260

atcccatcca tcatcgattt ggattctttg aaagttactg gtgatgtctg gtttggttct    1320

ggtgttactt tgaaaggtaa agttaccgtt gctgctaagt caggtgttaa gttggaaatt    1380

ccagatggtg ctgttattgc caacaaggat attaacggtc cagaagatat ctaa          1434


<210> SEQ ID NO 139
<211> LENGTH: 477
```

<212> TYPE: PRT
<213> ORGANISM: Solanum tuberosum

<400> SEQUENCE: 139

```
Met Ala Thr Ala Thr Thr Leu Ser Pro Ala Asp Ala Glu Lys Leu Asn
1               5                   10                  15

Asn Leu Lys Ser Ala Val Ala Gly Leu Asn Gln Ile Ser Glu Asn Glu
            20                  25                  30

Lys Ser Gly Phe Ile Asn Leu Val Gly Arg Tyr Leu Ser Gly Glu Ala
        35                  40                  45

Gln His Ile Asp Trp Ser Lys Ile Gln Thr Pro Thr Asp Glu Val Val
    50                  55                  60

Val Pro Tyr Asp Lys Leu Ala Pro Leu Ser Glu Asp Pro Ala Glu Thr
65                  70                  75                  80

Lys Lys Leu Leu Asp Lys Leu Val Val Leu Lys Leu Asn Gly Gly Leu
                85                  90                  95

Gly Thr Thr Met Gly Cys Thr Gly Pro Lys Ser Val Ile Glu Val Arg
            100                 105                 110

Asn Gly Leu Thr Phe Leu Asp Leu Ile Val Lys Gln Ile Glu Ala Leu
        115                 120                 125

Asn Ala Lys Phe Gly Cys Ser Val Pro Leu Leu Leu Met Asn Ser Phe
    130                 135                 140

Asn Thr His Asp Asp Thr Leu Lys Ile Val Glu Lys Tyr Ala Asn Ser
145                 150                 155                 160

Asn Ile Asp Ile His Thr Phe Asn Gln Ser Gln Tyr Pro Arg Leu Val
                165                 170                 175

Thr Glu Asp Phe Ala Pro Leu Pro Cys Lys Gly Asn Ser Gly Lys Asp
            180                 185                 190

Gly Trp Tyr Pro Pro Gly His Gly Asp Val Phe Pro Ser Leu Met Asn
        195                 200                 205

Ser Gly Lys Leu Asp Ala Leu Leu Ala Lys Gly Lys Glu Tyr Val Phe
    210                 215                 220

Val Ala Asn Ser Asp Asn Leu Gly Ala Ile Val Asp Leu Lys Ile Leu
225                 230                 235                 240

Asn His Leu Ile Leu Asn Lys Asn Glu Tyr Cys Met Glu Val Thr Pro
                245                 250                 255

Lys Thr Leu Ala Asp Val Lys Gly Gly Thr Leu Ile Ser Tyr Glu Gly
            260                 265                 270

Lys Val Gln Leu Leu Glu Ile Ala Gln Val Pro Asp Glu His Val Asn
        275                 280                 285

Glu Phe Lys Ser Ile Glu Lys Phe Lys Ile Phe Asn Thr Asn Asn Leu
    290                 295                 300

Trp Val Asn Leu Ser Ala Ile Lys Arg Leu Val Glu Ala Asp Ala Leu
305                 310                 315                 320

Lys Met Glu Ile Ile Pro Asn Pro Lys Glu Val Asp Gly Val Lys Val
                325                 330                 335

Leu Gln Leu Glu Thr Ala Ala Gly Ala Ala Ile Lys Phe Phe Asp Arg
            340                 345                 350

Ala Ile Gly Ala Asn Val Pro Arg Ser Arg Phe Leu Pro Val Lys Ala
        355                 360                 365

Thr Ser Asp Leu Leu Leu Val Gln Ser Asp Leu Tyr Thr Leu Thr Asp
    370                 375                 380

Glu Gly Tyr Val Ile Arg Asn Pro Ala Arg Ser Asn Pro Ser Asn Pro
385                 390                 395                 400
```

```
Ser Ile Glu Leu Gly Pro Glu Phe Lys Lys Val Ala Asn Phe Leu Gly
                405                 410                 415

Arg Phe Lys Ser Ile Pro Ser Ile Ile Asp Leu Asp Ser Leu Lys Val
            420                 425                 430

Thr Gly Asp Val Trp Phe Gly Ser Gly Val Thr Leu Lys Gly Lys Val
        435                 440                 445

Thr Val Ala Ala Lys Ser Gly Val Lys Leu Glu Ile Pro Asp Gly Ala
    450                 455                 460

Val Ile Ala Asn Lys Asp Ile Asn Gly Pro Glu Asp Ile
465                 470                 475


<210> SEQ ID NO 140
<211> LENGTH: 1818
<212> TYPE: DNA
<213> ORGANISM: Arabidopsis thaliana

<400> SEQUENCE: 140

atgttcttgt tggttacctc ttgcttcttg ccagattctg gttcttctgt taaggtcagt      60

ttgttcatct tcggtgtctc attggtttct acctctccaa ttgatggtca aaaaccaggt     120

acttctggtt tgagaaagaa ggtcaaggtt ttcaagcaac ctaactactt ggaaaacttc     180

gttcaagcta ctttcaacgc tttgactacc gaaaaagtta agggtgctac tttggttgtt     240

tctggtgatg gtagatatta ctccgaacaa gccattcaaa tcatcgttaa gatggctgct     300

gctaacggtg ttagaagagt ttgggttggt caaaactctt tgttgtctac tccagctgtt     360

tccgccatta ttagagaaag agttggtgct gatggttcta aagctactgg tgctttcatt     420

ttgactgctt ctcataatcc aggtggtcca actgaagatt tcggtattaa gtacaacatg     480

gaaaatggtg gtccagcccc agaatctatt actgataaga tatacgaaaa caccaagacc     540

atcaaagaat acccaattgc agaagatttg ccaagagttg atatctctac tatcggtatc     600

acttctttcg aaggtcctga aggtaaattc gacgttgaag tttttgattc cgctgatgat     660

tacgtcaagt tgatgaagtc catcttcgac ttcgaatcca tcaagaagtt gttgtcttac     720

ccaaagttca ccttttgtta cgatgcattg catggtgttg ctggtgctta tgctcataga     780

attttcgttg aagaattggg tgctccagaa tcctctttat tgaactgtgt tccaaaagaa     840

gattttggtg gtggtcatcc agatccaaat ttgacttatg ccaaagaatt ggttgccaga     900

atgggtttgt ctaagactga tgatgctggt ggtgaaccac ctgaatttgg tgctgctgca     960

gatggtgatg ctgatagaaa tatgatcttg ggtaaaagat tcttcgtcac cccatctgat    1020

tccgttgcta ttattgctgc taatgctgtt ggtgctattc catacttttc atccggtttg    1080

aaaggtgttg ctagatctat gccaacttct gctgctttgg atgttgttgc taagaatttg    1140

ggtttgaagt tcttcgaagt tccaactggt tggaaattct tcggtaattt gatggatgca    1200

ggtatgtgtt ctgtttgcgg tgaagaatca tttggtactg gttccgatca tatcagagaa    1260

aaggatggta tttgggctgt tttggcttgg ttgtctattt tggctcacaa gaacaaagaa    1320

accttggatg gtaatgccaa gttggttact gttgaagata tcgttagaca acattgggct    1380

acttacggta gacattacta cactagatac gactacgaaa acgttgatgc tacagctgct    1440

aaagaattga tgggtttatt ggtcaagttg caatcctcat tgccagaagt taacaagatc    1500

atcaagggta tccatcctga agttgctaat gttgcttctg ctgatgaatt cgaatacaag    1560

gatccagttg atggttccgt ttctaaacat caaggtatca gatacttgtt tgaagatggt    1620

tccagattgg ttttcagatt gtctggtaca ggttctgaag gtgctactat tagattgtac    1680
```

atcgaacaat acgaaaagga cgcctctaag attggtagag attctcaaga tgctttgggt 1740
ccattggttg atgttgcttt gaagttgtcc aagatgcaag aattcactgg tagatcttct 1800
ccaaccgtta ttacctga 1818

<210> SEQ ID NO 141
<211> LENGTH: 605
<212> TYPE: PRT
<213> ORGANISM: Arabidopsis thaliana

<400> SEQUENCE: 141

Met Phe Leu Leu Val Thr Ser Cys Phe Leu Pro Asp Ser Gly Ser Ser
1 5 10 15

Val Lys Val Ser Leu Phe Ile Phe Gly Val Ser Leu Val Ser Thr Ser
20 25 30

Pro Ile Asp Gly Gln Lys Pro Gly Thr Ser Gly Leu Arg Lys Lys Val
35 40 45

Lys Val Phe Lys Gln Pro Asn Tyr Leu Glu Asn Phe Val Gln Ala Thr
50 55 60

Phe Asn Ala Leu Thr Thr Glu Lys Val Lys Gly Ala Thr Leu Val Val
65 70 75 80

Ser Gly Asp Gly Arg Tyr Tyr Ser Glu Gln Ala Ile Gln Ile Ile Val
85 90 95

Lys Met Ala Ala Ala Asn Gly Val Arg Arg Val Trp Val Gly Gln Asn
100 105 110

Ser Leu Leu Ser Thr Pro Ala Val Ser Ala Ile Ile Arg Glu Arg Val
115 120 125

Gly Ala Asp Gly Ser Lys Ala Thr Gly Ala Phe Ile Leu Thr Ala Ser
130 135 140

His Asn Pro Gly Gly Pro Thr Glu Asp Phe Gly Ile Lys Tyr Asn Met
145 150 155 160

Glu Asn Gly Gly Pro Ala Pro Glu Ser Ile Thr Asp Lys Ile Tyr Glu
165 170 175

Asn Thr Lys Thr Ile Lys Glu Tyr Pro Ile Ala Glu Asp Leu Pro Arg
180 185 190

Val Asp Ile Ser Thr Ile Gly Ile Thr Ser Phe Glu Gly Pro Glu Gly
195 200 205

Lys Phe Asp Val Glu Val Phe Asp Ser Ala Asp Asp Tyr Val Lys Leu
210 215 220

Met Lys Ser Ile Phe Asp Phe Glu Ser Ile Lys Lys Leu Leu Ser Tyr
225 230 235 240

Pro Lys Phe Thr Phe Cys Tyr Asp Ala Leu His Gly Val Ala Gly Ala
245 250 255

Tyr Ala His Arg Ile Phe Val Glu Glu Leu Gly Ala Pro Glu Ser Ser
260 265 270

Leu Leu Asn Cys Val Pro Lys Glu Asp Phe Gly Gly Gly His Pro Asp
275 280 285

Pro Asn Leu Thr Tyr Ala Lys Glu Leu Val Ala Arg Met Gly Leu Ser
290 295 300

Lys Thr Asp Asp Ala Gly Gly Glu Pro Pro Glu Phe Gly Ala Ala Ala
305 310 315 320

Asp Gly Asp Ala Asp Arg Asn Met Ile Leu Gly Lys Arg Phe Phe Val
325 330 335

Thr Pro Ser Asp Ser Val Ala Ile Ile Ala Ala Asn Ala Val Gly Ala

```
            340                 345                 350

Ile Pro Tyr Phe Ser Ser Gly Leu Lys Gly Val Ala Arg Ser Met Pro
        355                 360                 365

Thr Ser Ala Ala Leu Asp Val Val Ala Lys Asn Leu Gly Leu Lys Phe
    370                 375                 380

Phe Glu Val Pro Thr Gly Trp Lys Phe Phe Gly Asn Leu Met Asp Ala
385                 390                 395                 400

Gly Met Cys Ser Val Cys Gly Glu Glu Ser Phe Gly Thr Gly Ser Asp
                405                 410                 415

His Ile Arg Glu Lys Asp Gly Ile Trp Ala Val Leu Ala Trp Leu Ser
            420                 425                 430

Ile Leu Ala His Lys Asn Lys Glu Thr Leu Asp Gly Asn Ala Lys Leu
        435                 440                 445

Val Thr Val Glu Asp Ile Val Arg Gln His Trp Ala Thr Tyr Gly Arg
    450                 455                 460

His Tyr Tyr Thr Arg Tyr Asp Tyr Glu Asn Val Asp Ala Thr Ala Ala
465                 470                 475                 480

Lys Glu Leu Met Gly Leu Leu Val Lys Leu Gln Ser Ser Leu Pro Glu
                485                 490                 495

Val Asn Lys Ile Ile Lys Gly Ile His Pro Glu Val Ala Asn Val Ala
            500                 505                 510

Ser Ala Asp Glu Phe Glu Tyr Lys Asp Pro Val Asp Gly Ser Val Ser
        515                 520                 525

Lys His Gln Gly Ile Arg Tyr Leu Phe Glu Asp Gly Ser Arg Leu Val
    530                 535                 540

Phe Arg Leu Ser Gly Thr Gly Ser Glu Gly Ala Thr Ile Arg Leu Tyr
545                 550                 555                 560

Ile Glu Gln Tyr Glu Lys Asp Ala Ser Lys Ile Gly Arg Asp Ser Gln
                565                 570                 575

Asp Ala Leu Gly Pro Leu Val Asp Val Ala Leu Lys Leu Ser Lys Met
            580                 585                 590

Gln Glu Phe Thr Gly Arg Ser Ser Pro Thr Val Ile Thr
        595                 600                 605


<210> SEQ ID NO 142
<211> LENGTH: 1641
<212> TYPE: DNA
<213> ORGANISM: Escherichia coli

<400> SEQUENCE: 142

atggccattc ataatagagc tggtcaacca gcacaacaat ccgatttgat taacgttgct      60

caattgaccg cccaatatta cgttttgaaa cctgaagctg gtaacgctga acatgctgtt     120

aagtttggta cttctggtca tagaggttct gctgctagac attcttttaa cgaaccacat     180

attttggcta tcgctcaagc tattgctgaa gaaagagcta agaacggtat tactggtcca     240

tgttacgttg gtaaagatac ccatgctttg tctgaaccag ctttcatttc tgttttggaa     300

gttttggctg ctaacggtgt tgatgttatc gttcaagaaa acaacggttt cactccaact     360

ccagctgttt ctaatgctat tttggttcac aacaaaaagg gtggtccatt ggctgatggt     420

atagttatta ctccatctca taacccacct gaagatggtg gtattaagta caatccacca     480

aatggtggtc cagctgatac aaatgttact aaggttgttg aagatagagc caacgctttg     540

ttagctgatg gtttgaaagg tgtcaagaga atctctttgg atgaagctat ggcttcaggt     600

catgtcaaag aacaagattt ggttcaacca ttcgttgaag gtttggctga tatagttgat     660
```

atggctgcta ttcaaaaggc tggtttgact ttgggtgttg atccattggg tggttctggt 720
attgaatact ggaaaagaat cggtgaatat tacaacttga acttgaccat cgtcaacgat 780
caagttgacc aaactttcag attcatgcac ttggataagg atggtgctat tagaatggac 840
tgttcttctg aatgtgctat ggctggttta ttggctttga gagataagtt cgatttggct 900
tttgctaacg atccagatta cgatagacat ggtatcgtta ctccagcagg tttgatgaat 960
ccaaatcatt acttggctgt tgccatcaac tacttgtttc aacatagacc acaatggggt 1020
aaggatgttg ctgttggtaa aactttggtt tcctccgcta tgatcgatag agttgttaac 1080
gatttgggta gaaagttggt tgaagttcca gttggtttca agtggtttgt tgacggtttg 1140
tttgatggtt cttttggttt tggtggtgaa gaatctgctg gtgcttcatt tttgagattt 1200
gatggtactc catggtccac tgacaaagat ggtattatca tgtgtttgtt ggctgctgaa 1260
attactgctg ttactggtaa gaatccacaa gaacactaca acgaattggc taagagattt 1320
ggtgctccat cttacaatag attgcaagct gctgctactt ctgctcaaaa agctgcttta 1380
tctaagttgt ccccagaaat ggtttctgct tctactttag ctggtgatcc aattacagct 1440
agattgactg ctgctccagg taatggtgct tctattggtg gtttaaaggt tatgactgat 1500
aacggttggt ttgctgcaag accatctggt actgaagatg cttacaaaat ctactgcgaa 1560
tccttcttgg gtgaagaaca tagaaagcaa attgaaaaag aagccgtcga aatcgtcagt 1620
gaagttttga agaatgccta a 1641

<210> SEQ ID NO 143
<211> LENGTH: 546
<212> TYPE: PRT
<213> ORGANISM: Escherichia coli

<400> SEQUENCE: 143

Met Ala Ile His Asn Arg Ala Gly Gln Pro Ala Gln Gln Ser Asp Leu
1 5 10 15

Ile Asn Val Ala Gln Leu Thr Ala Gln Tyr Tyr Val Leu Lys Pro Glu
20 25 30

Ala Gly Asn Ala Glu His Ala Val Lys Phe Gly Thr Ser Gly His Arg
35 40 45

Gly Ser Ala Ala Arg His Ser Phe Asn Glu Pro His Ile Leu Ala Ile
50 55 60

Ala Gln Ala Ile Ala Glu Glu Arg Ala Lys Asn Gly Ile Thr Gly Pro
65 70 75 80

Cys Tyr Val Gly Lys Asp Thr His Ala Leu Ser Glu Pro Ala Phe Ile
85 90 95

Ser Val Leu Glu Val Leu Ala Ala Asn Gly Val Asp Val Ile Val Gln
100 105 110

Glu Asn Asn Gly Phe Thr Pro Thr Pro Ala Val Ser Asn Ala Ile Leu
115 120 125

Val His Asn Lys Lys Gly Gly Pro Leu Ala Asp Gly Ile Val Ile Thr
130 135 140

Pro Ser His Asn Pro Pro Glu Asp Gly Gly Ile Lys Tyr Asn Pro Pro
145 150 155 160

Asn Gly Gly Pro Ala Asp Thr Asn Val Thr Lys Val Val Glu Asp Arg
165 170 175

Ala Asn Ala Leu Leu Ala Asp Gly Leu Lys Gly Val Lys Arg Ile Ser
180 185 190

-continued

```
Leu Asp Glu Ala Met Ala Ser Gly His Val Lys Glu Gln Asp Leu Val
        195                 200                 205

Gln Pro Phe Val Glu Gly Leu Ala Asp Ile Val Asp Met Ala Ala Ile
    210                 215                 220

Gln Lys Ala Gly Leu Thr Leu Gly Val Asp Pro Leu Gly Gly Ser Gly
225                 230                 235                 240

Ile Glu Tyr Trp Lys Arg Ile Gly Glu Tyr Tyr Asn Leu Asn Leu Thr
                245                 250                 255

Ile Val Asn Asp Gln Val Asp Gln Thr Phe Arg Phe Met His Leu Asp
            260                 265                 270

Lys Asp Gly Ala Ile Arg Met Asp Cys Ser Ser Glu Cys Ala Met Ala
        275                 280                 285

Gly Leu Leu Ala Leu Arg Asp Lys Phe Asp Leu Ala Phe Ala Asn Asp
    290                 295                 300

Pro Asp Tyr Asp Arg His Gly Ile Val Thr Pro Ala Gly Leu Met Asn
305                 310                 315                 320

Pro Asn His Tyr Leu Ala Val Ala Ile Asn Tyr Leu Phe Gln His Arg
                325                 330                 335

Pro Gln Trp Gly Lys Asp Val Ala Val Gly Lys Thr Leu Val Ser Ser
            340                 345                 350

Ala Met Ile Asp Arg Val Val Asn Asp Leu Gly Arg Lys Leu Val Glu
        355                 360                 365

Val Pro Val Gly Phe Lys Trp Phe Val Asp Gly Leu Phe Asp Gly Ser
    370                 375                 380

Phe Gly Phe Gly Gly Glu Glu Ser Ala Gly Ala Ser Phe Leu Arg Phe
385                 390                 395                 400

Asp Gly Thr Pro Trp Ser Thr Asp Lys Asp Gly Ile Ile Met Cys Leu
                405                 410                 415

Leu Ala Ala Glu Ile Thr Ala Val Thr Gly Lys Asn Pro Gln Glu His
            420                 425                 430

Tyr Asn Glu Leu Ala Lys Arg Phe Gly Ala Pro Ser Tyr Asn Arg Leu
        435                 440                 445

Gln Ala Ala Ala Thr Ser Ala Gln Lys Ala Ala Leu Ser Lys Leu Ser
    450                 455                 460

Pro Glu Met Val Ser Ala Ser Thr Leu Ala Gly Asp Pro Ile Thr Ala
465                 470                 475                 480

Arg Leu Thr Ala Ala Pro Gly Asn Gly Ala Ser Ile Gly Gly Leu Lys
                485                 490                 495

Val Met Thr Asp Asn Gly Trp Phe Ala Ala Arg Pro Ser Gly Thr Glu
            500                 505                 510

Asp Ala Tyr Lys Ile Tyr Cys Glu Ser Phe Leu Gly Glu Glu His Arg
        515                 520                 525

Lys Gln Ile Glu Lys Glu Ala Val Glu Ile Val Ser Glu Val Leu Lys
    530                 535                 540

Asn Ala
545


<210> SEQ ID NO 144
<211> LENGTH: 1749
<212> TYPE: DNA
<213> ORGANISM: Rubus suavissimus

<400> SEQUENCE: 144

atgtcctccg gtaagattaa gagagttcaa actactccat tcgacggtca aaaaccaggt      60
```

-continued

```
acttctggtt tgagaaagaa ggttaaggtt ttcacccaac ctaactactt gcaaaacttc    120
gttcaatcta ccttcaacgc tttgccatct gataaggtaa aaggtgctag attggttgtt    180
tctggtgatg gtagatactt ctccaaagaa gccattcaaa tcatcattaa gatggctgct    240
ggtaacggtg ttaagtctgt ttgggttggt caaaatggtt tgttgtctac tccagctgtt    300
tctgctgttg ttagagaaag agttggtgct gatggttgta aagcttctgg tgctttcatt    360
ttgactgctt ctcataatcc aggtggtcca aatgaagatt tcggtatcaa gtacaacatg    420
gaaaatggtg gtccagctcc agaatctatt accaacaaaa tctacgaaaa caccacccaa    480
atcaaagaat acttgaccgt tgatttgcca gaagttgata ttactaagcc aggtgttact    540
accttcgaag ttgaaggtgg tactttcact gttgatgttt tcgattctgc ttccgattac    600
gtcaagttga tgaagtccat tttcgacttc gaatccatca gaaagttgtt gtcctctcca    660
aagttcacct tttgttttga tgcattgcat ggtgttggtg gtgcttacgc taaaagaatt    720
ttcgttgaag aattgggtgc caaagaatcc tctttgttga actgtgttcc taaagaagat    780
tttggtggtg gtcatccaga tccaaatttg acatatgcta aagaattggt cgccagaatg    840
ggtttgtcta agtctaatac tcaaaacgaa ccaccagaat ttggtgctgc tgcagatggt    900
gatgctgata gaaatatggt tttgggtaag agattcttcg ttaccccatc tgattccgtt    960
gctattattg ctgctaatgc tgttgaagct atcccatact tttctactgg tttgaaaggt   1020
gttgctagat ctatgccaac ttctgctgct ttggatgttg ttgctaaaca cttgaacttg   1080
aagttcttcg aagtaccaac tggttggaag tttttcggta atttgatgga tgctggtttg   1140
tgttctgttt gcggtgaaga atcttttggt actggttccg atcatatcag agaaaaggat   1200
ggtatttggg ctgttttggc ttggttgtca attattgcca tcaagaacaa ggataacatc   1260
ggtggtgata agttggttac cgttgaagat atcgttagaa aacattgggc tacttacggt   1320
agacattact acactagata cgattacgaa aacgttgatg ctggtaaggc taaagatttg   1380
atggcatcat tggtcaactt gcaatcatct ttgcctgaag ttaacaagat cgttaagggt   1440
atctgttccg atgttgcaaa tgttgttggt gccgatgaat tcgaatacaa ggattctgtt   1500
gatggttcca tctccaaaca tcaaggtatc agatacttgt tcgaagatgg ttcaagattg   1560
gttttcagat tgtctggtac aggttctgaa ggtgctacta ttagattgta catcgaacaa   1620
tacgaaaatg acccatccaa gatctccaga gaatcttctg aagctttggc tccattggtt   1680
gaagttgctt tgaaattgtc caagatgcaa gaattcactg gtagatcagc tccaactgtt   1740
attacctga                                                           1749
```

<210> SEQ ID NO 145
<211> LENGTH: 582
<212> TYPE: PRT
<213> ORGANISM: Rubus suavissimus

<400> SEQUENCE: 145

```
Met Ser Ser Gly Lys Ile Lys Arg Val Gln Thr Thr Pro Phe Asp Gly
1               5                   10                  15

Gln Lys Pro Gly Thr Ser Gly Leu Arg Lys Lys Val Lys Val Phe Thr
            20                  25                  30

Gln Pro Asn Tyr Leu Gln Asn Phe Val Gln Ser Thr Phe Asn Ala Leu
        35                  40                  45

Pro Ser Asp Lys Val Lys Gly Ala Arg Leu Val Val Ser Gly Asp Gly
    50                  55                  60

Arg Tyr Phe Ser Lys Glu Ala Ile Gln Ile Ile Ile Lys Met Ala Ala
```

```
65                  70                  75                  80

Gly Asn Gly Val Lys Ser Val Trp Val Gly Gln Asn Gly Leu Leu Ser
                85                  90                  95

Thr Pro Ala Val Ser Ala Val Val Arg Glu Arg Val Gly Ala Asp Gly
            100                 105                 110

Cys Lys Ala Ser Gly Ala Phe Ile Leu Thr Ala Ser His Asn Pro Gly
        115                 120                 125

Gly Pro Asn Glu Asp Phe Gly Ile Lys Tyr Asn Met Glu Asn Gly Gly
    130                 135                 140

Pro Ala Pro Glu Ser Ile Thr Asn Lys Ile Tyr Glu Asn Thr Thr Gln
145                 150                 155                 160

Ile Lys Glu Tyr Leu Thr Val Asp Leu Pro Glu Val Asp Ile Thr Lys
                165                 170                 175

Pro Gly Val Thr Thr Phe Glu Val Glu Gly Gly Thr Phe Thr Val Asp
            180                 185                 190

Val Phe Asp Ser Ala Ser Asp Tyr Val Lys Leu Met Lys Ser Ile Phe
        195                 200                 205

Asp Phe Glu Ser Ile Arg Lys Leu Leu Ser Ser Pro Lys Phe Thr Phe
    210                 215                 220

Cys Phe Asp Ala Leu His Gly Val Gly Gly Ala Tyr Ala Lys Arg Ile
225                 230                 235                 240

Phe Val Glu Glu Leu Gly Ala Lys Glu Ser Ser Leu Leu Asn Cys Val
                245                 250                 255

Pro Lys Glu Asp Phe Gly Gly Gly His Pro Asp Pro Asn Leu Thr Tyr
            260                 265                 270

Ala Lys Glu Leu Val Ala Arg Met Gly Leu Ser Lys Ser Asn Thr Gln
        275                 280                 285

Asn Glu Pro Pro Glu Phe Gly Ala Ala Ala Asp Gly Asp Ala Asp Arg
    290                 295                 300

Asn Met Val Leu Gly Lys Arg Phe Phe Val Thr Pro Ser Asp Ser Val
305                 310                 315                 320

Ala Ile Ile Ala Ala Asn Ala Val Glu Ala Ile Pro Tyr Phe Ser Thr
                325                 330                 335

Gly Leu Lys Gly Val Ala Arg Ser Met Pro Thr Ser Ala Ala Leu Asp
            340                 345                 350

Val Val Ala Lys His Leu Asn Leu Lys Phe Phe Glu Val Pro Thr Gly
        355                 360                 365

Trp Lys Phe Phe Gly Asn Leu Met Asp Ala Gly Leu Cys Ser Val Cys
    370                 375                 380

Gly Glu Glu Ser Phe Gly Thr Gly Ser Asp His Ile Arg Glu Lys Asp
385                 390                 395                 400

Gly Ile Trp Ala Val Leu Ala Trp Leu Ser Ile Ile Ala Ile Lys Asn
                405                 410                 415

Lys Asp Asn Ile Gly Gly Asp Lys Leu Val Thr Val Glu Asp Ile Val
            420                 425                 430

Arg Lys His Trp Ala Thr Tyr Gly Arg His Tyr Tyr Thr Arg Tyr Asp
        435                 440                 445

Tyr Glu Asn Val Asp Ala Gly Lys Ala Lys Asp Leu Met Ala Ser Leu
    450                 455                 460

Val Asn Leu Gln Ser Ser Leu Pro Glu Val Asn Lys Ile Val Lys Gly
465                 470                 475                 480

Ile Cys Ser Asp Val Ala Asn Val Val Gly Ala Asp Glu Phe Glu Tyr
                485                 490                 495
```

```
Lys Asp Ser Val Asp Gly Ser Ile Ser Lys His Gln Gly Ile Arg Tyr
            500                 505                 510

Leu Phe Glu Asp Gly Ser Arg Leu Val Phe Arg Leu Ser Gly Thr Gly
        515                 520                 525

Ser Glu Gly Ala Thr Ile Arg Leu Tyr Ile Glu Gln Tyr Glu Asn Asp
    530                 535                 540

Pro Ser Lys Ile Ser Arg Glu Ser Ser Glu Ala Leu Ala Pro Leu Val
545                 550                 555                 560

Glu Val Ala Leu Lys Leu Ser Lys Met Gln Glu Phe Thr Gly Arg Ser
                565                 570                 575

Ala Pro Thr Val Ile Thr
            580


<210> SEQ ID NO 146
<211> LENGTH: 1749
<212> TYPE: DNA
<213> ORGANISM: Stevia rebaudiana

<400> SEQUENCE: 146

atggcctctt tcaaggttaa cagagttgaa tcctctccaa tcgaaggtca aaaaccaggt      60

acttctggtt tgagaaagaa ggttaaggtt ttcacccaac cacattactt gcacaacttc     120

gttcaatcta ctttcaacgc tttgtctgcc gaaaaagtta agggttctac tttggttgtt     180

tccggtgatg gtagatatta ctccaaggat gccattcaaa tcatcattaa gatggctgct     240

gctaacggtg ttagaagagt ttgggttggt caaaatggtt tgttgtctac tccagctgtt     300

tctgctgttg ttagagaaag agttggtgct gatggttcta aatctaacgg tgctttcatt     360

ttgactgcct ctcataatcc aggtggtcca aatgaagatt tcggtatcaa gtacaacatg     420

gaaaatggtg gtccagctcc agaaggtatt actgataaga tttttgaaaa caccaagacc     480

atcaaagaat acttcattgc tgaaggtttg ccagacgttg atatttccgc tattggtatc     540

tcttcattct ctggtccaga tggtcaattc gatgttgatg ttttcgattc ctcttccgac     600

tacgtcaaat tgatgaagtc catcttcgac ttccaatcca tcaagaagtt gattacctcc     660

ccacaatttt ctttctgtta cgatgcttta catggtgttg gtggtgctta tgctaagcca     720

atttttgttg atgaattggg tgccaaagaa tcctctttgt tgaactgtgt tcctaaagaa     780

gattttggtg gtggtcatcc agatccaaat ttgacttacg ctaaagaatt ggtttccaga     840

atgggtttgg gtaagaatcc agattctaat ccaccagaat ttggtgctgc tgcagatggt     900

gatgctgata gaaatatgat cttgggtaaa agattcttcg tcaccccatc tgattccgtt     960

gctattattg ctgctaatgc cgttcaatca atcccatact tttcatccgg tttgaaaggt    1020

gttgctagat ctatgccaac ttctgctgct ttggatgttg ttgctaagtc tttgaacttg    1080

aagttcttcg aagttccaac tggttggaag tttttcggta atttgatgga tgctggtttg    1140

tgttctgttt gcggtgaaga atcatttggt actggttccg atcatatcag agaaaaggat    1200

ggtatttggg ctgttttggc ttggttgtct attttggctc ataagaacaa ggacaacttg    1260

aacggtggta acttggttac tgttgaagat atcgttaagc aacattgggc tacttacggt    1320

agacattact acactagata cgactacgaa aacgttgatg ctggtgctgc aaaagaattg    1380

atggctcatt tggttaagtt gcaatcctcc atctctgatg ttaacacctt cattaagggt    1440

atcagatccg atgttgctaa tgttgcatct gctgatgaat tcgaatacaa ggatccagtt    1500

gacggttcta tttccaaaca tcaaggtatt agatacttgt ttgaagatgg ttccagattg    1560
```

gttttcagat tgtctggtac aggttctgaa ggtgctacta ttagattgta catcgaacaa 1620
tacgaaaagg attcctctaa gaccggtaga gattctcaag aagctttggc tccattagtt 1680
gaagttgcct tgaaattgtc caagatgcaa gaattcactg gtagatctgc tccaactgtt 1740
attacctga 1749

<210> SEQ ID NO 147
<211> LENGTH: 582
<212> TYPE: PRT
<213> ORGANISM: Stevia rebaudiana

<400> SEQUENCE: 147

Met Ala Ser Phe Lys Val Asn Arg Val Glu Ser Ser Pro Ile Glu Gly
1 5 10 15

Gln Lys Pro Gly Thr Ser Gly Leu Arg Lys Lys Val Lys Val Phe Thr
20 25 30

Gln Pro His Tyr Leu His Asn Phe Val Gln Ser Thr Phe Asn Ala Leu
35 40 45

Ser Ala Glu Lys Val Lys Gly Ser Thr Leu Val Val Ser Gly Asp Gly
50 55 60

Arg Tyr Tyr Ser Lys Asp Ala Ile Gln Ile Ile Ile Lys Met Ala Ala
65 70 75 80

Ala Asn Gly Val Arg Arg Val Trp Val Gly Gln Asn Gly Leu Leu Ser
85 90 95

Thr Pro Ala Val Ser Ala Val Val Arg Glu Arg Val Gly Ala Asp Gly
100 105 110

Ser Lys Ser Asn Gly Ala Phe Ile Leu Thr Ala Ser His Asn Pro Gly
115 120 125

Gly Pro Asn Glu Asp Phe Gly Ile Lys Tyr Asn Met Glu Asn Gly Gly
130 135 140

Pro Ala Pro Glu Gly Ile Thr Asp Lys Ile Phe Glu Asn Thr Lys Thr
145 150 155 160

Ile Lys Glu Tyr Phe Ile Ala Glu Gly Leu Pro Asp Val Asp Ile Ser
165 170 175

Ala Ile Gly Ile Ser Ser Phe Ser Gly Pro Asp Gly Gln Phe Asp Val
180 185 190

Asp Val Phe Asp Ser Ser Ser Asp Tyr Val Lys Leu Met Lys Ser Ile
195 200 205

Phe Asp Phe Gln Ser Ile Lys Lys Leu Ile Thr Ser Pro Gln Phe Ser
210 215 220

Phe Cys Tyr Asp Ala Leu His Gly Val Gly Gly Ala Tyr Ala Lys Pro
225 230 235 240

Ile Phe Val Asp Glu Leu Gly Ala Lys Glu Ser Ser Leu Leu Asn Cys
245 250 255

Val Pro Lys Glu Asp Phe Gly Gly Gly His Pro Asp Pro Asn Leu Thr
260 265 270

Tyr Ala Lys Glu Leu Val Ser Arg Met Gly Leu Gly Lys Asn Pro Asp
275 280 285

Ser Asn Pro Pro Glu Phe Gly Ala Ala Ala Asp Gly Asp Ala Asp Arg
290 295 300

Asn Met Ile Leu Gly Lys Arg Phe Phe Val Thr Pro Ser Asp Ser Val
305 310 315 320

Ala Ile Ile Ala Ala Asn Ala Val Gln Ser Ile Pro Tyr Phe Ser Ser
325 330 335

-continued

```
Gly Leu Lys Gly Val Ala Arg Ser Met Pro Thr Ser Ala Ala Leu Asp
            340                 345                 350

Val Val Ala Lys Ser Leu Asn Leu Lys Phe Phe Glu Val Pro Thr Gly
        355                 360                 365

Trp Lys Phe Phe Gly Asn Leu Met Asp Ala Gly Leu Cys Ser Val Cys
    370                 375                 380

Gly Glu Glu Ser Phe Gly Thr Gly Ser Asp His Ile Arg Glu Lys Asp
385                 390                 395                 400

Gly Ile Trp Ala Val Leu Ala Trp Leu Ser Ile Leu Ala His Lys Asn
                405                 410                 415

Lys Asp Asn Leu Asn Gly Gly Asn Leu Val Thr Val Glu Asp Ile Val
            420                 425                 430

Lys Gln His Trp Ala Thr Tyr Gly Arg His Tyr Tyr Thr Arg Tyr Asp
        435                 440                 445

Tyr Glu Asn Val Asp Ala Gly Ala Ala Lys Glu Leu Met Ala His Leu
    450                 455                 460

Val Lys Leu Gln Ser Ser Ile Ser Asp Val Asn Thr Phe Ile Lys Gly
465                 470                 475                 480

Ile Arg Ser Asp Val Ala Asn Val Ala Ser Ala Asp Glu Phe Glu Tyr
                485                 490                 495

Lys Asp Pro Val Asp Gly Ser Ile Ser Lys His Gln Gly Ile Arg Tyr
            500                 505                 510

Leu Phe Glu Asp Gly Ser Arg Leu Val Phe Arg Leu Ser Gly Thr Gly
        515                 520                 525

Ser Glu Gly Ala Thr Ile Arg Leu Tyr Ile Glu Gln Tyr Glu Lys Asp
    530                 535                 540

Ser Ser Lys Thr Gly Arg Asp Ser Gln Glu Ala Leu Ala Pro Leu Val
545                 550                 555                 560

Glu Val Ala Leu Lys Leu Ser Lys Met Gln Glu Phe Thr Gly Arg Ser
                565                 570                 575

Ala Pro Thr Val Ile Thr
            580
```

<210> SEQ ID NO 148
<211> LENGTH: 426
<212> TYPE: DNA
<213> ORGANISM: Artificial Sequence
<220> FEATURE:
<223> OTHER INFORMATION: pTEF1 promoter nucleotide sequence

<400> SEQUENCE: 148

```
gcacacacca tagcttcaaa atgtttctac tcctttttta ctcttccaga ttttctcgga     60

ctccgcgcat cgccgtacca cttcaaaaca cccaagcaca gcatactaaa tttcccctct    120

ttcttcctct agggtgtcgt taattacccg tactaaaggt ttggaaaaga aaaaagagac    180

cgcctcgttt ctttttcttc gtcgaaaaag gcaataaaaa tttttatcac gtttcttttt    240

cttgaaaatt tttttttttg atttttttct ctttcgatga cctcccattg atatttaagt    300

taataaacgg tcttcaattt ctcaagtttc agtttcattt ttcttgttct attacaactt    360

tttttacttc ttgctcatta gaaagaaagc atagcaatct aatctaagtt ttaattacaa    420

ggatcc                                                               426
```

<210> SEQ ID NO 149
<211> LENGTH: 984
<212> TYPE: DNA
<213> ORGANISM: Artificial Sequence
<220> FEATURE:
<223> OTHER INFORMATION: pPGK1 promoter nucleotide sequence

<400> SEQUENCE: 149
ggaagtacct tcaaagaatg gggtcttatc ttgttttgca agtaccactg agcaggataa 60
taatagaaat gataatatac tatagtagag ataacgtcga tgacttccca tactgtaatt 120
gcttttagtt gtgtattttt agtgtgcaag tttctgtaaa tcgattaatt ttttttttctt 180
tcctcttttt attaacctta atttttattt tagattcctg acttcaactc aagacgcaca 240
gatattataa catctgcata ataggcattt gcaagaatta ctcgtgagta aggaaagagt 300
gaggaactat cgcatacctg catttaaaga tgccgatttg ggcgcgaatc ctttattttg 360
gcttcaccct catactatta tcagggccag aaaaaggaag tgtttccctc cttcttgaat 420
tgatgttacc ctcataaagc acgtggcctc ttatcgagaa agaaattacc gtcgctcgtg 480
atttgtttgc aaaaagaaca aaactgaaaa aacccagaca cgctcgactt cctgtcttcc 540
tattgattgc agcttccaat ttcgtcacac aacaaggtcc tagcgacggc tcacaggttt 600
tgtaacaagc aatcgaaggt tctggaatgg cgggaaaggg tttagtacca catgctatga 660
tgcccactgt gatctccaga gcaaagttcg ttcgatcgta ctgttactct ctctctttca 720
aacagaattg tccgaatcgt gtgacaacaa cagcctgttc tcacacactc ttttcttcta 780
accaaggggg tggtttagtt tagtagaacc tcgtgaaact tacatttaca tatatataaa 840
cttgcataaa ttggtcaatg caagaaatac atatttggtc ttttctaatt cgtagttttt 900
caagttctta gatgctttct ttttctcttt tttacagatc atcaaggaag taattatcta 960
ctttttacaa caaatataaa acaa 984

<210> SEQ ID NO 150
<211> LENGTH: 666
<212> TYPE: DNA
<213> ORGANISM: Artificial Sequence
<220> FEATURE:
<223> OTHER INFORMATION: pTDH3 promoter nucleotide sequence

<400> SEQUENCE: 150
cattatcaat actgccattt caaagaatac gtaaataatt aatagtagtg attttcctaa 60
ctttatttag tcaaaaaatt agccttttaa ttctgctgta acccgtacat gcccaaaata 120
gggggcgggt tacacagaat atataacatc gtaggtgtct gggtgaacag tttattcctg 180
gcatccacta aatataatgg agcccgcttt ttaagctggc atccagaaaa aaaaagaatc 240
ccagcaccaa aatattgttt tcttcaccaa ccatcagttc ataggtccat tctcttagcg 300
caactacaga gaacaggggc acaaacaggc aaaaaacggg cacaacctca atggagtgat 360
gcaacctgcc tggagtaaat gatgacacaa ggcaattgac ccacgcatgt atctatctca 420
ttttcttaca ccttctatta ccttctgctc tctctgattt ggaaaaagct gaaaaaaaag 480
gttgaaacca gttccctgaa attattcccc tacttgacta ataagtatat aaagacggta 540
ggtattgatt gtaattctgt aaatctattt cttaaacttc ttaaattcta cttttatagt 600
tagtcttttt tttagtttta aaacaccaag aacttagttt cgaataaaca cacataaaca 660
aacaaa 666

<210> SEQ ID NO 151
<211> LENGTH: 565
<212> TYPE: DNA
<213> ORGANISM: Artificial Sequence
<220> FEATURE:

<223> OTHER INFORMATION: pTEF2 promoter nucleotide sequence

<400> SEQUENCE: 151
gatctgggcc gtatacttac atatagtaga tgtcaagcgt aggcgcttcc cctgccggct 60
gtgagggcgc cataaccaag gtatctatag accgccaatc agcaaactac ctccgtacat 120
tcatgttgca cccacacatt tatacaccca gaccgcgaca aattacccat aaggttgttt 180
gtgacggcgt cgtacaagag aacgtgggaa ctttttaggc tcaccaaaaa agaaagaaaa 240
aatacgagtt gctgacagaa gcctcaagaa aaaaaaaatt cttcttcgac tatgctggag 300
gcagagatga tcgagccggt agttaactat atatagctaa attggttcca tcaccttctt 360
ttctggtgtc gctccttcta gtgctatttc tggcttttcc tatttttttt tttccatttt 420
tctttctctc tttctaatat ataaattctc ttgcattttc tatttttctc tctatctatt 480
ctacttgttt attcccttca aggttttttt ttaaggagta cttgttttta gaatatacgg 540
tcaacgaact ataattaact aaaca 565

<210> SEQ ID NO 152
<211> LENGTH: 532
<212> TYPE: DNA
<213> ORGANISM: Artificial Sequence
<220> FEATURE:
<223> OTHER INFORMATION: pTPI1 promoter nucleotide sequence

<400> SEQUENCE: 152
agttataata atcctacgtt agtgtgagcg ggatttaaac tgtgaggacc ttaatacatt 60
cagacacttc tgcggtatca ccctacttat tcccttcgag attatatcta ggaacccatc 120
aggttggtgg aagattaccc gttctaagac ttttcagctt cctctattga tgttacacct 180
ggacacccct tttctggcat ccagttttta atcttcagtg gcatgtgaga ttctccgaaa 240
ttaattaaag caatcacaca attctctcgg ataccacctc ggttgaaact gacaggtggt 300
ttgttacgca tgctaatgca aaggagccta tatacctttg gctcggctgc tgtaacaggg 360
aatataaagg gcagcataat ttaggagttt agtgaacttg caacatttac tattttccct 420
tcttacgtaa atatttttct ttttaattct aaatcaatct tttcaattt tttgtttgta 480 ttcttttctt gcttaaatct ataactacaa aaaacacata cataaactaa aa 532

<210> SEQ ID NO 153
<211> LENGTH: 805
<212> TYPE: DNA
<213> ORGANISM: Artificial Sequence
<220> FEATURE:
<223> OTHER INFORMATION: pPDC1 promoter nucleotide sequence

<400> SEQUENCE: 153
gatctatgcg actgggtgag catatgttcc gctgatgtga tgtgcaagat aaacaagcaa 60
ggcagaaact aacttcttct tcatgtaata aacacacccc gcgtttattt acctatctct 120
aaacttcaac accttatatc ataactaata tttcttgaga taagcacact gcacccatac 180
cttccttaaa aacgtagctt ccagtttttg gtggttccgg cttccttccc gattccgccc 240
gctaaacgca tatttttgtt gcctggtggc atttgcaaaa tgcataacct atgcatttaa 300
aagattatgt atgctcttct gacttttcgt gtgatgaggc tcgtggaaaa aatgaataat 360
ttatgaattt gagaacaatt ttgtgttgtt acggtatttt actatggaat aatcaatcaa 420
ttgaggattt tatgcaaata tcgtttgaat atttttccga ccctttgagt acttttcttc 480
ataattgcat aatattgtcc gctgcccctt tttctgttag acggtgtctt gatctacttg 540

-continued

```
ctatcgttca acaccacctt attttctaac tatttttttt ttagctcatt tgaatcagct    600

tatggtgatg gcacattttt gcataaacct agctgtcctc gttgaacata ggaaaaaaaa    660

atatataaac aaggctcttt cactctcctt gcaatcagat ttgggtttgt tccctttatt    720

ttcatatttc ttgtcatatt cctttctcaa ttattatttt ctactcataa cctcacgcaa    780

aataacacag tcaaatctat caaaa                                          805


<210> SEQ ID NO 154
<211> LENGTH: 192
<212> TYPE: DNA
<213> ORGANISM: Artificial Sequence
<220> FEATURE:
<223> OTHER INFORMATION: tCYC1 terminator nucleotide sequence

<400> SEQUENCE: 154

atccgctcta accgaaaagg aaggagttag acaacctgaa gtctaggtcc ctatttattt     60

tttttaatag ttatgttagt attaagaacg ttatttatat ttcaaatttt tctttttttt    120

ctgtacaaac gcgtgtacgc atgtaacatt atactgaaaa ccttgcttga gaaggttttg    180

ggacgctcga ag                                                         192


<210> SEQ ID NO 155
<211> LENGTH: 195
<212> TYPE: DNA
<213> ORGANISM: Artificial Sequence
<220> FEATURE:
<223> OTHER INFORMATION: tADH1 terminator nucleotide sequence

<400> SEQUENCE: 155

gtagatacgt tgttgacact tctaaataag cgaatttctt atgatttatg atttttatta     60

ttaaataagt tataaaaaaa ataagtgtat acaaatttta aagtgactct taggttttaa    120

aacgaaaatt cttattcttg agtaactctt tcctgtaggt caggttgctt tctcaggtat    180

agcatgaggt cgctc                                                      195
```

UNITED STATES PATENT AND TRADEMARK OFFICE
CERTIFICATE OF CORRECTION

PATENT NO. : 10,982,249 B2  
APPLICATION NO. : 16/091536  
DATED : April 20, 2021  
INVENTOR(S) : Veronique Douchin et al.

Page 1 of 1

It is certified that error appears in the above-identified patent and that said Letters Patent is hereby corrected as shown below:

In the Specification

Column 2, Line 64 – "an" should be deleted;  
Column 23, Line 67 – "sunthesizing" should be "synthesizing";  
Column 47, Line 64 – "microorgamism" should be "microorganism";  
Column 54, Lines 65-66 – "convertion" should be "conversion";  
Column 57, Line 51 – "disctinction" should be "distinction";  
Column 58, Line 67 – "quadrapole" should be "quadrupole"; and In the Claims Column 483, Line 26 – "an" should be deleted.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*